(12) United States Patent
Matsuura et al.

(10) Patent No.: US 7,544,835 B2
(45) Date of Patent: Jun. 9, 2009

(54) CARBOXYLIC ACID DERIVATIVE AND SALT THEREOF

(75) Inventors: Fumiyoshi Matsuura, Brookline, MA (US); Eita Emori, Ibaraki (JP); Masanobu Shinoda, Ibaraki (JP); Richard Clark, Ibaraki (JP); Shunji Kasai, Ibaraki (JP); Hideki Yoshitomi, Ibaraki (JP); Kazuto Yamazaki, Ibaraki (JP); Takashi Inoue, Ibaraki (JP); Sadakazu Miyashita, Ibaraki (JP); Taro Hihara, Ibaraki (JP); Hitoshi Harada, Ibaraki (JP); Kaya Ohashi, Toyko (JP)

(73) Assignee: Eisai R&D Management Co., Ltd., Bunkyo-Ku (JP)

( * ) Notice: Subject to any disclaimer, the term of this patent is extended or adjusted under 35 U.S.C. 154(b) by 886 days.

(21) Appl. No.: 10/472,543

(22) PCT Filed: Apr. 18, 2002

(86) PCT No.: PCT/JP02/03866

§ 371 (c)(1), (2), (4) Date: Oct. 22, 2003

(87) PCT Pub. No.: WO02/100812

PCT Pub. Date: Dec. 19, 2002

(65) Prior Publication Data

US 2004/0102634 A1 May 27, 2004

(30) Foreign Application Priority Data

Apr. 20, 2001 (JP) ............................ 2001-123346
Feb. 14, 2002 (JP) ............................ 2002-036274

(51) Int. Cl.
*C07C 55/28* (2006.01)
*C07C 63/00* (2006.01)

(52) U.S. Cl. .................. 562/489; 562/405; 562/488

(58) Field of Classification Search .................. 562/405, 562/488, 489
See application file for complete search history.

(56) References Cited

U.S. PATENT DOCUMENTS

| | | | |
|---|---|---|---|
| 6,506,797 B1 | 1/2003 | Nomura et al. | |
| 6,884,821 B1 | 4/2005 | Shinoda et al. | |
| 7,244,861 B2 | 7/2007 | Matsuura et al. | |
| 7,253,178 B2 | 8/2007 | Matsuura et al. | |
| 2004/0102634 A1 | 5/2004 | Matsuura et al. | |
| 2004/0116708 A1 | 6/2004 | Harada et al. | |
| 2004/0138271 A1 | 7/2004 | Matsuura et al. | |
| 2004/0214888 A1 | 10/2004 | Matsuura et al. | |
| 2005/0014833 A1 | 1/2005 | Clark et al. | |

FOREIGN PATENT DOCUMENTS

| | | | |
|---|---|---|---|
| DE | 3026924 A1 | 2/1982 | |
| EP | 0028063 A1 | 5/1981 | |
| EP | 0028063 | * | 6/1984 |
| EP | 219308 A2 | 4/1987 | |
| EP | 543662 A2 | 5/1993 | |
| EP | 1026149 A1 | 8/2000 | |
| JP | 57-64639 A | 4/1982 | |
| JP | 9-48771 A | 2/1997 | |
| JP | 11-152269 A | 6/1999 | |
| JP | 2001-55367 A | 2/2001 | |
| JP | 2001-261612 A | 9/2001 | |
| WO | WO 89/03819 A1 | 5/1989 | |
| WO | WO 90/06920 A1 | 6/1990 | |
| WO | WO 94/01420 A1 | 1/1994 | |
| WO | WO 94/13650 A1 | 6/1994 | |
| WO | WO 95/03288 A1 | 2/1995 | |
| WO | WO 99-04815 A1 | 2/1999 | |
| WO | WO 99/16758 A1 | 4/1999 | |
| WO | WO 99/18066 A1 | 4/1999 | |
| WO | WO-99/20275 A1 | 4/1999 | |
| WO | WO-99/36393 A1 | 7/1999 | |
| WO | WO-99/65897 A1 | 12/1999 | |
| WO | WO-00/04011 A1 | 1/2000 | |
| WO | WO 00/64876 A1 | 11/2000 | |

(Continued)

OTHER PUBLICATIONS

Paul W. Young et al., The Journal of Pharmacology and Experimental Therapeutics, 1997, vol. 284, No. 2, pp. 751 to 759.

(Continued)

*Primary Examiner*—Taylor Victor Oh
(74) *Attorney, Agent, or Firm*—Birch, Stewart, Kolasch & Birch, LLP

(57) ABSTRACT

Carboxylic acid compound or salt or hydrate thereof useful as insulin sensitizer, represented by the formula

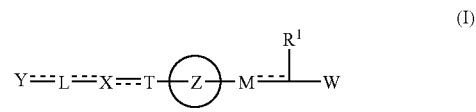

(I)

wherein $R^1$ represents hydrogen, hydroxyl, halogen, carboxyl, or $C_{1-6}$ alkyl, L represents single bond or $C_{1-6}$-alkylene, $C_{2-6}$-alkenylene, or $C_{2-6}$-alkynylene, M represents single bond or $C_{1-6}$-alkylene, $C_{2-6}$-alkenylene, or $C_{2-6}$-alkynylene, T represents single bond, or $C_{1-3}$-alkylene, $C_{2-3}$-alkenylene, or $C_{2-3}$-alkynylene, W represents carboxyl,

----- represents single bond, X represents single bond, oxygen, $-NR^{X1}CQ^1O-$, $-OCQ^1NR^{X1}-$, $-CQ^1NR^{X1}O-$, $ONR^{X1}CQ^1-$, $-Q^2SO_2-$, or $-SO_2Q^2-$, Y represents 5- to 14-membered aromatic group, and ring Z represents 5- to 14-membered aromatic group.

19 Claims, No Drawings

FOREIGN PATENT DOCUMENTS

| | | |
|---|---|---|
| WO | WO 00/64888 A1 | 11/2000 |
| WO | WO 00/75103 A1 | 12/2000 |
| WO | WO-01/21578 A1 | 3/2001 |
| WO | WO-01/25181 A1 | 4/2001 |
| WO | WO-01/25189 A1 | 4/2001 |
| WO | WO-01/38325 A1 | 5/2001 |
| WO | WO 01/55085 A1 | 8/2001 |
| WO | WO 01/55086 A1 | 8/2001 |
| WO | WO-01/92201 A1 | 12/2001 |
| WO | WO-02/12210 A1 | 2/2002 |
| WO | WO-02/34711 A1 | 5/2002 |
| WO | WO-02/42273 A2 | 5/2002 |
| WO | WO-02/079162 A1 | 10/2002 |
| WO | WO-02/080899 | 10/2002 |
| WO | WO-02/081428 A1 | 10/2002 |
| WO | WO-02/083616 A1 | 10/2002 |
| WO | WO-02/100812 A1 | 12/2002 |
| WO | WO-03/016265 A1 | 2/2003 |
| WO | WO-03/055867 A1 | 7/2003 |

OTHER PUBLICATIONS

David Haigh et al., Bioorganic & Medicinal Chemistry, 1999, vol. 7, No. 5, pp. 821 to 830.

"Nuovi Coloranti Per Miste Poliestere/Cotone" Tinctoria, 1996, vol. 93, No. 5, pp. 34 to 39.

D Gibson et al., European Journal of Medicinal Chemistry, 1997, vol. 32, No. 10, pp. 823 to 831.

Rico Lavoie et al., Bioorganic & Medicinal Chemistry Letters, 2001, vol. 11, No. 21, pp. 2847 to 2850.

Hulin et al., Current Pharmaceutical Design, 1996, 2, 85-102.

Buckle et al., Bioorganic & Medicinal Chemistry Letters, vol. 6, No. 17, pp. 2121-2126, 1996.

Bastie et al., The Journal of Biological Chemistry, vol. 274, No. 31, pp. 21920-21925, Jul. 30, 1999.

Lehmann et al., The Journal of Biological Chemistry, vol. 270, No. 22, 12953-12956, Jun. 2, 1995.

Willson et al., Journal of Medicinal Chemistry, vol. 43, No. 4, pp. 527-550 Feb. 24, 2000.

Barger et al., Trends in Cardiovasc. Med., vol. 10, No. 6, pp. 238-245, 2000.

Miyachi et al., Bioorganic & Medicinal Chemistry Letters, vol. 12, No. 1, Jan. 2002, pp. 77-80.

Kurtz, Hcaplus 2006:551484, "New treatment strategies for patients with hypertension and insulin resistance", American Journal of Medicine, 2006.

Li et al., Hcaplus 2006:256663, "Peroxisome proliferators-activated receptors: how their effects on macrophages can lead to the development of a new drug therapy against atherosclerosis", Annual Review of Pharmacology and Toxicology, 2006.

Demers et al., Journal of the American Pharmaceutical Association, Scientific Edition, vol. 41, No. 2, 1952, pp. 61-65.

Vasil'eva et al., Database Calpus, "Synthesis and Biological activity of acyl derivatives of 4-aminoantipyrine", 1984, XP002450796.

Aboul-Enein et al., Database Calpus, "Synthesis and biological activity of dibenz[c,e]azepines", 1990, XP002450797.

Richter et al., Tetrahedron Letters, vol. 39, 1998, pp. 8747-8750.

\* cited by examiner

CARBOXYLIC ACID DERIVATIVE AND SALT THEREOF

This application is the national phase under 35 U.S.C. § 371 of PCT International Application No. PCT/JP02/03866 which has an International filing date of Apr. 18, 2002, which designated the United States of America, the contents of which are hereby incorporated by reference.

TECHNICAL FIELD OF THE INVENTION

The present invention relates to a novel carboxylic acid compound useful for prevention or treatment of hyperglycemia, hyperlipemia and inflammatory disease, a salt thereof or a hydrate of them, and to a medicament comprising them.

PRIOR ART

Diabetes mellitus refers to a durable hyperglycemic condition attributable to the absolute or relative shortage of intrinsic insulin (blood glucose-depressing hormone produced and secreted from Langerhans islet β cells in the pancreas), and in this disease, metabolic abnormalities caused by this condition appear as various morbid states.

Diabetes mellitus is classified roughly into insulin dependent diabetes mellitus (IDDM) that is type 1 diabetes mellitus, for treatment of which insulin administration is absolutely necessary, non insulin dependent diabetes mellitus (NIDDM) that is type 2 diabetes mellitus, and other diabetes mellitus (secondary diabetes mellitus; diabetes mellitus occurs as one symptom of other diseases).

In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity and stress in addition to hereditary factors.

Since excessive intake of calories and obesity resulting from lack of exercise are related to diabetes mellitus as described above, the therapy is based on 3 kinds of therapies, that is, dietary therapy, exercise therapy and chemotherapy.

However, there are not a few cases where dietary therapy and exercise therapy are hardly to conduct because of an increase in the number of persons of advanced age in this aging society in recent years.

In chemotherapy of NIDDM, sulfonyl urea (SU) medicines such as Tolbutamide, Chlorpropamide and Tolazamide and Biguanide (BG) medicines such as Metformin hydrochloride and Buformin have been used as oral blood glucose depressants, but the morbid state of NIDDM is characterized by insulin deficiency and insulin resistance, and it cannot be said that the SU medicines stimulating insulin secretion from pancreatic β cells are effective therapeutic medicines for patients with NIDDM condition, where the insulin secretion potential is well but adequate blood glucose control is not achieved in target organs due to insulin registance, thus permitting hyperglycemia. Further, the BG medicines may permit the onset of lactic acid acidosis, so use of such medicines is limited to a certain extent. Further, these chemicals often caused severe hypoglycemia as a side effect.

To solve these problems, development of chemicals with a new working mechanism is advancing, and thiazolidine derivatives such as Troglitazone, Pioglitazone and Rosiglitazone are called insulin sensitizers, and these chemicals recently attract attention because they can ameliorate insulin resistance (or enhance the action of insulin) and lower blood glucose without promoting secretion of insulin from the pancreas.

It has been revealed that these thiazolidine-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953-12956, 1995). By the differentiation of preadipocytes, immature and small adipocytes with less secretion of TNFα, FFA and leptin are increased thus resulting in amelioration of insulin resistance.

Thiazolidine derivatives such as the above Troglitazone, Pioglitazone and Rosiglitazone also act as agonists for PPARγ, to exhibit the effect of ameliorating insulin resistance.

Besides PPARγ, PPAR subtypes such as α, β(δ) etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert glucose into lipid and storing the lipid, while PPARα mediates lipid catabolism by regulating expression of a gene group involved in intake of fatty acids into cells and oxidation thereof to decompose lipid.

Moreover, researches concerning relationships between particular subtypes of PPAR and various diseases have been widely conducted in recent years (J. Med. Chem., 2000, 43 (4), 527-550; Trends Cardiovasc. Med., 2000, 10, p 238-245).

As thiazolidine derivatives acting as PPARγ and α dual agonists, compounds disclosed in e.g. JP-A 9-48771 are known.

Further, some compounds are known as insulin sensitizers having a carboxylic acid moiety in their structure (Current Pharmaceutical Design, 2, No. 1, p 85-102, 1996; Bioorganic & Medicinal Chemistry Letters, 6, No. 17, p 2121-2126, 1996; WO200075103; WO9918066; WO9916758).

However, it has been reported that some chemicals acting as PPARγ agonists cause hepatic damage and thus should be carefully used, so chemicals satisfactory in both therapeutic effects and side effects such as toxicity are still not obtained.

Further, compounds having a carboxyl group instead of a thiazolidinyl group are merely presented in literatures and not marketed. Further, there is no report showing that such compounds can be used as PPARγ and a dual agonists, and as a matter of course, their γ, α and β(δ) triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful.

The conventional chemicals are still unsatisfactory in respect of neutral fat (triglyceride (TG)) related closely to arteriosclerosis.

Further, the action of PPARβ(δ) to induce differentiation of adipocytes is known (J. Biol. Chem., 274, No. 31, pp. 21920-21925), and by this action, cholesterol levels are reported to be lowered (WO9904815), and if a compound having an agonist action for this subtype can be found, this compound can be expected to exhibit a higher activity than that of the conventional insulin sensitizers and to reduce side effects such as hepatic toxicity.

Furthermore, as a PRAR receptor ligand, diarylic acid derivatives are disclosed in WO00/64888A and triarylic acid derivatives in WO00/64876A.

From the foregoing aspects, there is demand for development of excellent chemicals.

DISCLOSURE OF THE INVENTION

For the purpose of providing a medicament effective in prevention or treatment of hyperglycemia, which satisfies these various requirements, the present inventors made extensive study and, as a result, they found that a carboxylic acid derivative having a novel structure has an excellent anti-hyperglycemia and anti-hyperlipemia action, thus completing the present invention.

That is, the present invention relates to:

1) a carboxylic acid compound represented by the following formula:

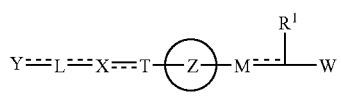
(I)

(wherein $R^1$ represents a hydrogen atom, hydroxyl group, halogen, carboxyl group, or a $C_{1-6}$ alkyl group, a $C_{1-6}$ alkoxy group, a $C_{1-6}$ alkylthio group, a $C_{1-6}$ hydroxyalkyl group, a $C_{1-6}$ hydroxyalkoxy group, a $C_{1-6}$ hydroxyalkylthio group, a $C_{1-6}$ aminoalkyl group, an amino $C_{1-6}$ alkoxy group, an amino $C_{1-6}$ alkylthio group, a halogeno $C_{1-6}$ alkyl group, a halogeno $C_{1-6}$ alkoxy group, a halogeno-$C_{1-6}$ alkylthio group, a $C_{2-12}$ alkoxyalkyl group, a $C_{2-12}$ alkoxyalkoxy group, a $C_{2-12}$ alkoxyalkylthio group, a $C_{3-7}$ cycloalkyl group, a $C_{3-7}$ cycloalkyloxy group, a $C_{4-13}$ cycloalkylalkyloxy group, a $C_{3-7}$ cycloalkylthio group, a $C_{2-6}$ alkenyl group, a $C_{2-6}$ alkenyloxy group, $C_{2-6}$ alkenylthio group, a $C_{2-6}$ alkynyl group, a $C_{2-6}$ alkynyloxy group, a $C_{2-6}$ alkynylthio group, a $C_{6-12}$ aryl group, a $C_{6-12}$ aryloxy group, a $C_{6-12}$ arylthio group, a $C_{7-18}$ alkylaryl group, a $C_{7-18}$ alkylaryloxy group, a $C_{7-18}$ alkylarylthio group, a $C_{7-18}$ aralkyl group, a $C_{7-18}$ aralkyloxy group or a $C_{7-18}$ aralkylthio group, each of which may have one or more substituents; L represents a single bond, or a $C_{1-6}$ alkylene group, a $C_{2-6}$ alkenylene group or a $C_{2-6}$ alkynylene group, each of which may have one or more substituents; M represents a single bond, or a $C_{1-6}$ alkylene group, a $C_{2-6}$ alkenylene group or a $C_{2-6}$ alkynylene group, each of which may have one or more substituents; T represents a single bond, or a $C_{1-3}$ alkylene group, a $C_{2-3}$ alkenylene group or a $C_{2-3}$ alkynylene group, each of which may have one or more substituents; W represents a carboxyl group;

----- represents a single bond or a double bond; X represents a single bond, oxygen atom, a group represented by —$NR^{X1}CQ^1O$— (wherein $Q^1$ represents an oxygen atom or sulfur atom; and $R^{X1}$ represents a hydrogen atom, formyl group, or a $C_{1-6}$ alkyl group, a $C_{1-6}$ hydroxyalkyl group, a $C_{1-6}$ aminoalkyl group, a halogeno $C_{1-6}$ alkyl group, a $C_{2-12}$ alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a $C_{7-19}$ aromatic acyl group, each of which may have one or more substituents), —$OCQ^1NR^{X1}$— (wherein $Q^1$ and $R^{X1}$ are as defined above), —$CQ^1NR^{X1}O$— (wherein $Q^1$ and $R^{X1}$ are as defined above), $ONR^{X1}CQ^1$— (wherein $Q^1$ and $R^{X1}$ areas defined above), —$Q^2SO_2$— (wherein $Q^2$ is an oxygen atom or —$NR^{X10}$— (wherein $R^{X10}$ represents a hydrogen atom, formyl group, or a $C_{1-6}$ alkyl group, a $C_{1-6}$ hydroxyalkyl group, a $C_{1-6}$ aminoalkyl group, a halogeno-$C_{1-6}$ alkyl group, a alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a aromatic acyl group, each of which may have one or more substituents)) or —$SO_2Q^2$— (wherein $Q^2$ is as defined above), or a group represented by the formula:

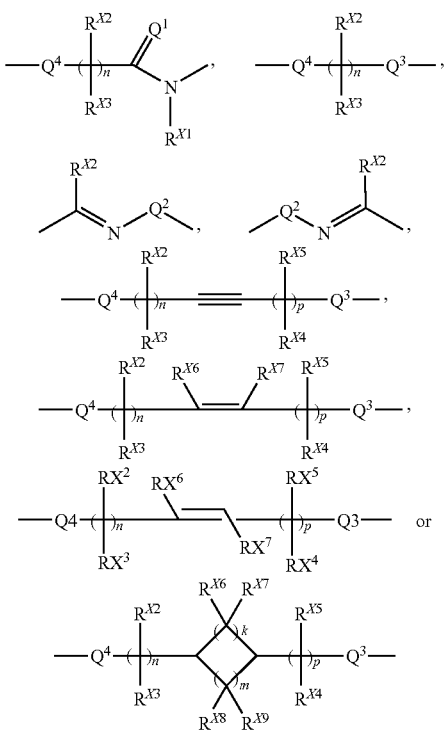

(wherein $Q^1$, $Q^2$ and $R^{X1}$ are as defined above; k represents 0 to 5; m represents 1 to 5; n and p are the same as or different from each other and each represents 1 to 5; $R^{X2}$, $R^{X3}$, $R^{X4}$, $R^{X5}$, $R^{X6}$, $R^{X7}$, $R^{X8}$ and $R^{X9}$ are the same as or different from each other and each represents a hydrogen atom, hydroxy group, halogen, —$N(R^{X11})R^{X12}$— (wherein $R^{X11}$ and $R^{X12}$ are the same as or different from each other and each represents a hydrogen atom, formyl group, or a $C_{1-6}$ alkyl group, a $C_{1-6}$ hydroxyalkyl group, a $C_{1-6}$ aminoalkyl group, a halogeno-$C_{1-6}$ alkyl group, a $C_{2-12}$ alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a $C_{7-19}$ aromatic acyl group, each of which may have one or more substituents), or a $C_{1-6}$ alkyl group, $C_{1-6}$ alkoxy group, a $C_{1-6}$ alkylthio group, a $C_{1-6}$ hydroxyalkyl group, a $C_{1-6}$ hydroxyalkoxy group, a $C_{1-6}$ hydroxyalkylthio group, a $C_{1-6}$ aminoalkyl group, a $C_{1-6}$ aminoalkoxy group, a $C_{1-6}$ aminoalkylthio group, a halogeno-$C_{1-6}$ alkyl group, a halogeno-$C_{1-6}$ alkoxy group, a halogeno-$C_{1-6}$ alkylthio group, a $C_{2-12}$ alkoxyalkyl group, a $C_{2-12}$ alkoxyalkoxy group, a $C_{2-12}$ alkoxyalkylthio group, a $C_{3-7}$ cycloalkyl group, a $C_{3-7}$ cycloalkyloxy group, a $C_{4-13}$ cycloalkylalkyloxy group, a $C_{3-7}$ cycloalkylthio group, a $C_{2-6}$ alkenyl group, a $C_{2-6}$ alkenyloxy group, a $C_{2-6}$ alkenylthio group, a $C_{2-6}$ alkynyl group, a $C_{2-6}$ alkynyloxy group, a $C_{2-6}$ alkynylthio group, a $C_{6-12}$ aryl group, a $C_{6-12}$ aryloxy group, a $C_{6-12}$ arylthio group, a $C_{7-18}$ alkylaryl group, a $C_{7-18}$ alkylaryloxy group, a $C_{7-18}$ alkylarylthio group, a $C_{7-18}$ aralkyl group, a $C_{7-18}$ aralkyloxy group or a $C_{7-18}$ aralkylthio group, each of which may have one or more substituents, provided that $R^{X2}$ and $R^{X3}$, and/or $R^{X4}$ and $R^{X5}$ may together form a ring; and $Q^3$ and $Q^4$ are the same as or different from each other and each represents an oxygen atom, (O)S(O) or $NR^{X10}$ (wherein $NR^{X10}$ is as defined above)); Y represents a 5- to 14-membered aromatic group or a $C_{3-7}$ alicyclic hydrocarbon group, each of which may have one or more substituents and one or more hetero atoms; and the ring Z represents a 5- to 14-membered aromatic group which may have 1 to 4 substituents and one or more hetero atoms, and wherein part of the ring may be saturated) a salt thereof, an ester thereof or a hydrate of them;

2) the carboxylic acid compound according to 1), a salt thereof, an ester thereof or a hydrate of them, wherein in the formula (I), Y is a 5- to 14-membered aromatic group which may have 1 to 4 substituents and one or more hetero atoms;

3) the carboxylic acid compound according to 1) or 2), a salt thereof, an ester thereof or a hydrate of them, wherein in the formula (I), X is a group represented by —$NR^{X1}CQ^1O$— (wherein $Q^1$ and $R^{X1}$ are as defined above), —$OCQ^1NR^{X1}$— (wherein $Q^1$ and $R^{X1}$ are as defined above), —$CQ^1NR^{X1}O$— (wherein $Q^1$ and $R^{X1}$ are as defined above), $ONR^{X1}CQ^1$— (wherein $Q^1$ and $R^{X1}$ are as defined above), —$Q^2SO_2$— (wherein $Q^2$ is as defined above) or $SO_2Q^2$ (wherein $Q^2$ is as defined above), or a group represented by the formula:

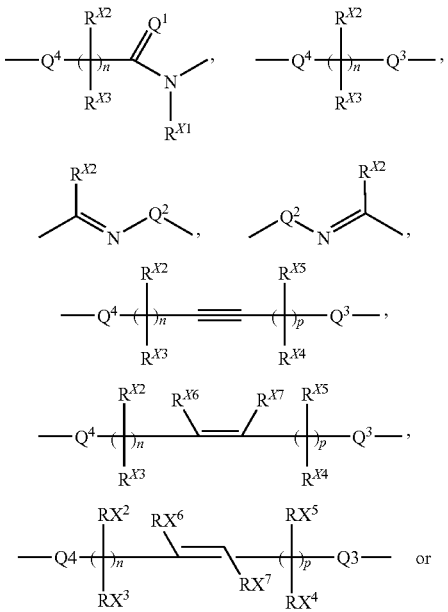

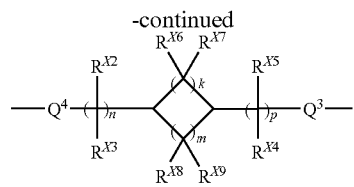

wherein $Q^1$, $Q^2$, k, m, n, p, $R^{X2}$, $R^{X3}$, $R^{X4}$, $R^{X5}$, $R^{X6}$, $R^{X7}$, $R^{X8}$ and $R^{X9}$ are as defined above;

4) the carboxylic acid compound according to any one of 1) to 3), a salt thereof, an ester thereof or a hydrate of them, wherein in the formula (I), X is —$NR^{X1}CQ^1O$— (wherein $Q^1$ and $R^{X1}$ are as defined above) or —$OCQ^1NR^{X1}$— ($Q^1$ and $R^{X1}$ are as defined above);

5) the carboxylic acid compound according to any one of 1) to 3), a salt thereof, an ester thereof or a hydrate of them, wherein in the formula (I), X is a group represented by the formula:

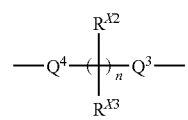

wherein n, $Q^3$, $Q^4$, $R^{X2}$ and $R^{X3}$ are as defined above;

6) the carboxylic acid compound according to 1), a salt thereof, an ester thereof or a hydrate of them, wherein in the formula (I), L is a single bond or a $C_{1-6}$ alkylene group which may have one or more substituents; X is a single bond or oxygen atom; and T is a $C_{2-6}$ alkynylene group which may have one or more substituents;

7) the carboxylic acid compound according to 1), a salt thereof, an ester thereof or a hydrate of them, wherein in the formula (I), L is a $C_{2-6}$ alkynylene which may have one or more substituents; X is a single bond or oxygen atom; and T is a single bond or a $C_{1-6}$ alkylene group which may have one or more substituents;

8) the carboxylic acid compound according to 1), a salt thereof, an ester thereof or a hydrate of them, wherein in the formula (I), X is a group represented by the formula:

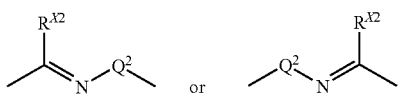

wherein $Q^2$ and $R^{X2}$ are as defined above;

9) the carboxylic acid compound according to 1), a salt thereof, an ester thereof or a hydrate of them, wherein in the formula (I), X is a group represented by the formula:

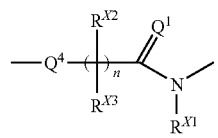

wherein n, $Q^1$, $Q^4$, $R^{X1}$, $R^{X2}$ and $R^{X3}$ are as defined above;

10) the carboxylic acid compound according to 1), a salt thereof, an ester thereof or a hydrate of them, wherein in the formula (I), X is a group represented by the formula:

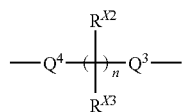

wherein $Q^3$ and $Q^4$ represent an oxygen atom; and n, $R^{X2}$ and $R^{X3}$ are as defined above;

11) the carboxylic acid according to 10), a salt thereof, an ester thereof or a hydrate of them, wherein in the formula (I), X is a group represented by the formula:

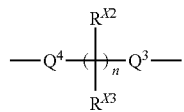

(wherein $Q^3$ and $Q^4$ represent an oxygen atom; n represents 2 to 5; and $R^{X2}$ and $R^{X3}$ are as defined above, provided that either one of $R^{X2}$ and $R^{X3}$ should be a group other than a hydrogen atom); L is a single bond or a $C_{1-3}$ alkylene group which may have one or more substituents; and T is a single bond or a $C_{1-3}$ alkylene group which may have one or more substituents;

12) the carboxylic acid compound according to 4), a salt thereof, an ester thereof or a hydrate of them, wherein in the formula (I), X is a group represented by the formula —$NR^{X1}CQ^1O$— (wherein $Q^1$ represents an oxygen atom, $R^{X1}$ is as defined above) or —$OCQ^1NR^{X1}$— (wherein $Q^1$ represents an oxygen atom, $R^{X1}$ is as defined above), L is a single bond or a $C_{1-3}$ alkylene group which may have one or more substituents, and T is a single bond or a $C_{1-3}$ alkylene group which may have one or more substituents;

13) the carboxylic acid compound according to 8), a salt thereof, an ester thereof or a hydrate of them, wherein in the formula (I), X is a group represented by the formula:

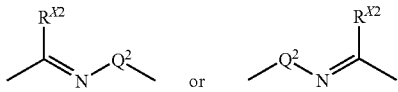

(wherein, $Q^2$ represents an oxygen atom and $R^{X2}$ is as defined above) L is a single bond or a $C_{1-3}$ alkylene group which may have one or more substituents; and T is a single bond or a $C_{1-3}$ alkylene group which may have one or more substituents;

14) the carboxylic acid compound according to 9), a salt thereof, an ester thereof or a hydrate of them, wherein in the formula (I), X is a group represented by the formula:

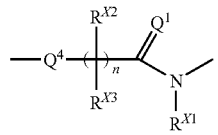

(wherein, $Q^1$ and $Q^4$ represent an oxygen atom; $R^{X1}$, $R^{X2}$ and $R^{X3}$ are as defined above; and n represents 1 to 5); L is a single bond or a $C_{1-3}$ alkylene group which may have one or more substituents; and T is a single bond or a $C_{1-3}$ alkylene group which may have one or more substituents;

15) the carboxylic acid compound according to 3), a salt thereof, an ester thereof or a hydrate of them, wherein in the formula (I), X is —$Q^2SO_2$— or —$SO_2Q^2$— (wherein $Q^2$ represents an oxygen atom); L is a single bond or a $C_{1-3}$ alkylene group which may have one or more substituents; and T is a single bond or a $C_{1-3}$ alkylene group which may have one or more substituents;

16) the carboxylic acid compound according to 3), a salt thereof, an ester thereof or a hydrate of them, wherein in the formula (I), X is —$CQ^1NR^{X1}O$— or —$ONR^{X1}CQ^1$— (wherein $Q^1$ represents an oxygen atom; and $R^{X1}$ is as defined above); L is a single bond or a $C_{1-3}$ alkylene group which may have one or more substituents; and T is a single bond or a $C_{1-3}$ alkylene group which may have one or more substituents;

17) the carboxylic acid compound according to 11), a salt thereof, an ester thereof or a hydrate of them, wherein in the formula (I), wherein M is a $C_{1-6}$ alkylene group; $R^1$ is a carboxyl group, or a $C_{1-6}$ alkyl group, a $C_{1-6}$ alkoxy group, a $C_{1-6}$ alkylthio group, a $C_{6-12}$ aryloxy group or a $C_{7-18}$ aralkyloxy group, each of which may have one or more substituents;

18) the carboxylic acid compound according to 17), a salt thereof, an ester thereof or a hydrate of them, wherein in the formula (I), the ring Z is a 1,3-phenylene group which may have 1 to 4 substituents;

19) the carboxylic acid compound according to 11) or 18), a salt thereof, an ester thereof or a hydrate of them, wherein in the formula (I), X is a group represented by the formula:

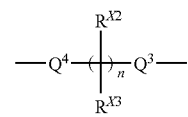

wherein $Q^3$ and $Q^4$ represent an oxygen atom; n represents 3 to 5; and $R^{X2}$ and $R^{X3}$ represent a hydrogen atom, hydroxyl group or fluorine atom, provided that either one of $R^{X2}$ and $R^{X3}$ should be a group other than a hydrogen atom;

20) the carboxylic acid compound according to 19), a salt thereof, an ester thereof or a hydrate of them, wherein in the formula (I), X is represented by the formula:

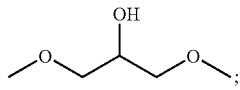

21) the carboxylic acid compound according to 19), a salt thereof, an ester thereof or a hydrate of them, wherein in the formula (I), X is represented by the formula:

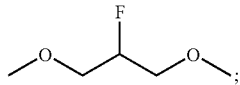

22) the carboxylic acid compound according to any one of 19) to 21), a salt thereof, an ester thereof or a hydrate of them, wherein in the formula (I), M is a methylene group; and $R^1$ is a $C_{1-6}$ alkoxy group which may have one or more substituents; 23) the carboxylic acid compound according to 12), a salt thereof, an ester thereof or a hydrate of them, wherein in the formula (I), M is a $C_{1-6}$ alkylene group; and $R^1$ is a carboxyl group, or a $C_{1-6}$ alkyl group, a $C_{1-6}$ alkoxy group, a $C_{1-6}$ alkylthio group, a $C_{6-12}$ aryloxy group or a $C_{7-18}$ aralkyloxy group, each of which may have one or more substituents;

24) the carboxylic acid compound according to 23), a salt thereof, an ester thereof or a hydrate of them, wherein in the formula (I), L is a $C_{1-3}$ alkylene group which may have one or more substituents; and T is a $C_{1-3}$ alkylene group which may have one or more substituents;

25) the carboxylic acid compound according to 24), a salt thereof, an ester thereof or a hydrate of them, wherein in the formula (I), the ring Z is a 1,3-phenylene group which may have 1 to 4 substituents;

26) the carboxylic acid compound according to 25), a salt thereof, an ester thereof or a hydrate of them, wherein in the formula (I), M is a methylene group; and $R^1$ is a $C_{1-6}$ alkoxy group which may have one or more substituents;

27) the carboxylic acid compound according to any one of 6), 7), 13), 14), 15) and 16), a salt thereof, an ester thereof or a hydrate of them, wherein in the formula (I), M is a $C_{1-6}$ alkylene group; $R^1$ is a carboxyl group, or a $C_{1-6}$ alkyl group, a $C_{1-6}$ alkoxy group, a $C_{1-6}$ alkylthio group, a $C_{6-12}$ aryloxy group or a $C_{7-18}$ aralkyloxy group, each of which may have one or more substituents;

28) the carboxylic acid compound according to any one of 11) to 27), a salt thereof, an ester thereof or a hydrate of them, wherein in the formula (I), Y is a phenyl group which may have 1 or 2 substituents;

29) the carboxylic acid compound according to 1), a salt thereof, an ester thereof or a hydrate of them, wherein in the formula (I), a group represented by the formula:

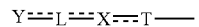

(wherein each symbol represents a group as defined above) and a group represented by the formula:

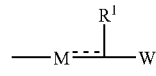

(wherein each symbol represents a group as defined above) are bound with each other on the ring Z via from 2 to 8 atoms;

30) the carboxylic acid compound according to 1), a salt thereof, an ester thereof or a hydrate of them, wherein the compound represented by the formula (I) is one selected from:
(1) 2-isopropoxy-3-(3-[3-(2,4-dichlorophenyl)-2-propynyl] oxyphenyl)propanoic acid;
(2) 3-3-[3-(4-trifluoromethylphenyl)-1-hydroxy-1-methyl-2-propynyl]phenyl-2-isopropoxypropanoic acid;
(3) 2-isopropoxy-3-[3-([4-(trifluoromethyl)benzyl]-oxyehtaneimidoyl)phenyl]propanoic acid;
(4) 2-ethoxy-3-{3-[2-({[4-(trifluoromethyl)anilino]-carbonyl}oxy)ethyl]phenyl}propanoic acid;
(5) 3-{3-[3-(4-chloro-2-cyanophenoxy)-2-hydroxypropoxy]phenyl}-2-isopropoxypropanoic acid;
(6) 2-isopropoxy-3-(3-{[({[4-trifluoromethoxybenzyl]-oxy}carbonyl)amino]methyl}phenyl)propanoic acid;
(7) 3-{3-[3-(2,4-dichlorophenoxy)-2(S)-hydroxypropoxy]phenyl}-2(S)-isopropoxypropanoic acid;
(8) 3-{3-[3-(4-chloro-2-cyanophenoxy)-2(S)-hydroxypropoxy]phenyl}-2(S)-isopropoxypropanoic acid;
(9) 3-(3-{2(S)-hydroxy-3-[3-(1-hydroxy-1-methylethyl)-phenoxy]-propoxy}phenyl)-2(S)-isopropoxypropanoic acid;
(10) 3-(3-{2(R)-hydroxy-3-[4-chlorophenoxy]propoxy}-phenyl)-2(S)-isopropoxypropanoic acid;
(11) 3-(3-{2(S)-hydroxy-3-[2,4-dimethylphenoxy]-propoxy}phenyl)-2(S)-isopropoxypropanoic acid;
(12) 3-(3-{2(S)-hydroxy-3-[4-chloro-2-fluorophenoxy]-propoxy}phenyl)-2(S)-isopropoxypropanoic acid;
(13) 3-{3-[3-(2,4-dichlorophenoxy)-2 (R)-hydroxypropoxy]phenyl}-2(S)-isopropoxypropanoic acid;
(14) 3-{3-[3-(4-chloro-2-cyanophenoxy)-2 (R)-hydroxypropoxy]phenyl}-2(S)-isopropoxypropanoic acid;
(15) 3-(3-{2(R)-hydroxy-3-[2,4-dimethylphenoxy]-propoxy}phenyl)-2(S)-isopropoxypropanoic acid;
(16) 3-{3-[3-(2,4-dichlorophenoxy)-2 (R)-fluoropropyl]phenyl}-2(S)-isopropoxypropanoic acid;
(17) 3-{3-[3-(4-chlorophenoxy)-2(S)-fluoropropyl]phenyl}-2(S)-isopropoxypropanoic acid;
(18) 3-{3-[3-(4-chloro-2-cyanophenoxy)-2 (R)-fluoropyl]phenyl}-2(S)-isopropoxypropanoic acid;
(19) 3-{3-[3-(2,4-dichlorophenoxy)-2(S)-fluoropropyl]phenyl}-2(S)-isopropoxypropanoic acid;
(20) 3-{3-[3-(4-chlorophenoxy)-2 (R)-fluoropropyl]phenyl}-2(S)-isopropoxypropanoic acid;
(21) 3-{3-[3-(4-chloro-2-cyanophenoxy)-2(S)-fluoropropyl]phenyl}-2(S)-isopropoxypropanoic acid;
(22) 3-{3-[3-(2,4-dimethylphenoxy)-2(S)-fluoropropyl]phenyl}-2(S)-isopropoxypropanoic acid;
(23) 2 (S)-isopropoxy-3-{3-[(4-trifluoromethylbenzyloxycarbonylamino)methyl]phenyl}-propanoic acid;
(24) 2 (S)-isopropoxy-3-{3-[(3-trifluoromethylbenzyloxycarbonylamino)methyl]phenyl}-propanoic acid;
(25) 2 (S)-isopropoxy-3-{3-[(4-trifluoromethoxybenzyloxycarbonylamino)methyl]phenyl}-propanoic acid;
(26) 3-(3-{[4-(1-hydroxy-1-methylethyl)-benzyloxycarbonylamino]methyl}phenyl)-2(S)-isopropoxypropanoic acid;

(27) 3-(3-{[2,5-dichlorobenzyloxycarbonylamino]-methyl}phenyl)-2(S)-isopropoxypropanoic acid;
(28) 3-(3-{[4-ethoxybenzyloxycarbonylamino]methyl}-phenyl)-2(S)-isopropoxypropanoic acid;
(29) 3-(3-{[3-trifluoromethoxybenzyloxycarbonylamino]-methyl}phenyl)-2(S)-isopropoxypropanoic acid;
(30) 3-(3-{[2-(4-chlorophenyl)ethoxycarbonylamino]-methyl}phenyl)-2(S)-isopropoxypropanoic acid;
(31) 2 (S)-isopropoxy-3-{3-[(quinolin-2-ylmethoxycarbonylamino)methyl]phenyl}propanoic acid;
(32) 3-{[3-(2,4-dichlorophenyl)carbamoyloxymethyl-4-ethoxy]phenyl}-2-isopropoxypropanoic acid;
(33) 3-({4-[5-(benzo[1,3]dioxolyl)]-carbamoyloxymethyl}phenyl)-2-isopropoxypropanoic acid;
(34) 3-{3-[3-(2,4-dichlorophenoxy)-1-propynyl]phenyl}-2 (S)-isopropoxypropanoic acid;
(35) 3-{3-[3-(2,4-dichlorophenyl)-2-propionyloxy]-phenyl}-2 (s)-isopropoxypropanoic acid;
(36) 3-{3-[3-(4-chlorophenyl)-2-propionyloxy]phenyl}-2 (S)-isopropoxypropanoic acid;
(37) 2 (S)-3-{[3-(2,4-dichlorophenyl)carbamoyloxymethyl-4-ethoxy]phenyl}-2-isopropoxypropanoic acid;
(38) 3-{3-[2-(4-chlorophenoxy)acetylamino]-4-ethoxyphenyl}-2-isopropoxypropanoic acid;
(39) 3-{3-[2-(2,4-dichlorophenoxy)acetylamino]-4-ethoxyphenyl}-2-isopropoxypropanoic acid; and
(40) 3-{4-[3-(4-chloro-2-cyanophenoxy)-2-hydroxypropoxy]phenyl}-2-isopropoxypropanoic acid;

31) a medicament comprising a carboxylic acid compound represented by the following formula:

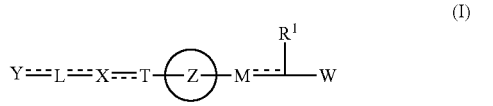

(I)

(wherein $R^1$ represents a hydrogen atom, hydroxyl group, halogen, carboxyl group, or a $C_{1-6}$ alkyl group, a $C_{1-6}$ alkoxy group, a $C_{1-6}$ alkylthio group, a $C_{1-6}$ hydroxyalkyl group, a $C_{1-6}$ hydroxyalkoxy group, a $C_{1-6}$ hydroxyalkylthio group, a $C_{1-6}$ aminoalkyl group, an amino $C_{1-6}$ alkoxy group, an amino $C_{1-6}$ alkylthio group, a halogeno $C_{1-6}$ alkyl group, a halogeno $C_{1-6}$ alkoxy group, a halogeno-$C_{1-6}$ alkylthio group, a $C_{2-12}$ alkoxyalkyl group, a $C_{2-12}$ alkoxyalkoxy group, a $C_{2-12}$ alkoxyalkylthio group, a $C_{3-7}$ cycloalkyl group, a $C_{3-7}$ cycloalkyloxy group, a $C_{4-13}$ cycloalkylalkyloxy group, a $C_{3-7}$ cycloalkylthio group, a $C_{2-6}$ alkenyl group, a $C_{2-6}$ alkenyloxy group, $C_{2-6}$ alkenylthio group, a $C_{2-6}$ alkynyl group, a $C_{2-6}$ alkynyloxy group, a $C_{2-6}$ alkynylthio group, a $C_{6-12}$ aryl group, a $C_{6-12}$ aryloxy group, a $C_{6-12}$ arylthio group, a $C_{7-18}$ alkylaryl group, a $C_{7-18}$ alkylaryloxy group, a $C_{7-18}$ alkylarylthio group, a $C_{7-18}$ aralkyl group, a $C_{7-18}$ aralkyloxy group or a $C_{7-18}$ aralkylthio group, each of which may have one or more substituents; L represents a single bond, or a $C_{1-6}$ alkylene group, a $C_{2-6}$ alkenylene group or a $C_{2-6}$ alkynylene group, each of which may have one or more substituents; M represents a single bond, or a $C_{1-6}$ alkylene group, a $C_{2-6}$ alkenylene group or a $C_{2-6}$ alkynylene group, each of which may have one or more substituents; T represents a single bond, or a $C_{1-3}$ alkylene group, a $C_{2-3}$ alkenylene group or a $C_{2-3}$ alkynylene group, each of which may have one or more substituents; W represents a carboxyl group;

represents a single bond or a double bond; X represents a single bond, oxygen atom, a group represented by —$NR^{X1}CQ^{10}$— (wherein $Q^1$ represents an oxygen atom or sulfur atom; and $R^{X1}$ represents a hydrogen atom, formyl group, or a $C_{1-6}$ alkyl group, a $C_{1-6}$ hydroxyalkyl group, a $C_{1-6}$ aminoalkyl group, a halogeno $C_{1-6}$ alkyl group, a $C_{2-12}$ alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a $C_{7-19}$ aromatic acyl group, each of which may have one or more substituents), —$OCQ^1NR^{X1}$— (wherein $Q^1$ and $R^{X1}$ are as defined above), —$CQ^1NR^{X1}O$— (wherein $Q^1$ and $R^{X1}$ are as defined above), $ONR^{X1}CQ^1$— (wherein $Q^1$ and $R^{X1}$ are as defined above), —$Q^2SO_2$— (wherein $Q^2$ is an oxygen atom or —$NR^{X10}$— (wherein $R^{X1}$ represents a hydrogen atom, formyl group, or a $C_{1-6}$ alkyl group, a $C_{1-6}$ hydroxyalkyl group, a $C_{1-6}$ aminoalkyl group, a halogeno-$C_{1-6}$ alkyl group, a $C_{2-12}$ alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a $C_{7-19}$ aromatic acyl group, each of which may have one or more substituents)) or —$SO_2Q^2$— (wherein $Q^2$ is as defined above), or a group represented by the formula:

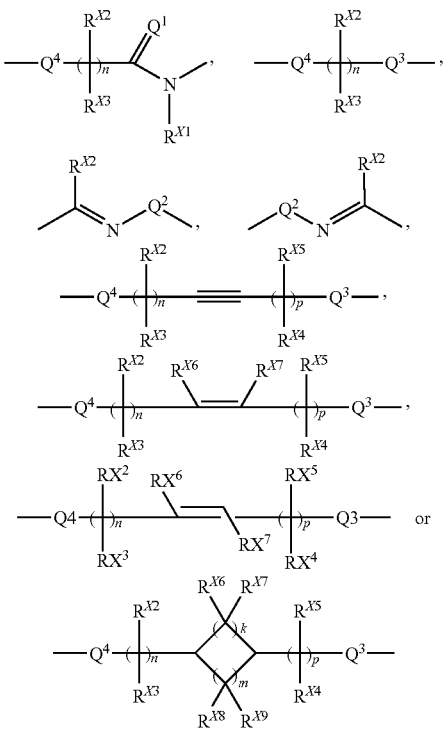

(wherein $Q^1$, $Q^2$ and $R^{X1}$ are as defined above; k represents 0 to 5; m represents 1 to 5; n and p are the same as or different from each other and each represents 1 to 5; $R^{X2}$, $R^{X3}$, $R^{X4}$, $R^{X5}$, $R^{X6}$, $R^{X7}$, $R^{X8}$ and $R^{X9}$ are the same as or different from each other and each represents a hydrogen atom, hydroxy group, halogen, —$N(R^{X11})R^{X12}$ (wherein $R^{X11}$ and $R^{X12}$ are the same as or different from each other and each represents a hydrogen atom, formyl group, or a $C_{1-6}$ alkyl group, a $C_{1-6}$ hydroxyalkyl group, a $C_{1-6}$ aminoalkyl group, a halogeno-$C_{1-6}$ alkyl group, a $C_{2-12}$ alkoxyalkyl group, a $C_{3-7}$ cycloalkyl group, a $C_{2-6}$ alkenyl group, a $C_{2-6}$ alkynyl group, a $C_{6-12}$ aryl group, a $C_{7-18}$ alkylaryl group, a $C_{7-18}$ aralkyl group, a $C_{2-7}$ aliphatic acyl group or a $C_{7-19}$ aromatic acyl group, each of which may have one or more substituents), or a $C_{1-6}$ alkyl group, $C_{1-6}$ alkoxy group, a $C_{1-6}$ alkylthio group, a $C_{1-6}$ hydroxyalkyl group, a $C_{1-6}$ hydroxyalkoxy group, a $C_{1-6}$ hydroxyalkylthio group, a $C_{1-6}$ aminoalkyl group, a $C_{1-6}$ aminoalkoxy group, a $C_{1-6}$ aminoalkylthio group, a halogeno-$C_{1-6}$ alkyl group, a halogeno-$C_{1-6}$ alkoxy group, a halogeno-$C_{1-6}$ alkylthio group, a $C_{2-12}$ alkoxyalkyl group, a $C_{2-12}$ alkoxyalkoxy group, a $C_{2-12}$ alkoxyalkylthio group, a $C_{3-7}$ cycloalkyl group, a $C_{3-7}$ cycloalkyloxy group, a $C_{4-13}$ cycloalkylalkyloxy group, a $C_{3-7}$ cycloalkylthio group, a $C_{2-6}$ alkenyl group, a $C_{2-6}$ alkenyloxy group, a $C_{2-6}$ alkenylthio group, a $C_{2-6}$ alkynyl group, a $C_{2-6}$ alkynyloxy group, a $C_{2-6}$ alkynylthio group, a $C_{6-12}$ aryl group, a $C_{6-12}$ aryloxy group, a $C_{6-12}$ arylthio group, a $C_{7-18}$ alkylaryl group, a $C_{7-18}$ alkylaryloxy group, a $C_{7-18}$ alkylarylthio group, a $C_{7-18}$ aralkyl group, a $C_{7-18}$ aralkyloxy group or a $C_{7-18}$ aralkylthio group, each of which may have one or more substituents, provided that $R^{X2}$ and $R^{X3}$, and/or $R^{X4}$ and $R^{X5}$ may together form a ring; and $Q^3$ and $Q^4$ are the same as or different from each other and each represents an oxygen atom, (O)S(O) or $NR^{X10}$ (wherein $NR^{X10}$ is as defined above)); Y represents a 5- to 14-membered aromatic group or a $C_{3-7}$ alicyclic hydrocarbon group, each of which may have one or more substituents and one or more hetero atoms; and the ring Z represents a 5- to 14-membered aromatic group which may have 1 to 4 substituents and one or more hetero atoms, and wherein part of the ring may be saturated), a salt thereof, an ester thereof or a hydrate of them;

32) the medicament according to 31), which is based on PPAR α and γ dual agonism;

33) the medicament according to 31), which is based on PPAR α, β(δ) and γ triple agonism;

34) the medicament according to any one of 31) to 33), which is an insulin sensitizer;

35) the medicament according to any one of 31) to 33), which is an agent for preventing or treating diabetes mellitus;

36) the medicament according to any one of 31) to 33), which is an agent for preventing or treating syndrome X;

37) the medicament according to any one of 31) to 33), which is an agent for preventing or treating diabetic complications;

38) the medicament according to any one of 31) to 33), which is an agent for preventing or treating hyperlipemia;

39) the medicament according to any one of 31) to 33), which is a lipid-lowering agent;

40) the medicament according to any one of 31) to 33), which is an agent for preventing or treating obesity;

41) the medicament according to any one of 31) to 33), which is an agent for treating osteoporosis;

42) the medicament according to any one of 31) to 33), which is an anti-inflammatory agent;

43) the medicament according to any one of 31) to 33), which is an agent for preventing or treating digestive disease;

44) the medicament according to 43), wherein the digestive disease is a disease selected from the group consisting of 1) inflammatory diseases of the digestive organs; 2) proliferative diseases of the digestive organs; and 3) ulcerative diseases of the digestive organs;

45) the medicament according to 44), wherein the inflammatory disease of the digestive organs is a disease selected from the group consisting of 1) ulcerative colitis; 2) Crohn's disease; 3) pancreatitis; and (4) gastritis;

46) the medicament according to 44), wherein the inflammatory disease of the digestive organs is ulcerative colitis;

47) an agent for preventing or treating a disease against which an insulin sensitizing action is efficacious, which comprises the compound according to any one of 1) to 30) as the active ingredient;

48) the agent for preventing or treating digestive disease according to 44), wherein the proliferative diseases of the digestive organs is a disease selected from the group consisting of 1) benign tumor of the digestive organs; 2) digestive polyp; 3) hereditary polyposis syndrome; 4) colon cancer; 5) rectum cancer and 6) stomach cancer;

49) the medicament according to any one of 31) to 33) whose action is improving energy metabolism, which is an agent for preventing or treating 1) stenocardia and myocardial infarction, and sequelae thereof; 2) senile dementia; or 3) cerebrovascular dementia;

50) the medicament according to any one of 31) to 33) which is an immunomodulatory agent;

51) the medicament according to any one of 31) to 33) which is an agent for preventing or treating cancer;

52) a method of preventing or treating a disease against which an insulin sensitizing action is efficacious, which comprises administering to a patient a pharmaceutically effective amount of the carboxylic acid compound according to any one of 1) to 30), a salt thereof, an ester thereof or a hydrate of them; and 53) use of the carboxylic acid compound according to any one of 1) to 30), a salt thereof, an ester thereof or a hydrate of them, for producing an agent for preventing or treating a disease against which an insulin sensitizing action is efficacious.

The present invention provides a pharmaceutical composition comprising a carboxylic acid compound represented by the formula (I), a salt thereof, an ester thereof or a hydrate of them, and a pharmaceutically acceptable carrier.

The present invention also provides a method of preventing or treating a disease against which PPAR α and γ dual agonism or PPAR α, β(δ) and γ triple agonism is efficacious, which comprises administering to a patient a pharmaceutically effective amount of the carboxylic acid compound according to anyone of 1) to 30), a salt thereof, an ester thereof or a hydrate of them.

Further, the present invention provides use of the carboxylic acid compound according to any one of 1) to 30), a salt thereof, an ester thereof or a hydrate of them, for producing an agent for preventing or treating a disease against which PPAR α and γ dual agonism or PPAR α, β(δ) and γ triple agonism is efficacious.

In the present invention, "disease against which PPAR α and γ dual agonism or PPAR α, β(δ) and γ triple agonism is efficacious" includes diabetes mellitus; syndrome X; diabetic complications; hyperlipemia; a disease against which a lipid-lowering action is efficacious; obesity; osteoporosis; a disease against which an anti-inflammatory action is efficacious, digestive diseases including 1) inflammatory diseases of digestive organs including ulcerative colitis, Crohn's disease, pancreatitis and gastritis; 2) the proliferative diseases of digestive organs including benign tumor of digestive organs, digestive polyp, hereditary polyposis syndrome, colon cancer, rectum cancer and stomach cancer; and 3) ulcerative diseases of digestive organs; 1) stenocardia and myocardial infarction, and sequelae thereof; 2) senile dementia; or 3) cerebrovascular dementia based on energy metabolism improving effect, respectively, a disease against which an immunomodulatory action is efficacious, and tumor disease.

In this specification, the structural formulae of the compounds may, for convenience' sake, indicate a certain isomer, but the present invention encompasses every possible isomer such as geometric isomer, optical isomer based on asymmetric carbon, stereoisomer and tautomer, which can occur in the structures of the compounds of the present invention, and mixtures of these isomers, and therefore, the compounds of the present invention are not limited by the formulae shown for convenience' sake.

Now, the terms used in this specification are described in detail.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ each represents a $C_{1-6}$ alkyl group which may have one or more substituents, the alkyl group means a $C_{1-6}$ linear or branched alkyl group, and specific examples thereof include methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group, preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group and i-hexyl group, more preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group and 1,2-dimethylpropyl group, further preferably methyl group, ethyl group, n-propyl group, i-propyl group, n-butyl group, i-butyl group, sec-butyl group and t-butyl group, and most preferably methyl group, ethyl group, n-propyl group and i-propyl group.

Herein, the phrase "which may have a substituent" specifically means that the group may be substituted with a substituent such as hydroxyl group; thiol group; nitro group; morpholino group; thiomorpholino group; a halogen atom such as fluorine atom, chlorine atom, bromine atom and iodine atom; nitrile group; azide group; formyl group; alkyl group such as methyl group, ethyl group, propyl group, isopropyl group and butyl group; alkenyl group such as vinyl group, allyl group and propenyl group; alkynyl group such as ethynyl group, butynyl group and propargyl group; alkoxy group such as methoxy group, ethoxy group, propoxy group and butoxy group; halogenoalkyl group such as fluoromethyl group, difluoromethyl group, trifluoromethyl group and fluoroethyl group; hydroxyalkyl group such as hydroxymethyl group, hydroxyethyl group and hydroxypropyl group; guanidino group; formimidoyl group; acetoimidoyl group; carbamoyl group; thiocarbamoyl group; carbamoylalkyl group such as carbamoylmethyl group and carbamoylethyl group; alkyl carbamoyl group such as methylcarbamoyl group and dimethylcarbamoyl group; carbamide group; alkanoyl group such as acetyl group; amino group; alkylamino group such as methylamino group, ethylamino group and isopropylamino group; dialkylamino group such as dimethylamino group, methylethylamino group and diethylamino group; amino alkyl group such as aminomethyl group, aminoethyl group and aminopropyl group; carboxyl group; alkoxycarbonyl group such as methoxycarbonyl group, ethoxycarbonyl group and propoxycarbonyl group; alkoxycarbonylalkyl group such as methoxycarbonylmethyl group, ethoxycarbonylmethyl group, propoxycarbonylmethyl group, methoxycarbonylethyl group, ethoxycarbonylethyl group and propoxycarbonylethyl group; alkyloxyalkyl group such as methyloxymethyl group, methyloxyethyl group, ethyloxymethyl group and ethyloxyethyl group; alkylthioalkyl group such as methylthiomethyl group, methylthioethyl group, ethylthiomethyl group and ethylthioethyl group; aminoalkylaminoalkyl group such as aminomethylaminomethyl group and aminoethylaminomethyl group; alkylcarbonyloxy group such as methylcarbonyloxy group, ethylcarbonyloxy group and isopropylcarbonyloxy group; arylalkoxyalkoxyalkyl group such as benzyloxyethyloxymethyl group and benzyloxyethyloxyethyl group; hydroxyalkoxyalkyl group such as hydroxyethyloxymethyl group and hydroxyethyloxyethyl group; arylalkoxyalkyl group such as benzyloxymethyl group, benzyloxyethyl group and benzyloxypropyl group; quaternary ammonio group such as trimethylammonio group, methylethylmethylammonio group and triethyl ammonio group; cycloalkyl group such as cyclopropyl group, cyclobutyl group, cyclopentyl group and cyclohexyl group; cycloalkenyl group such as cyclopropenyl group, cyclobutenyl group, cyclopentenyl group and cylohexenyl group; aryl group such as phenyl group, pyridinyl group, thienyl group, furyl group and pyrrolyl group; alkylthio group such as methylthio group, ethylthio group, propylthio group and butylthio group; arylthio group such as phenylthio group, pyridinylthio group, thienylthio group, furylthio group and pyrrolylthio group; aryl lower alkyl group such as benzyl group, trityl group and dimethoxytrityl group; substituted sulfonyl group such as sulfonyl group, mesyl group and p-toluene sulfonyl group; aryloyl group such as benzoyl group; halogenoaryl group such as fluorophenyl group and bromophenyl group; and oxyalkoxy group such as methylene dioxy group.

The phrase "which may have one or more substituents" means that the group may have one or more of these groups in an arbitrary combination, and includes e.g. an alkyl group, alkenyl group, alkynyl group and alkoxy group substituted with hydroxyl group, thiol group, nitro group, morpholino group, thiomorpholino group, a halogen atom, nitrile group, azide group, formyl group, amino group, alkylamino group, dialkylamino group, carbamoyl group and sulfonyl group.

Hereinafter, the phrases "which may have a substituent" and "which may have one or more substituents" in the present invention have the meanings as defined above.

When $R^1$, $R^{X2}$, $R^{X3}$, $R^{X4}$, $R^{X5}$, $R^{X6}$, $R^{X7}$, $R^{X8}$ and $R^{X9}$ represents a $C_{1-6}$ alkoxy group which may have one or more substituents, the alkoxy group means a $C_{1-6}$ linear or branched alkoxy group and refers to a group having an oxygen atom bound to the end of the alkyl group. Specific examples thereof include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; further preferably methoxy group, ethoxy group, n-propoxy group, i-propoxy group, n-butoxy group, i-butoxy group, sec-butoxy group and t-butoxy group; and most preferably a methoxy group, ethoxy group, n-propoxy group and i-propoxy group.

When $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ alkylthio group which may have one or more substituents, the alkylthio group represents a $C_{1-6}$ linear or branched alkylthio group and refers to a group having a sulfur atom bound to the end of the alkyl group. Specific examples thereof include methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group and 1-ethyl-2-methylpropylthio group, preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group and i-hexylthio group; more preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group and 1,2-dimethylpropylthio group; further preferably methylthio group, ethylthio group, n-propylthio group, i-propylthio group, n-butylthio group, i-butylthio group, sec-butylthio group and t-butylthio group; and most preferably a methylthio group, ethylthio group, n-propylthio group and i-propylthio group.

When $R^1$, $R^{X1}$, $R^{X2}R^{X3}$, $R^{X4}$, $R^{X5}$, $R^{X6}$, $R^{X7}$, $R^{X8}$, $R^{X9}$ and $R^{X10}$ represent a $C_{1-6}$ hydroxyalkyl group which may have one or more substituents, the hydroxyalkyl group represents a group having the $C_{1-6}$ linear or branched alkyl group substituted at a substitutable site with a hydroxy group. Specific examples thereof include hydroxymethyl group, 2-hydroxyethyl group and 1-hydroxyethyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ hydroxyalkoxy group which may have one or more substituents, the hydroxyalkoxy group represents a group having the $C_{1-6}$ linear or branched alkoxy group substituted at a substitutable site with a hydroxy group. Specific examples thereof include hydroxymethoxy group, 2-hydroxyethoxy group and 1-hydroxyethoxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ hydroxyalkylthio group which may have one or more substituents, the hydroxyalkylthio group represents a group having the $C_{1-6}$ linear or branched alkylthio group substituted at a substitutable site with a hydroxy group. Specific examples thereof include hydroxymethylthio group, 2-hydroxyethylthio group and 1-hydroxyethylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{1-6}$ aminoalkyl group which may have one or more substituents, the aminoalkyl group represents a group having the $C_{1-6}$ linear or branched alkyl group substituted at a substitutable site with an amino group. Specific examples thereof include aminomethyl group, 2-aminoethyl group and 1-aminoethyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ aminoalkoxy group which may have one or more substituents, the aminoalkoxy group represents a group having the $C_{1-6}$ linear or branched alkoxy group substituted at a substitutable site with an amino group. Specific examples thereof include aminomethoxy group, 2-aminoethoxy group and 1-aminoethoxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ aminoalkylthio group which may have one or more substituents, the aminoalkylthio group represents a group having the $C_{1-6}$ linear or branched alkylthio group substituted at a substitutable site with an amino group. Specific examples thereof include aminomethylthio group, 2-aminoethylthio group and 1-aminoethylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a halogeno $C_{1-6}$ alkyl group which may have one or more substituents, the halogenoalkyl group represents a group having the $C_{1-6}$ linear or branched alkyl group substituted at substitutable sites with one or more halogen atoms. Herein, the halogen atoms refer to fluorine atom, chlorine atom, bromine atom and iodine atom. Specific examples of such a group include fluoromethyl group, trifluoromethyl group, 2-fluoroethyl group and 1-fluoroethyl group.

Similarly when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ halogenated alkoxy group which may have one or more substituents, the halogenated alkoxy group represents a group having the $C_{1-6}$ linear or branched alkoxy group substituted at substitutable sites with one or more halogen atoms. Specific examples thereof include fluoromethoxy group, trifluoromethoxy group, 2-fluoroethoxy group and 1-fluoroethoxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{1-6}$ halogenated alkylthio group which may have one or more substituents, the halogenated alkylthio group represents a group having the $C_{1-6}$ linear or branched alkylthio group substituted at substitutable sites with one or more halogen atoms. Specific examples thereof include fluoromethylthio group, trifluoromethylthio group, 2-fluoroethylthio group and 1-fluoroethylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{2-12}$ alkoxyalkyl group which may have one or more substituents, the alkoxyalkyl group represents a group having the $C_{1-6}$ linear or branched alkyl group substituted at a substitutable site with the $C_{1-6}$ linear or branched alkoxy group. Specific examples thereof include methoxymethyl group, ethoxymethyl group, 1-methoxyethyl group, 2-methoxyethyl group, 1-ethoxyethyl group and 2-ethoxyethyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{2-12}$ alkoxyalkoxy group which may have one or more substituents, the alkoxyalkoxy group represents a group having the $C_{1-6}$ linear or branched alkoxy group substituted at a substitutable site with the $C_{1-6}$ linear or branched alkoxy group. Specific examples thereof include methoxymethoxy group, ethoxymethoxy group, 1-methoxyethoxy group, 2-methoxyethoxy group, 1-ethoxyethoxy group and 2-ethoxyethoxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{2-12}$ alkoxyalkylthio group which may have one or more substituents, the alkoxyalkylthio group represents a group having the $C_{1-6}$ linear or branched alkylthio group substituted at a substitutable site with the $C_{1-6}$ linear or branched alkoxy group. Specific examples thereof include methoxymethylthio group, ethoxymethylthio group, 1-methoxyethylthio group, 2-methoxyethylthio group, 1-ethoxyethylthio group and 2-ethoxyethylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{3-7}$ cycloalkyl group which may have one or more substituents, the cycloalkyl group means a $C_{3-7}$ cyclic alkyl group, and specific examples thereof include cyclopropyl group, cyclobutyl group, cyclopentyl group, cyclohexyl group and cycloheptyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{3-7}$ cycloalkyloxy group which may have one or more substituents, the cycloalkyloxy group refers to a group having an oxygen atom bound to the end of the $C_{3-7}$ cyclic alkyl group, and specific examples thereof include cyclopropyloxy group, cyclobutyloxy group, cyclopentyloxy group, cyclohexyloxy group and cycloheptyloxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent $C_{3-7}$ cycloalkylthio group which may have one or more substituents, the cycloalkylthio group refers to a group having a sulfur atom bound to the end of the $C_{3-7}$ cycloalkyl group, and specific examples thereof include cyclopropylthio group, cyclobutylthio group, cyclopentylthio group, cyclohexylthio group and cycloheptylthio group.

When $R^1$, $R^{X1}$, $R^{X2}$, $R^{X3}$, $R^{X4}$, $R^{X5}$, $R^{X6}$, $R^7$, $R^{X8}$, $R^{X9}$ and $R^{X10}$ represent a $C_{2-6}$ alkenyl group which may have one or more substituents, the alkenyl group is a $C_{2-6}$ linear or branched alkenyl group and refers to a compound residue having a double bond in the alkyl group containing 2 or more carbon atoms. Specific examples of thereof include ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,2-dimethyl-1-butene-1-yl group, 1,3-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-methyl-1-pentene-1-yl group, 2-methyl-1-pentene-1-yl group, 3-methyl-1-pentene-1-yl group, 4-methyl-1-pentene-1-yl group, 1-methyl-2-pentene-1-yl group, 2-methyl-2-pentene-1-yl group, 3-methyl-2-pentene-1-yl group, 4-methyl-2-pentene-1-yl group, 1-methyl-3-pentene-1-yl group, 2-methyl-3-pentene-1-yl group, 3-methyl-3-pentene-1-yl group, 4-methyl-3-pentene-1-yl group, 1-methyl-4-pentene-1-yl group, 2-methyl-4-pentene-1-yl group, 3-methyl-4-pentene-1-yl group, 4-methyl-4-pentene-1-yl group, 1-methyl-1-pentene-2-yl group, 2-methyl-1-pentene-2-yl group, 3-methyl-1-pentene-2-yl group, 4-methyl-1-pentene-2-yl group, 1-methyl-2-pentene-2-yl group, 3-methyl-2-pentene-2-yl group, 4-methyl-2-pentene-2-yl group, 1-methyl-3-pentene-2-yl group, 2-methyl-3-pentene-2-yl group, 3-methyl-3-pentene-2-yl group, 4-methyl-3-pentene-2-yl group, 1-methyl-4-pentene-2-yl group, 2-methyl-4-pentene-2-yl group, 3-methyl-4-pentene-2-yl group, 4-methyl-4-pentene-2-yl group, 1-methyl-1-pentene-3-yl group, 2-methyl-1-pentene-3-yl group, 3-methyl-1-pentene-3-yl group, 4-methyl-1-pentene-3-yl group, 1-methyl-2-pentene-3-yl group, 2-methyl-2-pentene-3-yl group, 4-methyl-2-pentene-3-yl group, 1-hexene-1-yl group, 1-hexene-2-yl group, 1-hexene-3-yl group, 1-hexene-4-yl group, 1-hexene-5-yl group, 1-hexene-6-yl group, 2-hexene-1-yl group, 2-hexene-2-yl group, 2-hexene-3-yl group, 2-hexene-4-yl group, 2-hexene-5-yl group, 2-hexene-6-yl group, 3-hexene-1-yl group, 3-hexene-2-yl group and 3-hexene-3-yl group; preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,2-dimethyl-1-butene-1-yl group, 1,3-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 1,1-dimethyl-3-butene-1-yl group, 1,2-dimethyl-3-butene-1-yl group, 1,3-dimethyl-3-butene-1-yl group and 2,2-dimethyl-3-butene-1-yl group;

more preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, and 3-methyl-3-butene-1-yl group; and most preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group and 2-butene-2-yl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{2-6}$ alkenyloxy group which may have one or more substituents, the alkenyloxy group refers to a group having an oxygen atom bound to the end of the $C_{2-6}$ linear or branched alkenyl group. Specific examples thereof include ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,2-dimethyl-1-butene-1-yloxy group, 1,3-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 1,1-dimethyl-3-butene-1-yloxy group, 1,2-dimethyl-3-butene-1-yloxy group, 1,3-dimethyl-3-butene-1-yloxy group, 2,2-dimethyl-3-butene-1-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-methyl-1-pentene-1-yloxy group, 2-methyl-1-pentene-1-yloxy group, 3-methyl-1-pentene-1-yloxy group, 4-methyl-1-pentene-1-yloxy group, 1-methyl-2-pentene-1-yloxy group, 2-methyl-2-pentene-1-yloxy group, 3-methyl-2-pentene-1-yloxy group, 4-methyl-2-pentene-1-yloxy group, 1-methyl-3-pentene-1-yloxy group, 2-methyl-3-pentene-1-yloxy group, 3-methyl-3-pentene-1-yloxy group, 4-methyl-3-pentene-1-yloxy group, 1-methyl-4-pentene-1-yloxy group, 2-methyl-4-pentene-1-yloxy group, 3-methyl-4-pentene-1-yloxy group, 4-methyl-4-pentene-1-yloxy group, 1-methyl-1-pentene-2-yloxy group, 2-methyl-1-pentene-2-yloxy group, 3-methyl-1-pentene-2-yloxy group, 4-methyl-1-pentene-2-yloxy group, 1-methyl-2-pentene-2-yloxy group, 2-methyl-2-pentene-2-yloxy group, 3-methyl-2-pentene-2-yloxy group, 4-methyl-2-pentene-2-yloxy group, 1-methyl-3-pentene-2-yloxy group, 2-methyl-3-pentene-2-yloxy group, 3-methyl-3-pentene-2-yloxy group, 4-methyl-3-pentene-2-yloxy group, 1-methyl-4-pentene-2-yloxy group, 2-methyl-4-pentene-2-yloxy group, 3-methyl-4-pentene-2-yloxy group, 4-methyl-4-pentene-2-yloxy group, 1-methyl-1-pentene-3-yloxy group, 2-methyl-1-pentene-3-yloxy group, 3-methyl-1-pentene-3-yloxy group, 4-methyl-1-pentene-3-yloxy group, 1-methyl-2-pentene-3-yloxy group, 2-methyl-2-pentene-3-yloxy group, 3-methyl-2-pentene-3-yloxy group, 4-methyl-2-pentene-3-yloxy group, 1-hexene-1-yloxy group, 1-hexene-2-yloxy group, 1-hexene-3-yloxy group, 1-hexene-4-yloxy group, 1-hexene-5-yloxy group, 1-hexene-6-yloxy group, 2-hexene-1-yloxy group, 2-hexene-2-yloxy group, 2-hexene-3-yloxy group, 2-hexene-4-yloxy group, 2-hexene-5-yloxy group, 2-hexene-6-yloxy group, 3-hexene-1-yloxy group, 3-hexene-2-yloxy group and 3-hexene-3-yloxy group; preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,1-dimethyl-1-butene-1-yloxy group, 1,2-dimethyl-1-butene-1-yloxy group, 1,3-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 1,1-dimethyl-3-butene-1-yloxy group, 1,2-dimethyl-3-butene-1-yloxy group, 1,3-dimethyl-3-butene-1-yloxy group and 2,2-dimethyl-3-butene-1-yloxy group; more preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group and 3-methyl-3-butene-1-yloxy group; further preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group and 2-butene-2-yloxy group; and most preferably ethenyloxy group, 1-propene-1-yloxy group, 2-propene-1-yloxy group and 3-propene-1-yloxy group.

Similarly when $R^1$, $R^{X2}$, $R^{X3}$, $R^{X4}$, $R^{X5}$, $R^{X6}$, $R^{X7}$, $R^{X8}$ and $R^{X9}$ represent a $C_{2-6}$ alkenylthio group which may have one or more substituents, the alkenylthio group refers to a group having sulfur atom bound to the end of the $C_{2-6}$ linear or branched alkenyl group, and specific examples thereof include ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,2-dimethyl-1-butene-1-ylthio group, 1,3-dimethyl-1-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group, 2,2-dimethyl-3-butene-1-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-methyl-1-pentene-1-ylthio group, 2-methyl-1-pentene-1-ylthio group, 3-methyl-1-pentene-1-ylthio group, 4-methyl-1-pentene-1-ylthio group, 1-methyl-2-pentene-1-ylthio group, 2-methyl-2-pentene-1-ylthio group, 3-methyl-2-pentene-1-ylthio group, 4-methyl-2-pentene-1-ylthio group, 1-methyl-3-pentene-1-ylthio group, 2-methyl-3-pentene-1-ylthio group, 3-methyl-3-pentene-1-ylthio group, 4-methyl-3-pentene-1-ylthio group, 1-methyl-4-pentene-1-ylthio group, 2-methyl-4-pentene-1-ylthio group, 3-methyl-4-pentene-1-ylthio group, 4-methyl-4-pentene-1-ylthio group, 1-methyl-1-pentene-2-ylthio group, 2-methyl-1-pentene-2-ylthio group, 3-methyl-1-pentene-2-ylthio group, 4-methyl-1-pentene-2-ylthio group, 1-methyl-2-pentene-2-ylthio group, 3-methyl-2-pentene-2-ylthio group, 4-methyl-2-pentene-2-ylthio group, 1-methyl-3-pentene-2-ylthio group, 2-methyl-3-pentene-2-ylthio group, 3-methyl-3-pentene-2-ylthio group, 4-methyl-3-pentene-2-ylthio group, 1-methyl-4-pentene-2-ylthio group, 2-methyl-4-pentene-2-ylthio group, 3-methyl-4-pentene-2-ylthio group, 4-methyl-4-pentene-2-ylthio group, 1-methyl-1-pentene-3-ylthio group, 2-methyl-1-pentene-3-ylthio group, 3-methyl-1-pentene-3-ylthio group, 4-methyl-1-pentene-3-ylthio group, 1-methyl-2-pentene-3-ylthio group, 2-methyl-2-pentene-3-ylthio group, 4-methyl-2-pentene-3-ylthio group, 1-hexene-1-ylthio group, 1-hexene-2-ylthio group, 1-hexene-3-ylthio group, 1-hexene-4-ylthio group, 1-hexene-5-ylthio group, 1-hexene-6-ylthio group, 2-hexene-1-ylthio group, 2-hexene-2-ylthio group, 2-hexene-3-ylthio group, 2-hexene-4-ylthio group, 2-hexene-5-ylthio group, 2-hexene-6-ylthio group, 3-hexene-1-ylthio group, 3-hexene-2-ylthio group and 3-hexene-3-ylthio group; preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,2-dimethyl-1-butene-1-ylthio group, 1,3-dimethyl-1-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group and 2,2-dimethyl-3-butene-1-ylthio group; more preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group and 3-methyl-3-butene-1-ylthio group; further preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group and 2-butene-2-ylthio group; and most preferably ethenylthio group, 1-propene-1-ylthio group, 2-propene-1-ylthio group and 3-propene-1-ylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{10}$ represent a $C_{2-6}$ alkynyl group which may have one or more substituents, the alkynyl group is a $C_{2-6}$ linear or branched alkynyl group and refers to a compound residue having a triple bond in the alkyl group containing 2 or more carbon atoms. Specific examples thereof include ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 1-methyl-2-propyn-1-yl group, 3-methyl-1-butyn-1-yl group, 1-methyl-2-butyn-1-yl group, 1-methyl-3-butyn-1-yl group, 2-methyl-3-butyn-1-yl group, 1-ethyl-2-butyn-1-yl group, 1-ethyl-3-butyn-1-yl group, 2-ethyl-3-butyn-1-yl group, 3,3-dimethyl-1-butyn-1-yl group, 1,1-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group, 1-pentyn-1-yl group, 2-pentyn-1-yl group, 3-pentyn-1-yl group, 4-pentyn-1-yl group, 3-pentyn-2-yl group, 4-pentyn-2-yl group, 1-pentyn-3-yl group, 1-pentyn-1-yl group, 2-pentyn-1-yl group, 3-pentyn-1-yl group, 4-pentyn-1-yl group, 3-pentyn-2-yl group, 4-pentyn-2-yl group, 1-pentyn-3-yl group, 3-methyl-1-pentyn-1-yl group, 4-methyl-1-pentyn-1-yl group, 1-methyl-2-pentyn-1-yl group, 4-methyl-2-pentyn-1-yl group, 1-methyl-3-pentyn-1-yl group, 2-methyl-3-pentyn-1-yl group, 3-methyl-3-pentyn-1-yl group, 4-methyl-3-pentyn-1-yl group, 1-methyl-4-pentyn-1-yl group, 2-methyl-4-pentyn-1-yl group, and 3-methyl-4-pentyn-1-yl group; preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 1-methyl-2-propyn-1-yl group, 3-methyl-1-butyn-1-yl group, 1-methyl-2-butyn-1-yl group, 1-methyl-3-butyn-1-yl group, 2-methyl-3-butyn-1-yl group, 1-ethyl-2-butyn-1-yl group, 1-ethyl-3-butyn-1-yl group, 2-ethyl-3-butyn-1-yl group, 3,3-dimethyl-1-butyn-1-yl group, 1,1-dimethyl-2-butyn-1-yl group, 1,1-dimethyl-3-butyn-1-yl group, 1,2-dimethyl-3-butyn-1-yl group and 2,2-dimethyl-3-butyn-1-yl group; more preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 1-methyl-2-propyn-1-yl group, 3-methyl-1-butyn-1-yl group, 1-methyl-2-butyn-1-yl group, 1-methyl-3-butyn-1-yl group and 2-methyl-3-butyn-1-yl group; further preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group and 2-butyn-1-yl group; and most preferably ethynyl group, 1-propyn-1-yl group, 2-propyn-1-yl group and 3-propyn-1-yl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{2-6}$ alkynyloxy group which may have one or more substituents, the alkynyloxy group refers to a group having oxygen atom bound to the end of the $C_{2-6}$ linear or branched alkynyl group, and specific examples thereof include ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 1-methyl-2-propyn-1-yloxy group, 3-methyl-1-butyn-1-yloxy group, 1-methyl-2-butyn-1-yloxy group, 1-methyl-3-butyn-1-yloxy group, 2-methyl-3-butyn-1-yloxy group, 1-ethyl-2-butyn-1-yloxy group, 1-ethyl-3-butyn-1-yloxy group, 2-ethyl-3-butyn-1-yloxy group, 3,3-dimethyl-1-butyn-1-yloxy group, 1,1-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group, 1-pentyn-1-yloxy group, 2-pentyn-1-yloxy group, 3-pentyn-1-yloxy group, 4-pentyn-1-yloxy group, 3-pentyn-2-yloxy group, 4-pentyn-2-yloxy group, 1-pentyn-3-yloxy group, 1-pentyn-1-yloxy group, 2-pentyn-1-yloxy group, 3-pentyn-1-yloxy group, 4-pentyn-1-yloxy group, 3-pentyn-2-yloxy group, 4-pentyn-2-yloxy group, 1-pentyn-3-yloxy group, 3-methyl-1-pentyn-1-yloxy group, 4-methyl-1-pentyn-1-yloxy group, 1-methyl-2-pentyn-1-yloxy group, 4-methyl-2-pentyn-1-yloxy group, 1-methyl-3-pentyn-1-yloxy group, 2-methyl-3-pentyn-1-yloxy group, 3-methyl-3-pentyn-1-yloxy group, 4-methyl-3-pentyn-1-yloxy group, 1-methyl-4-pentyn-1-yloxy group, 2-methyl-4-pentyn-1-yloxy group and 3-methyl-4-pentyn-1-yloxy group; preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 1-methyl-2-propyn-1-yloxy group, 3-methyl-1-butyn-1-yloxy group, 1-methyl-2-butyn-1-yloxy group, 1-methyl-3-butyn-1-yloxy group, 2-methyl-3-butyn-1-yloxy group, 1-ethyl-2-butyn-1-yloxy group, 1-ethyl-3-butyn-1-yloxy group, 2-ethyl-3-butyn-1-yloxy group, 3,3-dimethyl-1-butyn-1-yloxy group, 1,1-dimethyl-2-butyn-1-yloxy group, 1,1-dimethyl-3-butyn-1-yloxy group, 1,2-dimethyl-3-butyn-1-yloxy group and 2,2-dimethyl-3-butyn-1-yloxy group; more preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 1-methyl-2-propyn-1-yloxy group, 3-methyl-1-butyn-1-yloxy group, 1-methyl-2-butyn-1-yloxy group, 1-methyl-3-butyn-1-yloxy group and 2-methyl-3-butyn-1-yloxy group; further preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group and 2-butyn-1-yloxy group; and most preferably ethynyloxy group, 1-propyn-1-yloxy group, 2-propyn-1-yloxy group and 3-propyn-1-yloxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{2-6}$ alkynylthio group which may have one or more substituents, the alkynylthio group refers to a group having sulfur atom bound to the end of the $C_{2-6}$ linear or branched alkynyl group, and specific examples thereof include ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 1-methyl-2-propyn-1-ylthio group, 3-methyl-1-butyn-1-ylthio group, 1-methyl-2-butyn-1-ylthio group, 1-methyl-3-butyn-1-ylthio group, 2-methyl-3-butyn-1-ylthio group, 1-ethyl-2-butyn-1-ylthio group, 1-ethyl-3-butyn-1-ylthio group, 2-ethyl-3-butyn-1-ylthio group, 3,3-dimethyl-1-butyn-1-ylthio group, 1,1-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group, 1-pentyn-1-ylthio group, 2-pentyn-1-ylthio group, 3-pentyn-1-ylthio group, 4-pentyn-1-ylthio group, 3-pentyn-2-ylthio group, 4-pentyn-2-ylthio group, 1-pentyn-3-ylthio group, 2-pentyn-3-ylthio group, 1-pentyn-1-ylthio group, 2-pentyn-1-ylthio group, 3-pentyn-1-ylthio group, 4-pentyn-1-ylthio group, 3-pentyn-2-ylthio group, 4-pentyn-2-ylthio group, 1-pentyn-3-ylthio group, 3-methyl-1-pentyn-1-ylthio group, 4-methyl-1-pentyn-1-ylthio group, 1-methyl-2-pentyn-1-ylthio group, 4-methyl-2-pentyn-1-ylthio group, 1-methyl-3-pentyn-1-ylthio group, 2-methyl-3-pentyn-1-ylthio group, 3r-methyl-3-pentyn-1-ylthio group, 4-methyl-3-pentyn-1-ylthio group, 1-methyl-4-pentyn-1-ylthio group, 2-methyl-4-pentyn-1-ylthio group and 3-methyl-4-pentyn-1-ylthio group; preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 1-methyl-2-propyn-1-ylthio group, 3-methyl-1-butyn-1-ylthio group, 1-methyl-2-butyn-1-ylthio group, 1-methyl-3-butyn-1-ylthio group, 2-methyl-3-butyn-1-ylthio group, 1-ethyl-2-butyn-1-ylthio group, 1-ethyl-3-butyn-1-ylthio group, 2-ethyl-3-butyn-1-ylthio group, 3,3-dimethyl-1-butyn-1-ylthio group, 1,1-dimethyl-2-butyn-1-ylthio group, 1,1-dimethyl-3-butyn-1-ylthio group, 1,2-dimethyl-3-butyn-1-ylthio group and 2,2-dimethyl-3-butyn-1-ylthio group; more preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 1-methyl-2-propyn-1-ylthio group, 3-methyl-1-butyn-1-ylthio group, 1-methyl-2-butyn-1-ylthio group, 1-methyl-3-butyn-1-ylthio group and 2-methyl-3-butyn-1-ylthio group; further preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group and 2-butyn-1-ylthio group; and most preferably ethynylthio group, 1-propyn-1-ylthio group, 2-propyn-1-ylthio group and 3-propyn-1-ylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{6-12}$ aryl group which may have one or more substituents, the aryl group refers to an aromatic cyclic group, and specific examples thereof include phenyl group, 1-naphthyl group, 2-naphthyl group, as-indacenyl group, s-indacenyl group and acenapthylenyl group; preferably phenyl group, 1-naphthyl group and 2-naphthyl group; more preferably phenyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{6-12}$ aryloxy group which may have one or more substituents, the aryloxy group refers to a group having an oxygen atom bound to the end of the $C_{6-12}$ aryl group, and specific examples thereof include phenyloxy group, 1-naphthyloxy group, 2-naphthyloxy group, as-indacenyloxy group, s-indacenyloxy group and acenapthylenyloxy group; preferably phenyloxy group, 1-naphthyloxy group and 2-naphthyloxy group; more preferably phenyloxy group.

Similarly, $R^1$, $R^{X2}$, $R^{X3}$, $R^{X4}$, $R^{X5}$, $R^{X6}$, $R^{X7}$, $R^{X8}$ and $R^{X9}$ represent a $C_{6-12}$ arylthio group which may have one or more substituents, the arylthio group refers to a group having a sulfur atom bound to the end of the $C_{6-12}$ aryl group, and specific examples thereof include phenylthio group, 1-naphthylthio group, 2-naphthylthio group, as-indacenylthio group, s-indacenylthio group and acenapthylenylthio group; preferably phenylthio group, 1-naphthylthio group and 2-naphthylthio group; more preferably phenylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{7-18}$ alkylaryl group which may have one or more substituents, the alkylaryl group refers to a group having the $C_{6-12}$ aryl group substituted at a substitutable site with the $C_{1-6}$ alkyl group. Specific examples thereof include tolyl group, xylyl group, cumenyl group, mesityl group, cymenyl group and styryl group; preferably tolyl group, xylyl group, cumenyl group, mesityl group, cymenyl group and styryl group; more preferably tolyl group, xylyl group, cumenyl group and mesityl group; and further preferably tolyl group, xylyl group and cumenyl group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{7-18}$ alkylaryloxy group which may have one or more substituents, the alkylaryloxy group refers to a group having an oxygen atom bound to the end of the $C_{7-18}$ alkylaryl group. Specific examples thereof include o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group and mesityloxy group; and most preferably o-tolyloxy group, m-tolyloxy group and p-tolyloxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{7-18}$ alkylarylthio group which may have one or more substituents, the alkylarylthio group refers to a group having a sulfur atom bound to the end of the $C_{7-18}$ alkylaryl group. Specific examples thereof include o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; more preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, o-styrylthio group, m-styrylthio group and p-styrylthio group; further preferably o-tolylthio group, m-tolylthio group, p-tolylthio group, 2,3-xylyl-1-thio group, 2,4-xylyl-1-thio group, 2,5-xylyl-1-thio group and mesitylthio group; and most preferably o-tolylthio group, m-tolylthio group and p-tolylthio group.

When $R^1$, $R^{X1}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{7-18}$ aralkyl group which may have one or more substituents, the aralkyl group refers to a group having the $C_{1-6}$ alkyl group substituted at a substitutable site with the $C_{6-12}$ aryl group. Specific examples thereof include benzyl group, phenetyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; preferably benzyl group, phenetyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; more preferably benzyl group, phenetyl group, 3-phenylpropyl group, 4-phenylbutyl group, 5-phenylpentyl group, 6-phenylhexyl group, 1-naphthylmethyl group and 2-naphthylmethyl group; further preferably benzyl group, phenetyl group, 3-phenylpropyl group and 4-phenylbutyl group; and most preferably benzyl group and phenetyl group.

Similarly, when $R^1$, $R^{X2}R^{X3}$, $R^{X4}$, $R^{X5}R^{X6}$, $R^{X7}$, $R^{X8}$ and $R^{X9}$ represent a $C_{7-18}$ aralkyloxy group which may have one or more substituents, the aralkyloxy group refers to a group having an oxygen atom bound to the $C_{7-18}$ aralkyl group. Specific examples thereof include benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; more preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group and 2-naphthylmethyloxy group; further preferably benzyloxy group, phenetyloxy group, 3-phenylpropyloxy group and 4-phenylbutyloxy group; and most preferably benzyloxy group and phenetyloxy group.

Similarly, when $R^1$, $R^{X2}$, $R^{X3}$, $R^{X4}$, $R^{X5}$, $R^{X6}$, $R^{X7}$, $R^{X8}$ and $R^{X9}$ represent a $C_{7-18}$ aralkylthio group which may have one or more substituents, the aralkylthio group refers to a group having a sulfur atom bound to the end of the $C_{7-18}$ aralkyl group. Specific examples thereof include benzylthio group, phenetylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; preferably benzylthio group, phenetylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; more preferably benzylthio group, phenetylthio group, 3-phenylpropylthio group, 4-phenylbutylthio group, 5-phenylpentylthio group, 6-phenylhexylthio group, 1-naphthylmethylthio group and 2-naphthylmethylthio group; further preferably benzylthio group, phenetylthio group, 3-phenylpropylthio group and 4-phenylbutylthio group; and most preferably benzylthio group and phenetylthio group.

Similarly, when $R^1$, $R^{X1}$, $R^{X2}$, $R^{X3}$, $R^{X4}$, $R^{X5}$, $R^{X6}$, $R^{X7}$, $R^{X8}$ and $R^{X9}$ represent a $C_{4-13}$ cycloalkylalkyloxy group which may have one or more substituents, the cycloalkylalkyloxy group refers to a group having the linear or branched $C_{1-6}$ alkoxy group wherein a substitutable site is substituted with the $C_{3-7}$ cyclic alkyl group, and specific examples thereof include cyclopropylmethoxy group, cyclobutylmethoxy group, cyclopentylmethoxy group, cyclohexylmethoxy group, cycloheptylmethoxy group, 1-cyclopropylethoxy group, 2-cyclopropylethoxy group, 1-cyclopropyl-n-propoxy group, 2-cyclopropyl-n-propoxy group, 3-cyclopropyl-n-propoxy group, cyclopropyl-1-propoxy group, cyclopropyl-n-butoxy group, cyclopropyl-1-butoxy group, cyclopropyl-sec-butoxy group, cyclopropyl-t-butoxy group, cyclopropyl-n-pentyloxy group, cyclopropyl-1-pentyloxy group, cyclopropyl-sec-pentyloxy group, cyclopropyl-t-pentyloxy group and cyclopropyl-neopentyloxy group; more preferably cyclopropyl-methoxy group, cyclopropyl-ethoxy group, cyclopropyl-n-propoxy group, cyclopropyl-i-propoxy group, cyclopropyl-n-butoxy group, cyclopropyl-i-butoxy group, cyclopropyl-sec-butoxy group, cyclopropyl-t-butoxy group, cyclopropyl-n-pentyloxy group, cyclopropyl-i-pentyloxy group, cyclopropyl-sec-pentyloxy group, cyclopropyl-t-pentyloxy group, cyclopropyl-neopentyloxy group; and most preferably cyclopropyl-methoxy group, cyclopropyl-ethoxy group, cyclopropyl-n-propoxy group, cyclopropyl-i-propoxy group and the like.

Herein, specific examples of "hetero atom" include oxygen atom, sulfur atom, nitrogen atom, phosphorus, aresevic, antimony, silicon, germanium, tin, lead, boron, mercury and the like, oxygen atom, sulfur atom, nitrogen atom and phosphorus are preferred, and oxygen atom, sulfur atom and nitrogen atom are more preferred.

Hereinafter, when expressed as "which may have a hetero atom", the hetero atom is as defined above.

In the expression "Y and the ring Z is a 5- to 14-membered aromatic group which may have one or more hetero atoms", the aromatic group means the $C_{6-12}$ aryl group, or the $C_{6-12}$ aryl groups wherein a substitutable site is substituted with the $C_{1-6}$ aliphatic hydrocarbon group, and specific examples of which include phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group, acenaphthylenyl group and the like. Phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group and acenaphthylenyl group are preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group and 2-naphthylmethyl group are more preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group and cinnamylidene group are still preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group and phenethyl group are further preferred; and phenyl group, o-tolyl group, m-tolyl group, p-tolyl group, 2,3-xylyl group, 2,4-xylyl group, 2,5-xylyl group and benzyl group are most preferred. Therefore, specific examples of the aromatic group having a hetero atom include furyl group, thienyl group, pyrrolyl group, pyridyl group, quinolyl group, isoquinolyl group, cinnolyl group, quinazolyl group, quinoxalyl group, indolyl group, indazolyl group, oxazolyl group, isoxazolyl group, thiazolyl group, isothiazolyl group, imidazolyl group, pyrazolyl group, furazanyl group, pyridazinyl group, pyrimidyl group, pyrazyl group and the like.

When expressed as "the ring Z is a 5- to 14-membered aromatic group whose ring may be partially saturated", the aromatic group means 9- to 14-membered aromatic group wherein two or three rings are condensed, with 1 or 2 rings being nonaromatic, and specific examples of which include dihydrobenzofuranyl group, phthalanyl group, chromanyl group, chromanonyl group, isochromanyl group, tetrahydronaphthalenyl group, dihydrobenzothiophenyl group, indolinyl group, isatinyl group, indanyl group, indanonyl group, tetralonyl group, coumarinyl group, naphthoquinonyl group and anthraquinonyl group; preferably dihydrobenzofuranyl group, phthalanyl group, chromanyl group, chromanonyl group, tetrahydronaphthalenyl group and indanyl group; and more preferably dihydrobenzofuranyl group and chromanyl group.

The expression "Y represents a $C_{3-7}$ alicyclic hydrocarbon" refers to that the alicyclic hydrocarbon group means a $C_{3-7}$ cyclic aliphatic hydrocarbon group, and specific examples of which include cyclopropyl group, cyclobutyl group, cyclopentyl group, cyclohexyl group, cycloheptyl group, cyclopropenyl group, cyclobutenyl group, cyclopentenyl group, cyclohexenyl group, cycloheptenyl group and the like. Cyclopropyl group, cyclobutyl group, cyclopentyl group, cyclohexyl group, cycloheptyl group, cyclopropenyl group, cyclobutenyl group, cyclopentenyl group, cyclohexenyl group and cycloheptenyl group are preferred; cyclopropyl group, cyclobutyl group, cyclopentyl group, cyclohexyl group and cycloheptyl group are more preferred; cyclopropyl group, cyclobutyl group, cyclopentyl group and cyclohexyl group are still preferred; and cyclopropyl group, cyclobutyl group and cyclopentyl group are most preferred. Therefore, specific examples of the alicyclic hydrocarbon having a hetero atom include pyrrolynyl group, pyrrolidinyl group, imidazolinyl group, imidazolidinyl group, pyrazolinyl group, pyrazolidinyl group, piperidinyl group, piperazinyl group, morpholinyl group, dihydrofuranyl group and tetrahydrofuranyl group, with dihydrofuranyl group and tetrahydrofuranyl group being preferred.

When L represents a single bond, the compounds of the invention are exemplified by carboxylic acid derivatives having group X bound via a single bond to the group Y, represented by the following formula:

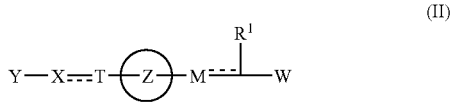

(II)

(wherein each symbol has the same meaning as defined above), a salts thereof, an ester thereof or a hydrate of them.

When M represents a single bond, the compounds of the invention are exemplified by carboxylic acid derivatives represented by the following formula:

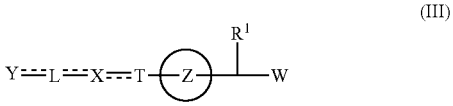

(III)

(wherein each symbol has the same meaning as defined above), a salt thereof, an ester thereof or a hydrate of them.

When T represents a single bond, the compounds of the invention are exemplified by carboxylic acid derivatives represented by the following formula:

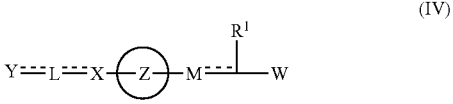

(IV)

(wherein each symbol has the same meaning as defined above), a salt thereof, an ester thereof or a hydrate of them.

When X represents a single bond, the compounds of the invention are exemplified by carboxylic acid derivatives represented by the following formula:

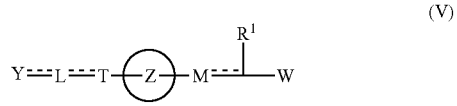

(V)

(wherein each symbol has the same meaning as defined above), a salt thereof, an ester thereof or a hydrate of them.

When L, T and M represent a $C_{1-6}$ alkylene group which may have one or more substituents, the alkylene group means a bivalent group derived by removing one hydrogen atom from the $C_{1-6}$ alkyl group, and specific examples of which include methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group, hexamethylene group and the like. Methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group and hexamethylene group are preferred; methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group and 1,1-dimethyltrimethylene group are more preferred; methylene group, ethylene group, methylethylene group, propylene group, ethylethylene group, 1,1-dimethylethylene group, 1,2-dimethylethylene group and trimethylene group are still preferred; and methylene group, ethylene group, methylethylene group and propylene group are most preferred.

Similarly, when T represents a $C_{1-3}$ alkylene group which may have one or more substituents, the alkylene group means a bivalent group derived by removing one hydrogen atom from the $C_{1-3}$ alkyl group, and specific examples of which include the $C_{1-3}$ alkylene group as recited above. Methylene group, ethylene group and propylene group are preferred; methylene group and ethylene group are more preferred; and methylene group is most preferred.

When L, T and M represent a $C_{2-6}$ alkenylene group which may have one or more substituents, the alkenylene group means a bivalent group derived by removing one hydrogen atom from the alkenyl group of 2 to 6 carbons, and specific examples of which include vinylene group, propenylene group, butenylene group, pentenylene group, hexenylene group and the like. Vinylene group, propenylene group, butenylene group and pentenylene group are preferred; vinylene group, propenylene group and butenylene group are more preferred; vinylene group and propenylene group are still preferred; and vinylene group is most preferred.

When L and T represent a $C_{2-6}$ alkynylene group which may have one or more substituents, the alkynylene group means a bivalent group derived by removing one hydrogen atom from the $C_{2-6}$ alkynyl group, and specific examples of which include ethynylene group, propynylene group, butynylene group, pentynylene group, hexynylene group and the like. Ethynylene group, propynylene group, butynylene group and pentynylene group are preferred; ethynylene group, propynylene group and butynylene group are more preferred; butynylene group and propynylene group are still preferred; and propynylene group is most preferred.

Similarly, when M represents a $C_{2-6}$ alkynylene group which may have one or more substituents, the alkynylene group means a bivalent group derived by removing one hydrogen atom from the $C_{2-6}$ alkynyl group, and specific examples of which include the $C_{2-6}$ alkynylene group as recited above. Ethynylene group and propynylene group are preferred, and ethynylene group is more preferred.

When $R^{X1}$, $R^{X1}$, $R^{X11}$ and $R^{X12}$ represent a $C_{2-7}$ aliphatic acyl group which may have one or more substituents, the aliphatic acyl group represents the $C_{1-6}$ alkyl group, the $C_{2-6}$ alkenyl group or the $C_{2-6}$ alkynyl group wherein a carbonyl group is bound to their terminal end, and specific examples of which include acetyl group, propionyl group, butyryl group, isobutyryl group, valeryl group, isovaleryl group, pivaloyl group, hexanoyl group, octanoyl group, acryloyl group, methacryloyl group, crotonoyl group and the like. Acetyl group, propionyl group, butyryl group, isobutyryl group, valeryl group, isovaleryl group, pivaloyl group, hexanoyl group, octanoyl group, acryloyl group, methacryloyl group and crotonoyl group are preferred; acetyl group, propionyl group, butyryl group, isobutyryl group, valeryl group, isovaleryl group, pivaloyl group, hexanoyl group and octanoyl group are more preferred; acetyl group, propionyl group, butyryl group and isobutyryl group are still preferred; and acetyl group and propionyl group are most preferred.

When $R^{X1}$, $R^{X10}$, $R^{X11}$ and $R^{X1}$ represent a $C_{7-19}$ aromatic acyl group which may have one or more substituents, the $C_{5-12}$ aromatic acyl group means the $C_{5-12}$ aryl group wherein a carbonyl group or a group derived by removing one hydrogen atom from the $C_{2-7}$ aliphatic acyl group is bound to their terminal end, and specific examples of which include benzoyl group, o-toluoyl group, m-toluoyl group, p-toluoyl group, cinnamoyl group, 1-naphthoyl group, 2-naphthoyl group and the like. Benzoyl group, o-toluoyl group, m-toluoyl group, p-toluoyl group, cinnamoyl group, 1-naphthoyl group and 2-naphthoyl group are preferred; benzoyl group, o-toluoyl group, m-toluoyl group, p-toluoyl group and cinnamoyl group are more preferred; benzoyl group and cinnamoyl group are still preferred; and benzoyl group is most preferred.

----- represents a single bond or a double bond. Therefore, compounds of the present invention represented by the following formula (I):

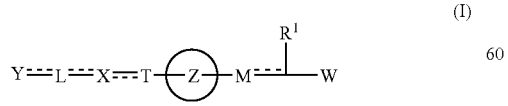

(I)

(wherein each symbol represents a group as defined above) comprehend carboxylic acid compound represented by the following formulae:

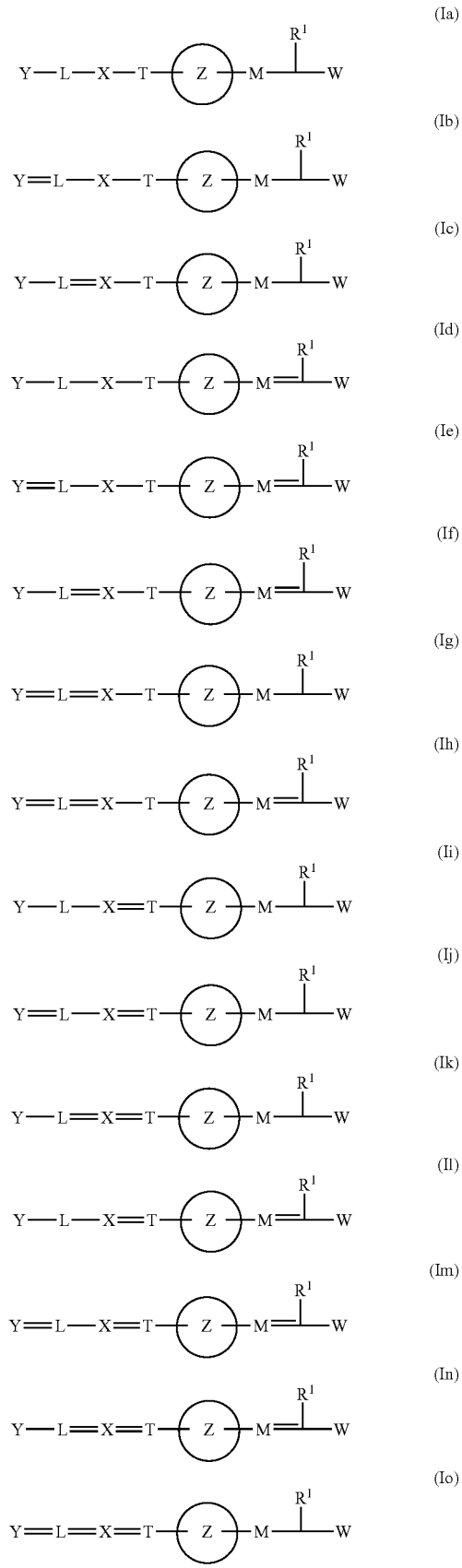

-continued

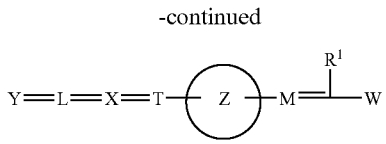 (Ip)

(wherein symbols are as described above), a salt thereof, an ester thereof or a hydrate of them.

The group represented by the formula:

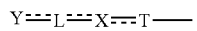

(wherein each symbol represents a group as defined above) and the group represented by the formula:

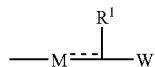

(wherein each symbol represents a group as defined above) are bound with each other on the ring Z via from 2 to 8 atoms. In the case where such wording is used, "bound with each other on the ring Z via from 2 to 8 atoms" represents the following cases.

For example, when the ring Z is benzene, and 2 atoms are involved in binding, the formula is as follows:

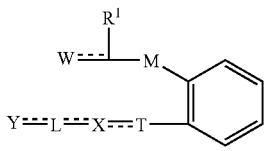

wherein each symbol represents a group as defined above.

When the ring Z is anthracene and 8 atoms are involved in binding, the formula is as follows:

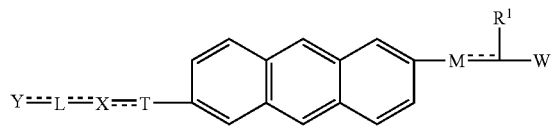

(wherein each symbol represents a group as defined above). Therefore, those defined by the ring Z, and the group represented by the formula:

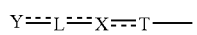

(wherein each symbol represents a group as defined above), and the group represented by the formula:

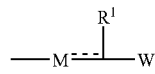

(wherein each symbol represents a group as defined above) may be bound in any positions. Preferably the compound represented by the formula:

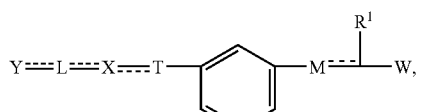

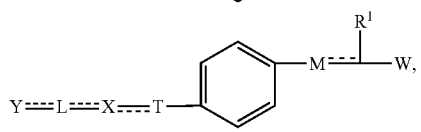

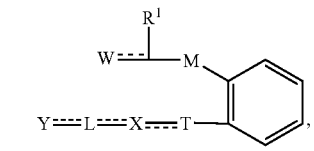

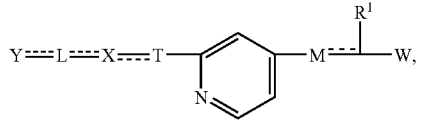

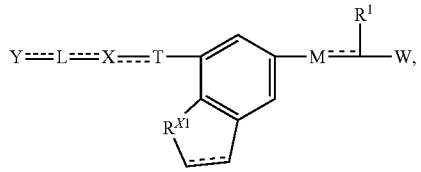

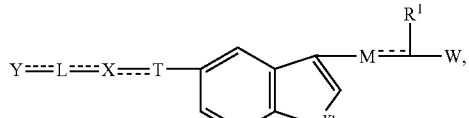

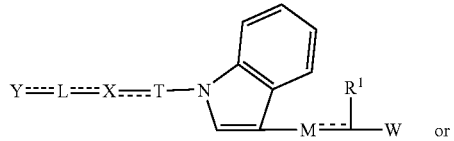

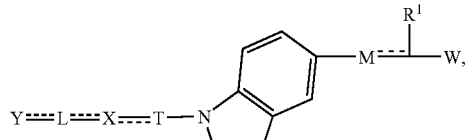

(wherein each symbol represents a group as defined above, and the aromatic group may further have 1 to 4 substituents), and more preferably the formula:

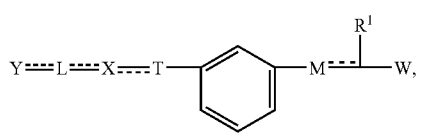

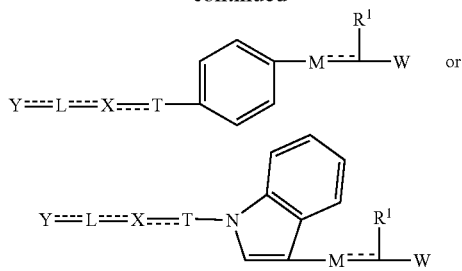

(wherein each symbol represents a group as defined above, and the aromatic group may further have 1 to 4 substituents).

"Salts" used herein are not particularly limited with regard to the kind, and specific examples include additive salts of inorganic acid such as hydrofluoride, hydrochloride, sulfate, nitrate, perchlorate, phosphate, carbonate, bicarbonate, hydrobromide or hydroiodide; additive salts of organic carboxylic acid such as acetate, maleate, fumarate, oxalate, lactate, tartrate or trifluoroacetate; additive salts of organic sulfonic acid such as methanesulfonate, trifluoromethanesulfonate, ethanesulfonate, hydroxymethanesulfonate, hydroxyethanesulfonate, benzensulfonate, toluenesulfonate or taurine salt and the like; additive salts of amine such as trimethylamine salt, triethylamine salt, pyridine salt, procaine salt, picoline salt, dicyclohexylamine salt, N,N'-dibenzyldiaminoethane salt, N-methylglucamine salt, diethanolamine salt, triethanolamine salt, tris (hydroxymethylamino)methane salt or phenethyl benzyl amine salt; additive salts of alkaline metal such as sodium salt or potassium salt; additive salts of alkaline earth metal such as magnesium salt or calcium salt; and additive salts of amino acid such as arginine salt, lysine salt, serine salt, glycine salt, aspartate or glutamate and the like. Pharmaceutically acceptable salt is preferred.

Pharmaceutically acceptable salts are not particularly limited with regard to the kind, and specific examples include additive salts of inorganic acid such as hydrochloride, sulfate, carbonate, bicarbonate, hydrobromide or hydroiodide; additive salts of organic carboxylic acid such as acetate, maleate, lactate, tartrate or trifluoroacetate; additive salts of organic sulfonic acid such as methanesulfonate, hydroxymethanesulfonate, hydroxyethanesulfonate, benzensulfonate, toluenesulfonate or taurine salt; additive salts of amine such as trimethylamine salt, triethylamine salt, pyridine salt, procaine salt, picoline salt, dicyclohexylamine salt, N,N'-dibenzyldiaminoethane salt, N-methylglucamine salt, diethanolamine salt, triethanolamine salt, tris(hydroxymethylamino)methane salt or phenethyl benzyl amine; additive salts of alkaline metal such as sodium salt or potassium salt; additive salts of amino acid such as arginine salt, lysine salt, serine salt, glycine salt, aspartate or glutamate.

"Ester" used in the present invention refers to esters of carboxyl group of W in the general formula (I). These are not particularly limited insofar as they are commonly used inorganic synthesis, and physiologically acceptable ester groups which are hydrolyzed under physiological conditions are comprehended. Specific examples include $C_{1-6}$ alkyl groups, $C_{6-12}$ aryl groups, $C_{7-20}$ aralkyl groups such as benzyl group, $C_{7-20}$ heteroarylalkyl groups, 4-methoxybenzyl group, alkanoyloxyalkyl groups such as acetoxymethyl group, propionyloxymethyl group or pivaloxymethyl group, alkoxycarbonyloxyalkyl groups such as methoxycarbonyloxymethyl group, ethoxycarbonyloxymethyl group or 2-methoxycarbonyloxyethyl group, (5-methyl-2-oxo-1,3-dioxo-4-yl)methyl group and the like.

It is to be noted that if the carboxylic acid derivative having the above general formula (I), a salt pharmacologically acceptable salt thereof or a pharmacologically acceptable ester thereof form solvates, all such solvates are comprehended in the present invention.

Salts, hydrates or esters of compounds of the present invention are preferably those pharmaceutically acceptable.

The compound of the present invention represented by the formula (I):

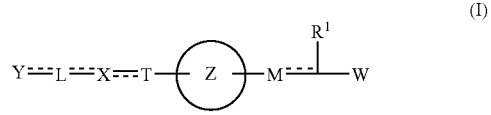

(wherein each symbol represents a group as defined above) can be synthesized in a conventional method, and can be synthesized, for example, in the manner as described below.

General production example A

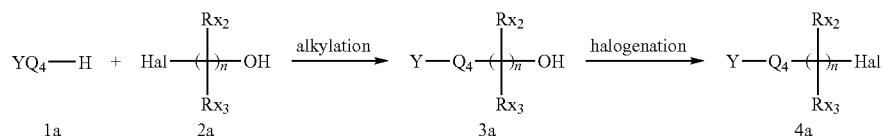

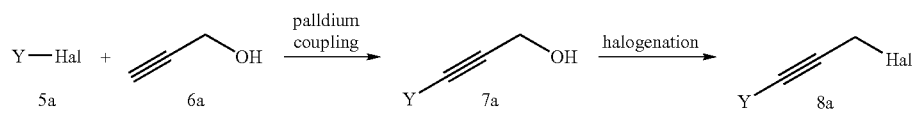

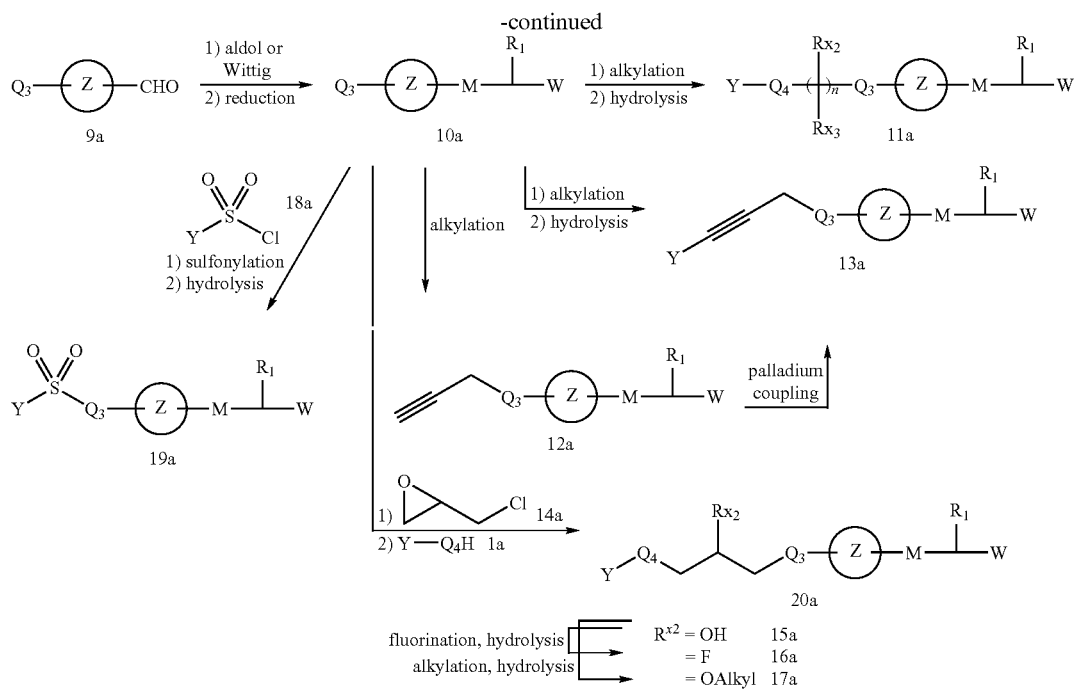

wherein each symbol represents a group as defined above, and "Hal" represents a halogen.

The compound represented by the formula (3a) is obtained by treating the compound represented by the formula (2a) with the compound represented by the formula (1a).

The reaction condition is not particularly limited, and for example, the reaction is conducted in a solvent such as methanol, ethanol, propanol, dimethylsulfoxide, N,N-dimethylformamide, N-methylpyrrolidone, dioxane, tetrahydrofuran or toluene, in the presence of a base such as lithium hydroxide, sodium hydroxide, potassium hydroxide, lithium carbonate, sodium carbonate, potassium carbonate, cesium carbonate, lithium hydride, sodium hydride or potassium hydride at a temperature from 0° C. to 150° C.

The compound represented by the formula (4a) can be obtained by halogenation of the compound represented by the formula (3a).

The reaction condition is not particularly limited, and for example, it can be obtained by making phosphorus oxychloride, thionyl chloride, phosphorus trichloride or phosphorus tribromide in a solvent such as dioxane, tetrahydrofuran or dimethoxyethane. The reaction temperature is from 0° C. to 150° C. Conditions which combine triphenyl phosphine, carbon tetrachloride, carbon tetrabromide, N-bromo succinimide and the like may be used as well.

The compound represented by the formula (7a) can be obtained by treating the compound represented by the formula (6a) with the compound represented by the formula (5a).

The reaction condition is not particularly limited, and the reaction may be conducted in a solvent such as methanol, ethanol, propanol, dimethylsulfoxide, N,N-dimethylformamide N-methylpyrrolidone, dioxane, tetrahydrofuran or toluene, in the presence of from 0.0001 to 0.5 mole equivalent of copper halide, from 0.0001 to 0.5 mole equivalent of palladium catalyst such as tetrakis(triphenylphosphine)palladium or dichlorobis(triphenylphosphine) palladium, and an organic base such as triethylamine, N,N-diisopropylethylamine, butylamine or tributylamine at a temperature from 0° C. to 150° C.

The compound represented by the formula (8a) can be obtained by halogenation of the compound represented by the formula (7a).

The reaction condition corresponds to that of production example of the formula (4a) in Production example A.

The compound represented by the formula (10a) is obtained by aldol reaction between the compound represented by the formula (9a) and aliphatic esters, alkoxyacetic acid esters (these alkyl or alkoxy groups correspond to $R^1$ of the formula, and ester groups correspond to W of the formula) and the like, or Wittig-Horner-Emmons reaction of alkylphosphonic acid esters, alkoxyphosphonic acid esters (these alkyl or alkoxy groups correspond to $R^1$ of the formula, and ester groups correspond to W of the formula) and the like followed by reduction of alcohol or double bond.

The reaction condition for aldol reaction and Wittig-Horner-Emmons reaction is not particularly limited, and for example, the reaction may be conducted in a solvent such as methanol, ethanol, propanol, dimethylsulfoxide, N,N-dimethylformamide, N-methylpyrrolidone, dioxane, tetrahydrofuran or toluene, in a presence of a base such as lithium hydroxide, sodium hydroxide, potassium hydroxide, lithium carbonate, sodium carbonate, potassium carbonate, cesium carbonate, lithium hydride, sodium hydride, potassium hydride, butyl lithium, methyl lithium, lithium bistrimethylsilylamide, sodium bistrimethylsilylamide or potassium bistrimethylsilyl amide and the like at a temperature from 0° C. to 150° C.

As to the condition of reduction reaction and the like, the reaction may be conducted in a solvent such as methanol, ethanol, propanol, dimethylsulfoxide, N,N-dimethylformamide, N-methylpyrrolidone, dioxane, tetrahydrofuran or toluene, in the presence of a metal catalyst such as palladium carbon, platinum oxide or Raney's nickel, in hydrogen atmosphere, at temperature between 0° C. and 150° C. Optionally, the reduction may be conducted after acylation or sulfonylation of an alcohol group on an aldol adduct.

The compound represented by the formula (11a) can be obtained by hydrolyzing an ester in the molecule after alkylation between the compound represented by the formula (10a) and the compound represented by the formula (4a).

The condition for alkylation corresponds to that of the production example of the formula (4a) in Production example A.

The condition for hydrolysis reaction is not particularly limited, and the reaction may be conducted by treating an aqueous solution of lithium hydroxide, sodium hydroxide, potassium hydroxide and the like, for example, in a solvent such as methanol, ethanol, propanol, dimethylsulfoxide, N,N-dimethylformamide, N-methylpyrrolidone, dioxane or tetrahydrofuran, at a temperature from 0° C. to 150° C.

The compound represented by the formula (13a) can be obtained by hydrolyzing the ester in the molecule after alkylation of the compound represented by the formula (10a) and the compound represented by the formula (8a), or by hydrolyzing the ester in the molecule after reaction between the compound represented by the formula (10a) and propargyl bromide followed by a coupling reaction using palladium catalyst.

The conditions for the alkylation reaction and hydrolysis reaction correspond to those of the production example of the formula (11a) of Production example A.

The reaction condition for the coupling reaction corresponds to that of the production example of the formula (7a) in Production example A.

The compound represented by the formula (15a) can be obtained by treating the compound represented by the formula (1a) after alkylation of the compound represented by the formula (10a) with the compound represented by the formula (14a).

The reaction condition for alkylation of the formula (14a) follows the production example of the formula (3a) in Production example A.

The reaction condition for the treatment of the formula (1a) is not particularly limited, and it can be achieved by reacting in a solvent such as methanol, ethanol, propanol, dimethylsulfoxide, N,N-dimethylformamide, N-methylpyrrolidone, dioxane or tetrahydrofuran, in the presence of 0.0001 to 1.0 mole equivalent of catalyst such as potassium carbonate, triethylamine or cesium fluoride at a temperature from 0° C. to 150° C.

The compound represented by the formula (16a) can be obtained by hydrolyzing the ester in the molecule after fluorination of the compound represented by the formula (15a).

The reaction condition of fluorination is not particularly limited, and the reaction can be achieved, for example, by treating a reagent such as (diethylamino) sulfur trifluoride in a solvent such as dichloromethane or chloroform at a temperature from 0° C. to 150° C.

The condition for hydrolysis reaction corresponds to that of the production example of the formula (11a) in Production example A.

The compound represented by the formula (17a) can be obtained by hydrolyzing the ester in the molecule after alkylation of the compound represented by the formula (15a) with an alkyl halide.

The reaction condition corresponds to that of the production example of the formula (3a) in Production example A.

The compound represented by the formula (19a) can be obtained by hydrolyzing the ester of the molecule after modifying the compound represented by the formula (10a) into a sulfonates using sulfonyl chloride represented by the formula (18a).

The reaction condition for sulfonylation is not particularly limited, and the reaction can be conducted in a solvent such as pyridine, dichloromethane or chloroform, in the presence of an organic base such as triethylamine, N,N-diisopropylethylamine or tributylamine at a temperature from 0° C. to 150° C.

The condition for hydrolysis reaction corresponds to that of the production example of the formula (11a) in Production example A.

The compound represented by the formula (20a) can be obtained by hydrolyzing the compound represented by the formula (15a).

The condition for hydrolysis reaction corresponds to that of the production example of the formula (11a) in Production example A.

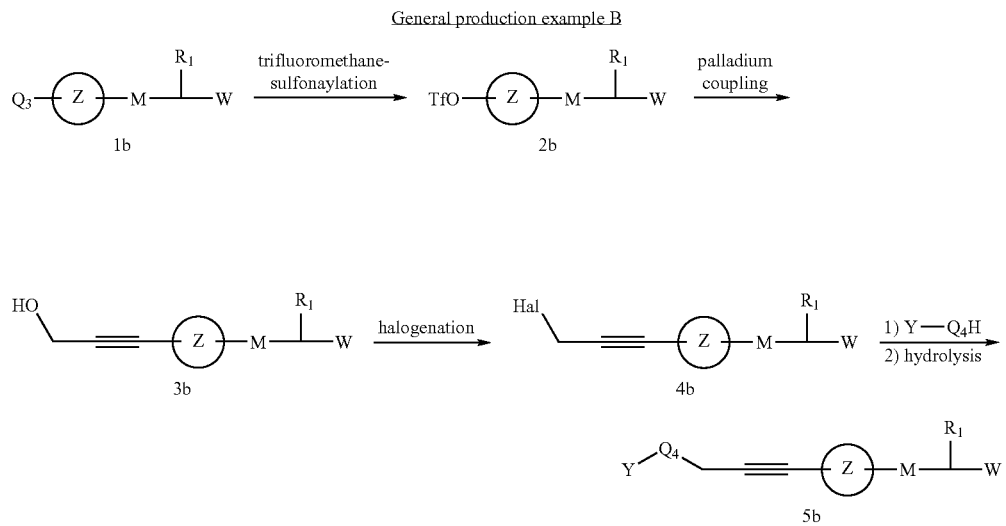

General production example B

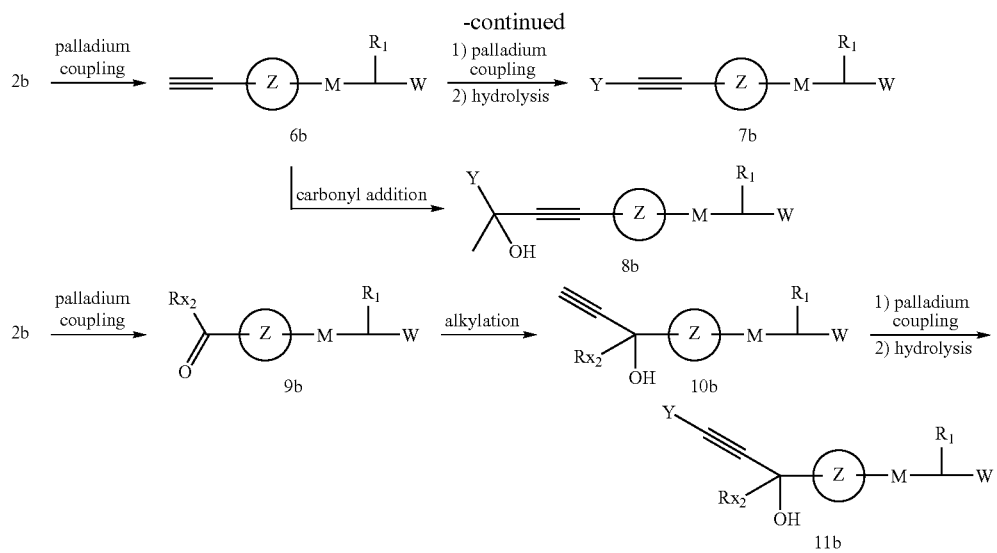

wherein each symbol represents a group as defined above; and Tf represents a trifluoromethanesulfonyl group.

The compound represented by the formula (2b) can be obtained by trifluoromehtanesulfonylation of the compound represented by the formula (1b).

The reaction condition is not particularly limited, and it can be synthesized by treating N,N-bistrifluoromethanesulfonamide, trifluoromehtanesulfonic anhydride, trifluoromehtanesulfonyl chloride and the like in a solvent such as pyridine, dichloromethane or chloroform, in the presence of an organic base such as triethylamine, N,N-diisopropylethylamine or tributylamine at a temperature from 0° C. to 150°.

The compound represented by the formula (3b) can be obtained by palladium coupling of the compound represented by the formula (2b).

The reaction condition corresponds to that of the production example of the formula (7a) in Production example A.

The compound represented by the formula (4b) can be obtained by halogenation of the compound represented by the formula (3b).

The reaction condition corresponds to that of the production example of the formula (4a) in Production example A.

The compound represented by the formula (5b) can be obtained by alkylation of the compound represented by the formula (4b).

The reaction condition corresponds to that of the production example of the formula (3a) in Production example A.

The compound represented by the formula (6b) can be obtained by palladium coupling of the compound represented by the formula (2b).

The reaction condition corresponds to that of the production example of the formula (7a) in Production example A.

The compound represented by the formula (7b) can be obtained by hydrolyzing the ester in the molecule after palladium coupling of the compound represented by the formula (6b).

The reaction conditions for palladium coupling and hydrolysis correspond to those of the production example of the formula (7a) in Production example A, and the production example of the formula (11a) in Production example A, respectively.

The compound represented by the formula (8b) can be obtained by treating a carbonyl compound such as ketone or aldehyde with the compound represented by the formula (6b).

The reaction condition is not particularly limited, and the reaction can be conducted, for example, in a solvent such as dioxane, tetrahydrofuran or dimethoxyethane, in the presence of a base such as lithium bistrimethylsilylamide, sodium bistrimethylsilylamide or potassium bistrimethylsilyl amide at a temperature from 0° C. to room temperature.

The compound represented by the formula (9b) can be obtained by palladium coupling of the compound represented by the formula (2b).

The reaction condition is not particularly limited, and it can be synthesized, for example, in a solvent such as dioxane, tetrahydrofuran, dimethoxyethane or toluene, by reacting 1,1-ethoxyvinyltributyltin, butylvinyl ether and the like in the presence of from 0.0001 to 0.5 mole equivalent of palladium catalyst such as tetrakis(triphenylphosphine)palladium or dichlorobis(triphenylphosphine)palladium, and lithium chloride, at a temperature from 0° C. to 150° C.

The compound represented by the formula (10b) can be obtained by adding acetylene to the compound represented by the formula (9b).

The reaction condition is not particularly limited, and the reaction can be conducted, for example in a solvent such as dioxane, tetrahydrofuran or dimethoxyethane, in the presence of a base such as butyl lithium, methyl lithium, ethyl magnesium hydride, lithium bistrimethylsilylamide, sodium bistrimethylsilylamide or potassium bistrimethylsilylamide, and a Lewis acid such as boron trifluoride ether complex, at a temperature from 0° C. to room temperature.

The compound represented by the formula (11b) can be obtained by hydrolysis after palladium coupling to the compound represented by the formula (10b).

The reaction condition corresponds to that of the production example of the formula (7b) in Production example B.

General production example C

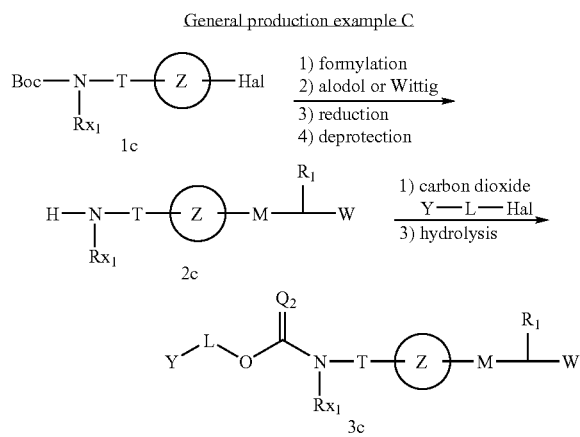

wherein each symbol represents a group as defined above; Boc represents a t-butoxycarbonyl group; and Hal represents a halogen.

The compound represented by the formula (2c) can be obtained by formylation of the compound represented by the formula (1c), followed by aldol reaction or Wittig-Horner-Emmons reaction, reduction and deprotection.

The reaction condition for formylation is not particularly limited, and it may be achieved by acting butyl lithium in a solvent such as dioxane, tetrahydrofuran or dimethoxyethane, followed by acting N,N-dimethylformamide, and the like at a temperature from −78° C. to 0° C.

The reaction conditions for aldol reaction or Wittig-Horner-Emmons reaction corresponds to that of the production example of the formula (10a) in Production example A.

The reaction condition for reduction reaction corresponds to that of the production example of the formula (10a) in Production example A.

The reaction condition for deprotection is not particularly limited, and it can be achieved by causing an acid such as hydrogen chloride or trifluoroacetic acid in an organic solvent such as dichloromethane, chloroform, tetrahydrofuran or dioxane, at a temperature from 0° C. to 150° C.

The compound represented by the formula (3c) can be obtained by causing carbon dioxide and Y-L-Hal to act on the compound represented by the formula (2c), to form carbamate, and hydrolyzing the ester in the molecule.

As to reaction condition for synthesis of carbamate follows, but not particularly limited thereto, the document (*J. Org. Chem.* 2000, 66, 1035.).

The reaction condition for hydrolysis follows the production example of the formula (11a) in Production example A.

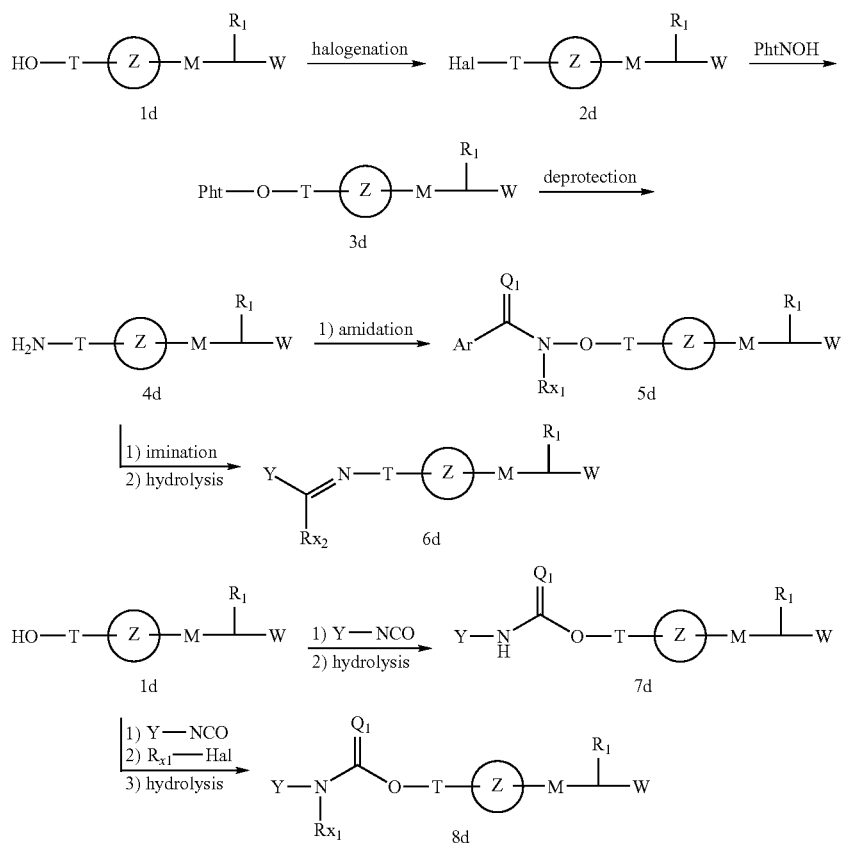

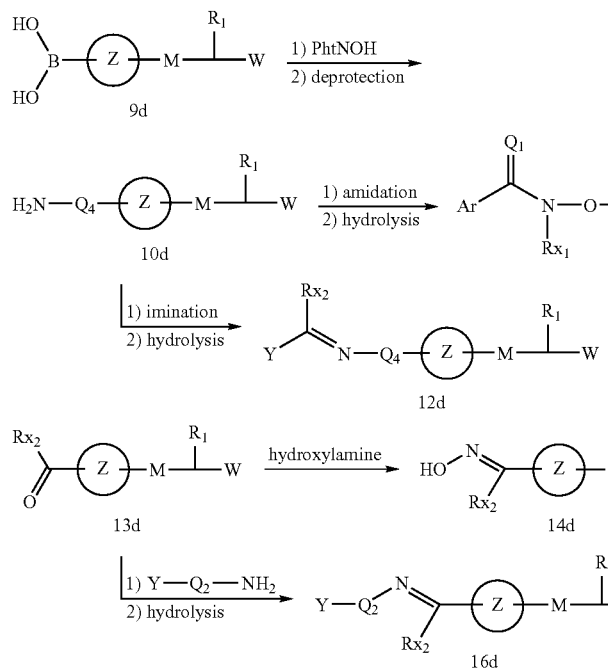

wherein each symbol represents a group as described above; Hal represents a halogen; PhtNOH represents N-hydroxyphthalimide; and —NCO represents an isocyanate group.

The compound represented by the formula (2d) can be obtained by halogenation of the compound represented by the formula (1d).

The reaction condition follows the production example of the formula (4a) in Production example A.

The compound represented by the formula (3d) can be obtained by causing N-hydroxyphthalimide to act on the compound represented by the formula (2d).

The reaction condition is not particularly limited, and the reaction can be conducted, for example, in a solvent such as methanol, ethanol, propanol, dimethylsulfoxide, N,N-dimethylformamide, N-methylpyrrolidone, dioxane, tetrahydrofuran or toluene in the presence of a base such as lithium carbonate, sodium carbonate, potassium carbonate, cesium carbonate, lithium hydride, sodium hydride, potassium hydride, triethylamine, N,N-diisopropylethylamine or tributylamine at a temperature from 0° C. to 150° C.

The compound represented by the formula (4d) can be obtained by deprotection of the phthalimide group of the compound represented by the formula (3d).

The reaction condition is not particularly limited, and for example, hydrazine, N-methyl hydrazine and the like may be caused to act in a solvent such as methanol, ethanol, propanol, dimethylsulfoxide, N,N-dimethylformamide, N-methylpyrrolidone, dioxane, tetrahydrofuran or toluene at a temperatures from 0° C. to 150° C.

The compound represented by the formula (5d) can be obtained by amidation of the compound represented by the formula (4d), and hydrolysis of the ester in the molecule.

The reaction condition for amidation is not particularly limited, and it can be achieved by causing an appropriate carboxylic acid to act in a solvent such as N,N-dimethylformamide, N-methylpyrrolidone, dioxane, tetrahydrofuran, toluene, dichloromethane or chloroform, in the presence of a condensing agent such as diphenylphospholylazide, diethylphospholylcyanide or dicyclohexylcarbodiimide, and a base such as triethylamine, N,N-diisopropylethylamine, tributylamine, sodium hydrogencarbonate or potassium hydrogen carbonate at a temperature from 0° C. to 150° C.

The reaction condition of hydrolysis reaction follows the production example of the formula (11a) in Production example A.

The compound represented by the formula (6d) can be obtained by imitation of the compound represented by the formula (4d) followed by hydrolysis of the ester in the molecule.

The reaction condition for the imination is not particularly limited, and it can be synthesized, for example, by causing an appropriate carbonyl compound such as ketone or aldehyde in a solvent such as methanol, ethanol, propanol, dimethylsulfoxide, N,N-dimethylformamide, N-methylpyrrolidone, dioxane, tetrahydrofuran or toluene at a temperature from 0° C. to 150° C. An acid such as acetic acid, trifluoroaceteic acid or hydrogen chloride may also exist.

The reaction condition for hydrolysis corresponds to that of the production example of the formula (11a) in Production example A.

The compound represented by the formula (7d) can be obtained by treating Y—NCO with the compound represented by the formula (1d) to form a carbamate, and hydrolyzing the ester in the molecule.

The reaction condition for synthesis of the carbamate is not particularly limited, and it can be achieved by causing an organic base such as pyridine or triethylamine to act in a solvent such as tetrahydrofuran, toluene, ether or dioxane at a temperature from 0° C. to 150° C.

The reaction condition for hydrolysis reaction corresponds to that of the production example of the formula (11a) in Production example A.

The compound represented by the formula (8d) can be obtained by causing Y—NCO to act on the compound represented by the formula (1d), thereby forming a carbamate, followed by alkylation by causing $R_{x1}$-Hal to act thereon, and hydrolysis of the ester in the molecule.

The reaction condition for synthesis of the carbamate corresponds to that of the production example of the formula (7d) in Production example D.

The reaction condition for alkylation corresponds to that of the production example of the formula (4a) in Production example A.

The reaction condition for hydrolysis reaction corresponds to that of the production example of the formula (11a) in Production example A.

The compound represented by the formula (10d) can be obtained by treating N-hydroxyphthalimide with the compound represented by the formula (9d), followed by deprotection of the phthalimide group.

The hydroxyphthalimidation can be conducted in accordance with the document (*Org. Lett.* 2001, 3, 139).

The reaction condition for deprotection corresponds to that of the production example of the formula (4d) in Production example D.

The compound represented by the formula (11d) can be obtained by amidation of the compound represented by the formula (10d) followed by hydrolysis of the ester in the molecule.

The reaction condition corresponds to that of the production example of the formula (5d) in Production example D.

The compound represented by the formula (12d) can be obtained by the imination of the compound represented by the formula (10d) followed by hydrolysis of the ester in the molecule.

The reaction condition corresponds to that of the production example of the formula (6d) in Production example D.

The compound represented by the formula (14d) can be obtained by imination of the compound represented by the formula (13d).

The reaction condition corresponds to that of the production example of the formula (6d) in Production example D.

The compound represented by the formula (15d) can be obtained by alkylation of the compound represented by the formula (14d) with Y-L-Hal.

The reaction condition corresponds to that of the production example of the formula (3a) in Production example A.

The compound represented by the formula (16d) can be obtained by imination of the compound represented by the formula (13d) with Y—$Q_2$—$NH_2$, and followed by hydrolysis of the ester in the molecule.

The reaction condition corresponds to that of the production example of the formula (6d) in Production example D.

General production example E

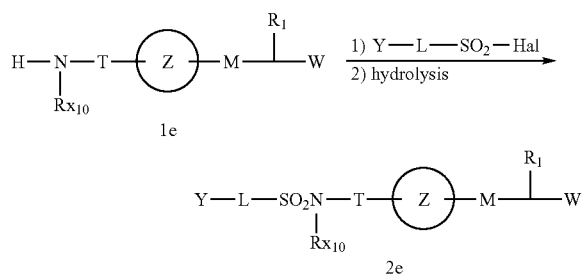

wherein each symbol represents a group as defined above; and Hal represents a halogen.

The compound represented by the formula (2e) can be obtained by sulfonamidation by causing Y—L—$SO_2$-Hal to act on the compound represented by the formula (1e), and hydrolyzing the ester in the molecule.

The reaction condition for synthesis of sulfonamide is not particularly limited, and it can be achieved, for example, by causing an organic base such as pyridine or triethylamine to act in an organic solvent such as dichloromethane or chloroform at a temperature from 0° C. to 150° C.

The reaction condition for hydrolysis reaction corresponds to that of the production example of the formula (11a) in Production example A.

General production example F

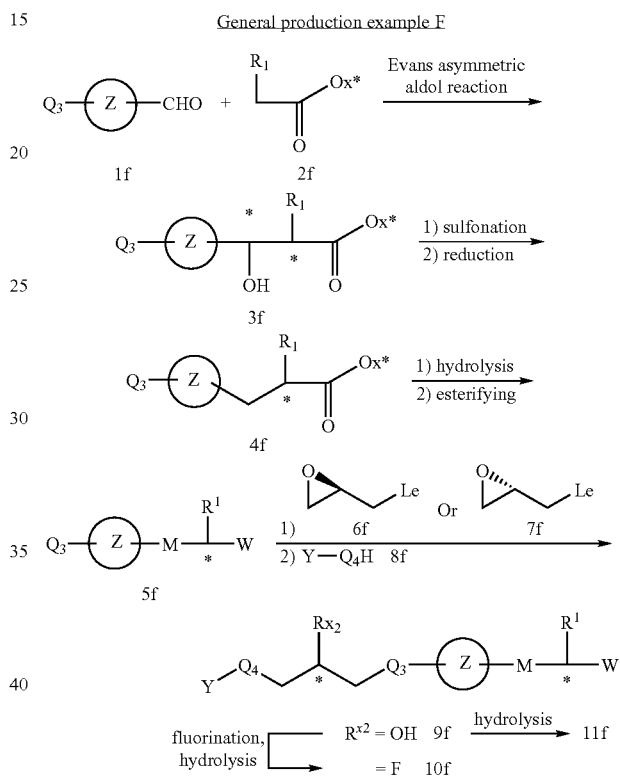

wherein each symbol represents a group as defined above; and t Ox* represents an Evans aldol asymmetric auxiliary group (chiral oxazolidinone), Le represents a leaving group such as halogen or sulfonate; and symbol * represents an asymmetric carbon.

The compound represented by the formula (3f) can be obtained by treating the compound represented by the formula (2f) with the compound represented by the formula (1f) in an Evans asymmetrical aldol condition.

The reaction condition is not particularly limited, but for example, the reaction is conducted in a solvent such as dichloromethane, chloroform, dioxane, tetrahydrofuran or toluene, in the presence of a base such as triethylamine or diisopropylethylamine, at a temperature from 0° C. to 150° C.

The compound represented by the formula (4f) can be obtained by sulfonylation of the compound represented by the formula (3f), followed by reduction of the sulfonate group.

The reaction condition for sulfonylation is not particularly limited, and for example, it can be achieved by treating methanesulfonyl chloride, tosyl chloride, 4-nitrobenzenesulfonyl chloride and the like in a solvent such as dichloromethane, chloroform, dioxane, tetrahydrofuran, toluene or pyridine, in the presence of a base such as trimethyl amine, diisopropylethylamine, pyridine or N,N-dimethylaminopyridine, at a temperature from 0° C. to 150° C.

The condition for reduction is conducted in a solvent such as methanol, ethanol, propanol, dimethylsulfoxide, N,N-dimethylformamide, N-methylpyrrolidone, dioxane, tetrahydrofuran or toluene, in the presence of a metal catalyst such as palladium carbon, platinum oxide or Raney's nickel, in hydrogen atmosphere, at a temperature from 0° C. to 1500. A base such as sodium acetate, potassium acetate or pyridine may exist as the case requires.

The compound represented by the formula (5f) can be obtained by hydrolysis of the compound represented by the formula (4f), followed by esterification of the carboxyl group.

The condition for hydrolysis reaction is not particularly limited, and for example, it can be achieved by causing an aqueous solution of lithium hydroxide, sodium hydroxide, potassium hydroxide and the like to act in a solvent such as methanol, ethanol, propanol, dimethylsulfoxide, N,N-dimethylformamide, N-methylpyrrolidone, dioxane or tetrahydrofuran, in the presence of hydrogen peroxide solution at a temperature from 0° C. to 150° C.

The reaction condition for esterification is not particularly limited, and for example, it can be achieved, for example, by treating an alkyl halide such as iodomethane, iodoethane, iodopropane or benzyl bromide in a solvent such as methanol, ethanol, propanol, dimethylsulfoxide, N,N-dimethylformamide, N-methylpyrrolidone, dioxane, tetrahydrofuran or toluene, in the presence of a base such as lithium hydroxide, sodium hydroxide, potassium hydroxide, lithium carbonate, sodium carbonate, potassium carbonate, cesium carbonate potassium bicarbonate, (sodium) bicarbonate, lithium hydride, sodium hydride, potassium hydride, butyl lithium, methyl lithium, lithium bistrimethylsilylamide, sodium bistrimethylsilyl amide or potassium bistrimethylsilylamide at a temperature from 0° C. to 150° C.

The compound of the formula (9f) can be obtained by treating an alkylation agent containing epoxy represented by the formula (6f) or the formula (7f) or the like with the compound represented by the formula (5f), and opening the epoxy group with phenol represented by (8f) and the like.

The reaction condition for alkylation of the formula (6f), the formula (7f) or the like is not particularly limited, and for example, it can be achieved by conducting the reaction in a solvent such as methanol, ethanol, propanol, dimethylsulfoxide, N,N-dimethylformamide, N-methylpyrrolidone, dioxane, tetrahydrofuran or toluene, in the presence of a base such as lithium hydroxide, sodium hydroxide, potassium hydroxide, lithium carbonate, sodium carbonate, potassium carbonate, cesium carbonate, lithium hydride, sodium hydride, potassium hydride, butyl lithium, methyl lithium, lithium bistrimethylsilylamide, sodium bistrimethylsilylamide, potassium bistrimethylsilylamide or cesium fluoride at a temperature from 0° C. to 150° C.

The reaction condition for the treatment of the formula (8f) is not particularly limited, and for example, it can be achieved by conducting the reaction in a solvent such as methanol, ethanol, propanol, dimethylsulfoxide, N,N-dimethylformamide, N-methylpyrrolidone, dioxane or tetrahydrofuran, in the presence of 0.0001 to 1.0 mole equivalent of a catalyst such as potassium carbonate, triethylamine or cesium fluoride at a temperature from 0° C. to 150° C.

The compound represented by the formula (10f) can be obtained by fluorination of the compound represented by the formula (9f), followed by hydrolysis of the ester in the molecule.

The reaction condition for fluorination is not particularly limited, and for example, it can be achieved by treating a reagent such as diethylaminosulfur trifluoride in a solvent such as dichloromethane or chloroform, at a temperature from 0° C. to 150° C.

The compound represented by the formula (11f) can be obtained by hydrolyzing the ester in the compound represented by the formula (9f) or (10f).

The condition for hydrolysis reaction is not particularly limited, and for example, it can be achieved by treating an aqueous solution of lithium hydroxide, sodium hydroxide, potassium hydroxide and the like in a solvent such as methanol, ethanol, propanol, dimethylsulfoxide, N,N-dimethylformamide, N-methylpyrrolidone, dioxane or tetrahydrofuran, in the presence of hydrogen peroxide solution at a temperature from 0° C. to 150° C.

General production example G

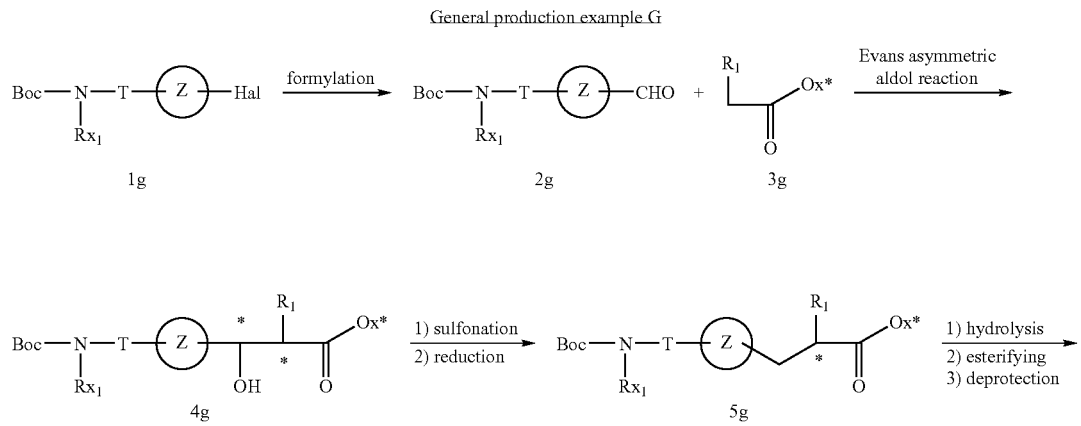

-continued

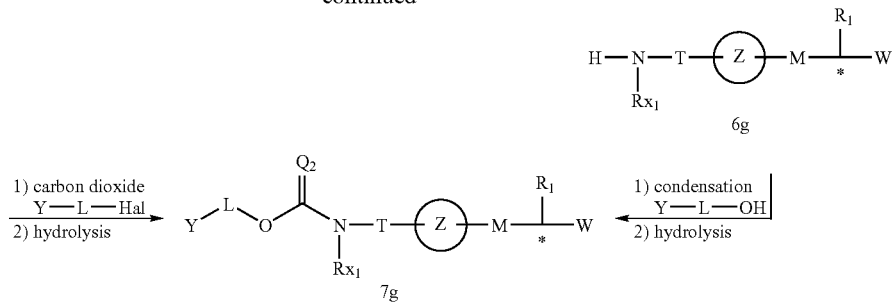

wherein each symbol represents a group as defined above; Ox* represents an Evans aldol asymmetric auxiliary group (chiral oxazolidinone); Le represents a leaving group such as halogen or sulfonate; and symbol * represents an asymmetric carbon.

The compound represented by the formula (2 g) can be obtained by formylation of the compound represented by the formula (1 g).

The reaction condition for formylation is not particularly limited, and for example, it can be achieved by treating butyl lithium in a solvent such as dioxane, tetrahydrofuran or dimethoxyethane, followed by reacting N,N-dimethylformamide, N-formylmorpholine and the like at a temperature from −78° C. to 0° C.

The compound represented by the formula (4 g) can be obtained by causing the compound represented by the formula (3 g) to act on the compound represented by the formula (2 g) in Evans asymmetric aldol condition.

The Evans asymmetric aldol condition corresponds to that of the production example of the compound represented by the formula (3f) in General production example F.

The compound represented by the formula (5 g) can be obtained by sulfonylation of the compound represented by the formula (4 g), followed by reduction of the sulfonate group.

The reaction condition for sulfonylation corresponds to that of the production example of the formula (4f) in General production example F.

The reaction condition for reduction corresponds to that of the production example of the formula (4f) in General production example F.

The compound represented by the formula (6 g) can be obtained by hydrolyzing the compound represented by the formula (5 g), and esterifying the carboxyl group, followed by deprotection of the amino group.

The reaction condition for hydrolysis corresponds to that of the production example of the formula (5f) in General production example F.

The reaction condition for esterification corresponds to that of the production example of the formula (5f) in General production example F.

As to deprotection of amino group, though the method differs depending on the employed protecting group, for example, deprotection of t-butylcarbonyl group can be achieved by using a solution of anhydrous hydrochloric acid in methanol, a solution of anhydrous hydrochloric acid in ethanol, a solution of anhydrous hydrochloric acid in dioxane, trifluoroacetic acid, formic acid and the like.

The compound represented by the formula (7 g) can be obtained by treating carbon dioxide and Y-L-Hal with the compound represented by the formula (6 g) or treating phosgene, diphosgene, triphosgene and the like with the compound represented by the formula (6 g), to give a corresponding isocyanate, acting a benzyl alcohol such as Y—L—OH so as to form a carbamate, and hydrolyzing the ester in the molecule.

The reaction condition for synthesis of the carbamate is not particularly limited, and it can be achieved in accordance with the document (*J. Org. Chem.* 2000, 66, 1035.), or can be achieved by causing phosgene, diphosgene, triphosgene and the like to act in a solvent such as dichloromethane, chloroform, dioxane, tetrahydrofuran or toluene, in the presence of a base such as triethylamine, diisopropylethylamine, pyridine or N,N-dimethylaminopyridine at a temperature from 0° C. to 150° C., and thereafter causing a benzyl alcohol such as Y—L—OH to act at a temperature from 0° C. to 150° C. Alternatively, it may be obtained by treating a carbonyldiimidazole with Y—L—OH in a solvent such as dichloromethane, chloroform, tetrahydrofuran, toluene or acetonitrile at a temperature from 0° C. to 50° C., and then causing the compound represented by the formula (6 g) to act at a temperature from 0° C. to 50° C.

The reaction condition for hydrolysis corresponds to that of the production example of the formula (I of) in Production example F.

General production example H

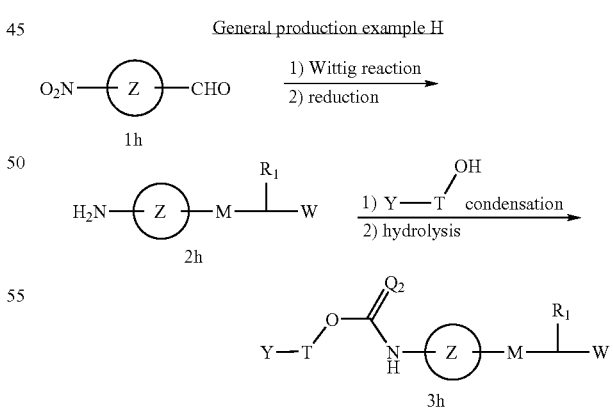

The compound represented by the formula (2h) can be obtained by conducting Wittig-Horner-Emmons reaction on the compound represented by the formula (1h) and reducing the resultant compound. The condition for Wittig-Horner-Emmons reaction corresponds to that of the production example of the formula (10a) in Production example A.

The reaction condition for reduction corresponds to that of the production example of the formula (10a) in Production example A.

The compound represented by the formula (3h) can be obtained by treating phosgene, diphosgene, triphosgene, di-tert-butyldicarbonate and the like with the compound represented by the formula (2h) in a solvent such as dichloromethane, tetrahydrofuran or acetonitrile, in the presence of a base such as pyridine, triethylamine or 4-dimethylaminopyridine, thereby generating an isocyanate, and by treating Y—T—OH with the isocyanate, to give a carbamate, and followed by the subsequent alkaline hydrolysis of the carbamate. The reaction temperature at the time of generating isocyanate is from 0° C. to 5° C.

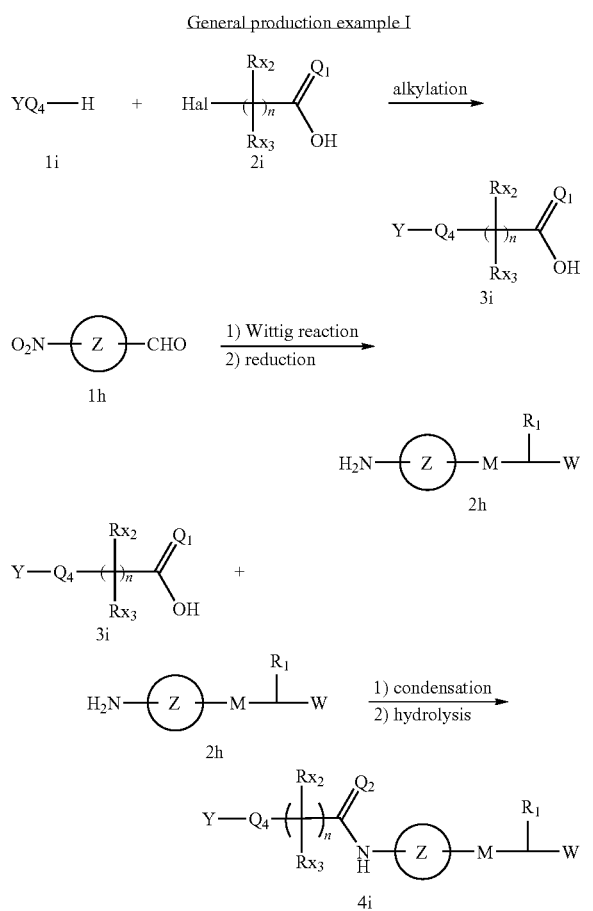

The compound represented by the formula (3I) can be obtained by reacting the compound represented by the formula (1i) and the compound represented by the formula (2i). The reaction condition is not particularly limited, and for example, it can be achieved by treating a base such as potassium carbonate or sodium hydride with the compound represented by the formula (1i) in a solvent such as tetrahydrofuran, N,N-dimethylformamide or dioxane and the like, and further treating the compound represented by the formula (2i) The reaction temperature is from 0° C. to 100° C.

The compound represented by the formula (4i) can be obtained by reacting the compound represented by the formula (3i) and the compound represented by the formula (2h), followed by hydrolyzing. The reaction condition is not particularly limited, and the condensing reaction can be achieved by treating the compound represented by the formula (3i) with the compound represented by the formula (2h) in a solvent such as tetrahydrofuran or N,N-dimethylformamide, in the presence of a base such as triethylamine or pyridine, and in the presence of a condensing agent such as 1,1-carbonyldiimidazole, diethylcyanophosphonate or carbodiimide. The reaction temperature is from 0° C. to 100° C. The reaction condition for hydrolysis corresponds to that of the production example of the formula (11a) in Production example A.

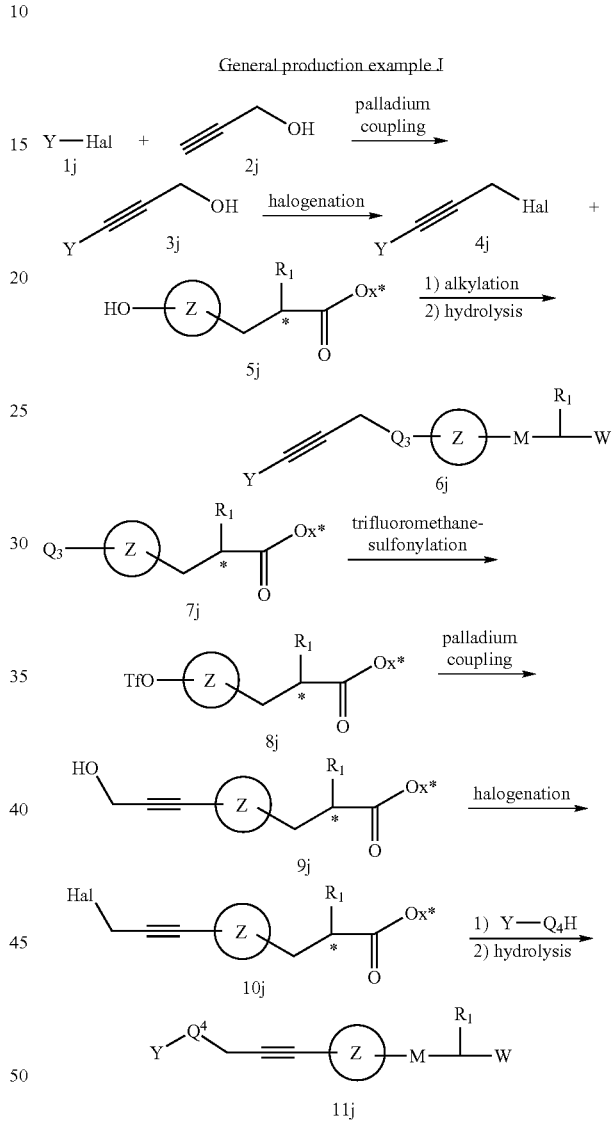

wherein each symbol represents a group as defined above; Ox* represents an Evans aldol asymmetric auxiliary group (chiral oxazolidinone); Tf represents a trifluoromethanesulfonyl group; Hal represents a leaving group such as halogen or sulfonate; and symbol * represents an asymmetric carbon.

The compound represented by the formula (3j) can be obtained by treating the compound represented by the formula (2j) with the compound represented by the formula (1j).

The reaction condition is not particularly limited, and for example, the reaction can be conducted in a solvent such as methanol, ethanol, propanol, dimethylsulfoxide, N,N-dimethylformamide, N-methylpyrrolidone, dioxane, tetrahydrofuran or toluene, in the presence of from 0.0001 to 0.5 mole equivalent of copper halide, from 0.0001 to 0.5 mole equivalent of a palladium catalyst such as tetrakis(triphenylphosphine)palladium or dichlorobis(triphenylphosphine) palladium in the presence of an organic base such as triethylamine, N,N-diisopropylethylamine, butylamine or tributylamine at a temperature from 0° C. to 150° C.

The compound represented by the formula (4j) can be obtained by halogenation of the compound represented by the formula (3j).

The compound represented by the formula (6j) can be obtained by causing the compound represented by the formula (5j) to act on the compound represented by the formula (4j), followed by hydrolysis.

The reaction condition for alkylation corresponds to that of the production example of the formula (4a) in Production example A.

The reaction condition for hydrolysis corresponds to that of the production example of the formula (5f) in Production example F.

The compound represented by the formula (8j) can be obtained by trifluoromethanesulfonylation of the compound represented by the formula (7j).

The reaction condition corresponds to that of the production example of the formula (2b) in Production example B.

The compound represented by the formula (9j) can be obtained by palladium coupling of the compound represented by the formula (8j).

The reaction condition corresponds to that of the production example of the formula (7a) in Production example A.

The compound represented by the formula (10j) can be obtained by halogenation of the compound represented by the formula (9j).

The reaction condition corresponds to that of the production example of the formula (4a) in Production example A.

The compound represented by the formula (11j) can be obtained by alkylation of the compound represented by the formula (10j) with the compound of Y—QH, followed by hydrolysis.

The condition for alkylation reaction corresponds to that of the production example of the formula (4a) in Production example A.

The reaction condition for hydrolysis corresponds to the production example of the formula (5f) in Production example F.

General production example K

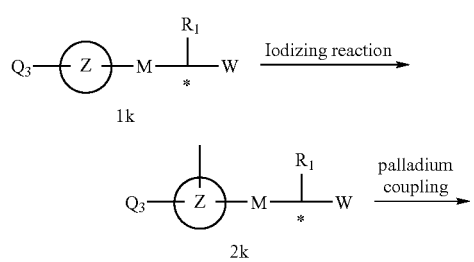

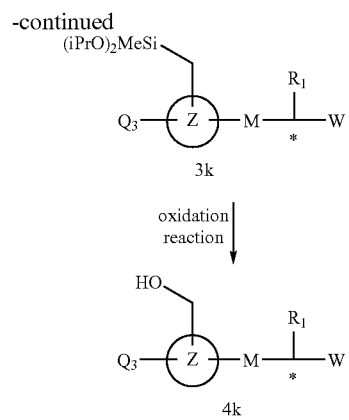

wherein each symbol represents a group as defined above.

The compound represented by the formula (2k) can be obtained by treating an iodizing agent with the compound represented by the formula (1k).

The reaction condition is not particularly limited, and for example, it can be achieved by treating iodine or an iodizing agent such as N-iodosuccinimide in a solvent such as methanol, ethanol, propanol, dimethylsulfoxide, N,N-dimethylformamide, N-methylpyrrolidone, dioxane, tetrahydrofuran or toluene, or a mixed solvent thereof, in the presence of a silver salt such as silver sulfate, at a temperature from 0° C. to 100° C.

The compound represented by the formula (3k) can be obtained by causing an organic zinc compound to react with the compound represented by the formula (2k) in the presence of a palladium catalyst.

The reaction condition is not particularly limited, and for example, it can be achieved by causing an organic zinc reagent such as dialkoxymethylsilylmethylzinc to react in an ether solvent such as tetrahydrofuran, in the presence of a palladium catalyst such as palladium acetate or dichlorophosphinoferrocene palladium, at a temperature from 0° C. to 100° C.

The compound represented by the formula (4k) can be obtained by oxidizing the compound represented by the formula (3k).

The reaction condition is not particularly limited, and for example, hydrogen peroxide may be caused to react in a mixed solvent of an alcohol solvent such as methanol, ethanol or propanol and an ether solvent such as tetrahydrofuran, or in a solvent of N,N-dimethylformamide at a temperature from 0° C. to 80° C.

Although compounds of the present invention can be synthesized in the above methods, they may be also synthesized in commonly used general organic synthesizing methods. As for protecting groups for a hydroxyl group which may be used herein, any hydroxyl groups are possible without limitation insofar as they are protected by groups which are generally known as a protecting group for a hydroxyl group in organic synthesis, and specific examples of protecting groups for a hydroxyl group include lower alkylsilyl groups such as trimethylsilyl group or t-butyldimethylsilyl; lower alkoxymethyl groups such as methoxymethyl group or 2-methoxyethoxymethyl group; tetrahydropyranyl group; aralkyl groups such as benzyl group, p-methoxybenzyl group, 2,4-dimethoxybenzyl group, o-nitrobenzyl group, p-nitrobenzyl group or trityl group; acyl groups such as formyl group or acetyl group; lower alkoxycarbonyl groups such as t-butoxycarbonyl group, 2-iodoethoxycarbonyl group or 2,2,2-trichloroethoxycarbonyl group; alkenyloxycarbonyl groups such as 2-propenyloxycarbonyl group, 2-chloro-2-propenyloxycarbonyl group, 3-methoxycarbonyl-2-propenyloxycarbonyl group, 2-methyl-2-propenyloxycarbonyl group, 2-butenyloxycarbonyl group or cinnamyloxycarbonyl group; aralkyloxycarbonyl groups such as benzyloxycarbonyl group, p-methoxybenzyloxycarbonyl group, o-nitrobenzyloxycarbonyl group or p-nitrobenzyloxycarbonyl group and the like.

These protecting groups may be eliminated by conventional methods such as hydrolysis and reduction depending on the kind of the employed protecting group.

Although compounds of the present invention can be synthesized by the methods as described above, they may be also synthesized in commonly used general organic synthesizing methods. Specific examples of protecting groups for an amino group which may be used herein include, but not limited to, any groups which are generally known as a protecting group for an amino group in organic synthesis. For example, substituted or unsubstituted lower alkanoyl groups such as formyl group, acetyl group, chloroacetyl group, dicholroacetyl group, propionyl group, phenylacetyl group, phenoxyacetyl group or thienylacetyl group; substituted or unsubstituted lower alkoxycarbonyl groups such as benzyloxycarbonyl group, t-butoxycarbonyl group or p-nitrobenzyloxycarbonyl group; substituted lower alkyl groups such as methyl group, t-butyl group, 2,2,2-trichloroethyl group, trityl group, p-methoxybenzyl group, p-nitrobenzyl group, diphenylmethyl group or pivaloyloxymethyl group; substituted silyl groups such as trimethylsilyl group or t-butyldimethylsilyl group; substituted silylalkoxyalkyl groups such as trimethylsilylmethoxymethyl group, trimethylsilylethoxymethyl group, t-butyldimethylsilylmethoxymethyl group or t-butyldimethylsilylethoxymethyl group; substituted or unsubstituted benzylidene groups such as benzylidene group, salicylidene group, p-nitrobenzylidene group, m-chlorobenzylidene group, 3,5-di(t-butyl)-4-hydroxybenzylidene group or 3,5-di(t-butyl)benzylidene group may be proposed.

These protecting groups may be eliminated by conventional methods such as hydrolysis and reduction depending on the kind of the employed protecting group.

Although compounds of the present invention can be synthesized in the above methods, they may be also synthesized in commonly used general organic synthesizing methods. As for protecting groups for a carboxyl group which may be used herein, any carboxyl groups are possible without limitation insofar as they are protected by groups which are generally known as a protecting group for a carboxyl group in organic synthesis, and specific examples of a protecting group for a carboxyl group include linear or branched lower alkyl groups of from 1 to 4 carbon atoms such as methyl group, ethyl group, isopropyl group or t-butyl group; halogeno lower alkyl groups such as 2-iodoethyl group or 2,2,2-trichloroethyl group; lower alkoxymethyl groups such as methoxymethyl group, ethoxymethyl group or isobutoxymethyl group; lower aliphatic acyloxymethyl groups such as butylyloxymethyl group or pivaloyloxymethyl group; lower alkoxycarbonyloxyethyl groups such as 1-methoxycarbonyloxyethyl group or 1-ethoxycarbonyloxyethyl group; aralkyl groups such as benzyl, p-methoxybenzyl group, o-nitrobenzyl group or p-nitrobenzyl group; benzhydryl group; phthalidyl group, etc.

Elimination of such a protective group can be carried out in a conventional method such as hydrolysis and reduction etc, depending on the type of the protective group used.

Although compounds of the present invention can be synthesized by the methods as described above, they may be synthesized in commonly used general organic synthesizing methods. Specific examples of solvents which may be used herein include, but not limited to, any solvents which do not inhibit the reaction and are generally used in organic synthesis, for example, lower alcohols such as methanol, ethanol, propanol or butanol; polyalcohols such as ethylene glycol or glycerin; ketones such as acetone, methyl ethyl ketone, diethyl ketone or cyclohexanone; ethers such as diethyl ether, isopropyl ether, tetrahydrofuran, dioxane, 2-methoxyethanol or 1,2-dimethoxyethane; nitriles such as acetonitrile or propionitrile; esters such as methyl acetate, ethyl acetate, isopropyl acetate, butyl acetate or diethyl phthalate; hydrocarbon halides such as dichloromethane, chloroform, carbon tetrachloride, 1,2-dichloroethane, trichloroethylene or tetrachloroethylene; aromatic compounds such as benzene, toluene, xylene, monochlorobenzene, nitrobenzene, indene, pyridine, quinoline, collidine or phenol; hydrocarbons such as pentane, cyclohexane, hexane, heptane, octane, isooctane, petroleum benzine or petroleum ether; amines such as ethanolamine, diethylamine, triethylamine, pyrrolidine, piperidine, piperazine, morpholine, aniline, dimethylaniline, benzylamine or toluidine; amides such as formamide, N-methylpyrrolidone, N,N-dimethylimidazolone, N,N-dimethylacetamide or N,N-dimethylformamide; phosphate amides such as hexamethylphosphate triamide or hexamethylphosphite triamide; water; and mixed solvents of one or more kinds of commonly used solvents. The mixing ratio is not particularly limited.

Although compounds of the present invention can be synthesized by the methods as described above, they may be synthesized in commonly used general organic synthesizing methods. Specific examples of bases which may be used herein include, but not limited to, any bases which do not inhibit the reaction and are generally used inorganic synthesis, for example, sodium carbonate, sodium hydrogencarbonate, potassium carbonate, sodium hydride, potassium hydride, potassium t-butoxide, pyridine, dimethylaminopyridine, trimethylamine, triethylamine, N,N-diisopropylethylmine, N-methylmorpholine, N-methylpyrrolidine, N-methylpiperidine, N,N-dimethylaniline, 1,8- diazabicyclo[5,4,0]undec-7-ene(DBU), pyridine, 4-dimethylaminopyridine, picoline, lutidine, quinoline, isoquinoline, sodium hydroxide, potassium hydroxide, lithium hydroxide, butyl lithium, sodium or potassium alcoholates such as sodium methylate, potassium methylate or sodium ethylate, and the like.

Although compounds of the present invention can be synthesized by the methods as described above, they may be synthesized in commonly used general organic synthesizing methods. Specific examples of reducing agents which may be used herein include, but not limited to, any reducing agents which do not inhibit the reaction and are generally used in organic synthesis, for example, $NaBH_4$, $LiBH_4$, $Zn(BH_4)_2$, $Me_4NBH(OAc)_3$, $NaBH_3CN$, Selectride, Super Hydride $(LiBHEt_3)$, $LiAlH_4$, DIBAL, $LiAlH(t-BuO)_3$, Red-al, binap, as well as catalysts such as platinum, palladium, rhodium, ruthenium, nickel and the like.

After the reaction is completed, the product can be purified if necessary by usual methods such as column chromatography on silica gel or adsorption resin, or by re-crystallization from a suitable solvent.

The medicament according to the present invention improves insulin resistance by the agonism of PPAR as described above, and the present invention can be applied not only as an insulin sensitizer but also as various medicaments based on PPAR ($\alpha$, $\beta$, $\gamma$) agonism (based on e.g. PPAR $\alpha$ and $\gamma$ dual agonism or on PPAR $\alpha$, $\beta$ and $\gamma$ triple agonism).

For example, the relationship of PPAR not only with insulin resistance but also with blood lipid or inflammatory diseases is known (Current Opinion in Lipidol. 10:245-257, 1999; Jiang, C., et al., PPAR-gamma agonists inhibit production of monocyte inflammatory cytokines, Nature 391:82-86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094-2104 (1999); Su, C. G., et al., A novel therapy for colitis utilizing PPAR-gamma ligands to inhibit the epithelial inflammatory response., J Clin Invest 1999 August; 104 (4):383-9; Ricote, M., et al., The peroxisome proliferator-activated receptor-gamma is a negative regulator of macrophage activation., Nature 1998 Jan. 1; 391 (6662):79-82), and the medicament of the present invention can be applied to diseases against which it is reported to be effective in these literatures.

The dose of the pharmaceutical preparation of the present invention, though being varied depending on the severeness of symptom, age, sex, bodyweight, administration form and the type of disease, is usually 100 μg to 10g/day/adult, and this dose is administered in one or divided portions.

The administration form of the medicament of the present invention is not particularly limited, and it can be administered orally or parenterally by an ordinarily used method.

For manufacturing of the medicament, ordinarily used fillers, binders, lubricants, coloring agents, flavoring agents and if necessary stabilizers, emulsifiers, absorption promoters, surfactants etc. can be used, and ingredients used generally as starting materials for medicament are compounded in a usual manner.

These ingredients include e.g. animal and vegetable oils (such as soybean oil, tallow and synthetic glyceride), hydrocarbons (such as liquid paraffin, squalene and solid paraffin), ester oils (such as octyldodecyl myristate and isopropyl myristate), higher alcohols (such as cetostearyl alcohol and behenyl alcohol), silicon resin, silicon oil, surfactants (polyoxyethylene fatty ester, sorbitan fatty ester, glycerin fatty ester, polyoxyethylene sorbitan fatty ester, polyoxyethylene hardened castor oil and polyoxyethylene-polyoxypropylene block copolymer), water-soluble polymers (such as hydroethyl cellulose, polyacrylic acid, carboxyvinyl polymer, polyethylene glycol, polyvinyl pyrrolidone and methyl cellulose), alcohols (such as ethanol and isopropanol), polyvalent alcohols (such as glycerin, propyleneglycol, dipropyleneglycol and sorbitol), sugars (such as glucose and sucrose), inorganic powder (such as silicic anhydride, aluminum magnesium silicate and aluminum silicate), and pure water. For pH adjustment, it is possible to use inorganic acids (such as hydrochloric acid and phosphoric acid), alkali metal salt of inorganic acid (such as sodium phosphate), inorganic bases (such as sodium hydroxide), organic acids (such as lower fatty acids, citric acid and lactic acid), alkali metal salts of organic acid (such as sodium citrate and sodium lactate) and organic bases (such as arginine and ethanolamine). If necessary, preservatives, antioxidants etc. can be added.

Hereinafter, pharmacological experiment examples are shown to show the usefulness of this invention.

EXPERIMENT EXAMPLE 1

Measurement of Blood Glucose Reduction, Blood Triglyceride Reduction and Blood Non-Esterified Fatty Acids Reduction (Evaluation of Sugar and Lipid Metabolism Improving Effect in Mouse)

A chemical suspended in 0.5% methyl cellulose was orally administered via a sonde into male db/db mice (Nippon Charles River, Yokohama, JP) once a day (0.3 to 30 mg/kg/day). Before treatment and after 4 and 9 days treatment, blood was collected through a tail vein after the mice were fasted for 1 hour, respectively. On Day 10, an oral glucose loading test was conducted; in this test, the mice were fasted overnight from the previous day, and in the next morning, 2 g/kg glucose was given to the mice. Plasma glucose, triglycerides (TG), non-esterified fatty acid (NEFA) were measured by using commercial kits, that is, Glucose C-II Test Wako (trade name) (Wako Pure Chemical Industries, Ltd., Tokyo), Determiner L TG II (trade name) (Kyowa Medex, Tokyo) and NEFA C-Test Wako (Wako Pure Chemical Industries, Ltd., Tokyo), respectively.

The determined blood glucose reduction, blood triglyceride reduction and blood non-esterified fatty acid reduction at day 9 after administration are shown in Table 1.

TABLE 1

| in vivo db/db mice day 9 after administration | | | |
|---|---|---|---|
| | Dose (mg/kg) | Blood sugar reduction (%) | Blood triglyceride reduction (%) | Blood free fatty acid reduction (%) |
| Ex 100 | 6 | 65.1 | 79.3 | 60.7 |
| Ex 132 | 6 | 50.4 | 75.5 | 72.5 |
| Ex 113 | 6 | 70.0 | 81.8 | 39.5 |
| Ex 320 | 3 | 56.3 | 80.3 | 35.4 |
| Ex 335 | 3 | 57.2 | 81.4 | 40.0 |
| Ex 282 | 3 | 17.9 | 59.7 | 18.4 |
| Ex 344 | 3 | 45.8 | 61.8 | 58.1 |
| Ex 329 | 3 | 37.7 | 36.8 | 47.5 |

Compounds of the present invention showed excellent blood glucose reduction, blood triglyceride reduction and blood non-esterified fatty acid reduction.

EXPERIMENT EXAMPLE 2

Measurement of Blood Triglyceride Reduction and Blood Cholesterol Reduction (Evaluation of Lipid Metabolism Improving Effect in Dog)

A chemical suspended in 0.5% methyl cellulose was orally administered via a sonde into male beagle (Nosan Corporation, YOKOHAMA) once a day. The dosage of drug was increased every week. Blood was collected from forefoot vein prior to administration of drug and every time the dosage was increased, and levels of triglyceride and cholesterol in non-HDL and HDL fractions were measured by ultracentrifugation. At the day of collecting blood, the animal was fasted and blood was collected. Compounds of the present invention showed excellent blood triglyceride reduction and cholesterol reduction.

EXPERIMENT EXAMPLE 3

Measurement of Transcriptional Activity

A GAL4-PPAR LBD chimera expression vector was constructed by ligating human PPAR 167-468 (PPARα), 138-440 (NUC-1) and 174-475 (PPARγ) amino acid regions (LBD: Ligand Binding Domain) to a yeast transcriptional factor GAL4 1-147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70) was used. That is, CV-1 cells were spread at a density of $5\times10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. 24 hours after this transfection, the cells were spread again on a 96-well plate at a density of $1\times10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The PLAP activity was determined after adding 50 μl assay buffer and 50 μl chemoluminescence substrate to 10 μl culture supernatant and incubating the mixture at room temperature for 1 hour. In this way, transcription activities with respect to PPARα, PPARβ and PPARγ could be determined. Transcription activities with respect to PPARα, PPARβ and PPARγ are shown in Table 2.

TABLE 2

| | Transcription activity $EC_{50}$ (nM) | | |
|---|---|---|---|
| | PPARα | PPARβ | PPARγ |
| Ex 100 | 0.008 | 1.249 | 0.008 |
| Ex 132 | 0.604 | 1.544 | 0.001 |
| Ex 113 | 0.027 | 0.954 | 0.115 |
| Ex 320 | 0.064 | 0.686 | 0.024 |
| Ex 335 | 0.119 | >30 | 0.031 |
| Ex 282 | 0.062 | 1.521 | 0.114 |
| Ex 344 | 0.020 | 1.742 | 0.038 |
| Ex 329 | 0.117 | 1.290 | 0.053 |

The Compounds of the present invention showed an excellent transcription activity.

As described above, the compounds of the present invention have an excellent blood glucose- and blood lipid-ameliorating action and are very useful as anti-diabetes agents, anti-hyperlipemia agents and insulin sensitizers.

EXPERIMENT EXAMPLE 4

Anti-Inflammatory Effect

Experimental colitis was induced to female ICR mice (10 mice/group, Charles River Japan, Yokohama) by giving 4% dextran sodium in drinking water for 5 days. After 8 days, the mice were grouped into sections from "0" (normal) to "4" (severe) based on change in diarrhea, hematochezia and weight loss as described by Cooper H S et al., (Laboratory Invest (69), pp. 238-249, 1993) and the average of the values was used as the Disease Activity Index for colitis. Each test compound was suspended in a 0.5% methylcellulose solution and administered to the mice orally once a day via a sonde from the day when the induction of colitis was initiated. The compounds of the present invention had an excellent anti-inflammatory effect.

EXAMPLES

The present invention will be explained more specifically and more concretely by way of the following Examples which are not intended to limit the present invention.

Example 1

3-(3-2-Hydroxy-3-[4-(trifluoromethyl)phenoxy]-propoxyphenyl)-2-isopropoxypropanoic acid Production Example 1a)

Ethyl 3-(3-hydroxyphenyl)-2-isopropoxypropanoate

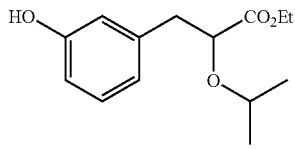

9.5 g of Ethyl 2-isopropoxyacetate was dissolved in 200 ml of tetrahydrofuran anhydride, and the mixture was cooled to −78° C. under nitrogen atmosphere. After adding 6.5 ml of lithium bis(trimethylsilyl)amide (1M solution in tetrahydrofuran), 15 g of 3-benzyloxybenzaldehyde in tetrahydrofuran (50 ml) was added via a cannula. The temperature of the solution was elevated to room temperature, and the mixture was stirred for 3 hours. The reaction solution was treated with saturated aqueous ammonium chloride, and extracted with ethyl acetate. The organic layer was dried over anhydrous magnesium sulfate, filtered and the solvent was distilled off. The residue was purified by silica gel column chromatography, to give 10.8 g of ethyl 3-[3-(benzyloxy)phenyl]-3-hydroxy-2-isopropoxypropanoate as a mixture of erythro and threo in the 3:1 hexane-ethyl acetate fraction. This product was dissolved in 50 ml of pyridine and 3.5 ml of methanesulfonyl chloride was added under ice-cooling. After stirring overnight at room temperature, the reaction mixture was diluted with ethyl acetate, and washed with 1N hydrochloric acid. The organic layer was dried over anhydrous magnesium sulfate, filtered and the solvent was distilled off, to give 13.7 g of ethyl 3-[3-(benzyloxy)phenyl]-2-isopropoxy-3-[(methylsulfonyl) oxy]propanoate. This product was dissolved in 450 ml of ethanol, 3.9 g of 10% palladium carbon was added, and the mixture was stirred overnight at room temperature under hydrogen atmosphere. The reaction mixture was filtered through Celite, and the filtrate was concentrated, to give 7.5 g of the title compound.

$^1$H NMR (CDCl$_3$)

δ: 0.98 (d, J=6.4 Hz, 3H) 1.16 (d, J=6.4 Hz, 3H) 1.24 (t, J=7.2 Hz, 3H) 2.89 (dd, J=8.8, 14.0 Hz, 1H) 2.97 (dd, J=4.8, 13.6 Hz, 1H) 3.52 (Sept, J=6.0 Hz, 1H) 4.05 (dd, J=4.8, 8.8 Hz, 1H) 4.12-4.19 (m, 2H) 5.01 (br, 1H) 6.09-6.72 (m, 1H) 6.81-6.83 (m, 1H) 6.75 (t, J=1.6 Hz, 1H) 7.15 (t, J=7.6 Hz, 1H)

Production Example 1b

Ethyl 2-isopropoxy-3-[3-(2-oxilanylmethoxy)phenyl]propanoate

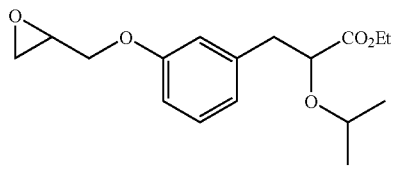

519 mg of Ethyl 3-(3-hydroxyphenyl)-2-isopropoxypropanoate was dissolved in 7 ml of N,N-dimethylformamide, and 250 mg of epichlorohydrin and 400 mg of potassium carbonate were successively added, and the mixture was stirred overnight at 50° C. The reaction mixture was diluted with ethyl acetate and washed with water. The organic layer was dried over anhydrous magnesium sulfate, filtered and the solvent was distilled off. Then, the residue was purified by silica gel column chromatography, to give 465 mg of the title compound in the 5:1 hexane-ethyl acetate fraction.

$^1$H NMR (CDCl$_3$)

δ: 0.96 (d, J=6.4 Hz, 3H) 1.15 (d, J=6.4 Hz, 3H) 1.24 (t, J=7.2 Hz, 3H) 2.75 (dd, J=2.8, 4.8 Hz, 1H) 2.87-2.93 (m, 2H) 2.96 (dd, J=8.8, 13.6 Hz, 1H) 3.34 (dt, J=2.8, 9.6 Hz, 1H) 3.50 (Sept, J=6.0 Hz, 1H) 3.94 (ddd, J=2.0, 5.6, 11.2 Hz, 1H) 4.04 (dd, J=4.8, 8.8 Hz, 1H) 4.15-4.22 (m, 2H) 6.78 (d, J=8.0 Hz, 1H) 6.82 (s, 1H) 6.86 (d, J=7.6 Hz, 1H) 7.19 (t, J=8.0 Hz, 1H)

Example 1c)

3-(3-2-Hydroxy-3-[4-(trifluoromethyl)phenoxy]-propoxyphenyl)-2-isopropoxypropanoic acid

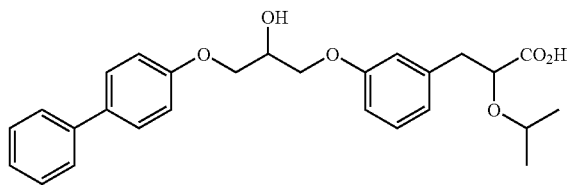

41 mg of Ethyl 2-isopropoxy-3-[3-(2-oxilanylmethoxy)phenyl]propanoate was dissolved in 2 ml of ethanol, 22 mg of 4-hydroxybenzotrifluoride and two drops of triethylamine were added, and the mixture was stirred overnight at 80° C. The reaction solution was evaporated, and the residue was purified by silica gel column chromatography, to give 6 mg of ethyl 3-(3-2-hydroxy-3-[4-(trifluoromethyl)phenoxy]-propoxyphenyl)-2-isopropoxypropanoate in the 4:1 hexane-ethyl acetate fraction. This product was dissolved in 0.4 ml of ethanol, and 0.1 ml of 5N-sodium hydroxide was added, and the mixture was kept still overnight at room temperature. The reaction solution was acidified by adding 1N-hydrochloric acid, and extracted with ethyl acetate. The residue was purified by reverse-phase high performance liquid chromatography, to give 3.15 mg of the title compound.

MS m/e (ESI) 443 (MH$^+$)

Example 2

3-(3-3-[4-(t-Butyl)phenoxy]-2-hydroxypropoxyphenyl)-2-isopropoxypropanoic acid

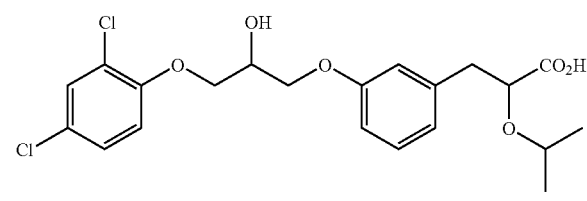

Using 4-t-butylphenol, the title compound was obtained in the same manner as described in Example 1c).

MS m/e (ESI) 431 (MH$^+$)

Example 3

3-(3-3-[4-(Phenyl)phenoxy]-2-hydroxypropoxyphenyl)-2-isopropoxypropanoic acid

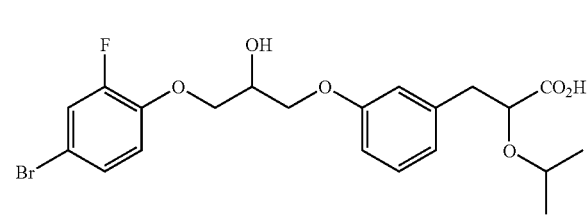

Using 4-hydroxybiphenyl, the title compound was obtained in the same manner as described in Example 1c).

MS m/e (ESI) 451 (MH$^+$)

Example 4

3-(3-3-[4-(2,4-Dichlorophenoxy)]-2-hydroxypropoxyphenyl)-2-isopropoxypropanoic acid Using 2,4-dichlorophenol, the title compound was obtained in the same manner as described in Example 1c).

$^1$H NMR (CDCl$_3$)

δ: 1.03 (d, J=6.0 Hz, 3H) 1.17 (d, J=6.0 Hz, 3H) 2.93 (dd, J=8.0, 14.0 Hz, 1H) 3.11 (dd, J=4.0, 14.0 Hz, 1H) 3.55 (Sept, J=6.0 Hz, 1H) 4.14 (dd, J=4.0, 8.0 Hz, 1H) 4.16-4.23 (m, 4H) 4.42 (Sept, J=6.4 Hz, 1H) 6.82-6.85 (m, 2H) 6.87 (d, J=7.6 Hz, 1H) 6.90 (d, J=8.8 Hz, 1H) 7.19 (dd, J=2.8, 8.8 Hz, 1H) 7.22 (dd, J=7.6, 8.8 Hz, 1H) 7.37 (d, J=2.8 Hz, 1H)

MS m/e (ESI) 443 (MH$^+$)

Example 5

3-(3-3-[4-(4-Bromo-2-fluorophenoxy)]-2-hydroxypropoxyphenyl)-2-isopropoxypropanoic acid Using 4-bromo-2-fluorophenol, the title compound was obtained in the same manner as described in Example 1c).

MS m/e (ESI) 471 (MH$^+$)

Example 6

3-(3-3-[4-(4-Cyanophenoxy)]-2-hydroxypropoxyphenyl)-2-isopropoxypropanoic acid

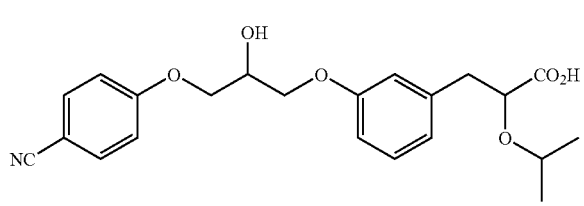

Using 4-hydroxybenzonitrile, the title compound was obtained in the same manner as described in Example 1c).
MS m/e (ESI) 400 (MH$^+$)

Example 7

3-3-[3-(4-Cyano-3-fluorophenoxy)-2-hydroxypropoxy]phenyl-2-isopropoxypropanoic acid

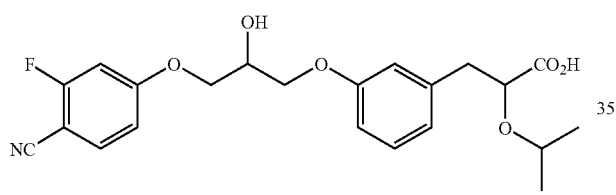

Using 2-fluoro-4-hydroxybenzonitrile, the title compound was obtained in the same manner as described in Example 1c)
MS m/e (ESI) 418 (MH$^+$)

Example 8

3-3-[3-(4-Cyano-2-methoxyphenoxy)-2-hydroxypropoxy]phenyl-2-isopropoxypropanoic acid

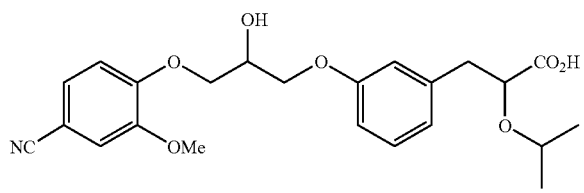

Using 3-methoxy-4-hydroxybenzonitrile, the title compound was obtained in the same manner as described in Example 1c)
MS m/e (ESI) 430 (MH$^+$)

Example 9

3-3-[3-(3-Cyanophenoxy)-2-hydroxypropoxy]phenyl-2-isopropoxypropanoic acid

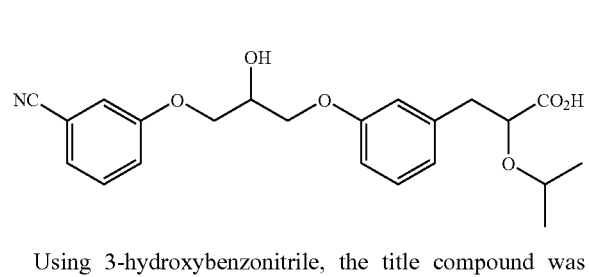

Using 3-hydroxybenzonitrile, the title compound was obtained in the same manner as described in Example 1c).
MS m/e (ESI) 400 (MH$^+$)

Example 10

3-3-[3-(4-Acetoaminophenoxy)-2-hydroxypropoxy]phenyl-2-isopropoxypropanoic acid

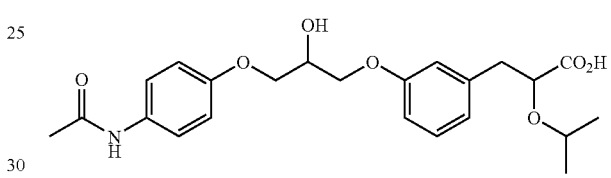

Using 4-acetamidophenol, the title compound was obtained in the same manner as described in Example 1c).
MS m/e (ESI) 432 (MH$^+$)

Example 11

3-3-[3-(3-Acetaminophenoxy)-2-hydroxypropoxy]phenyl-2-isopropoxypropanoic acid

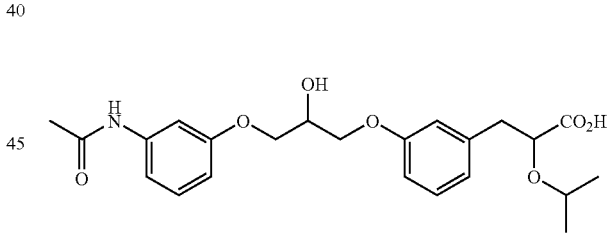

Using 3-acetamidophenol, the title compound was obtained in the same manner as described in Example 1c).
MS m/e (ESI) 432 (MH$^+$)

Example 12

3-3-[3-(3-t-Butoxycarbonylaminophenoxy)-2-hydroxypropoxy]phenyl-2-isopropoxypropanoic acid

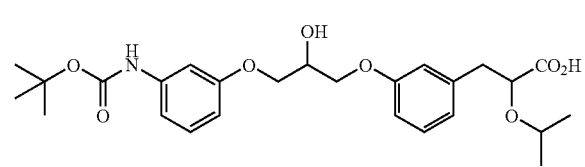

Using 3-t-butoxycarbonylaminophenol, the title compound was obtained in the same manner as described in Example 1c).
MS m/e (ESI) 490 (MH+)

Example 13

3-(3-2-Hydroxy-3-[(2-oxo-1,2,3,4-tetrahydro-5-quinolinyl)oxy]propoxyphenyl)-2-isopropoxypropanoic acid

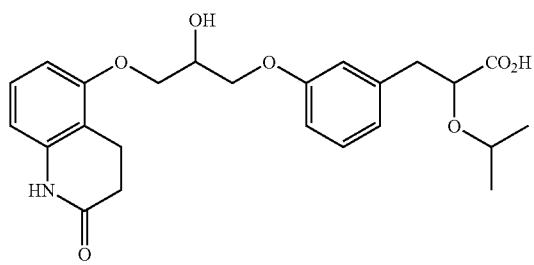

Using 5-hydroxy-1,2,3,4-tetrahydro-2-quinolinone, the title compound was obtained in the same manner as described in Example 1c).
MS m/e (ESI) 444 (MH+)

Example 14

3-(3-2-Hydroxy-3-[4-(tetrahydro-1H-1-pyrrolylcarbonyl)-phenoxy]propoxyphenyl)-2-isopropoxypropanoic acid

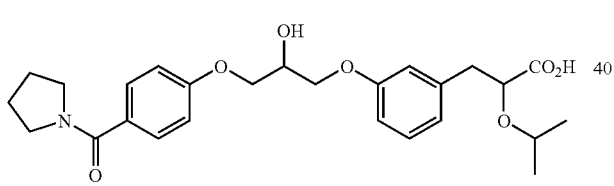

Using (4-hydroxyphenyl)(tetrahydro-1H-1-pyrrolyl) methanone, the title compound was obtained in the same manner as described in Example 1c).
MS m/e (ESI) 472 (MH+)

Example 15

3-(3-2-Hydroxy-3-[4-(1-hydroxy-1-methyl-2-oxopropyl)phenoxy]propoxyphenyl)-2-isopropoxypropanoic acid

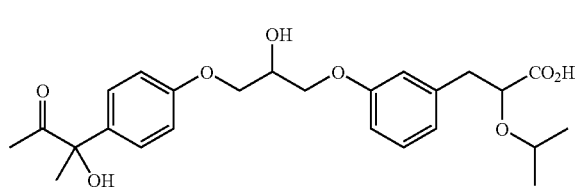

Using 3-hydroxy-3-(4-hydroxyphenyl)-2-butanone, the title compound was obtained in the same manner as described in Example 1c).
MS m/e (ESI) 461 (MH+)

Example 16

3-(3-3-[(7-Cyano-1-naphthyl)oxy]-2-hydroxypropoxyphenyl)-2-isopropoxypropanoic acid

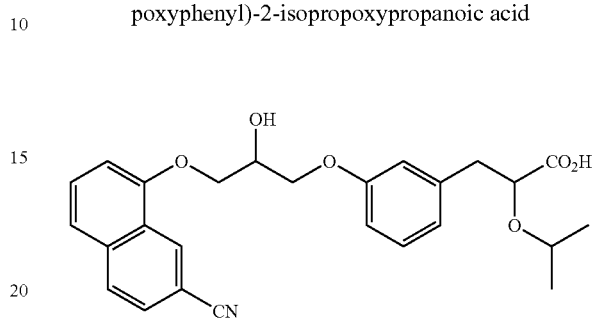

Using 8-hydroxy-2-naphthonitrile, the title compound was obtained in the same manner as described in Example 1c).
MS m/e (ESI) 450 (MH+)

Example 17

3-3-[2-Hydroxy-3-(1,2,3,4-tetrahydro-8-quinolinyloxy)propoxy]phenyl-2-isopropoxypropanoic acid

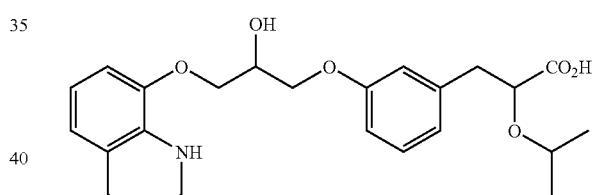

1,2,3,4-Tetrahydro-8-quinolinol, the title compound was obtained in the same manner as described in Example 1c).
MS m/e (ESI) 430 (MH+)

Example 18

3-3-[2-Hydroxy-3-(2-bromo-3-pyridyloxy)propoxy]phenyl-2-isopropoxypropanoic acid

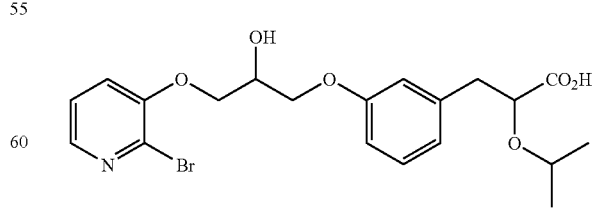

Using 2-bromo-3-pyridinol, the title compound was obtained in the same manner as described in Example 1c).
MS m/e (ESI) 454 (MH+)

Example 19

3-3-[2-Hydroxy-3-(5-methyl-8-quinolinyloxy)propoxy]phenyl-2-isopropoxypropanoic acid

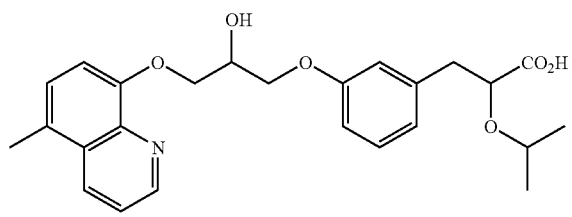

Using 5-methyl-8-quinolinol, the title compound was obtained in the same manner as described in Example 1c).

MS m/e (ESI) 440 (MH$^+$)

Example 20

3-(3-2-Hydroxy-3-[4-(methylsulfanyl)phenoxy]-propoxyphenyl)-2-isopropoxypropanoic acid

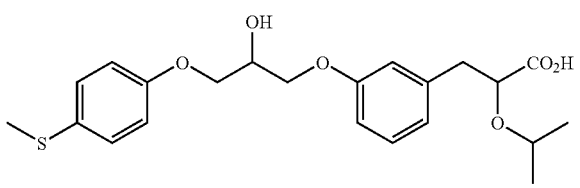

Using 4-methylthiophenol, the title compound was obtained in the same manner as described in Example 1c).

MS m/e (ESI) 421 (MH$^+$)

Example 21

3-(3-2-Hydroxy-3-[4-(methylsulfonyl)phenoxy]-propoxyphenyl)-2-isopropoxypropanoic acid

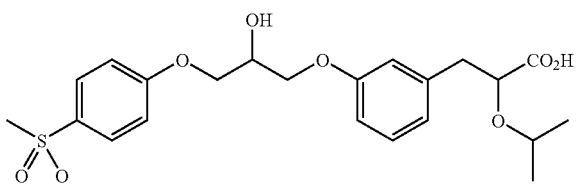

3-(3-2-Hydroxy-3-[4-(methylsulfanyl)phenoxy]-propoxyphenyl)-2-isopropoxypropanoic acid was dissolved in 2 ml of methanol and 0.5 ml of water, and 100 mg of oxone was added. After stirring was continued at room temperature for 2 hours, the reaction mixture was diluted with ethyl acetate and washed with water. The organic layer was evaporated, and the residue was purified by reverse-phase high performance liquid chromatography, to give 1.86 mg of the title compound.

MS m/e (ESI) 453 (MH$^+$)

Example 22

3-[3-(2-Hydroxy-3-[5-(trifluoromethyl)-2-pyridyl]oxypropoxy)phenyl]-2-isopropoxypropanoic acid

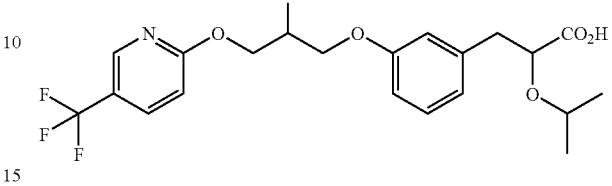

Using 2-hydroxy-5-trifluoromethyl pyridine, the title compound was obtained in the same manner as described in Example 1c).

$^1$H NMR (CDCl$_3$)

δ: 1.05 (d, J=6.0 Hz, 3H) 1.16 (d, J=6.0 Hz, 3H) 2.93 (dd, J=7.6, 14.0 Hz, 1H) 3.11 (dd, J=3.6, 14.4 Hz, 1H) 3.56 (Sept, J=6.0 Hz, 1H) 4.11 (d, J=5.6 Hz, 2H) 4.14 (dd, J=4.0, 8.0 Hz, 1H) 4.36-4.43 (m, 1H) 4.57 (dd, J=6.0, 12.8 Hz, 1H) 6.43 (dd, J=4.0, 11.6 Hz, 1H) 6.80-6.83 (m, 2H) 6.86 (d, J=7.6 Hz, 1H) 6.91 (d, J=8.4 Hz, 1H) 7.19-7.26 (m, 1H) 7.82 (dd, J=2.8, 8.8 Hz, 1H) 8.42 (s, 1H)

MS m/e (ESI) 444 (MH$^+$)

Example 23

3-[3-(2-Hydroxy-3-[5-chloro-2-pyridyl]-oxypropoxy)phenyl]-2-isopropoxypropanoic acid

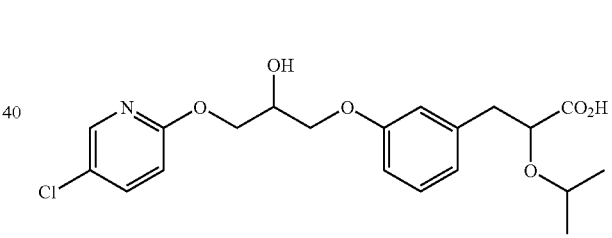

Using 2-hydroxy-5-chloropyridine, the title compound was obtained in the same manner as described in Example 1c).

MS m/e (ESI) 410 (MH$^+$)

Example 24

3-3-[2-Hydroxy-3-(2-quinolyloxy)propoxy]phenyl-2-isopropoxypropanoic acid

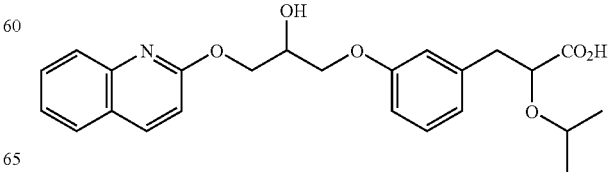

Using 2-hydroxyquinoline, the title compound was obtained in the same manner as described in Example 1c).

$^1$H NMR (CDCl$_3$)

δ: 1.03, 1.04 (each d, J=6.0 Hz and 6.4 Hz, 3H) 1.15 (d, J=6.0 Hz, 3H) 2.91 (dd, J=8.0, 13.6 Hz, 1H) 3.12 (dd, J=4.0, 14.0 Hz, 1H) 3.53 (Sept, J=6.4 Hz, 1H) 4.09-4.12 (m, 2H) 4.14 (dd, J=4.0, 8.4 Hz, 1H) 4.37-4.44 (m, 1H) 4.72 (dd, J=5.6, 12.0 Hz, 1H) 4.78 (ddd, J=1.2, 3.2, 12.8 Hz, 2H) 6.83-6.87 (m, 3H) 6.98-7.01 (m, 1H) 7.22 (dd, J=7.2, 8.4 Hz, 1H) 7.42 (ddd, J=1.2, 6.8, 8.0 Hz, 1H) 7.65 (dt, J=1.6, 8.4 Hz, 1H) 7.75 (d, J=6.8 Hz, 1H) 7.82 (d, J=8.4 Hz, 1H) 8.06 (d, J=8.8 Hz, 1H)

MS m/e (ESI) 426 (MH$^+$)

Example 25

3-3-[3-(2-Bromo-4-cyanophenoxy)-2-hydroxypropoxy]phenyl-2-isopropoxypropanoic acid

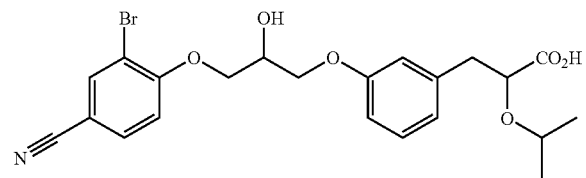

Using 3-bromo-4-hydroxybenzonitrile, the title compound was obtained in the same manner as described in Example 1c).

MS m/e (ESI) 478 (MH$^+$)

Example 26

3-(3-3-[(2,4-Dichlorophenyl)sulfinyl]-2-hydroxypropoxyphenyl)-2-isopropoxypropanoic acid

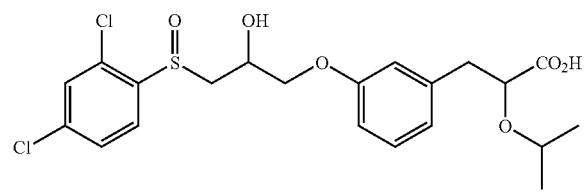

Example 27

3-(3-3-[(2,4-Dichlorophenyl)sulfonyl]-2-hydroxypropoxyphenyl)-2-isopropoxypropanoic acid

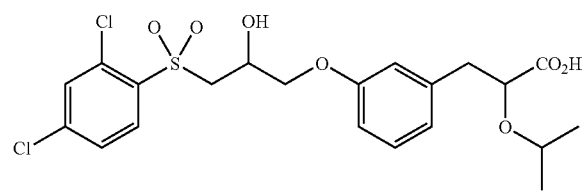

15 mg of 2,4-Dichlorothiophenol and 10 mg of ethyl 2-isopropoxy-3-[3-(2-oxilanylmethoxy)phenyl]propanoate were dissolved in 0.4 ml of ethanol, and 2 drops of triethylamine were added, and the mixture was stirred at 80° C. overnight. The reaction solution was evaporated, to give ethyl 3-(3-2-hydroxy-3-[2,4-dichlorophenoxy]propoxyphenyl)-2-isopropoxypropanoate. This product was dissolved in 2 ml of methanol and 0.5 ml of water, and 100 mg of oxone was added, and the mixture was stirred at room temperature for 2 hours. The reaction mixture was diluted with ethyl acetate and washed with water. The organic layer was concentrated, and the residue was treated with 0.4 ml of ethanol and 0.1 ml of 5N-sodium hydroxide, and the mixture was kept still overnight at room temperature. The reaction solution was acidified by adding 1N-hydrochloric, and then extracted with ethylacetate. The residue was purified by reverse-phase high performance liquid chromatography, to give 5.81 mg of the title compound (Example 26) (MS m/e (ESI) 475 (MH$^+$)), and 3.44 mg of the title compound (Example 27).

$^1$H NMR (CDCl$_3$)

δ: 1.04 (d, J=6.0 Hz, 3H) 1.17 (d, J=6.0 Hz, 3H) 2.92 (dd, J=8.0, 14.4 Hz, 1H) 3.09 (dd, J=4.0, 13.6 Hz, 1H) 3.56 (Sept, J=6.0 Hz, 1H) 3.73 (dd, J=8.0, 14.8 Hz, 1H) 3.79 (dd, J=3.2, 14.4 Hz, 1H) 3.97-4.05 (m, 2H) 4.13 (dd, J=4.0, 7.6 Hz, 1H) 4.52 (dt, J=2.8, 8.0 Hz, 4H) 6.73 (d, J=6.8 Hz, 1H) 6.74 (s, 1H) 6.86 (d, J=6.8 Hz, 1H) 7.19 (dd, J=7.6, 8.8 Hz, 1H) 7.46 (ddd, J=0.8, 2.0, 8.4 Hz, 1H) 7.57 (d, J=2.0 Hz, 1H) 8.07 (d, J=8.8 Hz, 1H)

MS m/e (ESI) 491 (MH$^+$)

Example 28

3-(3-3-[4-t-Butylphenoxy]-2-fluoropropoxyphenyl)-2-isopropoxypropanoic acid

Using 4-t-butyl phenol, the process was conducted in the same manner as described in Example 1c), to give 32 mg of ethyl 3-(3-2-hydroxy-3-[4-t-butylphenoxy]propoxyphenyl)-2-isopropoxypropanoate. 16 mg of this compound was dissolved in 1 ml of dichloromethane and 10 mg of DAST was added. After stirring was continued overnight at room temperature, the reaction mixture was diluted with ethyl acetate and washed with water. The organic layer was evaporated, to give ethyl 3-(3-3-[4-t-butylphenoxy]-2-fluoropropoxyphenyl)-2-isopropoxypropanoate. This product was dissolved in 0.4 ml of ethanol, and 0.1 ml of 5N-sodium hydroxide was added, and the mixture was kept still overnight at room temperature. The reaction solution was acidified by adding 1N-hydrochloric acid, and extracted with ethyl acetate. The residue was purified by reverse-phase high performance liquid chromatography, to give 2.22 mg of the title compound.

MS m/e (ESI) 433 (MH$^+$)

Example 29

3-(3-3-[4-Phenylphenoxy]-2-fluoropropoxyphenyl)-2-isopropoxypropanoic acid

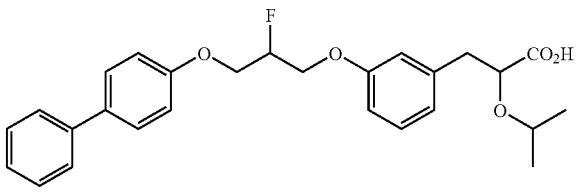

Using 4-hydroxybiphenyl, the title compound was obtained in the same manner as described in Example 28.

MS m/e (ESI) 453 (MH$^+$)

Example 30

3-(3-3-[4-(2,4-Dichlorophenoxy)]-2-fluoropropoxyphenyl)-2-isopropoxypropanoic acid

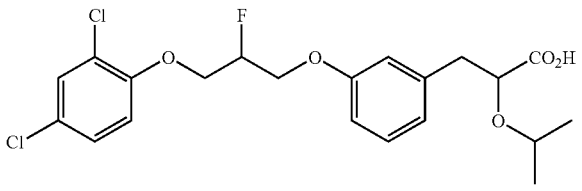

Using 2,4-dichlorophenol, the title compound was obtained in the same manner as described in Example 28.

$^1$H NMR (CDCl$_3$)

δ: 1.03, 1.03 (each d, J=6.0 Hz, 3H) 1.16 (d, J=6.0 Hz, 3H) 2.93 (dd, J=8.0, 13.6 Hz, 1H) 3.12 (dd, J=4.0, 14.0 Hz, 1H) 3.55, 3.55 (each Sept, J=6.0 Hz, 1H) 4.11-4.16 (m, 1H) 4.29-4.41 (m, 4H) 5.18 (dSept, J=4.8, 46.8 Hz, 1H) 6.81-6.85 (m, 2H) 6.98 (d, J=7.6 Hz, 1H) 6.91 (d, J=9.2 Hz, 1H) 7.20 (dd, J=2.4, 8.8 Hz, 1H) 7.23 (dd, J=7.6, 9.2 Hz, 1H) 7.38 (d, J=2.4 Hz, 1H)

MS m/e (ESI) 445 (MH$^+$)

Example 31

3-(3-3-[4-(4-Bromo-2-fluorophenoxy)]-2-fluoropropoxyphenyl)-2-isopropoxypropanoic acid

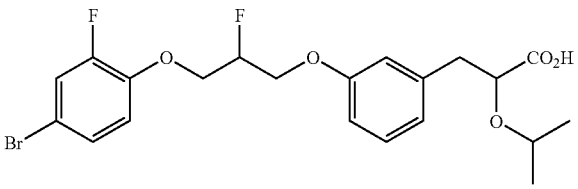

Using 4-bromo-2-fluorophenol, the title compound was obtained in the same manner as described in Example 28.

MS m/e (ESI) 473 (MH$^+$)

Example 32

3-(3-3-[4-(2,4-Dichlorophenoxy)]-2-methoxypropoxyphenyl)-2-isopropoxypropanoic acid

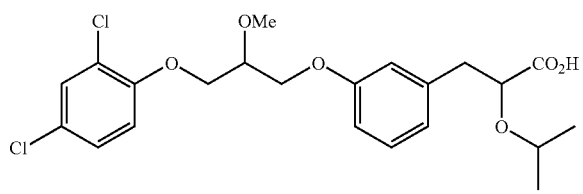

15 mg of Ethyl 3-(3-3-[4-(2,4-dichlorophenoxy)]-2-hydroxypropoxyphenyl)-2-isopropoxypropanoate was dissolved in 0.4 ml of tetrahydrofuran, and 0.1 ml of methyl iodide and 10 mg of sodium hydride were added, and the mixture was stirred overnight at room temperature. To the reaction solution were added ethanol and 0.1 ml of 5N-sodium hydroxide, after stirring was continued at room temperature for 3 hours, the mixture was neutralized with 1N-hydrochloric acid, and extracted with ethyl acetate. The organic layer was evaporated, and the residue was purified by reverse-phase high performance liquid chromatography, to give 4.32 mg of the title compound.

$^1$H NMR (CDCl$_3$)

δ: 1.02 (d, J=6.0 Hz, 3H) 1.15 (d, J=6.0 Hz, 3H) 2.91 (dd, J=7.6, 12.8 Hz, 1H) 3.11 (dd, J=3.2, 13.6 Hz, 1H) 3.53 (dSept, J=3.2, 6.6 Hz, 1H) 3.61 (s, 3H) 3.99 (dd, J=4.8, 10.0 Hz, 1H) 4.09-4.26 (m, 5H) 6.80-6.85 (m, 2H) 6.85 (d, J=8.0 Hz, 1H) 6.89 (d, J=8.8 Hz, 1H) 7.18 (dd, J=2.4, 8.8 Hz, 1H) 7.21 (dd, J=7.2, 9.2 Hz, 1H) 7.36 (d, J=2.4 Hz, 1H)

MS m/e (ESI) 457 (MH$^+$)

Example 33

3-3-[2-(2,4-Dichlorophenoxy)ethoxy]phenyl-2-isopropoxypropanoic acid

Production Example 33a)

2-(2,4-Dichlorophenoxy)-1-ethanol

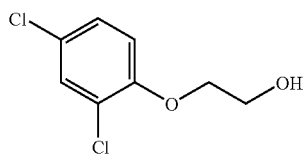

To a solution of 15.0 g of 2,4-dichlorophenoxyacetic acid in tetrahydrofuran (300 ml) was added dropwise 96 ml of 1.0 M borane-tetrahydrofuran complex/tetrahydrofuran solution under ice-cooling over 1.5 hours. The reaction solution was stirred at room temperature for 22 hours. After the reaction solution was concentrated, the residue was diluted with saturated aqueous ammonium chloride and ethyl acetate. The organic layer was washed with saturated ammonium chloride, saturated aqueous sodium hydrogen carbonate (×2) and saturated ammonium chloride, then dried over anhydrous sodium sulfate and concentrated, to give 14 g the title compound as a colorless oil.

¹H-NMR (CDCl₃)

δ: 2.21 (d, J=6.4 Hz, 1H) 3.99 (dt, J=4.4, 6.4 Hz, 2H) 4.12 (t, J=4.4 Hz, 2H) 6.87 (d, J=8.8 Hz, 1H) 7.20 (dd, J=2.4, 8.8 Hz, 1H) 7.37 (d, J=2.4 Hz, 1H)

Production Example 33b 1-(2-Bromoethoxy)-2,4-dichlorobenzene

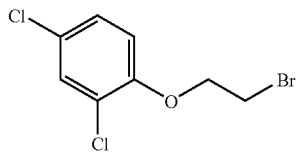

To a solution of 10.0 g of 2-(2,4-dichlorophenoxy)-1-ethanol in 1,2-dimethoxyethane (200 ml) was added dropwise a solution of 14 g of phosphorus tribromide in 1,2-dimethoxyethane (20 ml) under ice-cooling. The reaction solution was stirred at room temperature for 20 hours. After the reaction solution was concentrated, the residue was diluted with water and ethyl acetate. Saturated aqueous sodium hydrogencarbonate was added to the organic layer, and the resulting emulsion formed was subjected to Celite filtration. The filtrate was diluted with diethyl ether and saturated aqueous ammonium chloride. The organic layer was dried over anhydrous magnesium sulfate and concentrated. The residue was purified by silica gel column chromatography, to give 6.15 g of the title compound as a pale yellow oil.

¹H-NMR (CDCl₃)

δ: 3.67 (t, J=6.4 Hz, 2H) 4.32 (t, J=6.4 Hz, 2H) 6.87 (d, J=8.8 Hz, 1H) 7.19 (dd, J=2.6, 8.8 Hz, 1H) 7.39 (d, J=2.6 Hz, 1H)

Example 33c 3-3-[2-(2,4-Dichlorophenoxy)ethoxy]phenyl-2-isopropoxypropanoic acid

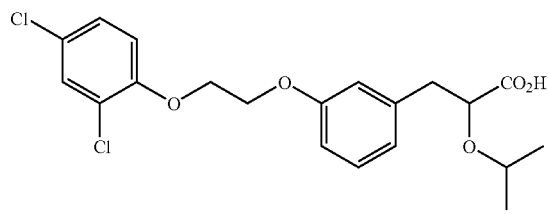

140 mg of 1-(2-Bromoethoxy)-2,4-dichlorobenzene, 100 mg of ethyl 3-(3-hydroxyphenyl)-2-isopropoxypropanoate and 110 mg of potassium carbonate were dissolved in N,N-dimethylformamide, and the mixture was stirred overnight at 60° C. The reaction solution was diluted with saturated aqueous ammonium chloride and ethyl acetate. The organic layer was washed with saturated ammonium chloride, saturated aqueous sodium hydrogen carbonate (×2) and saturated ammonium chloride, dried over anhydrous sodium sulfate and concentrated. The residue was dissolved in 4 ml of methanol, and 1 ml of 5N-sodium hydroxide was added thereto, and the mixture was stirred at room temperature for 2 hours. The reaction mixture was neutralized with 1N-hydrochloric acid and extracted with ethyl acetate. The organic layer was dried over anhydrous sodium sulfate and concentrated. The residue was purified by silica gel column chromatography, to give 83.6 mg of the title compound in the 4:1→1:2 hexane-ethyl acetate fraction.

¹H-NMR (CDCl₃)

δ: 1.02 (d, J=6.0 Hz, 3H) 1.16 (d, J=6.0 Hz, 3H) 2.93 (dd, J=8.2, 13.8 Hz, 1H) 3.12 (dd, J=3.8, 13.8 Hz, 1H) 3.55 (sept, J=6.0 Hz, 1H) 4.14 (dd, J=3.8, 8.2 Hz, 1H) 4.33-4.38 (m, 4H) 6.81-6.89 (m, 3H) 6.95 (d, J=8.8 Hz, 1H) 7.18-7.25 (m, 2H) 7.37 (d, J=2.8 Hz, 1H)

MS m/e (ESI) 435 (MNa⁺)

Example 34

3-3-[2-(4-Trifluoromethylphenoxy)ethoxy]phenyl-2-isopropoxypropanoic acid

Production Example 34a 1-(2-Bromoethoxy)-4-trifluoromethylbenzene

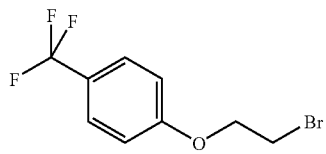

A suspension of 5.0 g of 4-hydroxybenzotrifluoride, 17.4 g of 1,2-dibromoethane and 2.6 g potassium carbonate in acetone (100 ml) was heated under reflux for 3 days. The reaction solution was diluted with water and ethyl acetate. The organic layer was washed with saturated aqueous sodium hydrogen carbonate and saturated ammonium chloride (×2), dried over anhydrous sodium sulfate and concentrated. The residue was purified by silica gel column chromatography to give 1.78 g of the title compound as a colorless oil.

¹H-NMR (CDCl₃)

δ: 3.66 (t, J=6.4 Hz, 2H) 4.34 (t, J=6.4 Hz, 2H) 6.98 (d, J=8.4 Hz, 2H) 7.56 (d, J=8.4 Hz, 1H)

Example 34b 3-3-[2-(4-Trifluoromethylphenoxy)ethoxy]phenyl-2-isopropoxypropanoic acid

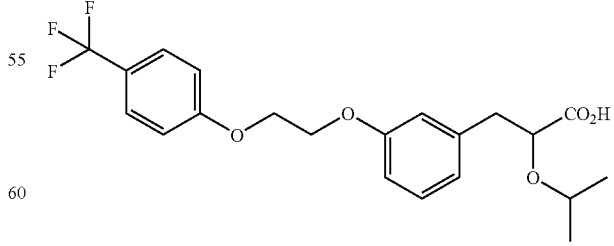

Using 1-(2-bromoethoxy)-4-trifluoromethylbenzene, the title compound was obtained in the same manner as described in Example 33c)

MS m/e (ESI) 435 (MNa⁺).

Example 35

3-3-[2-(4-Cyclohexylphenoxy)ethoxy]phenyl-2-isopropoxypropanoic acid

Production Example 35a

1-[2-(Benzyloxy)ethoxy]-4-cyclohexylbenzene

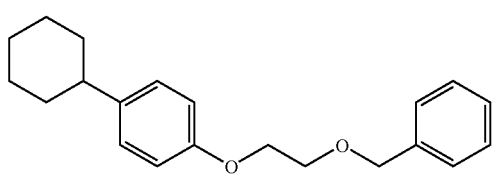

A suspension of 2.5 g of 4-cyclohexylphenol, 3.0 g of benzyl 2-bromoethyl ether and 2.4 g of potassium carbonate in N,N-dimethylformamide (50 ml) was stirred at 60° C. for 23 hours. The reaction solution was diluted with water and ethyl acetate. The organic layer was washed with saturated aqueous potassium carbonate and saturated ammonium chloride (×2), dried over anhydrous sodium sulfate and concentrated. The residue was purified by silica gel column chromatography, to give 3.9 g of the title compound as a colorless oil.

$^1$H-NMR (CDCl$_3$)

δ: 1.20-1.44 (m, 5H) 1.70-1.90 (m, 5H) 2.39-2.48 (m, 1H) 3.82 (t, J=4.8 Hz, 2H) 4.13 (t, J=4.8 Hz, 2H) 4.63 (s, 2H) 6.83-6.88 (m, 2H) 7.09-7.14 (m, 2H) 7.26-7.38 (m, 5H)

Production Example 35b 1-(2-Hydroxyethoxy)-4-cyclohexylbenzene

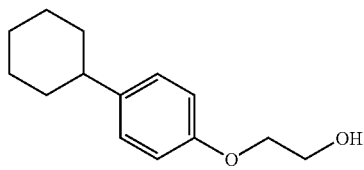

3.2 g of 1-[2-(Benzyloxy)ethoxy]-4-cyclohexylbenzene was dissolved in 100 ml of ethanol, and 300 mg of 20% palladium hydroxide was added, and the mixture was stirred at room temperature under hydrogen atmosphere for 25 hours. The catalyst was filtered off and washed with ethyl acetate. The filtrate was evaporated, and the residue was subjected to azeotropy with toluene (×2), to give 2.34 g of the title compound as a colorless solid.

$^1$H-NMR (CDCl$_3$)

δ: 1.17-1.44 (m, 5H) 1.70-1.90 (m, 5H) 2.40-2.50 (m, 1H) 3.62 (t, J=6.4 Hz, 2H) 4.27 (t, J=6.4 Hz, 2H) 6.82-6.87 (m, 2H) 7.11-7.15 (m, 2H)

Production Example 35c 1-(2-Bromoethoxy)-4-cyclohexylbenzene

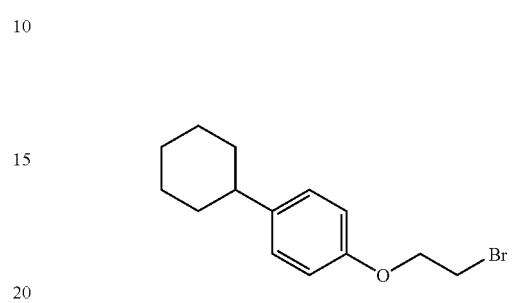

The compound of Production example 35c) was synthesized in the same manner as described in Production example 33b).

$^1$H-NMR (CDCl$_3$)

δ: 1.17-1.44 (m, 5H) 1.70-1.90 (m, 5H) 2.40-2.50 (m, 1H) 3.62 (t, J=6.4 Hz, 2H) 4.27 (t, J=6.4 Hz, 2H) 6.82-6.87 (m, 2H) 7.11-7.15 (m, 2H)

Example 35d 3-3-[2-(4-Cyclohexylphenoxy)ethoxy]phenyl-2-isopropoxypropanoic acid

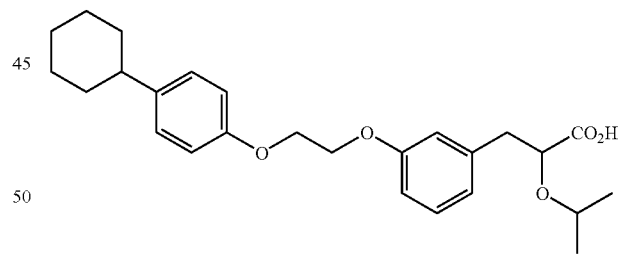

Using 1-(2-bromoethoxy)-4-cyclohexylbenzene, the title compound was obtained in the same manner as described in Example 33c).

$^1$H-NMR (CDCl$_3$)

δ: 1.02 (d, J=6.0 Hz, 3H) 1.16 (d, J=6.0 Hz, 3H) 1.19-1.45 (m, 5H) 1.70-1.90 (m, 5H) 2.41-2.50 (m, 1H) 2.92 (dd, J=8.4, 14.0 Hz, 1H) 3.12 (dd, J=4.0, 14.0 Hz, 1H) 3.54 (sept, J=6.0 Hz, 1H) 4.13 (dd, J=4.0, 8.4 Hz, 1H) 4.30 (brs, 4H) 6.82-6.91 (m, 4H) 7.11-7.16 (m, 2H) 7.19-7.24 (m, 2H)

MS m/e (ESI) 449 (MNa$^+$)

Example 36

3-3-[2-(4-Cyclopentylphenoxy)ethoxy]phenyl-2-isopropoxypropanoic acid

Production Example 36a 1-(2-Bromoethoxy)-4-cyclopentylbenzene

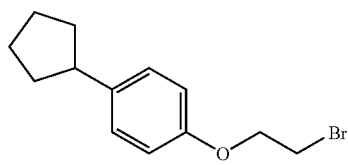

Using cyclopentylphenol, the title compound was obtained in the same manner as described in Production examples 35a), 35b) and 35c).
$^1$H-NMR (CDCl$_3$)
δ: 1.48-1.84 (m, 6H) 2.00-2.08 (m, 2H) 2.90-2.98 (m, 1H) 3.63 (t, J=6.4 Hz, 2H) 4.27 (t, J=6.4 Hz, 2H) 6.83-6.86 (m, 2H) 7.14-7.18 (m, 2H)

Example 36b 3-3-[2-(4-Cyclohexylphenoxy)ethoxy]phenyl-2-isopropoxypropanoic acid

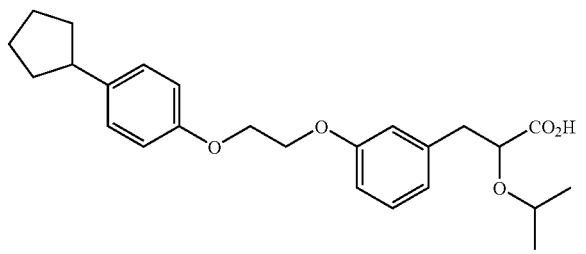

Using 1-(2-bromoethoxy)-4-cyclopentylbenzene, the title compound was obtained in the same manner as described in Example 33c).
MS m/e (ESI) 435 (MNa$^+$)

Example 37

3-3-[2-(4-t-Butylphenoxy)ethoxy]phenyl-2-isopropoxypropanoic acid

Production Example 37a 1-(2-Bromoethoxy)-4-t-butylbenzene

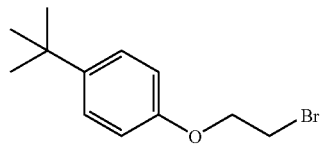

Using 4-t-butylphenol, the title compound was obtained in the same manner as described in Production examples 35a), 35b) and 35c).
$^1$H-NMR (CDCl$_3$)
δ: 1.31 (s, 9H) 3.64 (t, J=6.4 Hz, 2H) 4.29 (t, J=6.4 Hz, 2H) 6.84-6.89 (m, 2H) 7.30-7.34 (m, 2H)

Example 37b 3-3-[2-(4-t-Butylphenoxy)ethoxy]phenyl-2-isopropoxypropanoic acid

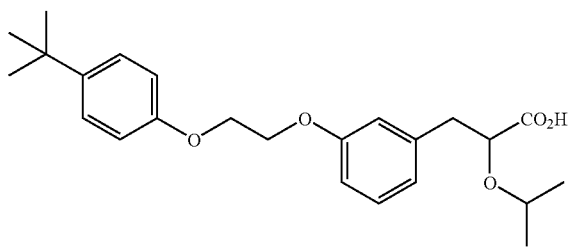

Using 1-(2-bromoethoxy)-4-t-butylbenzene, the title compound was obtained in the same manner as described in Example 33c).
MS m/e (ESI) 423 (MNa$^+$)

Example 38

3-3-[2-(4-Isopropylphenoxy)ethoxy]phenyl-2-isopropoxypropanoic acid

Production Example 38a 1-(2-Bromoethoxy)-4-isopropylbenzene

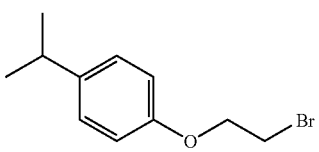

Using 4-isopropylphenol, the title compound was obtained in the same manner as described in Production examples 35a) 35b) and 35c).
$^1$H-NMR (CDCl$_3$)
δ: 1.23 (d, J=6.8 Hz, 6H) 2.87 (sept, J=6.8 Hz, 1H) 3.63 (t, J=6.4 Hz, 2H) 4.27 (t, J=6.4 Hz, 2H) 6.83-6.88 (m, 2H) 7.13-7.17 (m, 2H)

Example 38b 3-3-[2-(4-Isopropylphenoxy)ethoxy]phenyl-2-isopropoxypropanoic acid

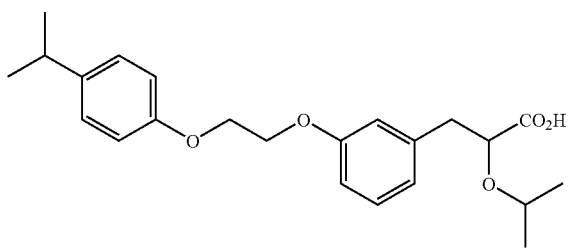

Using 1-(2-bromoethoxy)-4-isopropylbenzene, the title compound was obtained in the same manner as described in Example 33c).

MS m/e (ESI) 409 (MNa+)

Example 39

3-3-[2-(Phenoxy)ethoxy]phenyl-2-isopropoxypropanoic acid

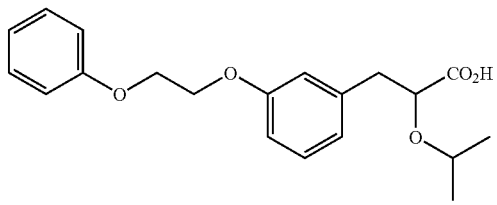

Using 2-(bromoethoxy)benzene, the title compound was obtained in the same manner as described in Example 33c).

MS m/e (ESI) 367 (MNa+)

Example 40

3-3-[2-(4-Fluorophenoxy)ethoxy]phenyl-2-isopropoxypropanoic acid

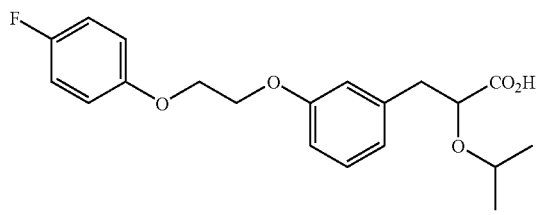

Using 1-(2-bromoethoxy)-4-fluorobenzene, the title compound was obtained in the same manner as described in Example 33c).

MS m/e (ESI) 385 (MNa+)

Example 41

3-3-[2-(4-Benzyloxy)ethoxy]phenyl-2-isopropoxypropanoic acid

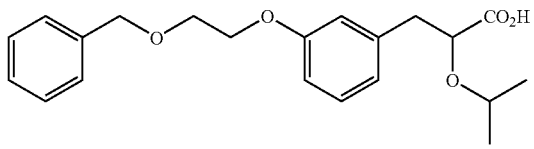

Using 1-[(2-bromoethoxy)methyl]benzene, the title compound was obtained in the same manner as described in Example 33c).

MS m/e (ESI) 381 (MNa+)

Example 42

2-Isopropoxy-3-[3-(3-phenylpropoxy)phenyl]propanoic acid

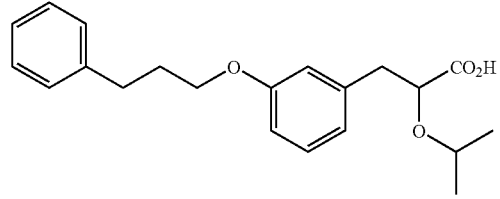

Using 3-phenylpropylbromide, the title compound was obtained in the same manner as described in Example 33c).

MS m/e (ESI) 365 (MNa+)

Example 43

2-Isopropoxy-3-[3-(3-phenoxypropoxy)phenyl]propanoic acid

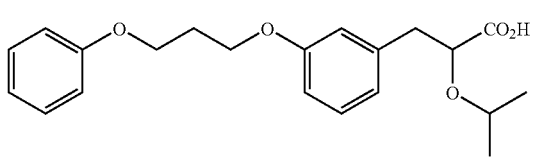

Using 1-(3-bromopropoxy)benzene, the title compound was obtained in the same manner as described in Example 33c).

$^1$H-NMR (CDCl$_3$)

δ: 1.01 (d, J=6.0 Hz, 3H) 1.15 (d, J=6.0 Hz, 3H) 2.26 (quint, J=6.0 Hz, 2H) 2.90 (dd, J=8.8, 13.8 Hz, 1H) 3.10 (dd, J=3.6, 13.8 Hz, 1H) 3.52 (sept, J=6.0 Hz, 1H) 4.10-4.19 (m, 5H) 6.89-6.96 (m, 3H) 6.78-6.85 (m, 3H) 7.20 (t, J=8.2 Hz, 1H) 7.25-7.31 (m, 2H)

MS m/e (ESI) 381 (MNa+)

Example 44

3-{3-[3-(2,4-Dichlorophenoxy)propoxy]phenyl}-2-isopropoxypropanoic acid

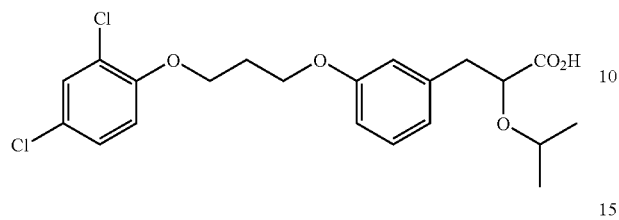

Using 1-(3-bromopropoxy)-2,4-dichlorobenzene, the title compound was obtained in the same manner as described in Example 33c).
MS m/e (ESI) 449 (MNa+)

Example 45

3-{3-[3-(4-Acetyl-3-hydroxy-2-propylphenoxy)propoxy]phenyl}-2-isopropoxypropanoic acid

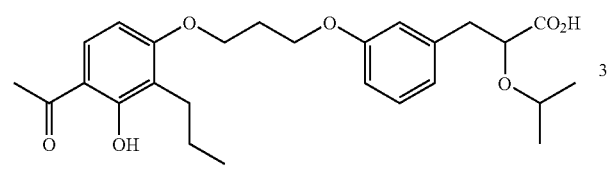

Using 1-[4-(3-bromopropoxy)-2-hydroxy-3-propylphenyl]-1-ethanone, the title compound was obtained in the same manner as described in Example 33c).
MS m/e (ESI) 481 (MNa+)

Example 46

3-3-[2-(2,4-Dichlorophenoxy)ethoxy]phenyl-2-ethoxypropanoic acid

Production Example 46a

Ethyl (E,Z)-3-[3-(benzyloxy)phenyl]-2-ethoxy-2-propenoate

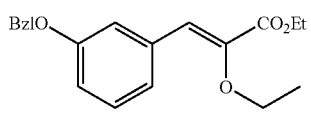

3.6 g of Ethyl 2-(diethoxyphosphoryl)-2-ethoxyacetate was dissolved in tetrahydrofuran, and 520 mg of 60% sodium hydride was added, and the mixture was stirred for 10 minutes. A solution of 2.5 g of 3-benzyloxybenzaldehyde in 10 ml of N,N-dimethylformamide was added and the mixture was stirred overnight at room temperature. The reaction mixture was diluted with ethyl acetate. Saturated aqueous sodium hydrogencarbonate was added to the organic layer, and the resulting emulsion formed was subjected to Celite filtration. The filtrate was diluted with diethyl ether and saturated aqueous ammonium chloride. The organic layer was dried over anhydrous magnesium sulfate and concentrated, to give 4.5 g of the title compound.

Production Example 46b

Ethyl 2-ethoxy-3-(3-hydroxyphenyl)propanoate

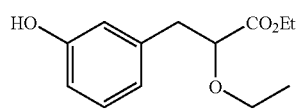

4.5 g of Ethyl (E,Z)-3-[3-(benzyloxy)phenyl]-2-ethoxy-2-propenoate was dissolved in ethyl acetate, and 450 mg of 10% palladium carbon was added thereto and the mixture was stirred overnight at room temperature under hydrogen atmosphere. The reaction solution was filtered through Celite and the filtrate was evaporated. The residue was purified by silica gel column chromatography, to give 3.7 g of the title compound in the 5:1 hexane-ethyl acetate fraction.

δ: 1.16 (t, J=7.2 Hz, 3H) 1.23 (t, J=7.2 Hz, 3H) 2.95-2.98 (m, 2H) 3.37 (dq, J=7.2, 9.2 Hz, 1H) 3.61 (dq, J=7.2, 9.2 Hz, 1H) 4.02 (dd, J=5.6, 7.6 Hz, 1H) 4.18 (q, J=7.2 Hz, 2H) 5.14 (s, 1H) 6.69-6.73 (m, 1H) 6.74-6.76 (m, 1H) 6.79-6.82 (m, 1H) 7.15 (t, J=8.0 Hz, 1H)

Example 46c 3-3-[2-(2,4-Dichlorophenoxy)ethoxy]phenyl-2-ethoxypropanoic acid

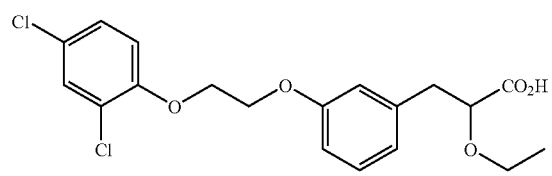

Using 1-(2-bromoethoxy)-2,4-dichlorobenzene and ethyl 2-ethoxy-3-(3-hydroxyphenyl)propanoate, the title compound was obtained in the same manner as described in Example 33c).
MS m/e (ESI) 421 (MNa+)

Example 47

3-3-[2-(4-Trifluoromethylphenoxy)ethoxy]phenyl-2-ethoxypropanoic acid

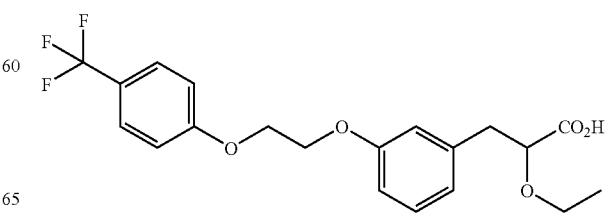

Using 1-(2-bromoethoxy)-4-trifluoromethylbenzene, the title compound was obtained in the same manner as described in Example 46c).
MS m/e (ESI) 421 (MNa⁺)

Example 48

3-3-[2-(4-Cyclohexylphenoxy)ethoxy]phenyl-2-ethoxypropanoic acid

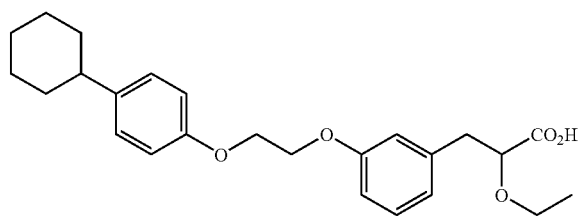

Using 1-(2-bromoethoxy)-4-cyclohexylbenzene, the title compound was obtained in the same manner as described in Example 46c).
MS m/e (ESI) 435 (MNa⁺)

Example 49

3-3-[2-(4-Cyclopentylphenoxy)ethoxy]phenyl-2-ethoxypropanoic acid

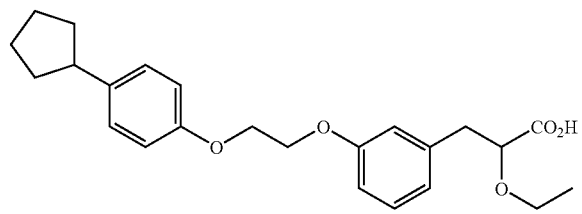

Using 1-(2-bromoethoxy)-4-cyclopentylbenzene, the title compound was obtained in the same manner as described in Example 46c).
MS m/e (ESI) 421 (MNa⁺)

Example 50

3-3-[2-(4-t-Butylphenoxy)ethoxy]phenyl-2-ethoxypropanoic acid

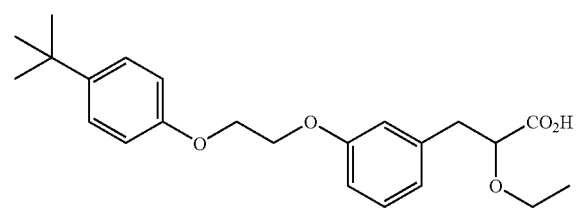

Using 1-(2-bromoethoxy)-4-t-butylbenzene, the title compound was obtained in the same manner as described in Example 46c).
MS m/e (ESI) 409 (MNa⁺)

Example 51

3-3-[2-(4-Isopropylphenoxy)ethoxy]phenyl-2-ethoxypropanoic acid

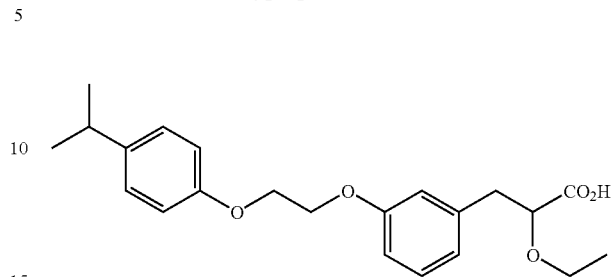

Using 1-(2-bromoethoxy)-4-isopropylbenzene, the title compound was obtained in the same manner as described in Example 46c).
MS m/e (ESI) 395 (MNa⁺)

Example 52

3-{3-[2-(2,4-Dichlorophenoxy)ethoxy]-4-methoxyphenyl}-2-isopropoxypropanoic acid Production Example 52a Ethyl 3-(3-hydroxy-4-methoxyphenyl)-2-isopropoxypropanoate

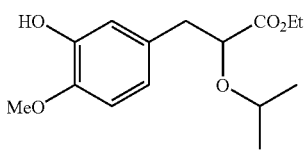

Using 3-benzyloxy-4-methoxybenzaldehyde and ethyl 2-(diethoxyphosphoryl)-2-isopropoxyacetate, the title compound was obtained in the same manner as described in Example 46b).
δ: 0.99 (d, J=6.0 Hz, 3H) 1.16 (d, J=6.0 Hz, 3H) 1.23 (t, J=7.2 Hz, 3H) 2.85 (dd, J=8.4, 14.0 Hz, 1H) 2.91 (dd, J=4.8, 14.0 Hz, 1H) 3.45-3.55 (m, 1H) 3.87 (s, 3H) 4.01 (dd, J=4.8, 8.4 Hz, 1H) 4.14-4.20 (m, 2H) 5.55 (s, 1H) 6.70-6.78 (m, 2H) 6.84 (d, J=2.0 Hz, 1H)

Example 52b

3-{3-[2-(2,4-Dichlorophenoxy)ethoxy]-4-methoxyphenyl}-2-isopropoxypropanoic acid

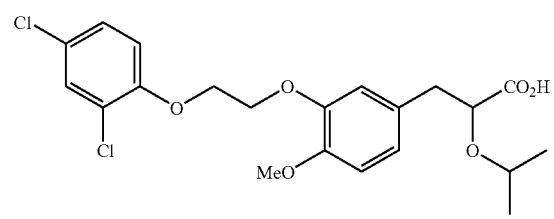

Using 1-(2-bromoethoxy)-2,4-dichlorobenzene and ethyl 3-(3-hydroxy-4-methoxyphenyl)-2-isopropoxypropanoate, the title compound was obtained in the same manner as described in Example 33c).

$^{1}$H-NMR (CDCl$_{3}$)

δ: 1.04 (d, J=6.0 Hz, 3H) 1.16 (d, J=6.0 Hz, 3H) 2.89 (dd, J=8.0, 14.0 Hz, 1H) 3.07 (dd, J=4.0, 14.0 Hz, 1H) 3.56 (sept, J=6.0 Hz, 1H) 3.84 (s, 3H) 4.13 (dd, J=4.0, 8.0 Hz, 1H) 4.37-4.44 (m, 4H) 6.83 (s, 1H) 6.83 (d, J=1.2 Hz, 1H) 6.91 (d, J=1.2 Hz, 1H) 6.98 (d, J=8.6 Hz, 1H) 7.18 (dd, J=2.6, 8.6 Hz, 1H) 7.37 (d, J=2.6 Hz, 1H)

MS m/e (ESI) 465 (MNa$^{+}$)

Example 53

3-{3-[2-(4-Trifluoromethylphenoxy)ethoxy]-4-methoxyphenyl}-2-isopropoxypropanoic acid

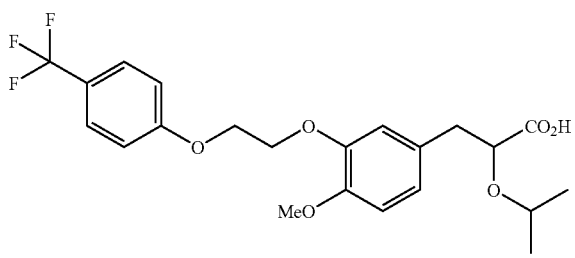

Using 1-(2-bromoethoxy)-4-trifluoromethylbenzene, the title compound was obtained in the same manner as described in Example 52b).

MS m/e (ESI) 465 (MNa$^{+}$)

Example 54

3-{3-[2-(4-Cyclohexylphenoxy)ethoxy]-4-methoxyphenyl}-2-isopropoxypropanoic acid

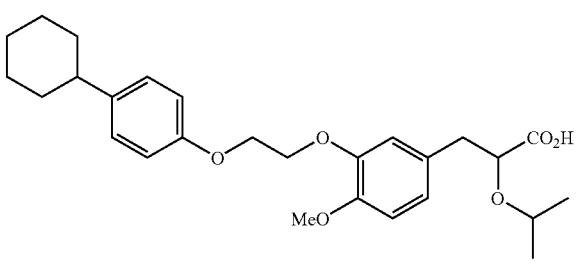

Using 1-(2-bromoethoxy)-4-cyclohexylbenzene, the title compound was obtained in the same manner as described in Example 52b).

MS m/e (ESI) 479 (MNa$^{+}$)

Example 55

3-{3-[2-(4-Cyclopentylphenoxy)ethoxy]-4-methoxyphenyl}-2-isopropoxypropanoic acid

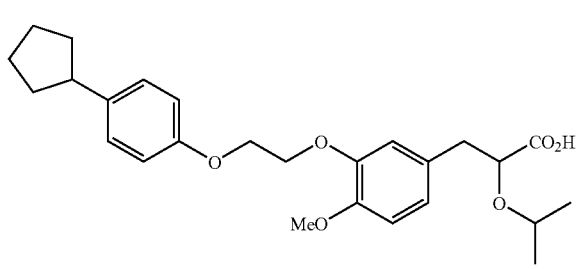

Using 1-(2-bromoethoxy)-4-cyclopentylbenzene, the title compound was obtained in the same manner as described in Example 52b).

MS m/e (ESI) 465 (MNa$^{+}$)

Example 56

3-{3-[2-(4-t-Butylphenoxy)ethoxy]-4-methoxyphenyl}-2-isopropoxypropanoic acid

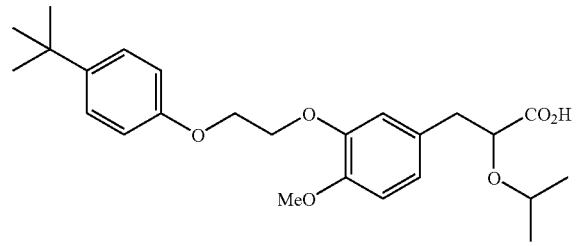

Using 1-(2-bromoethoxy)-4-t-butylbenzene, the title compound was obtained in the same manner as described in Example 52b).

MS m/e (ESI) 453 (MNa$^{+}$)

Example 57

3-{3-[2-(4-Isopropylphenoxy)ethoxy]-4-methoxyphenyl}-2-isopropoxypropanoic acid

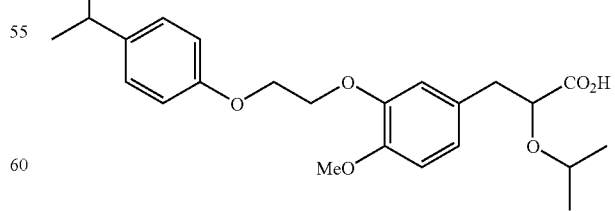

Using 1-(2-bromoethoxy)-4-isopropylbenzene, the title compound was obtained in the same manner as described in Example 52b)

MS m/e (ESI) 439 (MNa$^{+}$).

Example 58

3-{3-[2-(2,4-Dichlorophenoxy)ethoxy]phenyl}-2-methylpropanoic acid

Production Example 58a

Ethyl 3-(3-hydroxyphenyl)-2-methylpropanoate

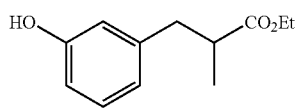

Using 3-benzyloxybenzaldehyde and ethyl 2-(diethoxyphosphoryl)-2-methylacetate, the title compound was obtained in the same manner as described in Production examples 46a) and 46b).
$^1$H-NMR (CDCl$_3$)
δ: 1.15 (d, J=6.8 Hz, 3H) 1.20 (t, J=7.2 Hz, 3H) 2.62 (dd, J=7.6, 13.2 Hz, 1H) 2.67-2.76 (m, 1H) 2.96 (dd, J=7.2, 13.2 Hz, 1H) 4.10 (q, J=7.2 Hz, 2H) 5.28 (s, 1H) 6.66-6.70 (m, 2H) 6.72-6.75 (m, 1H) 7.14 (t, J=6.8 Hz, 1H)

Example 58b

3-{3-[2-(2,4-Dichlorophenoxy)ethoxy]phenyl}-2-methylpropanoic acid

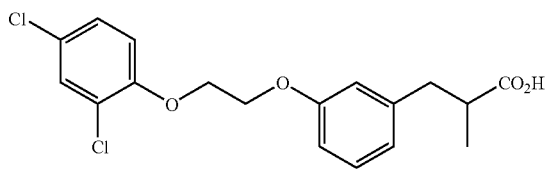

Using 1-(2-bromoethoxy)-2,4-dichlorobenzene and ethyl 3-(3-hydroxy-4-methoxyphenyl)-2-methylpropanoate, the title compound was obtained in the same manner as described in Example 33c).
MS m/e (ESI) 391 (MNa$^+$)

Example 59

3-{3-[2-(4-Trifluoromethylphenoxy)ethoxy]-phenyl}-2-methylpropanoic acid

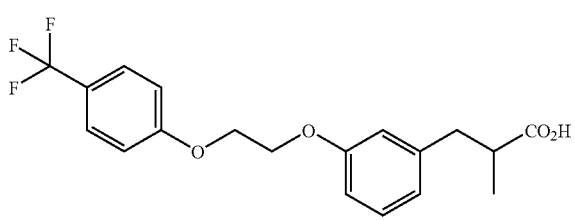

Using 1-(2-bromoethoxy)-4-trifluoromethylbenzene, the title compound was obtained in the same manner as described in Example 58b).
$^1$H-NMR (CDCl$_3$)
δ: 1.18 (d, J=6.8 Hz, 3H) 2.64 (dd, J=8.0, 13.6 Hz, 1H) 2.72-2.81 (m, 1H) 3.05 (dd, J=6.8, 13.6 Hz, 1H) 4.30-4.37 (m, 4H) 6.77-6.84 (m, 3H) 6.99-7.04 (m, 2H) 7.19-7.24 (m, 1H) 7.53-7.58 (m, 2H)
MS m/e (ESI) 391 (MNa$^+$)

Example 60

3-{3-[2-(4-Cyclohexylphenoxy)ethoxy]phenyl}-2-methylpropanoic acid

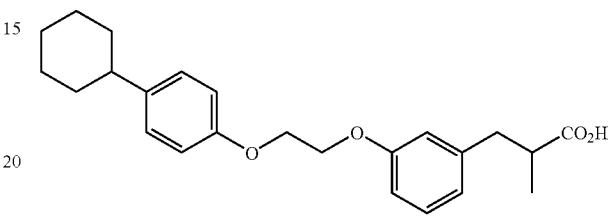

Using 1-(2-bromoethoxy)-4-cyclohexylbenzene, the title compound was obtained in the same manner as described in Example 58b).
MS m/e (ESI) 405 (MNa$^+$)

Example 61

3-{3-[2-(4-Cyclopentylphenoxy)ethoxy]phenyl}-2-methylpropanoic acid

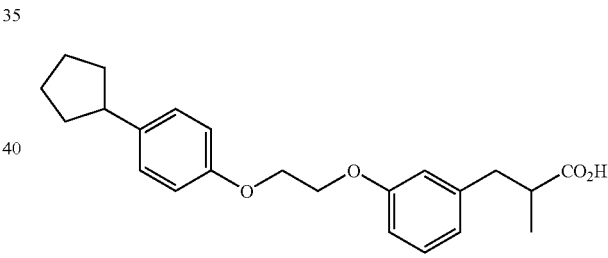

Using 1-(2-bromoethoxy)-4-cyclopentylbenzene, the title compound was obtained in the same manner as described in Example 58b).
MS m/e (ESI) 391 (MNa$^+$)

Example 62

3-{3-[2-(4-t-Butylphenoxy)ethoxy]phenyl}-2-methylpropanoic acid

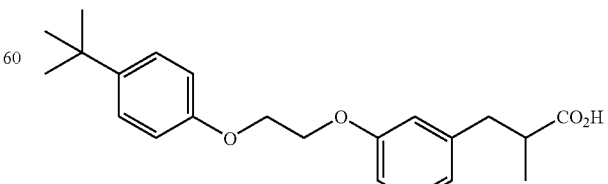

Using 1-(2-bromoethoxy)-4-t-butylbenzene, the title compound was obtained in the same manner as described in Example 58b).
MS m/e (ESI) 379 (MNa⁺)

Example 63

3-{3-[2-(4-Isopropylphenoxy)ethoxy]phenyl}-2-methylpropanoic acid

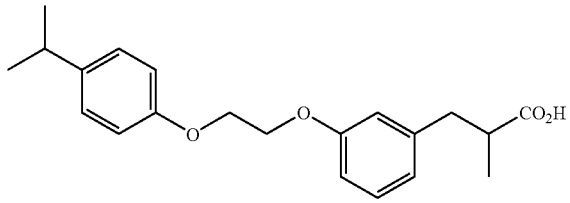

Using 1-(2-bromoethoxy)-4-isopropylbenzene, the title compound was obtained in the same manner as described in Example 58b).
MS m/e (ESI) 365 (MNa⁺)

Example 64

3-{3-[2-(2,4-Dichlorophenoxy)ethoxy]phenyl}-2-ethylpropanoic acid

Production Example 64a

Ethyl 3-(3-hydroxyphenyl)-2-ethylpropanoate

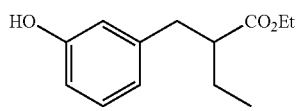

Using 3-benzyloxybenzaldehyde, ethyl 2-(diethoxyphosphoryl)-2-ethylacetate, the title compound was obtained in the same manner as described in Production examples 46a) and 46b).
¹H-NMR (CDCl₃)
δ: 0.92 (t, J=7.2 Hz, 3H) 1.16 (t, J=7.2 Hz, 3H) 1.50-1.70 (m, 2H) 2.53-2.60 (m, 1H) 2.70 (dd, J=6.4, 13.6 Hz, 1H) 2.87 (dd, J=8.6, 13.6 Hz, 1H) 4.08 (q, J=7.2 Hz, 2H) 5.26 (s, 1H) 6.64-6.69 (m, 2H) 6.71-6.75 (m, 1H) 7.14 (t, J=7.8 Hz, 1H)

Example 64b

3-{3-[2-(2,4-Dichlorophenoxy)ethoxy]phenyl}-2-ethylpropanoic acid

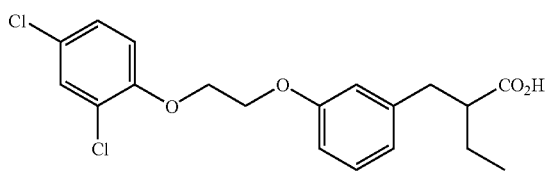

Using 1-(2-bromoethoxy)-2,4-dichlorobenzene and ethyl 3-(3-hydroxy-4-methoxyphenyl)-2-ethylpropanoate, the title compound was obtained in the same manner as described in Example 33c).
MS m/e (ESI) 405 (MNa⁺)

Example 65

3-{3-[2-(4-Trifluoromethylphenoxy)ethoxy]-phenyl}-2-ethylpropanoic acid

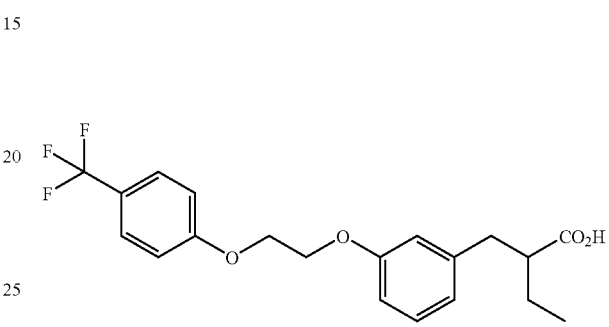

Using 1-(2-bromoethoxy)-4-trifluoromethylbenzene, the title compound was obtained in the same manner as described in Example 64b).
¹H-NMR (CDCl₃)
δ: 0.95 (t, J=7.2 Hz, 3H) 1.53-1.72 (m, 2H) 2.57-2.65 (m, 1H) 2.73 (dd, J=6.8, 13.6 Hz, 1H) 2.96 (dd, J=8.0, 13.6 Hz, 1H) 4.29-4.36 (m, 4H) 6.77-6.82 (m, 3H) 6.99-7.03 (m, 2H) 7.18-7.23 (m, 1H) 7.53-7.58 (m, 2H)
MS m/e (ESI) 405 (MNa⁺)

Example 66

3-{3-[2-(4-Cyclohexylphenoxy)ethoxy]phenyl}-2-ethylpropanoic acid

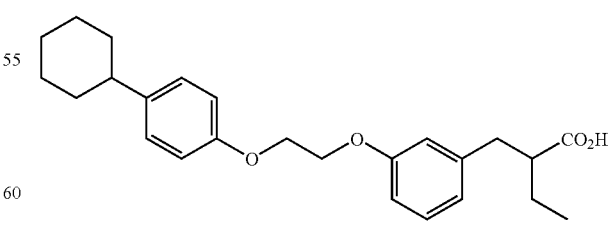

Using 1-(2-bromoethoxy)-4-cyclohexylbenzene, the title compound was obtained in the same manner as described in Example 64b).
MS m/e (ESI) 419 (MNa⁺)

Example 67

3-{3-[2-(4-Cyclopentylphenoxy)ethoxy]phenyl}-2-ethylpropanoic acid

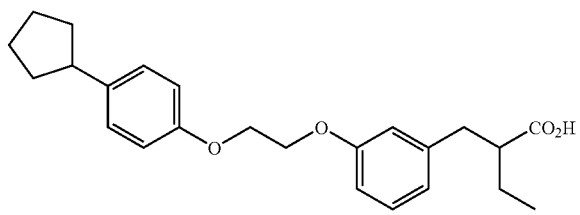

Using 1-(2-bromoethoxy)-4-cyclopentylbenzene, the title compound was obtained in the same manner as described in Example 64b).

MS m/e (ESI) 405 (MNa$^+$)

Example 68

3-{3-[2-(4-t-Butylphenoxy)ethoxy]phenyl}-2-ethylpropanoic acid

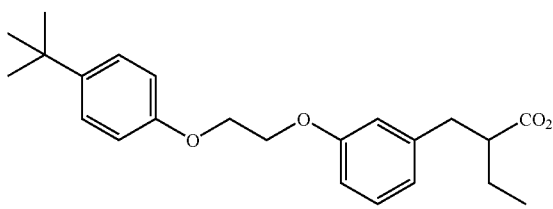

Using 1-(2-bromoethoxy)-4-t-butylbenzene, the title compound was obtained in the same manner as described in Example 64b).

MS m/e (ESI) 393 (MNa$^+$)

Example 69

3-{3-[2-(4-Isopropylphenoxy)ethoxy]phenyl}-2-ethylpropanoic acid

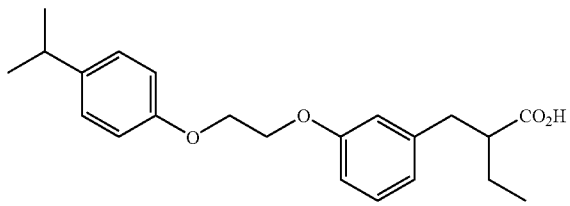

Using 1-(2-bromoethoxy)-4-isopropylbenzene, the title compound was obtained in the same manner as described in Example 64b).

MS m/e (ESI) 379 (MNa$^+$)

Example 70

3-3-[2-(Phenoxy)ethoxy]phenyl-2-ethylpropanoic acid

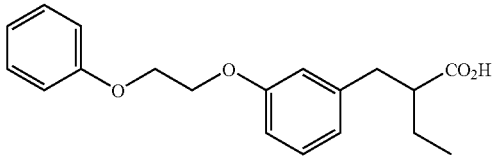

Using 1-(2-bromoethoxy)benzene, the title compound was obtained in the same manner as described in Example 64b).

MS m/e (ESI) 337 (MNa$^+$)

Example 71

3-3-[2-(4-Fluorophenoxy)ethoxy]phenyl-2-ethylpropanoic acid

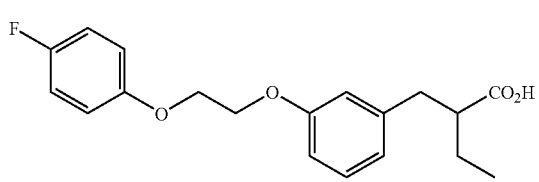

Using 1-(2-bromoethoxy)-4-fluorobenzene, the title compound was obtained in the same manner as described in Example 64b).

MS m/e (ESI) 355 (MNa$^+$)

Example 72

3-3-[2-(4-Benzyloxy)ethoxy]phenyl-2-ethylpropanoic acid

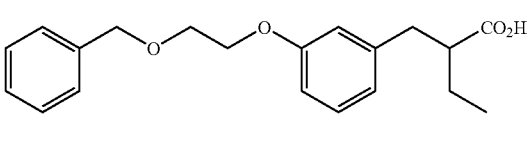

Using 1-[(2-bromoethoxy)methyl]benzene, the title compound was obtained in the same manner as described in Example 64b).

MS m/e (ESI) 351 (MNa$^+$)

Example 73

2-Ethyl-3-[3-(3-phenylpropoxy)phenyl]propanoic acid

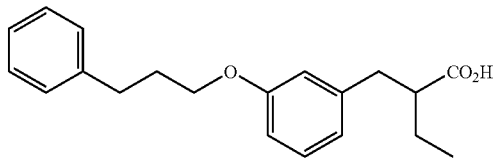

Using 3-phenylpropyl bromide, the title compound was obtained in the same manner as described in Example 64b).
MS m/e (ESI) 335 (MNa$^+$)

Example 74

2-Ethyl-3-[3-(3-phenoxypropoxy)phenyl]propanoic acid

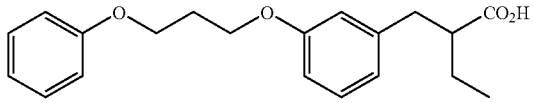

Using 1-(3-bromopropoxy)benzene, the title compound was obtained in the same manner as described in Example 64b).
MS m/e (ESI) 351 (MNa$^+$)

Example 75

3-{3-[3-(2,4-Dichlorophenoxy)propoxy]phenyl}-2-ethylpropanoic acid

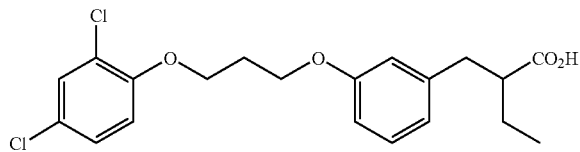

Using 1-(3-bromopropoxy)-2,4-dichlorobenzene, the title compound was obtained in the same manner as described in Example 64b).
MS m/e (ESI) 419 (MNa$^+$)

Example 76

3-{3-[3-(4-Acetyl-3-hydroxy-2-propylphenoxy)propoxy]phenyl}-2-ethylpropanoic acid

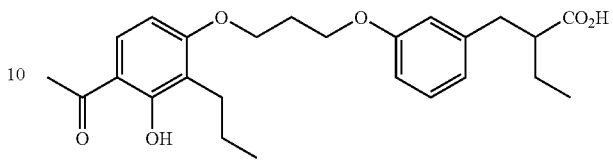

Using 1-[4-(3-bromopropoxy)-2-hydroxy-3-propylphenyl]-1-ethanone, the title compound was obtained in the same manner as described in Example 64b).
MS m/e (ESI) 451 (MNa$^+$)

Example 77

2-Isopropoxy-3-(4-methoxy-3-[3-(2-methylphenyl)-2-propynyl]oxyphenyl)propanoic acid

Production Example 77a

Ethyl 2-isopropoxy-3-[3-(2-propynyloxy)-4-methoxyphenyl]propanoate

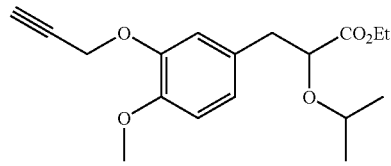

685 mg of Ethyl 3-(3-hydroxy-4-methoxyphenyl)-2-isopropanoate was dissolved in 10 ml of N,N-dimethylformamide, and 350 mg of propargyl bromide and 500 mg of potassium carbonate were added, and the mixture was stirred at room temperature for 3 hours. The reaction mixture was diluted with ethyl acetate, and washed with water and 1N hydrochloric acid. The organic layer was dried over anhydrous magnesium sulfate, filtered and the solvent was distilled off, to give 660 mg of the title compound.

Example 77b

2-Isopropoxy-3-(4-methoxy-3-[3-(2-methylphenyl)-2-propynyl]oxyphenyl)propanoic acid

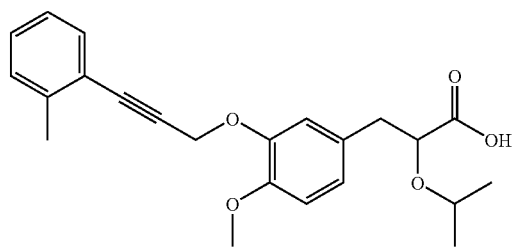

15.5 mg of Ethyl 2-isopropoxy-3-[3-(2-propynyloxy)phenyl]propanoate, 20 mg of 2-iodotoluene, 5 mg of copper iodide, 5 mg of tetrakis(triphenylphosphine) palladium and 50 μl triethylamine were dissolved in 0.2 ml of N,N-dimethylformamide, and the mixture was stirred at room temperature for two days under nitrogen atmosphere. The reaction mixture was diluted with ethyl acetate, and washed with water and 1N hydrochloric acid. The organic layer was dried over anhydrous magnesium sulfate, filtered, and the solvent was distilled off, to give ethyl 2-isopropoxy-3-(3-[3-(2-methylphenyl)-2-propynyl]-oxyphenyl)propanoate. This product was dissolved in 0.4 ml of ethanol, and 0.1 ml of 5N-sodium hydroxide was added, and the mixture was kept still overnight at room temperature. The reaction solution was acidified by adding 1N-hydrochloric acid and extracted with ethyl acetate. The residue was purified by reverse-phase high performance liquid chromatography, to give 1.10 mg of the title compound.

MS m/e (ESI) 383 (MH$^+$)

Example 78

2-Isopropoxy-3-(4-methoxy-3-[3-(3-methylphenyl)-2-propynyl]oxyphenyl)propanoic acid

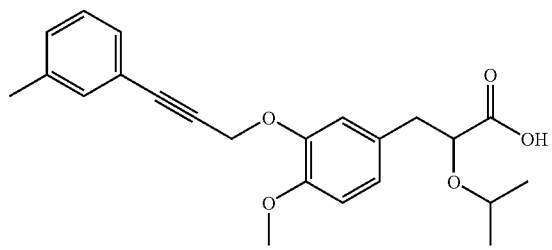

Using 3-iodotoluene, the title compound was obtained in the same manner as described in Example 77b).

MS m/e (ESI) 383 (MH$^+$)

Example 79

2-Isopropoxy-3-(4-methoxy-3-[3-(3-methyophenyl)-2-propynyl]oxyphenyl)propanoic acid

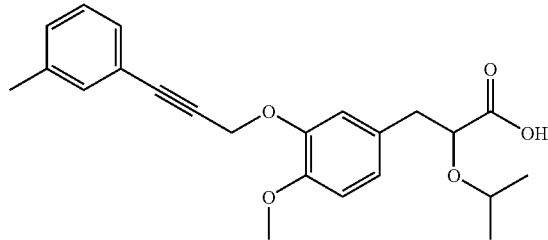

Using 3-iodotoluene, the title compound was obtained in the same manner as described in Example 77b).

MS m/e (ESI) 383 (MH$^+$)

Example 80

2-Isopropoxy-3-(4-methoxy-3-[3-(4-methylphenyl)-2-propynyl]oxyphenyl)propanoic acid

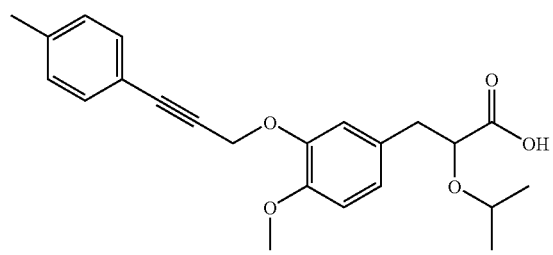

Using 4-iodotoluene, the title compound was obtained in the same manner as described in Example 77b).

MS m/e (ESI) 383 (MH$^+$)

Example 81

2-Isopropoxy-3-(4-methoxy-3-[3-(4-butylphenyl)-2-propynyl]oxyphenyl)propanoic acid

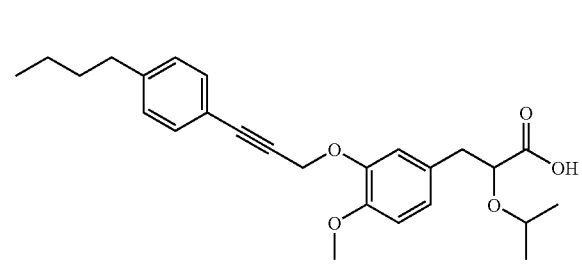

Using 4-butyliodobenzene, the title compound was obtained in the same manner as described in Example 77b).

MS m/e (ESI) 425 (MH$^+$)

Example 82

2-Isopropoxy-3-(4-methoxy-3-[3-(3-trifluoromethylphenyl)-2-propynyl]oxyphenyl)propanoic acid

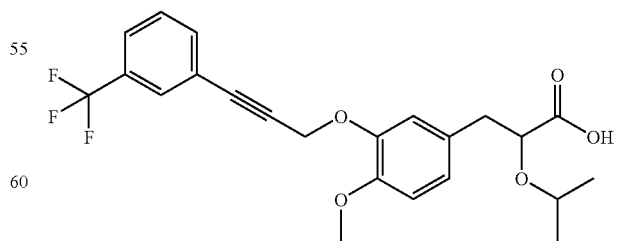

Using 3-iodobenzene trifluoride, the title compound was obtained in the same manner as described in Example 77b).

MS m/e (ESI) 437 (MH$^+$)

Example 83

2-Isopropoxy-3-(4-methoxy-3-[3-(3-methoxyphenyl)-2-propynyl]oxyphenyl)propanoic acid

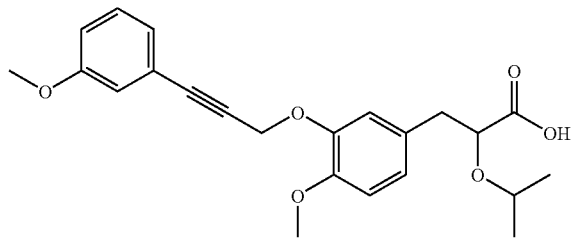

Using 3-methoxyiodobenzene, the title compound was obtained in the same manner as described in Example 77b). MS m/e (ESI) 399 (MH⁺)

Example 84

2-Isopropoxy-3-(4-methoxy-3-[3-(4-methoxyphenyl)-2-propynyl]oxyphenyl)propanoic acid

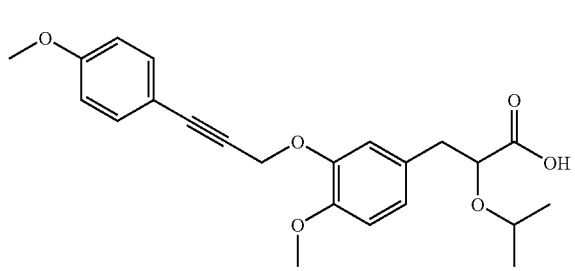

Using 4-methoxyiodobenzene, the title compound was obtained in the same manner as described in Example 77b). MS m/e (ESI) 399 (MH⁺)

Example 85

2-Isopropoxy-3-(4-methoxy-3-[3-(3-fluorophenyl)-2-propynyl]oxyphenyl)propanoic acid

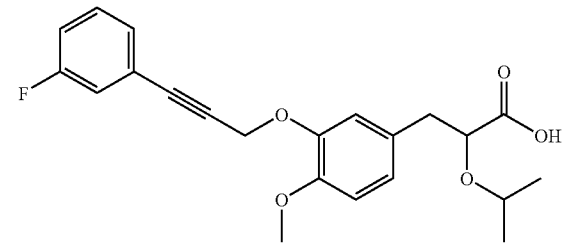

Using 3-fluoroiodobenzene, the title compound was obtained in the same manner as described in Example 77b) MS m/e (ESI) 387 (MH⁺).

Example 86

2-Isopropoxy-3-(4-methoxy-3-[3-(4-fluorophenyl)-2-propynyl]oxyphenyl)propanoic acid

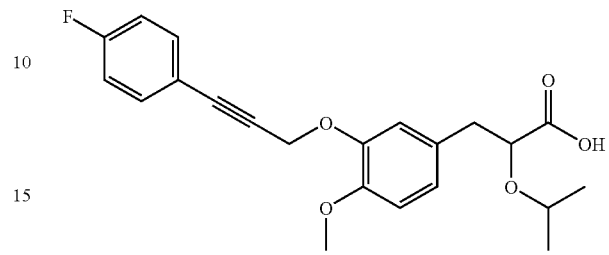

Using 4-fluoroiodobenzene, the title compound was obtained in the same manner as described in Example 77b). MS m/e (ESI) 387 (MH⁺)

Example 87

2-Isopropoxy-3-(4-methoxy-3-[3-(4-chlorophenyl)-2-propynyl]oxyphenyl)propanoic acid

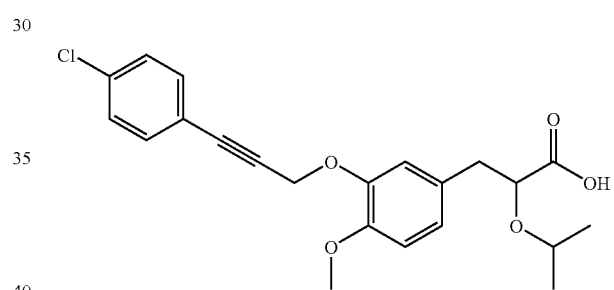

Using 4-chloroiodobenzene, the title compound was obtained in the same manner as described in Example 77b). MS m/e (ESI) 403 (MH⁺)

Example 88

2-Isopropoxy-3-(4-methoxy-3-[3-(3-bromophenyl)-2-propynyl]oxyphenyl)propanoic acid

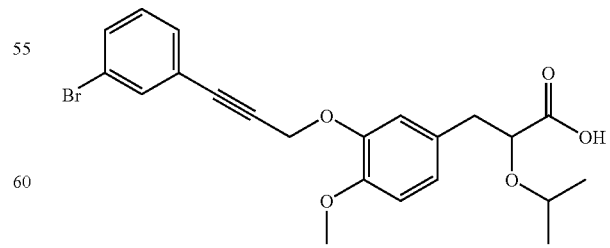

Using 3-bromoiodobenzene, the title compound was obtained in the same manner as described in Example 77b). MS m/e (ESI) 447 (MH⁺)

Example 89

2-Isopropoxy-3-(4-methoxy-3-[3-(3,5-bistrifluoromethylphenyl)-2-propynyl]oxyphenyl)propanoic acid

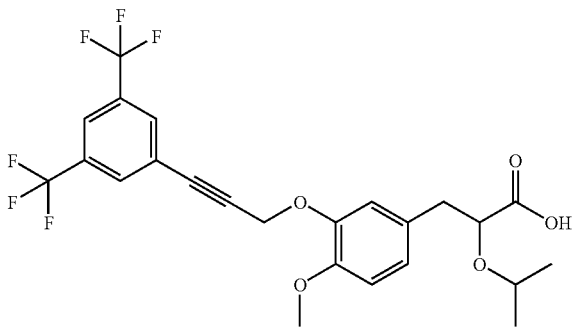

Using 3,5-bistrifluoromethyliodobenzene, the title compound was obtained in the same manner as described in Example 77b).
MS m/e (ESI) 505 (MH$^+$)

Example 90

2-Isopropoxy-3-(4-methoxy-3-[3-(2,4-dichlorophenyl)-2-propynyl]oxyphenyl)propanoic acid

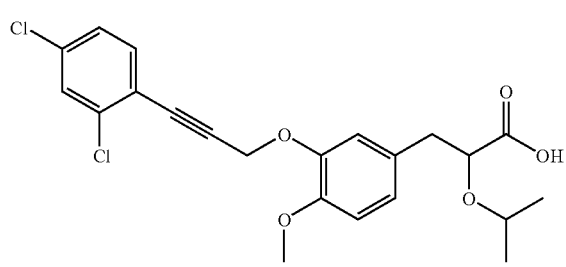

Using 2,4-dichloroiodobenzene, the title compound was obtained in the same manner as described in Example 77b).
MS m/e (ESI) 437 (MH$^+$)

Example 91

2-Isopropoxy-3-(4-methoxy-3-[3-(3,4-dichlorophenyl)-2-propynyl]oxyphenyl)propanoic acid

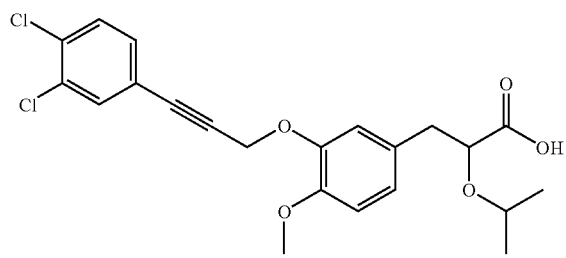

Using 3,4-dichloroiodobenzene, the title compound was obtained in the same manner as described in Example 77b).
MS m/e (ESI) 437 (MH$^+$)

Example 92

2-Isopropoxy-3-(4-methoxy-3-[3-(3,5-dimethylphenyl)-2-propynyl]oxyphenyl)propanoic acid

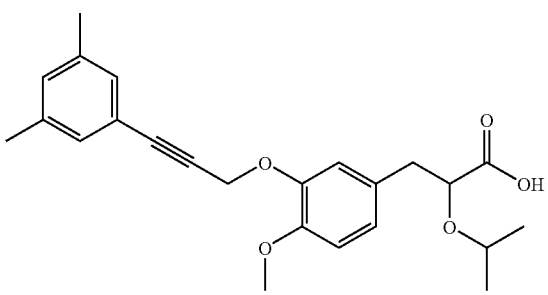

Using 3,5-dimethyliodobenzene, the title compound was obtained in the same manner as described in Example 77b).
MS m/e (ESI) 397 (MH$^+$)

Example 93

2-Isopropoxy-3-(4-methoxy-3-[3-(1-naphthyl)-2-propynyl]oxyphenyl)propanoic acid

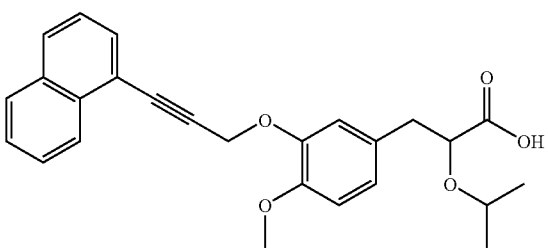

Using 1-iodonaphthalene, the title compound was obtained in the same manner as described in Example 77b).
MS m/e (ESI) 419 (MH$^+$)

Example 94

2-Isopropoxy-3-(4-methoxy-3-[3-(2-thienyl)-2-propynyl]oxyphenyl)propanoic acid

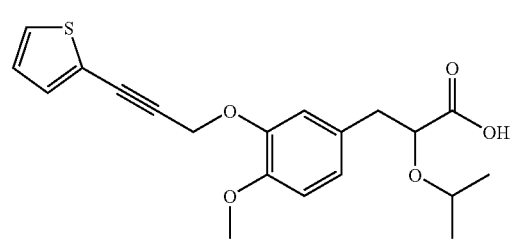

Using 2-iodothiophene, the title compound was obtained in the same manner as described in Example 77b)
MS m/e (ESI) 375 (MH$^+$).

Example 95

2-Isopropoxy-3-(3-[3-(4-methylphenyl)-2-propynyl]oxyphenyl)propanoic acid

Production Example 95a) Ethyl 2-isopropoxy-3-[3-(2-propynyloxy)phenyl]propanoate

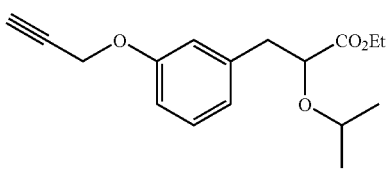

Using ethyl 3-(3-hydroxyphenyl)-2-isopropoxypropanoate, the title compound was obtained in the same manner as described in Example 77a).

$^1$H NMR (CDCl$_3$)
δ: 0.96 (d, J=6.4 Hz, 3H) 1.16 (d, J=6.0 Hz, 3H) 1.25 (t, J=7.2 Hz, 3H) 2.51 (t, J=2.4 Hz, 1H) 2.92 (dd, J=8.8, 14.0 Hz, 1H) 2.99 (dd, J=4.8, 13.6 Hz, 1H) 3.51 (Sept, J=6.4 Hz, 1H) 4.05 (dd, J=4.4, 8.8 Hz, 1H) 4.14-4.23 (m, 2H) 4.68 (d, J=2.4 Hz, 2H) 6.83-6.86 (m, 1H) 6.88-6.90 (m, 1H) 6.90 (s, 1H) 7.21 (dt, J=0.8, 8.0 Hz, 1H)

Example 95b

2-Isopropoxy-3-(3-[3-(4-methylphenyl)-2-propynyl]oxyphenyl)propanoic acid

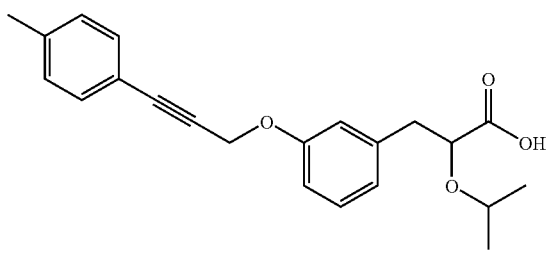

Using 4-iodotoluene, the title compound was obtained in the same manner as described in Example 77b).
MS M/e(ESI) 353 (MH$^+$)

Example 96

2-Isopropoxy-3-(3-[3-(4-chlorophenyl)-2-propynyl]oxyphenyl)propanoic acid

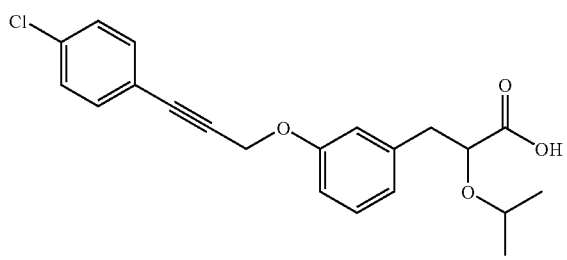

Using 4-iodochlorobenzene, the title compound was obtained in the same manner as described in Example 77b).
$^1$H NMR (CDCl$_3$)
δ: 0.99 (d, J=6.4 Hz, 3H) 1.13 (d, J=6.0 Hz, 3H) 2.93 (dd, J=8.4, 14.0 Hz, 1H) 3.13 (dd, J=3.6, 13.6 Hz, 1H) 3.52 (Sept, J=6.4 Hz, 1H) 4.14 (dd, J=3.6, 8.4 Hz, 1H) 4.89 (s, 2H) 6.87-6.93 (m, 3H) 7.22-7.30 (m, 3H) 7.36 (d, J=8.4 Hz, 2H)
MS m/e (ESI) 373 (MH$^+$)

Example 97

2-Isopropoxy-3-(3-[3-(3-bromophenyl)-2-propynyl]oxyphenyl)propanoic acid

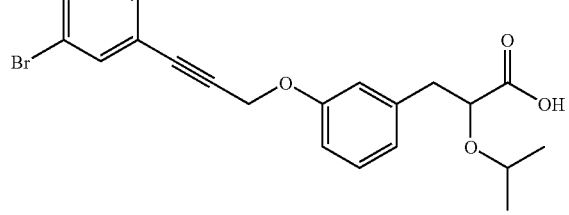

Using 3-bromoiodobenzene, the title compound was obtained in the same manner as described in Example 77b).
MS m/e (ESI) 417 (MH$^+$)

Example 98

2-Isopropoxy-3-(3-[3-(3-trifluoromethylphenyl)-2-propynyl]oxyphenyl)propanoic acid

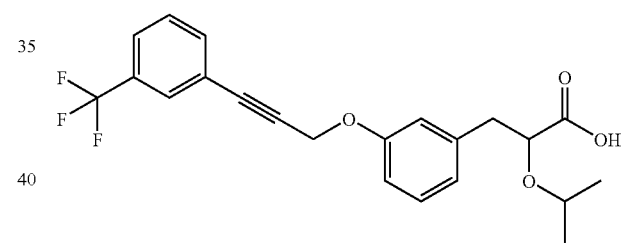

Using 3-iodobenzotrifluoride, the title compound was obtained in the same manner as described in Example 77b).
MS m/e (ESI) 407 (MH$^+$)

Example 99

2-Isopropoxy-3-(3-[3-(3,4-dichlorophenyl)-2-propynyl]oxyphenyl)propanoic acid

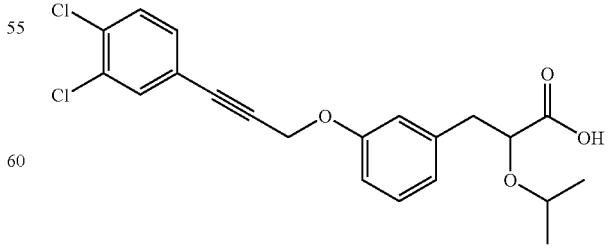

Using 3,4-dichloroiodobenzene, the title compound was obtained in the same manner as described in Example 77b)
MS m/e (ESI) 407 (MH$^+$).

Example 100

2-Isopropoxy-3-(3-[3-(2,4-dichlorophenyl)-2-propynyl]oxyphenyl)propanoic acid

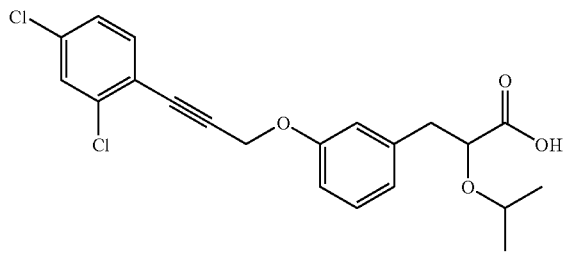

Using 2,4-dichloroiodobenzene, the title compound was obtained in the same manner as described in Example 77b).

$^1$H NMR (CDCl$_3$)
δ: 0.99 (d, J=6.0 Hz, 3H) 1.14 (d, J=6.0 Hz, 3H) 2.92 (dd, J=8.4, 14.0 Hz, 1H) 3.13 (dd, J=3.6, 14.0 Hz, 1H) 3.52 (Sept, J=6.0 Hz, 1H) 4.14 (dd, J=3.6, 8.0 Hz, 1H) 4.94 (s, 2H) 6.89 (d, J=7.6 Hz, 1H) 6.91-6.95 (m, 2H) 7.19 (dd, J=2.0, 8.4 Hz, 1H) 7.24 (dd, J=7.2, 8.8 Hz, 1H) 7.39 (d, J=8.4 Hz, 1H) 7.40 (d, J=2.0 Hz, 1H)
MS m/e (ESI) 407 (MH$^+$)

Example 101

2-Isopropoxy-3-(3-[3-(4-trifluoromethylphenyl)-2-propynyl]oxyphenyl)propanoic acid

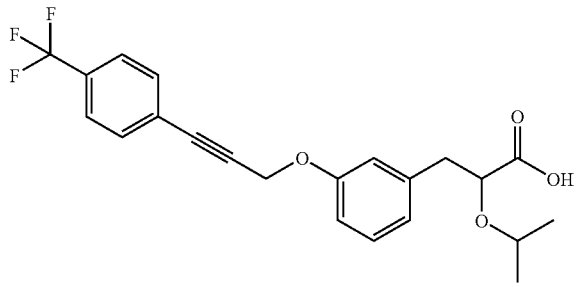

Using 4-iodobenzotrifluoride, the title compound was obtained in the same manner as described in Example 77b).
MS m/e (ESI) 407 (MH$^+$)

Example 102

2-Isopropoxy-3-(3-3-[4-(trifluoromethyl)phenoxy]-1-propynylphenyl)propanoic acid Production Example 102a Ethyl 2-isopropoxy-3-(3-[(trifluoromethyl)sulfonyl]oxyphenyl)-propanoate

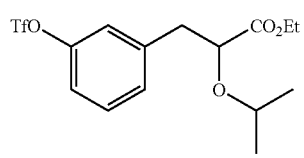

688 mg of Ethyl 3-(3-hydroxyphenyl)-2-isopropoxypropanoate was dissolved in dichloromethane, and 600 μl of triethylamine, 15 mg of 4-dimethylaminopyridine and 1.045 g of N,N-bistrifluoromethanesulfonyl aniline were added. The solution was stirred at room temperature overnight and the solvent was evaporated. The residue was purified by silica gel column chromatography, to give 1.132 g of the title compound in the 10:1 hexane-ethyl acetate fraction.

Production Example 102b

Ethyl 3-[3-(3-hydroxy-1-propynyl)phenyl]-2-isopropoxypropanoate

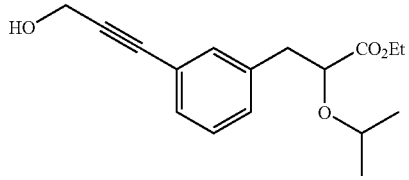

550 mg of Ethyl 2-isopropoxy-3-(3-[(trifluoromethyl)sulfonyl]oxyphenyl)propanoate was dissolved in 5 ml of N,N-dimethylformamide, and 160 mg of propargyl alcohol, 13 mg of copper iodide, 83 mg of tetrakis(triphenylphosphine)palladium and 1 ml of triethylamine were added. After stirring was continued at 50° C. for 4 hours under nitrogen atmosphere, the reaction mixture was diluted with ethyl acetate and washed with water and 1N hydrochloric acid. The organic layer was dried over anhydrous magnesium sulfate, filtered, and the solvent was distilled off. Then, the residue was purified by silica gel column chromatography, to give 184 mg of the title compound in the 4:1→2:1 hexane-ethyl acetate fraction.

$^1$H NMR (CDCl$_3$)
δ 0.94 (d, J=6.0 Hz, 3H) 1.15 (d, J=6.4 Hz, 3H) 1.24 (t, J=7.6 Hz, 3H) 1.70 (t, J=6.0 Hz, 1H) 2.90 (dd, J=8.8, 14.0 Hz, 1H) 2.98 (dd, J=4.8, 14.0 Hz, 1H) 3.49 (Sept, J=6.0 Hz, 1H) 4.02 (dd, J=4.8, 8.4 Hz, 1H) 4.14-4.22 (m, 2H) 4.50 (d, J=5.6 Hz, 2H) 7.22-7.25 (m, 2H) 7.27-7.34 (m, 2H)

Production Example 102c

Ethyl 3-[3-(3-bromo-1-propynyl)phenyl]-2-isopropoxypropanoate

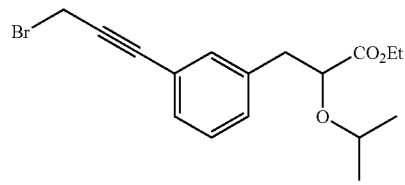

184 mg of Ethyl 3-[3-(3-hydroxy-1-propynyl)phenyl]-2-isopropoxypropanoate was dissolved in 4 ml of dimethoxyethane, and 50 μl of phosphorous tribromide was added. After stirring was continued at room temperature overnight, the reaction mixture was diluted with ethyl acetate and washed with water and 1N hydrochloric acid. The organic layer was dried over anhydrous magnesium sulfate, filtered and the solvent was distilled off. Then, the residue was purified by silica gel column chromatography, to give 209 mg of the title compound in the 20:1 hexane-ethyl acetate fraction.

$^1$H NMR (CDCl$_3$)

δ: 0.94 (d, J=6.4 Hz, 3H) 1.15 (d, J=6.4 Hz, 3H) 1.24 (t, J=7.2 Hz, 3H) 2.90 (dd, J=8.4, 14.0 Hz, 1H) 2.98 (dd, J=4.8, 13.6 Hz, 1H) 3.47 (Sept, J=6.0 Hz, 1H) 4.02 (dd, J=4.8, 8.8 Hz, 1H) 4.14-4.22 (m, 2H) 4.16 (s, 2H) 7.23-7.25 (m, 2H) 7.30-7.35 (m, 2H)

Example 102d

2-Isopropoxy-3-(3-3-[4-(trifluoromethyl)phenoxy]-1-propynylphenyl)propanoic acid

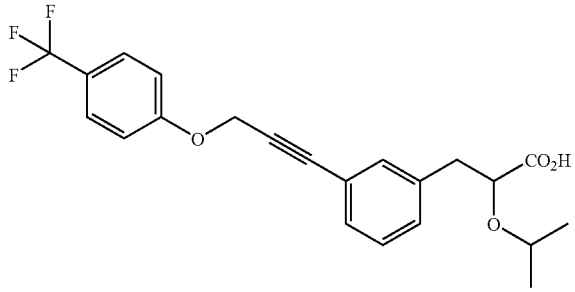

10 mg of Ethyl 3-[3-(3-bromo-1-propynyl)phenyl]-2-isopropoxypropanoate was dissolved in 0.3 ml of N,N-dimethylformamide, and 10 mg of 4-hydroxybenzotrifluoride and 20 mg of potassium carbonate were added. After stirring was continued at room temperature overnight, the reaction mixture was diluted with ethyl acetate and washed with water. After distilling off the solvent from the organic layer, the residue was dissolved in 0.4 ml of ethanol, and 0.1 ml of 5N-sodium hydroxide was added, and the mixture was kept still at room temperature overnight. The reaction solution was acidified by adding 1N-hydrochloric acid, and extracted with ethyl acetate. The solvent was concentrated, and the residue was purified by reverse-phase high performance liquid chromatography, to give 3.55 mg of the title compound.

MS m/e (ESI) 407 (MH$^+$)

Example 103

2-Isopropoxy-3-(3-3-[4-t-butylphenoxy]-1-propynylphenyl)propanoic acid

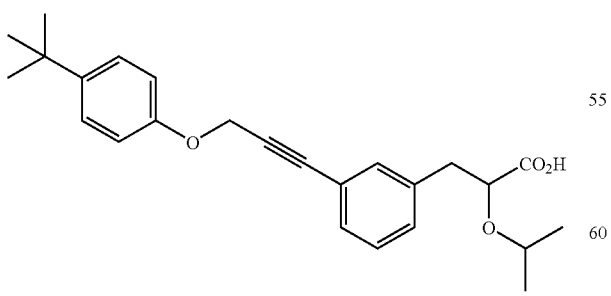

Using 4-t-butylphenol, the title compound was obtained in the same manner as described in Example 102d).

MS m/e (ESI) 395 (MH$^+$)

Example 104

2-Isopropoxy-3-(3-3-[4-(phenyl)phenoxy]-1-propynylphenyl)propanoic acid

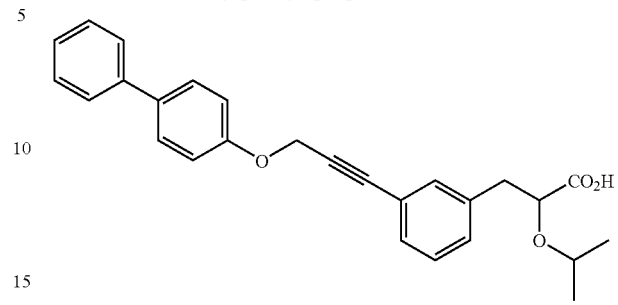

Using 4-hydroxybiphenyl, the title compound was obtained in the same manner as described in Example 102d).

MS m/e (ESI) 415 (MH$^+$)

Example 105

2-Isopropoxy-3-{3-[3-(2,4-dichlorophenoxy)-1-propyl]phenyl}propanoic acid

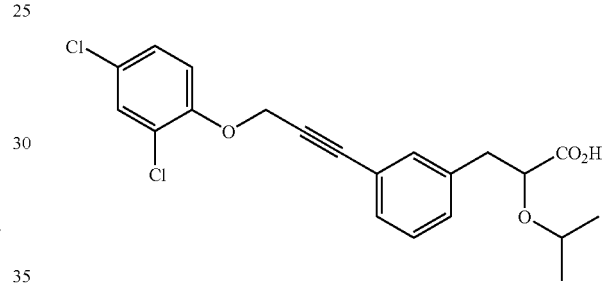

Using 2,4-dichlorophenol, the title compound was obtained in the same manner as described in Example 102d).

$^1$H NMR (CDCl$_3$)

δ: 1.00 (d, J=6.0 Hz, 3H) 1.16 (d, J=6.4 Hz, 3H) 2.91 (dd, J=8.0, 13.6 Hz, 1H) 3.09 (dd, J=2.8, 13.6 Hz, 1H) 3.52 (Sept, J=6.0 Hz, 1H) 4.10 (dd, J=3.6, 8.0 Hz, 1H) 4.97 (s, 2H) 7.11 (d, J=8.8 Hz, 1H) 7.22 (dd, J=2.8, 8.8 Hz, 1H) 7.23 (t, J=1.2 Hz, 1H) 7.25 (t, J=7.6 Hz, 1H) 7.29-7.32 (m, 2H) 7.40 (d, J=2.4 Hz, 1H)

MS m/e (ESI) 407 (MH$^+$)

Example 106

2-Isopropoxy-3-(3-3-[4-bromo-2-fluorophenoxy]-1-propynylphenyl)propanoic acid

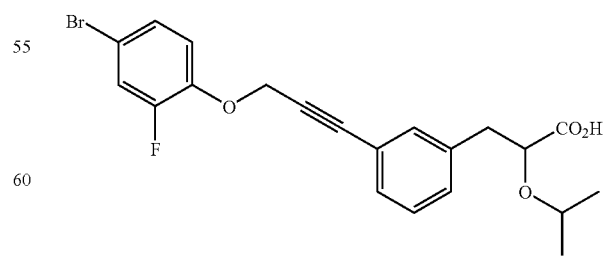

Using 4-bromo-2-fluorophenol, the title compound was obtained in the same manner as described in Example 102d).

MS m/e (ESI) 435 (MH$^+$)

Example 107

2-Isopropoxy-3-3-[2-(4-methylphenyl)-1-ethynyl]phenylpropanoic acid

Production Example 107a) Ethyl 3-[3-(2-trimethylsilyl-1-propynyl)phenyl]-2-isopropoxypropanoate

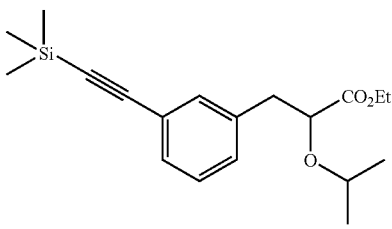

932 mg of Ethyl 2-isopropoxy 3-(3-[(trifluoromethyl)sulfonyl]oxyphenyl)propanoate was dissolved in 8 ml of N,N-dimethylformamide, and 480 mg of trimethylsilyl acetylene, 40 mg of copper iodide, 280 mg of tetrakis(triphenylphosphine)palladium and 1 ml of triethylamine were added. After stirring was continued at 50° C. for 8 hours under nitrogen atmosphere, and the reaction mixture was diluted with ethyl acetate, and washed with water and 1N hydrochloric acid. The organic layer was dried over anhydrous magnesium sulfate, and after filtration and distilling off the solvent. Then, the residue was purified by silica gel column chromatography, to give 442 mg of the title compound in the 30:1 hexane-ethyl acetate fraction.

$^1$H NMR (CDCl$_3$)
δ: 0.24 (s, 9H) 0.94 (d, J=6.0 Hz, 3H) 1.15 (d, J=6.0 Hz, 3H) 1.24 (t, J=7.2 Hz, 3H) 2.89 (dd, J=9.2, 14.0 Hz, 1H) 2.97 (dd, J=4.8, 13.6 Hz, 1H) 3.49 (Sept, J=6.0 Hz, 1H) 4.01 (dd, J=6.4, 12.4 Hz, 1H) 4.14-4.22 (m, 2H) 7.21 (dd, J=1.4, 4.0 Hz, 2H) 7.31-7.35 (m, 1H) 7.37 (s, 1H)

Production Example 107b

Ethyl 3-[3-(ethynyl)phenyl]-2-isopropoxypropanoate

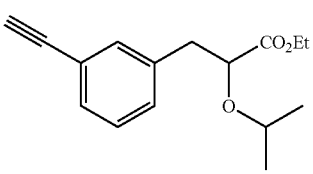

442 mg of Ethyl 3-[3-(2-trimethylsilyl-1-propynyl)phenyl]-2-isopropoxypropanoate was dissolved in 10 ml of tetrahydrofuran, and 0.5 ml of acetic acid and 2 ml of tetrabutylammonium fluoride (solution in 1M tetrahydrofuran) were added. The solution was stirred at 50° C. for 3 hours, and the reaction mixture was diluted with ethyl acetate, and washed with water and saturated sodium bicarbonate. The organic layer was dried over anhydrous magnesium sulfate, filtered, and the solvent was distilled off. Then, the residue was purified by silica gel column chromatography, to give 233 mg of the title compound in the 30:1 hexane-ethyl acetate fraction.

$^1$H NMR (CDCl$_3$)
δ: 0.94 (d, J=6.0 Hz, 3H) 1.15 (d, J=6.0 Hz, 3H) 1.24 (t, J=7.2 Hz, 3H) 2.91 (dd, J=8.8, 13.6 Hz, 1H) 2.99 (dd, J=4.8, 13.6 Hz, 1H) 3.05 (s, 1H) 3.50 (Sept, J=6.4 Hz, 1H) 4.02 (dd, J=4.8, 8.8 Hz, 1H) 4.14-4.22 (m, 2H) 7.22-7.26 (m, 2H) 7.35-7.37 (m, 1H) 7.40 (s, 1H)

Example 107c

2-Isopropoxy-3-3-[2-(4-methylphenyl)-1-ethynyl]phenylpropanoic acid

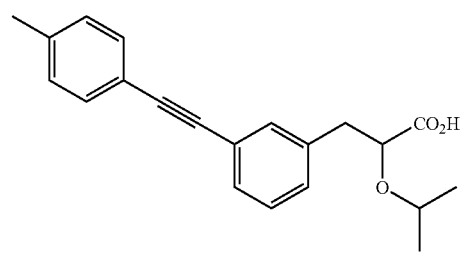

10 mg of Ethyl 3-[3-(2-trimethylsilyl-1-propynyl)phenyl]-2-isopropoxypropanoate, 20 mg of 4-iodotoluene, 5 mg of copper iodide, 5 mg of tetrakis(triphenylphosphine)palladium and 50 μl of triethylamine were dissolved in 0.2 ml of N,N-dimethylformamide, and the mixture was stirred at 50° C. overnight under nitrogen atmosphere. The reaction mixture was diluted with ethylacetate, and washed with water and 1N hydrochloric acid. The organic layer was dried over anhydrous magnesium sulfate, filtered, and the solvent was distilled off, to give ethyl 2-isopropoxy-3-3-[2-(4-methylphenyl)-1-ethynyl]phenylpropanoate. This product was dissolved in 0.4 ml of ethanol, and 0.1 ml of 5N-sodium hydroxide was added, and the mixture was kept still at room temperature overnight. The reaction solution was acidified by adding 1N-hydrochloric acid and extracted with ethyl acetate. The residue was purified by reverse-phase high performance liquid chromatography, to give 1.90 mg of the title compound.

MS m/e (ESI) 323 (MH$^+$)

Example 108

2-Isopropoxy-3-3-[2-(4-chlorophenyl)-1-ethynyl]phenylpropanoic acid

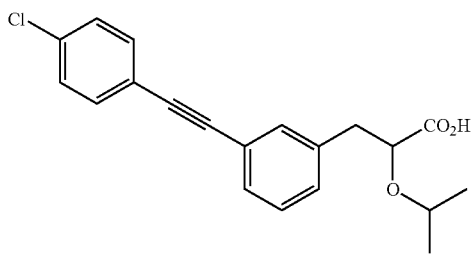

Using 4-chloroiodobenzene, 3.70 mg of the title compound was obtained in the same manner as described in Example 107c)

MS m/e (ESI) 343 (MH$^+$)

Example 109

2-Isopropoxy-3-3-[2-(3-bromophenyl)-1-ethynyl]phenylpropanoic acid

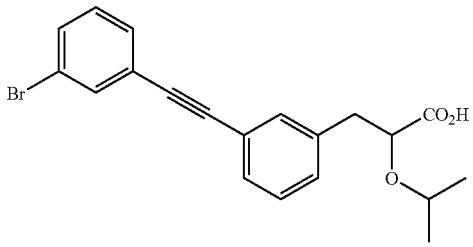

Using 3-bromoiodobenzene, the title compound was obtained in the same manner as described in Example 107c). MS m/e (ESI) 387 (MH⁺)

Example 110

2-Isopropoxy-3-3-[2-(3-trifluoromethylphenyl)-1-ethynyl]phenylpropanoic acid

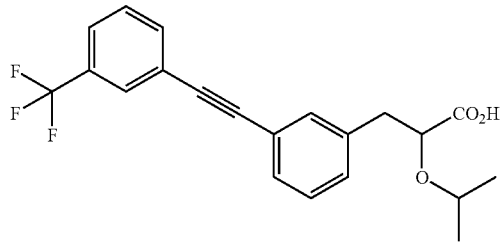

Using 3-iodobenzotrifluoride, the title compound was obtained in the same manner as described in Example 107c). MS m/e (ESI) 377 (MH⁺)

Example 111

2-Isopropoxy-3-3-[2-(3,4-dichlorophenyl)-1-ethynyl]phenylpropanoic acid

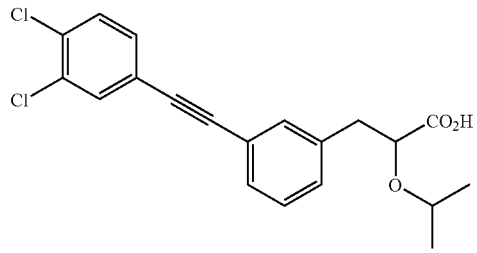

Using 3,4-dichloroiodobenzene, the title compound was obtained in the same manner as described in Example 107c). MS m/e (ESI) 377 (MH⁺)

Example 112

2-Isopropoxy-3-3-[2-(2,4-dichlorophenyl)-1-ethynyl]phenylpropanoic acid

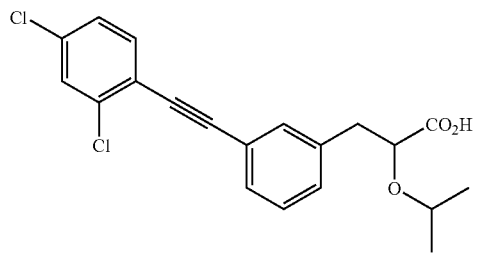

Using 2,4-dichloroiodobenzene, the title compound was obtained in the same manner as described in Example 107c). MS m/e (ESI) 377 (MH⁺)

Example 113

3-(3-2-[4-t-Butyl-1-hydroxycyclohexyl]-1-ethynylphenyl)-2-isopropoxypropanoic acid

Production Example 113a

3-[3-(1-Ethynyl)phenyl]-2-isopropoxypropanoic acid

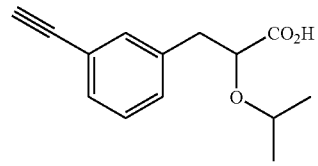

156 mg of Ethyl 3-[3-(propynyl)phenyl]-2-isopropoxy propanoate was dissolved in 2 ml of ethanol, and 0.5 ml of 5N-sodium hydroxide was added. After the mixture was kept at room temperature for 1 hour, the solution was neutralized with 1N-hydrochloric acid and extracted with ethyl acetate. The organic layer was dried over anhydrous magnesium sulfate, filtered and the solvent was distilled off, to give 138 mg of the title compound.

Example 113b trans-3-(3-2-[4-t-Butyl-1-hydroxycyclohexyl]-1-ethynylphenyl)-2-isopropoxypropanoic acid

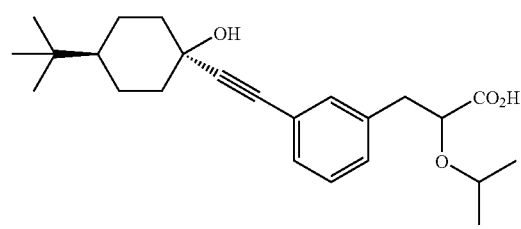

12 mg of 3-[3-(1-Ethynyl)phenyl]-2-isopropoxypropanoic acid was dissolved in 1 ml of tetrahydrofuran, and 130 μl of 1M-lithium bistrimethylsilylamide and 40 mg of 4-t-butylcyclohexanone were added. The solution was stirred at room temperature for 1 hour, neutralized with 1N-hydrochloric acid and extracted with ethyl acetate. The organic layer was concentrated, and the residue was purified by reverse-phase high performance liquid chromatography, to give 4.70 mg of the title compound.

MS m/e (ESI) 409 (MNa$^+$)

Example 114

3-3-[2-(8-Hydroxy-1,4-dioxaspiro[4.5]dec-8-yl)-1-ethynyl]phenyl-2-isopropoxypropanoic acid

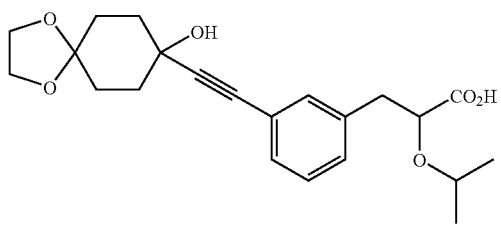

Using 1,4-dioxaspiro[4.5]decane-8-one, the title compound was obtained in the same manner as described in Example 113b)

MS m/e (ESI) 411 (MNa$^+$)

Example 115

3-(3-3-Hydroxy-3-[4-(trifluoromethyl)phenyl]-1-butynylphenyl)-2-isopropoxypropanoic acid

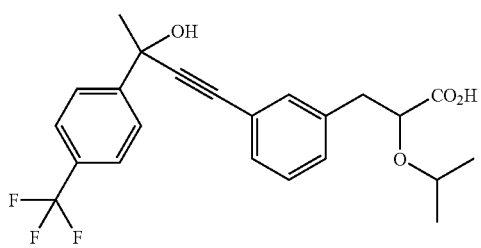

Using 4-trifluoromethylacetophenone, the title compound was obtained in the same manner as described in Example 113b)

MS m/e (ESI) 443 (MNa$^+$)

Example 116

3-3-[3-(2,4-Dichlorophenyl)-3-hydroxy-1-buthynyl]phenyl-2-isopropoxypropanoic acid

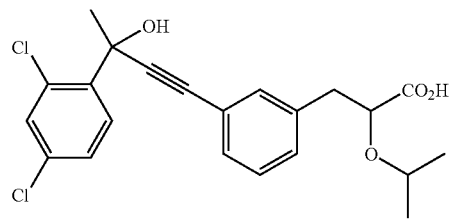

Using 2,4-dichloroacetophenone, the title compound was obtained in the same manner as described in Example 113b).

MS m/e (ESI) 443 (MNa$^+$)

Example 117

3-3-[3-Biphenyl-3-hydroxy-1-butynyl]phenyl-2-isopropoxypropanoic acid

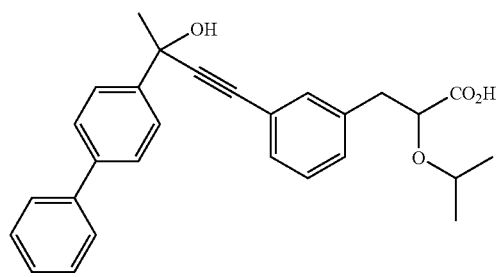

Using 4-phenylacetophenone, the title compound was obtained in the same manner as described in Example 113b).

MS m/e (ESI) 451 (MNa$^+$)

Example 118

3-3-[3-(4-cyclohexylphenyl)-3-hydroxy-1-butynyl]phenyl-2-isopropoxypropanoic acid

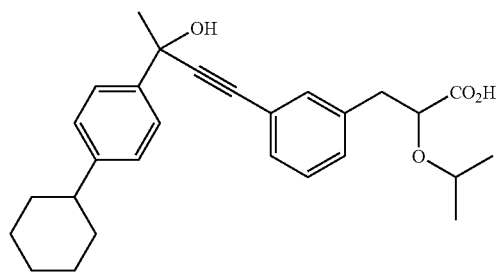

Using 4-cyclohexylacetophenone, the title compound was obtained in the same manner as described in Example 113b).

MS m/e (ESI) 457 (MNa$^+$)

Example 119

3-(3-3-Hydroxy-3-[4-(trifluoromethyl)phenyl]-1-propynyl)-2-isopropoxypropanoic acid

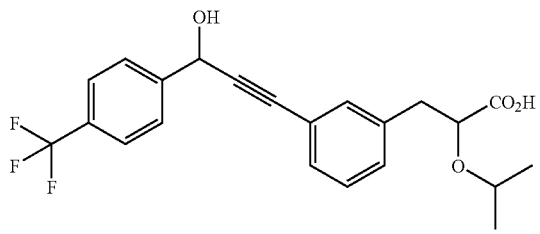

Using 4-trifluoromethylbenzaldehyde, 1.20 mg of the title compound was obtained in the same manner as described in Example 113b).
MS m/e (ESI) 429 (MNa$^+$)

Example 120

3-(3-3-Hydroxy-3-[2,4-dichlorophenyl]-1-propynyl)-2-isopropoxypropanoic acid

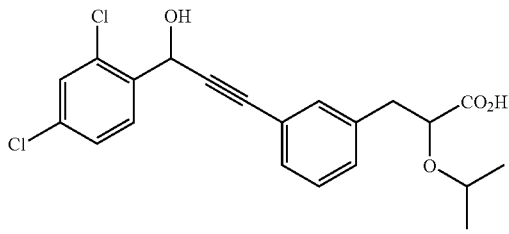

Using 2,4-dichlorobenzaldehyde, the title compound was obtained in the same manner as described in Example 113b).
MS m/e (ESI) 429 (MNa$^+$)

Example 121

3-(3-3-[4-t-Butylphenyl]-3-hydroxy-1-propynylphenyl)-2-isopropoxypropanoic acid

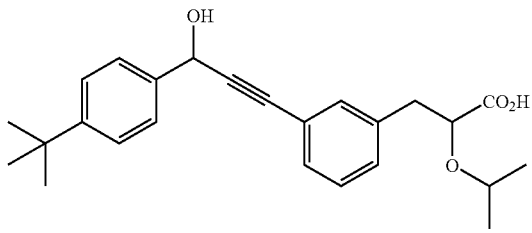

Using 4-t-butylbenzaldehyde, the title compound was obtained in the same manner as described in Example 113b).
MS m/e (ESI) 417 (MNa$^+$)

Example 122

3-3-[3-(4-Chlorophenyl)-1-hydroxy-1-methyl-2-propynyl]phenyl-2-isopropoxypropanoic acid Production Example 122a) Ethyl 3-(3-acetylphenyl)-2-isopropoxypropanoate

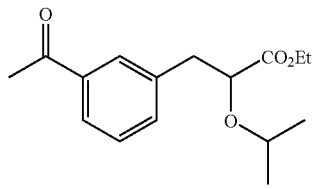

2.037 g of Ethyl 2-isopropoxy-3-(3-[(trifluoromethyl)sulfonyl]oxyphenyl)-propanoate, 2.5 g of ethyl [1-(1,1,1-tributylstannyl)vinyl]ether, 500 mg of lithium chloride and 186 mg of dichlorobis(triphenylphosphine) palladium were dissolved in 15 ml of dioxane, and the mixture was stirred at 90° C. overnight under nitrogen atmosphere. The solution was cooled in ice bath, added with 1N-hydrochloric acid, and extracted with ethylacetate. The organic layer was dried over anhydrous magnesium sulfate, filtered, and the solvent was distilled off. The residue was purified by silica gel column chromatography, to give 1.041 g of the title compound in the 6:1 hexane-ethyl acetate fraction.

$^1$H NMR (CDCl$_3$)

δ: 0.91 (d, J=6.0 Hz, 3H) 1.15 (d, J=6.0 Hz, 3H) 1.25 (t, J=7.2 Hz, 3H) 2.59 (s, 3H) 2.94 (dd, J=8.8, 14.0 Hz, 1H) 3.08 (dd, J=4.8, 14.0 Hz, 1H) 3.50 (Sept, J=6.0 Hz, 1H) 4.05 (dd, J=4.8, 8.8 Hz, 1H) 4.15-4.22 (m, 2H) 7.38 (t, J=7.6 Hz, 1H) 7.47 (dt, J=1.6, 7.6 Hz, 1H) 7.82 (dt, J=1.6, 7.6 Hz, 1H) 7.87 (dd, J=1.2, 1.6 Hz, 1H)

Production Example 122b

Ethyl 3-3-[1-hydroxy-1-methyl-3-(1,1,1-trimethylsilyl)-2-propynyl]phenyl-2-isopropoxypropanoate

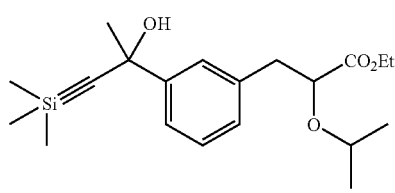

243 mg of Trimethylsilyl acetylene was dissolved in 5 ml of tetrahydrofuran, and 1.43 ml of butyl lithium (1.56 M solution in hexane) and 283 μl of boron trifluoride ether complex were added under nitrogen atmosphere at −78° C., and the mixture was then stirred for 30 minutes. A solution of 345 mg of ethyl 3-(3-acetylphenyl)-2-isopropoxypropanoate in tetrahydrofuran (2 ml) was added thereto, and stirring was continued for 30 minutes. A saturated aqueous ammonium chloride was added thereto, and the mixture was extracted with ethyl acetate. The organic layer was dried over anhydrous magnesium sulfate, filtered, and the solvent was distilled off. The residue was purified by silica gel column chromatography, to give 256 mg of the title compound in the 6:1 hexane-ethyl acetate fraction.

¹H NMR (CDCl₃)

δ: 0.21 (s, 9H) 0.94, 0.95 (each d, J=6.4 Hz, 3H) 1.15, 1.16 (each d, J=6.0 Hz, 3H) 1.24, 1.25 (each t, J=7.2 Hz, 3H) 1.74 (s, 3H) 2.35 (s, 1H) 2.93-3.05 (m, 2H) 3.47-3.54 (m, 1H) 4.06 (dd, J=4.8, 8.4 Hz, 1H) 4.12-4.19 (m, 2H) 7.18 (d, J=8.0 Hz, 1H) 7.26-7.29 (m, 1H) 7.46-7.55 (m, 2H)

Production Example 122c

Ethyl 3-3-[1-hydroxy-1-methyl-2-propynyl]phenyl-2-isopropoxypropanoate

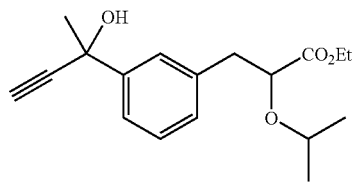

256 mg of Ethyl 3-3-[1-hydroxy-1-methyl-3-(1,1,1-trimethylsilyl)-2-propynyl]phenyl-2-isopropoxypropanoate was dissolved in 4 ml of tetrahydrofuran, and 0.1 ml of acetic acid and 1 ml of tetrabutylammonium fluoride (1M solution in tetrahydrofuran) were added under ice-cooling, and the mixture was stirred overnight. The reaction mixture was diluted with ethylacetate, and washed with saturated aqueous sodium bicarbonate and water. The organic layer was dried over anhydrous magnesium sulfate, filtered and the solvent was distilled off. The residue was purified by silica gel column chromatography, to give 185 mg of the title compound in the 4:1 hexane-ethyl acetate fraction.

¹H NMR (CDCl₃)

δ: 0.94 (d, J=6.4 Hz, 3H) 1.15 (d, J=6.0 Hz, 3H) 1.25 (t, J=7.2 Hz, 3H) 1.78 (s, 3H) 2.43 (s, 1H) 2.67 (s, 1H) 2.98 (dd, J=2.0, 8.8 Hz, 1H) 3.03 (dd, J=4.8, 13.6 Hz, 1H) 3.50 (Sept, J=6.0 Hz, 1H) 4.06 (ddd, J=2.8, 4.8, 8.8 Hz, 1H) 4.14-4.22 (m, 2H) 7.20 (dd, J=1.2, 7.6 Hz, 1H) 7.26 (s, 1H) 7.29 (t, J=7.6 Hz, 1H) 7.51-7.57 (m, 1H)

Production Example 122d 3-3-[3-(4-Chlorophenyl)-1-hydroxy-1-methyl-2-propynyl]phenyl-2-isopropoxypropanoic acid

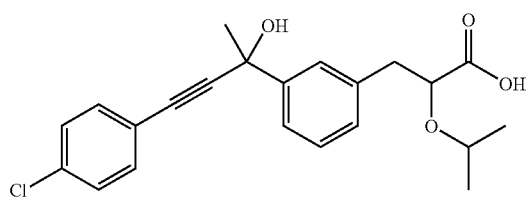

12 mg of Ethyl 3-3-[1-hydroxy-1-methyl-2-propynyl]phenyl-2-isopropoxypropanoate, 20 mg of 4-iodochlorobenzene, 5 mg of copper iodide, 5 mg of tetrakis(triphenylphosphine)palladium and 50 μl of triethylamine were dissolved in 0.2 ml of N,N-dimethylformamide, and the mixture was stirred at room temperature for 2 days under nitrogen atmosphere. The reaction mixture was diluted with ethyl acetate and washed with water and 1N hydrochloric acid. The organic layer was dried over anhydrous magnesium sulfate, filtered, and the solvent was distilled off, to give ethyl 3-3-[3-(4-chlorophenyl)-1-hydroxy-1-methyl-2-propynyl]phenyl-2-isopropoxypropanoate. This product was dissolved in 0.4 ml of ethanol, and 0.1 ml of 5N-sodium hydroxide was added, and the mixture was kept still at room temperature overnight. The reaction solution was acidified by adding 1N-hydrochloric acid, and extracted with ethyl acetate. The residue was purified by reverse-phase high performance liquid chromatography, to give 4.07 mg of the title compound.

MS m/e (ESI) 409 (MNa⁺)

Example A-113

3-3-[3-(4-Trifluoromethylphenyl)-1-hydroxy-1-methyl-2-propynyl]phenyl-2-isopropoxypropanoic acid

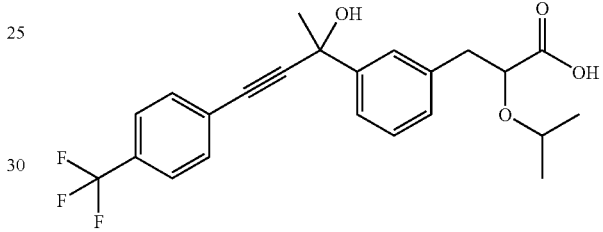

Using 4-iodobenzotrifluoride, the title compound was obtained in the same manner as described in Production Example 122d).

¹H NMR (CDCl₃)

δ: 1.06 (d, J=6.4 Hz, 3H) 1.15 (d, J=6.0 Hz, 3H) 1.87 (s, 3H) 2.27 (s, 1H) 3.00 (ddd, J=2.4, 8.0, 13.6 Hz, 1H) 3.17 (dd, J=3.6, 14.0 Hz, 1H) 3.52-3.59 (m, 1H) 4.14-4.18 (m, 1H) 7.21 (d, J=7.6 Hz, 1H) 7.33 (dd, J=7.6, 8.8 Hz, 1H) 7.57-7.61 (m, 6H)

MS m/e (ESI) 443 (MNa⁺)

Example A-114

3-3-[3-(3-Trifluoromethylphenyl)-1-hydroxy-1-methyl-2-propynyl]phenyl-2-isopropoxypropanoic acid

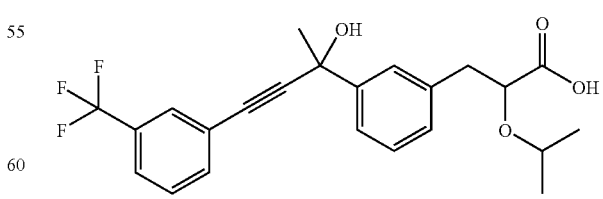

Using 3-iodobenzotrifluoride, the title compound was obtained in the same manner as described in Production Example 122d).

MS m/e (ESI) 443 (MNa⁺)

Example A-115

3-3-[3-(2,4-Dichlorophenyl)-1-hydroxy-1-methyl-2-propynyl]phenyl-2-isopropoxypropanoic acid

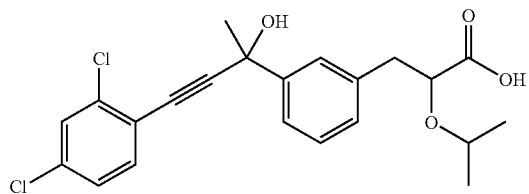

Using 2,4-dichloroiodobenzene, the title compound was obtained in the same manner as described in Production Example 122d).

MS m/e (ESI) 443 (MNa$^+$)

Example A-116

3-3-[3-(3,4-Dichlorophenyl)-1-hydroxy-1-methyl-2-propynyl]phenyl-2-isopropoxypropanoic acid

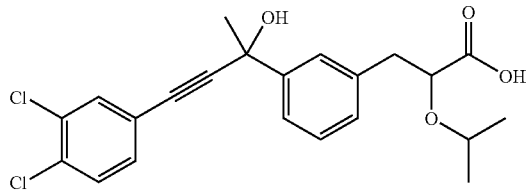

Using 3,4-dichloroiodobenzene, the title compound was obtained in the same manner as described in Production Example 122d).

$^1$H NMR (CDCl$_3$)
δ: 1.01, 1.02 (each d, J=6.4 Hz and 6.0 Hz, 3H) 1.15 (d, J=6.4 Hz, 3H) 1.85 (s, 3H) 2.05 (s, 1H) 3.01 (dd, J=8.0, 14.0 Hz, 1H) 3.18 (dd, J=4.0, 13.2 Hz, 1H) 3.56 (Sept, J=6.0 Hz, 1H) 4.17 (dd, J=3.6, 7.6 Hz, 1H) 7.21 (d, J=8.0 Hz, 1H) 7.28-7.35 (m, 2H) 7.40 (d, J=8.8 Hz, 1H) 7.54-7.59 (m, 3H)

MS m/e (ESI) 443 (MNa$^+$)

Example A-117

2-Isopropoxy-3-4-methoxy-3-[([2-(trifluoromethyl)benzyl]oxyimino)methyl]phenylpropanoic acid

Production Example A-117a

[(5-Bromo-2-methoxybenzyl)oxy](t-butyl)dimethylsilane

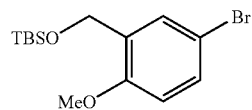

14 g of 2-Methoxybenzyl alcohol was dissolved in 200 ml of N,N-dimethylformamide, and 19.5 g of t-butyl chlorodimethylsilane and 13.6 g of imidazole were added. After stirring was continued at room temperature overnight, the solution was diluted with ethyl acetate, and washed successively with 1N hydrochloric acid and saturated brine. The organic layer was dried over anhydrous magnesium sulfate, and the solvent was evaporated. Then, the resulting crude product was dissolved in 200 ml of acetonitrile, and 21 g of N-bromosuccinimide was added under ice-cooling. After stirring was continued at room temperature for 5 hours, the solvent was evaporated. The residue was dissolved in ethyl acetate, and washed successively with water and saturated brine. The organic layer was dried over anhydrous magnesium sulfate, and the solvent was evaporated. The residue was purified by silica gel column chromatography, to give 26 g of the title compound in the 2:1 hexane-diethyl ether fraction.

$^1$H-NMR (CDCl$_3$)
δ: 0.12 (s, 6H) 0.96 (s, 9H) 3.80 (s, 3H) 4.70 (s, 2H) 6.68 (d, J=8.4 Hz, 1H) 7.31 (dd, J=1.6, 8.4 Hz, 1H) 7.56 (d, J=1.6 Hz, 1H)

Production Example A-117b 3-({[1-t-Butyl-1,1-dimethylsilyl]oxy}methyl)-4-methoxybenzaldehyde

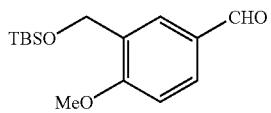

12 g of [(5-Bromo-2-methoxybenzyl)oxy](t-butyl)dimethylsilane was dissolved in 150 ml of tetrahydrofuran, and the mixture was cooled to −78° C. under nitrogen atmosphere. To the mixture was added 28 ml of butyl lithium (1.52M solution in hexane), and the mixture was stirred for 30 minutes, and then a solution of 8.3 g of 4-formylmorpholine in 10 ml of tetrahydrofuran was added. After stirring was continued at −78° C. for 1 hour, 1N-hydrochloric acid was added thereto. The mixture was extracted with ethylacetate, and the organic layer was washed with water and saturated brine, dried over anhydrous magnesium sulfate, and the solvent was evaporated. The residue was purified by silica gel column chromatography, to give 5.8 g of the title compound in the hexane-ethyl acetate (5:1) fraction.

$^1$H-NMR (CDCl$_3$)
δ: 0.12 (s, 6H) 0.93 (s, 9H) 3.91 (s, 3H) 4.76 (s, 2H) 6.94 (d, J=8.4 Hz, 1H) 7.80 (dd, J=1.6, 8.4 Hz, 1H) 8.01 (d, J=1.6 Hz, 1H) 9.90 (s, 1H)

Production Example A-117c

Ethyl 3-[3-({[1-t-butyl-1,1-dimethylsilyl]oxy}methyl)-4-methoxyphenyl]-2-isopropoxypropanoate

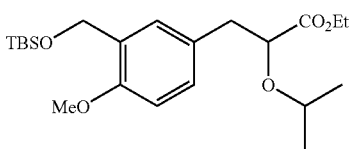

Using 3-({[1-t-butyl-1,1-dimethylsilyl]oxy}methyl)-4-methoxybenzaldehyde and diethyl 2-isopropoxyphosphonoacetate, the title compound was obtained in the same manner as described in Production examples 46a) and 46b).

Production Example A-117d

Ethyl 3-[3-(hydroxymethyl)-4-methoxyphenyl]-2-isopropoxypropanoate

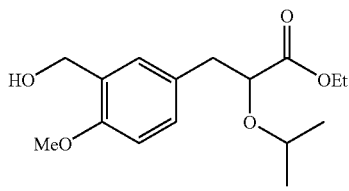

3.4 g of Ethyl 3-[3-({[1-t-butyl-1,1-dimethylsilyl]oxy}methyl)-4-methoxyphenyl]-2-isopropoxypropanoate was dissolved in 40 ml of tetrahydrofuran, and 9.4 ml of tetrabutylammonium fluoride (1M solution in tetrahydrofuran) was added. After stirring was continued at room temperature overnight, the reaction mixture was diluted with ethyl acetate, and the organic layer was washed with water and saturated brine, and dried over anhydrous magnesium sulfate. After evaporating the solvent, the residue was purified by silica gel column chromatography, to give 1.5 g of the title compound in the 2:1 hexane-ethyl acetate fraction.

$^1$H-NMR (CDCl$_3$)
δ: 0.97 (d, J=6.0 Hz, 3H) 1.15 (d, J=6.0 Hz, 3H) 1.24 (t, J=7.2 Hz, 3H) 2.88 (dd, J=8.4, 14.0 Hz, 1H) 2.95 (dd, J=5.2, 14.0 Hz, 1H) 3.50 (sept, J=6.0 Hz, 1H) 3.85 (s, 3H) 4.00 (dd, J=5.2, 8.4 Hz, 1H) 4.11-4.21 (m, 2H) 4.65 (d, J=6.4 Hz, 2H) 6.79 (d, J=8.8 Hz, 1H) 7.14-7.15 (m, 2H)

Production Example A-117e

Ethyl 3-[3-(formyl)-4-methoxyphenyl]-2-isopropoxypropanoate

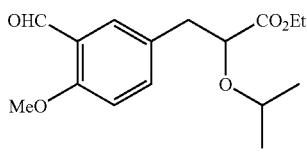

826 mg of Ethyl 3-[3-(hydroxymethyl)-4-methoxyphenyl]-2-isopropoxypropanoate was dissolved in 20 ml of dichloromethane, and 390 mg of N-methylmorpholine N-oxide, 1.4 g of molecular sieve 4A and 49 mg of tetrapropylammonium perruthenate were added, and the mixture was stirred at room temperature overnight. The reaction mixture was filtered through Celite, the filtrate was concentrated, and the residue was purified by silica gel column chromatography, to give 782 mg of the title compound in the 5:1→2:1 hexane-ethyl acetate fraction.

$^1$H NMR (CDCl$_3$)
δ: 0.95 (d, J=6.0 Hz, 3H) 1.15 (d, J=6.0 Hz, 3H) 1.25 (t, J=7.2 Hz, 3H) 2.91 (dd, J=8.8, 14.0 Hz, 1H) 2.99 (dd, J=4.8, 14.0 Hz, 1H) 3.51 (Sept, J=6.0 Hz, 1H) 3.91 (s, 3H) 4.02 (dd, J=4.4, 8.4 Hz, 1H) 4.11-4.20 (m, 2H) 6.92 (dd, J=2.4, 8.4 Hz, 1H) 7.46 (dd, J=2.4, 8.4 Hz, 1H) 7.72 (d, J=2.4 Hz, 1H) 10.45 (s, 1H)

Production Example A-117f

2-Isopropoxy-3-4-methoxy-3-[([2-(trifluoromethyl)benzyl]oxyimino)methyl]phenylpropanoic acid

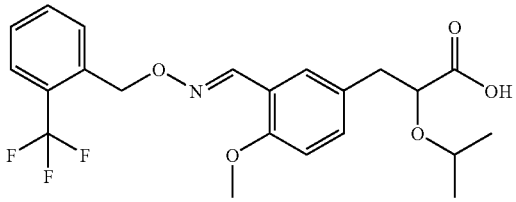

138 mg of Ethyl 3-[3-(formyl)-4-methoxyphenyl]-2-isopropoxypropanoate was dissolved in 2 ml of ethanol and 0.5 ml of water, and 40 mg of hydroxylamine hydrochloride and 70 ml sodium acetate were added, and the mixture was stirred at room temperature for 15 minutes. The reaction mixture was diluted with ethyl acetate, and washed with water and 1N hydrochloric acid. The organic layer was dried over anhydrous magnesium sulfate, filtered, and the solvent was distilled off, to give 178 mg of ethyl 3-[3-(hydroxyiminomethyl)-4-methoxyphenyl]-2-isopropanoate. 12 mg of this compound was dissolved in 0.2 ml of tetrahydrofuran, and 20 mg of 2-trifluoromethylbenzyl bromide and 10 mg sodium hydride were added, and the mixture was stirred at room temperature overnight. To the reaction mixture were added 0.4 ml of ethanol and 0.1 ml of 5N-sodium hydroxide, and the mixture was stirred at room temperature for 4 hours. Then the reaction mixture was neutralized with 1N-hydrochloric acid, extracted with ethyl acetate, and the solvent was concentrated. The residue was purified by reverse-phase high performance liquid chromatography, to give 2.1 mg of the title compound.

MS m/e (ESI) 440 (MH$^+$)

Example A-118

2-Isopropoxy-3-4-methoxy-3-[([3-(trifluoromethyl)benzyl]-oxyimino)methyl]phenylpropanoic acid

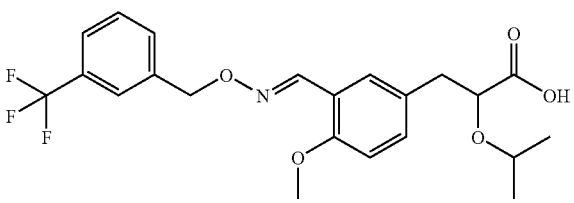

Using 3-trifluoromethylbenzyl bromide, the title compound was obtained in the same manner as described in Production Example A-117f).

MS m/e (ESI) 440 (MH$^+$)

Example A-119

2-Isopropoxy-3-4-methoxy-3-[([4-(trifluoromethyl)benzyl]oxyimino)methyl]-phenylpropanoic acid

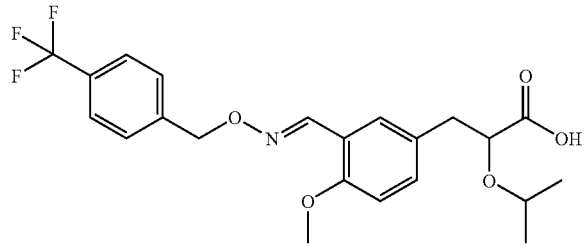

Using 4-trifluoromethylbenzyl bromide, the title compound was obtained in the same manner as described in Production Example A-117f).

MS m/e (ESI) 440 (MH⁺)

Example A-120

2-Isopropoxy-3-4-methoxy-3-[([4-bromo-2-fluorobenzyl]oxyimino)methyl]phenylpropanoic acid

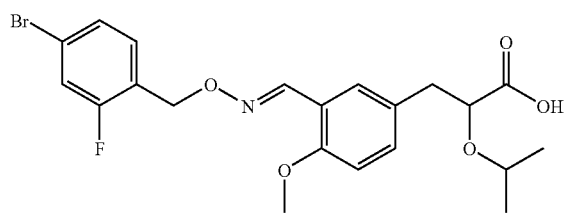

Using 4-bromo-2-fluorobenzyl bromide, the title compound was obtained in the same manner as described in Production Example A-117f).

MS m/e (ESI) 468 (MH⁺)

Example A-121

2-Isopropoxy-3-4-methoxy-3-[([2,6-dichlorobenzyl]oxyimino)methyl]phenylpropanoic acid

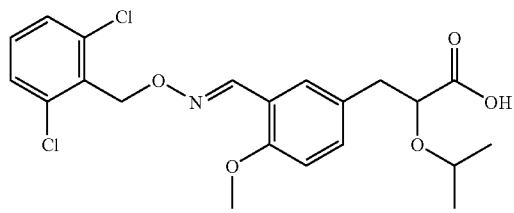

Using 2,6-dichlorobenzyl bromide, the title compound was obtained in the same manner as described in Production Example A-117f)

MS m/e (ESI) 440 (MH⁺).

Example A-122

2-Isopropoxy-3-4-methoxy-3-[([3,4-dichlorobenzyl]oxyimino)methyl]phenylpropanoic acid

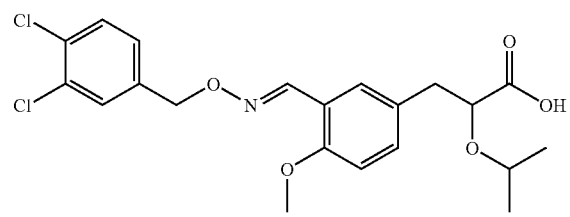

Using 3,4-dichlorobenzyl bromide, the title compound was obtained in the same manner as described in Production Example A-117f).

MS m/e (ESI) 440 (MH⁺)

Example 123

2-Isopropoxy-3-4-methoxy-3-[([4-ethylbenzyl]oxyimino)methyl]phenylpropanoic acid

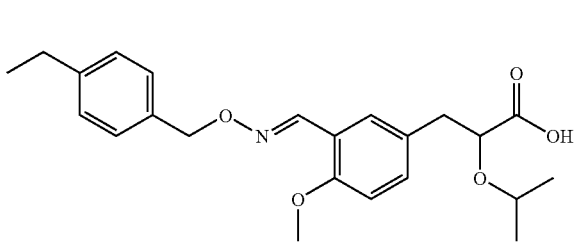

Using 4-ethylbenzyl bromide, the title compound was obtained in the same manner as described in Production Example A-117f).

MS m/e (ESI) 400 (MH⁺)

Example 124

2-Isopropoxy-3-4-methoxy-3-[([2-naphytyl]oxyimino)methyl]phenylpropanoic acid

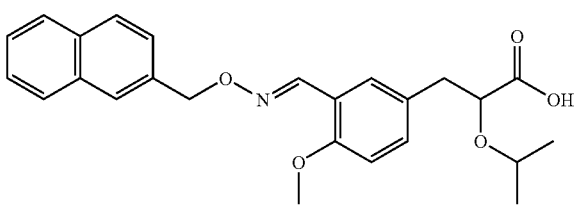

Using 2-bromomethylnaphthalene, the title compound was obtained in the same manner as described in Production Example A-117f)

MS m/e (ESI) 422 (MH⁺).

Example 125

2-Isopropoxy-3-4-methoxy-3-[([2-phenylbenzyl]oxyimino)methyl]phenylpropanoic acid

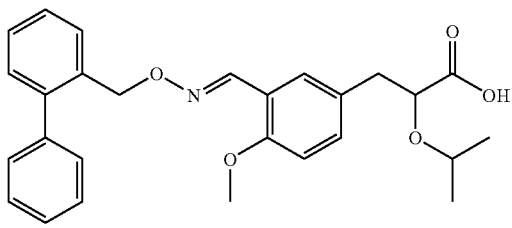

Using 2-phenylbenzyl bromide, the title compound was obtained in the same manner as described in Production Example A-117f).

MS m/e (ESI) 448 (MH$^+$)

Example 126

2-Isopropoxy-3-4-methoxy-3-[([4-t-butylbenzyl]oxyimino)methyl]phenylpropanoic acid

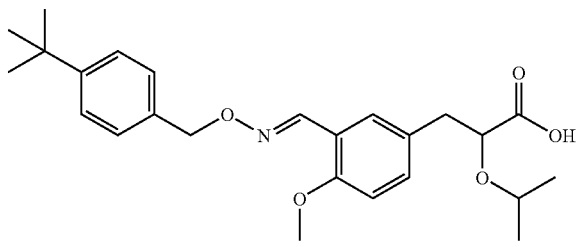

Using 4-t-butylbenzyl chloride, the title compound was obtained in the same manner as described in Production Example A-117f).

MS m/e (ESI) 428 (MH$^+$)

Example 127

2-Isopropoxy-3-4-methoxy-3-[([4-phenylbenzyl]oxyimino)methyl]phenylpropanoic acid

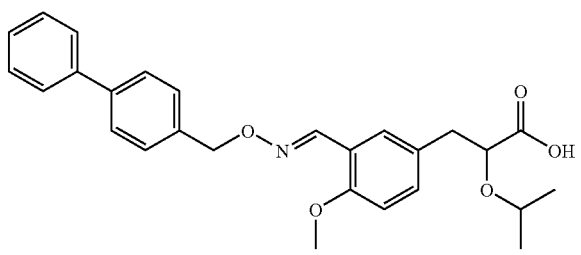

Using 4-phenylbenzyl chloride, the title compound was obtained in the same manner as described in Production Example A-117f)

MS m/e (ESI) 448 (MH$^+$).

Example 128

2-Isopropoxy-3-4-methoxy-3-[([2,4-dichlorobenzyl]oxyimino)methyl]phenylpropanoic acid

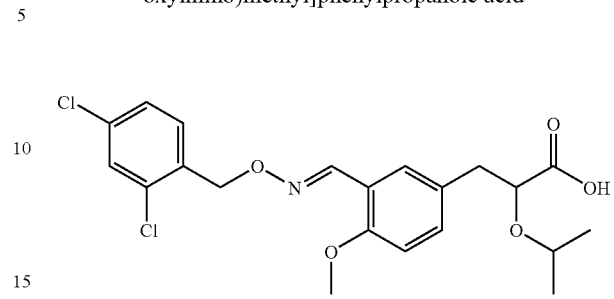

Using 2,4-dichlorobenzyl chloride, the title compound was obtained in the same manner as described in Production Example A-117f).

MS m/e (ESI) 440 (MH$^+$)

Example 129

2-Isopropoxy-3-4-methoxy-3-[([4-benzyloxybenzyl]oxyimino)methyl]phenylpropanoic acid

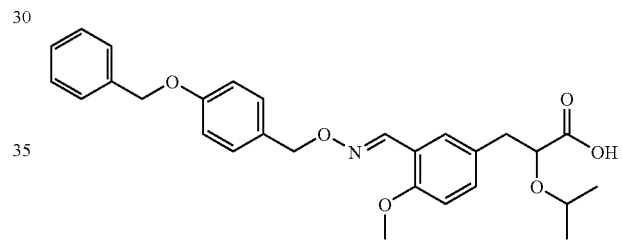

Using 4-benzyloxybenzyl chloride, the title compound was obtained in the same manner as described in Production. Example A-117f).

MS m/e (ESI) 478 (MH$^+$)

Example 130

2-Isopropoxy-3-[3-([2-(trifluoromethyl)benzyl]-oxy-ethaneimidoyl)phenyl]propanoic acid

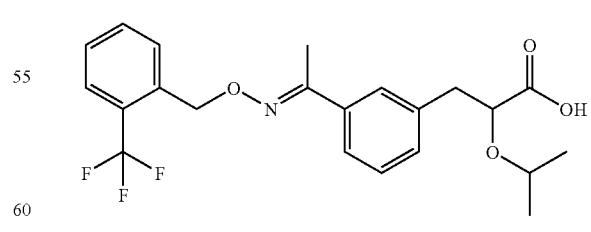

Using ethyl 3-(3-acetylphenyl)-2-isopropanoate and 2-trifluoromethylbenzyl bromide, the title compound was obtained in the same manner as described in Production Example A-117f).

MS m/e (ESI) 424 (MH$^+$)

Example 131

2-Isopropoxy-3-[3-([3-(trifluoromethyl)-benzyl]oxy-ethaneimidoyl)phenyl]propanoic acid

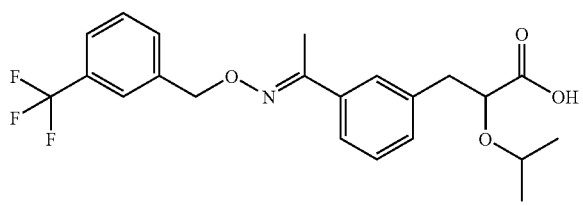

Using 3-trifluoromethylbenzyl bromide, the title compound was obtained in the same manner as described in Production Example A-117f).
MS m/e (ESI) 424 (MH$^+$)

Example 132

2-Isopropoxy-3-[3-([4-(trifluoromethyl)benzyl]-oxy-ethaneimidoyl)phenyl]propanoic acid

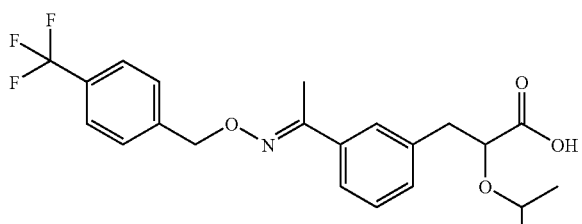

Using 4-trifluoromethylbenzyl bromide, the title compound was obtained in the same manner as described in Production Example A-117f).
$^1$H NMR (CDCl$_3$)
δ: 0.98 (d, J=6.0 Hz, 3H) 1.14 (d, J=6.4 Hz, 3H) 2.28 (s, 3H) 2.96 (dd, J=8.0, 14.0 Hz, 1H) 3.15 (dd, J=3.6, 14.0 Hz, 1H) 3.52 (Sept, J=6.4 Hz, 1H) 4.13 (dd, J=4.0, 8.4 Hz, 1H) 5.29 (s, 2H) 7.23-7.27 (m, 2H) 7.30 (t, J=7.2 Hz, 1H) 7.51 (d, J=7.6 Hz, 1H) 7.53 (d, J=6.0 Hz, 1H) 7.62 (d, J=8.0 Hz, 1H)
MS m/e (ESI) 424 (MH$^+$)

Example 133

2-Isopropoxy-3-[3-([3,4-(dichloro)benzyl]-oxyetha-neimidoyl)phenyl]propanoic acid

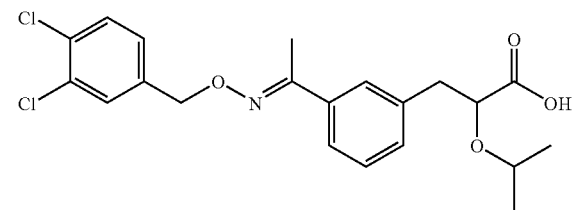

Using 3,4-dichlorobenzyl bromide, the title compound was obtained in the same manner as described in Production Example A-117f).
MS m/e (ESI) 424 (MH$^+$)

Example 134

2-Isopropoxy-3-[3-([2,6-(dichloro)benzyl]-oxyetha-neimidoyl)phenyl]propanoic acid

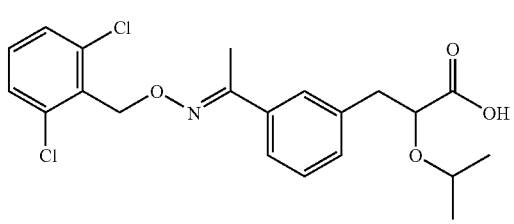

Using 2,6-dichlorobenzyl bromide, the title compound was obtained in the same manner as described in Production Example A-117f).
MS m/e (ESI) 424 (MH$^+$)

Example 135

2-Isopropoxy-3-[3-([2,4-(dichloro)benzyl]-oxyetha-neimidoyl)phenyl]propanoic acid

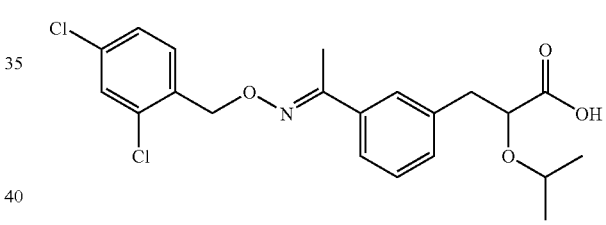

Using 2,4-dichlorobenzyl chloride, the title compound was obtained in the same manner as described in Production Example A-117f).
MS m/e (ESI) 424 (MH$^+$)

Example 136

2-Isopropoxy-3-[3-([4-bromo-2-fluorobenzyl]-oxy-ethaneimidoyl)phenyl]propanoic acid

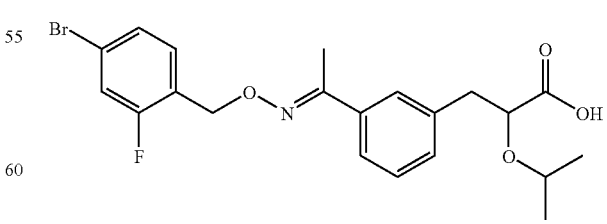

Using 4-bromo-2-fluorobenzyl bromide, the title compound was obtained in the same manner as described in Production Example A-117f).
MS m/e (ESI) 452 (MH$^+$).

Example 137

3-[3-({[(Benzyloxy)carbonyl]amino}methyl)-4-methoxyphenyl]-2-isopropoxypropanoic acid Production Example 137a) t-Butyl N-(2-methoxybenzyl) carbamate

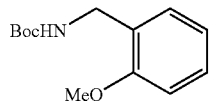

13.0 g of 2-methoxybenzylamine was dissolved in 80 ml of tetrahydrofuran, and a solution of 16 g of t-butyl dicarbonate in tetrahydrofuran (20 ml) was added. After stirring was continued at room temperature for 1 hour, the solvent was evaporated. The residue was dissolved in ethyl acetate, and successively washed with 1N hydrochloric acid and saturated brine. The organic layer was dried over anhydrous magnesium sulfate, and the solvent was evaporated, to give 19.0 g of the title compound.

$^1$H-NMR (CDCl$_3$)

δ: 1.45 (s, 9H) 3.84 (s, 3H) 4.27-4.33 (m, 2H) 5.01 (br, 1H) 6.84 (d, J=8.8 Hz, 1H) 6.94 (t, J=8.8 Hz, 1H) 7.23-7.29 (m, 2H)

Production Example 137b t-Butyl N-(5-bromo-2-methoxybenzyl)carbamate

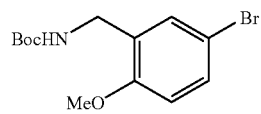

6.04 g of t-Butyl N-(2-methoxybenzyl)carbamate was dissolved in 50 ml of acetonitrile, and 4.6 g of N-bromosuccinimide was added. After stirring was continued at room temperature for 3 hours, the solvent was evaporated. The residue was dissolved in ethyl acetate, and washed successively with water and saturated brine. The organic layer was dried over anhydrous magnesium sulfate, and the solvent was evaporated. The residue was washed with a mixed solution of methyl t-butyl ether and hexane, to give 6.97 g of the title compound.

$^1$H-NMR (CDCl$_3$)

δ: 1.45 (s, 9H) 3.62 (s, 3H) 4.26 (d, J=6.4 Hz, 2H) 4.97 (br, 1H) 6.72 (d, J=8.8 Hz, 1H) 7.34 (dd, J=2.8, 11.2 Hz) 7.35 (s, 1H)

Production Example 137c t-Butyl N-(5-formyl-2-methoxybenzyl)carbamate

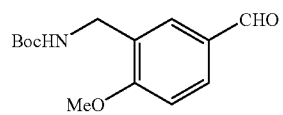

1.015 g of t-Butyl N-(5-bromo-2-methoxybenzyl) carbamate, 45 mg of dichlorobis(triphenylphosphine)palladium (II), 330 mg of sodium formate and 17 mg of triphenylphosphine were dissolved in anhydrous N,N-dimethylformamide, and the mixture was stirred at 110° C. for 2 hours under carbon monoxide atmosphere. The reaction mixture was diluted with ethyl acetate, and washed with water and saturated aqueous sodium bicarbonate. The organic layer was dried over anhydrous magnesium sulfate, and the solvent was evaporated. The residue was purified by silica gel column chromatography, to give 640 mg of the title compound in the hexane-ethyl acetate (3:1) fraction.

$^1$H-NMR (CDCl$_3$)

δ: 1.45 (s, 9H) 3.94 (s, 3H) 4.36 (d, J=6.0 Hz, 2H) 5.00 (br, 1H) 6.98 (d, J=8.4 Hz, 1H) 7.80-7.83 (m, 2H) 9.88 (s, 1H)

Production Example 137d

Ethyl 3-(3-[t-butoxycarbonylamino]methyl-4-methoxyphenyl)-3-hydroxy-2-isopropoxypropanoate

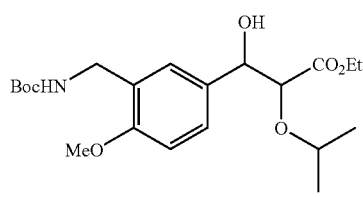

Under nitrogen atmosphere, 80 ml of sodium hexamethyldisilazane (1M solution in tetrahydrofuran) was diluted with 40 ml of tetrahydrofuran, and the mixture was cooled to −78° C., and a solution of 11.68 g of ethyl 2-isopropoxyacetate in tetrahydrofuran (10 ml) was added. After stirring was continued for 30 minutes, a solution containing 10.73 g of t-butyl N-(5-formyl-2-methoxybenzyl) carbamate in tetrahydrofuran (10 ml) was added. After stirring for another 1 hour, 100 ml of saturated aqueous ammonium chloride was added. The reaction solution was poured into 400 ml of water and 500 ml of ethyl acetate for separation, and the organic layer was dried over anhydrous magnesium sulfate. The solvent was evaporated, and the residue was purified by silica gel column chromatography (elution solvent: hexane-ethyl acetate), to give 12.8 g of the title compound (mixture of erythro form and threo form) as a colorless oil.

$^1$H-NMR (CDCl$_3$)

δ: 0.99 (d, J=6.1 Hz, 3H) 1.15 (d, J=6.1 Hz, 3H) 1.19 (t, J=7.6 Hz, 3H) 1.44 (s, 9H) 2.91 (d, J=5.2 Hz, 1H) 3.43 (sept, J=6.1 Hz, 1H) 3.83 (s, 3H) 4.03 (d, J=6.3 Hz, 1H) 4.12 (q, J=7.6 Hz, 2H) 4.29 (d, J=6.6 Hz, 2H) 4.86 (dd, J=5.2, 6.3 Hz, 1H) 4.99 (t, J=6.6 Hz, 1H) 6.81 (d, J=8.7 Hz, 1H) 7.23-7.29 (m, 2H) δ: 1.11 (t, J=6.9 Hz, 3H) 1.17 (d, J=6.1 Hz, 3H) 1.19 (d, J=6.1 Hz, 3H) 1.44 (s, 9H) 3.00 (d, J=4.4 Hz, 1H) 3.63 (sept, J=6.1 Hz, 1H) 3.83 (s, 3H) 3.95 (d, J=5.9 Hz, 1H) 4.08 (q, J=6.9 Hz, 2H) 4.29 (d, J=6.6 Hz, 2H) 4.80 (dd, J=4.4, 5.9 Hz, 1H) 4.99 (t, J=6.6 Hz, 1H) 6.81 (d, J=8.7 Hz, 1H) 7.23-7.29 (m, 2H)

Production Example 137e

Ethyl 3-[3-(aminomethyl)-4-methoxyphenyl]-2-isopropoxypropanoate

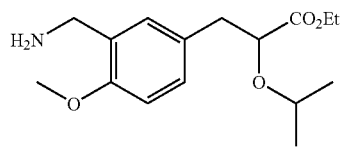

24.7 g of Ethyl 3-(3-[(t-butoxycarbonyl)amino]methyl-4-methoxyphenyl)-3-hydroxy-2-isopropoxypropanoate (mixture of erythro form and threo form) was dissolved in 400 ml of trifluoroacetic acid, and 96 ml of triethylsilane was added, and the mixture was stirred for 38 hours. The solvent was evaporated, and the residue was dissolved in 300 ml of 3N hydrochloric acid and 200 ml of hexane. The aqueous layer was washed with 100 ml of hexane, basified with 5N sodium hydroxide solution, and extracted with dichloromethane (200 ml×4). The organic layers were combined and dried over anhydrous magnesium sulfate, to give 13.0 g of the title compound as a pale yellow oil.

$^1$H-NMR (CDCl$_3$)

δ: 0.96 (d, J=6.0 Hz, 3H) 1.15 (d, J=6.0 Hz, 3H) 1.25 (t, J=7.2 Hz, 3H) 2.88 (dd, J=8.8, 13.6 Hz, 1H) 2.95 (dd, J=4.8, 13.6 Hz, 1H) 3.50 (sept, J=6.0 Hz, 1H) 3.84 (s, 3H) 4.00 (dd, J=4.8, 8.8 Hz, 1H) 4.15-4.21 (m, 2H) 4.32 (s, 2H) 6.83 (d, J=8.0 Hz, 1H) 7.14 (d, J=2.0 Hz, 1H) 7.20 (dd, J=2.0, 8.0 Hz, 1H)

Example 137f

3-[3-({[(Benzyloxy)carbonyl]amino}methyl)-4-methoxyphenyl]-2-isopropoxypropanoic acid

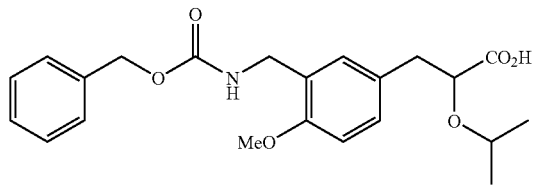

4.327 g of Ethyl 3-[3-(aminomethyl)-4-methoxyphenyl]-2-isopropanoate was dissolved in 30 ml of ethyl acetate and 10 ml of water, and 2 g of sodium hydrogen carbonate and 2 ml of benzylchloroformate were added, and the mixture was stirred at room temperature for 1 hour. The reaction mixture was diluted with ethyl acetate, washed with water and saturated brine, dried over anhydrous magnesium sulfate, filtered, and the solvent was distilled off, to give ethyl 3-[3-({[(benzyloxy)carbonyl]amino}methyl)-4-methoxyphenyl]-2-isopropoxypropanoate. This product was dissolved in 60 ml of ethanol and 15 ml of 5N-sodium hydroxide, and the mixture was kept still at room temperature for 1 hour. The reaction mixture was acidified with 1N-hydrochloric acid, and extracted with ethyl acetate. The organic layer was dried over anhydrous magnesium sulfate, filtered, and the solvent was distilled off, to give 4.75 g of the title compound.

MS m/e (ESI) 401 (MH$^+$)

Example 138

2-Isopropoxy-3-(3-{[({[3-(trifluoromethyl)benzyl]oxy}carbonyl)amino]methyl}phenyl)propanoic acid Production Example 138a t-Butyl N-(3-bromobenzyl)carbamate

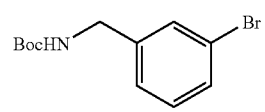

26.25 g of 3-Bromobenzylamine hydrochloride was suspended in 250 ml of dichloromethane, and the mixture was cooled to 0° C. 33.5 g of N,N-diisopropylethylamine and 28.3 g of t-butyl dicarbonate were added. After stirring was continued at room temperature overnight, the reaction mixture was diluted with ethyl acetate. The solution was washed with water and saturated brine, dried over anhydrous magnesium sulfate, filtered, and the solvent was distilled off, to give 31.28 g of the title compound.

$^1$H-NMR (CDCl$_3$)

δ: 1.45 (s, 9H) 4.28 (d, J=6.0 Hz, 2H) 4.87 (brs, 1H) 7.20 (m, 2H) 7.38 (m, 1H) 7.43 (brs, 1H)

Production Example 138b t-Butyl N-(3-formylbenzyl) carbamate

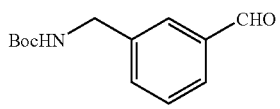

8.58 g of t-Butyl N-(3-bromobenzyl) carbamate was dissolved in 100 ml of tetrahydrofuran, and the mixture was cooled to −78° C. under nitrogen atmosphere. 41 ml of butyl lithium (1.56 M solution in hexane) was added. After stirring was continued for 30 minutes, 6.91 g of N-formylmorpholine was added. After stirring was continued at −78° C. for 30 minutes, 1N-hydrochloric acid was added, and the mixture was extracted with ethyl acetate. The solution was dried over anhydrous magnesium sulfate, filtered, and the solvent was distilled off, and the residue was purified by silica gel column chromatography, to give 4.762 g of the title compound in the 3:1→3:2 hexane-ethyl acetate fraction.

$^1$H-NMR (CDCl$_3$)

δ: 1.44 (s, 9H) 4.40 (d, J=6.0 Hz, 2H) 4.95 (br, 1H) 7.50 (m, 1H) 7.56-7.59 (m, 1H) 7.78-7.80 (m, 1H) 7.80 (s, 1H) 10.01 (s, 1H)

Production Example 138c

Ethyl (E,Z)-3-(3-{[(t-butoxycarbonyl)amino]methyl}phenyl)-2-isopropoxy-2-propenoate

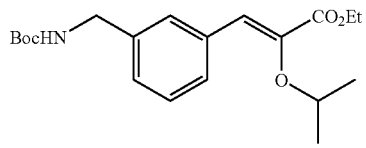

Using t-butyl N-(3-formylbenzyl)carbamate and ethyl 2-(diethoxyphosphoryl)-2-isopropoxyacetate, the title compound was obtained in the same manner as described in Production example 46a).

Production Example 138d

Ethyl 3-(3-{[(t-butoxycarbonyl)amino]methyl}phenyl)-2-isopropoxypropanoate

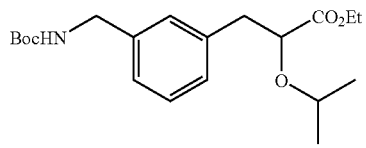

Using ethyl (E,Z)-3-(3-{[(t-butoxycarbonyl)amino]methyl}phenyl)-2-isopropoxy-2-propenoate, the title compound was obtained in the same manner as described in Production example 46b).

$^1$H-NMR (CDCl$_3$)

δ: 0.95 (d, J=6.0 Hz, 3H) 1.15 (d, J=6.0 Hz, 3H) 1.24 (t, J=7.2 Hz, 3H) 1.46 (s, 9H) 2.93 (dd, J=8.4, 14.0 Hz, 1H) 3.07 (dd, J=4.8, 14.0 Hz, 1H) 3.49 (sept, J=6.4 Hz, 1H) 4.04 (dd, J=4.8, 8.4 Hz, 1H) 4.12-4.19 (m, 2H) 4.30 (d, J=5.2 Hz, 2H) 4.80 (br, 1H) 7.12-7.16 (m, 3H) 7.23 (d, J=8.0 Hz, 1H)

Production Example 138e

Ethyl 3-[3-(ammoniomethyl)phenyl]-2-isopropoxypropanoate hydrochloride

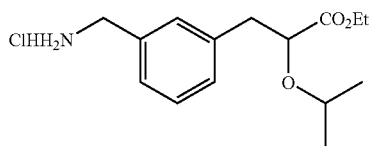

4.67 g of Ethyl 3-(3-{[(t-butoxycarbonyl)amino]methyl}phenyl)-2-isopropoxypropanoate was dissolved in 50 ml of trifluoroacetic acid, and the mixture was kept still at room temperature overnight. The solvent was concentrated and dried, and concentrated by adding 10 ml of 4N-hydrogen chloride ethyl acetate solution, to give 6.931 g of the title compound.

$^1$H-NMR (CDCl$_3$)

δ: 0.97 (d, J=6.0 Hz, 3H) 1.10 (d, J=6.0 Hz, 3H) 1.25 (t, J=7.2 Hz, 3H) 2.87 (m, 2H) 3.52 (m, 1H) 4.10 (t, J=6.0 Hz, 2H) 4.50 (q, J=7.2 Hz, 2H) 7.20 (m, 2H) 7.34 (m, 1H)

Example 138f

2-Isopropoxy-3-(3-{[({[3-(trifluoromethyl)benzyl]oxy}-carbonyl)amino]methyl}phenyl)propanoic acid

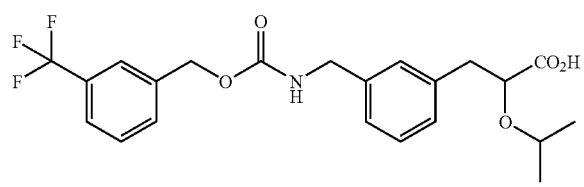

20 mg of Ethyl 3-[3-(ammoniomethyl)phenyl]-2-isopropoxypropanoate chloride was dissolved in 0.5 ml of N,N-dimethylformamide which was saturated in advance with carbon dioxide by adding dry ice, and 150 mg of cesium carbonate and 200 mg of tetrabutylammonium iodide were added, and the mixture was stirred at room temperature for 30 minutes. 40 mg of 3-trifluoromethylbenzyl bromide was added, and stirring was continued at room temperature for 3 hours. To the reaction mixture was added ethyl acetate, and the mixture was washed with water. The solvent was concentrated, and the residue was treated with 0.4 ml of ethanol and 0.1 ml of 5N-sodium hydroxide, and the mixture was kept still at room temperature for 30 minutes. The solution was neutralized with 1N-hydrochloric acid, and extracted with ethyl acetate. The solvent was distilled off, and the residue was purified by reverse-phase high performance liquid chromatography, to give 1.09 mg of the title compound.

MS m/e (ESI) 440 (MH$^+$)

Example 139

2-Isopropoxy-3-(3-{[({[4-(trifluoromethyl)benzyl]oxy}-carbonyl)amino]methyl}phenyl)propanoic acid

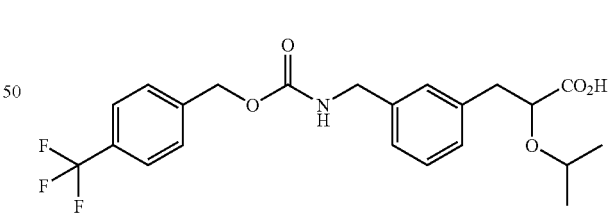

Using 4-trifluoromethylbenzyl bromide, the title compound was obtained in the same manner as described in Example 138f)

$^1$H-NMR (CDCl$_3$)

δ: 1.01 (d, J=6.0 Hz, 3H) 1.15 (d, J=6.0 Hz, 3H) 2.95 (dd, J=8.0, 14.4 Hz, 1H) 3.12 (dd, J=1.6, 14.8 Hz, 1H) 3.54 (sept, J=6.4 Hz, 1H) 4.13 (dd, J=4.0, 8.0 Hz, 1H) 4.38 (d, J=6.4 Hz, 2H) 5.11 (br, 1H) 5.19 (s, 2H) 7.15-7.19 (m, 3H) 7.25-7.30 (m, 1H) 7.48 (d, J=8.8 Hz, 2H) 7.62 (d, J=8.4 Hz, 2H)

MS m/e (ESI) 440 (MH$^+$)

Example 140

2-Isopropoxy-3-(3-{[({[2,4-dichlorobenzyl] oxy}carbonyl)-amino]methyl}phenyl)propanoic acid

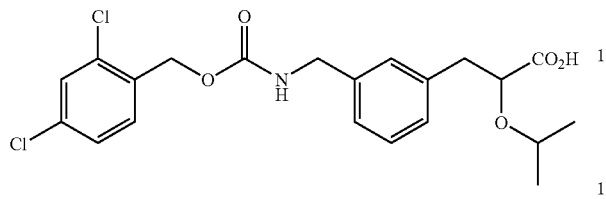

Using 2,4-dichlorobenzyl bromide, the title compound was obtained in the same manner as described in Example 138f).
MS m/e (ESI) 440 (MH⁺)

Example 141

2-Isopropoxy-3-(3-{[({[2,6-dichlorobenzyl] oxy}carbonyl)-amino]methyl}phenyl)propanoic acid

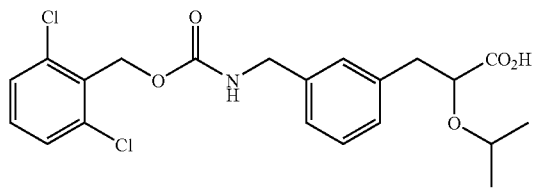

Using 2,6-dichlorobenzyl bromide, the title compound was obtained in the same manner as described in Example 138f).
MS m/e (ESI) 440 (MH⁺)

Example 142

2-Isopropoxy-3-(3-{[({[3,4-dichlorobenzyl] oxy}carbonyl)-amino]methyl}phenyl)propanoic acid

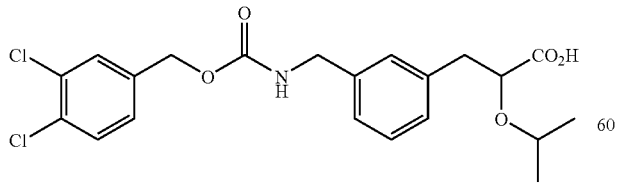

Using 3,4-dichlorobenzyl bromide, the title compound was obtained in the same manner as described in Example 138f).
MS m/e (ESI) 440 (MH⁺)

Example 143

2-Isopropoxy-3-[4-methoxy-3-({[5-(2-methyl-1,3-thiazol-4-yl)-2-thienyl]sulfonyl}oxy)phenyl]propanoic acid

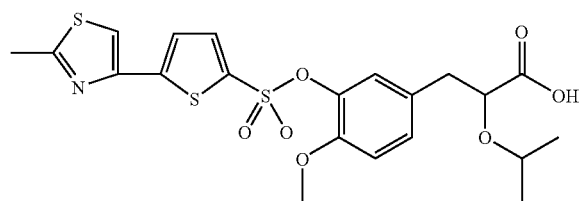

15 mg of Ethyl 3-(3-hydroxy-4-methoxyphenyl)-2-isopropoxypropanoate and 25 mg of 5-(2-methyl-1,3-thiazol-4-yl)-2-thiophenesulfonyl chloride were dissolved in 0.4 ml of dichloromethane, and 50 µl of triethylamine was added, and the mixture was kept still at room temperature overnight. To the reaction mixture was added ethyl acetate and the mixture was washed with water. The solvent was concentrated, and the residue was treated with 0.4 ml of ethanol and 0.1 ml of 5N-sodium hydroxide, and the mixture was kept still at room temperature for 30 minutes. The reaction mixture was neutralized with 1N-hydrochloric acid, extracted with ethyl acetate. The solvent was distilled off, and the residue was purified by reverse-phase high performance liquid chromatography, to give 5.8 mg of the title compound.
MS m/e (ESI) 498 (MH⁺)

Example 144

2-Isopropoxy-3-[3-({[5-(3-isoxazolyl)-2-thienyl] sulfonyl}-oxy)-4-methoxyphenyl]propanoic acid

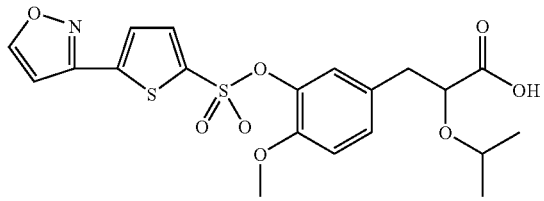

Using 5-(3-isoxazolyl)-2-thiophenesulfonyl chloride, the title compound was obtained in the same manner as described in Example 143.
MS m/e (ESI) 468 (MH⁺)

Example 145

3-(3-{[(4-Butoxyphenyl)sulfonyl]oxy}-4-methoxyphenyl)-2-isopropoxypropanoic acid

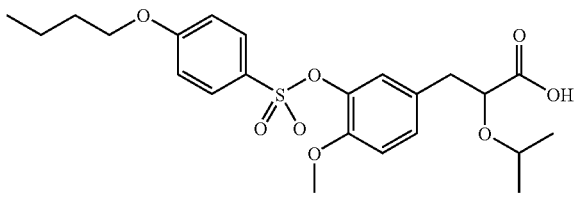

Using 4-butoxybenzenesulfonyl chloride, the title compound was obtained in the same manner as described in Example 143.

MS m/e (ESI) 467 (MH⁺)

Example 146

3-(3-{[(4-Biphenylsulfonyl)oxy]-4-methoxyphenyl]-2-isopropoxypropanoic acid

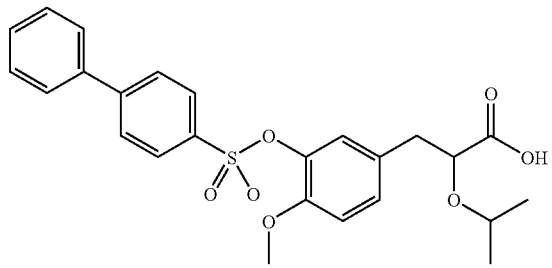

Using 4-biphenylsulfonyl chloride, the title compound was obtained in the same manner as described in Example 143.

MS m/e (ESI) 471 (MH⁺)

Example 147

2-Isopropoxy-3-{3-[({[4-(trifluoromethyl)anilino]-carbonyl}oxy)methyl]phenyl}propanoic acid

Production Example 147a 3-({[1-(t-Butyl)-1,1-dimethylsilyl]oxy}methyl)benzaldehyde

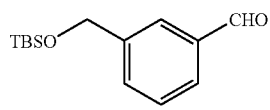

14 g of 3-Bromobenzyl alcohol was dissolved in 200 ml of N,N-dimethylformamide, and 15 g of t-butylchlorodimethyl silane and 10 g of imidazole were added. After stirring was continued at room temperature overnight, the solution was diluted with ethyl acetate, and washed successively with 1N hydrochloric acid and saturated brine. After drying the organic layer over anhydrous magnesium sulfate, the solvent was evaporated. The residue was purified by silica gel column chromatography, and 21 g of [(3-bromobenzyl)oxy] (t-butyl) dimethylsilane was obtained in the 4:1 hexane-ethyl acetate fraction. Then, the obtained 21 g of [(3-bromobenzyl)oxy] (t-butyl)dimethylsilane was dissolved in 300 ml of tetrahydrofuran, and the mixture was cooled to −78° C. under nitrogen atmosphere. 55 ml of butyl lithium (1.52 M solution in hexane) was added thereto, and the mixture was stirred for 30 minutes. A solution of 11.5 g of 4-formylmorpholine solution in 20 ml of tetrahydrofuran was added. After stirring was continued at −78° C. for 1 hour, 1N-hydrochloric acid was added, and the mixture was extracted with ethyl acetate. The organic layer was washed with water and saturated brine, dried over anhydrous magnesium sulfate, and the solvent was evaporated. The residue was purified by silica gel column chromatography, to give 14.7 g of the title compound in the 4:1 hexane-ethyl acetate fraction.

¹H-NMR (CDCl₃)

δ: 0.12 (s, 6H) 0.93 (s, 9H) 4.81 (s, 2H) 7.49-7.53 (m, 1H) 7.60-7.62 (m, 1H) 7.77 (d, J=7.6 Hz, 1H) 7.87 (s, 1H) 10.02 (s, 1H)

Production Example 147b

Ethyl 3-[3-(hydroxymethyl)phenyl]-2-isopropoxypropanoate

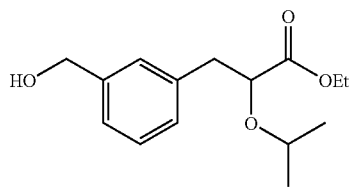

600 mg of Sodium hydride was suspended in 20 ml of tetrahydrofuran, and a solution of 4.2 g diethyl 2-isopropoxy-phosphonoacetate in 25 ml tetrahydrofuran was added under ice-cooling. After stirring was continued at room temperature for 30 minutes, a solution of 3.0 g of 3-({[1-(t-butyl)-1,1-dimethylsilyl]oxy}methyl)benzaldehyde in 25 ml of tetrahydrofuran was added. After stirring was continued at room temperature for 15 hours, to the reaction mixture was added 1N hydrochloric acid, and the mixture was extracted with ethylacetate. The organic layer was washed with water and saturated brine, dried over anhydrous magnesium sulfate, and the solvent was evaporated. The residue was purified by silica gel column chromatography, to give 3.4 g of ethyl (E,Z)-3-[3-({[1-(t-butyl)-1,1-dimethylsilyl]oxy}methyl)-phenyl]-2-isopropoxy 2-propenoate in the 4:1 hexane-ethyl fraction. Then the obtained 3.4 g of ethyl (E,Z)-3-[3-({[1-(t-butyl)-1,1-dimethylsilyl]oxy}methyl)-phenyl]-2-isopropoxy-2-propenoate was dissolved in 30 ml of tetrahydrofuran, and 13.5 ml tetrabutylammonium fluoride (1M solution in tetrahydrofuran) was added. After stirring was continued at room temperature overnight, the reaction mixture was diluted with ethyl acetate, and the organic layer was washed with water and saturated brine, and dried over anhydrous magnesium sulfate. The solvent was evaporated, and then the obtained crude product was dissolved in 25 ml of ethanol, and 0.30 g of 10% palladium carbon was added, and the mixture was stirred for 5 hours under hydrogen atmosphere. The catalyst was filtered off and the solvent was evaporated. The residue was purified by silica gel column chromatography, to give 1.1 g of the title compound in the 3:1 hexane-ethyl acetate fraction.

¹H-NMR (CDCl₃)

δ: 0.95 (d, J=6.4 Hz, 3H) 1.15 (d, J=6.4 Hz, 3H) 1.24 (t, J=6.8 Hz, 3H) 2.95 (dd, J=8.8, 13.6 Hz, 1H) 3.02 (dd, J=5.2, 13.6 Hz, 1H) 3.50 (sept, J=6.4 Hz, 1H) 4.05 (dd, J=5.2, 8.8 Hz, 1H) 4.14-4.20 (m, 2H) 4.67 (s, 2H) 7.17-7.30 (m, 4H)

Production Example 147c

Ethyl 2-isopropoxy-3-{3-[({[4-(trifluoromethyl)anilino]carbonyl}-oxy)methyl]phenyl}propanoate

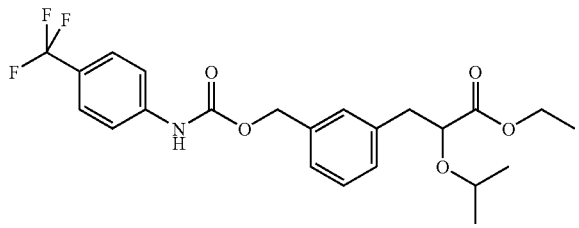

A suspension in tetrahydrofuran (2.0 ml) containing 100 mg of ethyl 3-[3-(hydroxymethyl)phenyl]-2-isopropoxypropanoate, 150 mg of α,α,α-trifluoro-p-tolylisocyanate and 35 μl of pyridine was stirred at room temperature for 14 hours. The solvent was removed, and the residue was treated with dichloromethane. After filtering off insoluble substances, the residue was purified by silica gel column chromatography, to give 149 mg of the title compound.
$^1$H-NMR (CDCl$_3$)
δ: 0.93 (d, J=6.0 Hz, 3H) 1.14 (d, J=6.0 Hz, 3H) 1.23 (t, J=7.2 Hz, 3H) 2.95 (dd, J=8.8, 13.6 Hz, 1H) 3.02 (dd, 4.8, 13.6 Hz, 1H) 3.49 (sept, J=6.0 Hz, 2H) 4.06 (dd, J=4.8, 8.8 Hz, 1H) 4.12-4.23 (m, 2H) 5.19 (s, 2H) 7.00 (br s, 1H) 7.22-7.32 (m, 4H) 7.51 (d, J=8.8 Hz, 2H) 7.56 (d, J=8.8 Hz, 2H)

Example 147d

2-Isopropoxy-3-{3-[({[4-(trifluoromethyl)anilino]carbonyl}-oxy)methyl]phenyl}propanoic acid

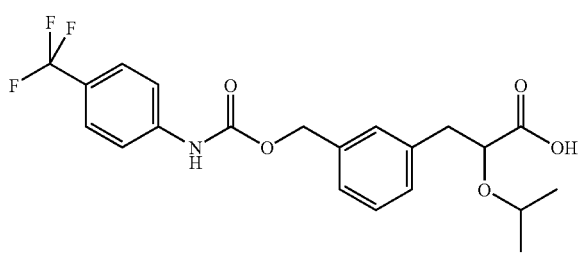

To 149 mg of Ethyl 2-isopropoxy-3-{3-[({[4-(trifluoromethyl)anilino]carbonyl}-oxy)methyl]phenyl}propanoate were added 4 ml of ethanol and 1.0 ml of 5N sodium hydroxide aqueous solution, and the mixture was stirred at room temperature for 20 hours. After the reaction solution was diluted with water, pH was adjusted to 5 with 5N hydrochloric acid, and the solution was diluted with ethyl acetate and saturated aqueous ammonium chloride. The organic layer was washed with saturated aqueous ammonium chloride, dried over anhydrous sodium sulfate, and concentrated. The residue was purified by silica gel column chromatography, to give 26 mg of the title compound
$^1$H-NMR (CDCl$_3$).

δ: 1.02 (d, J=6.0 Hz, 3H) 1.16 (d, J=6.0 Hz, 3H) 2.99 (dd, J=7.6, 14.0 Hz, 1H) 3.15 (dd, J=4.0, 14.0 Hz, 1H) 3.50-3.60 (m, 1H) 4.15 (dd, J=4.0, 7.6 Hz, 1H) 5.20 (s, 2H) 6.93 (br s, 1H) 7.16-7.35 (m, 4H) 7.51 (d, J=8.8 Hz, 2H) 7.57 (d, J=8.8 Hz, 2H)

MS m/e (ESI) 426 (MH$^+$)

Example 148

3-(3-{[(Anilinocarbonyl)oxy]methyl}phenyl)-2-isopropoxypropanoic acid

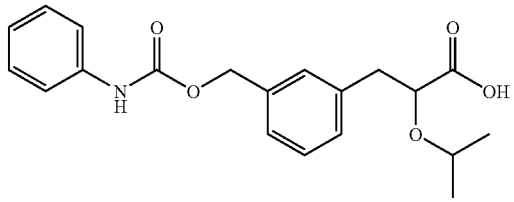

A suspension in tetrahydrofuran (0.6 ml) containing 20 μl of ethyl 3-[3-(hydroxymethyl)phenyl]-2-isopropoxypropanoate, 20 μl of phenylisocyanate and 5 μl of pyridine was stirred at room temperature for 11 hours. After the solvent was distilled off, the residue was treated with 0.4 ml of ethanol and 0.1 ml of 5N sodium hydroxide aqueous solution, and the mixture was stirred at room temperature for 1.5 hours. The reaction solution was diluted with water, and neutralized with 5N hydrochloric acid. The mixture was extracted with ethyl acetate and concentrated. Then, a half volume of the residue was purified by HPLC using a reverse-phase column and an elution solvent of water-acetonitrile-trifluoroacetic acid system, to give 6.02 mg of the title compound.

MS m/e (ESI) 358 (MH$^+$)

Example 149

3-[3-({[(4-Chloroanilino)carbonyl]oxy}methyl)phenyl]-2-isopropoxypropanoic acid

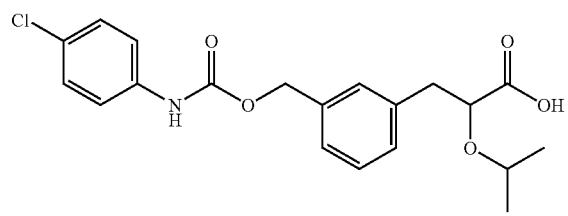

Using ethyl 3-[3-(hydroxymethyl)phenyl]-2-isopropoxypropanoate and 4-chlorophenylisocyanate, the title compound was obtained in the same manner as described in Example 148.

MS m/e (ESI) 392 (MH$^+$)

Example 150

2-Isopropoxy-3-(3-{[(4-toluidinocarbonyl)oxy]methyl}-phenyl)propanoic acid

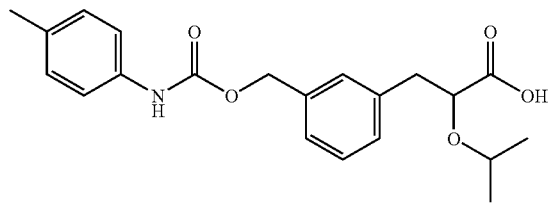

Using ethyl 3-[3-(hydroxymethyl)phenyl]-2-isopropoxypropanoate and p-tolylisocyanate, the title compound was obtained in the same manner as described in Example 148.

MS m/e (ESI) 372 (MH$^+$)

Example 151

2-Isopropoxy-3-[3-({[(4-methoxyanilino)carbonyl]oxy}-methyl)phenyl]propanoic acid

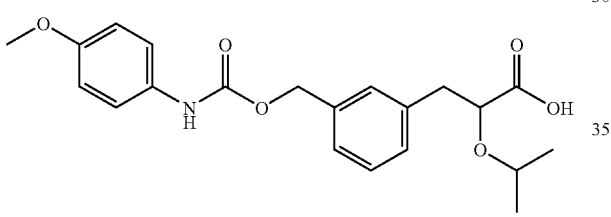

Using ethyl 3-[3-(hydroxymethyl)phenyl]-2-isopropoxypropanoate and 4-methoxyphenylisocyanate, the title compound was obtained in the same manner as described in Example 148.

MS m/e (ESI) 388 (MH$^+$)

Example 152

2-Isopropoxy-3-{3-[({[3-(trifluoromethyl)anilino]carbonyl}-oxy)methyl]phenyl}propanoic acid

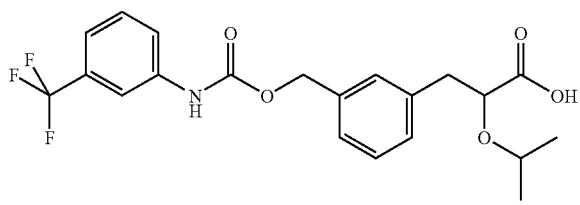

Using ethyl 3-[3-(hydroxymethyl)phenyl]-2-isopropoxypropanoate and α,α,α-trifluoro-m-tolylisocyanate, the title compound was obtained in the same manner as described in Example 148.

MS m/e (ESI) 426 (MH$^+$)

Example 153

3-[3-({[(2,4-Dichloroanilino)carbonyl]oxy}methyl)phenyl]-2-isopropoxypropanoic acid

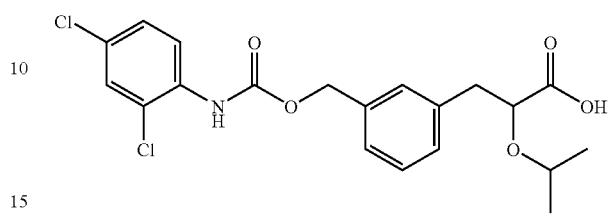

Using ethyl 3-[3-(hydroxymethyl)phenyl]-2-isopropoxypropanoate and 2,4-dichlorophenylisocyanate, the title compound was obtained in the same manner as described in Example 148.

MS m/e (ESI) 426 (MH$^+$)

Example 154

2-Isopropoxy-3-{3-[2-({[4-(trifluoromethyl)anilino]-carbonyl}oxy)ethyl]phenyl}propanoic acid Production Example 154a 3-(2-{[1-(t-Butyl)-1,1-diphenylsilyl]oxy}ethyl)benzaldehyde

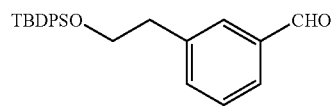

3-Bromophenethyl alcohol was dissolved in 110 ml of N,N-dimethylformamide, and 16 ml of t-butyl chlorodiphenyl silane and 8.3 g of imidazole were added. After stirring was continued at room temperature overnight, the solution was diluted with ethyl acetate, and washed successively with 1N hydrochloric acid and saturated brine. After drying the organic layer over anhydrous magnesium sulfate, the solvent was evaporated. The residue was purified by silica gel column chromatography, to give 22.1 g of [(3-bromophenethyl)oxy](t-butyl)diphenyl silane in the 4:1 hexane-ethyl acetate fraction. Then, the obtained 22.1 g of [(3-bromophenethyl)oxy](t-butyl) diphenyl silane was dissolved in 200 ml of tetrahydrofuran, and the mixture was cooled to −78° C. under nitrogen atmosphere. 37 ml of Butyl lithium (1.52 M solution in hexane) was added thereto, and the mixture was stirred for 30 minutes, and then 10 ml of 4-formylmorpholine was added. After stirring was continued at −78° C. for 1 hour, 1N-hydrochloric acid was added, and the mixture was extracted with ethyl acetate. The organic layer was washed with water and saturated brine, dried over anhydrous magnesium sulfate, and the solvent was evaporated. The residue was purified by silica gel column chromatography, to give 17 g of the title compound in the 4:1 hexane-ethyl acetate fraction.

$^1$H-NMR (CDCl$_3$)

δ: 0.12 (s, 6H) 0.93 (s, 9H) 4.81 (s, 2H) 7.49-7.53 (m, 1H) 7.60-7.62 (m, 1H) 7.77 (d, J=7.6 Hz, 1H) 7.87 (s, 1H) 10.02 (s, 1H)

Production Example 154b

Ethyl 3-[3-(2-hydroxyethyl)phenyl]-2-isopropoxypropanoate

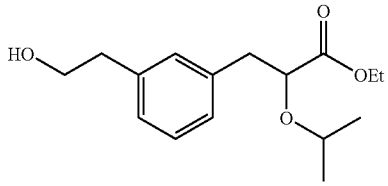

Using 3-(2-{[1-(t-butyl)-1,1-diphenylsilyl]oxy}ethyl) benzaldehyde and diethyl 2-isopropoxyphosphonoacetate, the title compound was obtained in the same manner as described in Production example 147b).

$^1$H-NMR (CDCl$_3$)

δ: 0.95 (d, J=6.4 Hz, 3H) 1.15 (d, J=6.4 Hz, 3H) 1.24 (t, J=6.8 Hz, 3H) 2.84 (t, J=6.4 Hz, 2H) 2.93 (dd, J=8.4, 14.0 Hz, 1H) 2.99 (dd, J=4.8, 14.0 Hz, 1H) 3.50 (sept, J=6.4 Hz, 1H) 3.84 (br, 2H) 4.05 (dd, J=4.8, 8.4 Hz, 1H) 4.14-4.20 (m, 2H) 7.08-7.13 (m, 3H) 7.22 (d, J=7.6 Hz, 1H)

Example 154c

2-Isopropoxy-3-{3-[2-({[4-(trifluoromethyl)anilino]-carbonyl}oxy)ethyl]phenyl}propanoic acid

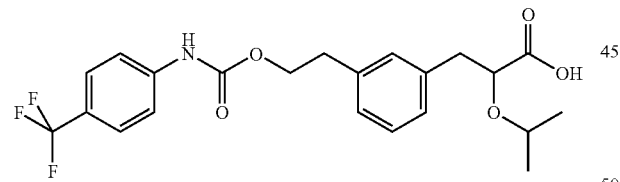

Using ethyl 3-[3-(2-hydroxyethyl)phenyl]-2-isopropoxypropanoate and α,α,α-trifluoro-p-tolylisocyanate, the title compound was obtained in the same manner as described in Example 148.

$^1$H-NMR (CDCl$_3$)

δ: 1.18 (d, J=6.0 Hz, 3H) 1.21 (d, J=6.0 Hz, 3H) 2.87-2.99 (m, 1H) 3.09 (d, J=5.2 Hz, 2H) 3.76 (sept, J=6.0 Hz, 1H) 4.14-4.23 (m, 1H) 4.26 (t, J=5.2 Hz, 1H) 4.46-4.53 (m, 1H) 7.09-7.15 (m, 3H) 7.25 (t, J=7.2 Hz, 1H) 7.53 (d, J=9.0 Hz, 2H) 7.56 (d, J=9.0 Hz, 2H) 7.67 (br s, 1H)

MS m/e (ESI) 440 (MH$^+$)

Example 155

3-(3-{2-[(Anilinocarbonyl)oxy]ethyl}phenyl)-2-isopropoxypropanoic acid

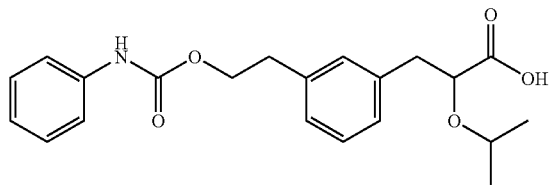

Using ethyl 3-[3-(2-hydroxyethyl)phenyl]-2-isopropoxypropanoate and phenylisocyanate, the title compound was obtained in the same manner as described in Example 148.

MS m/e (ESI) 372 (MH$^+$)

Example 156

3-[3-(2-{[(4-Chloroanilino)carbonyl]oxy}ethyl)phenyl]-2-isopropoxypropanoic acid

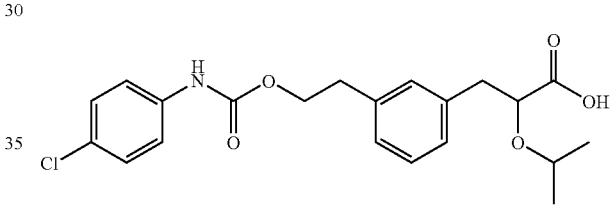

Using ethyl 3-[3-(2-hydroxyethyl)phenyl]-2-isopropoxypropanoate and 4-chlorophenylisocyanate, the title compound was obtained in the same manner as described in Example 148.

MS m/e (ESI) 406 (MH$^+$)

Example 157

2-Isopropoxy-3-(3-{2-[(4-toluidinocarbonyl)-oxy] ethyl}phenyl)propanoic acid

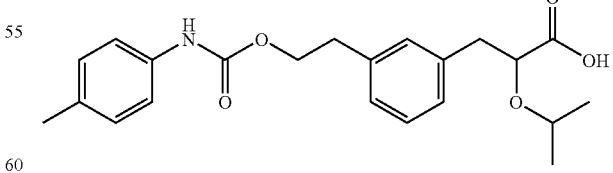

Using ethyl 3-[3-(2-hydroxyethyl)phenyl]-2-isopropoxypropanoate and p-tolylisocyanate, the title compound was obtained in the same manner as described in Example 148.

MS m/e (ESI) 386 (MH$^+$)

Example 158

2-Isopropoxy-3-[3-(2-{[(4-methoxyanilino)carbonyl]oxy}-ethyl)phenyl]propanoic acid

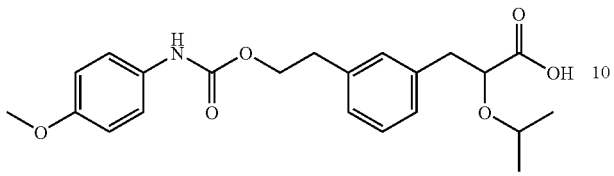

Using ethyl 3-[3-(2-hydroxyethyl)phenyl]-2-isopropoxypropanoate and 4-methoxyphenylisocyanate, the title compound was obtained in the same manner as described in Example 148.

MS m/e (ESI) 402 (MH$^+$)

Example 159

2-Isopropoxy-3-{3-[2-({[3-(trifluoromethyl)anilino]carbonyl}oxy)ethyl]phenyl}propanoic acid

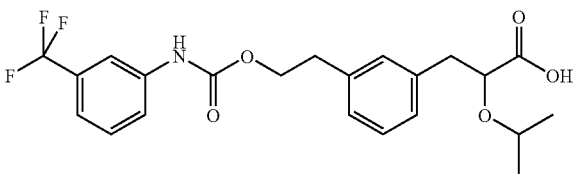

Using ethyl 3-[3-(2-hydroxyethyl)phenyl]-2-isopropoxypropanoate and α,α,α-trifluoro-m-tolylisocyanate, the title compound was obtained in the same manner as described in Example 148.

MS m/e (ESI) 440 (MH$^+$)

Example 160

2-Ethoxy-3-{3-[2-({[4-(trifluoromethyl)anilino]carbonyl}-oxy)ethyl]phenyl}propanoic acid

Production Example 160a

Ethyl 2-ethoxy-3-[3-(2-hydroxyethyl)phenyl]propanoate

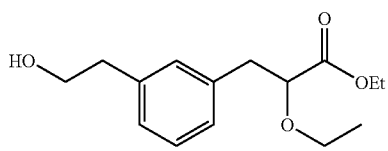

Using 3-(2-{[1-(t-butyl)-1,1-diphenylsilyl]oxy)ethyl)benzaldehyde and diethyl 2-ethoxyphosphono acetate, the title compound was obtained in the same manner as described in Production example 147b).

$^1$H-NMR (CDCl$_3$)

δ: 1.13 (t, J=6.8 Hz, 3H) 1.22 (t, J=7.2 Hz, 3H) 2.97 (t, J=6.8 Hz, 2H) 3.05 (dd, J=5.2, 14.0 Hz, 1H) 3.11 (dd, J=8.4, 14.0 Hz, 1H) 3.31 (dq, J=6.8, 8.8 Hz, 1H) 3.59 (dq, J=6.8, 8.8 Hz, 1H) 3.87 (dt, J=1.6, 6.8 Hz, 2H) 4.06 (dd, J=5.2, 8.4 Hz, 1H) 4.17 (q, J=7.2 Hz, 2H) 7.16-7.25 (m, 4H)

Example 160b

2-Ethoxy-3-{3-[2-({[4-(trifluoromethyl)anilino]carbonyl}-oxy)ethyl]phenyl}propanoic acid

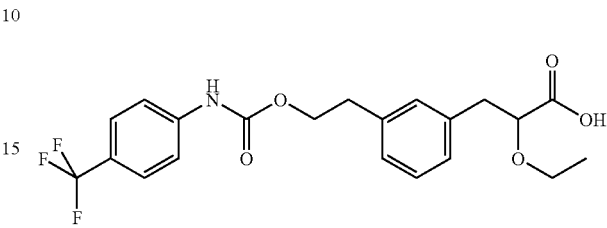

A suspension in tetrahydrofuran (0.6 ml) containing 14 mg of ethyl 2-ethoxy-3-[3-(2-hydroxyethyl)phenyl]propanoate, 20 μl of α,α,α-trifluorotolylisocyanate and 5 μl of pyridine was stirred at room temperature for 11 hours. After the solvent was distilled off, the residue was treated with 0.4 ml of ethanol and 0.1 ml of 5N sodium hydroxide aqueous solution, and the mixture was stirred at room temperature for 1.5 hours. The reaction solution was diluted with water, and neutralized with 5N hydrochloric acid. The mixture was extracted with ethylacetate, and concentrated. Then, a half volume of the residue was purified by HPLC using a reverse-phase column and an elution solvent of water-acetonitrile-trifluoroacetic acid system, to give 7.8 mg of the title compound.

MS m/e (ESI) 426 (MH$^+$)

Example 161

3-(3-{2-[(Anilinocarbonyl)oxy]ethyl}phenyl)-2-ethoxypropanoic acid

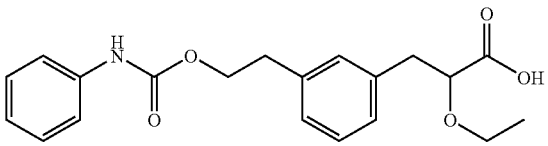

Using ethyl 2-ethoxy-3-[3-(2-hydroxyethyl)phenyl]propanoate and phenylisocyanate, the title compound was obtained in the same manner as described in Example 160b).

MS m/e (ESI) 358 (MH$^+$)

Example 162

3-[3-(2-{[(4-Chloroanilino)carbonyl]oxy}ethyl)phenyl]-2-ethoxypropanoic acid

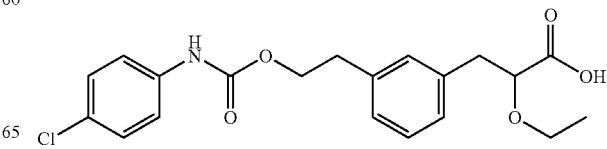

Using ethyl 2-ethoxy-3-[3-(2-hydroxyethyl)phenyl]propanoate and 4-chlorophenylisocyanate, the title compound was obtained in the same manner as described in Example 160b).

MS m/e (ESI) 392 (MH+)

Example 163

2-Ethoxy-3-(3-{2-[(4-toluidinocarbonyl)oxy]ethyl}phenyl)-propanoic acid

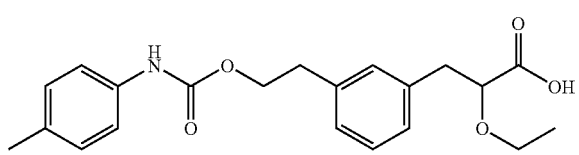

Using ethyl 2-ethoxy-3-[3-(2-hydroxyethyl)phenyl]propanoate and p-tolylisocyanate, the title compound was obtained in the same manner as described in Example 160b).

MS m/e (ESI) 372 (MH+)

Example 164

2-Ethoxy-3-[3-(2-{[(4-methoxyanilino)carbonyl]oxy}ethyl)-phenyl]propanoic acid

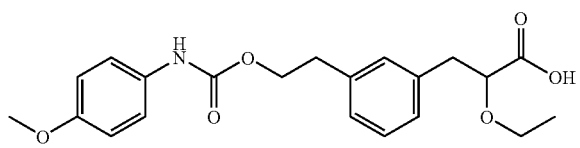

Using ethyl 2-ethoxy-3-[3-(2-hydroxyethyl)phenyl]propanoate and 4-methoxyphenylisocyanate, the title compound was obtained in the same manner as described in Example 160b).

MS m/e (ESI) 388 (MH+)

Example 165

2-Ethoxy-3-{3-[2-({[3-(trifluoromethyl)anilino]carbonyl}-oxy)ethyl]phenyl}propanoic acid

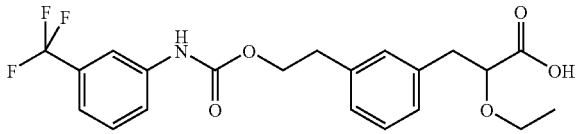

Using ethyl 2-ethoxy-3-[3-(2-hydroxyethyl)phenyl]propanoate and α,α,α-trifluoro-m-tolylisocyanate, the title compound was obtained in the same manner as described in Example 160b).

MS m/e (ESI) 426 (MH+)

Example 166

3-[3-(2-{[(2,4-Dichloroanilino)carbonyl]oxy}ethyl)phenyl]-2-ethoxypropanoic acid

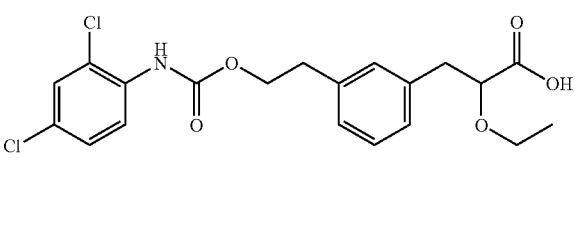

Using ethyl 2-ethoxy-3-[3-(2-hydroxyethyl)phenyl]propanoate and 2,4-dichlorophenylisocyanate, the title compound was obtained in the same manner as described in Example 160b).

MS m/e (ESI) 426 (MH+)

Example 167

2-Ethoxy-3-{3-[2-({[methyl-4-(trifluoromethyl)anilino]-carbonyl}oxy)ethyl]phenyl}propanoic acid

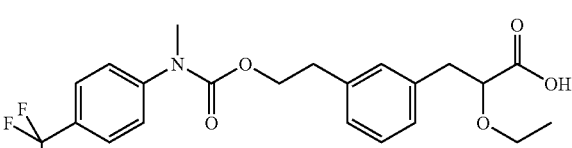

To a solution of another half amount of the residue in dimethylsulfoxide (0.5 ml) prior to HPLC purification in synthesis of 2-ethoxy-3-{3-[2-({[4-(trifluoromethyl)anilino]carbonyl}-oxy)ethyl]phenyl}propanoic acid were added 0.1 ml of methyl iodide and 10 ml sodium hydride in oil under ice-cooling, and the mixture was stirred for 12 hours while gradually raising the temperature to room temperature. The reaction solution was diluted with water and extracted with ethyl acetate. After concentrating the organic layer, the residue was treated with 0.4 ml of ethanol and 0.1 ml of 5N aqueous sodium hydroxide, and the mixture was stirred at room temperature for 1 hour. The reaction solution was diluted with water and neutralized with 5N hydrochloric acid. After extracting with ethyl acetate and concentration, the residue was purified by HPLC using a reverse-phase column and an elution solvent of water-acetonitrile-trifluoroacetic acid system, to give 3.4 mg of the title compound.

MS m/e (ESI) 440 (MH+)

Example 168

2-Ethoxy-3-[3-(2-{[(methylanilino)carbonyl]oxy}ethyl)-phenyl]propanoic acid

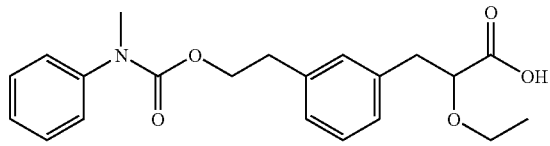

The title compound was obtained in the same manner as described in Example 167.
MS m/e (ESI) 372 (MH⁺)

Example 169

3-{3-[2-({[4-Chloro(methyl)anilino]carbonyl}oxy)ethyl]-phenyl}-2-ethoxypropanoic acid

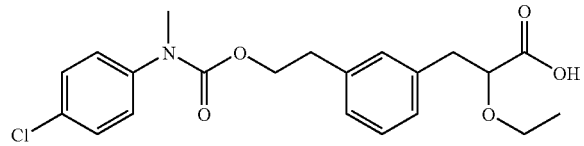

The title compound was obtained in the same manner as described in Example 167.
MS m/e (ESI) 406 (MH⁺)

Example 170

3-[3-(2-{[(N-Methyl-4-methylanilino)carbonyl]oxy}ethyl)-phenyl]-2-ethoxypropanoic acid

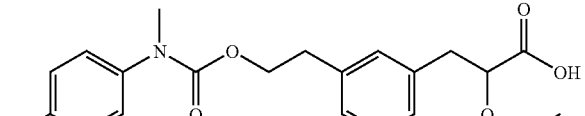

The title compound was obtained in the same manner as described in Example 167.
MS m/e (ESI) 386 (MH⁺)

Example 171

2-Ethoxy-3-{3-[2-({[4-methoxy(methyl)anilino]carbonyl}oxy)-ethyl]phenyl}propanoic acid

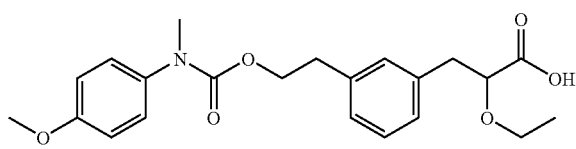

The title compound was obtained in the same manner as described in Example 167.
MS m/e (ESI) 402 (MH⁺)

Example 172

2-Ethoxy-3-{3-[2-({[methyl-3-(trifluoromethyl)anilino]-carbonyl}oxy)ethyl]phenyl}propanoic acid

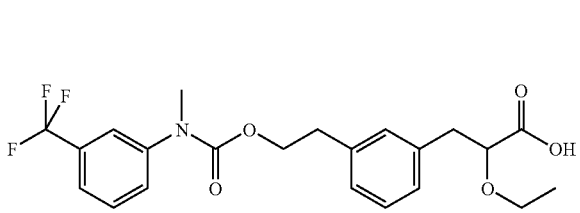

The title compound was obtained in the same manner as described in Example 167.
MS m/e (ESI) 440 (MH⁺)

Example 173

3-{3-[2-({[2,4-Dichloro(methyl)anilino]carbonyl}oxy)ethyl]-phenyl}-2-ethoxypropanoic acid

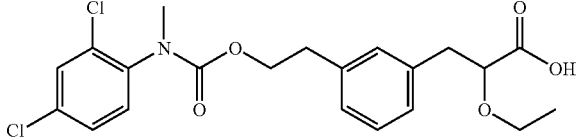

The title compound was obtained in the same manner as described in Example 167.
MS m/e (ESI) 440 (MH⁺)

Example 174

2-Isopropoxy-3-{4-methoxy-3-[({[4-(trifluoromethyl)-anilino]carbonyl}oxy)methyl]phenyl}propanoic acid

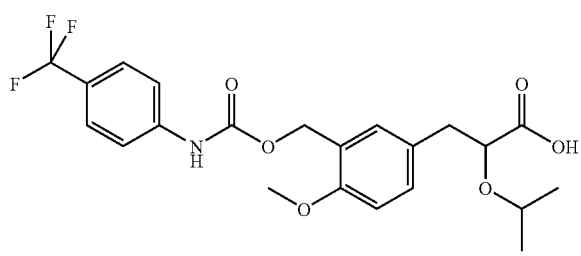

Using ethyl 3-[3-(hydroxymethyl)-4-methoxyphenyl]-2-isopropoxypropanoate and α,α,α-trifluoro-p-tolylisocyanate, the title compound was obtained in the same manner as described in Example 148.
MS m/e (ESI) 456 (MH$^+$)

Example 175

3-(3-{[(Anilinocarbonyl)oxy]methyl}-4-methoxyphenyl)-2-isopropoxypropanoic acid

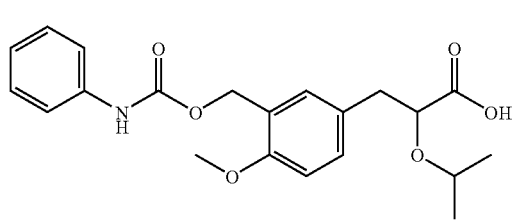

Using ethyl 3-[3-(hydroxymethyl)-4-methoxyphenyl]-2-isopropoxypropanoate and phenylisocyanate, the title compound was obtained in the same manner as described in Example 148.
MS m/e (ESI) 388 (MH$^+$)

Example 176

3-[3-({[(4-Chloroanilino)carbonyl]oxy}methyl)-4-methoxyphenyl]-2-isopropoxypropanoic acid

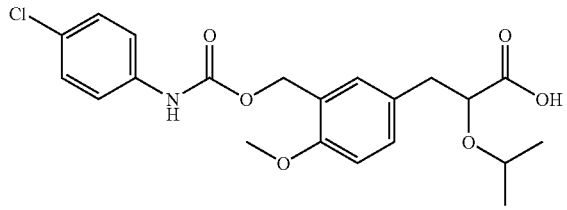

Using ethyl 3-[3-(hydroxymethyl)-4-methoxyphenyl]-2-isopropoxypropanoate and 4-chlorophenylisocyanate, the title compound was obtained in the same manner as described in Example 148.
MS m/e (ESI) 422 (MH$^+$)

Example 177

2-Isopropoxy-3-[4-methoxy-3-({[(4-methoxyanilino)carbonyl]-oxy}methyl)phenyl]propanoic acid

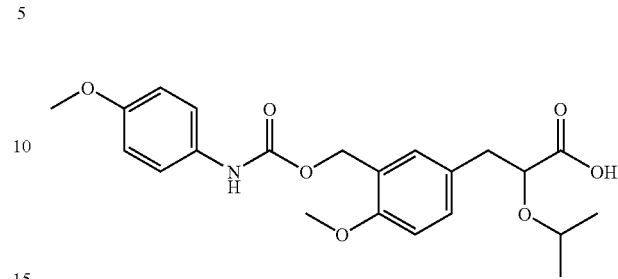

Using ethyl 3-[3-(hydroxymethyl)-4-methoxyphenyl]-2-isopropoxypropanoate and 4-methoxyphenylisocyanate, the title compound was obtained in the same manner as described in Example 148.
MS m/e (ESI) 418 (MH$^+$)

Example 178

2-Isopropoxy-3-{4-methoxy-3-[({[3-(trifluoromethyl)-anilino]carbonyl}oxy)methyl]phenyl}propanoic acid

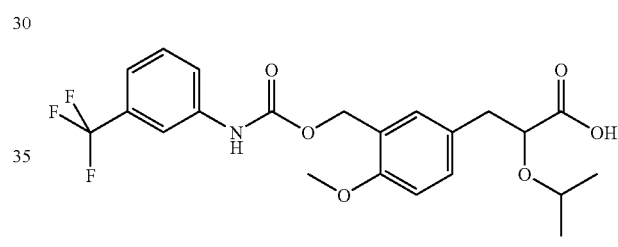

Using ethyl 3-[3-(hydroxymethyl)-4-methoxyphenyl]-2-isopropoxypropanoate and α,α,α-trifluoro-m-tolylisocyanate, the title compound was obtained in the same manner as described in Example 148.
MS m/e (ESI) 456 (MH$^+$)

Example 179

3-[3-({[(2,4-Dichloro)anilinocarbonyl]oxy}methyl)-4-methoxyphenyl]-2-isopropoxypropanoic acid

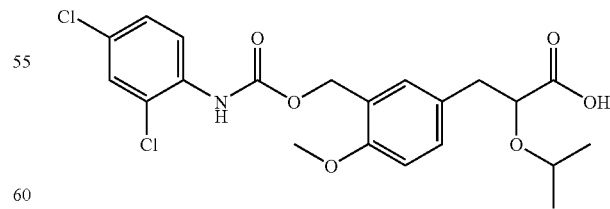

Using ethyl 3-[3-(hydroxymethyl)-4-methoxyphenyl]-2-isopropoxypropanoate and 2,4-dichlorophenylisocyanate, the title compound was obtained in the same manner as described in Example 148.
MS m/e (ESI) 456 (MH$^+$)

Example 180

2-Isopropoxy-3-[4-methoxy-3-(2-{[(3-methoxyanilino)-carbonyl]oxy}ethyl)phenyl]propanoic acid

Production Example 180a

[(5-Bromo-2-methoxyphenethyl)oxy]-(t-butyl)dimethylsilane

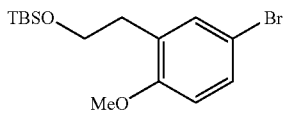

Using 2-methoxyphenethyl alcohol, the title compound was obtained in the same manner as described in Production example A-117a).
$^1$H-NMR (CDCl$_3$)
δ: 0.07 (s, 6H) 0.88 (s, 9H) 2.82 (t, J=6.8 Hz, 2H) 3.79 (t, J=6.8 Hz, 2H) 3.81 (s, 3H) 6.73 (d, J=8.4 Hz, 1H) 7.26-7.30 (m, 1H)

Production Example 180b 3-(2-{[1-(t-Butyl)-1,1-dimethylsilyl]oxy}ethyl)-4-methoxybenzaldehyde

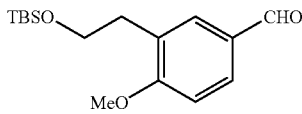

Using [(5-bromo-2-methoxyphenethyl)oxy](t-butyl)-dimethylsilane, the title compound was obtained in the same manner as described in Production example A-117b).
$^1$H-NMR (CDCl$_3$)
δ: 0.07 (s, 6H) 0.88 (s, 9H) 2.93 (t, J=6.8 Hz, 2H) 3.83 (t, J=6.8 Hz, 2H) 3.94 (s, 3H) 6.98 (d, J=8.4 Hz, 1H) 7.74 (d, J=2.4 Hz, 1H) 7.78 (dd, J=2.4, 8.4 Hz, 1H) 7.26-7.30 (m, 1H) 9.90 (s, 1H)

Production Example 180c

Ethyl 3-[3-(2-hydroxyethyl)-4-methoxyphenyl]-2-isopropoxypropanoate

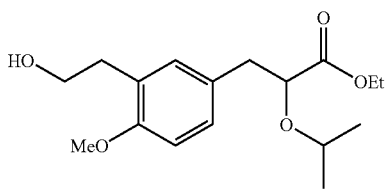

Using 3-(2-{[1-(t-butyl)-1,1-dimethylsilyl]oxy}ethyl)-4-methoxybenzaldehyde and diethyl 2-isopropoxyphosphonoacetate, the title compound was obtained in the same manner as described in Production example 147b)
$^1$H-NMR (CDCl$_3$).

δ: 0.98 (d, J=6.0 Hz, 3H) 1.15 (d, J=6.0 Hz, 3H) 1.24 (t, J=6.8 Hz, 3H) 2.85-2.95 (m, 4H) 3.51 (sept, J=6.0 Hz, 1H) 3.78-3.84 (m, 2H) 3.80 (s, 3H) 4.01 (dd, J=4.8, 8.0 Hz, 1H) 4.14-4.20 (m, 2H) 6.78 (d, J=8.4 Hz, 1H) 7.04 (d, J=2.0 Hz, 1H) 7.08 (dd, J=2.0, 8.4 Hz, 1H)

Example 180d

2-Isopropoxy-3-[4-methoxy-3-(2-{[(3-methoxyanilino)-carbonyl]oxy}ethyl)phenyl]propanoic acid

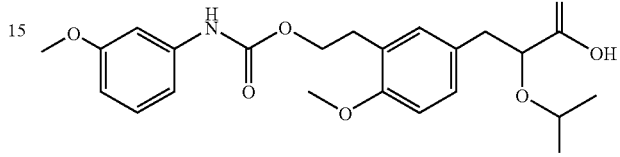

Using ethyl 3-[3-(2-hydroxyethyl)-4-methoxyphenyl]-2-isopropoxypropanoate and 3-methoxyphenylisocyanate, the title compound was obtained in the same manner as described in Example 148.
MS m/e (ESI) 432 (MH$^+$)

Example 181

3-[3-(2-{[(2,4-Difluoroanilino)carbonyl]oxy}ethyl)-4-methoxyphenyl]-2-isopropoxypropanoic acid

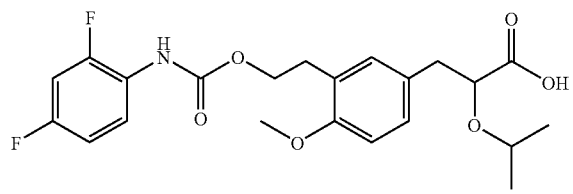

Using ethyl 3-[3-(2-hydroxyethyl)-4-methoxyphenyl]-2-isopropoxypropanoate and 2,4-difluorophenylisocyanate, the title compound was obtained in the same manner as described in Example 148.
MS m/e (ESI) 438 (MH$^+$)

Example 182

2-Isopropoxy-3-[4-methoxy-3-(2-{[(4-phenoxyanilino)-carbonyl]oxy}ethyl)phenyl]propanoic acid

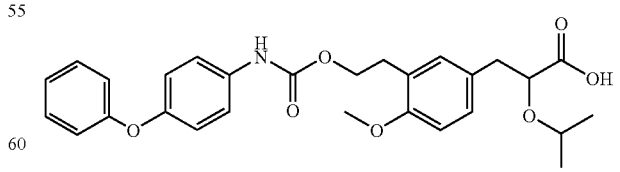

Using ethyl 3-[3-(2-hydroxyethyl)-4-methoxyphenyl]-2-isopropoxypropanoate and 4-phenoxyphenylisocyanate, the title compound was obtained in the same manner as described in Example 148.
MS m/e (ESI) 494 (MH$^+$)

Example 183

3-[3-(2-{[(4-Fluoroanilino)carbonyl]oxy}ethyl)-4-methoxyphenyl]-2-isopropoxypropanoic acid

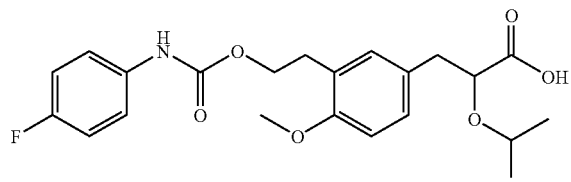

Using ethyl 3-[3-(2-hydroxyethyl)-4-methoxyphenyl]-2-isopropoxypropanoate and 4-fluorophenylisocyanate, the title compound was obtained in the same manner as described in Example 148.
MS m/e (ESI) 420 (MH$^+$)

Example 184

2-Isopropoxy-3-{4-methoxy-3-[2-({[4-(trifluoromethyl)-anilino]carbonyl}oxy)ethyl]phenyl}propanoic acid

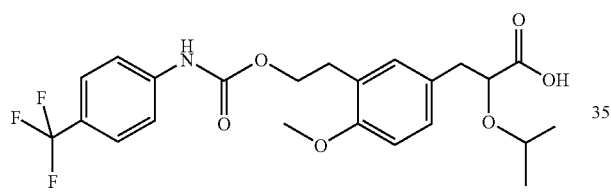

Using ethyl 3-[3-(2-hydroxyethyl)-4-methoxyphenyl]-2-isopropoxypropanoate and α,α,α-trifluoro-p-tolylisocyanate, the title compound was obtained in the same manner as described in Example 148.
MS m/e (ESI) 470 (MH$^+$)

Example 185

3-[3-(2-{[(3-Chloroanilino)carbonyl]oxy}ethyl)-4-methoxyphenyl]-2-isopropoxypropanoic acid

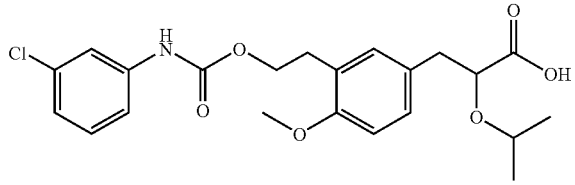

Using ethyl 3-[3-(2-hydroxyethyl)-4-methoxyphenyl]-2-isopropoxypropanoate and 3-chlorophenylisocyanate, the title compound was obtained in the same manner as described in Example 148.
MS m/e (ESI) 436 (MH$^+$)

Example 186

3-[3-(2-{[(2-Chloroanilino)carbonyl]oxy}ethyl)-4-methoxyphenyl]-2-isopropoxypropanoic acid

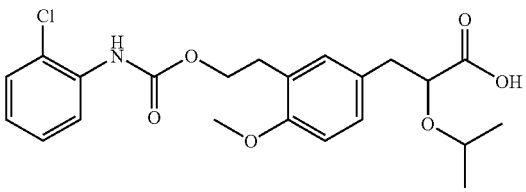

Using ethyl 3-[3-(2-hydroxyethyl)-4-methoxyphenyl]-2-isopropoxypropanoate and 2-chlorophenylisocyanate, the title compound was obtained in the same manner as described in Example 148.
MS m/e (ESI) 436 (MH$^+$)

Example 187

3-(3-{2-[(Anilinocarbonyl)oxy]ethyl}-4-methoxyphenyl)-2-isopropoxypropanoic acid

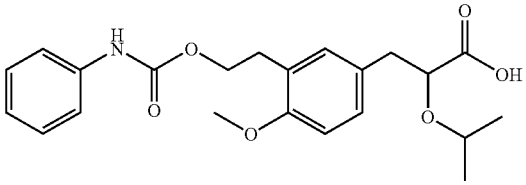

Using ethyl 3-[3-(2-hydroxyethyl)-4-methoxyphenyl]-2-isopropoxypropanoate and phenylisocyanate, the title compound was obtained in the same manner as described in Example 148.
MS m/e (ESI) 402 (MH$^+$)

Example 188

3-[3-(2-{[(4-Chloroanilino)carbonyl]oxy}ethyl)-4-methoxyphenyl]-2-isopropoxypropanoic acid

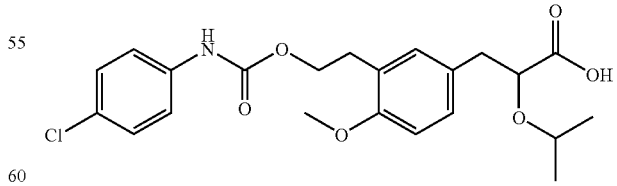

Using ethyl 3-[3-(2-hydroxyethyl)-4-methoxyphenyl]-2-isopropoxypropanoate and 4-chlorophenylisocyanate, the title compound was obtained in the same manner as described in Example 148.
MS m/e (ESI) 436 (MH$^+$)

Example 189

2-Isopropoxy-3-(4-methoxy-3-{2-[(4-toluidinocarbonyl)oxy]ethyl}phenyl)propanoic acid

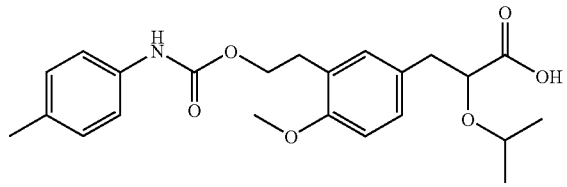

Using ethyl 3-[3-(2-hydroxyethyl)-4-methoxyphenyl]-2-isopropoxypropanoate and p-tolylisocyanate, the title compound was obtained in the same manner as described in Example 148.

MS m/e (ESI) 416 (MH+)

Example 190

2-Isopropoxy-3-[4-methoxy-3-(2-{[(4-methoxyanilino)-carbonyl]oxy}ethyl)phenyl]propanoic acid

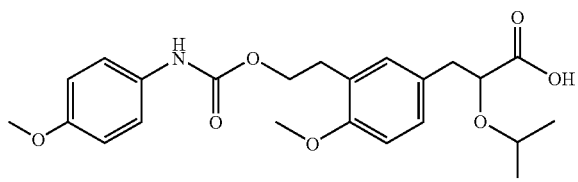

Using ethyl 3-[3-(2-hydroxyethyl)-4-methoxyphenyl]-2-isopropoxypropanoate and 4-methoxyphenylisocyanate, the title compound was obtained in the same manner as described in Example 148.

MS m/e (ESI) 432 (MH+)

Example 191

2-Isopropoxy-3-{4-methoxy-3-[2-({[3-(trifluoromethyl)-anilino]carbonyl}oxy)ethyl]phenyl}propanoic acid

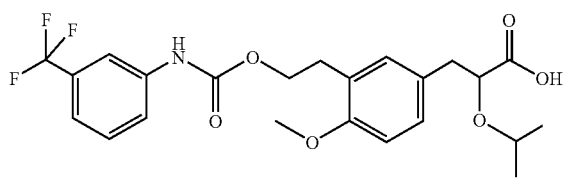

Using ethyl 3-[3-(2-hydroxyethyl)-4-methoxyphenyl]-2-isopropoxypropanoate and α,α,α-trifluoro-m-tolylisocyanate, the title compound was obtained in the same manner as described in Example 148.

MS m/e (ESI) 470 (MH+)

Example 192

Dimethyl 2-{3-[2-({[4-(trifluoromethyl)anilino]-carbonyl}oxy)methyl]benzyl}malonate

Production Example 192a

Dimethyl 2-[3-(hydroxymethyl)benzyl]malonate

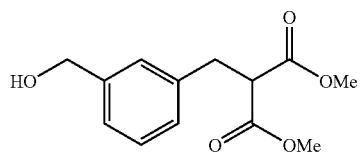

1.5 g of 3-({[1-(t-butyl)-1,1-dimethylsilyl]oxy}methyl)-benzaldehyde and 1.6 g of dimethyl malonate were dissolved in 20 ml of toluene, and 90 μl of piperidine and 52 μl of acetic acid were added thereto, and the mixture was heated at reflux using Dean-Stark equipment. After 9 hours, the solvent was evaporated, and the residue was purified by silica gel column chromatography, to give 5.8 g of dimethyl 2-{[3-({[1-(t-butyl)-1,1-dimethylsilyl]oxy}methyl)phenyl]methylene}malonate in the 4:1 hexane-ethyl acetate fraction. Then, the obtained 5.8 g of dimethyl 2-{[3-({[1-(t-butyl)-1,1-dimethylsilyl]oxy}-methyl)phenyl]methylene}malonate was dissolved in a mixture of 3 ml methanol and 15 ml of 1,4-dioxane, and 0.20 g of 10% palladium carbon was added thereto, and the mixture was stirred for 5 hours under hydrogen atmosphere. The catalyst was filtered off, and the solvent was evaporated. Then, the obtained crude product was dissolved in 12 ml of tetrahydrofuran, and 8.0 ml of tetrabutyl ammonium fluoride (1 M solution in tetrahydrofuran) was added thereto. After stirring was continued at room temperature overnight, the reaction mixture was diluted with ethyl acetate, and the organic layer was washed with water and saturated brine. After drying over anhydrous magnesium sulfate, the solvent was evaporated, and the residue was purified by silica gel column, to give 0.95 g of the title compound in the 2:1 hexane-ethyl acetate(2:1) fraction.

$^1$H-NMR (CDCl$_3$)

δ: 3.23 (d, J=8.0 Hz, 2H) 3.68 (t, J=8.0 Hz, 1H) 3.70 (s, 6H) 4.66 (d, J=4.4 Hz, 2H) 7.11-7.30 (m, 4H)

Example 192b

Dimethyl 2-{3-[2-({[4-(trifluoromethyl)-anilino]carbonyl}oxy)methyl]benzyl}malonate

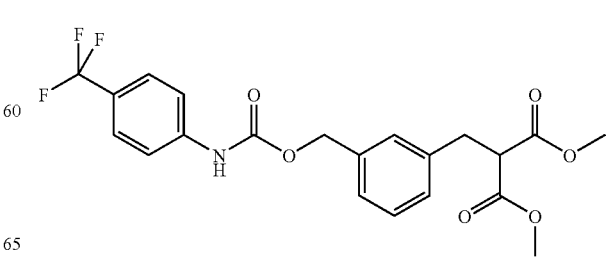

A suspension containing 63 mg of dimethyl 2-[3-(hydroxymethyl)benzyl]malonate, 47 mg of α,α,α-trifluoro-p-tolylisocyanate and 30 μl of pyridine in tetrahydrofuran (2.0 ml) was stirred at room temperature for 19 hours. After the solvent was distilled off, the residue was treated with dichloromethane. After filtering off insoluble substances and concentrating the filtrate, the residue was purified by HPLC using a reverse-phase column and an elution solvent of water-acetonitrile-trifluoroacetic acid system, to give 71 mg of the title compound.

$^1$H-NMR (CDCl$_3$)

δ: 3.24 (d, J=8.0 Hz, 2H) 3.68 (t, J=8.0 Hz, 1H) 3.70 (s, 6H) 5.18 (s, 2H) 7.17-7.31 (m, 4H) 7.50-7.59 (m, 4H)

MS m/e (ESI) 440 (MH$^+$)

Example 193

Dimethyl 2-(3-{[(anilinocarbonyl)oxy]methyl}benzyl)malonate

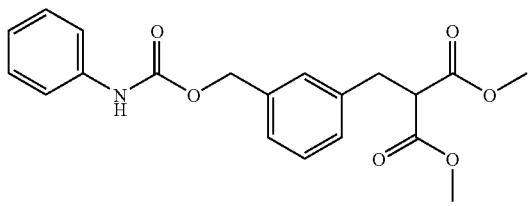

Using dimethyl 2-[3-(hydroxymethyl)benzyl]malonate and phenylisocyanate, the title compound was obtained in the same manner as described in Example 192b).

MS m/e (ESI) 372 (MH$^+$)

Example 194

Dimethyl 2-(3-{[(4-toluidinocarbonyl)oxy]methyl}benzyl)malonate

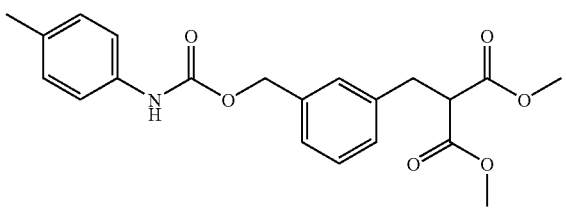

Using dimethyl 2-[3-(hydroxymethyl)benzyl]malonate and p-tolylisocyanate, the title compound was obtained in the same manner as described in Example 192b).

MS m/e (ESI) 386 (MH$^+$)

Example 195

Dimethyl 2-[3-({[(4-methoxyanilino)carbonyl]oxy}methyl)benzyl]malonate

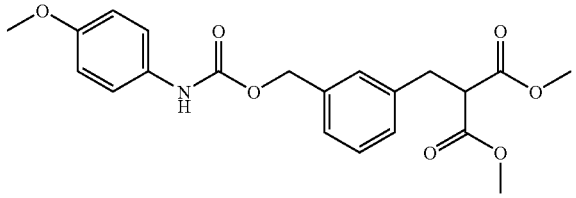

Using dimethyl 2-[3-(hydroxymethyl)benzyl]malonate and 4-methoxyphenylisocyanate, the title compound was obtained in the same manner as described in Example 192b).

MS m/e (ESI) 402 (MH$^+$)

Example 196

Dimethyl 2-[3-({[(3-methoxyanilino)carbonyl]oxy}methyl)benzyl]malonate

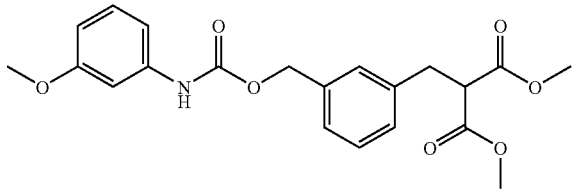

Using dimethyl 2-[3-(hydroxymethyl)benzyl]malonate and 3-methoxyphenylisocyanate, the title compound was obtained in the same manner as described in Example 192b).

MS m/e (ESI) 402 (MH$^+$)

Example 197

Dimethyl 2-[3-({[(4-chloroanilino)carbonyl]oxy}methyl)benzyl]malonate

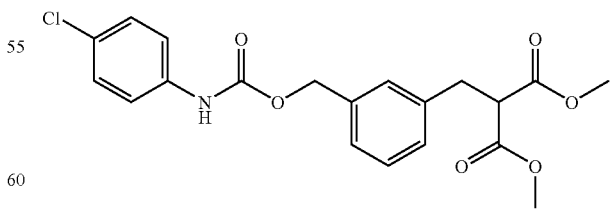

Using dimethyl 2-[3-(hydroxymethyl)benzyl]malonate and 4-chlorophenylisocyanate, the title compound was obtained in the same manner as described in Example 192b).

MS m/e (ESI) 406 (MH$^+$)

Example 198

Dimethyl 2-[3-({[(2,4-dichloroanilino)carbonyl]-oxy}methyl)benzyl]malonate

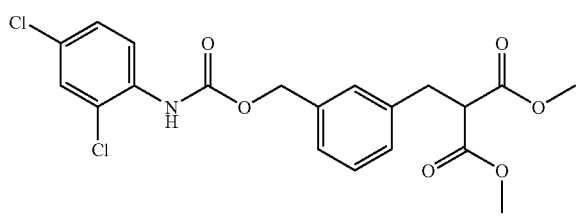

Using dimethyl 2-[3-(hydroxymethyl)benzyl]malonate and 2,4-dichlorophenylisocyanate, the title compound was obtained in the same manner as described in Example 192b).
MS m/e (ESI) 440 (MH+)

Example 199

Dimethyl 2-[3-({[(2-chloroanilino)carbonyl]oxy}-methyl)benzyl]malonate

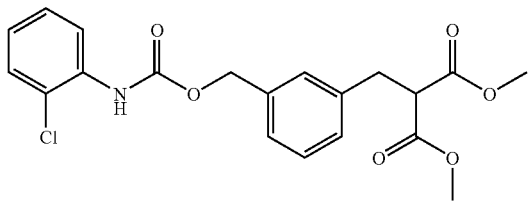

Using dimethyl 2-[3-(hydroxymethyl)benzyl]malonate and 2-chlorophenylisocyanate, the title compound was obtained in the same manner as described in Example 192b).
MS m/e (ESI) 406 (MH+)

Example 200

Dimethyl 2-[3-({[(2,4-difluoroanilino)carbonyl]-oxy}methyl)benzyl]malonate

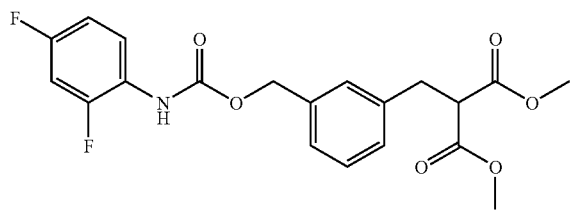

Using dimethyl 2-[3-(hydroxymethyl)benzyl]malonate and 2,4-difluorophenylisocyanate, the title compound was obtained in the same manner as described in Example 192b).
MS m/e (ESI) 408 (MH+)

Example 201

Dimethyl 2-[3-({[(3-chloroanilino)carbonyl]oxy}-methyl)benzyl]malonate

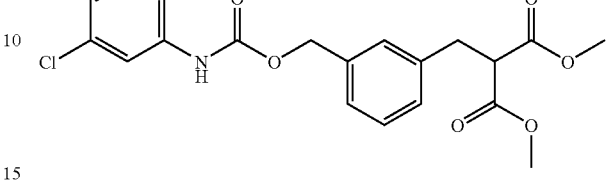

Using dimethyl 2-[3-(hydroxymethyl)benzyl]malonate and 3-chlorophenylisocyanate, the title compound was obtained in the same manner as described in Example 192b).
MS m/e (ESI) 406 (MH+)

Example 202

Dimethyl 2-{3-[2-({[4-(trifluoromethyl)anilino]-carbonyl}oxy)ethyl]benzyl}malonate

Production Example 202a

Dimethyl 2-[3-(2-hydroxyethyl)benzyl]malonate

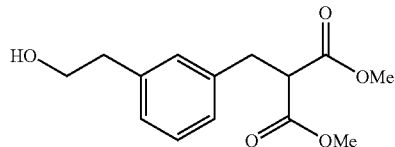

Using 3-(2-{[1-(t-butyl)-1,1-diphenylsilyl]oxy}ethyl)-benzaldehyde and dimethyl malonate, the title compound was obtained in the same manner as described in Production example 192a).
$^1$H-NMR (CDCl$_3$)
δ: 2.83 (t, J=6.4 Hz, 2H) 3.21 (d, J=8.0 Hz, 2H) 3.67 (t, J=8.0 Hz, 1H) 3.70 (s, 6H) 3.84 (t, J=6.4 Hz, 2H) 7.06-7.10 (m, 3H) 7.21-7.25 (m, 1H)

Example 202b

Dimethyl 2-(3-[2-({[4-(trifluoromethyl)-anilino]carbonyl}oxy)ethyl]benzyl}malonate

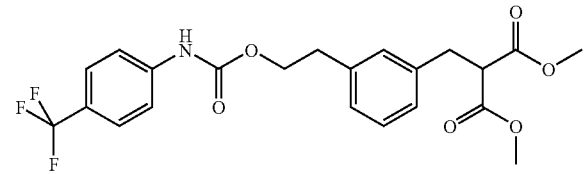

Using dimethyl 2-[3-(2-hydroxyethyl)benzyl]malonate and α,α,α-trifluoro-p-tolylisocyanate, the title compound was obtained in the same manner as described in Example 192b)
$^1$H-NMR (CDCl$_3$).

δ: 2.93 (t, J=6.4 Hz, 2H) 3.23 (d, J=7.6 Hz, 2H) 3.69 (t, J=7.6 Hz, 1H) 3.70 (s, 6H) 4.35 (t, J=6.4 Hz, 2H) 7.06-7.11 (m, 3H) 7.25 (t, J=7.2 Hz, 1H) 7.52-7.56 (m, 4H)
MS m/e (ESI) 454 (MH+)

Example 203

Dimethyl 2-(3-{2-[(anilinocarbonyl)oxy]ethyl}-benzyl)malonate

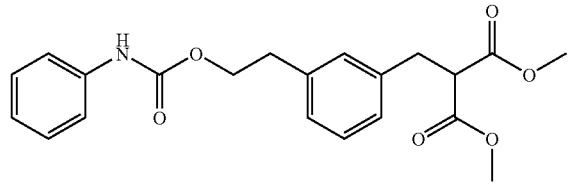

Using dimethyl 2-[3-(2-hydroxyethyl)benzyl]malonate and phenylisocyanate, the title compound was obtained in the same manner as described in Example 192b).
MS m/e (ESI) 386 (MH+)

Example 204

Dimethyl 2-(3-{2-[(4-toluidinocarbonyl)oxy]-ethyl}benzyl)malonate

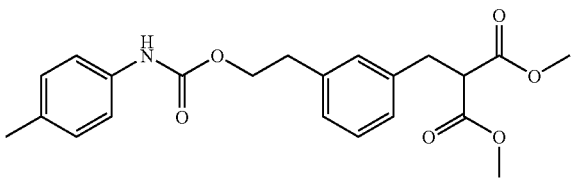

Using dimethyl 2-[3-(2-hydroxyethyl)benzyl]malonate and p-tolylisocyanate, the title compound was obtained in the same manner as described in Example 192b).
MS m/e (ESI) 400 (MH+)

Example 205

Dimethyl 2-(3-{2-[(4-methoxyanilinocarbonyl)-oxy]ethyl}benzyl)malonate

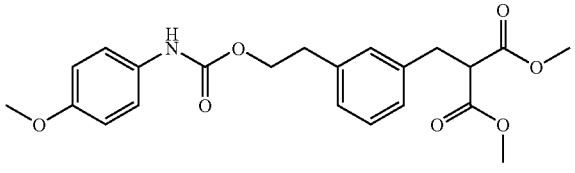

Using dimethyl 2-[3-(2-hydroxyethyl)benzyl]malonate and 4-methoxyphenylisocyanate, the title compound was obtained in the same manner as described in Example 192b)
MS m/e (ESI) 416 (MH+).

Example 206

Dimethyl 2-(3-{2-[(3-methoxyanilinocarbonyl)-oxy]ethyl}benzyl)malonate

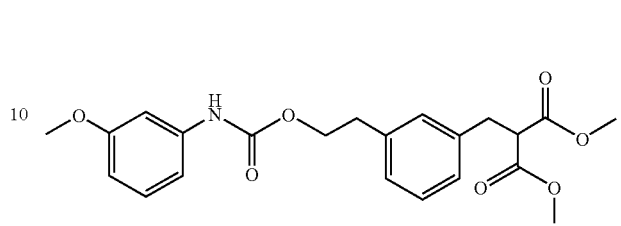

Using dimethyl 2-[3-(2-hydroxyethyl)benzyl]malonate and 3-methoxyphenylisocyanate, the title compound was obtained in the same manner as described in Example 192b).
MS m/e (ESI) 416 (MH+)

Example 207

Dimethyl 2-(3-{2-[(4-chloroanilinocarbonyl)oxy]-ethyl}benzyl)malonate

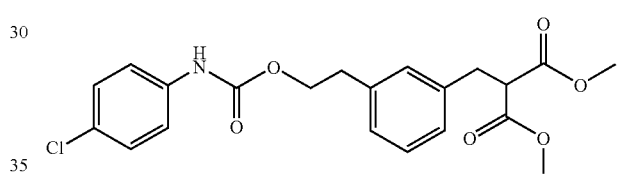

Using dimethyl 2-[3-(2-hydroxyethyl)benzyl]malonate and 4-chlorophenylisocyanate, the title compound was obtained in the same manner as described in Example 192b).
MS m/e (ESI) 420 (MH+)

Example 208

Dimethyl 2-(3-{2-[(2,4-dichloroanilinocarbonyl)-oxy]ethyl}benzyl)malonate

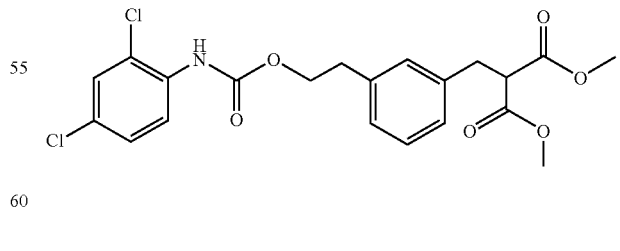

Using dimethyl 2-[3-(2-hydroxyethyl)benzyl]malonate and 2,4-dichlorophenylisocyanate, the title compound was obtained in the same manner as described in Example 192b).
MS m/e (ESI) 454 (MH+)

Example 209

Dimethyl 2-(3-{2-[(2-chloroanilinocarbonyl)oxy]-ethyl}benzyl)malonate

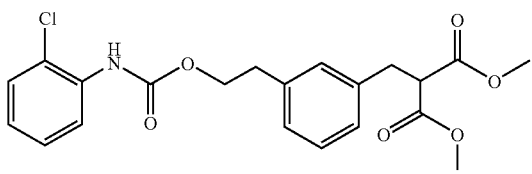

Using dimethyl 2-[3-(2-hydroxyethyl)benzyl]malonate and 2-chlorophenylisocyanate, the title compound was obtained in the same manner as described in Example 192b).
MS m/e (ESI) 420 (MH$^+$)

Example 210

Dimethyl 2-(3-{2-[(2,4-difluoroanilinocarbonyl)-oxy]ethyl}benzyl)malonate

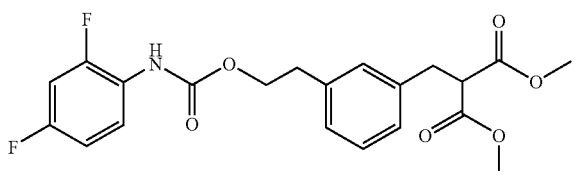

Using dimethyl 2-[3-(2-hydroxyethyl)benzyl]malonate and 2,4-difluorophenylisocyanate, the title compound was obtained in the same manner as described in Example 192b).
MS m/e (ESI) 422 (MH$^+$)

Example 211

Dimethyl 2-(3-{2-[(3-chloroanilinocarbonyl)oxy]ethyl}benzyl)malonate

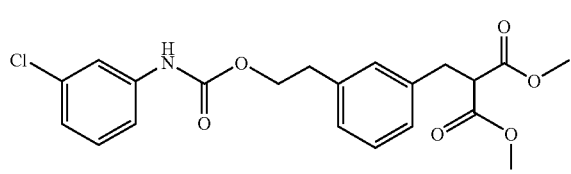

Using dimethyl 2-[3-(2-hydroxyethyl)benzyl]malonate and 3-chlorophenylisocyanate, the title compound was obtained in the same manner as described in Example 192b).
MS m/e (ESI) 420 (MH$^+$)

Example 212

Dimethyl 2-(3-{[(anilinocarbonyl)oxy]methyl}-4-methoxybenzyl)malonate

Production Example 212a

Dimethyl 2-[3-(hydroxymethyl)-4-methoxybenzyl]malonate

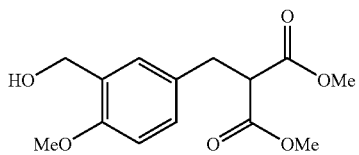

Using 3-({[1-(t-butyl)-1,1-dimethylsilyl]oxy}methyl)-4-methoxybenzaldehyde and dimethyl malonate, the title compound was obtained in the same manner as described in Production example 192a).
$^1$H-NMR (CDCl$_3$)
δ: 3.16 (d, J=8.0 Hz, 2H) 3.68 (t, J=8.0 Hz, 1H) 3.70 (s, 6H) 3.84 (s, 3H) 4.64 (d, J=6.0 Hz, 2H) 6.79 (d, J=9.2 Hz, 1H) 7.09-7.11 (m, 2H)

Example 212b

Dimethyl 2-(3-{[(anilinocarbonyl)oxy]methyl}-4-methoxybenzyl)malonate

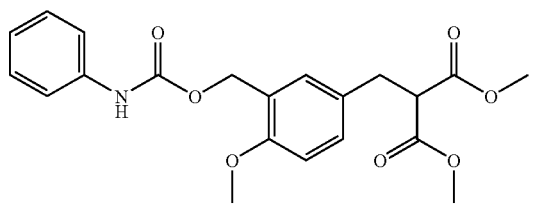

Using dimethyl 2-[3-(hydroxymethyl)-4-methoxybenzyl]malonate and phenylisocyanate, the title compound was obtained in the same manner as described in Example 192b).
MS m/e (ESI) 402 (MH$^+$)

Example 213

Dimethyl 2-(4-methoxy-3-{[(4-toluidinocarbonyl)oxy]methyl}benzyl)malonate

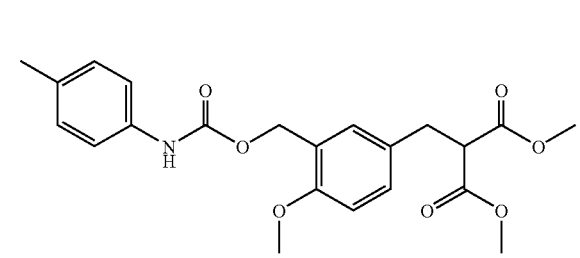

Using dimethyl 2-(3-(hydroxymethyl)-4-methoxybenzyl]malonate and p-tolylisocyanate, the title compound was obtained in the same manner as described in Example 192b).
MS m/e (ESI) 416 (MH+)

Example 214

Dimethyl 2-[4-methoxy-3-({[(4-methoxyanilino)-carbonyl]oxy}methyl)benzyl]malonate

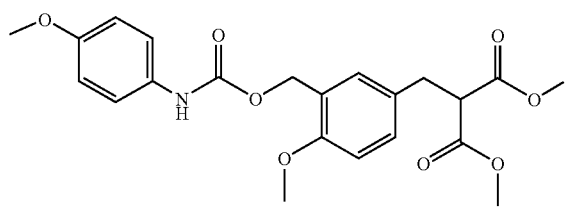

Using dimethyl 2-[3-(hydroxymethyl)-4-methoxybenzyl]malonate and 4-methoxyphenylisocyanate, the title compound was obtained in the same manner as described in Example 192b).
MS m/e (ESI) 432 (MH+)

Example 215

Dimethyl 2-[4-methoxy-3-({[(3-methoxyanilino)-carbonyl]oxy}methyl)benzyl]malonate

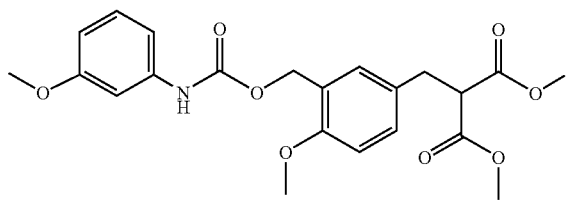

Using dimethyl 2-[3-(hydroxymethyl)-4-methoxybenzyl]malonate and 3-methoxyphenylisocyanate, the title compound was obtained in the same manner as described in Example 192b).
MS m/e (ESI) 432 (MH+)

Example 216

Dimethyl 2-[3-({[(4-chloroanilino)carbonyl]-oxy}methyl)-4-methoxybenzyl]malonate

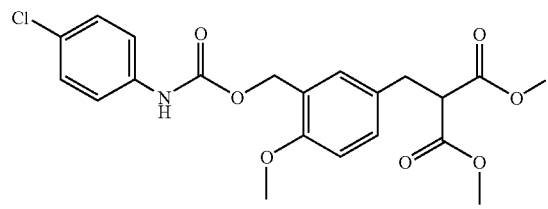

Using dimethyl 2-[3-(hydroxymethyl)-4-methoxybenzyl]malonate and 4-chlorophenylisocyanate, the title compound was obtained in the same manner as described in Example 192b).
MS m/e (ESI) 436 (MH+)

Example 217

Dimethyl 2-[3-({[(2,4-dichloroanilino)carbonyl]-oxy}methyl)-4-methoxy-benzyl]malonate

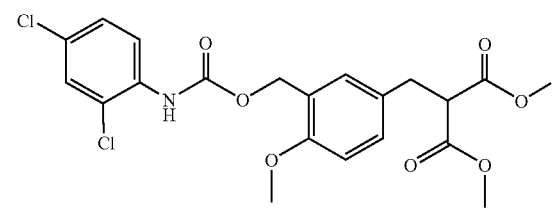

Using dimethyl 2-[3-(hydroxymethyl)-4-methoxybenzyl]malonate and 2,4-dichlorophenylisocyanate, the title compound was obtained in the same manner as described in Example 192b).
MS m/e (ESI) 470 (MH+)

Example 218

Dimethyl 2-[3-({[(2-chloroanilino)carbonyl]oxy}-methyl)-4-methoxybenzyl]malonate

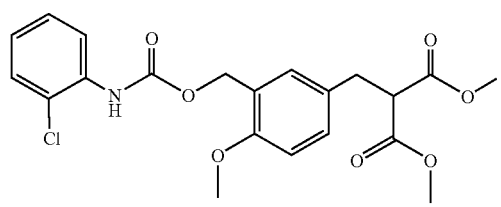

Using dimethyl 2-[3-(hydroxymethyl)-4-methoxybenzyl]malonate and 2-chlorophenylisocyanate, the title compound was obtained in the same manner as described in Example 192b).
MS m/e (ESI) 436 (MH+)

Example 219

Dimethyl 2-[3-({[(2,4-difluoroanilino)carbonyl]-oxy}methyl)-4-methoxybenzyl]malonate

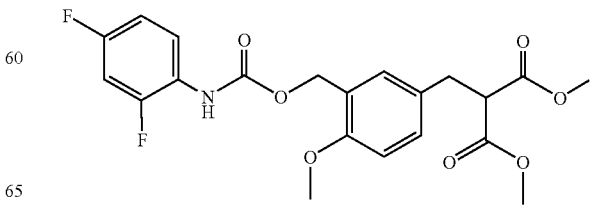

Using dimethyl 2-[3-(hydroxymethyl)-4-methoxybenzyl]malonate and 2,4-difluorophenylisocyanate, the title compound was obtained in the same manner as described in Example 192b).

MS m/e (ESI) 438 (MH+)

Example 220

Dimethyl 2-[3-({[(4-trifluoromethylanilino)carbonyl]-oxy}methyl)-4-methoxybenzyl]malonate

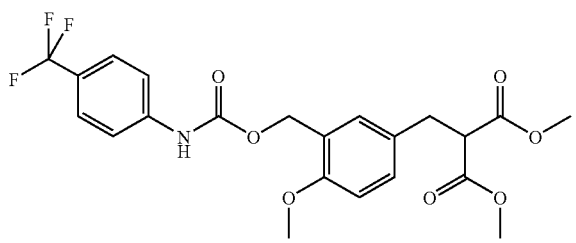

Using dimethyl 2-[3-(hydroxymethyl)-4-methoxybenzyl]malonate and α,α,α-trifluoro-p-tolylisocyanate, the title compound was obtained in the same manner as described in Example 192b).

MS m/e (ESI) 470 (MH+)

Example 221

Dimethyl 2-(3-{2-[(anilinocarbonyl)oxy]ethyl}-4-methoxybenzyl)malonate

Production Example 221a

Dimethyl 2-[3-(2-hydroxyethyl)-4-methoxybenzyl]malonate

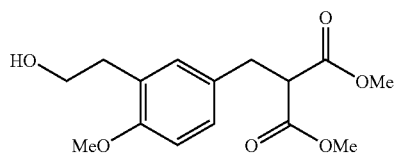

Using 3-(2-{[1-(t-butyl)-1,1-dimethylsilyl]oxy}ethyl)-4-methoxybenzaldehyde and dimethyl malonate, the title compound was obtained in the same manner as described in Production example 192a).

$^1$H-NMR (CDCl$_3$)

δ: 2.86 (t, J=6.4 Hz, 2H) 3.14 (d, J=8.0 Hz, 2H) 3.62 (t, J=8.0 Hz, 1H) 3.70 (s, 6H) 3.80 (s, 3H) 3.81 (t, J=6.4 Hz, 2H) 6.77 (d, J=8.4 Hz, 1H) 6.98 (d, J=2.4 Hz, 1H) 7.04 (dd, J=2.4, 8.4 Hz, 1H)

Example 221b

Dimethyl 2-(3-{2-[(anilinocarbonyl)oxy]ethyl}-4-methoxybenzyl)malonate

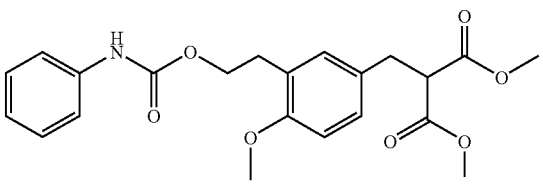

Using dimethyl 2-[3-(2-hydroxyethyl)-4-methoxybenzyl]malonate and phenylisocyanate, the title compound was obtained in the same manner as described in Example 192b).

MS m/e (ESI) 416 (MH+)

Example 222

Dimethyl 2-(4-methoxy-3-{2-[(4-toluidinocarbonyl)oxy]ethyl}benzyl)malonate

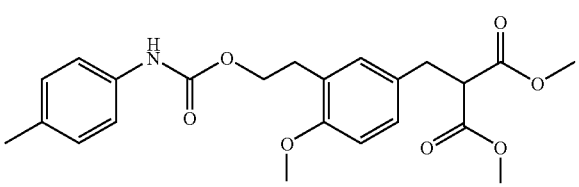

Using dimethyl 2-[3-(2-hydroxyethyl)-4-methoxybenzyl]malonate and p-tolylisocyanate, the title compound was obtained in the same manner as described in Example 192b).

MS m/e (ESI) 430 (MH+)

Example 223

Dimethyl 2-[4-methoxy-3-(2-{[(4-methoxyanilino)-carbonyl]oxy}ethyl)benzyl]malonate

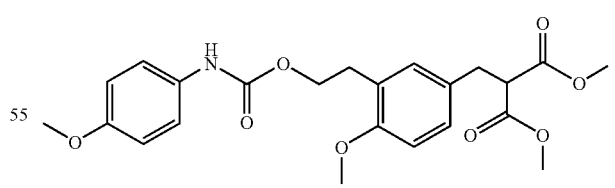

Using dimethyl 2-[3-(2-hydroxyethyl)-4-methoxybenzyl]malonate and 4-methoxyphenylisocyanate, the title compound was obtained in the same manner as described in Example 192b).

MS m/e (ESI) 446 (MH+)

Example 224

Dimethyl 2-[4-methoxy-3-(2-{[(3-methoxyanilino)-carbonyl]oxy}ethyl)benzyl]malonate

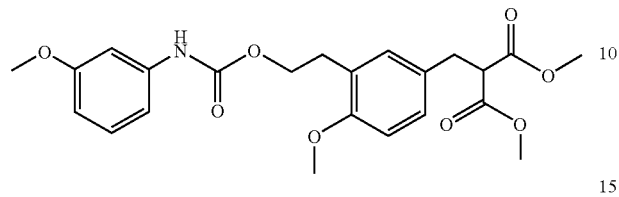

Using dimethyl 2-[3-(2-hydroxyethyl)-4-methoxybenzyl]malonate and 3-methoxyphenylisocyanate, the title compound was obtained in the same manner as described in Example 192b).

MS m/e (ESI) 446 (MH$^+$)

Example 225

Dimethyl 2-[3-(2-{[(4-chloroanilino)carbonyl]-oxy}ethyl)-4-methoxybenzyl]malonate

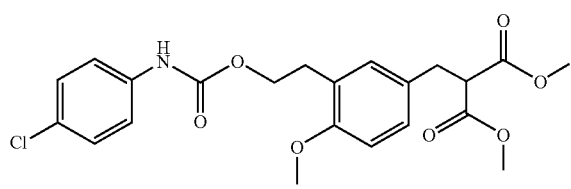

Using dimethyl 2-[3-(2-hydroxyethyl)-4-methoxybenzyl]malonate and 4-chlorophenylisocyanate, the title compound was obtained in the same manner as described in Example 192b).

MS m/e (ESI) 450 (MH$^+$)

Example 226

Dimethyl 2-[3-(2-{[(2,4-dichloroanilino)-carbonyl]oxy}ethyl)-4-methoxybenzyl]malonate

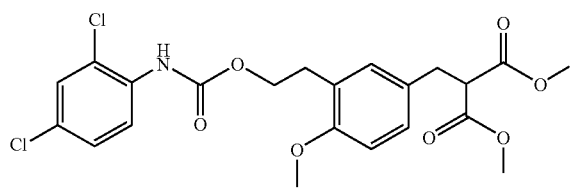

Using dimethyl 2-[3-(2-hydroxyethyl)-4-methoxybenzyl]malonate and 2,4-dichlorophenylisocyanate, the title compound was obtained in the same manner as described in Example 192b).

MS m/e (ESI) 484 (MH$^+$)

Example 227

Dimethyl 2-[3-(2-{[(2-chloroanilino)carbonyl]-oxy}ethyl)-4-methoxybenzyl]malonate

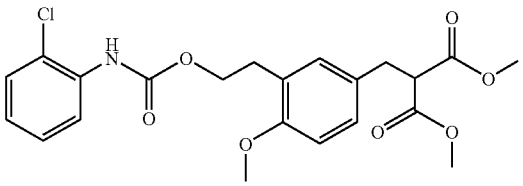

Using dimethyl 2-[3-(2-hydroxyethyl)-4-methoxybenzyl]malonate and 2-chlorophenylisocyanate, the title compound was obtained in the same manner as described in Example 192b).

MS m/e (ESI) 450 (MH$^+$)

Example 228

Dimethyl 2-[3-(2-{[(2,4-difluoroanilino)-carbonyl]oxy}ethyl)-4-methoxybenzyl]malonate

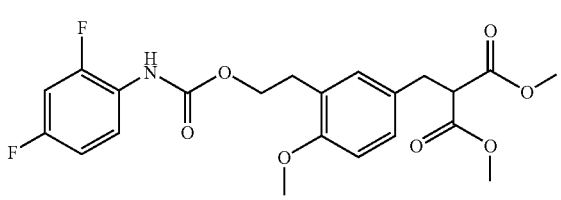

Using dimethyl 2-[3-(2-hydroxyethyl)-4-methoxybenzyl]-malonate and 2,4-difluorophenylisocyanate, the title compound was obtained in the same manner as described in Example 192b)

MS m/e (ESI) 452 (MH$^+$)

Example 229

Dimethyl 2-{4-methoxy-3-[2-({[4-(trifluoromethyl)anilino]carbonyl}-oxy)ethyl]benzyl}malonate

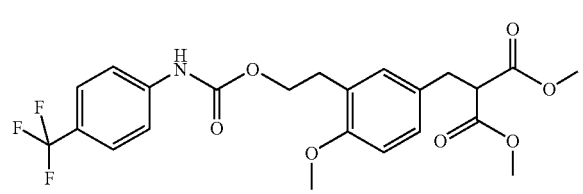

Using dimethyl 2-[3-(2-hydroxyethyl)-4-methoxybenzyl]malonate and α,α,α-trifluoro-p-tolylisocyanate, the title compound was obtained in the same manner as described in Example 192b).

MS m/e (ESI) 484 (MH$^+$)

Example 230

Dimethyl 2-(3-{[(anilinocarbonyl)oxy]methyl}-4-ethoxybenzyl)malonate

Production Example 230a

3-({[1-(t-butyl)-1,1-dimethylsilyl]-oxy}methyl)-4-ethoxybenzaldehyde

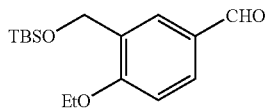

Using 2-ethoxybenzyl alcohol, the title compound was obtained in the same manner as described in Production example A-117a) followed by Production example A-117b).

$^1$H-NMR (CDCl$_3$)

δ: 0.12 (s, 6H) 0.93 (s, 9H) 1.40 (t, J=6.8 Hz, 3H) 4.11 (q, J=6.8 Hz, 2H) 4.74 (s, 2H) 6.90 (d, J=8.4 Hz, 1H) 7.76 (dd, J=1.6, 8.4 Hz, 1H) 7.97 (d, J=1.6 Hz, 1H) 9.86 (s, 1H)

Production Example 230b

Dimethyl 2-[4-ethoxy-3-(hydroxymethyl)benzyl]malonate

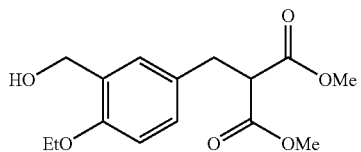

Using 3-({[1-(t-butyl)-1,1-dimethylsilyl]oxy}methyl)-4-ethoxybenzaldehyde and dimethyl malonate, the title compound was obtained in the same manner as described in Production example 192a).

$^1$H-NMR (CDCl$_3$)

δ: 1.42 (d, J=6.8 Hz, 3H) 3.15 (d, J=8.0 Hz, 2H) 3.63 (t, J=8.0 Hz, 1H) 3.70 (s, 6H) 4.05 (q, J=6.8 Hz, 2H) 4.65 (d, J=6.4 Hz, 2H) 6.77 (d, J=8.4 Hz, 1H) 7.06-7.09 (m, 2H)

Example 230c

Dimethyl 2-(3-{[(anilinocarbonyl)oxy]methyl}-4-ethoxybenzyl)malonate

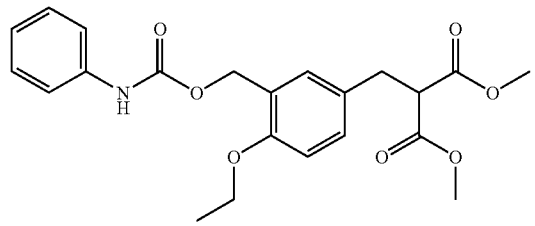

Using dimethyl 2-[4-ethoxy-3-(hydroxymethyl)benzyl]-malonate and phenylisocyanate, the title compound was obtained in the same manner as described in Example 192b).

MS m/e (ESI) 416 (MH$^+$)

Example 231

Dimethyl 2-(4-ethoxy-3-{[(4-toluidinocarbonyl)oxy]zmethyl}benzyl)malonate

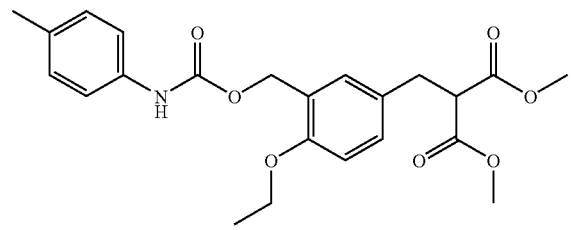

Using dimethyl 2-[4-ethoxy-3-(hydroxymethyl)benzyl]-malonate and p-tolylisocyanate, the title compound was obtained in the same manner as described in Example 192b).

MS m/e (ESI) 430 (MH$^+$)

Example 232

Dimethyl 2-[4-ethoxy-3-({[(4-methoxyanilino)-carbonyl]oxy}methyl)benzyl]malonate

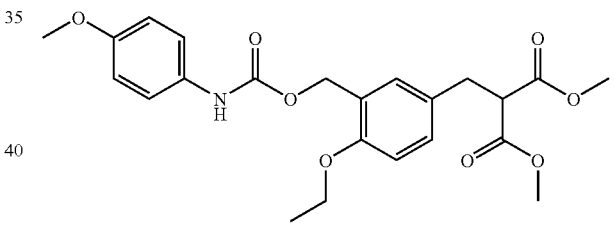

Using dimethyl 2-[4-ethoxy-3-(hydroxymethyl)benzyl] malonate and 4-methoxyphenylisocyanate, the title compound was obtained in the same manner as described in Example 192b).

MS m/e (ESI) 446 (MH$^+$)

Example 233

Dimethyl 2-[4-ethoxy-3-({[(3-methoxyanilino)-carbonyl]oxy}methyl)benzyl]malonate

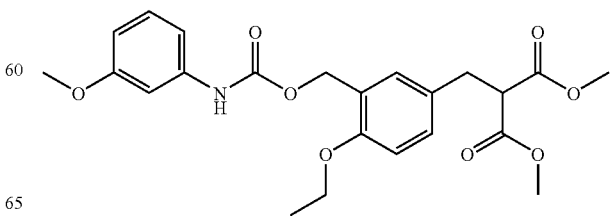

Using dimethyl 2-[4-ethoxy-3-(hydroxymethyl)benzyl]-malonate and 3-methoxyphenylisocyanate, the title compound was obtained in the same manner as described in Example 192b).

MS m/e (ESI) 446 (MH+)

Example 234

Dimethyl 2-[3-({[(4-chloroanilino)carbonyl]-oxy}methyl)-4-ethoxybenzyl]malonate

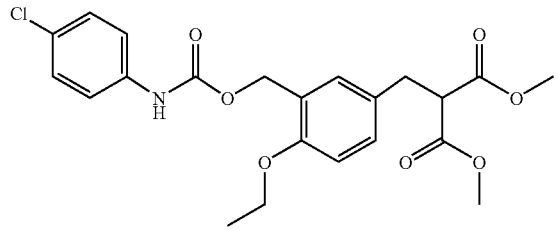

Using dimethyl 2-[4-ethoxy-3-(hydroxymethyl)benzyl]-malonate and 4-chlorophenylisocyanate, the title compound was obtained in the same manner as described in Example 192b).

MS m/e (ESI) 450 (MH+)

Example 235

Dimethyl 2-[3-({[(2,4-dichloroanilino)carbonyl]-oxy}methyl)-4-ethoxybenzyl]malonate

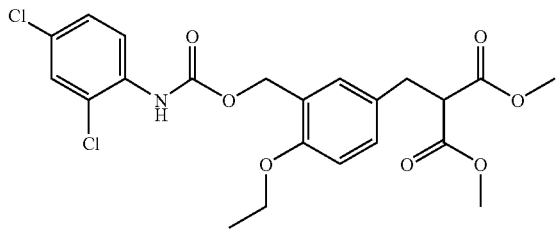

Using dimethyl 2-[4-ethoxy-3-(hydroxymethyl)benzyl]-malonate and 2,4-dichlorophenylisocyanate, the title compound was obtained in the same manner as described in Example 192b)

MS m/e (ESI) 484 (MH+)

Example 236

Dimethyl 2-[3-({[(2-chloroanilino)carbonyl]oxy}-methyl)-4-ethoxybenzyl]malonate

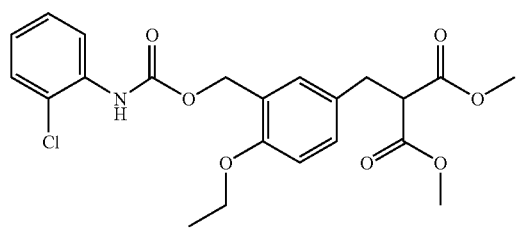

Using dimethyl 2-[4-ethoxy-3-(hydroxymethyl)benzyl]-malonate and 2-chlorophenylisocyanate, the title compound was obtained in the same manner as described in Example 192b).

MS m/e (ESI) 450 (MH+)

Example 237

Dimethyl 2-[3-({[(2,4-difluoroanilino)carbonyl]-oxy}methyl)-4-ethoxybenzyl]malonate

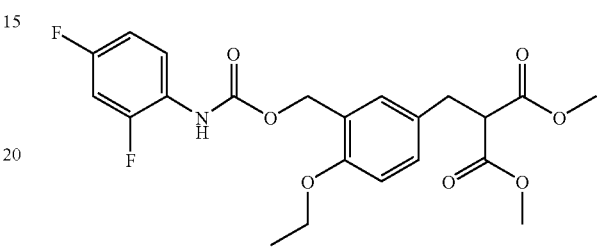

Using dimethyl 2-[4-ethoxy-3-(hydroxymethyl)benzyl]-malonate and 2,4-difluorophenylisocyanate, the title compound was obtained in the same manner as described in Example 192b)

MS m/e (ESI) 452 (MH+)

Example 238

Dimethyl 2-{4-ethoxy-3-[({[4-(trifluoromethyl)anilino]carbonyl}oxy)-methyl]benzyl}malonate

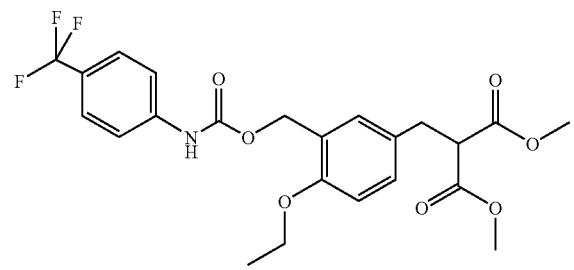

Using dimethyl 2-[4-ethoxy-3-(hydroxymethyl)benzyl]-malonate and α,α,α-trifluoro-p-tolylisocyanate, the title compound was obtained in the same manner as described in Example 192b).

MS m/e (ESI) 484 (MH+)

Example 239

Dimethyl 2-[3-({[(3-chloroanilino)carbonyl]oxy}-methyl)-4-ethoxybenzyl]malonate

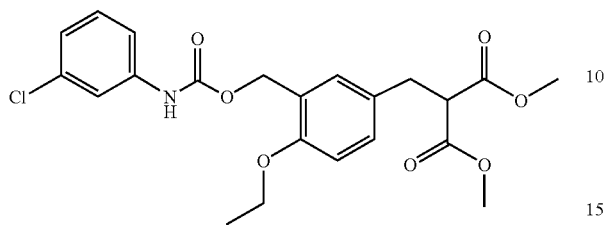

Using dimethyl 2-[4-ethoxy-3-(hydroxymethyl)benzyl]-malonate and 3-chlorophenylisocyanate, the title compound was obtained in the same manner as described in Example 192b).
MS m/e (ESI) 450 (MH$^+$)

Example 240

Ethyl 2-isopropoxy-3-[3-({[4-(trifluoromethyl)anilino]carbonyl}-oxy)phenyl]propanoate

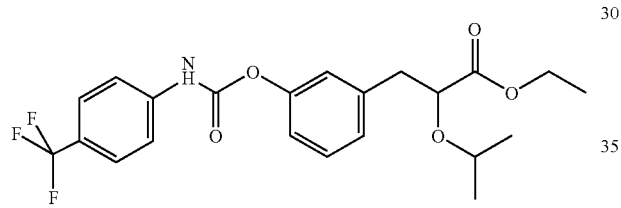

Using ethyl 3-(3-hydroxyphenyl)-2-isopropoxypropanoate and α,α,α-trifluoro-p-tolylisocyanate, the title compound was obtained in the same manner as described in Example 192b).
MS m/e (ESI) 484 (MH$^+$)

Example 241

3-[3-({[(2,4-Dichlorophenyl)sulfonyl]amino}methyl)-4-methoxyphenyl]-2-isopropoxypropanoic acid

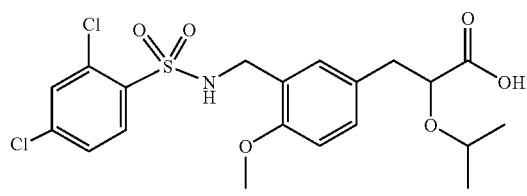

To a solution of 33 mg of ethyl 3-[3-(aminomethyl)-4-methoxyphenyl]-2-isopropoxypropanoate and 25 mg of 2,4-dichlorobenzenesulfonyl chloride in 0.8 ml of dichloromethane was added 40 μl of pyridine under ice-cooling, and stirring was continued at room temperature for 4 hours. After removing the solvent, to the residue were added 1.0 ml of ethanol and 0.3 ml of 2N aqueous sodium hydroxide, and the mixture was stirred at room temperature for 2 hours. The reaction solution was diluted with water, and neutralized with 2N hydrochloric acid. The mixture was extracted with ethyl acetate and concentrated. Then, the residue was purified by HPLC using a reverse-phase column by using an elution solvent of water-acetonitrile-trifluoroacetic acid system, to give 2.0 mg of the title compound.
MS m/e (ESI) 476 (MH$^+$)

Example 242

3-{3-[3-(3,4-Dimethylphenoxy)-2-hydroxypropoxy]phenyl}-2-isopropoxypropanoic acid

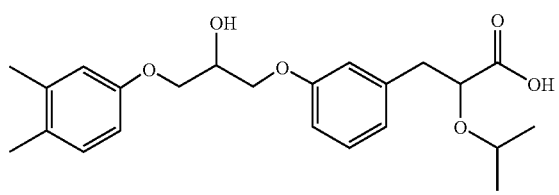

Using 3,4-dimethylphenol, the title compound was obtained in the same manner as described in Example 1c).
MS m/e (ESI) 425 (MNa$^+$)

Example 243

3-{3-[3-(4-Bromophenoxy)-2-hydroxypropoxy]phenyl}-2-isopropoxypropanoic acid

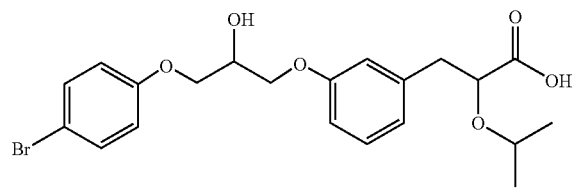

Using 4-bromophenol, the title compound was obtained in the same manner as described in Example 1c).
MS m/e (ESI) 475 (MNa$^+$)

Example 244

3-{3-[2-Hydroxy-3-(2-methoxy-5-methylphenoxy)propoxy]phenyl}-2-isopropoxypropanoic acid

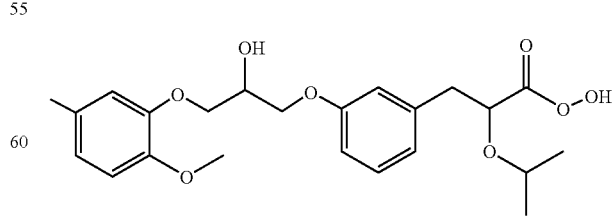

Using 2-methoxy-5-methylphenol, the title compound was obtained in the same manner as described in Example 1c).
MS m/e (ESI) 441 (MNa$^+$)

Example 245

3-{3-[3-(3-Chlorophenoxy)-2-hydroxypropoxy]phenyl}-2-isopropoxypropanoic acid

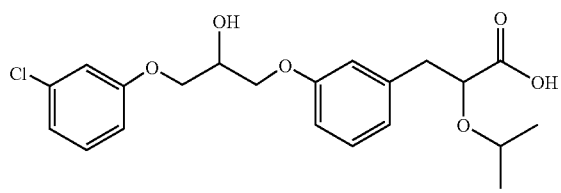

Using 3-chlorophenol, the title compound was obtained in the same manner as described in Example 1c).
MS m/e (ESI) 431 (MNa$^+$)

Example 246

3-[3-(2-Hydroxy-3-p-tolyloxypropoxy)phenyl]-2-isopropoxypropanoic acid

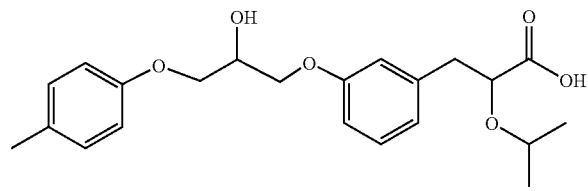

Using 4-methylphonol, the title compound was obtained in the same manner as described in Example 1c).
MS m/e (ESI) 411 (MNa$^+$)

Example 247

3-{3-[3-(2,4-Dimethylphenoxy)-2-hydroxypropoxy]phenyl}-2-isopropoxypropanoic acid

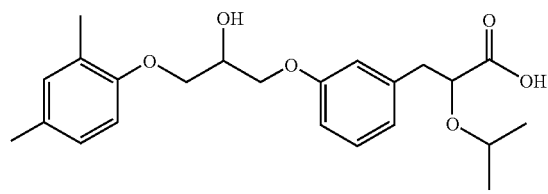

Using 2,4-dimethylphenol, the title compound was obtained in the same manner as described in Example 1c).
MS m/e (ESI) 425 (MNa$^+$)

Example 248

3-[3-(2-Hydroxy-3-m-tolyloxypropoxy)phenyl]-2-isopropoxypropanoic acid

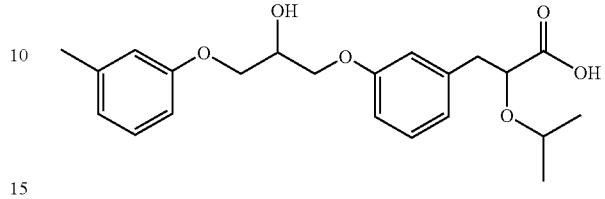

Using 3-methylphenol, the title compound was obtained in the same manner as described in Example 1c).
MS m/e (ESI) 411 (MNa$^+$)

Example 249

3-{3-[3-(3-Ethylphenoxy)-2-hydroxypropoxy]phenyl}-2-isopropoxypropanoic acid

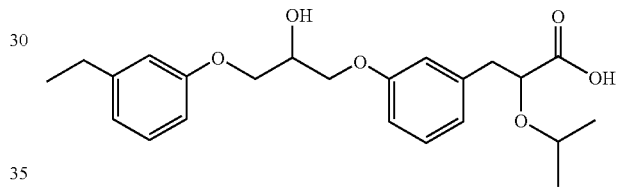

Using 3-ethylphenol, the title compound was obtained in the same manner as described in Example 1c).
MS m/e (ESI) 425 (MNa$^+$)

Example 250

3-{3-[3-(2,6-Difluorophenoxy)-2-hydroxypropoxy]phenyl}-2-isopropoxypropanoic acid

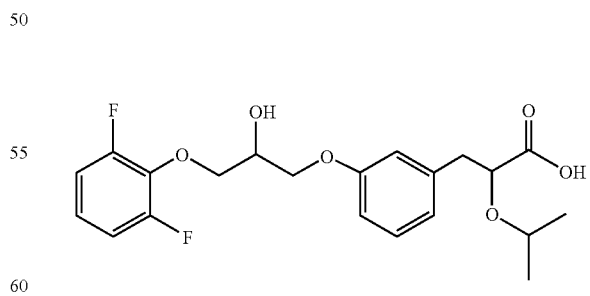

Using 2,6-difluorophenol, the title compound was obtained in the same manner as described in Example 1c).
MS m/e (ESI) 433 (MNa$^+$)

Example 251

3-{3-[3-(2-Chloro-5-trifluoromethylphenoxy)-2-hydroxypropoxy]phenyl}-2-isopropoxypropanoic acid

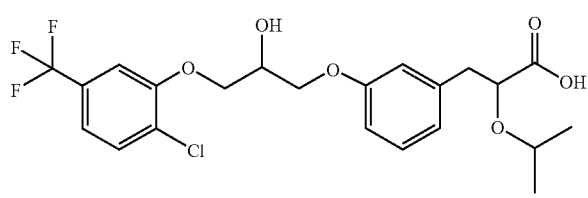

Using 2-chloro-5-trifluoromethylphenol, the title compound was obtained in the same manner as described in Example 1c).

MS m/e (ESI) 499 (MNa⁺)

Example 252

3-{3-[3-(3,4-Dichlorophenoxy)-2-hydroxypropoxy]phenyl}-2-isopropoxypropanoic acid

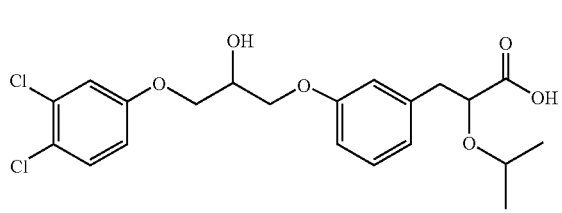

Using 3,4-dichlorophenol, the title compound was obtained in the same manner as described in Example 1c).

MS m/e (ESI) 465 (MNa⁺)

Example 253

3-{3-[3-(4-Chloro-3-methylphenoxy)-2-hydroxypropoxy]phenyl}-2-isopropoxypropanoic acid

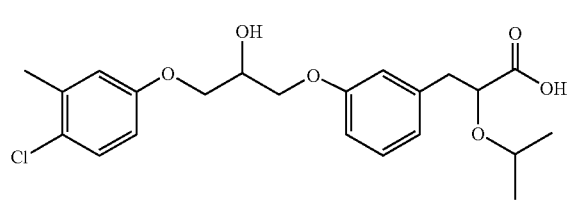

Using 4-chloro-3-methylphenol, the title compound was obtained in the same manner as described in Example 1c).

MS m/e (ESI) 445 (MNa⁺)

Example 254

3-{3-[3-(4-Cyanomethylphenoxy)-2-hydroxypropoxy]phenyl}-2-isopropoxypropanoic acid

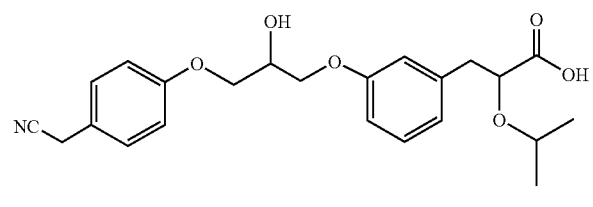

Using 4-cyanomethylphenol, the title compound was obtained in the same manner as described in Example 1c).

MS m/e (ESI) 435 (MNa⁺)

Example 255

3-{3-[3-(3-Chloro-4-fluorophenoxy)-2-hydroxypropoxy]phenyl}-2-isopropoxypropanoic acid

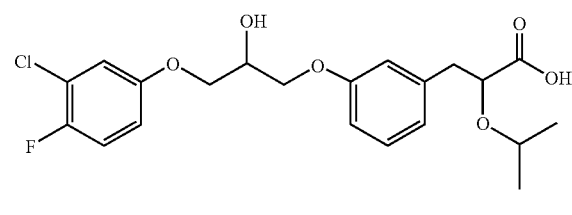

Using 3-chloro-4-fluorophenol, the title compound was obtained in the same manner as described in Example 1c).

MS m/e (ESI) 449 (MNa⁺)

Example 256

3-{3-[3-(4-Chlorophenoxy)-2-hydroxypropoxy]phenyl}-2-isopropoxypropanoic acid

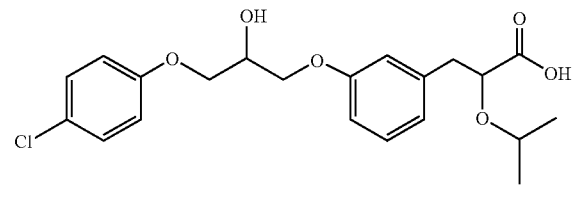

Using 4-chlorophenol, the title compound was obtained in the same manner as described in Example 1c).

MS m/e (ESI) 431 (MNa⁺)

Example 257

3-{3-[2-Hydroxy-3-(2-piperidino-1-yl-phenoxy)propoxy]phenyl}-2-isopropoxypropanoic acid

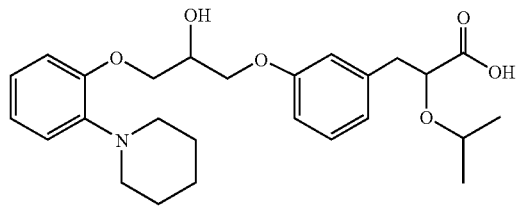

Using 2-piperidinophenol, the title compound was obtained in the same manner as described in Example 1c).
MS m/e (ESI) 480 (MNa$^+$)

Example 258

3-{3-[3-(4-Fluorophenoxy)-2-hydroxypropoxy]phenyl}-2-isopropoxypropanoic acid

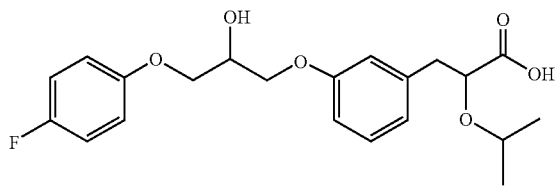

Using 4-fluorophenol, the title compound was obtained in the same manner as described in Example 1c).
MS m/e (ESI) 415 (MNa$^+$)

Example 259

3-{3-[3-(4-Ethylphenoxy)-2-hydroxy]propoxy}phenyl}-2-isopropoxypropanoic acid

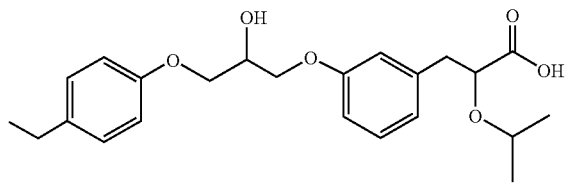

Using 4-ethylphenol, the title compound was obtained in the same manner as described in Example 1c).
MS m/e (ESI) 425 (MNa$^+$)

Example 260

3-{3-[3-(5-Chloro-2-methylphenoxy)-2-hydroxypropoxy]phenyl}-2-isopropoxypropanoic acid

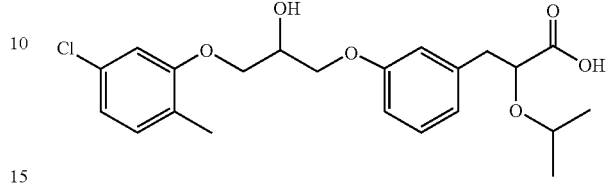

Using 2-methyl-3-chlorophenol, the title compound was obtained in the same manner as described in Example 1c).
MS m/e (ESI) 445 (MNa$^+$)

Example 261

3-{3-[2-Hydroxy-3-(3-methoxy-5-methylphenoxy)propoxy]phenyl}-2-isopropoxypropanoic acid

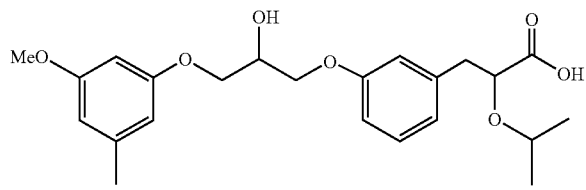

Using 3-methyl-5-methoxyphenol, the title compound was obtained in the same manner as described in Example 1c).
MS m/e (ESI) 441 (MNa$^+$)

Example 262

3-{3-[3-(3-Ethynylphenoxy)-2-hydroxypropoxy]phenyl}-2-isopropoxypropanoic acid

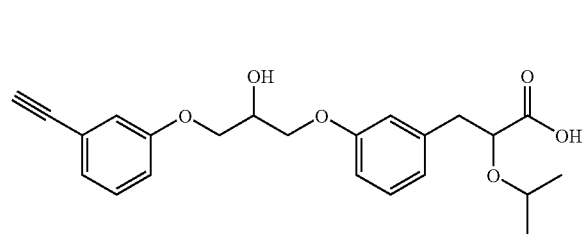

Using 3-ethynylphenol, the title compound was obtained in the same manner as described in Example 1c).
MS m/e (ESI) 421 (MNa$^+$)

Example 263

3-{3-[2-Hydroxy-3-(1H-indol-4-yloxy)propoxy]phenyl}-2-isopropoxypropanoic acid

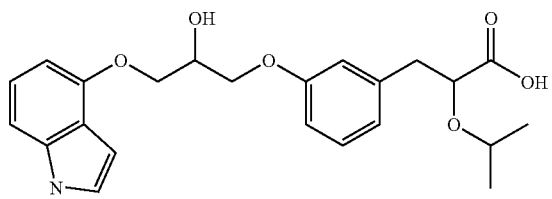

Using 4-hydroxyindole, the title compound was obtained in the same manner as described in Example 1c).
MS m/e (ESI) 435 (MNa+)

Example 264

3-{3-[3-(4-Chloro-2-cyanophenoxy)-2-hydroxypropoxy]phenyl}-2-isopropoxypropanoic acid

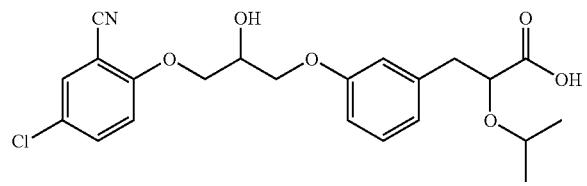

Using 4-chloro-2-cyanophenol, the title compound was obtained in the same manner as described in Example 1c).
MS m/e (ESI) 456 (MNa+)

Example 265

3-{3-[3-(4-Bromo-2-cyanophenoxy)-2-hydroxypropoxy]phenyl}-2-isopropoxypropanoic acid

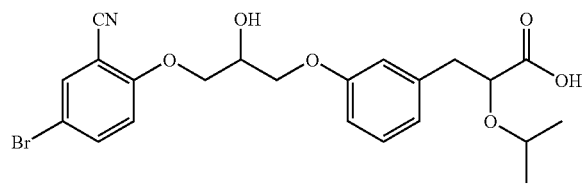

Using 4-bromo-2-cyanophenol, the title compound was obtained in the same manner as described in Example 1c).
MS m/e (ESI) 500 (MNa+)

Example 266

2-Isopropoxy-3-(3-{[({[4-chlorobenzyl]oxy}-carbonyl)amino]methyl}phenyl)propanoic acid

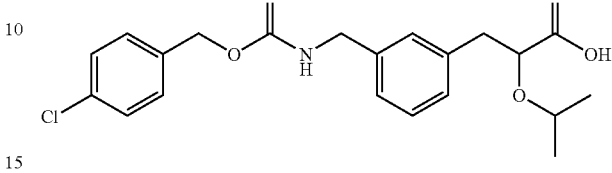

Using 4-chlorobenzyl bromide, the title compound was obtained in the same manner as described in Example 138f).
MS m/e (ESI) 428 (MH+)

Example 267

2-Isopropoxy-3-(3-{[({[3-chlorobenzyl]oxy}-carbonyl)amino]methyl}phenyl)propanoic acid

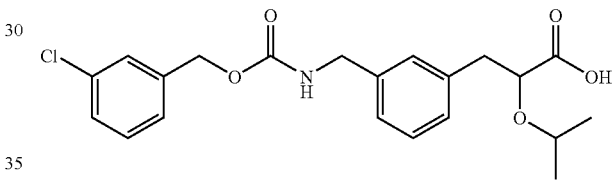

Using 3-chlorobenzyl bromide, the title compound was obtained in the same manner as described in Example 138f).
MS m/e (ESI) 428 (MH+)

Example 268

2-Isopropoxy-3-(3-{[({[2-chlorobenzyl]oxy}-carbonyl)amino]methyl}phenyl)propanoic acid

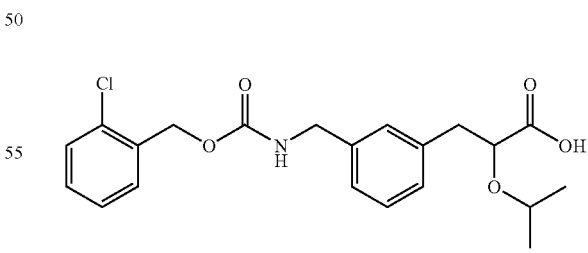

Using 2-chlorobenzyl bromide, the title compound was obtained in the same manner as described in Example 138f).
MS m/e (ESI) 428 (MH+)

Example 269

2-Isopropoxy-3-(3-{[({[4-fluorobenzyl]oxy}-carbonyl)amino]methyl}phenyl)propanoic acid

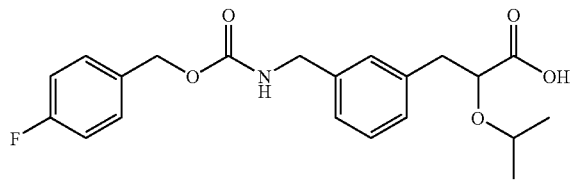

Using 4-fluorobenzyl bromide, the title compound was obtained in the same manner as described in Example 138f). MS m/e (ESI) 412 (MH$^+$)

Example 270

2-Isopropoxy-3-(3-{[({[3-fluorobenzyl]oxy}-carbonyl)amino]methyl}phenyl)propanoic acid

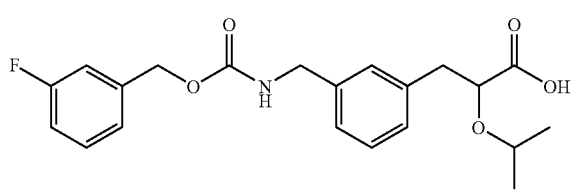

Using 3-fluorobenzyl bromide, the title compound was obtained in the same manner as described in Example 138f). MS m/e (ESI) 412 (MH$^+$)

Example 271

2-Isopropoxy-3-(3-{[({[4-cyanobenzyl]oxy}-carbonyl)amino]methyl}phenyl)propanoic acid

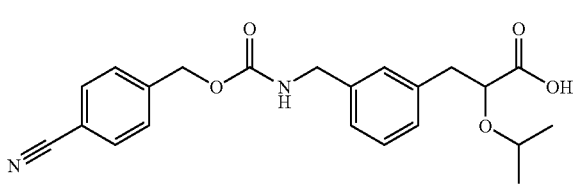

Using 4-cyanobenzyl bromide, the title compound was obtained in the same manner as described in Example 138f). MS m/e (ESI) 419 (MH$^+$)

Example 272

2-Isopropoxy-3-(3-{[({[3-cyanobenzyl]oxy}-carbonyl)amino]methyl}phenyl)propanoic acid

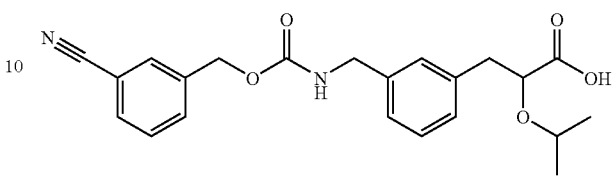

Using 3-cyanobenzyl bromide, the title compound was obtained in the same manner as described in Example 138f). MS m/e (ESI) 419 (MH$^+$)

Example 273

2-Isopropoxy-3-(3-{[({[2,4-difluorobenzyl]-oxy}carbonyl)amino]methyl}phenyl)propanoic acid

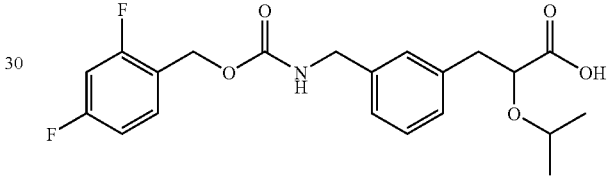

Using 2,4-difluorobenzyl bromide, the title compound was obtained in the same manner as described in Example 138f). MS m/e (ESI) 430 (MH$^+$)

Example 274

2-Isopropoxy-3-(3-{[({[4-methoxybenzyl]oxy}-carbonyl)amino]methyl}phenyl)propanoic acid

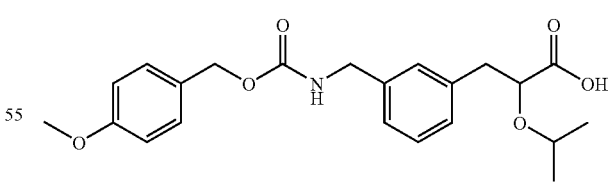

Using 4-methoxybenzyl chloride, the title compound was obtained in the same manner as described in Example 138f). MS m/e (ESI) 424 (MH$^+$)

Example 275

2-Isopropoxy-3-(3-{[({[2-fluoro-4-trifluoromethyl-benzyl]oxy}carbonyl)amino]methyl}phenyl)-propanoic acid

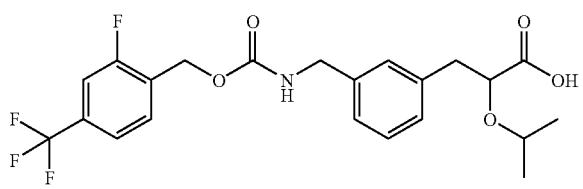

Using 2-fluoro-4-trifluoromethylbenzyl bromide, the title compound was obtained in the same manner as described in Example 138f).

MS m/e (ESI) 480 (MH$^+$)

Example 276

2-Isopropoxy-3-(3-{[({[2-chloro-4-propoxybenzyl]oxy}-carbonyl)amino]methyl}phenyl)propanoic acid

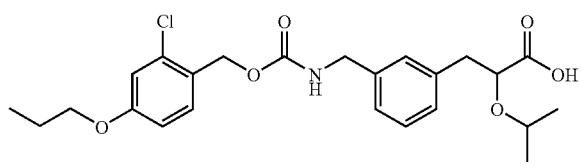

Using 2-chloro-4-propoxybenzyl bromide, the title compound was obtained in the same manner as described in Example 138f).

MS m/e (ESI) 486 (MH$^+$)

Example 277

2-Isopropoxy-3-(3-{[({[2-fluoro-4-chlorobenzyl]oxy}carbonyl)amino]methyl}phenyl)propanoic acid

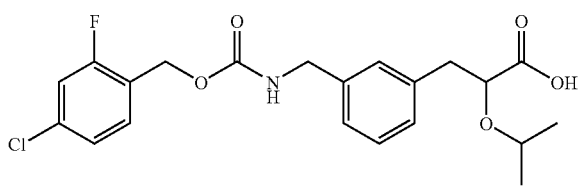

Using 2-fluoro-4-chlorobenzyl bromide, the title compound was obtained in the same manner as described in Example 138f).

MS m/e (ESI) 446 (MH$^+$)

Example 278

2-Isopropoxy-3-(3-{[({[4-trifluoromethoxybenzyl]oxy}-carbonyl)amino]methyl}phenyl)propanoic acid

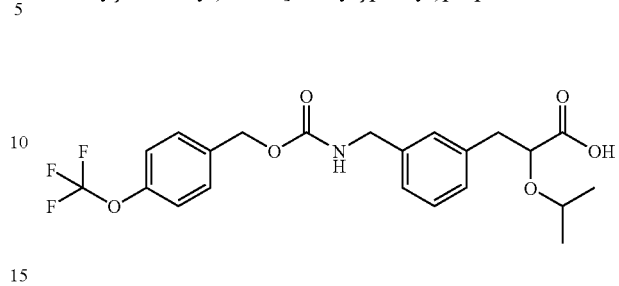

Using 4-trifluoromethoxybenzyl bromide, the title compound was obtained in the same manner as described in Example 138f).

MS m/e (ESI) 478 (MH$^+$)

Example 279

3-{3-[3-(2,4-Dichlorophenoxy)-2 (S)-hydroxypropoxy]phenyl}-2(S)-isopropoxypropanoic acid

Production Example 279a 4 (S)-Benzyl-3-(2-isopropoxyacetyl)oxazolidin-2-one

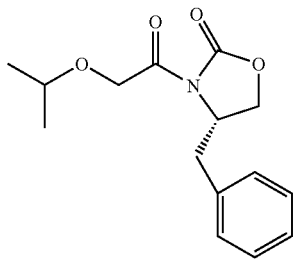

A solution containing 98 g of 2-isopropoxyacetic acid and 360 ml of triethylamine in tetrahydrofuran (4L) was cooled to −25° C. After 92 ml of 2,2-dimethylpropanoyl chloride was dropwise added, the reaction solution was stirred at −20° C. for 5 hours. Then, 50 g of anhydrous lithium chloride and 120 g of (4S)-4-benzyl-1,3-oxazolidin-2-one were successively added, and stirring was continued at room temperature overnight. Then, the reaction solution was filtered and evaporated. The residue was dissolved in 2 L of ethyl acetate, washed with saturated aqueous sodium hydrogen carbonate, and then dried over anhydrous magnesium sulfate. The solvent was evaporated, and the residue was purified by silica gel column chromatography (elution solvent: hexane-ethyl acetate), to give 106.6 g of (4S)-4-benzyl-3-(2-isopropoxyacetyl)-1,3-oxazolidin-2-one as a colorless oil.

$^1$H NMR (CDCl$_3$)

δ: 1.17 (d, J=6.0 Hz, 6H) 2.81 (dd, J=9.5, 13.4 Hz, 1H) 3.35 (dd, J=3.2, 13.4 Hz, 1H) 3.74 (sept, J=6.0 Hz, 1H) 4.24 (dd, J=3.5, 9.3 Hz, 1H) 4.29 (t, J=9.3 Hz, 1H) 4.65 (d, J=19.5 Hz, 1H) 4.69 (m, 1H) 4.70 (d, J=19.5 Hz, 1H) 7.22 (d, J=7.2 Hz, 2H) 7.30-7.45 (m, 3H)

Production Example 279b 4 (S)-Benzyl-3-[3-(3-benzyloxyphenyl)-3-hydroxy-2 (S)-isopropoxypropionyl]oxazolidin-2-one

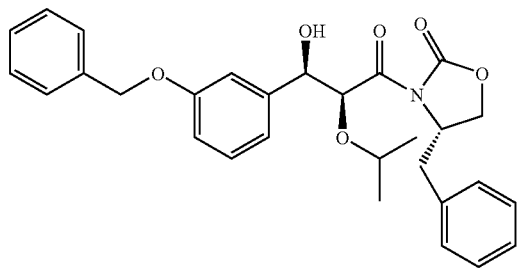

After cooling a solution containing 8.1 g of (4S)-4-benzyl-3-(2-isopropoxyacetyl)-1,3-oxazolidin-2-one in toluene (120 ml) was cooled to −75° C., 5.0 ml of triethylamine was added. 30.5 ml of dibutylboron triflate (1M solution in dichloromethane) was added dropwise at such a rate that the inside temperature did not exceed −70° C. After the dropwise addition, the mixture was stirred for 50 minutes. Then, the inside temperature was raised to 0° C. and the mixture was stirred for another 50 minutes, and again cooled to −75° C. To the reaction solution was added a solution containing 5.2 g of 3-benzyloxybenzaldehyde in dichloromethane (25 ml) by means of cannula, and stirring was continued at −75° C. for 30 minutes. Then, the inside temperature was raised to 0° C. over about 1 hour by 10° C. per 10 minutes. Again after cooling to −75° C., a solution containing 2.0 g of 3-benzyloxybenzaldehyde in dichloromethane (10 ml) was added. The temperature was gradually raised to room temperature and stirred for 3 days at room temperature. The reaction solution was poured into a mixed solution of 150 ml of methanol, 100 ml of pH 7 buffer (disodium hydrogen phosphate-citric acid) and 30 ml of hydrogen peroxide (30% aqueous solution), and extracted with ethyl acetate. The organic layer was washed with saturated brine, dried over anhydrous magnesium sulfate and the solvent was evaporated. The residue was purified by silica gel column chromatography, to give 13.1 g of 4 (S)-benzyl-3-[3-(3-benzyloxyphenyl)-3-hydroxy-2 (S)-isopropoxypropionyl]oxazolidin-2-one as a colorless oil in the 2:1→3:2 hexane-ethyl acetate fraction.

$^1$H NMR (CDCl$_3$)

δ: 1.11 (d, J=6.0 Hz, 3H) 1.19 (d, J=6.0 Hz, 3H) 2.75 (dd, J=9.6, 13.2 Hz, 1H) 3.08 (d, J=5.6 Hz, 1H) 3.26 (dd, J=3.2, 13.2 Hz, 1H) 3.60-3.69 (m, 2H) 3.99 (dd, J=1.6, 8.8 Hz, 1H) 4.27-4.33 (m, 1H) 4.84 (t, J=5.6 Hz, 1H) 5.07 (s, 2H) 5.44 (d, J=5.2 Hz, 1H) 6.88-6.90 (m, 1H) 7.00 (d, J=7.6 Hz, 1H) 7.09 (t, J=2.0 Hz, 1H) 7.16-7.24 (m, 3H) 7.28-7.35 (m, 6H) 7.39-7.43 (m, 2H)

Production Example 279c 4 (S)-Benzyl-3-[3-(3-hydroxyphenyl)-2 (S)-isopropoxypropionyl]oxazolidin-2-one

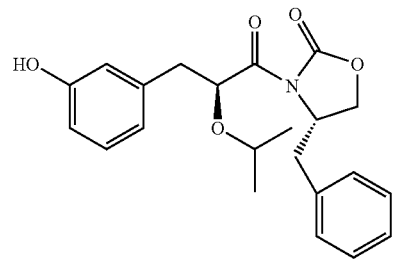

12.9 g of 4-Benzyl-3-(3-(3-benzyloxyphenyl)-3-hydroxy-2-isopropoxy propionyl]oxazolidin-2-one was dissolved in 30 ml of pyridine, and 3.06 ml of methanesulfonyl chloride was dropwise added thereto under ice-cooling. After stirring was continued at room temperature for 2 hours, the reaction solution was diluted with ethyl acetate and washed successively with 1N hydrochloric acid and saturated brine. The organic layer was dried over anhydrous magnesium sulfate, filtered, and the solvent was concentrated, to give 3-(4(S)-benzyl-2-oxooxazolidin-3-yl)-1(R)-(3-benzyloxyphenyl)-2 (S)-isopropoxy-3-oxopropyl methanesulfonate. This product was then dissolved in 300 ml of ethanol, and 2 g of 10% palladium carbon was added, and the mixture was stirred overnight under hydrogen atmosphere at room temperature. The reaction solution was filtered, and the filtrate was concentrated. The residue was diluted with ethyl acetate, and washed with saturated aqueous sodium hydrogen carbonate, The organic layer was dried over anhydrous magnesium sulfate, and the solvent was evaporated. The residue was purified by silica gel column chromatography, to give 5.87 g of the title compound as a colorless oil in the 2:1→3:2 hexane-ethyl acetate fraction.

$^1$H NMR (CDCl$_3$)

δ: 1.04 (d, J=6.0 Hz, 3H) 1.16 (d, J=6.0 Hz, 3H) 2.78 (dd, J=9.6, 13.2 Hz, 1H) 2.86-2.96 (m, 2H) 3.31 (dd, J=2.4, 13.6 Hz, 1H) 3.53 (Sept, J=6.0 Hz, 1H) 4.01 (t, J=8.0 Hz, 1H) 4.13 (dd, J=2.4, 9.2 Hz, 1H) 4.50-4.55 (m, 1H) 5.22 (s, 1H) 5.39 (dd, J=5.2, 8.4 Hz, 1H) 6.71 (dd, J=2.4, 8.0 Hz, 1H) 6.82 (t, J=2.0 Hz, 1H) 6.87 (d, J=7.6 Hz, 1H) 7.14 (t, J=8.0 Hz, 1H) 7.18-7.23 (m, 2H) 7.27-7.35 (m, 3H)

Production Example 279d 3-(3-Hydroxyphenyl)-2 (S)-isopropoxypropanoic acid ethyl ester

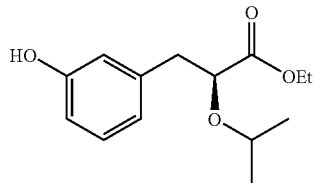

1.535 g of 4 (S)-Benzyl-3-[3-(3-hydroxyphenyl)-2 (S)-isopropoxypropionyl]oxazolidin-2-one was dissolved in 40 ml of tetrahydrofuran, and 3.3 ml of 30% aqueous hydrogen peroxide and 12 ml of 1N aqueous lithium hydroxide were successively added under ice-cooling, and stirring was continued at room temperature overnight. After adding water to the reaction solution, the mixture was extracted with dichloromethane and the aqueous layer was acidified by 1N hydrochloric acid. Following extraction (×3) was conducted with ethyl acetate, the organic layer was dried over anhydrous magnesium sulfate, and the solvent was distilled off under reduced pressures, to give 847 mg of 3-(3-hydroxyphenyl)-2(S)-isopropoxypropanoic acid. This product was then dissolved in 10 ml of N,N-dimethylformamide, and 400 mg of potassium hydrogencarbonate and 0.32 ml of ethyl iodide were successively added thereto, and stirring was continued at room temperature for 3 days. The reaction solution was diluted with ethylacetate and washed with water. The organic layer was dried over anhydrous magnesium sulfate, and the solvent was evaporated. The residue was purified by silica gel column chromatography, to give 567 mg of the title compound as a colorless oil in the 3:1 hexane-ethyl acetate fraction.

$^1$H NMR (CDCl$_3$)

δ: 0.98 (d, J=6.4 Hz, 3H) 1.16 (d, J=6.4 Hz, 3H) 1.24 (t, J=7.2 Hz, 3H) 2.89 (dd, J=8.8, 14.0 Hz, 1H) 2.97 (dd, J=4.8, 13.6 Hz, 1H) 3.52 (Sept, J=6.0 Hz, 1H) 4.05 (dd, J=4.8, 8.8 Hz, 1H) 4.12-4.19 (m, 2H) 5.01 (brs) 1H) 6.09-6.72 (m, 1H) 6.81-6.83 (m, 1H) 6.75 (t, J=1.6 Hz, 1H) 7.15 (t, J=7.6 Hz, 1H)

Production Example 279e 2 (S)-Isopropoxy-3-(3 (R)-oxilanylmethoxyphenyl)propanoic acid ethyl ester

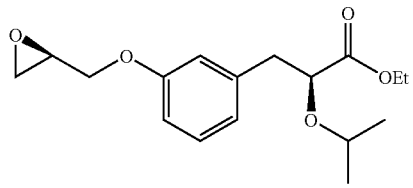

127 mg of 3-(3-hydroxyphenyl)-2(S)-isopropoxypropanoic acid ethyl ester was dissolved in 1.7 ml of N,N-dimethylformamide, and 83 mg of potassium carbonate, 15 mg of cesium fluoride and 156 mg of (R)-glycidylnosylate were added, and stirring was continued at room temperature overnight. The reaction solution was diluted with ethylacetate and washed with water. The organic layer was dried over anhydrous magnesium sulfate, and the solvent was evaporated. The residue was purified by silica gel column chromatography, to give 100 mg of the title compound as a colorless oil in the 4:1 hexane-ethyl acetate fraction.

$^1$H NMR (CDCl$_3$)

δ: 0.96 (d, J=6.0 Hz, 3H) 1.15 (d, J=6.0 Hz, 3H) 1.24 (t, J=7.2 Hz, 3H) 2.76 (dd, J=2.8, 4.8 Hz, 1H) 2.87-2.93 (m, 2H) 2.98 (dd, J=4.8, 14.0 Hz, 1H) 3.33-3.37 (m, 1H) 3.50 (Sept, J=6.0 Hz, 1H) 3.95 (dd, J=6.0, 11.2 Hz, 1H) 4.04 (dd, J=4.8, 9.2 Hz, 1H) 4.14-4.22 (m, 3H) 6.78 (dd, J=2.8, 8.4 Hz, 1H) 6.83 (d, J=2.0 Hz, 1H) 6.86 (d, J=7.6 Hz, 1H) 7.19 (t, J=8.4 Hz, 1H)

Production Example 279f

3-{3-[3-(2,4-Dichlorophenoxy)-2(S)-hydroxypropoxy]phenyl}-2(S)-isopropoxypropanoic acid ethyl ester

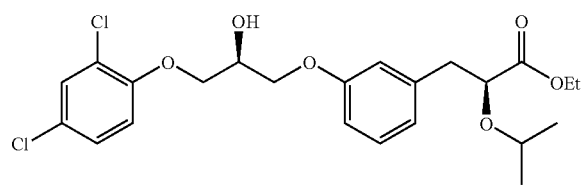

126 mg of 2-Isopropoxy-3-(3-oxilanylmethoxyphenyl)propanoic acid ethyl ester was dissolved in ethanol, and 130 mg of 2,4-dichlorophenol and 17 mg of potassium carbonate were added, and the mixture was stirred at 50° C. for 1.5 days. The reaction solution was diluted with ethyl acetate and washed with water. The organic layer was dried over anhydrous magnesium sulfate, and the solvent was evaporated. The residue was purified by silica gel column chromatography, to give 177 mg of the title compound as a colorless oil in the 3:1 hexane-ethyl acetate fraction.

Example 279g

3-{3-[3-(2,4-Dichlorophenoxy)-2(S)-hydroxypropoxy]phenyl}-2(S)-isopropoxypropanoic acid

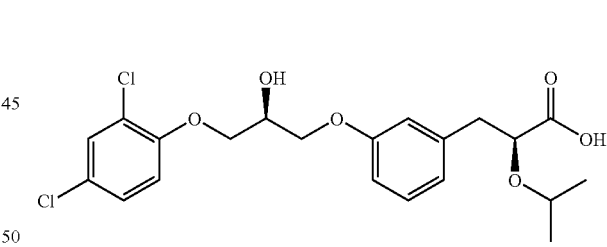

220 mg of 3-{3-[3-(2,4-Dichlorophenoxy)-2(S)-hydroxypropoxy]phenyl}-2(S)-isopropoxypropanoic acid ethyl ester was dissolved in 4 ml of ethanol, followed by adding 1 ml of 1N sodium hydroxide. After standing as it was at room temperature for 4 hours, the solution was neutralized with 1N hydrochloric acid and extracted with ethylacetate. The organic layer was dried over anhydrous magnesium sulfate, and the solvent was evaporated. The residue was purified by silica gel column chromatography, to give 200 mg of the title compound as a colorless oil in the 3:2→2:3 hexane-ethyl acetate fraction.

MS m/e (ESI) 465 (MNa$^+$)

Example 280

3-{3-[3-(4-Chloro-2-cyanophenoxy)-2(S)-hydroxypropoxy]phenyl}-2(S)-isopropoxypropanoic acid

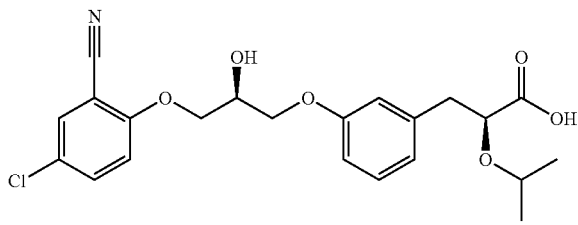

Using 4-chloro-2-cyanophenol, the title compound was obtained in the same manner as described in Production example 279f) and Example 279g).
MS m/e (ESI) 456 (MNa⁺)

Example 281

3-(3-{2(S)-Hydroxy-3-[3-(1-hydroxy-1-methylethyl)phenoxy]-propoxy}phenyl)-2(S)-isopropoxypropanoic acid

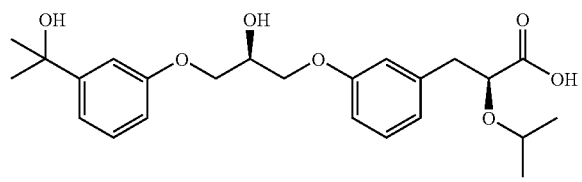

Using 3-(1-hydroxy-1-methylethyl)phenol, the title compound was obtained in the same manner as described in Production example 279f) and Example 279g).
¹H NMR (CDCl₃)
δ: 1.04 (d, J=6.0 Hz, 3H) 1.16 (d, J=6.0 Hz, 3H) 1.57 (s, 6H) 2.92 (dd, J=7.6, 14.0 Hz, 1H) 3.10 (dd, J=3.2, 13.6 Hz, 1H) 3.55 (Sept, J=6.0 Hz, 1H) 4.11-4.12 (m, 5H) 4.38 (Sept, J=5.2 Hz, 1H) 6.80-6.88 (m, 4H) 7.06 (d, J=7.2 Hz, 1H) 7.12 (t, J=2.4 Hz, 1H) 7.21 (dd, J=7.6, 8.0 Hz, 1H) 7.24 (m, 1H)
MS m/e (ESI) 453 (MNa⁺)

Example 282

3-(3-{2(R)-Hydroxy-3-[4-chlorophenoxy]propoxy}phenyl)-2(S)-isopropoxypropanoic acid

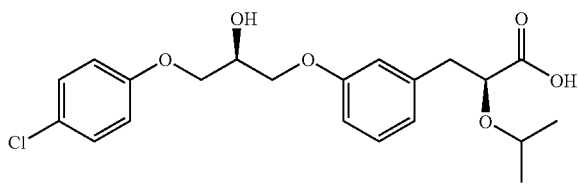

Using 4-chlorophenol, the title compound was obtained in the same manner as described in Production example 279f) and Example 279g)
¹H NMR (CDCl₃).
δ: 1.03 (d, J=6.0 Hz, 3H) 1.16 (d, J=6.0 Hz, 3H) 2.92 (dd, J=7.2, 13.6 Hz, 1H) 3.11 (dd, J=3.6, 13.6 Hz, 1H) 3.53 (Sept, J=6.0 Hz, 1H) 4.09-4.17 (m, 5H) 4.38 (Sept, J=5.6 Hz, 1H) 6.80-6.89 (m, 4H) 7.20-7.26 (m, 4H)
MS m/e (ESI) 431 (MNa⁺)

Example 283

3-(3-{2(S)-Hydroxy-3-[3,4-dichlorophenoxy]propoxy}phenyl)-2 (S)-isopropoxypropanoic acid

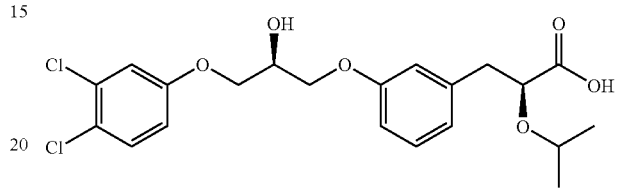

Using 3,4-dichlorophenol, the title compound was obtained in the same manner as described in Production example 279f) and Example 279g).
¹H NMR (CDCl₃)
δ: 1.04 (d, J=6.4 Hz, 3H) 1.17 (d, J=6.0 Hz, 3H) 2.93 (dd, J=7.6, 14.0 Hz, 1H) 3.11 (dd, J=4.0, 13.6 Hz, 1H) 3.56 (Sept, J=6.0 Hz, 1H) 4.09-4.16 (m, 5H) 4.38 (Sept, J=6.4 Hz, 1H) 6.80 (dd, J=2.8, 8.8 Hz, 1H) 6.83 (brs, 2H) 6.87 (d, J=7.6 Hz, 1H) 7.05 (d, J=2.8 Hz, 1H) 7.22 (dd, J=7.6, 8.8 Hz, 1H) 7.34 (d, 8.8 Hz, 1H)
MS m/e (ESI) 465 (MNa⁺)

Example 284

3-(3-{2(R)-Hydroxy-3-[4-methylphenoxy]-propoxy}phenyl)-2(S)-isopropoxypropanoic acid

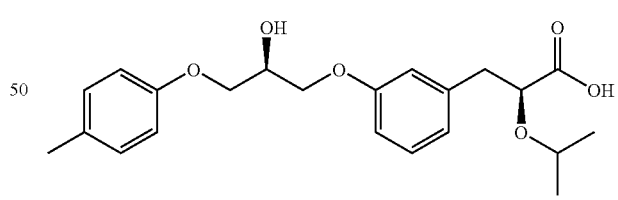

Using 4-methylphenol, the title compound was obtained in the same manner as described in Production example 279f) and Example 279g).
¹H NMR (CDCl₃)
δ: 1.03 (d, J=6.4 Hz, 3H) 1.15 (d, J=6.0 Hz, 3H) 2.29 (s, 3H) 2.91 (dd, J=8.0, 14.0 Hz, 1H) 3.11 (dd, J=3.6, 13.6 Hz, 1H) 3.54 (Sept, J=6.4 Hz, 1H) 4.09-4.17 (m, 5H) 4.37 (Sept, J=6.4 Hz, 1H) 6.80-6.87 (m, 5H) 7.09 (d, J=8.4 Hz, 2H) 7.21 (dd, J=7.6, 9.2 Hz, 1H)
MS m/e (ESI) 411 (MNa⁺)

Example 285

3-(3-{2(S)-Hydroxy-3-[2,4-dimethylphenoxy]-propoxy}phenyl)-2(S)-isopropoxypropanoic acid

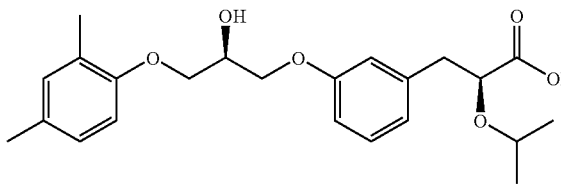

Using 2,4-dimethylphenol, the title compound was obtained in the same manner as described in Production example 279f) and Example 279g).

$^1$H NMR (CDCl$_3$)

δ: 1.03 (d, J=6.4 Hz, 3H) 1.15 (d, J=6.0 Hz, 3H) 2.20 (s, 3H) 2.26 (s, 3H) 2.91 (dd, J=8.0, 14.0 Hz, 1H) 3.11 (dd, J=4.0, 14.0 Hz, 1H) 3.54 (Sept, J=6.0 Hz, 1H) 4.10-4.20 (m, 5H) 4.39 (Sept, J=5.2 Hz, 1H) 6.75 (d, J=7.6 Hz, 1H) 6.81-6.87 (m, 3H) 6.93-6.97 (m, 2H) 7.22 (dd, J=8.0, 8.8 Hz, 1H)

MS m/e (ESI) 425 (MNa$^+$)

Example 286

3-(3-{2(S)-Hydroxy-3-[4-chloro-2-methylphenoxy]propoxy}phenyl)-2(S)-isopropoxypropanoic acid

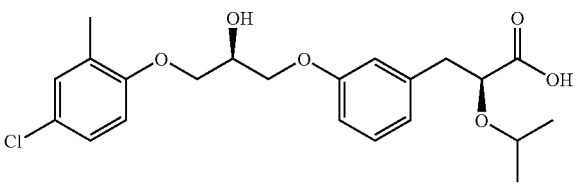

Using 4-chloro-2-methylphenol, the title compound was obtained in the same manner as described in Production example 279f) and Example 279g).

MS m/e (ESI) 445 (MNa$^+$)

Example 287

3-(3-{2(S)-Hydroxy-3-[4-chloro-2-fluorophenoxy]propoxy}phenyl)-2(S)-isopropoxypropanoic acid

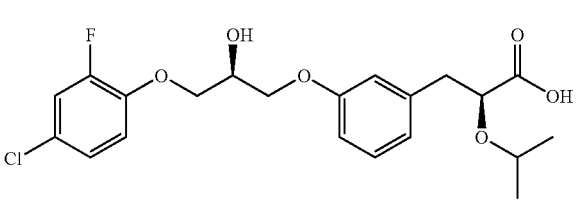

Using 4-chloro-2-fluorophenol, the title compound was obtained in the same manner as described in Production example 279f) and Example 279g).

MS m/e (ESI) 449 (MNa$^+$)

Example 288

3-(3-{2(S)-Hydroxy-3-[4-chloro-3-fluorophenoxy]propoxy}phenyl)-2(S)-isopropoxypropanoic acid

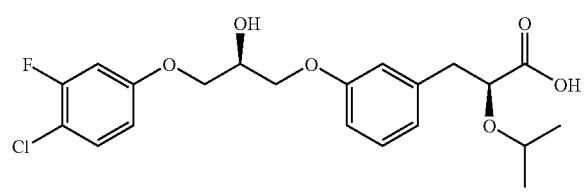

Using 4-chloro-3-fluorophenol, the title compound was obtained in the same manner as described in Production example 279f) and Example 279g).

MS m/e (ESI) 449 (MNa$^+$)

Example 289

3-(3-{2(S)-Hydroxy-3-[2,4,6-trimethylphenoxy]-propoxy}phenyl)-2(S)-isopropoxypropanoic acid

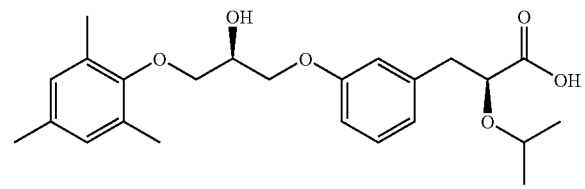

Using 2,4,6-trimethylphenol, the title compound was obtained in the same manner as described in Production example 279f) and Example 279g).

MS m/e (ESI) 439 (MNa$^+$)

Example 290

3-(3-{2(S)-Hydroxy-3-[4-fluoro-2-methylphenoxy]propoxy}phenyl)-2(S)-isopropoxypropanoic acid

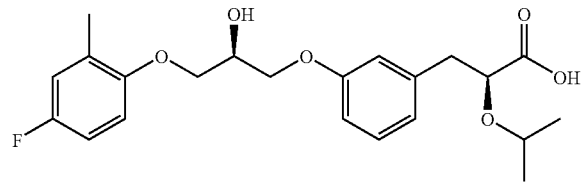

Using 4-fluoro-2-methylphenol, the title compound was obtained in the same manner as described in Production example 279f) and Example 279g).

MS m/e (ESI) 429 (MNa$^+$)

Example 291

3-(3-{2(S)-Hydroxy-3-[2-bromo-4-methylphenoxy]propoxy}phenyl)-2(S)-isopropoxypropanoic acid

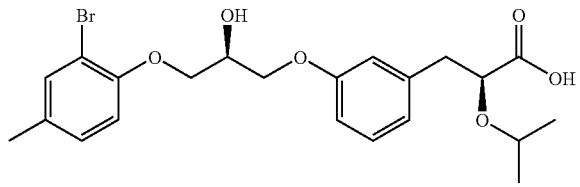

Using 2-bromo-4-methylphenol, the title compound was obtained in the same manner as described in Production example 279f) and Example 279g).

MS m/e (ESI) 489 (MNa$^+$)

Example 292

3-(3-{2(S)-Hydroxy-3-[2-acetyl-4-chlorophenoxy]propoxy}phenyl)-2(S)-isopropoxypropanoic acid

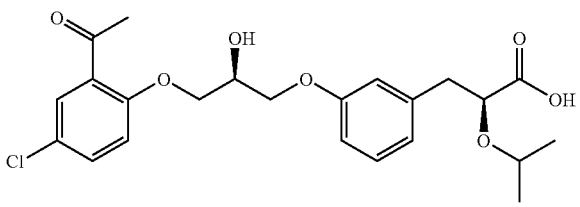

Using 2-acetyl-4-chlorophenol, the title compound was obtained in the same manner as described in Production example 279f) and Example 279g).

MS m/e (ESI) 473 (MNa$^+$)

Example 293

3-(3-{2(S)-Hydroxy-3-[2,5-dimethylphenoxy]propoxy}phenyl)-2(S)-isopropoxypropanoic acid

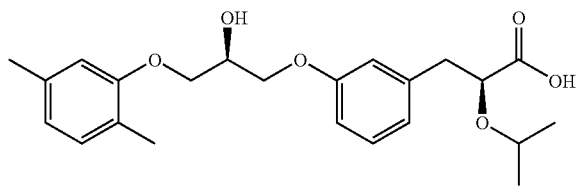

Using 2,5-dimethylphenol, the title compound was obtained in the same manner as described in Production example 279f) and Example 279g).

MS m/e (ESI) 425 (MNa$^+$)

Example 294

3-(3-{2(S)-Hydroxy-3-[2,5-dichlorophenoxy]propoxy}phenyl)-2(S)-isopropoxypropanoic acid

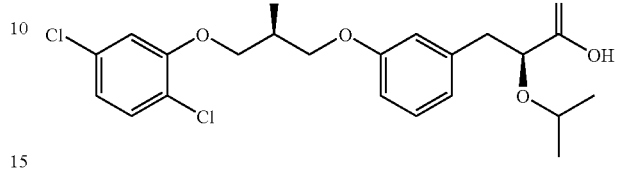

Using 2,5-dichlorophenol, the title compound was obtained in the same manner as described in Production example 279f) and Example 279g).

MS m/e (ESI) 465 (MNa$^+$)

Example 295

3-(3-{2(S)-Hydroxy-3-[2-fluoro-5-trifluoromethylphenoxy]-propoxy}phenyl)-2(S)-isopropoxypropanoic acid

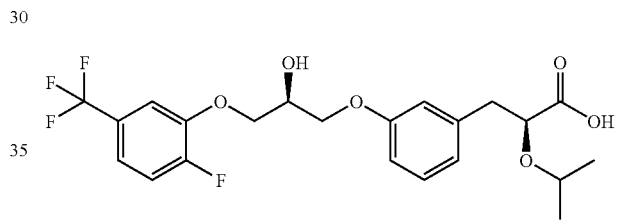

Using 2-fluoro-5-trifluoromethylphenol, the title compound was obtained in the same manner as described in Production example 279f) and Example 279g).

MS m/e (ESI) 483 (MNa$^+$)

Example 296

3-(3-{2(S)-Hydroxy-3-[5-fluoro-2-trifluoromethylphenoxy]-propoxy}phenyl)-2(S)-isopropoxypropanoic acid

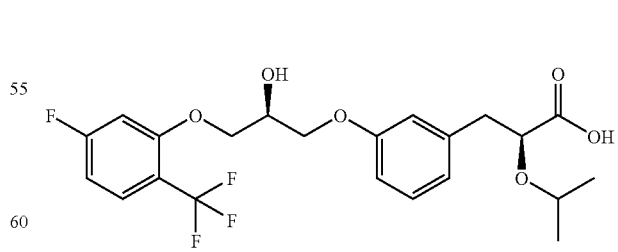

Using 5-fluoro-2-trifluoromethylphenol, the title compound was obtained in the same manner as described in Production example 279f) and Example 279g).

MS m/e (ESI) 483 (MNa$^+$)

Example 297

3-(3-{2(R)-Hydroxy-3-[2,4-dichlorophenoxy]-propoxy}phenyl)-2(S)-isopropoxypropanoic acid Production Example 297a 2 (S)-Isopropoxy-3-(3-(S)-oxilanylmethoxyphenyl)propanoic acid ethyl ester

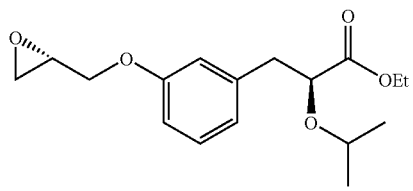

Using (S)-glycidylnosylate, the title compound was obtained as a colorless oil in the same manner as described in Production example 279e).

Production Example 297b

3-{3-[3-(2,4-Dichlorophenoxy)-2 (R)-hydroxypropoxy]phenyl}-2(S)-isopropoxypropanoic acid ethyl ester

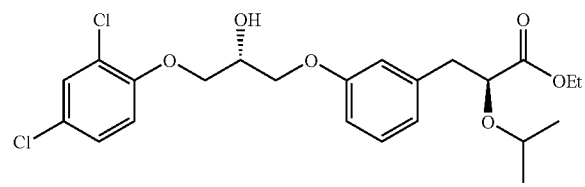

Using 2 (S)-isopropoxy-3-(3-(S)-oxilanylmethoxyphenyl)-propanoic acid ethyl ester, the title compound was obtained in the same manner as described in 279f).

Example 297c

3-{3-[3-(2,4-dichlorophenoxy)-2 (R)-hydroxypropoxy]phenyl}-2(S)-isopropoxypropanoic acid

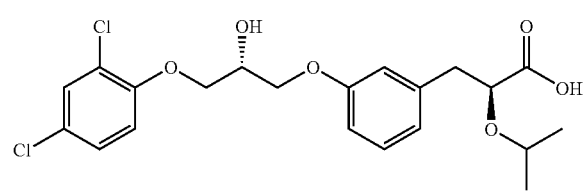

Using 3-{3-[3-(2,4-dichlorophenoxy)-2 (R)-hydroxypropoxy]phenyl}-2(S)-isopropoxypropanoic acid ethyl ester, the title compound was obtained in the same manner as described in Example 279g)

MS m/e (ESI) 465 (MNa$^+$).

Example 298

3-{3-[3-(4-Chloro-2-cyanophenoxy)-2 (R)-hydroxypropoxy]phenyl}-2(S)-isopropoxypropanoic acid

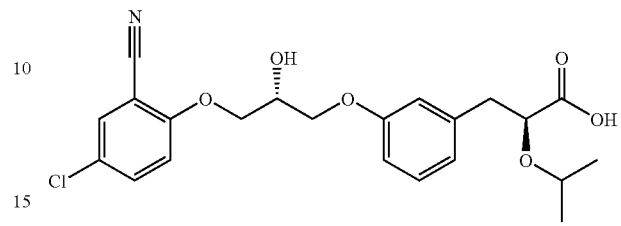

Using 4-chloro-2-cyanophenol, the title compound was obtained in the same manner as described in Production example 297b) and Example 297c).

MS m/e (ESI) 458 (MNa$^+$)

Example 299

3-(3-{2(R)-Hydroxy-3-[3-(1-hydroxy-1-methylethyl)phenoxy]propoxy}phenyl)-2(S)-isopropoxypropanoic acid

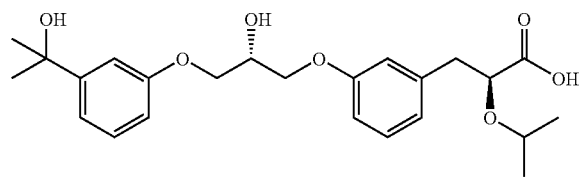

Using 3-dimethylhydroxyphenol, the title compound was obtained in the same manner as described in Production example 297b) and Example 297c).

$^1$H NMR (CDCl$_3$)

δ: 1.04 (d, J=6.0 Hz, 3H) 1.16 (d, J=6.0 Hz, 3H) 1.57 (s, 6H) 2.92 (dd, J=8.0, 14.0 Hz, 1H) 3.10 (dd, J=3.6, 13.6 Hz, 1H) 3.55 (Sept, J=6.0 Hz, 1H) 4.09-4.21 (m, 5H) 4.39 (Sept, J=5.2 Hz, 1H) 6.80-6.88 (m, 4H) 7.05-7.07 (m, 1H) 7.12 (t, J=2.4 Hz, 1H) 7.21 (dd, J=7.6, 8.0 Hz, 1H) 7.24-7.28 (m, 1H)

MS m/e (ESI) 453 (MNa$^+$)

Example 300

3-(3-{2(S)-Hydroxy-3-[4-chlorophenoxy]propoxy}phenyl)-2(S)-isopropoxypropanoic acid

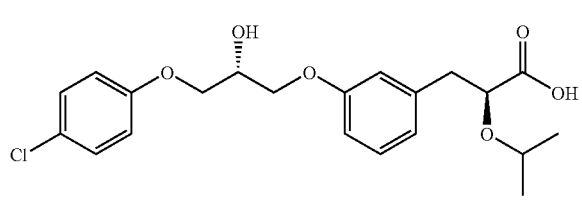

Using 4-chlorophenol, the title compound was obtained in the same manner as described in Production example 297b) and Example 297c).

$^1$H NMR (CDCl$_3$)

δ: 1.03 (d, J=6.0 Hz, 3H) 1.16 (d, J=6.0 Hz, 3H) 2.92 (dd, J=8.0, 13.6 Hz, 1H) 3.11 (dd, J=4.0, 13.6 Hz, 1H) 3.55 (Sept, J=6.0 Hz, 1H) 4.08-4.17 (m, 5H) 4.38 (Sept, J=4.8 Hz, 1H) 6.80-6.89 (m, 4H) 7.20-7.26 (m, 4H)

MS m/e (ESI) 431 (MNa$^+$)

Example 301

3-(3-{2(R)-Hydroxy-3-[3,4-dichlorophenoxy]-propoxy}phenyl)-2(S)-isopropoxypropanoic acid

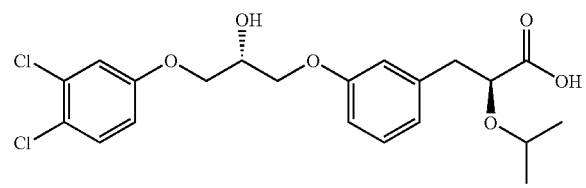

Using 3,4-dichlorophenol, the title compound was obtained in the same manner as described in Production example 297b) and Example 297c).

$^1$H NMR (CDCl$_3$)

δ: 1.03 (d, J=6.4 Hz, 3H) 1.16 (d, J=6.0 Hz, 3H) 2.93 (dd, J=8.0, 14.0 Hz, 1H) 3.11 (dd, J=6.0, 14.0 Hz, 1H) 3.56 (Sept, J=6.4 Hz, 1H) 4.09-4.16 (m, 5H) 4.37 (Sept, J=6.4 Hz, 1H) 6.78-6.84 (m, 3H) 6.87 (d, J=7.6 Hz, 1H) 7.04 (d, J=2.8 Hz, 1H) 7.22 (t, J=7.6 Hz, 1H) 7.33 (d, J=8.8 Hz, 1H)

MS m/e (ESI) 465 (MNa$^+$)

Example 302

3-(3-{2(S)-Hydroxy-3-[4-methylphenoxy]propoxy}phenyl)-2(S)-isopropoxypropanoic acid

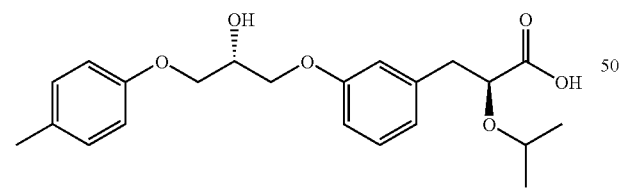

Using 4-methylphenol, the title compound was obtained in the same manner as described in Production example 297b) and Example 297c).

$^1$H NMR (CDCl$_3$)

δ: 1.03 (d, J=6.4 Hz, 3H) 1.16 (d, J=6.0 Hz, 3H) 2.29 (s, 3H) 2.91 (dd, J=8.0, 13.6 Hz, 1H) 3.11 (dd, J=4.0, 14.0 Hz, 1H) 3.54 (Sept, J=6.4 Hz, 1H) 4.09-4.17 (m, 5H) 4.37 (Sept, J=5.2 Hz, 1H) 6.80-6.88 (m, 5H) 7.09 (d, J=8.4 Hz, 2H) 7.21 (dd, J=7.6, 9.2 Hz, 1H)

MS m/e (ESI) 411 (MNa$^+$)

Example 303

3-(3-{2(R)-Hydroxy-3-[2,4-dimethylphenoxy]-propoxy}phenyl)-2(S)-isopropoxypropanoic acid

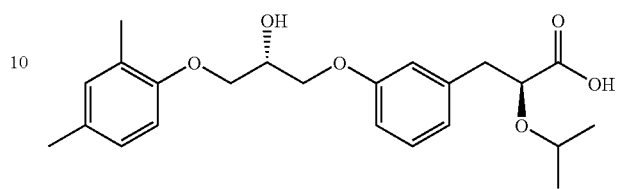

Using 2,4-dimethylphenol, the title compound was obtained in the same manner as described in Production example 297b) and Example 297c).

$^1$H NMR (CDCl$_3$)

δ: 1.02 (d, J=6.0 Hz, 3H) 1.16 (d, J=6.0 Hz, 3H) 2.20 (s, 3H) 2.26 (s, 3H) 2.91 (dd, J=8.0, 13.6 Hz, 1H) 3.11 (dd, J=3.6, 13.6 Hz, 1H) 3.54 (Sept, J=6.0 Hz, 1H) 4.09-4.20 (m, 5H) 4.39 (Sept, J=5.2 Hz, 1H) 6.75 (d, J=8.0 Hz, 1H) 6.80-6.87 (m, 3H) 6.93-6.97 (m, 2H) 7.22 (dd, J=8.0, 8.8 Hz, 1H)

MS m/e (ESI) 425 (MNa$^+$)

Example 304

3-(3-{2(S)-Hydroxy-3-[4-bromophenoxy]propoxy}-phenyl)-2(S)-isopropoxypropanoic acid

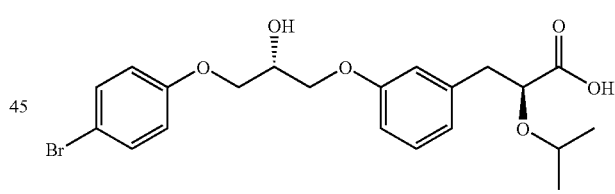

Using 4-bromophenol, the title compound was obtained in the same manner as described in Production example 297b) and Example 297c).

$^1$H NMR (CDCl$_3$)

δ: 1.04 (d, J=6.0 Hz, 3H) 1.16 (d, J=6.0 Hz, 3H) 2.92 (dd, J=7.6, 14.0 Hz, 1H) 3.11 (dd, J=4.0, 13.6 Hz, 1H) 3.55 (Sept, J=6.0 Hz, 1H) 4.08-4.17 (m, 5H) 4.38 (Sept, J=4.8 Hz, 1H) 6.80-6.84 (m, 4H) 6.87 (d, J=7.6 Hz, 1H) 7.22 (dd, J=7.6, 8.8 Hz, 1H) 7.39 (d, J=8.8 Hz, 1H)

MS m/e (ESI) 475 (MNa$^+$)

Example 305

3-(3-{2(S)-Hydroxy-3-[4-ethylphenoxy]propoxy}phenyl)-2(S)-isopropoxypropanoic acid

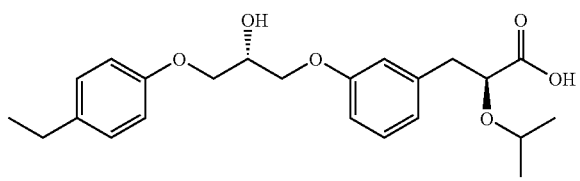

Using 4-ethylphenol, the title compound was obtained in the same manner as described in Production example 297b) and Example 297c).

$^1$H NMR (CDCl$_3$)

δ: 1.03 (d, J=6.0 Hz, 3H) 1.16 (d, J=6.0 Hz, 3H) 1.20 (t, J=7.2 Hz, 3H) 2.59 (q, J=7.6 Hz, 2H) 2.91 (dd, J=8.0, 14.0 Hz, 1H) 3.11 (dd, J=3.6, 13.6 Hz, 1H) 3.54 (Sept, J=6.0 Hz, 1H) 4.10-4.17 (m, 5H) 4.38 (Sept, J=5.2 Hz, 1H) 6.83 (t, J=6.8 Hz, 2H) 6.86 (d, J=8.4 Hz, 3H) 7.12 (d, J=8.4 Hz, 2H) 7.21 (dd, J=7.2, 9.2 Hz, 1H)

MS m/e (ESI) 425 (MNa$^+$)

Example 306

3-(3-{2(S)-Hydroxy-3-[4-chloro-3-methylphenoxy]propoxy}phenyl)-2(S)-isopropoxypropanoic acid

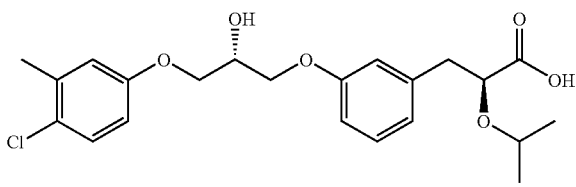

Using 4-chloro-3-methylphenol, the title compound was obtained in the same manner as described in Production example 297b) and Example 297c).

$^1$H NMR (CDCl$_3$)

δ: 1.03 (d, J=6.0 Hz, 3H) 1.16 (d, J=6.4 Hz, 3H) 2.26 (S, 3H) 2.92 (dd, J=7.6, 13.6 Hz, 1H) 3.11 (dd, J=3.6, 13.6 Hz, 1H) 3.55 (Sept, J=6.0 Hz, 1H) 4.08-4.16 (m, 5H) 4.37 (Sept, J=5.2 Hz, 1H) 6.71 (dd, J=2.8, 8.8 Hz, 1H) 6.80-6.84 (m, 3H) 6.87 (d, J=7.2 Hz, 1H) 7.19-7.24 (m, 2H)

MS m/e (ESI) 445 (MNa$^+$)

Example 307

3-(3-{2(R)-Hydroxy-3-[3-chloro-4-fluorophenoxy]propoxy}phenyl)-2(S)-isopropoxypropanoic acid

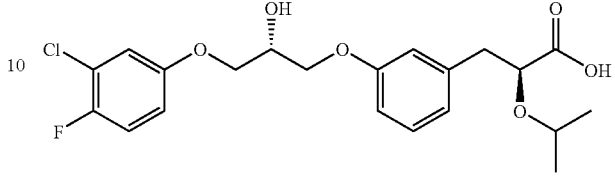

Using 3-chloro-4-fluorophenol, the title compound was obtained in the same manner as described in Production example 297b) and Example 297c).

$^1$H NMR (CDCl$_3$)

δ: 1.04 (d, J=6.0 Hz, 3H) 1.17 (d, J=6.0 Hz, 3H) 2.93 (dd, J=8.0, 14.0 Hz, 1H) 3.11 (dd, J=4.0, 14.0 Hz, 1H) 3.56 (Sept, J=6.4 Hz, 1H) 4.07-4.16 (m, 5H) 4.37 (Sept, J=4.8 Hz, 1H) 6.77-6.84 (m, 3H) 6.87 (d, J=7.6 Hz, 1H) 6.98 (dd, J=3.2, 6.0 Hz, 1H) 7.06 (t, J=8.8 Hz, 1H) 7.22 (dd, J=7.6, 9.2 Hz, 1H)

MS m/e (ESI) 449 (MNa$^+$)

Example 308

3-(3-{2(R)-Hydroxy-3-[4-chloro-2-methylphenoxy]propoxy}phenyl)-2(S)-isopropoxypropanoic acid

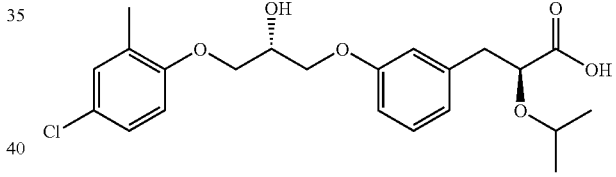

Using 4-chloro-2-methylphenol, the title compound was obtained in the same manner as described in Production example 297b) and Example 297c).

MS m/e (ESI) 445 (MNa$^+$)

Example 309

3-(3-{2(R)-Hydroxy-3-[4-chloro-2-fluorophenoxy]propoxy}phenyl)-2(S)-isopropoxypropanoic acid

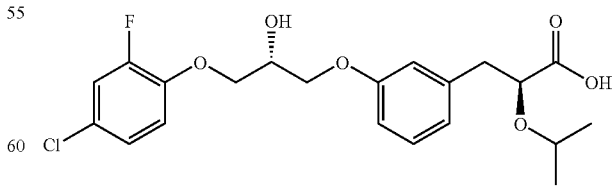

Using 4-chloro-2-fluorophenol, the title compound was obtained in the same manner as described in Production example 297b) and Example 297c).

MS m/e (ESI) 449 (MNa$^+$)

Example 310

3-(3-{2(R)-Hydroxy-3-[4-chloro-3-fluorophenoxy]propoxy}phenyl)-2(S)-isopropoxypropanoic acid

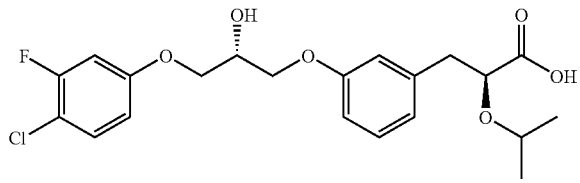

Using 4-chloro-3-fluorophenol, the title compound was obtained in the same manner as described in Production example 297b) and Example 297c).

MS m/e (ESI) 449 (MNa$^+$)

Example 311

3-(3-{2(R)-Hydroxy-3-[4-acetyl-2-methylphenoxy]propoxy}phenyl)-2(S)-isopropoxypropanoic acid

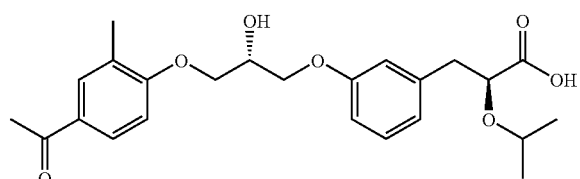

Using 4-acetyl-2-methylphenol, the title compound was obtained in the same manner as described in Production example 297b) and Example 297c).

MS m/e (ESI) 453 (MNa$^+$)

Example 312

3-(3-{2 (R)-Hydroxy-3-[2,4,6-trimethylphenoxy]-propoxy}phenyl)-2(S)-isopropoxypropanoic acid

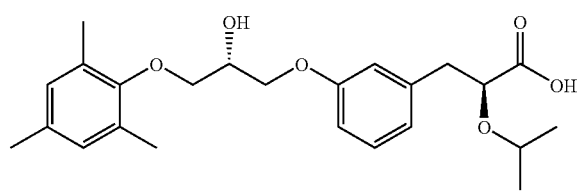

Using 2,4,6-trimethylphenol, the title compound was obtained in the same manner as described in Production example 297b) and Example 297c).

MS m/e (ESI) 439 (MNa$^+$)

Example 313

3-(3-{2(R)-Hydroxy-3-[4-fluoro-2-methylphenoxy]propoxy}phenyl)-2(S)-isopropoxypropanoic acid

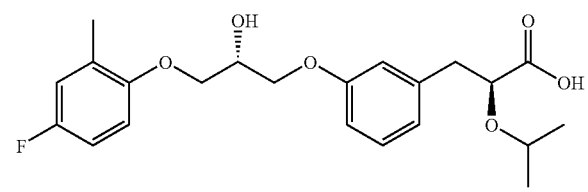

Using 4-fluoro-2-methylphenol, the title compound was obtained in the same manner as described in Production example 297b) and Example 297c).

MS m/e (ESI) 429 (MNa$^+$)

Example 314

3-(3-{2(R)-Hydroxy-3-[2-bromo-4-methylphenoxy]propoxy}phenyl)-2(S)-isopropoxypropanoic acid

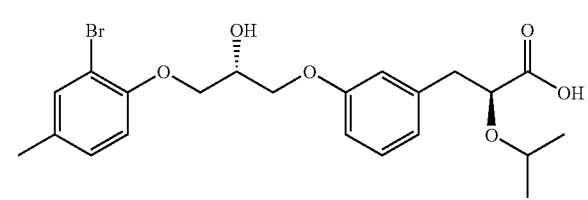

Using 2-bromo-4-methylphenol, the title compound was obtained in the same manner as described in Production example 297b) and Example 297c).

MS m/e (ESI) 489 (MNa$^+$)

Example 315

3-(3-{2(R)-Hydroxy-3-[2-acetyl-4-chlorophenoxy]propoxy}-phenyl)-2(S)-isopropoxypropanoic acid

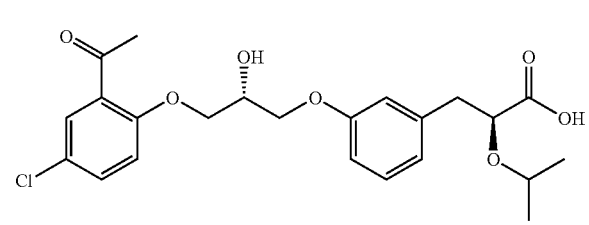

Using 2-acetyl-4-chlorophenol, the title compound was obtained in the same manner as described in Production example 297b) and Example 297c).

MS m/e (ESI) 473 (MNa$^+$)

Example 316

3-(3-{2 (R) —Hydroxy-3-[2,5-dimethylphenoxy]-propoxy}phenyl)-2(S)-isopropoxypropanoic acid

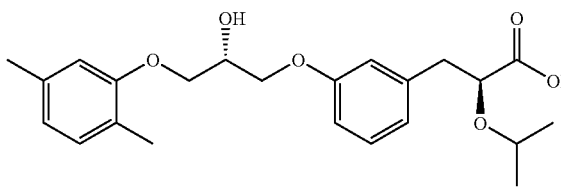

Using 2,5-dimethylphenol, the title compound was obtained in the same manner as described in Production example 297b) and Example 297c).

MS m/e (ESI) 425 (MNa$^+$)

Example 317

3-(3-{2(R)-Hydroxy-3-[2,5-dichlorophenoxy]-propoxy}phenyl)-2(S)-isopropoxypropanoic acid

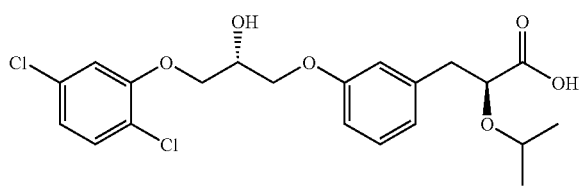

Using 2,5-dichlorophenol, the title compound was obtained in the same manner as described in Production example 297b) and Example 297c).

MS m/e (ESI) 465 (MNa$^+$)

Example 318

3-(3-{2(R)-Hydroxy-3-[2-fluoro-5-trifluoromethylphenoxy]-propoxy}phenyl)-2(S)-isopropoxypropanoic acid

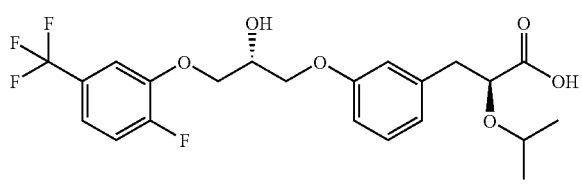

Using 2-fluoro-5-trifluoromethylphenol, the title compound was obtained in the same manner as described in Production example 297b) and Example 297c).

MS m/e (ESI) 483 (MNa$^+$)

Example 319

3-(3-{2(R)-Hydroxy-3-[5-fluoro-2-trifluoromethylphenoxy]propoxy}phenyl)-2(S)-isopropoxypropanoic acid Using 5-fluoro-2-trifluoromethylphenol, the title compound was obtained in the same manner as described in Production example 297b) and Example 297c).

MS m/e (ESI) 483 (MNa$^+$)

Example 320

3-{3-[3-(2,4-Dichlorophenoxy)-2 (R)-fluoropropoxy]phenyl}-2(S)-isopropoxypropanoic acid Using 174 mg of 3-{3-[3-(2,4-dichlorophenoxy)-2(S)-hydroxypropoxy]phenyl}-2(S)-isopropoxypropanoic acid ethyl ester (Production example 279e) was dissolved in 5 ml of dichloromethane, and the mixture was cooled to −78° C. To the solution was added 0.15 ml (diethylamino) sulfur trifluoride, and stirring was continued at room temperature for 2 days. Water was added thereto, and the mixture was extracted with dichloromethane. The organic layer was dried over anhydrous magnesium sulfate, filtered and the solvent was removed. The residue was purified by silica gel column chromatography, to give 79 mg of 3-{3-[3-(2,4-dichlorophenoxy)-2 (R)-fluoropropoxy]phenyl}-2(S)-isopropoxypropanoic acid ethyl ester in the 7:1→5:1 hexane-ethyl acetate fraction. This product was dissolved in 4 ml of ethanol and 0.5 ml of tetrahydrofuran and 0.5 ml of 1N lithium hydroxide were added, and stirring was continued overnight at room temperature. The solution was acidified with 1N hydrochloric acid, and extracted with ethyl acetate. The organic layer was dried over anhydrous magnesium sulfate, filtered and the solvent was removed. The residue was purified by silica gel column chromatography, to give 61 mg of the title compound in the 3:1→1:1 hexane-ethyl acetate fraction.

$^1$H NMR (CDCl$_3$)

δ: 1.03 (d, J=6.4 Hz, 3H) 1.16 (d, J=6.0 Hz, 3H) 2.92 (dd, J=8.0, 14.0 Hz, 1H) 3.11 (dd, J=3.6, 14.0 Hz, 1H) 3.54 (Sept, J=6.4 Hz, 1H) 4.13 (q, J=4.0 Hz, 1H) 4.28-4.39 (m, 4H) 5.18 (dt, J=4.0, 46.8 Hz, 1H) 6.82-6.92 (m, 4H) 7.19-7.29 (m, 3H)

MS m/e (ESI) 467 (MNa$^+$)

Example 321

3-{3-[3-(4-Chlorophenoxy)-2(S)-fluoropropoxy]phenyl}-2(S)-isopropoxypropanoic acid

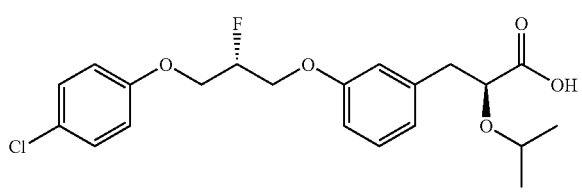

Using 4-chlorophenol, the title compound was obtained in the same manner as described in Production example 279e) and Example 319.

$^1$H NMR (CDCl$_3$)

δ: 1.02 (d, J=6.0 Hz, 3H) 1.16 (d, J=6.0 Hz, 3H) 2.92 (dd, J=8.0, 14.0 Hz, 1H) 3.11 (dd, J=3.6, 14.0 Hz, 1H) 3.55 (Sept, J=6.0 Hz, 1H) 4.13 (q, J=3.6 Hz, 1H) 4.26 (d, J=4.4 Hz, 2H) 4.31 (d, J=4.8 Hz, 2H) 5.14 (dsept, J=4.8, 47.2 Hz, 1H) 6.80-6.90 (m, 5H) 7.20-7.26 (m, 3H)

MS m/e (ESI) 433 (MNa$^+$)

Example 322

3-{3-[3-(3,4-Dichlorophenoxy)-2 (R)-fluoropropoxy]phenyl}-2(S)-isopropoxypropanoic acid

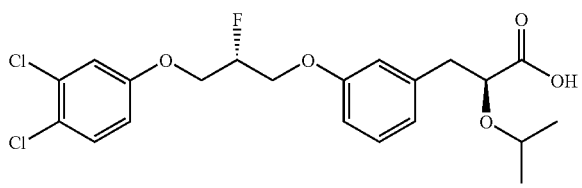

Using 3,4-dichlorophenol, the title compound was obtained in the same manner as described in Production example 279e) and Example 320.

$^1$H NMR (CDCl$_3$)

δ: 1.03 (d, J=6.4 Hz, 3H) 1.17 (d, J=6.4 Hz, 3H) 2.93 (dd, J=8.0, 14.0 Hz, 1H) 3.11 (dd, J=4.0, 14.0 Hz, 1H) 3.55 (Sept, J=6.4 Hz, 1H) 4.14 (q, J=3.6 Hz, 1H) 4.26 (d, J=4.4 Hz, 2H) 4.31 (t, J=4.8 Hz, 2H) 5.13 (dsept, J=4.8, 46.8 Hz, 1H) 6.79-6.84 (m, 3H) 6.88 (d, J=7.6 Hz, 1H) 7.05 (d, J=2.8 Hz, 1H) 7.23 (dt, J=1.2, 7.6 Hz, 1H) 7.34 (d, J=8.8 Hz, 1H)

MS m/e (ESI) 467 (MNa$^+$)

Example 323

3-{3-[3-(4-Chloro-2-cyanophenoxy)-2 (R)-fluoropropoxy]phenyl}-2(S)-isopropoxypropanoic acid

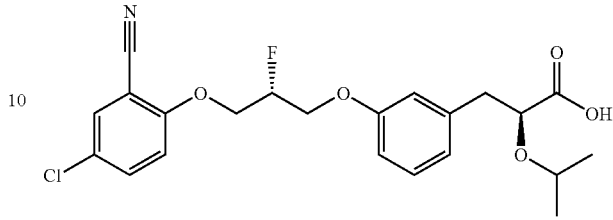

Using 4-chloro-2-cyanophenol, the title compound was obtained in the same manner as described in Production example 279e) and Example 320.

$^1$H NMR (CDCl$_3$)

δ: 1.04 (d, J=6.0 Hz, 3H) 1.17 (d, J=6.0 Hz, 3H) 2.94 (dd, J=7.6, 13.6 Hz, 1H) 3.10 (dd, J=4.0, 13.6 Hz, 1H) 3.57 (Sept, J=6.0 Hz, 1H) 4.14 (q, J=4.0 Hz, 1H) 4.28-4.50 (m, 4H) 5.20 (dsept, J=4.4, 46.4 Hz, 1H) 6.80-6.85 (m, 2H) 6.88 (d, J=7.6 Hz, 1H) 6.98 (d, J=8.8 Hz, 1H) 7.22 (dt, J=0.8, 7.6 Hz, 1H) 7.49-7.64 (m, 2H)

MS m/e (ESI) 458 (MNa$^+$)

Example 324

3-{3-[3-(2,4-Dimethylphenoxy)-2 (R)-fluoropropoxy]phenyl}-2(S)-isopropoxypropanoic acid

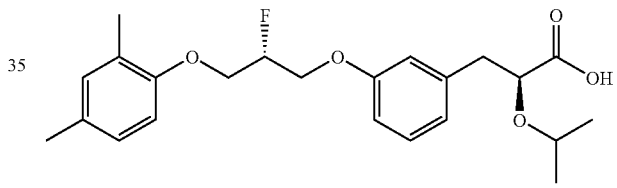

Using 2,4-dimethylphenol, the title compound was obtained in the same manner as described in Production example 279e) and Example 320.

$^1$H NMR (CDCl$_3$)

δ: 1.01 (d, J=6.4 Hz, 3H) 1.16 (d, J=6.4 Hz, 3H) 2.20 (s, 3H) 2.26 (s, 3H) 2.91 (dd, J=8.4, 14.0 Hz, 1H) 3.11 (dd, J=4.0, 13.6 Hz, 1H) 3.53 (Sept, J=6.0 Hz, 1H) 4.13 (q, J=4.0 Hz, 1H) 4.21-4.35 (m, 4H) 5.16 (dsept, J=4.4, 47.6 Hz, 1H) 6.74 (d, J=8.0 Hz, 1H) 6.80-6.84 (m, 2H) 6.87 (d, J=7.6 Hz, 1H) 6.93-6.97 (m, 2H) 7.22 (dt, J=0.6, 7.6 Hz, 1H) MS m/e (ESI) 458 (MNa$^+$)

Example 325

3-{3-[3-(4-Chloro-2-methylphenoxy)-2 (R)-fluoropropoxy]phenyl}-2(S)-isopropoxypropanoic acid

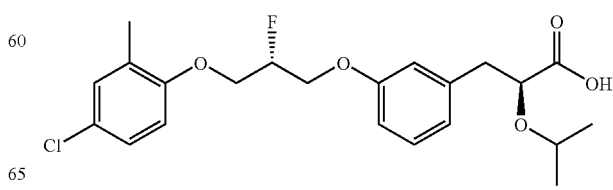

Using 4-chloro-2-methylphenol, the title compound was obtained in the same manner as described in Production example 279e) and Example 320.

MS m/e (ESI) 447 (MNa⁺)

Example 326

3-{3-[3-(2,4-Dichlorophenoxy)-2(S)-fluoropropoxy]phenyl}-2(S)-isopropoxypropanoic acid

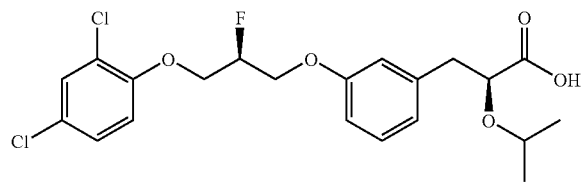

174 mg of 3-{3-[3-(2,4-dichlorophenoxy)-2 (R)-hydroxypropoxy]phenyl}-2(S)-isopropoxypropanoic acid ethyl ester (Production example 297b) was dissolved in 5 ml of dichloromethane, and the mixture was cooled to −78° C. 0.15 ml of (diethylamino)sulfur trifluoride was added thereto, and stirring was continued at room temperature for 2 days. Water was added and the mixture was extracted with dichloromethane. The organic layer was dried over anhydrous magnesium sulfate, filtered, and the solvent was removed. The residue was purified by silica gel column chromatography, to give 87 mg of 3-{3-[3-(2,4-dichlorophenoxy)-2(S)-fluoropropoxy]phenyl-2 (S)-isopropoxypropanoic acid ethyl ester in the 7:1→5:1 hexane-ethyl acetate fraction. This product was dissolved in 4 ml of ethanol and 0.5 ml of tetrahydrofuran, 0.5 ml of 1N lithium hydroxide was added, and the mixture was stirred overnight at room temperature. The solution was acidified with 1N hydrochloric acid, and extracted with ethyl acetate. The organic layer was dried over anhydrous magnesium sulfate, filtered, and the solvent was removed. The residue was purified by silica gel column chromatography, to give 83 mg of the title compound in the 3:1->1:1 hexane-ethyl acetate fraction.

¹H NMR (CDCl₃)

δ: 1.03 (d, J=6.4 Hz, 3H) 1.16 (d, J=6.4 Hz, 3H) 2.92 (dd, J=7.6, 13.6 Hz, 1H) 3.11 (dd, J=3.6, 13.6 Hz, 1H) 3.55 (Sept, J=6.0 Hz, 1H) 4.13 (q, J=4.0 Hz, 1H) 4.29-4.39 (m, 4H) 5.18 (dt, J=4.4, 46.8 Hz, 1H) 6.82-6.92 (m, 4H) 7.18-7.26 (m, 3H)

MS m/e (ESI) 467 (MNa⁺)

Example 327

3-{3-[3-(4-Chlorophenoxy)-2 (R)-fluoropropoxy]phenyl}-2(S)-isopropoxypropanoic acid

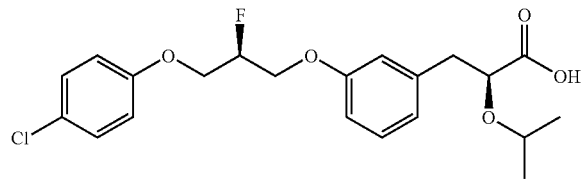

Using 4-chlorophenol, the title compound was obtained in the same manner as described in Production example 297b) and Example 326.

¹H NMR (CDCl₃)

δ: 1.02 (d, J=6.0 Hz, 3H) 1.16 (d, J=6.4 Hz, 3H) 2.93 (dd, J=8.4, 14.0 Hz, 1H) 3.10 (dd, J=4.0, 14.0 Hz, 1H) 3.55 (Sept, J=6.0 Hz, 1H) 4.13 (q, J=4.0 Hz, 1H) 4.26 (d, J=4.4 Hz, 2H) 4.31 (d, J=4.8 Hz, 2H) 5.11 (dsept, J=4.8, 47.4 Hz, 1H) 6.80-6.90 (m, 5H) 7.20-7.26 (m, 3H)

MS m/e (ESI) 433 (MNa⁺)

Example 328

3-{3-[3-(3,4-Dichlorophenoxy)-2(S)-fluoropropoxy]phenyl}-2(S)-isopropoxypropanoic acid

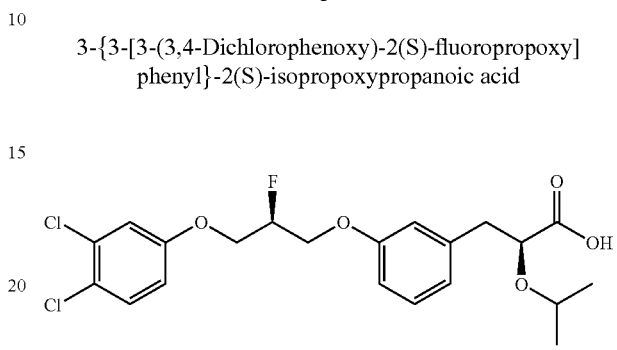

Using 3,4-dichlorophenol, the title compound was obtained in the same manner as described in Production example 297b) and Example 326.

¹H NMR (CDCl₃)

δ: 1.03 (d, J=6.0 Hz, 3H) 1.17 (d, J=6.4 Hz, 3H) 2.93 (dd, J=8.0, 14.0 Hz, 1H) 3.11 (dd, J=3.6, 14.0 Hz, 1H) 3.56 (Sept, J=6.0 Hz, 1H) 4.14 (q, J=4.0 Hz, 1H) 4.26 (d, J=4.4 Hz, 2H) 4.31 (t, J=4.4 Hz, 2H) 5.13 (dsept, J=4.8, 47.2 Hz, 1H) 6.79-6.85 (m, 3H) 6.88 (d, J=7.6 Hz, 1H) 7.05 (d, J=2.8 Hz, 1H) 7.23 (dt, J=7.6, 8.8 Hz, 1H) 7.34 (d, J=8.8 Hz, 1H)

MS m/e (ESI) 467 (MNa⁺)

Example 329

3-{3-[3-(4-Chloro-2-cyanophenoxy)-2(S)-fluoropropoxy]phenyl}-2(S)-isopropoxypropanoic acid

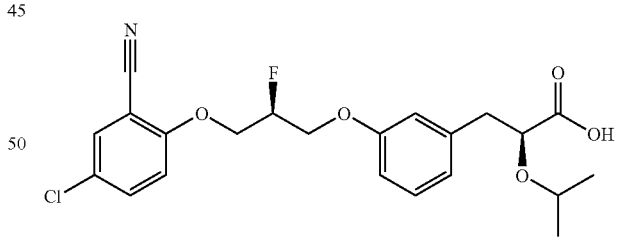

Using 4-chloro-2-cyanophenol, the title compound was obtained in the same manner as described in Production example 297b) and Example 326.

¹H NMR (CDCl₃)

δ: 1.04 (d, J=6.4 Hz, 3H) 1.17 (d, J=6.0 Hz, 3H) 2.94 (dd, J=8.0, 13.6 Hz, 1H) 3.10 (dd, J=3.6, 13.2 Hz, 1H) 3.57 (Sept, J=4.0 Hz, 1H) 4.15 (brs, 1H) 4.29-4.50 (m, 4H) 5.20 (dsept, J=4.4, 46.4 Hz, 1H) 6.81-6.85 (m, 2H) 6.88 (d, J=7.6 Hz, 1H) 6.98 (d, J=8.8 Hz, 1H) 7.22 (dt, J=8.0, 9.2 Hz, 1H) 7.50-7.54 (m, 2H)

MS m/e (ESI) 458 (MNa⁺)

Example 330

3-{3-[3-(2,4-Dimethylphenoxy)-2(S)-fluoropropoxy]phenyl}-2(S)-isopropoxypropanoic acid

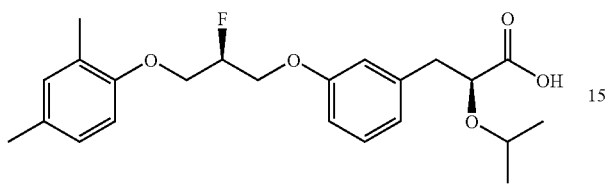

Using 2,4-dimethylphenol, the title compound was obtained in the same manner as described in Production example 297b) and Example 326.

$^1$H NMR (CDCl$_3$)

δ: 1.02 (d, J=6.4 Hz, 3H) 1.16 (d, J=6.4 Hz, 3H) 2.20 (s, 3H) 2.26 (s, 3H) 2.91 (dd, J=8.0, 14.0 Hz, 1H) 3.11 (dd, J=4.0, 14.0 Hz, 1H) 3.54 (Sept, J=6.0 Hz, 1H) 4.13 (q, J=4.0 Hz, 1H) 4.24-4.35 (m, 4H) 5.16 (dsept, J=4.8, 47.6 Hz, 1H) 6.74 (d, J=8.0 Hz, 1H) 6.81-6.89 (m, 3H) 6.93-6.97 (m, 2H) 7.22 (dt, J=7.6, 8.8 Hz, 1H)

MS m/e (ESI) 458 (MNa$^+$)

Example 331

3-{3-[3-(4-Chloro-2-methylphenoxy)-2(S)-fluoropropoxy]phenyl}-2(S)-isopropoxypropanoic acid

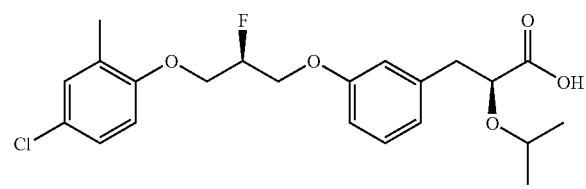

Using 4-chloro-2-methylphenol, the title compound was obtained in the same manner as described in Production example 297b) and Example 326.

MS m/e (ESI) 447 (MNa$^+$)

Example 332

2(S)-Isopropoxy-3-{3-[(4-trifluoromethylbenzyloxycarbonylamino)methyl]phenyl}-propanoic acid

Production Example 332a

{3-[3-(4 (S)-benzyl-2-oxooxazolidin-3-yl)-1 (R)-hydroxy-2(S)-isopropoxy-3-oxopropyl]benzyl}carbamic acid t-butyl ester

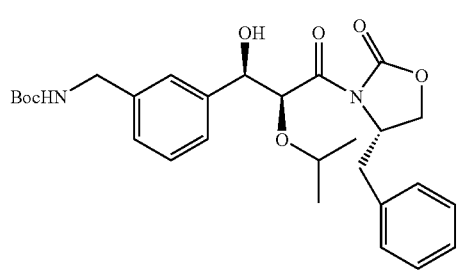

A solution of 15.3 g of (4S)-4-benzyl-3-(2-isopropoxyacetyl)-1,3-oxazolidin-2-one in toluene (250 ml) was cooled to −75° C., and 9.0 ml of triethylamine was added thereto. 55 ml of dibutylboron triflate (1M solution in dichloromethane) was added dropwise at such a rate that the inside temperature did not exceed −70° C. After the dropwise addition, the mixture was stirred for 50 minutes and then the inside temperature was raised to 0° C. The mixture was stirred for another 50 minutes, and again cooled to −75° C. To this reaction solution was added a solution containing 9.6 g of t-butyl N-(3-formylbenzyl) carbamate in dichloromethane (40 ml) by means of cannula and the mixture was stirred at −75° C. for 30 minutes. Then the temperature was raised to 0° C. over about 1 hour by 10° C. per 10 minutes. The temperature was gradually raised to room temperature and stirring was continued overnight at room temperature. The reaction solution was poured into a mixed solution of 200 ml of methanol, 200 ml of pH 7 buffer (disodium hydrogen phosphate-citric acid) and 60 ml of hydrogen peroxide (30% aqueous solution), and extracted with ethyl acetate. The organic layer was washed with saturated brine, dried over anhydrous magnesium sulfate, and the solvent was evaporated. The residue was purified by silica gel column chromatography, to give 19.2 g of the title compound as a colorless oil in the 1:1 hexane-ethyl acetate fraction.

$^1$H NMR (CDCl$_3$)

δ: 1.12 (d, J=6.0 Hz, 3H) 1.19 (d, J=6.0 Hz, 3H) 1.44 (s, 9H) 2.75 (dd, J=10.0, 13.6 Hz, 1H) 3.25 (dd, J=2.4, 13.6 Hz, 1H) 3.65 (Sept, J=6.0 Hz, 1H) 3.72 (t, J=8.0 Hz, 1H) 4.02 (d, J=8.4 Hz, 1H) 4.29 (d, J=6.0 Hz, 1H) 4.37-4.43 (m, 1H) 4.85 (t, J=4.8 Hz, 1H) 4.91 (m, 1H) 5.43 (d, J=5.6 Hz, 1H) 7.12-7.73 (m, 8H) 7.63 (s, 1H)

Production Example 332b

{3-[3-(4 (S)-Benzyl-2-oxooxazolidin-3-yl)-2(S)-isopropoxy-3-oxopropyl]benzyl}carbamic acid t-butyl ester

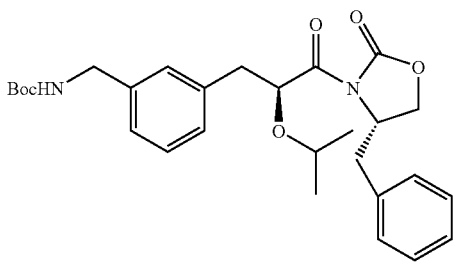

19.2 g of {3-[3-(4 (S)-Benzyl-2-oxooxazolidin-3-yl)-1-(R)-hydroxy-2(S)-isopropoxy-3-oxopropyl]benzyl}-carbamic acid t-butyl ester was dissolved in 100 ml of pyridine, and 4.35 ml of methanesulfonyl chloride was added dropwise under ice-cooling. After stirring was continued for 2 hours under ice-cooling and for 3 hours at room temperature, the reaction solution was diluted with ethyl acetate and washed successively with 1N hydrochloric acid and saturated brine. The organic layer was dried over anhydrous magnesium sulfate, filtered, and the solvent was concentrated, to give methanesulfonic acid 1 (R)-(3-aminomethylphenyl)-3-(4 (S)-benzyl-2-oxooxazolidin-3-yl)-2(S)-isopropoxy-3-oxopropyl ester. This product was dissolved in 500 ml of ethanol, and 10 g of 10% palladium carbon and 5 g of potassium acetate were added, and the mixture was stirred overnight at room temperature under hydrogen atmosphere. The reaction solution was filtered and the filtrate was concentrated. The residue was diluted with ethyl acetate and washed with saturated aqueous sodium hydrogencarbonate. The organic layer was dried over anhydrous magnesium sulfate, and the solvent was evaporated. The residue was purified by silica gel column chromatography, to give 15.3 g of the title compound as a white solid in the 2:1→3:2 hexane-ethyl acetate fraction.

$^1$H NMR (CDCl$_3$)

δ: 1.02 (d, J=6.0 Hz, 3H) 1.16 (d, J=6.4 Hz, 3H) 1.45 (s, 9H) 2.78 (dd, J=9.6, 13.6 Hz, 1H) 2.93-2.98 (m, 2H) 3.30 (dd, J=2.4, 13.2 Hz, 1H) 3.51 (Sept, J=6.0 Hz, 1H) 3.87-4.01 (m, 1H) 4.08-4.12 (m, 1H) 4.28 (d, J=6.0 Hz, 2H) 4.52-4.59 (m, 1H) 4.80-4.88 (m, 1H) 5.34-5.40 (m, 1H) 7.12-7.35 (m, 9H)

Production Example 332c

3-[3-(t-Butoxycarbonylaminomethyl)phenyl]-2(S)-isopropoxypropionic acid methyl ester

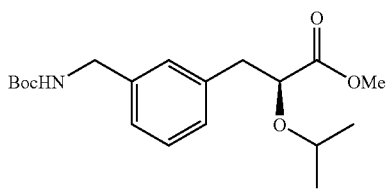

15.3 g of {3-[3-(4 (S)-Benzyl-2-oxooxazolidin-3-yl)-2(S)-isopropoxy-3-oxopropyl]benzyl}carbamic acid t-butyl ester was dissolved in 300 ml of tetrahydrofuran, and 15 ml of 30% aqueous hydrogen peroxide and 75 ml of 1N aqueous lithium hydroxide were successively added under ice-cooling, and stirring was continued overnight at room temperature. The reaction solution was treated with water, extracted with dichloromethane, and the aqueous layer was acidified with 1N hydrochloric acid. The mixture was extracted (×3) with ethyl acetate, and the organic layer was dried over anhydrous magnesium sulfate and the solvent was evaporated, to give 16.68 g of 3-[3-(t-butoxycarbonylaminomethyl)phenyl]-2(S)-isopropoxypropionic acid. The product was then dissolved in 100 ml of N,N-dimethylformamide, and 7 g of potassium hydrogen carbonate and 3.5 ml of iodomethane were successively added, and the mixture was stirred overnight at room temperature. The reaction solution was diluted with ethyl acetate and washed with water. The organic layer was dried over anhydrous magnesium sulfate, and the solvent was evaporated. The residue was purified by silica gel column chromatography, to give 8.58 g of the title compound as a white solid in the 4:1 hexane-ethyl acetate fraction.

$^1$H NMR (CDCl$_3$)

δ: 0.94 (d, J=6.0 Hz, 3H) 1.14 (d, J=6.4 Hz, 3H) 1.46 (s, 9H) 2.92 (dd, J=9.2, 14.0 Hz, 1H) 2.99 (dd, J=5.2, 14.0 Hz, 1H) 3.48 (Sept, J=6.0 Hz, 1H) 4.06 (dd, J=4.8, 8.8 Hz, 1H) 4.29 (brd, J=6.0 Hz, 2H) 4.80 (br, 1H) 7.13-7.15 (m, 3H) 7.24 (t, J=7.6 Hz, 1H)

Production Example 332d 2 (S)-Isopropoxy-3-{3-[(4-trifluoromethylbenzyloxycarbonylamino)methyl]phenyl}-propanoic acid methyl ester

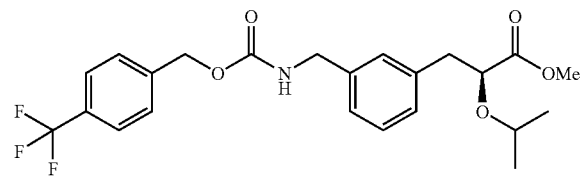

234 mg of 3-[3-(t-Butoxycarbonylaminomethyl)phenyl]-2(S)-isopropoxypropionic acid methyl ester was dissolved in 10 ml of 1,4-dioxane, and the mixture was stirred at room temperature for 1 hour. The reaction solution was concentrated, and the residue was treated with 320 mg of 4-trifluoromethylbenzyl bromide, 500 mg of tetrabutylammonium iodide and 650 mg cesium carbonate, and dissolved in 7 ml of N,N-dimethylformamide. While adding dry ice small by small, the solution was stirred overnight at room temperature. The reaction solution was dissolved in ethyl acetate, and washed with water. The organic layer was dried over anhydrous magnesium sulfate, and the solvent was evaporated. The residue was purified by silica gel column chromatography, to give 173 mg of the title compound in the 3:1 hexane-ethyl acetate fraction.

Example 332e 2 (S)-Isopropoxy-3-{3-[(4-trifluoromethylbenzyloxycarbonylamino)methyl]phenyl}-propanoic acid

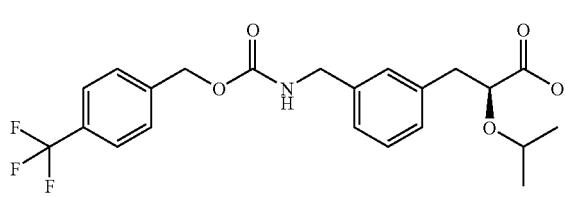

173 mg of 2 (S)-Isopropoxy-3-{3-[(4-trifluoromethylbenzyloxycarbonylamino)methyl]phenyl}-propanoic acid methyl ester was dissolved in 4 ml of ethanol, 1 ml of 1N lithium hydroxide was added, and the mixture was stirred at room temperature for 3 hours. The reaction solution was acidified with 1N hydrochloric acid, extracted with ethylacetate, and washed with water. The organic layer was dried over anhydrous magnesium sulfate, and the solvent was evaporated. The residue was purified by silica gel column chromatography, to give 168 mg of the title compound in the 3:2 hexane-ethylacetate fraction.

$^1$H NMR (CDCl$_3$)

δ: 1.00 (d, J=6.0 Hz, 3H) 1.15 (d, J=6.0 Hz, 3H) 2.95 (dd, J=8.0, 14.0 Hz, 1H) 3.11 (dd, J=2.4, 13.6 Hz, 1H) 3.54 (Sept, J=6.4 Hz, 1H) 4.13 (q, J=4.0 Hz, 1H) 4.37 (d, J=6.0 Hz, 2H) 5.12 (br, 1H) 5.19 (s, 2H) 7.15-7.19 (m, 3H) 7.25-7.27 (m, 1H) 7.48 (d, J=8.0 Hz, 1H) 7.62 (t, J=8.0 Hz, 1H)

MS m/e (ESI) 462 (MNa$^+$)

Example 333

2 (S)-Isopropoxy-3-{3-[(3-trifluoromethylbenzyloxycarbonylamino)methyl]phenyl}-propanoic acid

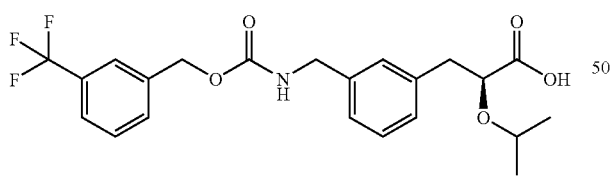

Using 3-trifluoromethylbenzyl bromide, the title compound was obtained in the same manner as described in Example 332e)

$^1$H NMR (CDCl$_3$)

δ: 0.99 (d, J=6.0 Hz, 3H) 1.15 (d, J=6.4 Hz, 3H) 2.94 (dd, J=8.4, 14.0 Hz, 1H) 3.11 (dd, J=4.0, 14.0 Hz, 1H) 3.53 (Sept, J=6.4 Hz, 1H) 4.12 (q, J=4.0 Hz, 1H) 4.38 (d, J=6.4 Hz, 2H) 5.13 (br, 1H) 5.19 (s, 2H) 7.11-7.18 (m, 3H) 7.24-7.29 (m, 1H) 7.48 (t, J=7.2 Hz, 1H) 7.53-7.64 (m, 2H)

MS m/e (ESI) 462 (MNa$^+$)

Example 334

2 (S)-Isopropoxy-3-{3-[(4-chlorobenzyloxycarbonylamino)methyl]phenyl}propanoic acid

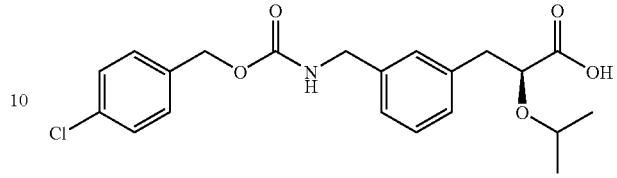

Using 4-chlorobenzyl chloride, the title compound was obtained in the same manner as described in Example 332e).

$^1$H NMR (CDCl$_3$)

δ: 1.00 (d, J=6.4 Hz, 3H) 1.15 (d, J=6.0 Hz, 3H) 2.94 (dd, J=8.0, 14.0 Hz, 1H) 3.11 (dd, J=4.0, 14.0 Hz, 1H) 3.53 (Sept, J=6.0 Hz, 1H) 4.12 (q, J=4.0 Hz, 1H) 4.36 (d, J=6.0 Hz, 2H) 5.07 (br, 1H) 5.09 (s, 2H) 7.11-7.18 (m, 3H) 7.24-7.34 (m, 5H)

MS m/e (ESI) 428 (MNa$^+$)

Example 335

2 (S)-Isopropoxy-3-{3-[(4-trifluoromethoxybenzyloxycarbonylamino)methyl]phenyl}-propanoic acid

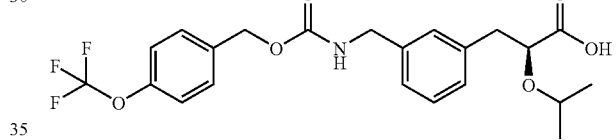

Using 4-trifluoromethoxybenzyl bromide, the title compound was obtained in the same manner as described in Example 332e)

$^1$H NMR (CDCl$_3$)

δ: 0.99 (d, J=6.0 Hz, 3H) 1.15 (d, J=6.0 Hz, 3H) 2.94 (dd, J=8.0, 14.0 Hz, 1H) 3.11 (dd, J=3.6, 14.0 Hz, 1H) 3.53 (Sept, J=6.0 Hz, 1H) 4.12 (q, J=4.0 Hz, 1H) 4.37 (d, J=6.0 Hz, 2H) 5.09 (br, 1H) 5.13 (s, 2H) 7.12-7.18 (m, 3H) 7.24-7.28 (m, 1H) 7.40 (d, J=8.0 Hz, 2H)

MS m/e (ESI) 478 (MNa$^+$)

Example 336

3-(3-{[4-(1-Hydroxy-1-methylethyl)-benzyloxycarbonylamino]methyl}phenyl)-2(S)-isopropoxypropanoic acid

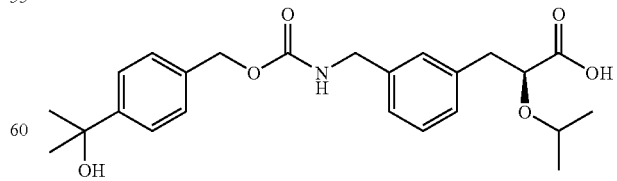

Using 1-hydroxy-1-methylethylbenzyl chloride, the title compound was obtained in the same manner as described in Example 332e).

$^1$H NMR (CDCl$_3$)

δ: 1.00 (d, J=6.4 Hz, 3H) 1.15 (d, J=6.4 Hz, 3H) 1.58 (s, 6H) 2.93 (dd, J=7.2, 12.8 Hz, 1H) 3.06-3.12 (m, 1H) 3.52 (Sept, J=6.0 Hz, 1H) 4.11 (t, J=7.2 Hz, 1H) 4.37 (d, J=5.6 Hz, 2H) 5.07 (br, 1H) 5.13 (s, 2H) 7.14-7.17 (m, 3H) 7.24-7.27 (m, 1H) 7.35 (d, J=8.4 Hz, 2H) 7.49 (d, J=8.0 Hz, 2H)

MS m/e (ESI) 452 (MNa⁺)

Example 337

3-{3-[(2,5-Dichlorobenzyloxycarbonylamino)-methyl]}phenyl}-2(S)-isopropoxypropanoic acid Production Example 337a 3-(3-Aminomethylphenyl)-2(S)-isopropoxypropanoic acid methyl ester

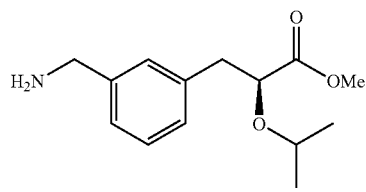

1.034 g of 3-[3-(t-Butoxycarbonylaminomethyl)phenyl]-2(S)-isopropoxypropionic acid methyl ester was dissolved in 20 ml of hydrogen chloride 1,4-dioxane, and the mixture was stirred at room temperature for 1 hour. The reaction solution was concentrated, the residue was dissolved in ethyl acetate, and washed with saturated aqueous sodium hydrogen carbonate. The organic layer was dried over anhydrous magnesium sulfate and the solvent was evaporated, to give 653 mg of the title compound as a colorless oil.

Example 337b

3-{3-[(2,5-Dichlorobenzyloxycarbonylamino)-methyl]}phenyl}-2(S)-isopropoxypropanoic acid

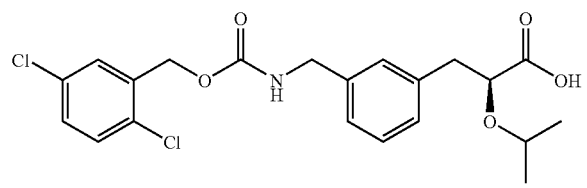

305 mg of 3-(3-Aminomethylphenyl)-2(S)-isopropoxypropanoic acid methyl ester was dissolved in 3 ml of dichloromethane, and a solution of 0.05 ml of pyridine and 180 mg triphosgen in dichloromethane (4 ml) were added under ice-cooling. 0.5 ml of triethylamine was added, and the mixture was stirred at room temperature for 30 minutes. The solution was filtered, and diluted so that the total amount was 5 ml. To the resultant 0.5 ml of solution (containing about 13 mg of isocyanate of 3-(3-aminomethylphenyl)-2(S)-isopropoxypropanoic acid methyl ester) was added 20 mg of 2,5-dichlorobenzyl alcohol. The reaction solution was concentrated and 0.4 ml of tetrahydrofuran was added, and the mixture was stirred at room temperature for 30 minutes. 0.5 ml of ethanol and 0.1 ml of 1N sodium hydroxide were added thereto, and stirring was continued overnight. The reaction solution was acidified with 1N hydrochloric acid, and extracted with ethyl acetate. The solvent was concentrated, and the residue was purified by reverse-phase high performance liquid chromatography, to give 10.27 mg of the title compound.

MS m/e (ESI) 462 (MNa⁺)

Example 338

3-(3-{[3,5-Dichlorobenzyloxycarbonylamino]-methyl}phenyl)-2(S)-isopropoxypropanoic acid

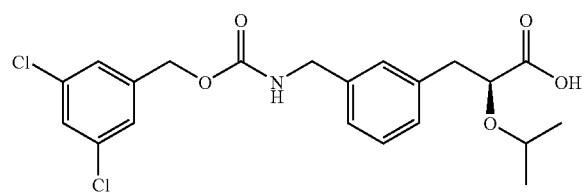

Using 2,5-dichlorobenzyl alcohol, the title compound was obtained in the same manner as described in Example 337b).

MS m/e (ESI) 462 (MNa⁺)

Example 339

3-(3-{[3,4-Difluorobenzyloxycarbonylamino]-methyl phenyl)-2(S)-isopropoxypropanoic acid

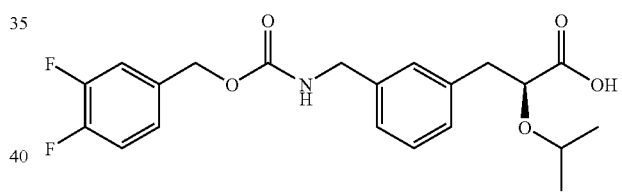

Using 3,4-difluorobenzyl alcohol, the title compound was obtained in the same manner as described in Example 337b).

MS m/e (ESI) 432 (MNa⁺)

Example 340

3-(3-{[4-Methylbenzyloxycarbonylamino]methyl}-phenyl)-2(S)-isopropoxypropanoic acid

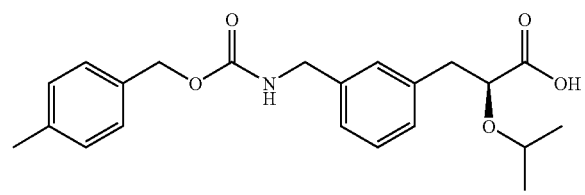

Using 4-methylbenzyl alcohol, the title compound was obtained in the same manner as described in Example 337b).

¹H NMR (CDCl₃)

δ: 0.99 (d, J=6.0 Hz, 3H) 1.15 (d, J=6.0 Hz, 3H) 2.35 (s, 3H) 2.93 (dd, J=8.0, 14.0 Hz, 1H) 3.11 (dd, J=3.6, 14.0 Hz, 1H) 3.52 (Sept, J=6.4 Hz, 1H) 4.11 (q, J=4.0 Hz, 1H) 4.36 (d, J=5.6 Hz, 2H) 5.05 (br, 1H) 5.09 (s, 2H) 7.14-7.18 (m, 5H) 7.23-7.28 (m, 3H)

MS m/e (ESI) 408 (MNa$^+$)

Example 341

3-(3-{[4-Ethylbenzyloxycarbonylamino]methyl}-phenyl)-2(S)-isopropoxypropanoic acid

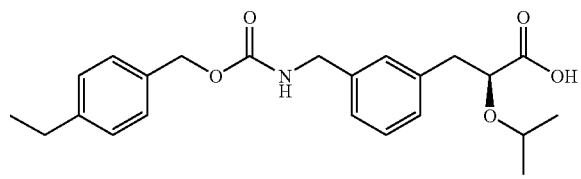

Using 4-ethylbenzyl alcohol, the title compound was obtained in the same manner as described in Example 337b).

$^1$H NMR (CDCl$_3$)

δ: 0.99 (d, J=6.0 Hz, 3H) 1.15 (d, J=6.0 Hz, 3H) 1.23 (t, J=7.2 Hz, 3H) 2.65 (q, J=7.6 Hz, 2H) 2.93 (dd, J=8.0, 14.0 Hz, 1H) 3.11 (dd, J=4.0, 14.0 Hz, 1H) 3.52 (Sept, J=6.4 Hz, 1H) 4.11 (q, J=4.0 Hz, 1H) 4.36 (d, J=6.0 Hz, 2H) 5.05 (br, 1H) 5.10 (s, 2H) 7.14-7.21 (m, 5H) 7.23-7.31 (m, 3H)

MS m/e (ESI) 422 (MNa$^+$)

Example 342

3-(3-{[3,4-Dimethylbenzyloxycarbonylamino]-methyl}phenyl)-2(S)-isopropoxypropanoic acid

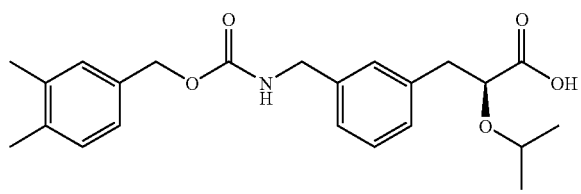

Using 3,4-dimethylbenzyl alcohol, the title compound was obtained in the same manner as described in Example 337b).

$^1$H NMR (CDCl$_3$)

δ: 0.99 (d, J=6.0 Hz, 3H) 1.15 (d, J=6.0 Hz, 3H) 2.26 (s, 6H) 2.93 (dd, J=8.0, 13.6 Hz, 1H) 3.10 (dd, J=3.6, 14.0 Hz, 1H) 3.52 (Sept, J=6.0 Hz, 1H) 4.11 (q, J=4.0 Hz, 1H) 4.36 (d, J=5.6 Hz, 2H) 5.07 (brs, 3H) 7.09-7.18 (m, 6H) 7.26-7.28 (m, 1H)

MS m/e (ESI) 422 (MNa$^+$)

Example 343

3-(3-{[4-Ethoxybenzyloxycarbonylamino]methyl}-phenyl)-2(S)-isopropoxypropanoic acid

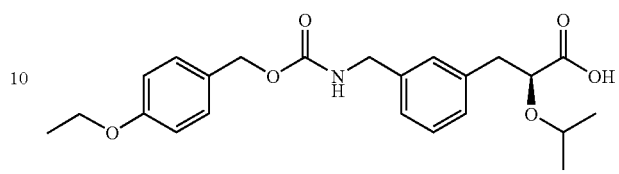

Using 4-ethoxybenzyl alcohol, the title compound was obtained in the same manner as described in Example 337b).

MS m/e (ESI) 438 (MNa$^+$)

Example 344

3-(3-{[3-Trifluoromethoxybenzyloxycarbonylamino] methyl}phenyl)-2(S)-isopropoxypropanoic acid

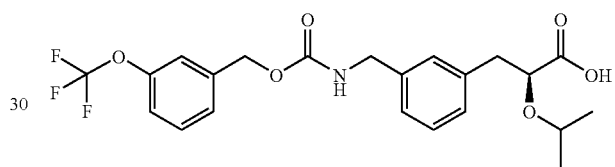

Using 3-trifluoromethoxybenzyl alcohol, the title compound was obtained in the same manner as described in Example 337b)

$^1$H NMR (CDCl$_3$)

δ: 0.99 (d, J=6.4 Hz, 3H) 1.15 (d, J=6.4 Hz, 3H) 2.94 (dd, J=8.0, 14.0 Hz, 1H) 3.11 (dd, J=4.0, 14.0 Hz, 1H) 3.53 (Sept, J=6.0 Hz, 1H) 4.12 (q, J=4.0 Hz, 1H) 4.38 (d, J=6.0 Hz, 2H) 5.13 (brs, 1H) 5.15 (s, 2H) 7.14-7.20 (m, 4H) 7.21-7.30 (m, 3H) 7.38 (t, J=8.0 Hz, 1H)

MS m/e (ESI) 478 (MNa$^+$)

Example 345

3-{3-[(Benzo[1,3]dioxol-5-ylmethoxycarbony-lamino)methyl]-phenyl}-2(S)-isopropoxypropanoic acid

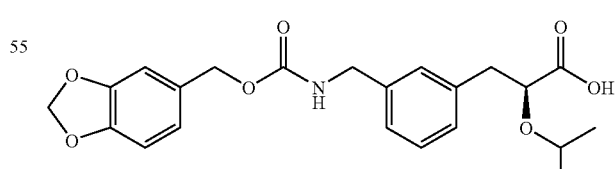

Using piperonyl alcohol, the title compound was obtained in the same manner as described in Example 337b).

$^1$H NMR (CDCl$_3$)

δ: 0.99 (d, J=6.0 Hz, 3H) 1.15 (d, J=6.4 Hz, 3H)) 2.93 (dd, J=8.4, 14.0 Hz, 1H) 3.11 (dd, J=3.6, 14.0 Hz, 1H) 3.52 (Sept, J=6.0 Hz, 1H) 4.11 (q, J=3.6 Hz, 1H) 4.36 (d, J=5.6 Hz, 2H) 5.03 (s, 3H) 5.96 (s, 2H) 6.76-6.89 (m, 3H) 7.12-7.18 (m, 3H) 7.23-7.28 (m, 1H)

MS m/e (ESI) 438 (MNa+)

Example 346

2 (S)-Isopropoxy-3-{3-[(6-methylpyridin-2-yl-methoxycarbonylamino)methyl]phenyl}propanoic acid

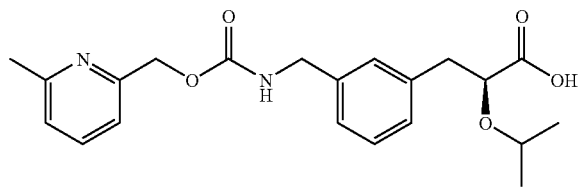

Using (6-methylpyridin-2-yl)methanol, the title compound was obtained in the same manner as described in Example 337b).

MS m/e (ESI) 409 (MNa+)

Example 347

2 (S)-Isopropoxy-3-{3-[(6-methylpyridin-3-yl-methoxycarbonylamino)methyl]phenyl}propanoic acid

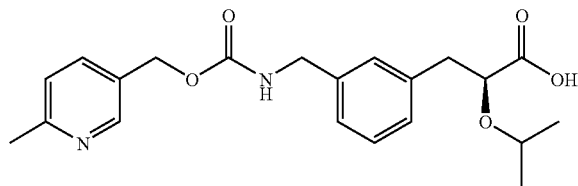

Using (6-methylpyridin-3-yl)methanol, the title compound was obtained in the same manner as described in Example 337b)

MS m/e (ESI) 409 (MNa+)

Example 348

2 (S)-Isopropoxy-3-{3-[(4-methoxy-3,5-dimethylpy-ridin-2-ylmethoxycarbonylamino)methyl]phenyl}-propanoic acid

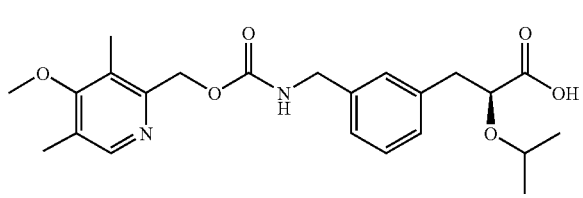

Using (4-methoxy-3,5-dimethylpyridin-2-yl)methanol, the title compound was obtained in the same manner as described in Example 337b).

MS m/e (ESI) 453 (MNa+)

Example 349

3-{3-[(6-t-Butoxycarbonylaminopyridin-3-yl-methoxycarbonylamino)methyl]phenyl}-2(S)-isopro-poxypropanoic acid

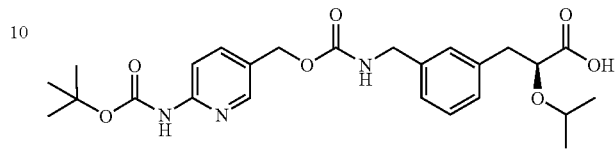

Using (5-hydroxymethylpyridin-2-yl) carbamic acid t-butyl ester, the title compound was obtained in the same manner as described in Example 337b).

MS m/e (ESI) 510 (MNa+)

Example 350

3-{3-[(6-Aminopyridin-3-ylmethoxycarbonylamino)methyl]phenyl}-2(S)-isopropoxypropanoic acid

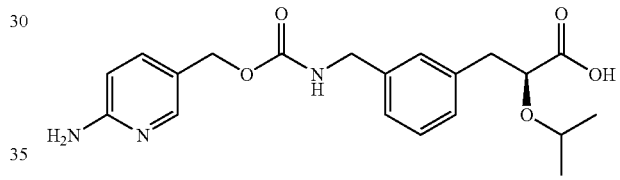

3-{3-[(6-t-Butoxycarbonylaminopyridin-3-ylmethoxy-carbonylamino)methyl]phenyl}-2(S)-isopropoxypropanoic acid was dissolved in trifluoroacetic acid, and the mixture was concentrated. The residue was purified by reverse-phase high performance liquid chromatography, to give the title compound.

MS m/e (ESI) 510 (MNa+)

Example 351

3-{3-[(1H-Benzoimidazol-2-ylmethoxycarbony-lamino)methyl]phenyl}-2(S)-isopropoxypropanoic acid

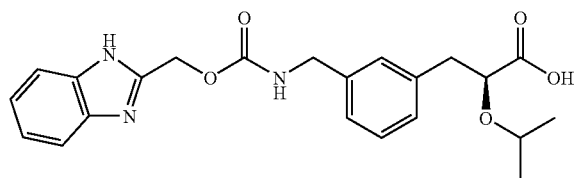

Using (1H-benzoimidazol-2-yl)methanol, the title compound was obtained in the same manner as described in Example 337b)

MS m/e (ESI) 434 (MNa+)

Example 352

2 (S)-Isopropoxy-3-{3-[(3-methyl-3H-benzoimidazol-5-ylmethoxycarbonylamino)methyl]phenyl}-propanoic acid

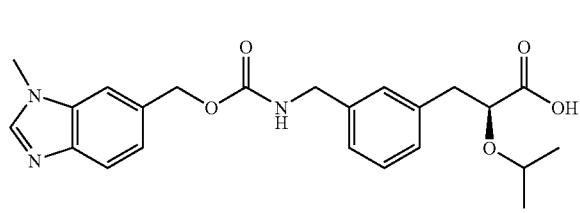

Using (3-methyl-3H-benzoimidazol-5-yl)methanol, the title compound was obtained in the same manner as described in Example 337b).

MS m/e (ESI) 449 (MNa+)

Example 353

3-(3-{[2-(4-Chlorophenyl)ethoxycarbonylamino]-methyl}phenyl)-2(S)-isopropoxypropanoic acid

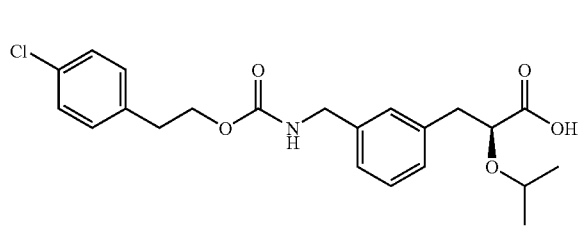

Using 4-chloro-2-phenethyl alcohol, the title compound was obtained in the same manner as described in Example 337b).

MS m/e (ESI) 442 (MNa+)

Example 354

3-(3-{[2-(3-Chlorophenyl)ethoxycarbonylamino]-methyl}phenyl)-2(S)-isopropoxypropanoic acid

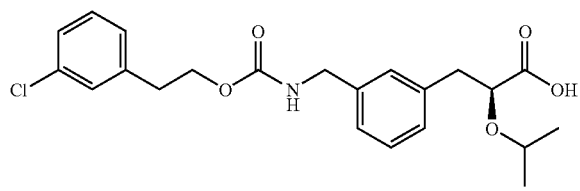

Using 3-chloro-2-phenethyl alcohol, the title compound was obtained in the same manner as described in Example 337b).

MS m/e (ESI) 442 (MNa+)

Example 355

3-(3-{[2-(4-Bromophenyl)ethoxycarbonylamino]-methyl}phenyl)-2(S)-isopropoxypropanoic acid

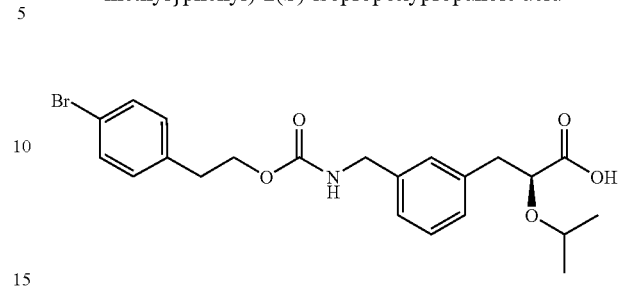

Using 4-bromo-2-phenethyl alcohol, the title compound was obtained in the same manner as described in Example 337b).

MS m/e (ESI) 486 (MNa+)

Example 356

3-(3-{[2-(2,4-Dichlorophenyl)ethoxycarbonylamino]methyl}-phenyl)-2(S)-isopropoxypropanoic acid

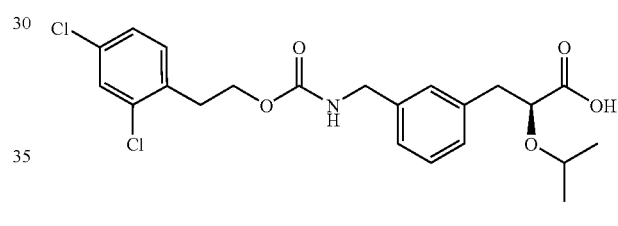

Using 2,4-dichloro-2-phenethylalcohol, the title compound was obtained in the same manner as described in Example 337b)

MS m/e (ESI) 476 (MNa+)

Example 357

2 (S)-Isopropoxy-3-{3-[(quinolin-2-ylmethoxycarbonylamino)methyl]phenyl}propanoic acid

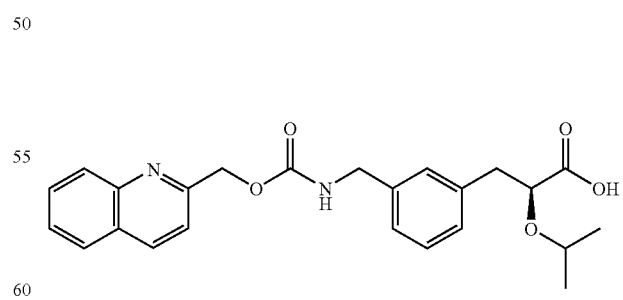

Using quinolin-2-yl-methanol, the title compound was obtained in the same manner as described in Example 337b).

MS m/e (ESI) 445 (MNa+)

Example 358

2 (S)-Isopropoxy-3-{3-[(quinolin-4-ylmethoxycarbonylamino)methyl]phenyl}propanoic acid

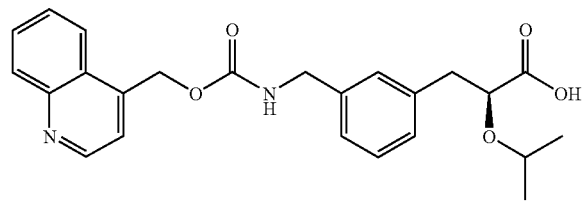

Using quinolin-4-yl-methanol, the title compound was obtained in the same manner as described in Example 337b).
MS m/e (ESI) 445 (MNa$^+$)

Example 359

2 (S)-Isopropoxy-3-{3-[(4-propoxybenzyloxycarbonylamino)-methyl]phenyl}propanoic acid

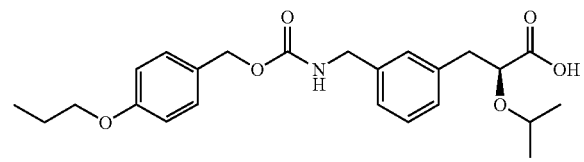

Using 4-propoxybenzyl alcohol, the title compound was obtained in the same manner as described in Example 337b).
MS m/e (ESI) 452 (MNa$^+$)

Example 360

2 (S)-Isopropoxy-3-{3-[(4-isopropoxybenzyloxycarbonylamino)-methyl]phenyl}propanoic acid

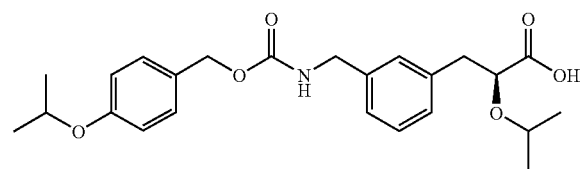

Using 4-isopropoxybenzyl alcohol, the title compound was obtained in the same manner as described in Example 337b).
MS m/e (ESI) 452 (MNa$^+$)

Example 361

2 (S)-Isopropoxy-3-{3-[(2-chloro-4-propoxybenzyloxycarbonylamino)methyl]phenyl}propanoic acid

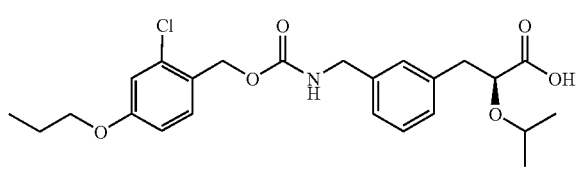

Using 2-chloro-4-propoxybenzyl alcohol, the title compound was obtained in the same manner as described in Example 337b)
MS m/e (ESI) 486 (MNa$^+$)

Example 362

2 (S)-Isopropoxy-3-{3-[(4-isopropylbenzyloxycarbonylamino)-methyl]phenyl}propanoic acid

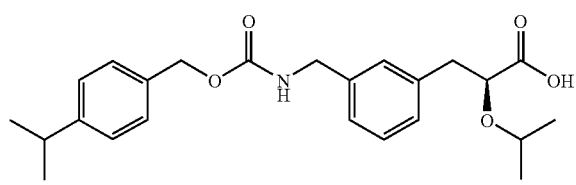

Using 4-isopropylbenzyl alcohol, the title compound was obtained in the same manner as described in Example 337b).
MS m/e (ESI) 436 (MNa$^+$)

Example 363

2 (S)-Isopropoxy-3-{3-[(4-butylbenzyloxycarbonylamino)methyl]phenyl}propanoic acid

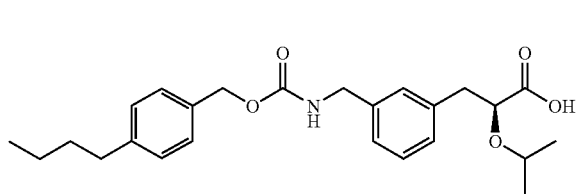

Using 4-butylbenzyl alcohol, the title compound was obtained in the same manner as described in Example 337b).
MS m/e (ESI) 450 (MNa$^+$)

Example 364

2 (S)-Isopropoxy-3-{3-[(2-fluoro-4-trifluoromethyl-benzyloxycarbonylamino)methyl]phenyl}-propanoic acid

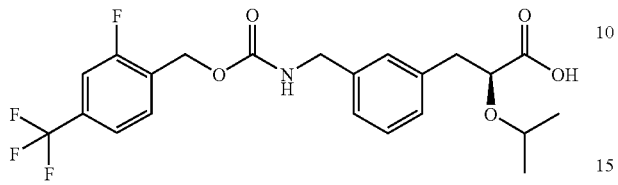

Using 2-fluoro-4-trifluoromethyl alcohol, the title compound was obtained in the same manner as described in Example 337b).

MS m/e (ESI) 480 (MNa+)

Example 365

2 (S)-Isopropoxy-3-{3-[(3-fluoro-4-trifluoromethyl-benzyloxycarbonylamino)methyl]phenyl}-propanoic acid

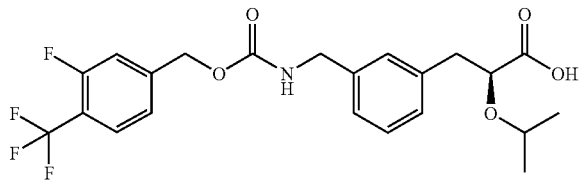

Using 3-fluoro-4-trifluoromethyl alcohol, the title compound was obtained in the same manner as described in Example 337b).

MS m/e (ESI) 480 (MNa+)

Example 366

2 (S)-Isopropoxy-3-{3-[(4-fluoro-3-trifluoromethyl-benzyloxycarbonylamino)methyl]phenyl}-propanoic acid

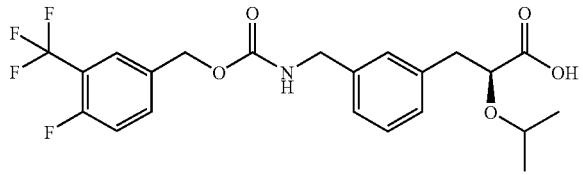

Using 4-fluoro-3-trifluoromethyl alcohol, the title compound was obtained in the same manner as described in Example 337b).

MS m/e (ESI) 480 (MNa+)
MS m/e (ESI) 440 (MH+)

Example 367

3-[(4-Ethoxy-3-phenylcarbamoyloxymethyl)-phenyl]-2-isopropoxypropanoic acid

Production Example 367a

Ethyl 3-[4-ethoxy-3-(hydroxymethyl)-phenyl]-2-isopropoxypropanoate

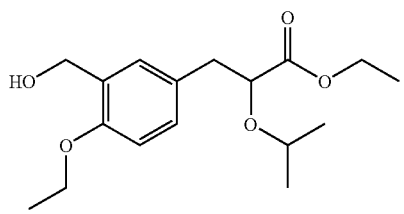

400 mg of sodium hydride was suspended in 10 ml of tetrahydrofuran, and 15 ml of a solution of 2.8 g of diethyl 2-isopropoxyphosphonoacetate in tetrahydrofuran was added under ice-cooling. The solution was stirred at room temperature for 30 minutes, and 25 ml of a solution of 2.4 g of 3-({[1-(t-butyl)-1,1-dimethylsilyl]oxy}methyl)-4-ethoxy-benzaldehyde in tetrahydrofuran was added. After stirring was continued overnight at room temperature, the reaction solution was treated with 1N hydrochloric acid and extracted with ethylacetate. The organic layer was washed with water and saturated brine, dried over anhydrous magnesium sulfate, and the solvent was evaporated. The residue was purified by silica gel column chromatography, to give ethyl (E,Z)-3-[3-({[1-(t-butyl)-1,1-dimethylsilyl]oxy}methyl)-4-ethoxyphenyl]-2-isopropoxy-2-propenoate in the 4:1 hexane-ethyl acetate fraction. Then, the obtained ethyl (E,Z)-3-[3-({[1-(t-butyl)-1,1-dimethylsilyl]oxy}methyl)-4-ethoxyphenyl]-2-isopropoxy-2-propenoate was dissolved in 25 ml of tetrahydrofuran, and 10 ml of tetrabutyl ammonium fluoride (1M solution in tetrahydrofuran) was added thereto. After stirring was continued at room temperature for 7 hours, the reaction mixture was diluted with ethyl acetate. The organic layer was washed with water and saturated brine, dried over anhydrous magnesium sulfate, and the solvent was evaporated. Then, the resulting crude product was dissolved in 25 ml of ethanol, and the mixture was treated with 0.40 g of rhodium-alumina, and stirred overnight under hydrogen atmosphere. The catalyst was filtered off, the solvent was evaporated, and then the residue was purified by silica gel column chromatography, to give 0.96 g of the title compound in the 3:1 hexane-ethyl acetate fraction.

$^1$H-NMR (CDCl$_3$)

δ: 0.97 (d, J=6.0 Hz, 3H) 1.15 (d, J=6.0 Hz, 3H) 1.24 (t, J=7.2 Hz, 3H) 1.43 (t, J=6.8 Hz, 3H) 2.87 (dd, J=8.4, 14.0 Hz, 1H) 2.94 (dd, J=5.2, 14.0 Hz, 1H) 3.50 (sept, J=6.0 Hz, 1H) 4.00 (dd, J=5.2, 8.4 Hz, 1H) 4.07 (q, J=6.8 Hz, 2H) 4.14-4.20 (m, 2H) 4.66 (s, 2H) 6.78 (d, J=8.0 Hz, 1H) 7.13 (d, J=8.0 Hz, 1H) 7.14 (s, 1H)

Production Example 367b

3-[(4-Ethoxy-3-phenylcarbornyloxymethyl)phenyl]-2-isopropoxypropanoic acid

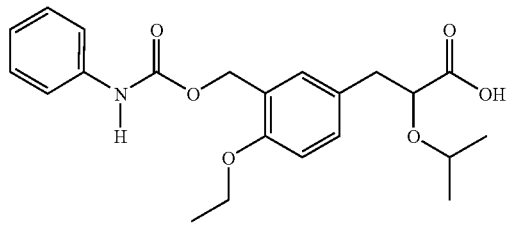

Using ethyl 3-[4-ethoxy-3-(hydroxymethyl)phenyl]-2-isopropoxypropanoate and phenylisocyanate, the title compound was obtained in the same manner as described in Example 148.
MS m/e (ESI) 402 (MH$^+$)

Example 368

3-[(4-Ethoxy-3-p-tolylcarbornyloxymethyl)phenyl]-2-isopropoxypropanoic acid

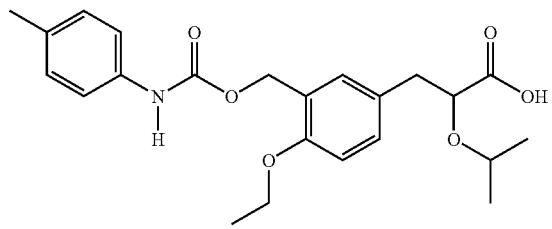

Using ethyl 3-[4-ethoxy-3-(hydroxymethyl)phenyl]-2-isopropoxypropanoate and p-tolylisocyanate, the title compound was obtained in the same manner as described in Example 148.
MS m/e (ESI) 416 (MH$^+$)

Example 369

3-{[4-Ethoxy-3-(4-methoxyphenyl)-carbamoyloxymethyl]phenyl}-2-isopropoxypropanoic acid

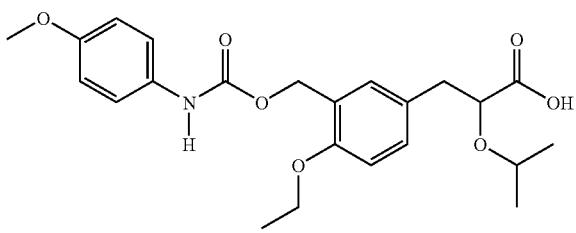

Using ethyl 3-[4-ethoxy-3-(hydroxymethyl)phenyl]-2-isopropoxypropanoate and 4-methoxyphenylisocyanate, the title compound was obtained in the same manner as described in Example 148.
MS m/e (ESI) 432 (MH$^+$)

Example 370

3-{[3-(4-Chlorophenyl)carbamoyloxymethyl-4-ethoxy]phenyl}-2-isopropoxypropanoic acid

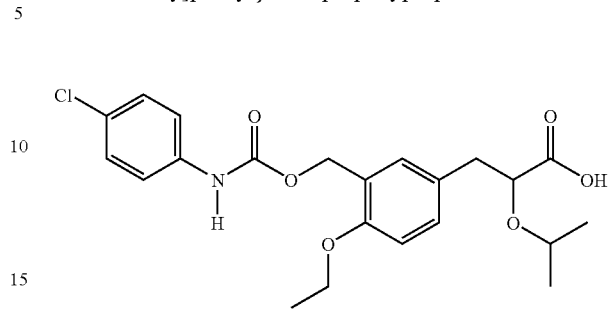

Using ethyl 3-[4-ethoxy-3-(hydroxymethyl)phenyl]-2-isopropoxypropanoate and 4-chlorophenylisocyanate, the title compound was obtained in the same manner as described in Example 148.
MS m/e (ESI) 436 (MH$^+$)

Example 371

3-{[3-(2,4-Dichlorophenyl)carbamoyloxymethyl-4-ethoxy]phenyl}-2-isopropoxypropanoic acid

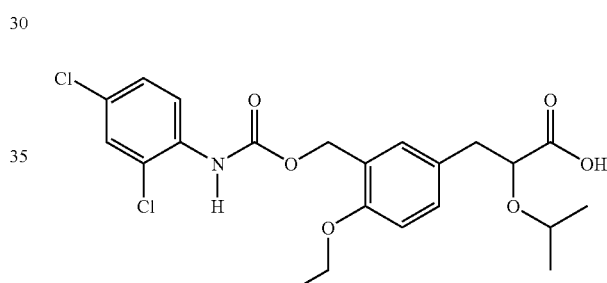

Using ethyl 3-[4-ethoxy-3-(hydroxymethyl)phenyl]-2-isopropoxypropanoate and 2,4-dichlorophenylisocyanate, the title compound was obtained in the same manner as described in Example 148.
MS m/e (ESI) 470 (MH$^+$)

Example 372

3-({4-Ethoxy-3-[4-(trifluoromethyl)phenyl]-carbamoyloxymethyl phenyl)-2-isopropoxypropanoic acid

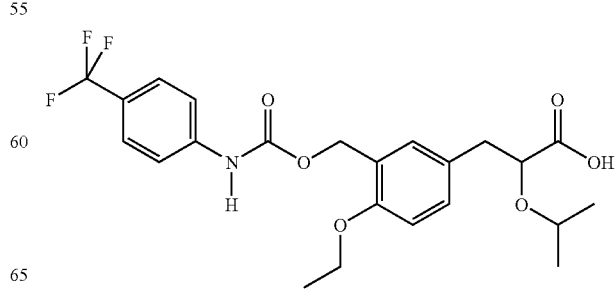

Using ethyl 3-[4-ethoxy-3-(hydroxymethyl)phenyl]-2-isopropoxypropanoate and α,α,α-trifluoro-p-tolylisocyanate, the title compound was obtained in the same manner as described in Example 148.
MS m/e (ESI) 470 (MH⁺)

Example 373

3-{[3-(2,4-Dimethoxyphenyl)carbamoyloxymethyl-4-ethoxy]phenyl}-2-isopropoxypropanoic acid

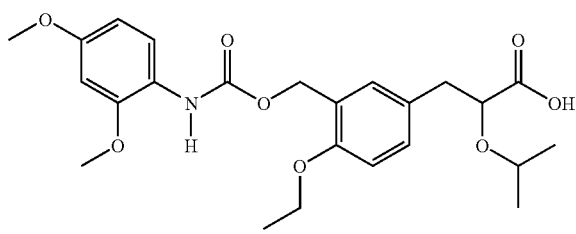

Using ethyl 3-[4-ethoxy-3-(hydroxymethyl)phenyl]-2-isopropoxypropanoate and 2,4-dimethoxyphenylisocyanate, the title compound was obtained in the same manner as described in Example 148.
MS m/e (ESI) 462 (MH⁺)

Example 374

3-{[3-(4-Dimethylaminophenyl)carbamoyloxymethyl-4-ethoxy]phenyl}-2-isopropoxypropanoic acid

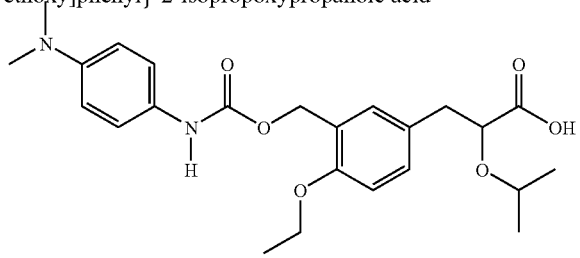

Using ethyl 3-[4-ethoxy-3-(hydroxymethyl)phenyl]-2-isopropoxypropanoate and 4-dimethylaminophenylisocyanate, the title compound was obtained in the same manner as described in Example 148.
MS m/e (ESI) 445 (MH⁺)

Example 375

3-{[3-(3,4-Dimethoxyphenyl)carbamoyloxymethyl-4-ethoxy]phenyl}-2-isopropoxypropanoic acid

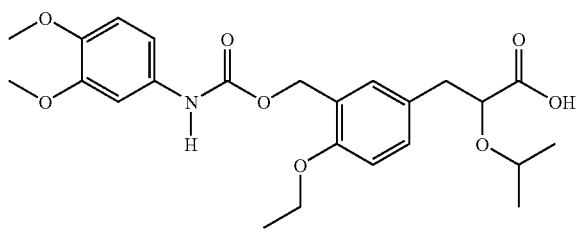

Using ethyl 3-[4-ethoxy-3-(hydroxymethyl)phenyl]-2-isopropoxypropanoate and 2,4-dimethoxyphenylisocyanate, the title compound was obtained in the same manner as described in Example 148.
MS m/e (ESI) 462 (MH⁺)

Example 376

3-({3-[5-(Benzo[1,3]dioxolyl)]carbamoyloxymethyl-4-ethoxy}phenyl)-2-isopropoxypropanoic acid

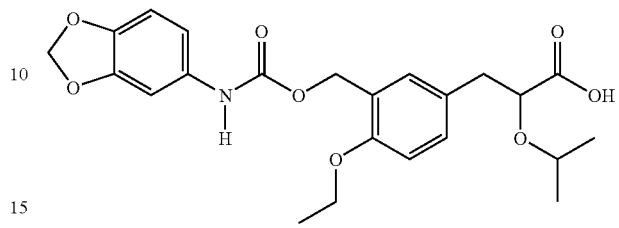

Using ethyl 3-[4-ethoxy-3-(hydroxymethyl)phenyl]-2-isopropoxypropanoate and 3,4-(methylenedioxy)phenylisocyanate, the title compound was obtained in the same manner as described in Example 148.
MS m/e (ESI) 446 (MH⁺)

Example 377

3-{[3-(2,4-Difluorophenyl) carbamoyloxymethyl-4-ethoxy]phenyl}-2-isopropoxypropanoic acid

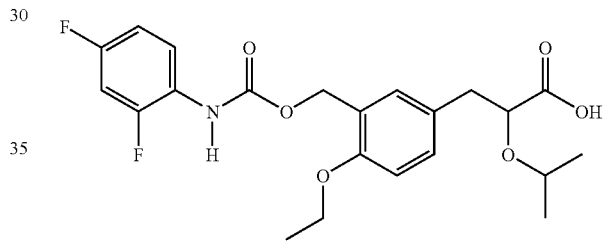

Using ethyl 3-[4-ethoxy-3-(hydroxymethyl)phenyl]-2-isopropoxypropanoate and 2,4-difluorophenylisocyanate, the title compound was obtained in the same manner as described in Example 148.
MS m/e (ESI) 438 (MH⁺)

Example 378

3-{[4-Ethoxy-3-(3-methoxyphenyl)carbamoyloxymethyl]phenyl}-2-isopropoxypropanoic acid

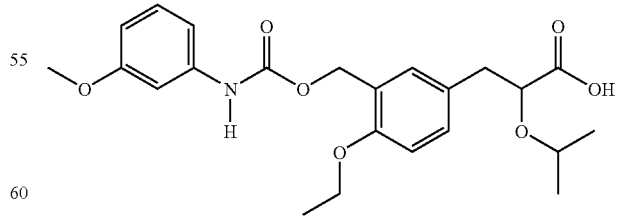

Using ethyl 3-[4-ethoxy-3-(hydroxymethyl)phenyl]-2-isopropoxypropanoate and 3-methoxyphenylisocyanate, the title compound was obtained in the same manner as described in Example 148.
MS m/e (ESI) 432 (MH⁺)

Example 379

3-{[3-(3-Chlorophenyl)carbamoyloxymethyl-4-ethoxy]phenyl}-2-isopropoxypropanoic acid

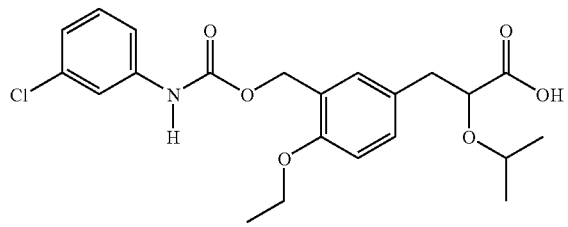

Using ethyl 3-[4-ethoxy-3-(hydroxymethyl)phenyl]-2-isopropoxypropanoate and 3-chlorophenylisocyanate, the title compound was obtained in the same manner as described in Example 148.

MS m/e (ESI) 436 (MH$^+$)

Example 380

3-([4-Ethoxy-3-(4-ethoxyphenyl)carbamoyloxymethyl]-phenyl}-2-isopropoxypropanoic acid

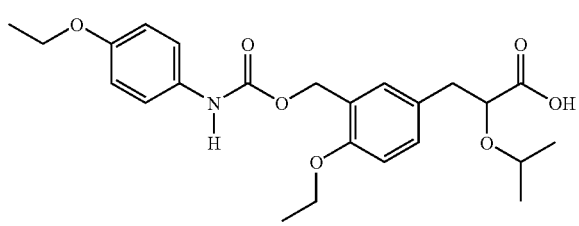

Using ethyl 3-[4-ethoxy-3-(hydroxymethyl)phenyl]-2-isopropoxypropanoate and 4-ethoxyphenylisocyanate, the title compound was obtained in the same manner as described in Example 148.

MS m/e (ESI) 446 (MH$^+$)

Example 381

3-({4-Ethoxy-3-[4-(trifluoromethoxy)phenyl]-carbamoyloxymethyl}phenyl)-2-isopropoxypropanoic acid

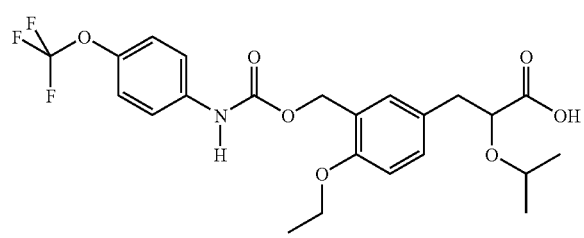

Using ethyl 3-[4-ethoxy-3-(hydroxymethyl)phenyl]-2-isopropoxypropanoate and 4-(trifluoromethoxy)phenylisocyanate, the title compound was obtained in the same manner as described in Example 148.

MS m/e (ESI) 486 (MH$^+$)

Example 382

3-{[4-Ethoxy-3-(4-fluorophenyl)carbamoyloxymethyl]phenyl}-2-isopropoxypropanoic acid

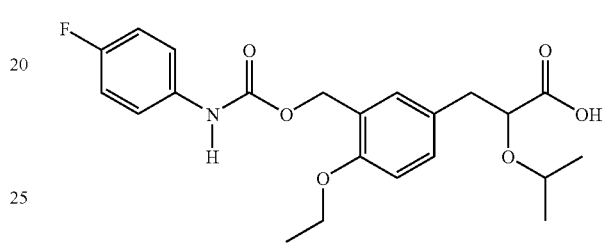

Using ethyl 3-[4-ethoxy-3-(hydroxymethyl)phenyl]-2-isopropoxypropanoate and 4-fluorophenylisocyanate, the title compound was obtained in the same manner as described in Example 148.

MS m/e (ESI) 420 (MH$^+$)

Example 383

3-{[3-(4-Cyanophenyl)carbamoyloxymethyl-4-ethoxy]phenyl}-2-isopropoxypropanoic acid

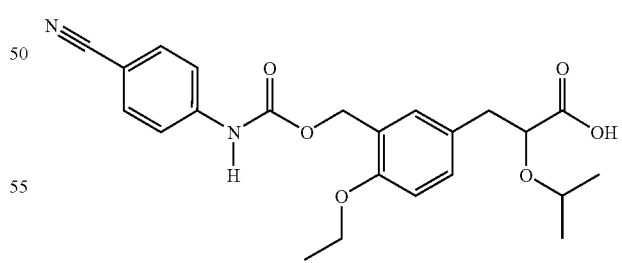

Using ethyl 3-[4-ethoxy-3-(hydroxymethyl)phenyl]-2-isopropoxypropanoate and 4-cyanophenylisocyanate, the title compound was obtained in the same manner as described in Example 148.

MS m/e (ESI) 427 (MH$^+$)

Example 384

3-({4-Ethoxy-3-[3-(trifluoromethyl)phenyl]-carbamoyloxymethyl}phenyl)-2-isopropoxypropanoic acid

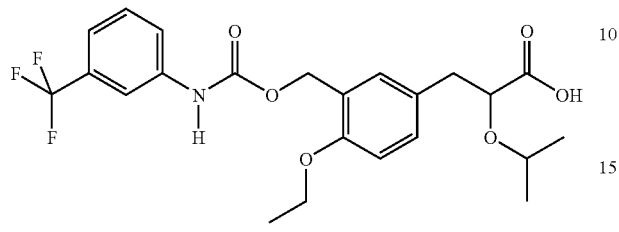

Using ethyl 3-[4-ethoxy-3-(hydroxymethyl)phenyl]-2-isopropoxypropanoate and α,α,α-trifluoro-m-tolylisocyanate, the title compound was obtained in the same manner as described in Example 148.

MS m/e (ESI) 470 (MH$^+$)

Example 385

3-{4-Ethoxy-3-[2-(phenylcarbamoyloxy)-ethyl]phenyl}-2-isopropoxypropanoic acid

Production Example 385a 2-(2-Ethoxyphenyl)ethanol

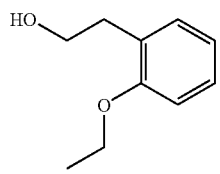

4.4 g of 2-hydroxyphenethyl alcohol was dissolved in 80 ml of N,N-dimethylformamide, and 15.3 g of ethyl iodide and 4.7 g of potassium carbonate were added. After stirring was continued at 70° C. overnight, the solution was diluted with ethyl acetate, and washed successively with water and saturated brine. The organic layer was dried over anhydrous magnesium sulfate, and then the solvent was evaporated. The residue was purified by silica gel column chromatography, to give 3.2 g of the title compound in the 4:1 hexane-ethyl acetate fraction.

$^1$H-NMR (CDCl$_3$)

δ: 1.43 (t, J=6.8 Hz, 3H) 2.92 (t, J=6.0 Hz, 2H) 3.85 (br, 2H) 4.05 (q, J=6.8 Hz, 2H) 6.85-6.91 (m, 2H) 7.15-7.22 (m, 1H)

Production Example 385b

3-[2-(t-Butyldimethylsilyloxy)ethyl]-4-ethoxybenzaldehyde

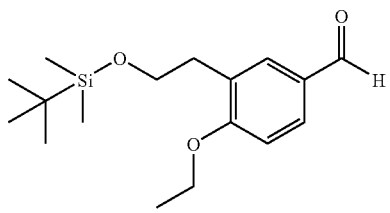

Using 2-(2-ethoxyphenyl)ethanol, the title compound was obtained in the same manner as described in Production example A-117a) followed by Production example A-117b).

$^1$H-NMR (CDCl$_3$)

δ: 0.00 (s, 6H) 0.88 (s, 9H) 1.48 (t, J=6.8 Hz, 3H) 2.92 (t, J=7.2 Hz, 2H) 3.83 (t, J=7.2 Hz, 2H) 4.15 (q, J=6.8 Hz, 2H) 6.94 (d, J=8.4 Hz, 1H) 7.72 (s, 1H) 7.75 (d, J=8.4 Hz, 1H) 9.87 (s, 1H)

Production Example 385c

Ethyl 3-[4-ethoxy-3-(2-hydroxyethyl)phenyl]-2-isopropoxypropanoate

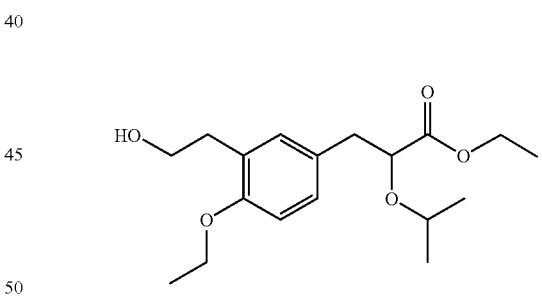

Using 3-[2-(t-butyldimethylsilyloxy)ethyl]-4-ethoxybenzaldehyde and triethyl 2-isopropoxyphosphonoacetate, the title compound was obtained in the same manner as described in Production example 147b).

$^1$H-NMR (CDCl$_3$)

δ: 0.97 (d, J=6.0 Hz, 3H) 1.15 (d, J=6.0 Hz, 3H) 1.24 (t, J=7.2 Hz, 3H) 1.41 (t, J=6.8 Hz, 3H) 2.86 (dd, J=8.4, 14.0 Hz, 1H) 2.88 (t, J=6.4 Hz, 2H) 2.92 (dd, J=5.2, 14.0 Hz, 1H) 3.50 (sept, J=6.0 Hz, 1H) 3.82 (t, J=6.4 Hz, 2H) 3.99-4.05 (m, 3H) 4.14-4.20 (m, 2H) 6.76 (d, J=8.4 Hz, 1H) 7.04-7.07 (m, 2H)

Production Example 385d

3-{4-Ethoxy-3-[2-(phenylcarbamoyloxy)ethyl]phenyl}-2-isopropoxypropanoic acid

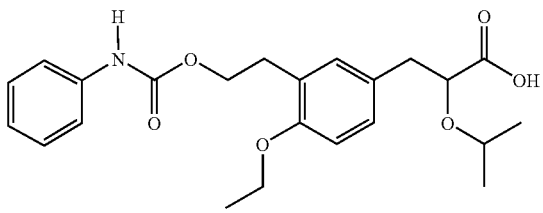

Using ethyl 3-[4-ethoxy-3-(2-hydroxyethyl)phenyl]-2-isopropoxypropanoate and phenylisocyanate, the title compound was obtained in the same manner as described in Example 148.

MS m/e (ESI) 416 (MH+)

Example 386

3-(4-Ethoxy-3-{2-[(4-methoxyphenyl)-carbamoyloxy]ethyl}phenyl)-2-isopropoxypropanoic acid

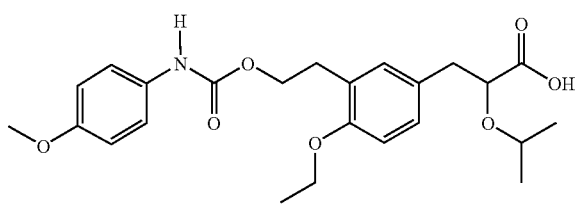

Using ethyl 3-[4-ethoxy-3-(2-hydroxyethyl)phenyl]-2-isopropoxypropanoate and 4-methoxyphenylisocyanate, the title compound was obtained in the same manner as described in Example 148.

MS m/e (ESI) 446 (MH+)

Example 387

3-(3-{2-[(4-Chlorophenyl)carbamoyloxy]ethyl}-4-ethoxyphenyl)-2-isopropoxypropanoic acid

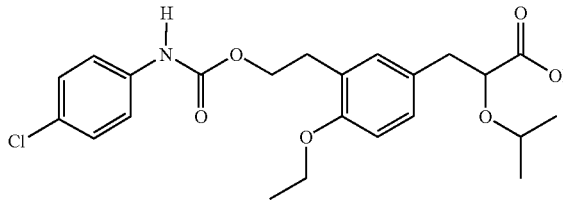

Using ethyl 3-[4-ethoxy-3-(2-hydroxyethyl)phenyl]-2-isopropoxypropanoate and 4-chlorophenylisocyanate, the title compound was obtained in the same manner as described in Example 148.

MS m/e (ESI) 450 (MH+)

Example 388

3-(3-{2-[(2,4-Dichlorophenyl)carbamoyloxy]ethyl}-4-ethoxyphenyl)-2-isopropoxypropanoic acid

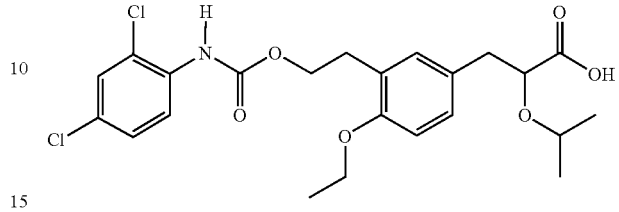

Using ethyl 3-[4-ethoxy-3-(2-hydroxyethyl)phenyl]-2-isopropoxy propanoate and 2,4-dichlorophenylisocyanate, the title compound was obtained in the same manner as described in Example 148.

MS m/e (ESI) 484 (MH+)

Example 389

3-[4-Ethoxy-3-(2-{[4-(trifluoromethyl)phenyl]-carbamoyloxy}ethyl)phenyl]-2-isopropoxypropanoic acid

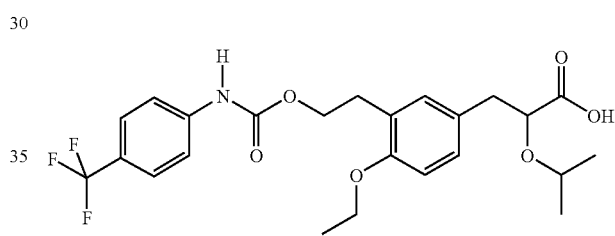

Using ethyl 3-[4-ethoxy-3-(2-hydroxyethyl)phenyl]-2-isopropoxy propanoate and α,α,α-trifluoro-p-tolylisocyanate, the title compound was obtained in the same manner as described in Example 148.

MS m/e (ESI) 484 (MH+)

Example 390

3-(3-{2-[(3-Chlorophenyl)carbamoyloxy]ethyl}-4-ethoxyphenyl)-2-isopropoxypropanoic acid

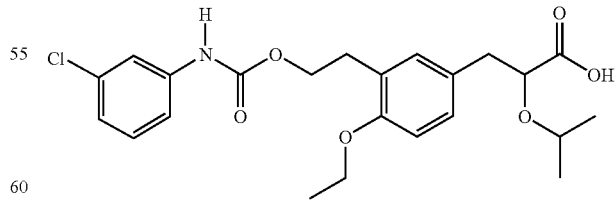

Using ethyl 3-[4-ethoxy-3-(2-hydroxyethyl)phenyl]-2-isopropoxypropanoate and 3-chlorophenylisocyanate, the title compound was obtained in the same manner as described in Example 148.

MS m/e (ESI) 450 (MH+)

Example 391

2-Isopropoxy-3-[(4-phenylcarbamoyloxymethyl)-phenyl]propanoic acid

Production Example 391a 4-(t-Butyldimethylsilyloxymethyl)benzaldehyde

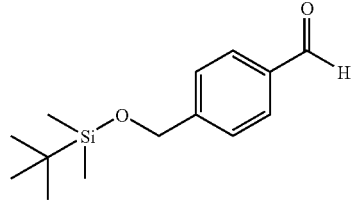

Using 4-bromobenzyl alcohol, the title compound was obtained in the same manner as described in Production example 147a).
$^1$H-NMR (CDCl$_3$)
δ: 0.12 (s, 6H) 0.96 (s, 9H) 4.82 (s, 2H) 7.49 (d, J=8.0 Hz, 2H) 7.85 (d, J=8.0 Hz, 2H) 9.88 (s, 1H)

Production Example 391b

Ethyl 3-[(4-hydroxymethyl)phenyl]-2-isopropoxypropanoate

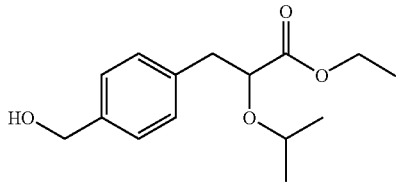

Using 4-(t-butyldimethylsilyloxymethyl)benzaldehyde and triethyl 2-isopropoxyphosphonoacetate, the title compound was obtained in the same manner as described in Production example 147b).
$^1$H-NMR (CDCl$_3$)
δ: 0.95 (d, J=6.0 Hz, 3H) 1.15 (d, J=6.0 Hz, 3H) 1.24 (t, J=7.2 Hz, 3H) 2.94 (dd, J=8.4, 14.0 Hz, 1H) 3.01 (dd, J=4.8, 14.0 Hz, 1H) 3.50 (sept, J=6.0 Hz, 1H) 4.05 (dd, J=4.8, 8.4 Hz, 1H) 4.15-4.23 (m, 2H) 4.67 (s, 2H) 7.25 (d, J=8.0 Hz, 2H) 7.28 (d, J=8.0 Hz, 2H)

Production Example 391c

2-Isopropoxy-3-[(4-phenylcarbamoyloxymethyl)phenyl]propanoic acid

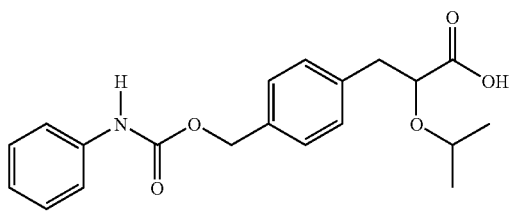

Using ethyl 3-[(4-hydroxymethyl)phenyl]-2-isopropoxypropanoate and phenylisocyanate, the title compound was obtained in the same manner as described in Example 148.
MS m/e (ESI) 358 (MH$^+$)

Example 392

2-Isopropoxy-3-{[4-(4-methoxyphenyl)carbamoyloxymethyl]phenyl}propanoic acid

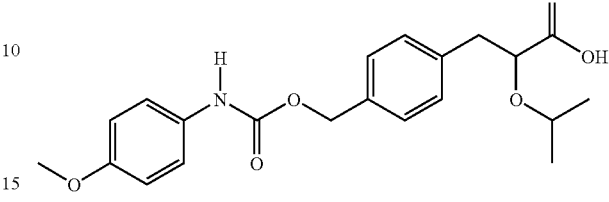

Using ethyl 3-[(4-hydroxymethyl)phenyl]-2-isopropoxypropanoate and 4-methoxyphenylisocyanate, the title compound was obtained in the same manner as described in Example 148.
MS m/e (ESI) 388 (MH$^+$)

Example 393

3-{[4-(4-Chlorophenyl)carbamoyloxymethyl]-phenyl}-2-isopropoxypropanoic acid

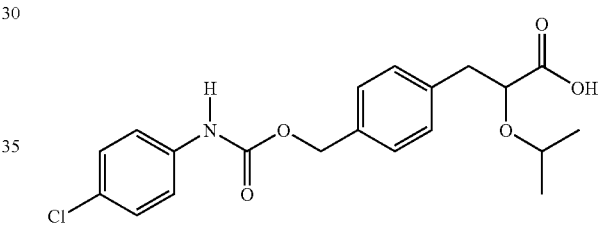

Using ethyl 3-[(4-hydroxymethyl)phenyl]-2-isopropoxypropanoate and 4-chlorophenylisocyanate, the title compound was obtained in the same manner as described in Example 148.
MS m/e (ESI) 392 (MH$^+$)

Example 394

3-{[4-(2,4-Dichlorophenyl)carbamoyloxymethyl]phenyl}-2-isopropoxypropanoic acid

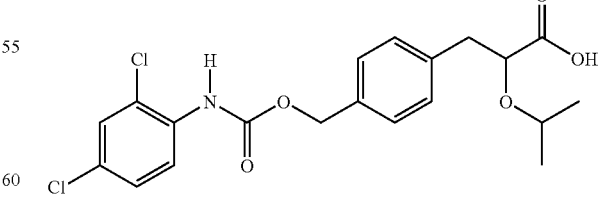

Using ethyl 3-[(4-hydroxymethyl)phenyl]-2-isopropoxypropanoate and 2,4-dichlorophenylisocyanate, the title compound was obtained in the same manner as described in Example 148.
MS m/e (ESI) 426 (MH$^+$)

Example 395

2-Isopropoxy-3-({4-[4-(trifluoromethyl)-phenyl]carbamoyloxymethyl}phenyl)propanoic acid

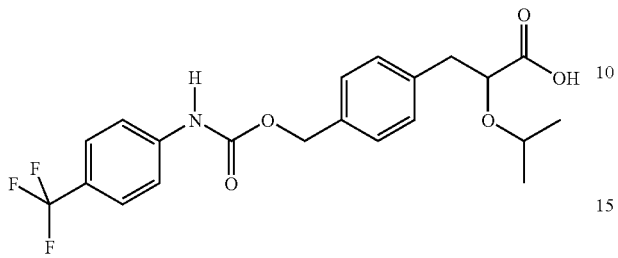

Using ethyl 3-[(4-hydroxymethyl)phenyl]-2-isopropoxypropanoate and α,α,α-trifluoro-p-tolylisocyanate, the title compound was obtained in the same manner as described in Example 148.
MS m/e (ESI) 426 (MH$^+$)

Example 396

3-{[4-(3-Chlorophenyl)carbamoyloxymethyl]-phenyl}-2-isopropoxypropanoic acid

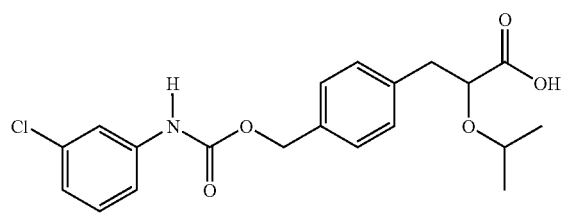

Using ethyl 3-[(4-hydroxymethyl)phenyl]-2-isopropoxypropanoate and 3-chlorophenylisocyanate, the title compound was obtained in the same manner as described in Example 148.
MS m/e (ESI) 392 (MH$^+$)

Example 397

3-{[4-(2,4-Dimethoxyphenyl)-carbamoyloxymethyl]phenyl}-2-isopropoxypropanoic acid

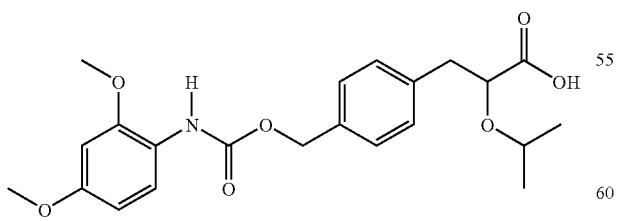

Using ethyl 3-[(4-hydroxymethyl)phenyl]-2-isopropoxypropanoate and 2,4-dimethoxyphenylisocyanate, the title compound was obtained in the same manner as described in Example 148.
MS m/e (ESI) 418 (MH$^+$)

Example 398

3-{[4-(4-Dimethylaminophenyl)-carbamoyloxymethyl]phenyl}-2-isopropoxypropanoic acid

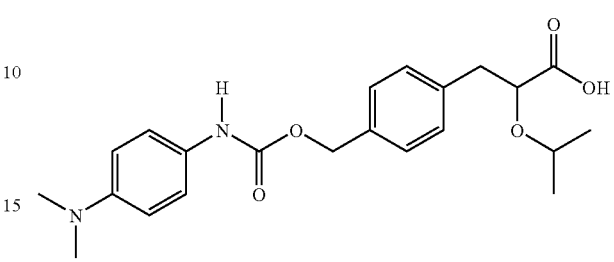

Using ethyl 3-[(4-hydroxymethyl)phenyl]-2-isopropoxypropanoate and 4-dimethylaminophenyl isocyanate, the title compound was obtained in the same manner as described in Example 148.
MS m/e (ESI) 401 (MH$^+$)

Example 399

3-{[4-(3,4-Dimethoxyphenyl)-carbamoyloxymethyl]phenyl}-2-isopropoxypropanoic acid

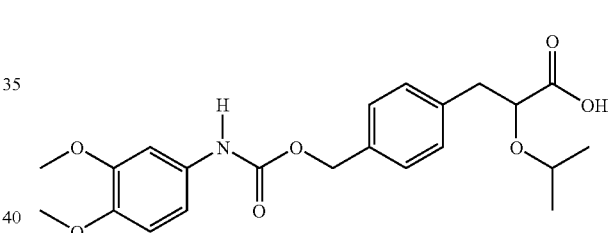

Using ethyl 3-[(4-hydroxymethyl)phenyl]-2-isopropoxypropanoate and 3,4-dimethoxyphenylisocyanate, the title compound was obtained in the same manner as described in Example 148.
MS m/e (ESI) 418 (MH$^+$)

Example 400

3-({4-[5-(Benzo[1,3]dioxolyl)]-carbamoyloxymethyl}phenyl)-2-isopropoxypropanoic acid

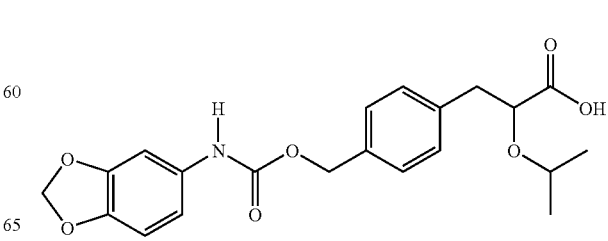

Using ethyl 3-[(4-hydroxymethyl)phenyl]-2-isopropoxypropanoate and 3,4-(methylenedioxy)phenylisocyanate, the title compound was obtained in the same manner as described in Example 148.
MS m/e (ESI) 402 (MH⁺)

Example 401

3-{[4-(2,4-Difluorophenyl)carbamoyloxymethyl]-phenyl}-2-isopropoxypropanoic acid

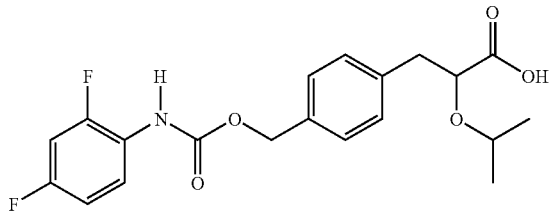

Using ethyl 3-[(4-hydroxymethyl)phenyl]-2-isopropoxypropanoate and 2,4-difluorophenylisocyanate, the title compound was obtained in the same manner as described in Example 148.
MS m/e (ESI) 394 (MH⁺)

Example 402

2-Isopropoxy-3-{[4-(3-methoxyphenyl)-carbamoyloxymethyl]phenyl}propanoic acid

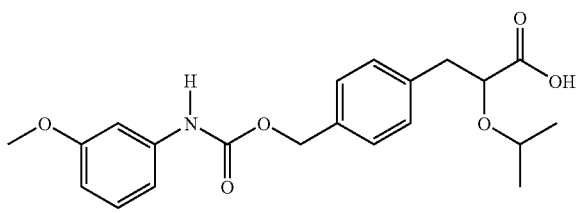

Using ethyl 3-[(4-hydroxymethyl)phenyl]-2-isopropoxypropanoate and 3-methoxyphenylisocyanate, the title compound was obtained in the same manner as described in Example 148.
MS m/e (ESI) 388 (MH⁺)

Example 403

2-Isopropoxy-3-[(4-p-tolylcarbamoyloxymethyl)phenyl]propanoic acid

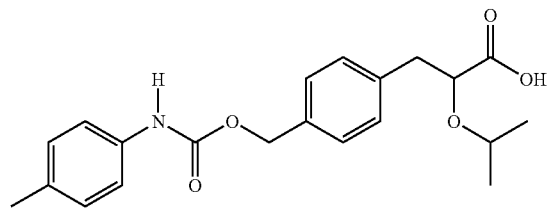

Using ethyl 3-[(4-hydroxymethyl)phenyl]-2-isopropoxypropanoate and p-tolylisocyanate, the title compound was obtained in the same manner as described in Example 148.
MS m/e (ESI) 372 (MH⁺)

Example 404

3-{[4-(4-Ethoxyphenyl)carbamoyloxymethyl]-phenyl}-2-isopropoxypropanoic acid

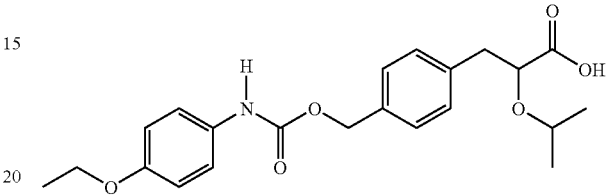

Using ethyl 3-[(4-hydroxymethyl)phenyl]-2-isopropoxypropanoate and 4-ethoxyphenylisocyanate, the title compound was obtained in the same manner as described in Example 148.
MS m/e (ESI) 402 (MH⁺)

Example 405

2-Isopropoxy-3-({4-[4-(trifluoromethoxy)-phenyl]carbamoyloxymethyl}phenyl)propanoic acid

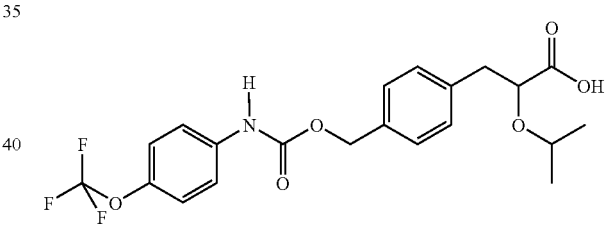

Using ethyl 3-[(4-hydroxymethyl)phenyl]-2-isopropoxypropanoate and 4-(trifluoromethoxy)phenylisocyanate, the title compound was obtained in the same manner as described in Example 148.
MS m/e (ESI) 442 (MH⁺)

Example 406

3-{[4-(4-Fluorophenyl)carbamoyloxymethyl]-phenyl}-2-isopropoxypropanoic acid

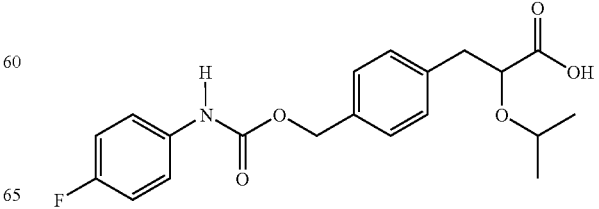

Using ethyl 3-[(4-hydroxymethyl)phenyl]-2-isopropoxypropanoate and 4-fluorophenylisocyanate, the title compound was obtained in the same manner as described in Example 148.

MS m/e (ESI) 376 (MH⁺)

Example 407

3-{[4-(4-Cyanophenyl)carbamoyloxymethyl]-phenyl}-2-isopropoxypropanoic acid

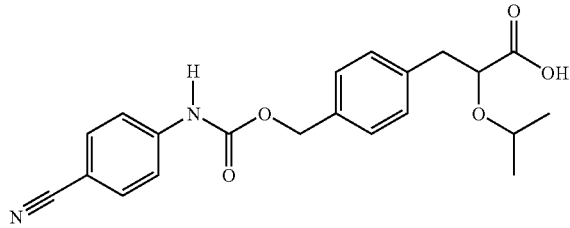

Using ethyl 3-[(4-hydroxymethyl)phenyl]-2-isopropoxypropanoate and 4-cyanophenylisocyanate, the title compound was obtained in the same manner as described in Example 148.

MS m/e (ESI) 383 (MH⁺)

Example 408

2-Isopropoxy-3-({4-[3-(trifluoromethyl)-phenyl]carbamoyloxymethyl}phenyl)propanoic acid

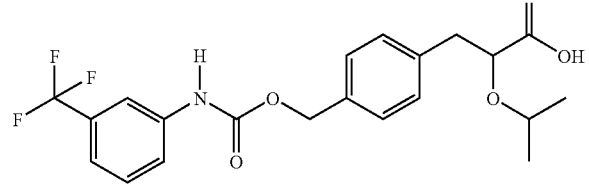

Using ethyl 3-[(4-hydroxymethyl)phenyl]-2-isopropoxypropanoate and α,α,α-trifluoro-m-tolyl isocyanate, the title compound was obtained in the same manner as described in Example 148.

MS m/e (ESI) 426 (MH⁺)

Example 409

2-Isopropoxy-3-{4-[2-(phenylcarbamoyloxy)-ethyl]phenyl}propanoic acid

Production Example 409a

4-[2-(t-Butyldimethylsilyloxy)ethyl]benzaldehyde

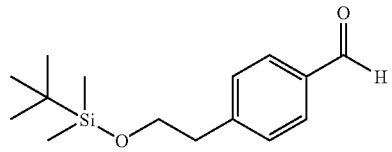

Using 4-bromophenethyl alcohol, the title compound was obtained in the same manner as described in Production example 147a).

¹H-NMR (CDCl₃)

δ: 0.00 (s, 6H) 0.89 (s, 9H) 2.94 (t, J=6.8 Hz, 2H) 3.89 (t, J=6.8 Hz, 2H) 7.42 (d, J=8.0 Hz, 2H) 7.85 (d, J=8.0 Hz, 2H) 9.88 (s, 1H)

Production Example 409b

Ethyl 3-[4-(2-hydroxyethyl)phenyl]-2-isopropoxypropanoate

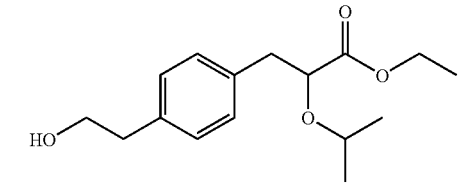

Using 4-[2-(t-butyldimethylsilyloxy)ethyl]benzaldehyde and triethyl 2-isopropoxyphosphonoacetate, the title compound was obtained in the same manner as described in Production example 147b).

¹H-NMR (CDCl₃)

δ: 0.96 (d, J=6.0 Hz, 3H) 1.15 (d, J=6.0 Hz, 3H) 1.23 (t, J=7.2 Hz, 3H) 2.84 (t, J=6.4 Hz, 2H) 2.92 (dd, J=8.4, 14.0 Hz, 1H) 2.98 (dd, J=5.2, 14.0 Hz, 1H) 3.51 (sept, J=6.0 Hz, 1H) 3.84 (t, J=6.4 Hz, 2H) 4.04 (dd, J=5.2, 8.4 Hz, 1H) 4.12-4.20 (m, 2H) 7.14 (d, J=8.0 Hz, 2H) 7.20 (d, J=8.0 Hz, 2H)

Production Example 409c

2-Isopropoxy-3-{4-[2-(phenylcarbamoyloxy)ethyl]phenyl}propanoic acid

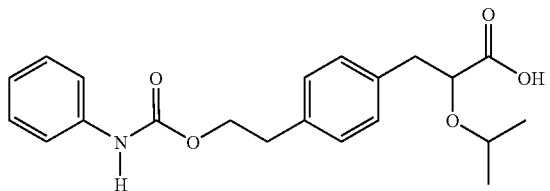

Using ethyl 3-[4-(2-hydroxyethyl)phenyl]-2-isopropoxypropanoate and phenylisocyanate, the title compound was obtained in the same manner as described in Example 148.

MS m/e (ESI) 372 (MH$^+$)

Example 410

2-Isopropoxy-3-(4-{2-[(4-methoxyphenyl)carbamoyloxy]ethyl}phenyl)propanoic acid

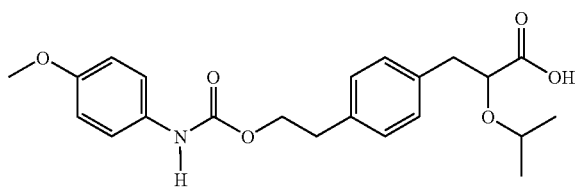

Using ethyl 3-[4-(2-hydroxyethyl)phenyl]-2-isopropoxypropanoate and 4-methoxyphenylisocyanate, the title compound was obtained in the same manner as described in Example 148.

MS m/e (ESI) 402 (MH$^+$)

Example 411

3-(4-{2-[(4-Chlorophenyl)carbamoyloxy]ethyl}phenyl)-2-isopropoxypropanoic acid

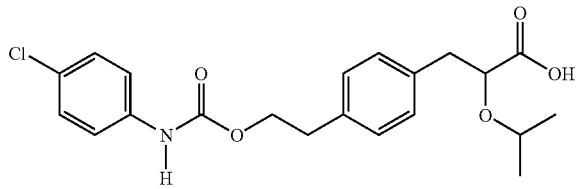

Using ethyl 3-[4-(2-hydroxyethyl)phenyl]-2-isopropoxypropanoate and 4-chlorophenylisocyanate, the title compound was obtained in the same manner as described in Example 148.

MS m/e (ESI) 406 (MH$^+$)

Example 412

3-(4-{2-[(2,4-Dichlorophenyl)carbamoyloxy]ethyl}phenyl)-2-isopropoxypropanoic acid

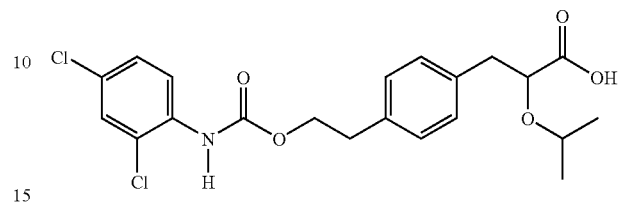

Using ethyl 3-[4-(2-hydroxyethyl)phenyl]-2-isopropoxypropanoate and 2,4-dichlorophenylisocyanate, the title compound was obtained in the same manner as described in Example 148.

MS m/e (ESI) 440 (MH$^+$)

Example 413

2-Isopropoxy-3-[4-(2-{[4-(trifluoromethyl)-phenyl]carbamoyloxy}ethyl)phenyl]propanoic acid

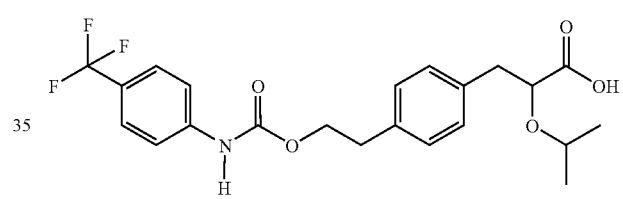

Using ethyl 3-[4-(2-hydroxyethyl)phenyl]-2-isopropoxypropanoate and α,α,α-trifluoro-p-tolylisocyanate, the title compound was obtained in the same manner as described in Example 148.

MS m/e (ESI) 440 (MH$^+$)

Example 414

3-(4-{2-[(3-Chlorophenyl)carbamoyloxy]ethyl}phenyl)-2-isopropoxypropanoic acid

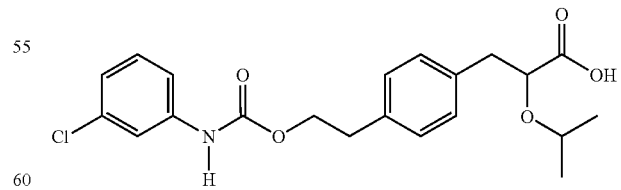

Using ethyl 3-[4-(2-hydroxyethyl)phenyl]-2-isopropoxypropanoate and 3-chlorophenylisocyanate, the title compound was obtained in the same manner as described in Example 148.

MS m/e (ESI) 406 (MH$^+$)

Example 415

3-{4-[({[(4-Chlorobenzyl)oxy]carbonyl}amino)-methyl]phenyl}-2-isopropoxypropanoic acid

Production Example 415a t-Butyl N-(4-formylbenzyl)carbamate

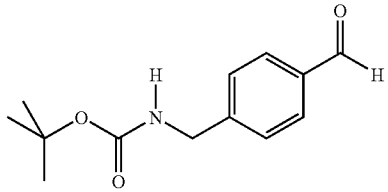

Using 4-bromobenzylamine hydrochloride, the title compound was obtained in the same manner as described in Production example 138a) followed by Production example 138b).

¹H-NMR (CDCl₃)

δ: 1.47 (s, 9H) 4.40 (d, J=6.0 Hz, 2H) 4.95 (br, 1H) 7.45 (d, J=8.0 Hz, 2H) 7.85 (d, J=8.0 Hz, 2H) 10.00 (s, 1H)

Production Example 415b

Ethyl 3-(4-{[(t-butoxycarbonyl)-amino]methyl}phenyl)-2-isopropoxypropanoate

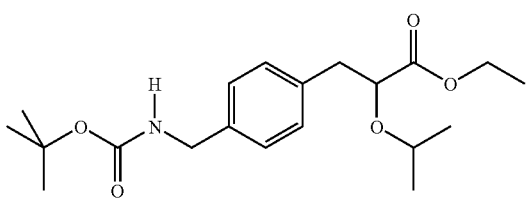

Using t-butyl N-(4-formylbenzyl)carbamate and triethyl 2-isopropoxyphosphonoacetate, the title compound was obtained in the same manner as described in Production example 46a) followed by Production example 46b).

¹H-NMR (CDCl₃)

δ: 0.95 (d, J=6.0 Hz, 3H) 1.15 (d, J=6.0 Hz, 3H) 1.24 (t, J=7.2 Hz, 3H) 1.46 (s, 9H) 2.92 (dd, J=8.4, 14.0 Hz, 1H) 2.99 (dd, J=4.8, 14.0 Hz, 1H) 3.50 (sept, J=6.0 Hz, 1H) 4.03 (dd, J=4.8, 8.4 Hz, 1H) 4.15-4.20 (m, 2H) 4.28 (d, J=6.0 Hz, 2H) 4.80 (br, 1H) 7.17-7.18 (m, 4H)

Example 415c

3-{4-[({[(4-Chlorobenzyl)oxy]carbonyl}amino)methyl]phenyl}-2-isopropoxypropanoic acid

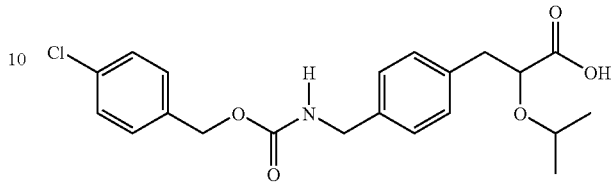

1.6 g of Ethyl 3-(4-{[(t-butoxycarbonyl)amino]methyl}-phenyl)-2-isopropoxypropanoate was dissolved in 10 ml of 4N hydrogen chloride-dioxane solution. After stirring was continued at room temperature for 1 hour, the solution was concentrated, to give 1.4 g of ethyl 3-[4-(ammoniomethyl)-phenyl]-2-isopropoxypropanoate hydrochloride. Next, 25 mg of the obtained ethyl 3-[4-(ammoniomethyl)phenyl]-2-isopropoxypropanoate chloride was dissolved in 0.8 ml of N,N-dimethylformamide which was saturated with carbon dioxide by adding dry ice, and 65 mg of cesium carbonate and 74 mg tetrabutylammonium iodide were added, and the mixture was stirred at room temperature for 30 minutes. Then 41 mg of 4-chlorobenzyl bromide was added thereto, and the mixture was stirred overnight at room temperature. The reaction mixture was diluted with ethyl acetate and washed with water. The solvent was concentrated, and the residue was treated with 1.0 ml of ethanol and 0.2 ml of 5N sodium hydroxide, and the mixture was stirred at room temperature for 3 hours. Then the solution was neutralized with 2N hydrochloric acid, extracted with ethyl acetate, and the solvent was removed. The residue was purified by reverse-phase high performance liquid chromatography, to give 9.27 mg of the title compound.

MS m/e (ESI) 406 (MH⁺)

Example 416

3-{4-[({[(2,4-Dichlorobenzyl)oxy]carbonyl}-amino)methyl]phenyl}-2-isopropoxypropanoic acid

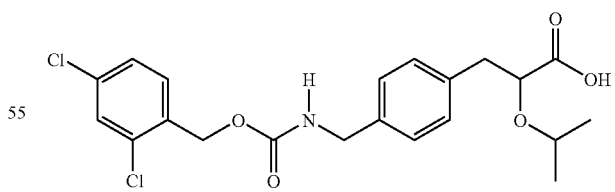

Using ethyl 3-[4-(ammoniomethyl)phenyl]-2-isopropoxypropanoate hydrochloride and 2,4-dichlorobenzyl bromide, the title compound was obtained in the same manner as described in Production example 415c).

MS m/e (ESI) 440 (MH⁺)

Example 417

2-Isopropoxy-3-(4-{[({[(4-trifluoromethyl)-benzyl]oxy}carbonyl)amino]methyl}phenyl)propanoic acid

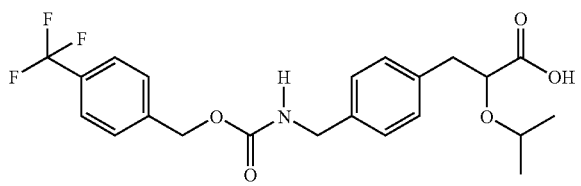

Using ethyl 3-[4-(ammoniomethyl)phenyl]-2-isopropoxypropanoate hydrochloride and 4-(trifluoromethyl)benzyl bromide, the title compound was obtained in the same manner as described in Production example 415c).
MS m/e (ESI) 440 (MH$^+$)

Example 418

2-Isopropoxy-3-{4-[({[(4-methoxybenzyl)-oxy]carbonyl}amino)methyl]phenyl}propanoic acid

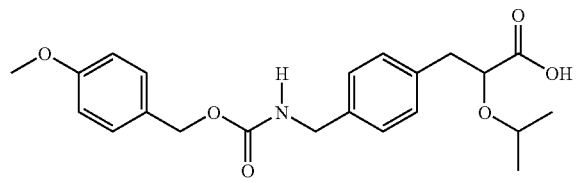

Using ethyl 3-[4-(ammoniomethyl)phenyl]-2-isopropoxypropanoate hydrochloride and 4-methoxybenzyl chloride, the title compound was obtained in the same manner as described in Production example 415c).
MS m/e (ESI) 402 (MH$^+$)

Example 419

3-{4-[({[(4-Chlorobenzyl)carbamoyloxy]-carbonyl}amino)methyl]phenyl}-2-isopropoxypropanoic acid

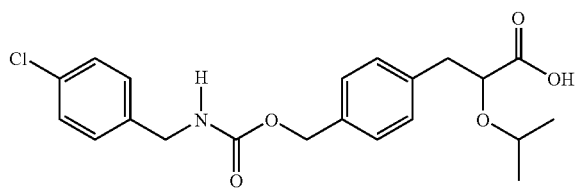

0.60 g of Ethyl 3-[(4-hydroxymethyl)phenyl]-2-isopropoxypropanoate was dissolved in 5 ml of dimethoxyethane, and 0.17 ml of phosphorous tribromide was added under ice-cooling. The solution was stirred at 0° C. for 1 hour, was diluted with ether, and successively washed with water and saturated brine. After drying the organic layer over anhydrous magnesium sulfate, the solvent was evaporated. The residue was purified by silica gel column chromatography, to give 0.51 g of ethyl 3-[(4-bromomethyl)phenyl]-2-isopropoxypropanoate from the 4:1 hexane-ethyl acetate fraction. Next 11 mg of 4-chlorobenzylamine was dissolved in 0.5 ml of N,N-dimethylformamide pre-saturated with carbon dioxide by adding dry ice, 33 mg of cesium carbonate and 37 mg of tetrabutylammonium iodide were added, and the mixture was stirred at room temperature for 30 minutes. 25 mg of the previously obtained ethyl 3-[(4-bromomethyl)phenyl]-2-isopropoxypropanoate was added and the mixture was stirred at room temperature for 4 hours. The reaction mixture was diluted with ethyl acetate and washed with water. The solvent was concentrated, and the residue was treated with 1.0 ml of ethanol and 0.2 ml of 5N-sodium hydroxide, and the mixture was stirred at room temperature for 3 hours. The solution was neutralized with 2N hydrochloric acid, then extracted with ethyl acetate. The solvent was removed, and the residue was purified by reverse-phase high performance liquid chromatography, to give 4.08 mg of the title compound.
MS m/e (ESI) 406 (MH$^+$)

Example 420

3-{4-[({[(2,4-Dichlorobenzyl)carbamoyloxy]carbonyl}-amino)methyl]phenyl}-2-isopropoxypropanoic acid

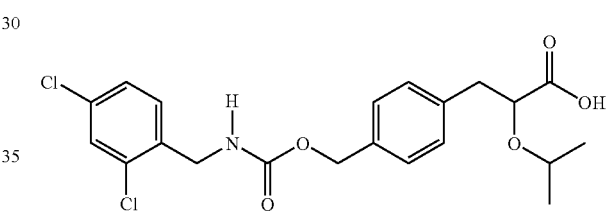

Using ethyl 3-[(4-bromomethyl)phenyl]-2-isopropoxypropanoate and 2,4-dichlorobenzylamine, the title compound was obtained in the same manner as described in Example 419.
MS m/e (ESI) 440 (MH$^+$)

Example 421

2-Isopropoxy-3-(4-{[({[(4-trifluoromethyl)benzyl]-carbamoyloxy}carbonyl)amino]methyl}phenyl)propanoic acid

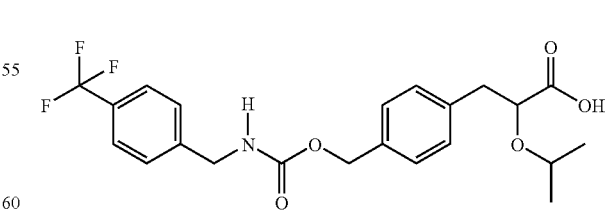

Using ethyl 3-[(4-bromomethyl)phenyl]-2-isopropoxypropanoate and 4-trifluoromethyl)benzylamine, the title compound was obtained in the same manner as described in Example 419.
MS m/e (ESI) 440 (MH$^+$)

Example 422

2-Isopropoxy-3-{4-[({[(4-methoxybenzyl)-carbamoyloxy]carbonyl}amino)methyl]phenyl}propanoic acid

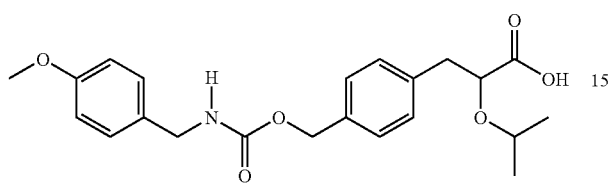

Using ethyl 3-[(4-bromomethyl)phenyl]-2-isopropoxypropanoate and 4-methoxybenzylamine, the title compound was obtained in the same manner as described in Example 419.

MS m/e (ESI) 402 (MH⁺)

Example 423 a) Ethyl 2-isopropoxy-3-(4-methoxy-3-nitrophenyl)-2-propanoate

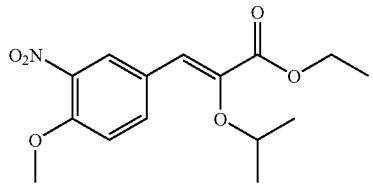

1.5 g of Ethyl 2-(diethylphosphoryl)-2-isopropylacetate was dissolved in 10 ml of tetrahydrofuran, and 0.22 g of 60% sodium hydride was added under ice-cooling. After stirring the reaction solution under ice-cooling for 20 minutes, 0.88 g of 4-methoxy-3-nitrobenzaldehyde was added and the mixture was stirred at room temperature for 2 hours. The reaction mixture was added with aqueous ammonium chloride, and extracted with ethyl acetate. The organic layer was washed with saturated brine, dried over anhydrous magnesium sulfate, and the solvent was evaporated. The residue was subjected to silica gel column chromatography, to give 0.85 g of the title compound from the 9:1 hexane-ethyl acetate fraction.

¹H-NMR (CDCl₃)

δ: 1.17+1.37 (t, J=6.0 Hz, 3H) 1.27+1.31 (d, J=6.0 Hz, 6H) 3.94+3.98 (s, 3H) 4.17+4.28 (q, J=6.0 Hz, 2H) 6.10+6.88 (s, 1H) 7.00+7.06 (d, J=8.0 Hz, 1H) 7.40+7.91 (dd, J=8.0, 2.0 Hz, 1H) 7.75+8.37 (d, J=2.0 Hz, 1H)

b) Ethyl 3-(3-amino-4-methoxyphenyl)-2-isopropoxypropanoate

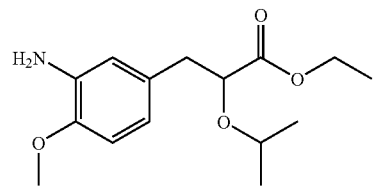

0.85 g of Ethyl 2-isopropoxy-3-(4-methoxy-3-nitrophenyl)-2-propanoate was dissolved in 15 ml of ethanol, 0.3 g of 10% palladium carbon was added, and the mixture was stirred for 4 hours under hydrogen atmosphere. The catalyst was filtered off, the solvent was evaporated, and then the residue was subjected to silica gel column chromatography, to give 0.72 g of the title compound from the 6:1 hexane-ethyl acetate fraction.

¹H-NMR (CDCl₃)

δ: 1.00 (d, J=6.0 Hz, 3H) 1.15 (d, J=6.0 Hz, 3H) 1.24 (t, J=6.0 Hz, 3H) 2.83 (m, 2H) 3.50 (dq, J=6.4, 6.4 Hz, 1H) 3.81 (s, 3H) 4.00 (dd, J=8.4, 4.8 Hz, 1H) 4.17 (q, J=6.0 Hz, 2H) 6.60 (dd, J=8.0, 2.0 Hz, 1H) 6.67 (d, J=2.0 Hz, 1H) 6.70 (d, J=8.0 Hz, 1H)

c) 3-{3-[2-(2,4-Dichlorophenoxy)acetylamino]-4-methoxyphenyl}-2-isopropoxypropanoic acid

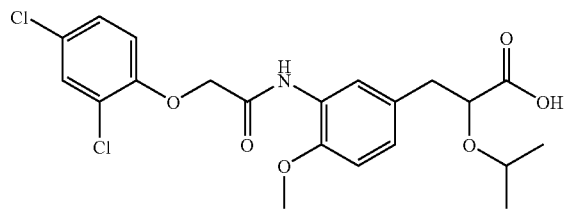

30 mg of Ethyl 3-(3-amino-4-methoxyphenyl)-2-isopropoxypropanoate and 20 mg of 2,4-dichlorophenoxyacetic acid were dissolved in 0.5 ml of tetrahydrofuran, and 30 mg of carbonyldiimidazole and 0.05 ml of triethylamine were added, and the mixture was stirred at 50° C. for 4 hours. The reaction mixture was then partitioned between water and ethyl acetate, and the organic layer was concentrated. The residue was dissolved in 0.6 ml of ethanol, and 0.12 ml of 5N sodium hydroxide was added, and the mixture was stirred at room temperature for 1 hour. The reaction solution was neutralized with dilute hydrochloric acid, and extracted with ethyl acetate. The organic layer was concentrated, and the residue was purified by HPLC using a reverse-phase column and a water-acetonitrile-trifluoroacetic acid elution solvent, to give 3.4 mg of the title compound.

¹H-NMR (CDCl₃)

δ: 1.02 (d, J=6.0 Hz, 3H) 1.11 (d, J=6.0 Hz, 3H) 2.86 (dd, J=14.0, 6.0 Hz, 1H) 3.05 (dd, J=14.0, 4.4 Hz, 1H) 3.53 (dq, J=6.0, 6.0 Hz, 1H) 3.81 (s, 3H) 4.09 (dd, J=7.6, 4.4 Hz, 1H) 4.55 (s, 2H) 6.75 (d, J=8.0 Hz, 1H) 6.81 (d, J=8.0 Hz, 1H) 6.90

(dd, J=8.0, 2.0 Hz, 1H) 7.18 (m, 1H) 7.38 (d, J=2.0 Hz, 2H) 8.24 (d, J=2.0 Hz, 1H) 9.19 (s, 1H)

Example 424

3-{3-[2-(4-t-Butylphenoxy)acetylamino]-4-methoxyphenyl}-2-isopropoxypropanoic acid

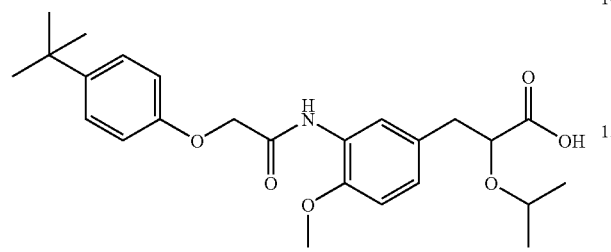

Using 4-t-butylphenoxyacetic acid, the title compound was obtained in the same manner as described in Example 423c).
MS m/e (ESI) 444 (MH$^+$)

Example 425

2-Isopropoxy-3-{4-methoxy-3-[2-(4-trifluoromethylphenoxy)acetylamino]phenyl}propanoic acid

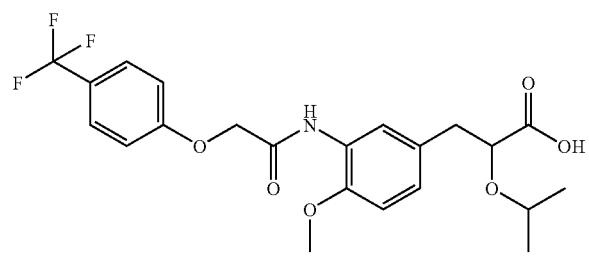

Using 4-trifluoromethylphenoxyacetic acid, the title compound was obtained in the same manner as described in Example 423c).
MS m/e (ESI) 478 (MNa$^+$)

Example 426 a) Ethyl-3-(3-aminophenyl)-2-isopropoxypropanoate

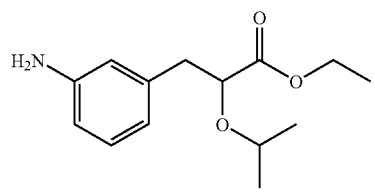

The title compound was obtained in the same manner as described in Examples 423a) and 423b).
$^1$H-NMR (CDCl$_3$)
δ: 0.97 (d, J=6.0 Hz, 3H) 1.15 (d, J=6.0 Hz, 3H) 1.24 (t, J=6.0 Hz, 3H) 2.86 (m, 2H) 3.50 (dq, J=6.4, 6.4 Hz, 1H) 4.03 (dd, J=8.4, 4.8 Hz, 1H) 4.17 (q, J=6.0 Hz, 2H) 6.55 (dd, J=8.0, 2.0 Hz, 1H) 6.59 (d, J=2.0 Hz, 1H) 6.65 (d, J=8.0 Hz, 1H) 7.06 (t, J=8.0 Hz, 1H)

b) 2-Isopropoxy-3-[3-(2-p-tolyloxyacetylamino)phenyl]-propanoic acid

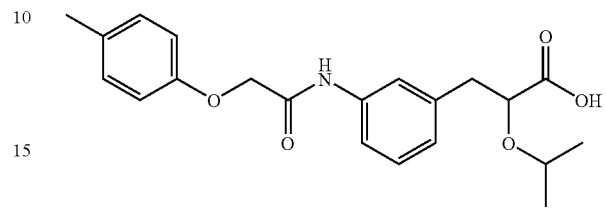

Using 4-methylphenoxyacetic acid, the title compound was obtained in the same manner as described in Example 423c).
MS m/e (ESI) 372 (MH$^+$)

Example 427

3-{3-[2-(2,4-Dichlorophenoxy)acetylamino]-phenyl}-2-isopropoxypropanoic acid

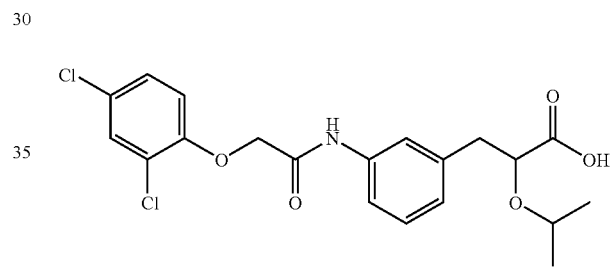

Using 2,4-dichlorophenoxyacetic acid, the title compound was obtained in the same manner as described in Example 423c).
MS m/e (ESI) 426 (MH$^+$)

Example 428

3-{3-[2-(4-t-Butylphenoxy)acetylamino]-phenyl}-2-isopropoxypropanoic acid

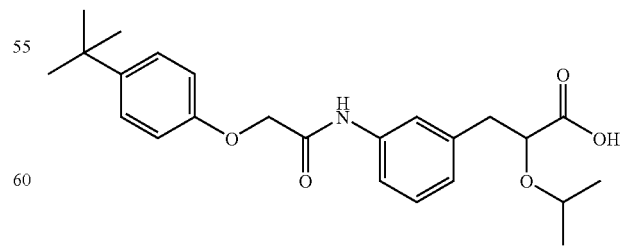

Using 4-t-butylphenoxyacetic acid, the title compound was obtained in the same manner as described in Example 423c).
MS m/e (ESI) 436 (MNa$^+$)

Example 429

2-Isopropoxy-3-{3-[2-(4-trifluoromethylphenoxy)acetylamino]phenyl}propanoic acid

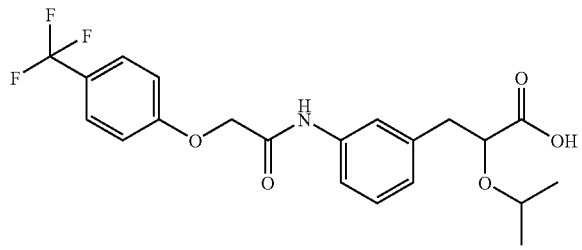

Using 4-trifluoromethylphenoxyacetic acid, the title compound was obtained in the same manner as described in Example 423c).
MS m/e (ESI) 448 (MNa+)

Example 430 a) Ethyl-3-(3-amino-4-ethoxyphenyl)-2-isopropoxypropanoate

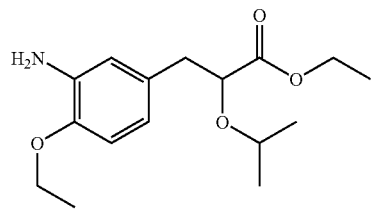

The title compound was obtained in the same manner as described in Examples 423a) and 423b).

$^1$H-NMR (CDCl$_3$)

δ: 0.98 (d, J=6.0 Hz, 3H) 1.14 (d, J=6.0 Hz, 3H) 1.24 (t, J=6.0 Hz, 3H) 1.40 (t, J=6.0 Hz, 3H) 2.83 (m, 2H) 3.50 (dq, J=6.4, 6.4 Hz, 1H) 4.00 (m, 3H) 4.17 (q, J=6.0 Hz, 2H) 6.55 (dd, J=8.0, 2.0 Hz, 1H) 6.62 (d, J=2.0 Hz, 1H) 6.67 (d, J=8.0 Hz, 1H)

b) 3-{3-[2-(2-Chlorophenoxy)acetylamino]-4-ethoxyphenyl}-2-isopropoxypropanoic acid

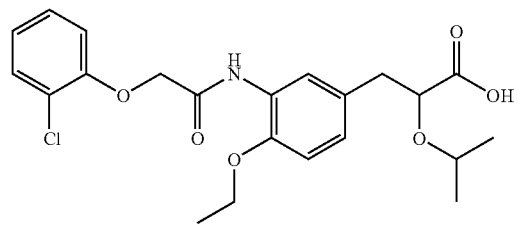

Using 2-chlorophenoxyacetic acid, the title compound was obtained in the same manner as described in Example 423c).
MS m/e (ESI) 436 (MH+)

Example 431

3-{3-[2-(3-Chlorophenoxy)acetylamino]-4-ethoxyphenyl}-2-isopropoxypropanoic acid

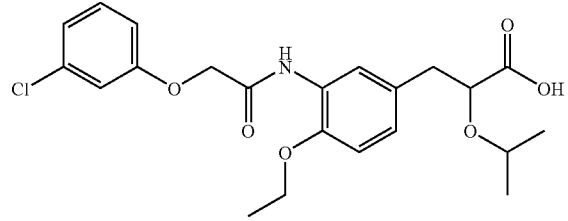

Using 3-chlorophenoxyacetic acid, the title compound was obtained in the same manner as described in Example 423c).
MS m/e (ESI) 436 (MH+)

Example 432

3-{3-[2-(4-Chlorophenoxy)acetylamino]-4-ethoxyphenyl}-2-isopropoxypropanoic acid

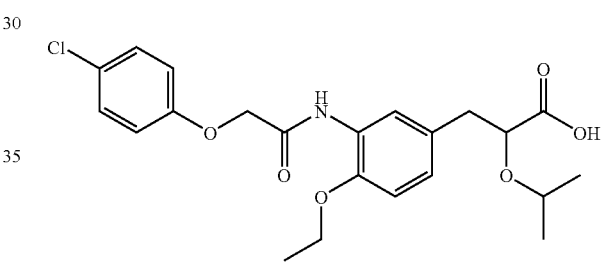

Using 4-chlorophenoxyacetic acid, the title compound was obtained in the same manner as described in Example 423c).
MS m/e (ESI) 436 (MH+)

Example 433

3-[4-Ethoxy-3-(2-p-tolyloxyacetylamino)-phenyl]-2-isopropoxypropanoic acid

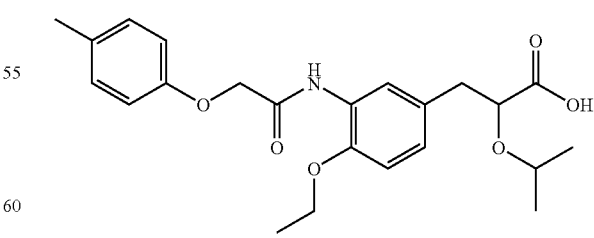

Using 4-methylphenoxyacetic acid, the title compound was obtained in the same manner as described in Example 423c).
MS m/e (ESI) 416 (MH+)

Example 434

3-{3-[2-(2,4-Dichlorophenoxy)acetylamino]-4-ethoxyphenyl}-2-isopropoxypropanoic acid

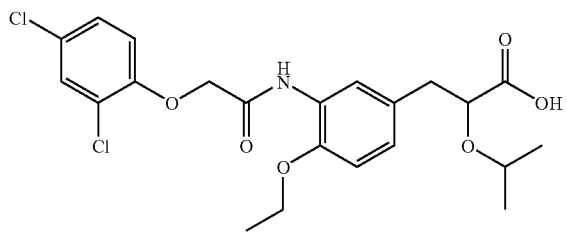

Using 2,4-dichlorophenoxyacetic acid, the title compound was obtained in the same manner as described in Example 423c)

MS m/e (ESI) 470 (MH+)

Example 435

3-{3-[2-(4-t-Butylphenoxy)acetylamino]-4-ethoxyphenyl}-2-isopropoxypropanoic acid

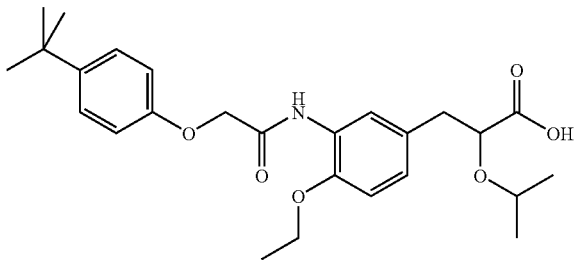

Using 4-t-butylphenoxyacetic acid, the title compound was obtained in the same manner as described in Example 423c).

MS m/e (ESI) 458 (MH+)

Example 436

3-{4-Ethoxy-3-[2-(4-trifluoromethylphenoxy)-acetylamino]phenyl}-2-isopropoxypropanoic acid

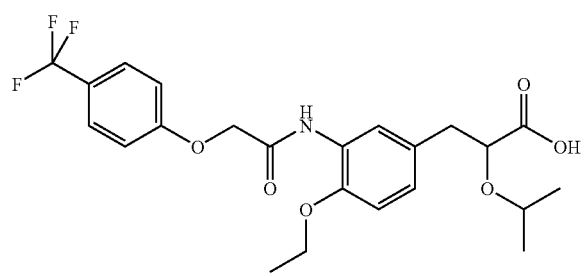

Using 4-trifluoromethylphenoxyacetic acid, the title compound was obtained in the same manner as described in Example 423c).

MS m/e (ESI) 492 (MNa+)

Example 437 a) 2-(2,4-Dichlorophenoxy)propanoic acid

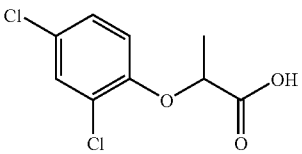

1 g of 2,4-Dichlorophenol was dissolved in 15 ml of N,N-dimethylformamide, and 0.27 g of 60% sodium hydride was added thereto under ice-cooling, and the mixture was stirred at room temperature for 30 minutes. 1.1 ml of Ethyl α-bromopropionate was added to the mixture, and stirring was continued at room temperature for another 1 hour. To the reaction solution was added aqueous ammonium chloride, and the mixture was extracted with ethyl acetate. The organic layer was washed with brine, dried over anhydrous magnesium sulfate, and then the solvent was evaporated. The residue was subjected to silica gel column chromatography, and the fraction eluted with 50:1 n-hexane:ethyl acetate was evaporated and the residue was dissolved in ethanol. To this solution was added 6.5 ml of 5N sodium hydroxide. It was then refluxed for 1 hour. The reaction solution was cooled, and water was added thereto. Then, the mixture was acidified with dilute hydrochloric acid, and extracted with ethyl acetate. The organic layer was washed with brine, dried over anhydrous magnesium sulfate, and the solvent was evaporated, to give 1.5 g of the title compound.

$^1$H-NMR (CDCl$_3$)

δ: 1.70 (d, J=6.0 Hz, 3H) 4.77 (q, J=6.0 Hz, 1H) 6.83 (d, J=8.0 Hz, 1H) 7.17 (dd, J=2.0, 8.0 Hz, 1H) 7.41 (d, J=2.0 Hz, 1H)

b) 3-{3-[2-(2,4-Dichlorophenoxy)propionylamino]-4-methoxyphenyl}-2-isopropoxypropanoic acid

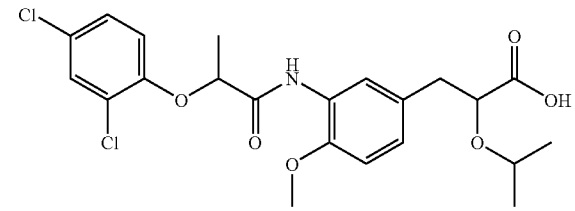

The title compound was obtained in the same manner as described in Example 423c)

MS m/e (ESI) 492 (MNa+).

Example 438 a) 2-(4-t-Butylphenoxy)propionic acid

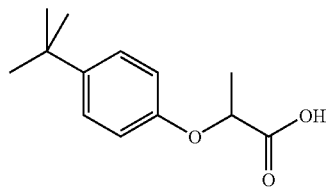

Using 4-t-butylphenol, the title compound was obtained in the same manner as described in Example 435a).
¹H-NMR (CDCl₃)
δ: 1.19 (s, 9H) 1.64 (d, J=6.0 Hz, 3H) 4.77 (q, J=6.0 Hz, 1H) 6.83 (d, J=8.0 Hz, 2H) 7.30 (d, J=8.0 Hz, 2H)

b) 3-{3-[2-(4-t-Butylphenoxy)propionylamino]-4-methoxyphenyl}-2-isopropoxypropanoic acid

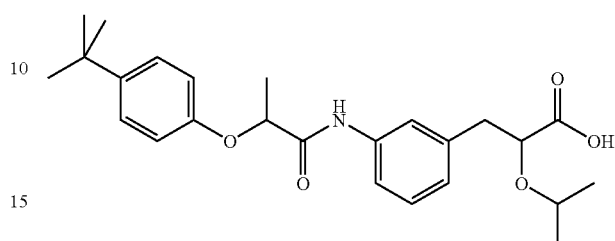

The title compound was obtained in the same manner as described in Example 423c).
MS m/e (ESI) 458 (MH⁺)

Example 439

3-{3-[2-(2,4-Dichlorophenoxy)propionylamino]-phenyl}-2-isopropoxypropanoic acid

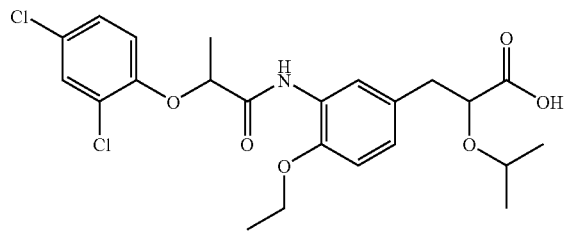

The title compound was obtained in the same manner as described in Example 423c).
¹H-NMR (CDCl₃)
δ: 0.97 (d, J=6.0 Hz, 3H) 1.09 (d, J=6.0 Hz, 3H) 1.64 (d, J=6.0 Hz, 3H) 2.88 (dd, J=14.0, 6.0 Hz, 1H) 3.07 (dd, J=14.0, 4.4 Hz, 1H) 3.49 (dq, J=6.0, 6.0 Hz, 1H) 4.08 (dd, J=7.6, 4.4 Hz, 1H) 4.74 (q, J=6.0 Hz, 1H) 6.86 (d, J=8.0 Hz, 1H) 6.97 (d, J=8.0 Hz, 2H) 7.16 (dd, J=8.0, 2.0 Hz, 1H) 7.20 (m, 1H) 7.38-7.43 (m, 2H) 8.48 (s, 1H)
MS m/e (ESI) 462 (MNa⁺)

Example 440

3-{3-[2-(4-t-Butylphenoxy)propionylamino]-phenyl}-2-isopropoxypropanoic acid

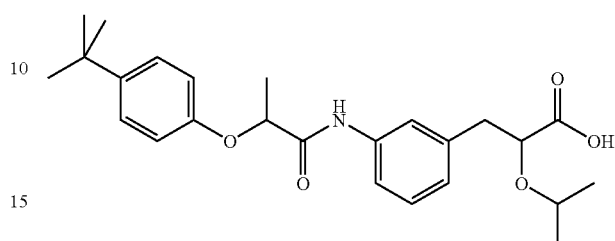

The title compound was obtained in the same manner as described in Example 423c).
MS m/e (ESI) 450 (MNa⁺)

Example 441

3-{3-[2-(2,4-dichlorophenoxy)propionylamino]-4-ethoxyphenyl}-2-isopropoxypropanoic acid

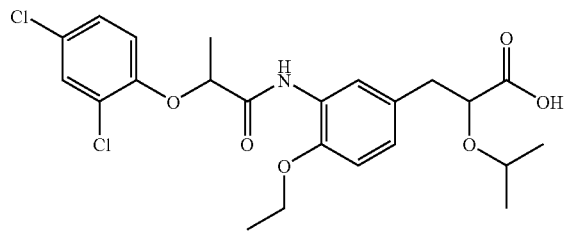

The title compound was obtained in the same manner as described in Example 423c).
MS m/e (ESI) 506 (MNa⁺)

Example 442

3-{3-[2-(4-t-Butylphenoxy)propionylamino]-4-ethoxyphenyl}-2-isopropoxypropanoic acid

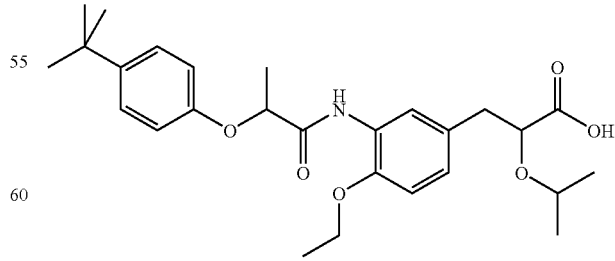

The title compound was obtained in the same manner as described in Example 423c)
MS m/e (ESI) 472 (MH⁺).

Example 443 a) 3-(2,4-Dichlorophenoxy)-dihydrofuran-2-one

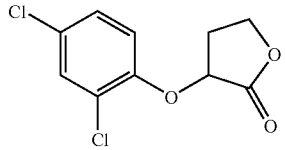

1 g of 2,4-Dichlorophenol was dissolved in 10 ml of N,N-dimethylformamide, and 0.27 g of 60% sodium hydride was added thereto under ice-cooling, and the mixture was stirred at room temperature for 30 minutes. 0.7 ml of Ethyl α-bromo-β-butyrolactone was added to the mixture which was then stirred at room temperature for another 1 hour. The reaction solution was diluted with aqueous ammonium chloride, and extracted with ethylacetate. The organic layer was washed with brine, dried over anhydrous magnesium sulfate, and the solvent was evaporated. The residue was subjected to silica gel column chromatography, to give 1 g of the title compound.

$^1$H-NMR (CDCl$_3$)

δ: 2.61 (m, 1H) 2.72 (m, 1H) 4.34 (m, 1H) 4.56 (m, 1H) 4.86 (t, J=6.0 Hz, 1H) 7.20 (m, 2H) 7.38 (m, 1H)

b) 3-{3-[2-(2,4-Dichlorophenoxy)-4-hydroxybutyrylamino]phenyl}-2-isopropoxypropanoic acid

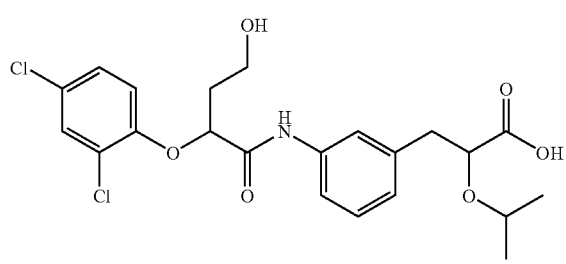

20 mg of 3-(2,4-Dichlorophenoxy)dihydrofuran-2-one and 30 mg of ethyl 3-(3-aminophenyl)-2-isopropoxypropanoate were dissolved in 1 ml of toluene, and the solution was heated under reflux for 8 hours. After removing the solvent under a stream of nitrogen, the residue was dissolved in 0.6 ml of ethanol, and 0.12 ml of 5N sodium hydroxide was added thereto, and the mixture was stirred at room temperature for 1 hour. The reaction solution was diluted with 2 ml of water and 0.14 ml of 5N hydrochloric acid, and extracted with ethyl acetate. The organic layer was collected, and the solvent was removed under a stream of nitrogen. The residue was purified by HPLC using a reverse-phase column and a water-acetonitrile-trifluoroacetic acid elution solvent, to give 6.8 mg of the title compound.

$^1$H-NMR (CDCl$_3$)

δ: 1.05 (d, J=6.0 Hz, 3H) 1.16 (d, J=6.0 Hz, 3H) 2.30 (d, J=6.0 Hz, 2H) 2.95 (m, 2H) 3.11 (dd, J=14.0, 4.4 Hz, 1H) 3.58 (dq, J=6.0, 6.0 Hz, 1H) 3.87-3.95 (m, 2H) 4.16 (dd, J=7.6, 4.4 Hz, 1H) 4.93 (d, J=6.0 Hz, 1H) 7.05 (m, 2H) 7.21-7.27 (m, 2H) 7.38 (m, 1H) 7.44 (dd, J=8.0, 2.0 Hz, 1H) 7.50 (d, J=2.0 Hz, 2H) 8.61 (s, 1H)

MS m/e (ESI) 470 (MH$^+$)

Example 444 a) 3-(4-t-Butylphenoxy)dihydrofuran-2-one

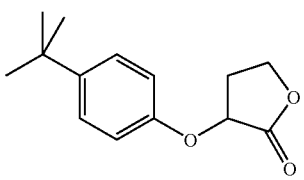

Using 4-t-butylphenol, the title compound was obtained in the same manner as described in Example 443a).

$^1$H-NMR (CDCl$_3$)

δ: 2.46 (m, 1H) 2.70 (m, 1H) 4.36 (m, 1H) 4.51 (m, 1H) 4.92 (t, J=6.0 Hz, 1H) 6.96 (d, J=8.0 Hz, 2H) 7.32 (d, J=8.0 Hz, 2H)

b) 3-{3-[2-(4-t-Butylphenoxy)-4-hydroxybutyrylamino]phenyl}-2-isopropoxypropanoic acid

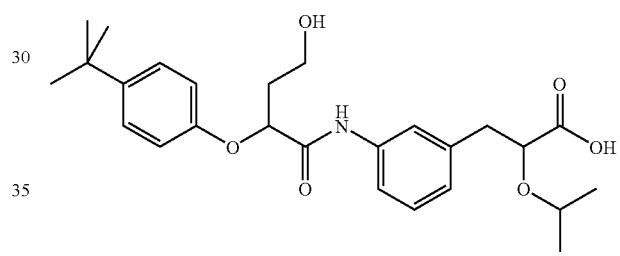

The title compound was obtained in the same manner as described in Example 443b).

MS m/e (ESI) 458 (MH$^+$)

Example 445

3-{3-[2-(2,4-Dichlorophenoxy)-4-hydroxybutyrylamino]-4-ethoxyphenyl}-2-isopropoxypropanoic acid

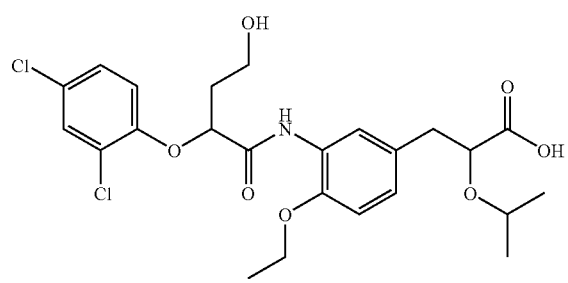

The title compound was obtained in the same manner as described in Example 443.

MS m/e (ESI) 514 (MH$^+$)

Example 446

3-{3-[2-(4-t-Butylphenoxy)-4-hydroxybutyry-lamino]-4-ethoxyphenyl}-2-isopropoxypropanoic acid

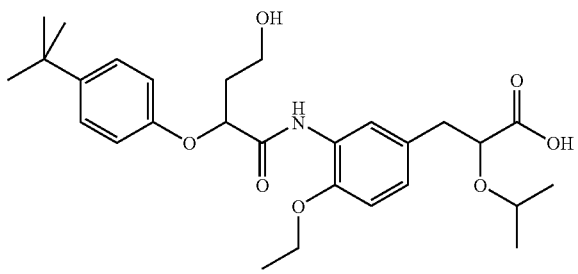

The title compound was obtained in the same manner as described in Example 443.

MS m/e (ESI) 502 (MH$^+$)

Example 447 a) Ethyl 3-(3-isocyanato-4-methoxyphenyl)-2-isopropoxypropanoate

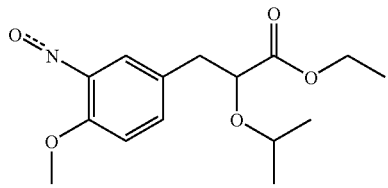

0.13 g of di-t-Butyl dicarbonate was dissolved in 2.5 ml of acetonitrile, and a solution containing 60 mg of 4-dimethylaminopyridine and 0.12 g of ethyl 3-(3-amino-4-methoxyphenyl)-2-isopropoxypropanoate in acetonitrile were added thereto, and the mixture was stirred at room temperature for 10 minutes. The reaction solution was cooled in ice, and 0.73 ml of 40% sulfuric acid-acetonitrile solution was added and stirring was continued at room temperature for 2 minutes, then the mixture was extracted with hexane. The organic layer was washed with saturated brine, dried over anhydrous magnesium sulfate, and the solvent was evaporated, to give 28 mg of the title compound.

$^1$H-NMR (CDCl$_3$)

δ: 0.98 (d, J=6.0 Hz, 3H) 1.15 (d, J=6.0 Hz, 3H) 1.24 (t, J=6.0 Hz, 3H) 2.83 (m, 2H) 3.50 (dq, J=6.4, 6.4 Hz, 1H) 3.89 (s, 3H) 3.97 (dd, J=8.4, 4.8 Hz, 1H) 4.17 (q, J=6.0 Hz, 2H) 6.77 (d, J=8.0 Hz, 1H) 6.89 (d, J=2.0 Hz, 1H) 7.02 (dd, J=8.0, 2.0 Hz, 1H)

b) 3-[3-(2,4-Dichlorobenzyloxycarbonylamino)-4-methoxyphenyl]-2-isopropoxypropanoic acid

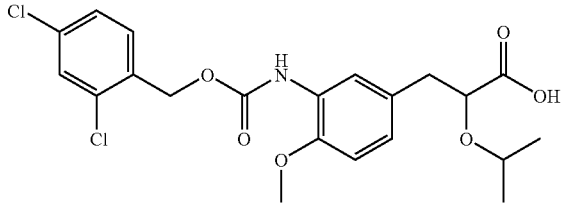

14 mg of Ethyl 3-(3-isocyanato-4-methoxyphenyl)-2-isopropoxypropanoate was dissolved in 1 ml of tetrahydrofuran, and 10 mg of 2,4-dichlorobenzyl alcohol and 5 μl of pyridine were added thereto, and the mixture was stirred at room temperature for 16 hours. The solvent was removed under a stream of nitrogen, and the residue was dissolved in 0.6 ml of ethanol, and 0.12 ml of 5N sodium hydroxide was added and stirred at room temperature for 1 hour. The reaction solution was diluted with 1 ml of water and 0.14 ml of 5N hydrochloric acid, and extracted with ethyl acetate. The organic layer was collected, and the solvent was removed under a stream of nitrogen. The residue was purified by HPLC using a reverse-phase column and a water-acetonitrile-trifluoroacetic acid elution solvent, to give 3.1 mg of the title compound.

MS m/e (ESI) 478 (MNa$^+$)

Example 448

3-{3-[2-(2,4-dichlorophenyl)ethoxycarbonylamino]-4-methoxy-phenyl}-2-isopropoxypropanoic acid

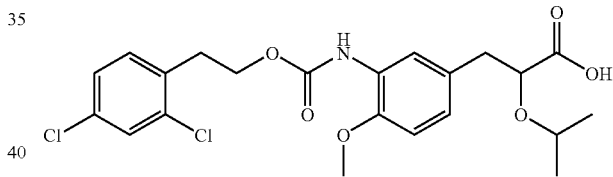

Using 2,4-dichlorophenethyl alcohol, the title compound was obtained in the same manner as described in Example 449b)

MS m/e (ESI) 492 (MNa$^+$)

Example 449

3-[3-(4-Chlorobenzyloxycarbonylamino)-4-ethoxyphenyl]-2-isopropoxypropanoic acid

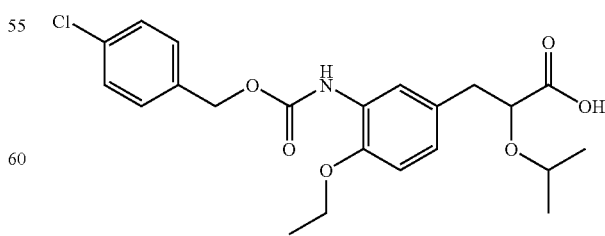

25 mg of di-t-Butyl dicarbonate was dissolved in 0.5 ml of acetonitrile, and a solution of 10 mg of 4-dimethylaminopyridine and 25 mg of ethyl 3-(3-amino-4-ethoxyphenyl)-2- isopropoxypropanoate in acetonitrile was added, and the mixture was stirred for 2 minutes. The reaction solution was treated with 20 mg of 4-chlorobenzyl alcohol, then stirred at 80° C. for 2 hours. The solvent was removed under a stream of nitrogen, and the residue was dissolved in 0.6 ml of ethanol, and 0.12 ml of 5N sodium hydroxide was added. The mixture was stirred at room temperature for 1 hour, and 1 ml of water and 0.14 ml of 5N hydrochloric acid were added, and the mixture was extracted with ethyl acetate. The organic layer was collected, and the solvent was removed under a stream of nitrogen. The residue was purified by HPLC on a reverse-phase column using a water-acetonitrile-trifluoroacetic acid solvent system, to give 19 mg of the title compound.

$^1$H-NMR (CDCl$_3$)

δ: 1.06 (d, J=6.0 Hz, 3H) 1.16 (d, J=6.0 Hz, 3H) 1.42 (t, J=6.0 Hz, 3H) 2.89 (dd, J=14.0, 6.0 Hz, 1H) 3.08 (dd, J=14.0, 4.4 Hz, 1H) 3.56 (dq, J=6.0, 6.0 Hz, 1H) 4.11 (m, 3H) 5.17 (s, 2H) 6.75 (d, J=8.0 Hz, 1H) 6.84 (dd, J=8.0, 2.0 Hz, 1H) 7.25-7.38 (m, 5H)

MS m/e (ESI) 436 (MH$^+$)

Example 450

3-[4-Ethoxy-3-(4-trifluoromethylbenzyloxycarbonylamino)-phenyl]-2-isopropoxypropanoic acid

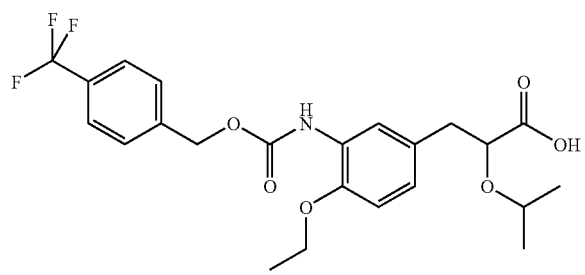

Using 4-trifluoromethylbenzyl alcohol, the title compound was obtained in the same manner as described in Example 449.

$^1$H-NMR (CDCl$_3$)

δ: 1.06 (d, J=6.0 Hz, 3H) 1.15 (d, J=6.0 Hz, 3H) 1.43 (t, J=6.0 Hz, 3H) 2.90 (dd, J=14.0, 6.0 Hz, 1H) 3.08 (dd, J=14.0, 4.4 Hz, 1H) 3.57 (dq, J=6.0, 6.0 Hz, 1H) 4.08 (q, J=6.0 Hz, 2H) 4.14 (dd, J=7.6, 4.4 Hz, 1H) 5.26 (s, 2H) 6.76 (d, J=8.0 Hz, 1H) 6.85 (dd, J=8.0, 2.0 Hz, 1H) 7.31 (s, 1H) 7.54 (d, J=8.0 Hz, 2H) 7.64 (d, J=8.0 Hz, 2H) 8.01 (s, 1H)

MS m/e (ESI) 470 (MH$^+$)

Example 451

3-[4-Ethoxy-3-(4-methoxybenzyloxycarbonylamino)phenyl]-2-isopropoxypropanoic acid

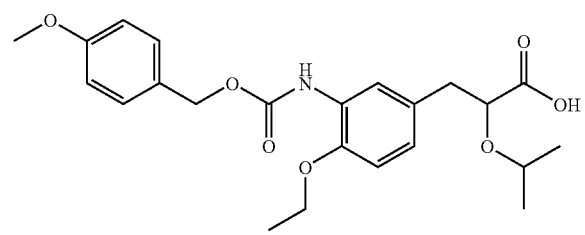

Using 4-methoxybenzyl alcohol, the title compound was obtained in the same manner as described in Example 449.

MS m/e (ESI) 454 (MNa$^+$)

Example 452

3-[4-Ethoxy-3-(4-trifluoromethoxybenzyloxycarbonylamino)-phenyl]-2-isopropoxypropanoic acid

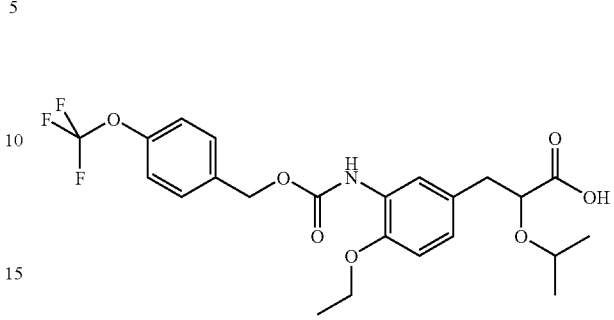

Using 4-trifluoromethoxybenzyl alcohol, the title compound was obtained in the same manner as described in Example 449.

MS m/e (ESI) 508 (MNa$^+$)

Example 453

3-[3-(3,4-Dichlorobenzyloxycarbonylamino)-4-ethoxyphenyl]-2-isopropoxypropanoic acid

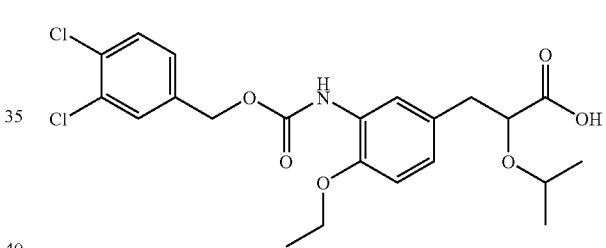

Using 3,4-dichlorobenzyl alcohol, the title compound was obtained in the same manner as described in Example 449.

MS m/e (ESI) 492 (MNa$^+$)

Example 454

3-{3-[2-(4-Chlorophenyl)ethoxycarbonylamino]-4-ethoxyphenyl}-2-isopropoxypropanoic acid

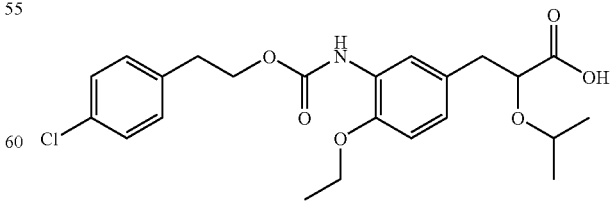

Using 4-chlorophenethyl alcohol, the title compound was obtained in the same manner as described in Example 449.

MS m/e (ESI) 472 (MNa$^+$)

Example 455

3-{4-Ethoxy-3-[2-(4-methoxyphenyl)ethoxycarbonylamino]-phenyl}-2-isopropoxypropanoic acid

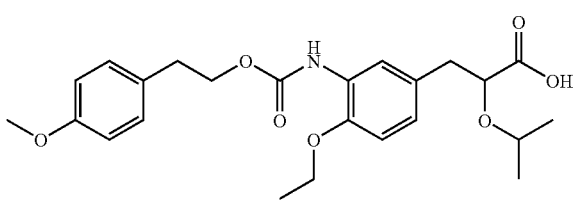

Using 4-methoxyphenethyl alcohol, the title compound was obtained in the same manner as described in Example 449.

MS m/e (ESI) 468 (MNa+)

Example 456

3-{3-[2-(2,4-Dichlorophenyl)ethoxycarbonylamino]-4-ethoxyphenyl}-2-isopropoxypropanoic acid

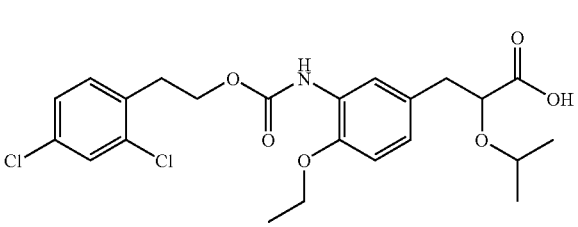

Using 2,4-dichlorophenethyl alcohol, the title compound was obtained in the same manner as described in Example 449.

MS m/e (ESI) 484 (MH+)

Example 457

3-[3-(2,4-Dichlorobenzyloxycarbonylamino)-4-ethoxyphenyl]-2-isopropoxypropanoic acid

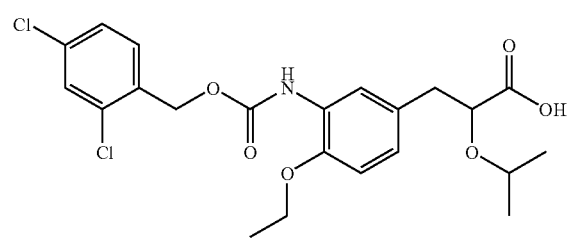

Using 2,4-dichlorobenzyl alcohol, the title compound was obtained in the same manner as described in Example 449.

MS m/e (ESI) 470 (MH+)

Example 458

3-[3-(4-Chlorobenzyloxycarbonylamino)phenyl]-2-isopropoxypropanoic acid

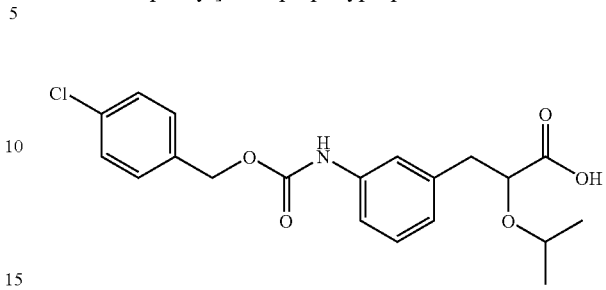

Using 4-chlorobenzyl alcohol, the title compound was obtained in the same manner as described in Example 449.

MS m/e (ESI) 414 (MNa+)

Example 459

2-Isopropoxy-3-[3-(4-trifluoromethylbenzyloxycarbonylamino)phenyl]propanoic acid

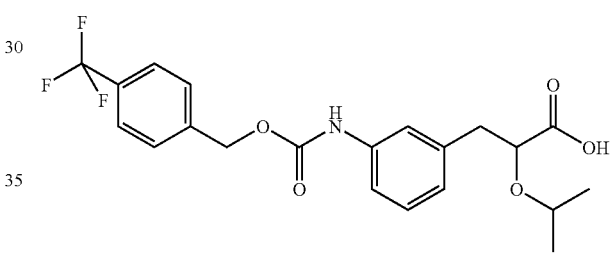

Using 4-trifluoromethylbenzyl alcohol, the title compound was obtained in the same manner as described in Example 449.

¹H-NMR (CDCl₃)

δ: 1.03 (d, J=6.0 Hz, 3H) 1.16 (d, J=6.0 Hz, 3H) 2.93 (dd, J=14.0, 6.0 Hz, 1H) 3.12 (dd, J=14.0, 4.4 Hz, 1H) 3.56 (dq, J=6.0, 6.0 Hz, 1H) 4.15 (dd, J=7.6, 4.4 Hz, 1H) 5.25 (s, 2H) 6.69 (s, 1H) 6.97 (d, J=8.0 Hz, 1H) 7.23 (d, J=8.0 Hz, 1H) 7.28 (m, 2H) 7.52 (d, J=8.0 Hz, 2H) 7.64 (d, J=8.0 Hz, 2H)

MS m/e (ESI) 448 (MNa+)

Example 460

2-Isopropoxy-3-[3-(3-trifluoromethylbenzyloxycarbonylamino)phenyl]propanoic acid

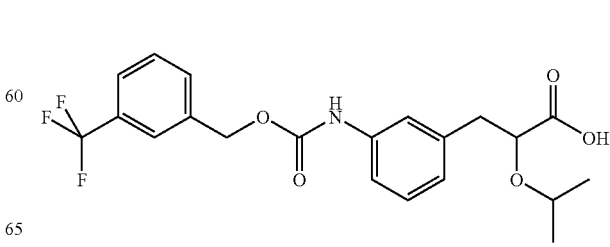

Using 3-trifluoromethylbenzyl alcohol, the title compound was obtained in the same manner as described in Example 449.

MS m/e (ESI) 448 (MNa⁺)

Example 461

2-Isopropoxy-3-[3-(4-trifluoromethoxybenzyloxy-carbonylamino)phenyl]propanoic acid

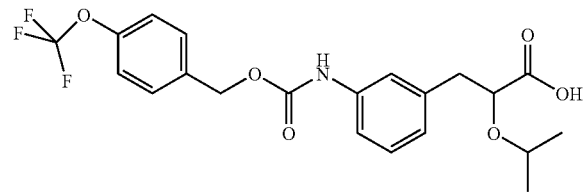

Using 4-trifluoromethoxybenzyl alcohol, the title compound was obtained in the same manner as described in Example 449.

MS m/e (ESI) 464 (MNa⁺)

Example 462

3-[3-(2,4-Dichlorobenzyloxycarbonylamino)-phenyl]-2-isopropoxypropanoic acid

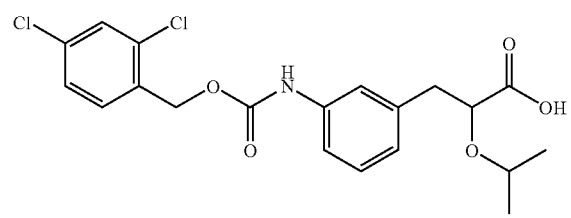

Using 2,4-dichlorobenzyl alcohol, the title compound was obtained in the same manner as described in Example 449.

MS m/e (ESI) 448 (MNa⁺)

Example 463

3-[3-(3,4-Dichlorobenzyloxycarbonylamino)-phenyl]-2-isopropoxypropanoic acid

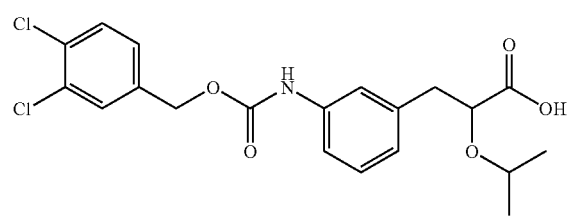

Using 3,4-dichlorobenzyl alcohol, the title compound was obtained in the same manner as described in Example 449.

MS m/e (ESI) 448 (MNa⁺)

Example 464

3-{3-[2-(3-Chlorophenyl)ethoxycarbonylamino]-phenyl}-2-isopropoxypropanoic acid

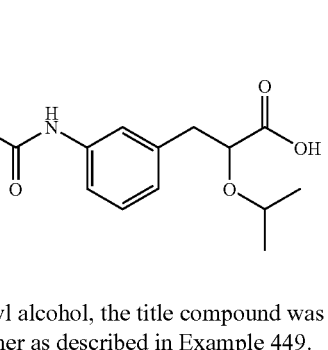

Using 3-chlorophenethyl alcohol, the title compound was obtained in the same manner as described in Example 449.

MS m/e (ESI) 428 (MNa⁺)

Example 465

3-{4-Ethoxy-[2-(6-methylpyridin-2-yl)ethoxycarbo-nylamino]phenyl}-2-isopropoxypropanoic acid

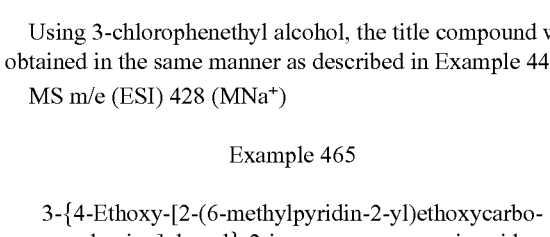

Using 2-(6-methylpyridin-2-yl)ethanol, the title compound was obtained in the same manner as described in Example 449.

MS m/e (ESI) 431 (MH⁺)

Example 466

3-[4-Ethoxy-3-(6-methylpyridin-2-ylmethoxycarbo-nylamino)phenyl]-2-isopropoxypropanoic acid

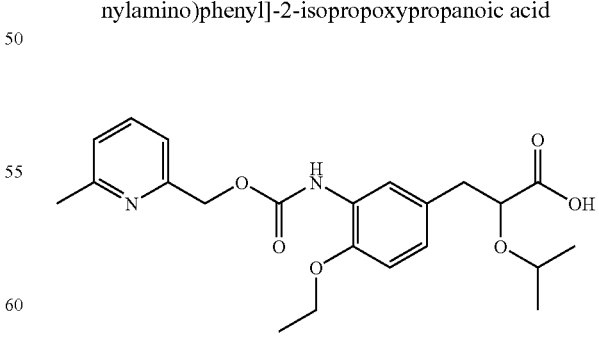

Using (6-methylpyridin-2-yl)methanol, the title compound was obtained in the same manner as described in Example 449.

MS m/e (ESI) 417 (MH⁺)

Example 467

3-[4-Ethoxy-3-(6-methylpyridin-3-ylmethoxycarbonylamino)phenyl]-2-isopropoxypropanoic acid

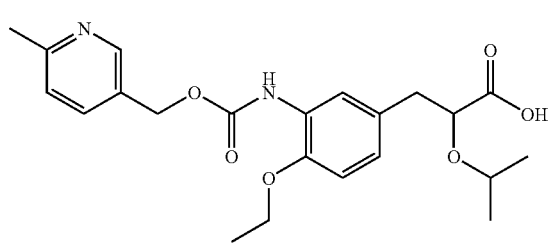

Using (6-methylpyridin-3-yl)methanol, the title compound was obtained in the same manner as described in Example 449.

MS m/e (ESI) 417 (MH$^+$)

Example 468

3-[4-Ethoxy-3-(quinolin-2-ylmethoxycarbonylamino)phenyl]-2-isopropoxypropanoic acid

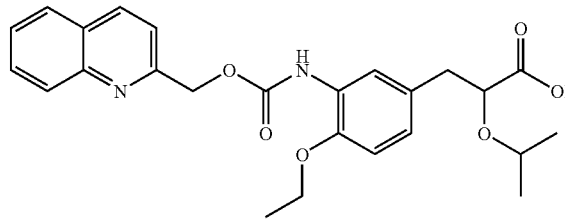

Using quinolin-2-yl methanol, the title compound was obtained in the same manner as described in Example 449.

MS m/e (ESI) 453 (MH$^+$)

Example 469

3-[4-Ethoxy-3-(quinolin-3-ylmethoxycarbonylamino)phenyl]-2-isopropoxypropanoic acid

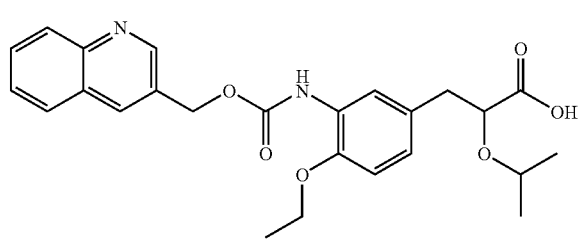

Using quinolin-3-yl methanol, the title compound was obtained in the same manner as described in Example 449.

MS m/e (ESI) 453 (MH$^+$)

Example 470

3-[4-Ethoxy-3-(quinolin-4-ylmethoxycarbonylamino)phenyl]-2-isopropoxypropanoic acid

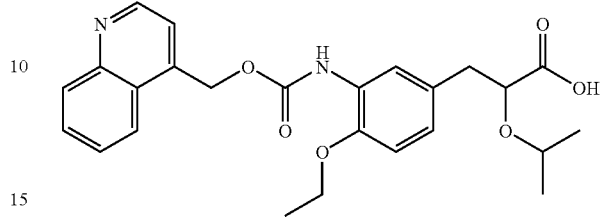

Using quinolin-4-yl methanol, the title compound was obtained in the same manner as described in Example 449.

MS m/e (ESI) 453 (MH$^+$)

Example 471

3-[3-(2-Chloroquinolin-3-ylmethoxycarbonylamino)-4-ethoxyphenyl]-2-isopropoxypropanoic acid

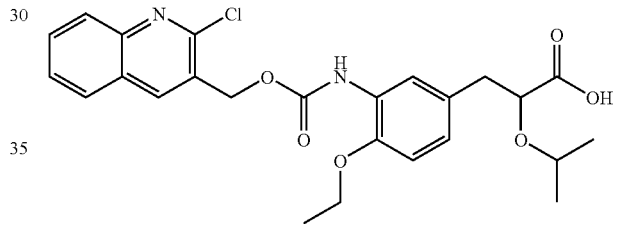

Using 2-chloroquinolin-3-yl methanol, the title compound was obtained in the same manner as described in Example 449.

MS ml/e(ESI) 487 (MH$^+$)

Example 472

3-[3-(2-Chloro-4-ethoxybenzyloxycarbonylamino)phenyl]-2-isopropoxypropanoic acid

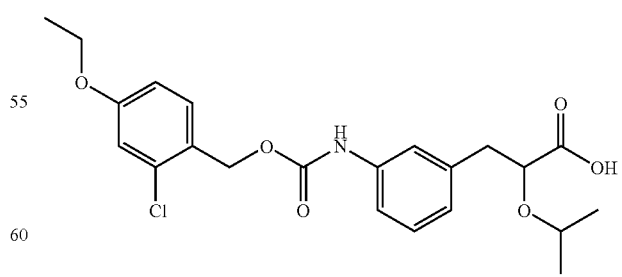

Using 2-chloro-3-ethoxybenzyl alcohol, the title compound was obtained in the same manner as described in Example 449.

MS m/e (ESI) 472 (MNa$^+$)

Example 473

3-[3-(2-Fluoro-4-trifluoromethylbenzyloxycarbonylamino)-phenyl]-2-isopropoxypropanoic acid

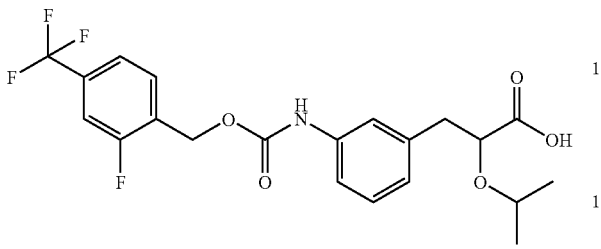

Using 2-fluoro-4-trifluoromethylbenzyl alcohol, the title compound was obtained in the same manner as described in Example 449.
MS m/e (ESI) 466 (MNa$^+$)

Example 474

3-[3-(4-Chloro-2-fluorobenzyloxycarbonylamino)phenyl]-2-isopropoxypropanoic acid

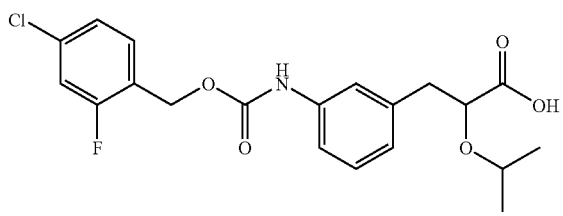

Using 4-chloro-2-fluorobenzyl alcohol, the title compound was obtained in the same manner as described in Example 449.
MS m/e (ESI) 432 (MNa$^+$)

Example 475

3-[3-(3-Bromo-4-methoxybenzyloxycarbonylamino)phenyl]-2-isopropoxypropanoic acid

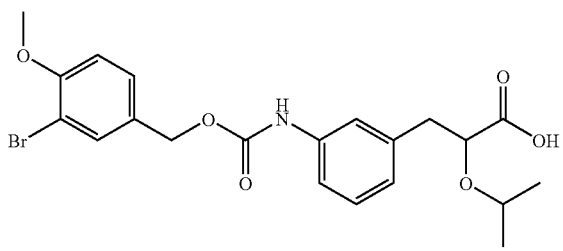

Using 3-bromo-4-methoxybenzyl alcohol, the title compound was obtained in the same manner as described in Example 449.
MS m/e (ESI) 488 (MNa$^+$)

Example 476

2-Isopropoxy-3-[3-(4-methoxy-3-methylbenzyloxycarbonylamino)phenyl]propanoic acid

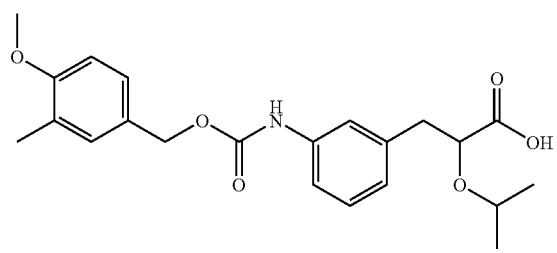

Using 4-methoxy-3-methylbenzylalcohol, the title compound was obtained in the same manner as described in Example 449.
MS m/e (ESI) 424 (MNa$^+$)

Example 477

3-[3-(2,3-Dihydrobenzofuran-5-ylmethoxycarbonylamino)phenyl]-2-isopropoxypropanoic acid

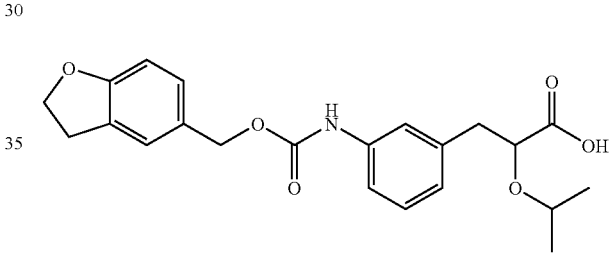

Using (2,3-dihydrobenzofuran-5-yl)methanol, the title compound was obtained in the same manner as described in Example 449.
MS m/e (ESI) 422 (MNa$^+$)

Example 478

3-[3-(Benzo[1,3]dioxol-5-ylmethoxycarbonylamino)phenyl]-2-isopropoxypropanoic acid

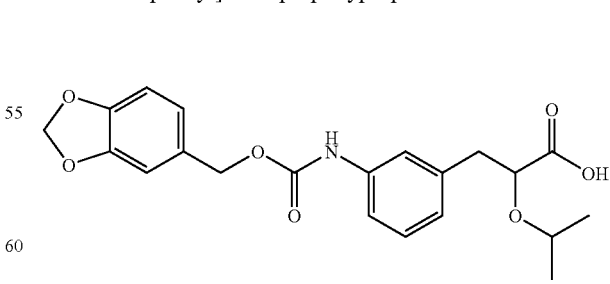

Using benzo[1,3]dioxol-5-yl methanol, the title compound was obtained in the same manner as described in Example 449.
MS m/e (ESI) 402 (MH$^+$)

Example 479

3-[3-(4-Ethoxybenzyloxycarbonylamino)phenyl]-2-isopropoxypropanoic acid

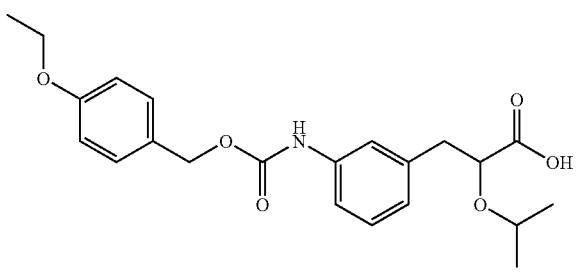

Using 4-ethoxybenzyl alcohol, the title compound was obtained in the same manner as described in Example 449.
MS m/e (ESI) 424 (MNa⁺)

Example 480 a) Ethyl 3-(5-amino-2-fluorophenyl)-2-isopropoxypropanoate

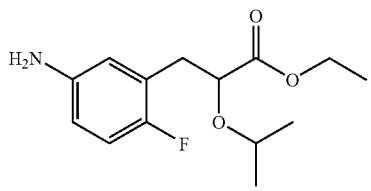

The title compound was obtained in the same manner as described in Examples 423a) and 423b).
¹H-NMR (CDCl₃)
δ: 0.98 (d, J=6.0 Hz, 3H) 1.14 (d, J=6.0 Hz, 3H) 1.24 (t, J=6.0 Hz, 3H) 2.83 (m, 1H) 3.05 (m, 1H) 3.55 (dq, J=6.0 Hz, 1H) 4.08 (dd, J=8.4, 4.8 Hz, 1H) 4.17 (q, J=6.0 Hz, 2H) 6.49 (m, 1H) 6.53 (d, J=8.0 Hz, 1H) 6.80 (d, J=8.0 Hz, 1H)

b) 3-[5-(4-Chlorobenzyloxycarbonylamino)-2-fluorophenyl]-2-isopropoxypropanoic acid

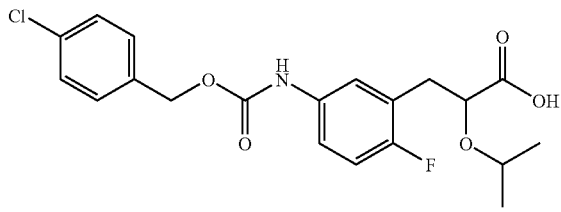

Using 4-chlorobenzyl alcohol, the title compound was obtained in the same manner as described in Example 449.
MS m/e (ESI) 432 (MNa⁺)

Example 481

3-[5-(2,4-Dichlorobenzyloxycarbonylamino)-2-fluorophenyl]-2-isopropoxypropanoic acid

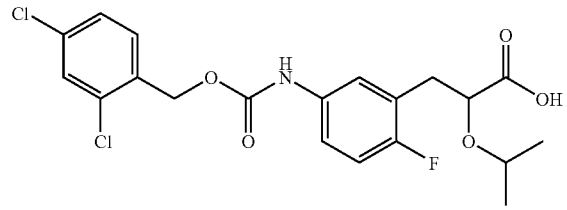

Using 2,4-dichlorobenzyl alcohol, the title compound was obtained in the same manner as described in Example 449.
MS m/e (ESI) 466 (MNa⁺)

Example 482

3-[5-(3,4-Dichlorobenzyloxycarbonylamino)-2-fluorophenyl]-2-isopropoxypropanoic acid

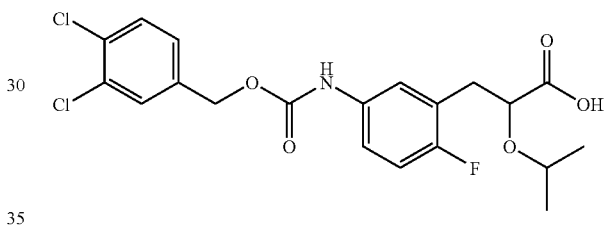

Using 3,4-dichlorobenzyl alcohol, the title compound was obtained in the same manner as described in Example 449.
MS m/e (ESI) 466 (MNa⁺)

Example 483

3-[2-Fluoro-5-(4-trifluoromethylbenzyloxycarbonylamino)-phenyl]-2-isopropoxypropanoic acid

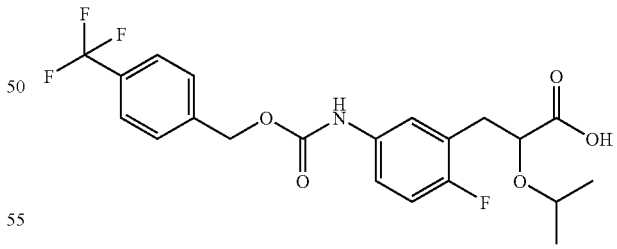

Using 4-trifluoromethylbenzyl alcohol, the title compound was obtained in the same manner as described in Example 449.
¹H-NMR (CDCl₃)
δ: 1.01 (d, J=6.0 Hz, 3H) 1.16 (d, J=6.0 Hz, 3H) 2.97 (dd, J=14.0, 6.0 Hz, 1H) 3.20 (dd, J=14.0, 4.4 Hz, 1H) 3.60 (dq, J=6.0, 6.0 Hz, 1H) 4.20 (dd, J=7.6, 4.4 Hz, 1H) 5.24 (s, 2H) 6.70 (bs, 1H) 6.99 (t, J=9.2 Hz, 1H) 7.23 (m, 2H) 7.28 (m, 1H) 7.50 (d, J=8.0 Hz, 2H) 7.64 (d, J=8.0 Hz, 2H)
MS m/e (ESI) 466 (MNa⁺)

Example 484

3-[2-Fluoro-5-(3-trifluoromethylbenzyloxycarbonylamino)-phenyl]-2-isopropoxypropanoic acid

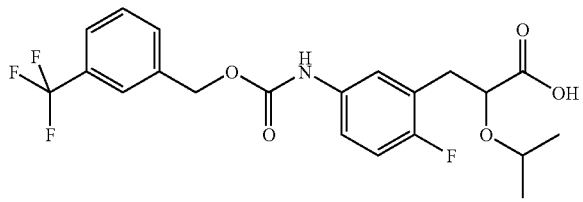

Using 3-trifluoromethylbenzyl alcohol, the title compound was obtained in the same manner as described in Example 449.

MS m/e (ESI) 466 (MNa$^+$)

Example 485

3-[2-Fluoro-5-(4-trifluoromethoxybenzyloxycarbonylamino)-phenyl]-2-isopropoxypropanoic acid

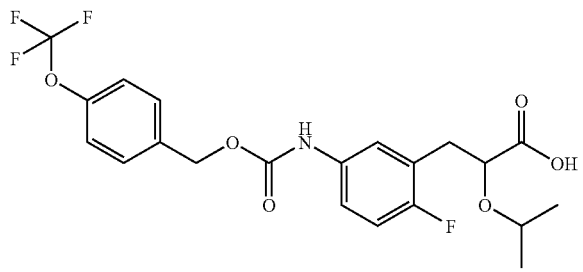

Using 4-trifluoromethoxybenzyl alcohol, the title compound was obtained in the same manner as described in Example 449.

MS m/e (ESI) 483 (MNa$^+$)

Example 486

3-[2-Fluoro-5-(quinolin-3-ylmethoxycarbonylamino)phenyl]-2-isopropoxypropanoic acid

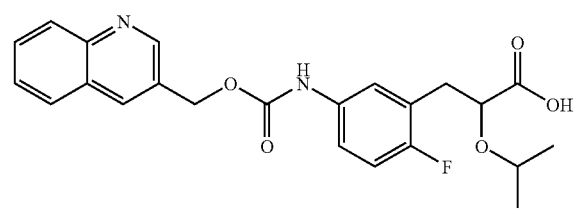

Using quinolin-3-yl methanol, the title compound was obtained in the same manner as described in Example 449.

MS m/e (ESI) 427 (MH$^+$)

Example 487

3-[5-(2-Chloroquinolin-3-ylmethoxycarbonylamino)-2-fluorophenyl]-2-isopropoxypropanoic acid

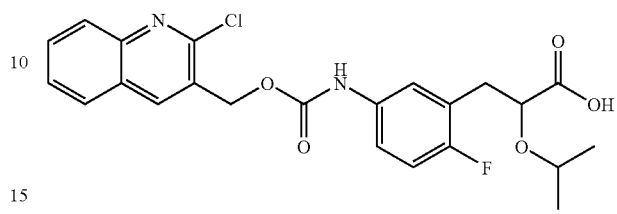

Using 2-chloroquinolin-3-yl methanol, the title compound was obtained in the same manner as described in Example 449.

MS m/e (ESI) 461 (MH$^+$)

Example 488

3-[5-(2-Chloro-4-propoxybenzyloxycarbonylamino)-2-fluorophenyl]-2-isopropoxypropanoic acid

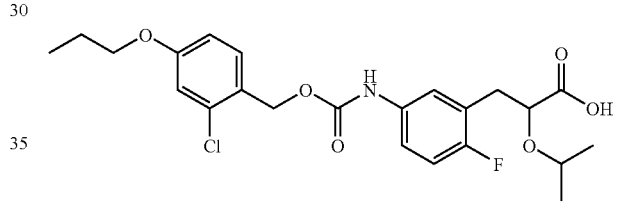

Using 2-chloro-4-propoxybenzyl alcohol, the title compound was obtained in the same manner as described in Example 449.

MS m/e (ESI) 490 (MNa$^+$)

Example 489

3-[2-Fluoro-5-(2-fluoro-4-trifluoromethylbenzyloxycarbonylamino)phenyl]-2-isopropoxypropanoic acid

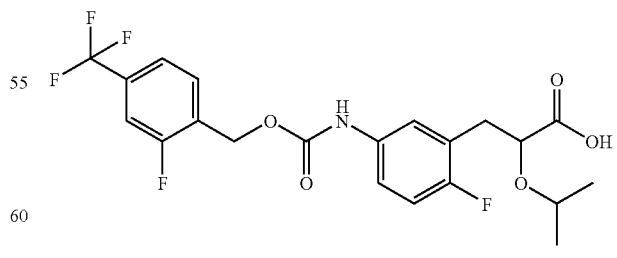

Using 2-fluoro-4-trifluoromethylbenzyl alcohol, the title compound was obtained in the same manner as described in Example 449.

MS m/e (ESI) 484 (MNa$^+$)

Example 490

3-[5-(3,4-Dimethylbenzyloxycarbonylamino)-2-fluorophenyl]-2-isopropoxypropanoic acid

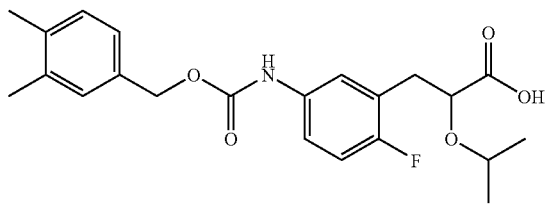

Using 3,4-dimethylbenzyl alcohol, the title compound was obtained in the same manner as described in Example 449.
MS m/e (ESI) 426 (MNa⁺)

Example 491

3-[2-Fluoro-5-(4-methoxy-3,5-dimethylpyridin-2-ylmethoxycarbonylamino)phenyl]-2-isopropoxypropanoic acid trifluoroacetate

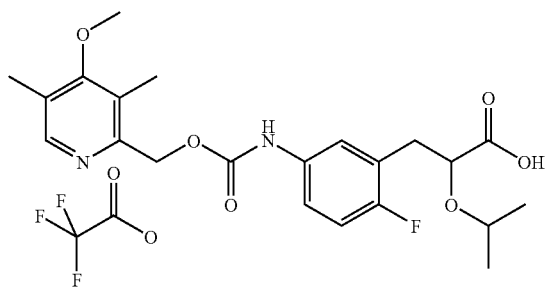

Using (4-methoxy-3,5-dimethylpyridin-2-yl)methanol, the title compound was obtained in the same manner as described in Example 449.
MS m/e (ESI) 435 (MH⁺)

Example 492

3-[5-(1H-Benzimidazol-2-ylmethoxycarbonylamino)-2-fluorophenyl]-2-isopropoxypropanoic acid trifluoroacetate

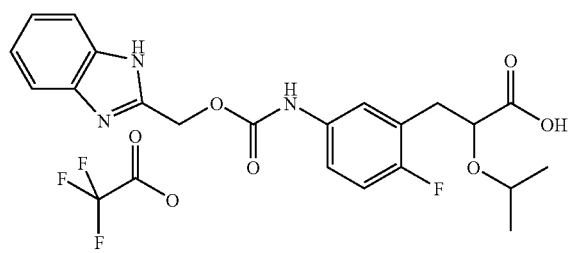

Using 1H-benzimidazol-2-yl methanol, the title compound was obtained in the same manner as described in Example 449.
MS m/e (ESI) 416 (MH⁺)

Example 493

3-[3-(4-Chloro-2-fluorobenzyloxycarbonylamino)phenyl]-2-isopropoxypropanoic acid

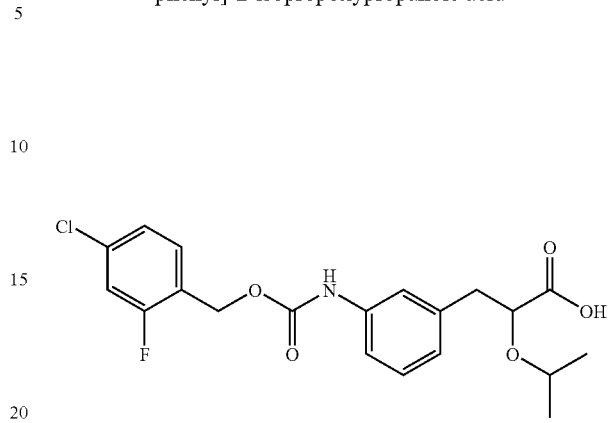

25 mg of Triphosgene was dissolved in 0.5 ml of dichloromethane, 5 µl of pyridine was added, and a solution of 20 mg of ethyl-3-(3-aminophenyl)-2-isopropoxypropanoate in dichloromethane and 50 µl of triethylamine were added under ice-cooling. After the insoluble substances had been removed by cotton plug filtration, 15 mg of 2-fluoro-4-chlorobenzyl alcohol was added. The solvent was removed under a stream of nitrogen, and the residue was dissolved in 0.6 ml of ethanol. 0.12 ml of 5N sodium hydroxide was added, followed by stirring at room temperature for 1 hour. The reaction solution was treated with 1 ml of water and 0.14 ml of 5N hydrochloric acid, then extracted with ethylacetate. The organic layers were collected, and the solvent was removed under a stream of nitrogen. The residue was purified by reverse-phase HPLC using a water-acetonitrile-trifluoroacetic acid solvent system, to give 1.4 mg of the title compound.
MS m/e (ESI) 438 (MNa⁺)

Example 494

2-Isopropoxy-3-[3-(4-isopropoxybenzyloxycarbonylamino)phenyl]propanoic acid

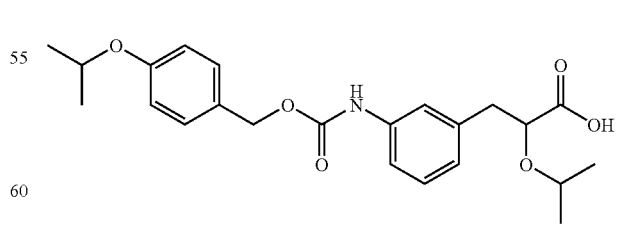

Using 4-isopropoxybenzyl alcohol, the title compound was obtained in the same manner as described in Example 493.
MS m/e (ESI) 464 (MNa⁺)

Example 495

2-Isopropoxy-3-[3-(3-trifluoromethoxybenzyloxy-carbonylamino)phenyl]propanoic acid

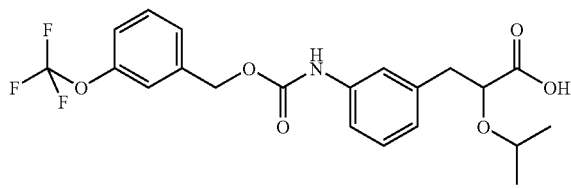

Using 3-trifluoromethoxybenzyl alcohol, the title compound was obtained in the same manner as described in Example 493.
MS m/e (ESI) 463 (MNa⁺)

Example 496

3-[3-(4-Fluoro-3-trifluoromethylbenzyloxycar-bonylamino)-phenyl]-2-isopropoxypropanoic acid

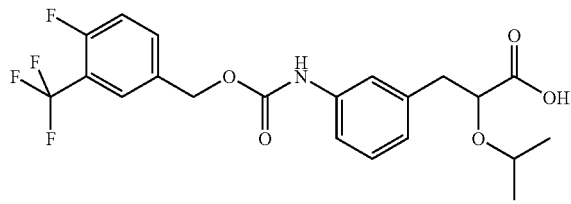

Using 4-fluoro-3-trifluoromethylbenzyl alcohol, the title compound was obtained in the same manner as described in Example 493.
MS ml/e(ESI) 466 (MNa⁺)

Example 497

3-[5-(4-Chloro-2-fluorobenzyloxycarbonylamino)-2-fluorophenyl]-2-isopropoxypropanoic acid

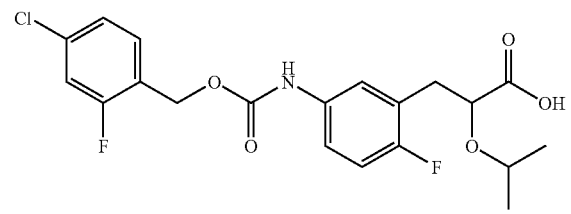

Using 4-chloro-2-fluorobenzyl alcohol, the title compound was obtained in the same manner as described in Example 493.
MS m/e (ESI) 450 (MNa⁺)

Example 498

3-[2-Fluoro-5-(4-isopropoxybenzyloxycarbony-lamino)phenyl]-2-isopropoxypropanoic acid

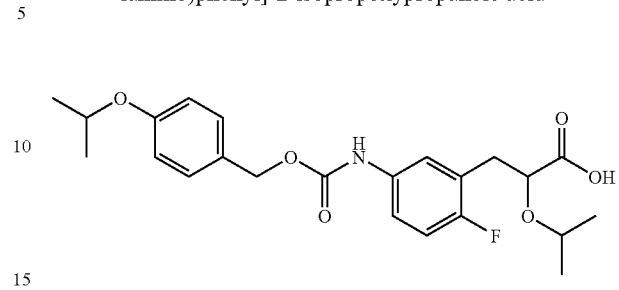

Using 4-isopropoxybenzyl alcohol, the title compound was obtained in the same manner as described in Example 493.
MS m/e (ESI) 456 (MNa⁺)

Example 499

3-[2-Fluoro-5-(4-propoxybenzyloxycarbonylamino)phenyl]-2-isopropoxypropanoic acid

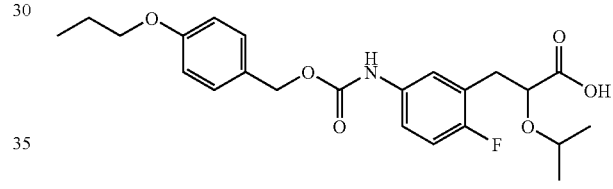

Using 4-propoxybenzyl alcohol, the title compound was obtained in the same manner as described in Example 493.
MS m/e (ESI) 456 (MNa⁺)

Example 500

3-[2-Fluoro-5-(4-methylbenzyloxycarbonylamino)phenyl]-2-isopropoxypropanoic acid

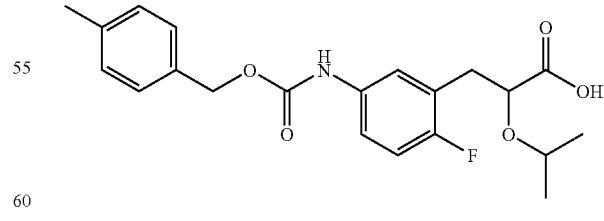

Using 4-methylbenzyl alcohol, the title compound was obtained in the same manner as described in Example 493.
MS m/e (ESI) 412 (MNa⁺)

Example 501

3-[2-Fluoro-5-(3-trifluoromethoxybenzyloxycarbonylamino)-phenyl]-2-isopropoxypropanoic acid

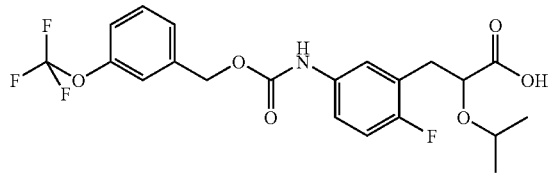

Using 3-trifluoromethoxybenzyl alcohol, the title compound was obtained in the same manner as described in Example 493.

MS m/e (ESI) 482 (MNa+)

Example 502 a) Ethyl 3-(5-amino-2-methoxyphenyl)-2-isopropoxypropionate

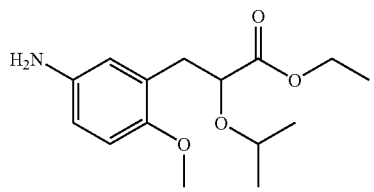

The title compound was obtained in the same manner as described in Examples 423a) and 423b).

$^1$H-NMR (CDCl$_3$)

δ: 0.98 (d, J=6.0 Hz, 3H) 1.14 (d, J=6.0 Hz, 3H) 1.20 (t, J=6.0 Hz, 3H) 2.84 (dd, J=14.0, 6.0 Hz, 1H) 3.00 (dd, J=14.0, 4.4 Hz, 1H) 3.52 (dq, J=6.0, 6.0 Hz, 1H) 3.76 (s, 3H) 4.15 (m, 3H) 6.54 (m, 2H) 6.67 (d, J=8.0 Hz, 1H)

b) 3-[5-(4-Chloro-2-fluorobenzyloxycarbonylamino)-2-methoxyphenyl]-2-isopropoxypropanoic acid

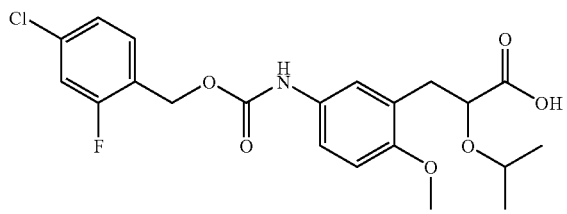

Using 4-chloro-2-fluorobenzyl alcohol, the title compound was obtained in the same manner as described in Example 493.

MS m/e (ESI) 440 (MH+)

Example 503

3-[5-(2-Fluoro-4-trifluoromethylbenzyloxycarbonylamino)-2-methoxyphenyl]-2-isopropoxypropanoic acid

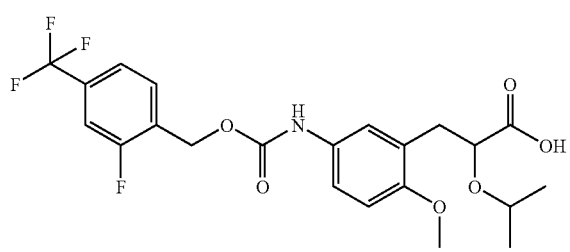

Using 2-fluoro-4-trifluoromethylbenzyl alcohol, the title compound was obtained in the same manner as described in Example 493.

MS m/e (ESI) 496 (MNa+)

Example 504

2-Isopropoxy-3-[2-methoxy-5-(4-trifluoromethylbenzyloxycarbonylamino)phenyl]propanoic acid

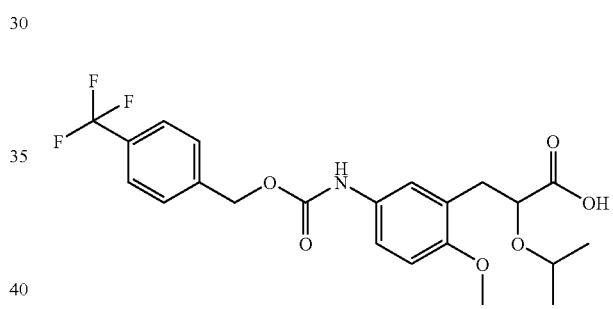

Using 4-trifluoromethylbenzyl alcohol, the title compound was obtained in the same manner as described in Example 493.

MS m/e (ESI) 478 (MNa+)

Example 505

2-Isopropoxy-3-[2-methoxy-5-(4-trifluoromethoxybenzyloxycarbonylamino)phenyl]propanoic acid

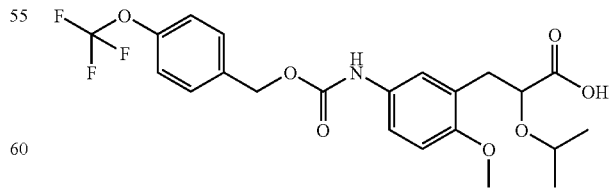

Using 4-trifluoromethoxybenzyl alcohol, the title compound was obtained in the same manner as described in Example 493.

MS m/e (ESI) 494 (MNa+)

Example 506

2-Isopropoxy-3-[2-methoxy-5-(3-trifluoromethoxy-benzyloxycarbonylamino)phenyl]propanoic acid

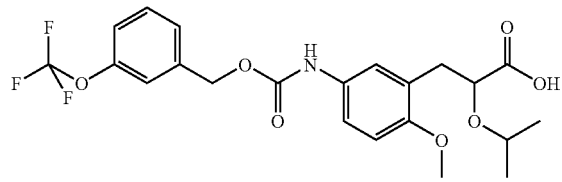

Using 3-trifluoromethoxybenzyl alcohol, the title compound was obtained in the same manner as described in Example 493.

MS m/e (ESI) 472 (MH$^+$)

Example 507

3-[5-(4-Ethylbenzyloxycarbonylamino)-2-methoxyphenyl]-2-isopropoxypropanoic acid

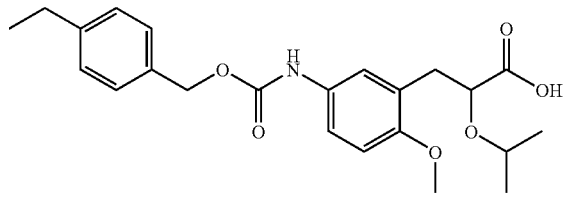

Using 4-ethylbenzyl alcohol, the title compound was obtained in the same manner as described in Example 493.

MS m/e (ESI) 438 (MNa$^+$)

Example 508

3-[5-(3,5-Dimethylbenzyloxycarbonylamino)-2-methoxyphenyl]-2-isopropoxypropanoic acid

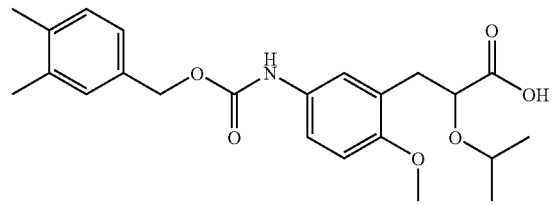

Using 3,4-dimethylbenzyl alcohol, the title compound was obtained in the same manner as described in Example 493.

MS m/e (ESI) 438 (MNa$^+$)

Example 509

3-[5-(3-Fluoro-4-trifluoromethylbenzyloxycarbonylamino)-2-methoxyphenyl]-2-isopropoxypropanoic acid

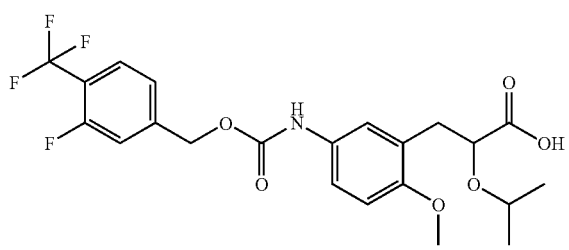

Using 3-fluoro-4-trifluoromethylbenzyl alcohol, the title compound was obtained in the same manner as described in Example 493.

MS m/e (ESI) 474 (MH$^+$)

Example 510

3-[5-(4-Fluoro-3-trifluoromethylbenzyloxycarbonylamino)-2-methoxyphenyl]-2-isopropoxypropanoic acid

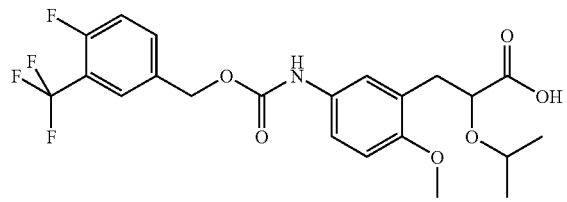

Using 4-fluoro-3-trifluoromethylbenzyl alcohol, the title compound was obtained in the same manner as described in Example 493.

MS m/e (ESI) 474 (MH$^+$)

Example 511

2-Isopropoxy-3-[2-methoxy-5-(4-propoxybenzyloxycarbonylamino)phenyl]propanoic acid

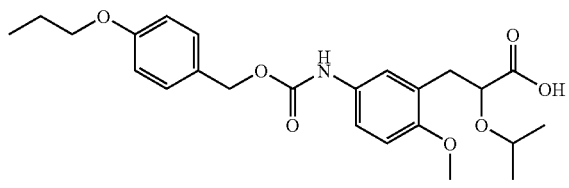

Using 4-propoxybenzyl alcohol, the title compound was obtained in the same manner as described in Example 493.

MS m/e (ESI) 468 (MNa$^+$)

Example 512

2-Isopropoxy-3-[5-(4-propoxybenzyloxycarbony-
lamino)-2-methoxyphenyl]propanoic acid

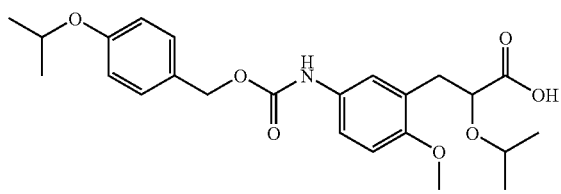

Using 4-isopropoxybenzyl alcohol, the title compound was obtained in the same manner as described in Example 493.

MS m/e (ESI) 468 (MNa⁺)

Example 513

3-[5-(2-Fluoro-4-methoxybenzyloxycarbonylamino)-
2-methoxyphenyl]-2-isopropoxypropanoic acid

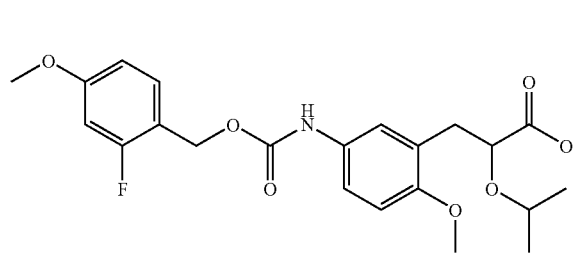

Using 2-fluoro-4-methoxybenzyl alcohol, the title compound was obtained in the same manner as described in Example 493.

MS m/e (ESI) 458 (MNa⁺)

Example 514

3-[5-(4-Ethoxybenzyloxycarbonylamino)-2-methox-
yphenyl]-2-isopropoxypropanoic acid

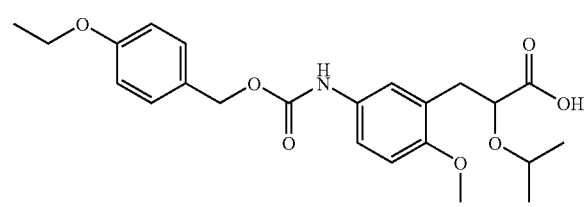

Using 4-ethoxybenzyl alcohol, the title compound was obtained in the same manner as described in Example 493.

MS m/e (ESI) 454 (MNa⁺)

Example 515

3-[5-(4-Butoxybenzyloxycarbonylamino)-2-methox-
yphenyl]-2-isopropoxypropanoic acid

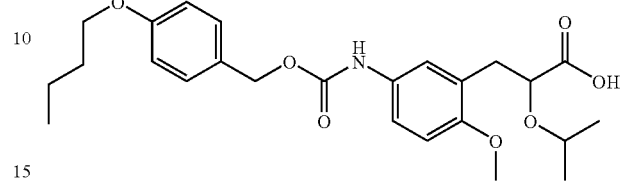

Using 4-butoxybenzyl alcohol, the title compound was obtained in the same manner as described in Example 493.

MS m/e (ESI) 482 (MNa⁺)

Example 516

2-Isopropoxy-3-[2-methoxy-5-(3-methoxybenzy-
loxycarbonylamino)phenyl]propanoic acid

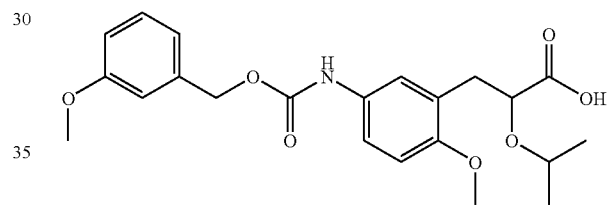

Using 3-methoxybenzyl alcohol, the title compound was obtained in the same manner as described in Example 493.

MS m/e (ESI) 440 (MNa⁺)

Example 517 a) Ethyl 3-(4-aminophenyl)-2-isopropoxypropionate

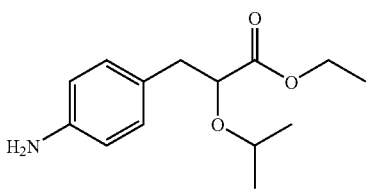

The title compound was obtained in the same manner as described in Examples 423a) and 423b).

¹H-NMR (CDCl₃)

δ: 0.98 (d, J=6.0 Hz, 3H) 1.14 (d, J=6.0 Hz, 3H) 1.22 (t, J=6.0 Hz, 3H) 2.84 (m, 2H) 3.48 (dq, J=6.0, 6.0 Hz, 1H) 3.98 (dd, J=7.6, 4.4 Hz, 1H) 4.15 (q, J=6.0 Hz, 2H) 6.60 (d, J=8.0 Hz, 2H) 7.02 (d, J=8.0 Hz, 2H)

b) 3-[4-(4-Chlorobenzyloxycarbonylamino)phenyl]-2-isopropoxypropanoic acid

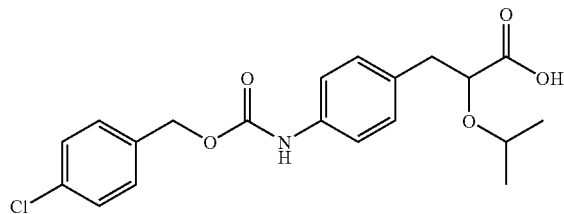

Using 4-chlorobenzyl alcohol, the title compound was obtained in the same manner as described in Example 493.
MS m/e (ESI) 414 (MNa$^+$)

Example 518

2-Isopropoxy-3-[4-(quinolin-3-ylmethoxycarbonylamino)-phenyl]propanoic acid

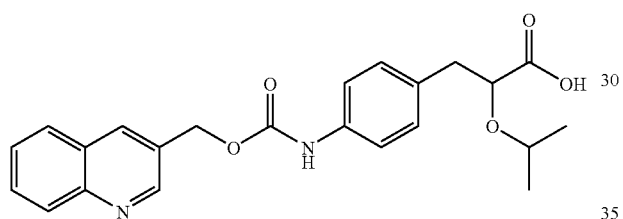

Using quinolin-3-yl methanol, the title compound was obtained in the same manner as described in Example 493.
MS m/e (ESI) 409 (MH$^+$)

Example 519

3-[4-(2-Chloroquinolin-3-ylmethoxycarbonylamino)phenyl]-2-isopropoxypropanoic acid

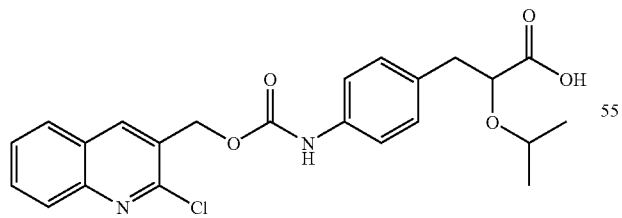

Using 2-chloroquinolin-3-yl methanol, the title compound was obtained in the same manner as described in Example 493.
MS m/e (ESI) 443 (MH$^+$)

Example 520

3-[4-(2-Chloro-4-propoxybenzyloxycarbonylamino)phenyl]-2-isopropoxypropanoic acid

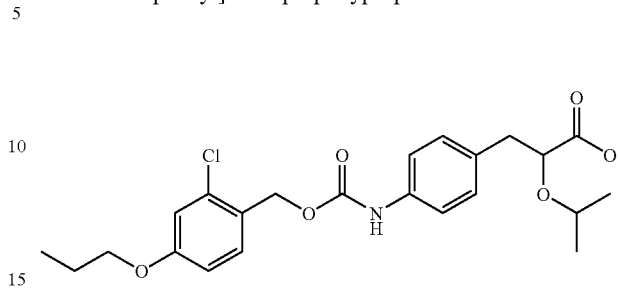

Using 2-chloro-4-propoxybenzyl alcohol, the title compound was obtained in the same manner as described in Example 493.
MS m/e (ESI) 472 (MNa$^+$)

Example 521

3-[4-(2-Fluoro-4-trifluoromethylbenzyloxycarbonylamino)-phenyl]-2-isopropoxypropanoic acid

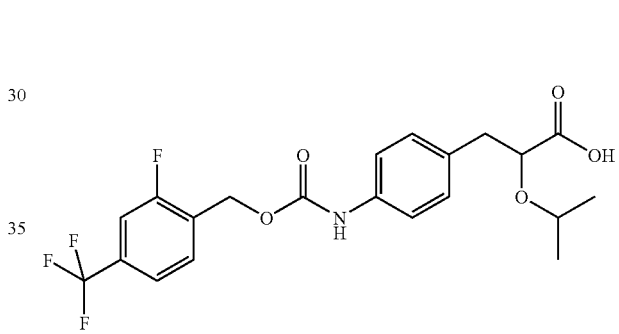

Using 2-fluoro-4-trifluoromethylbenzyl alcohol, the title compound was obtained in the same manner as described in Example 493.
MS m/e (ESI) 466 (MNa$^+$)

Example 522

3-[4-(2-Fluoro-4-chlorobenzyloxycarbonylamino)phenyl]-2-isopropoxypropanoic acid

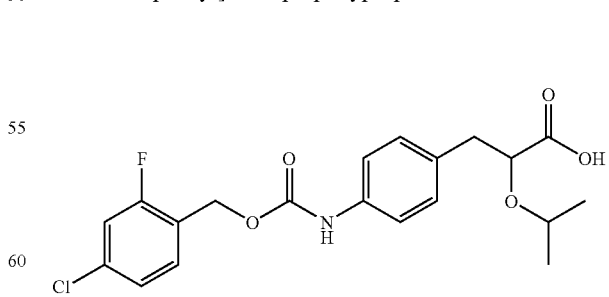

Using 4-chloro-2-methoxybenzyl alcohol, the title compound was obtained in the same manner as described in Example 493.
MS m/e (ESI) 432 (MNa$^+$)

Example 523

3-[4-(3-Bromo-4-methoxybenzyloxycarbonylamino)phenyl]-2-isopropoxypropanoic acid

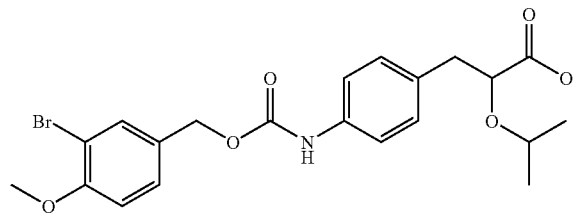

Using 3-bromo-4-methoxybenzyl alcohol, the title compound was obtained in the same manner as described in Example 493.

MS m/e (ESI) 488 (MNa$^+$)

Example 524

2-Isopropoxy-3-[4-(4-methoxy-3-methylbenzyloxycarbonylamino)phenyl]propanoic acid

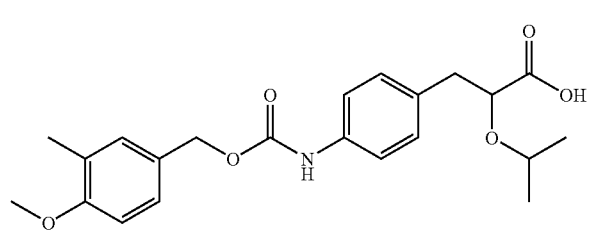

Using 4-methoxy-3-methylbenzyl alcohol, the title compound was obtained in the same manner as described in Example 493.

MS m/e (ESI) 424 (MNa$^+$)

Example 525

3-[4-(2,3-Dihydrobenzofuran-5-ylmethoxycarbonylamino)phenyl]-2-isopropoxypropanoic acid

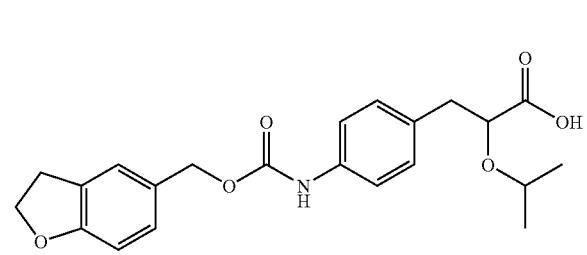

Using (2,3-dihydrobenzofuran-5-yl)methanol, the title compound was obtained in the same manner as described in Example 493.

MS m/e (ESI) 422 (MNa$^+$)

Example 526

3-[4-(Benzo[1,3]dioxol-5-ylmethoxycarbonylamino)phenyl]-2-isopropoxypropanoic acid

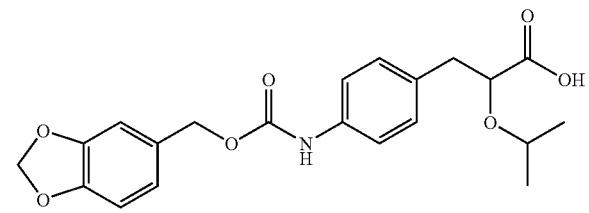

Using benzo[1,3]dioxol-5-yl methanol, the title compound was obtained in the same manner as described in Example 493.

MS m/e (ESI) 424 (MNa$^+$)

Example 527

3-[4-(4-Ethoxybenzyloxycarbonylamino)phenyl]-2-isopropoxypropanoic acid

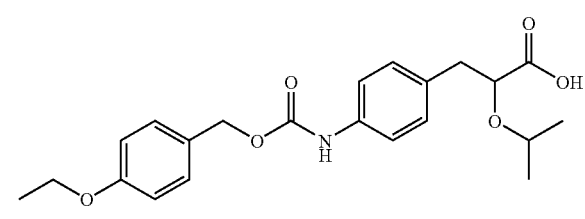

Using 4-ethoxybenzyl alcohol, the title compound was obtained in the same manner as described in Example 493.

MS m/e (ESI) 424 (MNa$^+$)

Example 528 a) Ethyl 3-(4-amino-3-methoxyphenyl)-2-isopropoxypropionate

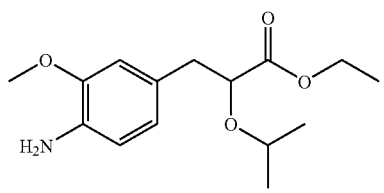

The title compound was obtained in the same manner as described in Examples 423a) and 423b).

$^1$H-NMR (CDCl$_3$)

δ: 0.98 (d, J=6.0 Hz, 3H) 1.14 (d, J=6.0 Hz, 3H) 1.25 (t, J=6.0 Hz, 3H) 2.86 (m, 2H) 3.48 (dq, J=6.0, 6.0 Hz, 1H) 3.82 (s, 3H) 3.98 (dd, J=7.6, 4.4 Hz, 1H) 4.16 (q, J=6.0 Hz, 2H) 6.65 (m, 2H) 6.71 (bs, 1H)

b) 3-[4-(3,4-Dichlorobenzyloxycarbonylamino)-3-methoxyphenyl]-2-isopropoxypropanoic acid

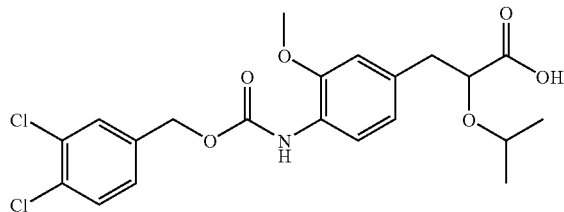

Using 3,4-dichlorobenzyl alcohol, the title compound was obtained in the same manner as described in Example 493.

MS m/e (ESI) 456 (MH$^+$)

Example 529

2-Isopropoxy-3-[3-methoxy-4-(4-trifluoromethylbenzyloxycarbonylamino)phenyl]propanoic acid

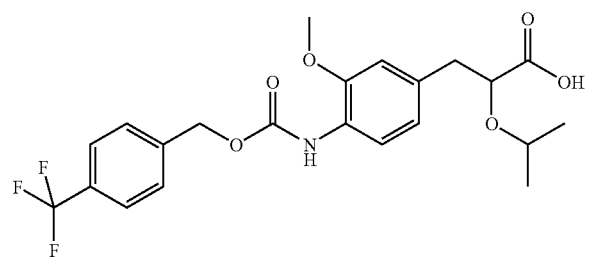

Using 4-trifluoromethylbenzyl alcohol, the title compound was obtained in the same manner as described in Example 493.

MS m/e (ESI) 456 (MH$^+$)

Example 530

3-[4-(2-Fluoro-4-trifluoromethylbenzyloxycarbonylamino)-3-methoxyphenyl]-2-isopropoxypropanoic acid

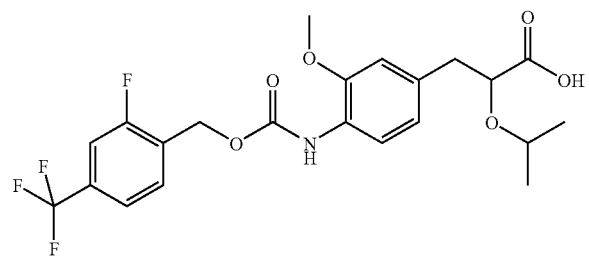

Using 2-fluoro-4-trifluoromethylbenzyl alcohol, the title compound was obtained in the same manner as described in Example 493.

MS m/e (ESI) 496 (MNa$^+$)

Example 531

3-[4-(4-Chlorobenzyloxycarbonylamino)-3-methoxyphenyl]-2-isopropoxypropanoic acid

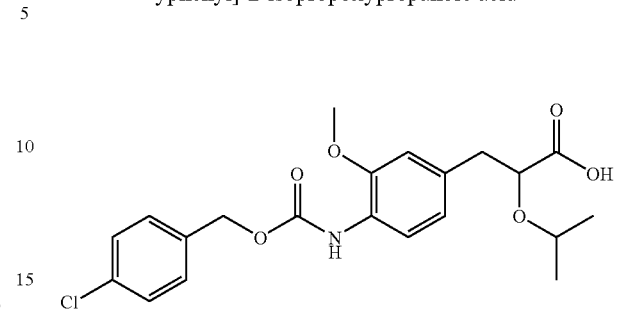

Using 4-chlorobenzyl alcohol, the title compound was obtained in the same manner as described in Example 493.

MS m/e (ESI) 462 (MNa$^+$)

Example 532.3-[4-(3-Bromo-4-methoxybenzyloxycarbonylamino)-3-methoxyphenyl]-2-isopropoxypropanoic acid

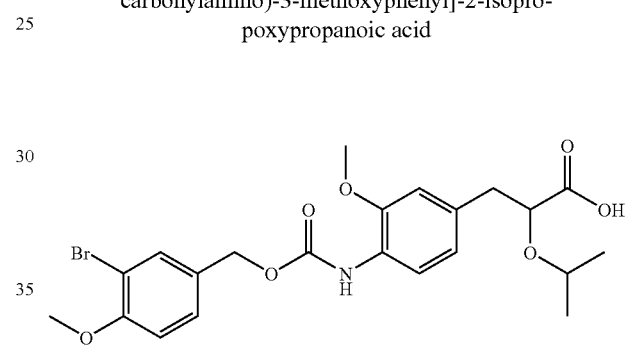

Using 3-bromo-4-methoxybenzyl alcohol, the title compound was obtained in the same manner as described in Example 493.

MS m/e (ESI) 518 (MNa$^+$)

Example 533

2-Isopropoxy-3-[3-methoxy-4-(4-methoxy-3-methylbenzyloxycarbonylamino)phenyl]propanoic acid

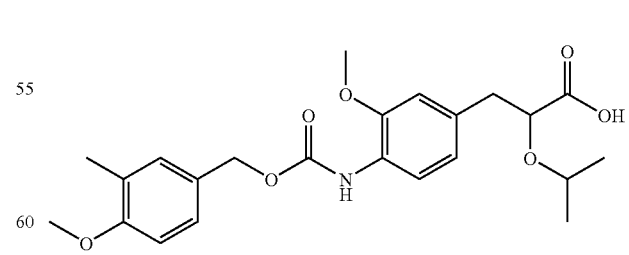

Using 4-methoxy-3-methylbenzylalcohol, the title compound was obtained in the same manner as described in Example 493.

MS m/e (ESI) 5 454 (MNa$^+$)

Example 534

3-[4-(2,3-Dihydrobenzofuran-5-ylmethoxycarbonylamino)-3-methoxyphenyl]-2-isopropoxypropanoic acid

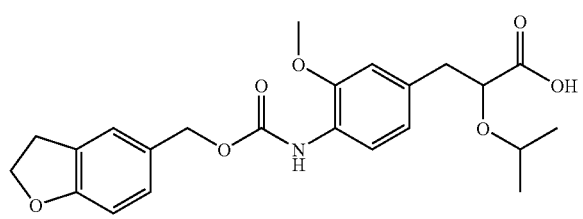

Using (2,3-dihydrobenzofuran-5-yl)methanol, the title compound was obtained in the same manner as described in Example 493.

MS m/e (ESI) δ 452 (MNa$^+$)

Example 535

3-[4-(Benzo[1,3]-dioxol-5-ylmethoxycarbonylamino)-3-methoxyphenyl]-2-isopropoxypropanoic acid

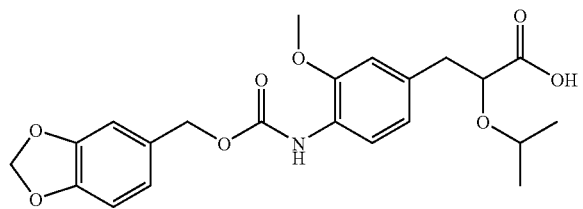

Using benzo[1,3]dioxol-5-yl methanol, the title compound was obtained in the same manner as described in Example 493.

MS m/e (ESI) 5 454 (MNa$^+$)

Example 536

3-[4-(4-Ethoxybenzyloxycarbonylamino)-3-methoxyphenyl]-2-isopropoxypropanoic acid

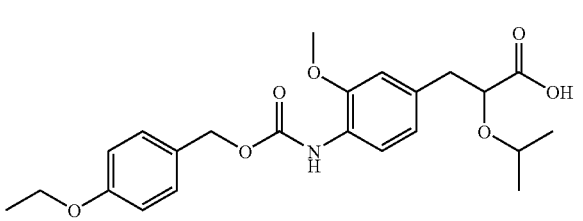

Using 4-ethoxybenzyl alcohol, the title compound was obtained in the same manner as described in Example 493.

MS m/e (ESI) 5 454 (MNa$^+$)

Example 537

3-[4-(2,4-Dichlorobenzyloxycarbonylamino)phenyl]-2-isopropoxypropanoic acid

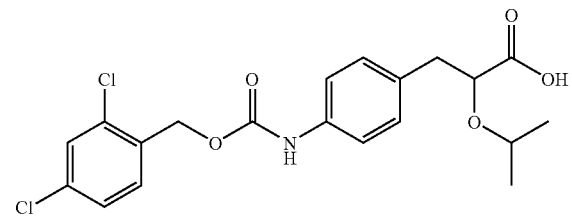

Using 2,4-dichlorobenzyl alcohol, the title compound was obtained in the same manner as described in Example 493.

MS m/e (ESI) δ 426 (MH$^+$)

Example 538 a) 2-Bromo-4-dimethoxymethyl-1-fluorobenzene

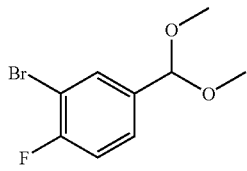

5 g of 3-Bromo-4-fluorobenzaldehyde was dissolved in 40 ml of methanol, and 7.8 g trimethyl o-formate and 0.42 g of p-toluene sulfonic acid were added thereto, and the mixture was stirred at room temperature for 4 hours. The reaction solution was diluted with water and sodium hydrogencarbonate, and extracted with ethylacetate. The organic layer was washed with saturated brine, dried over anhydrous magnesium sulfate, and evaporated, to give 6.2 g of the title compound.

$^1$H-NMR (DMDO-d$_6$)

δ: 3.20 (s, 3H) 3.31 (s, 3H) 5.48 (s, 1H) 7.40 (m, 2H) 7.65 (m, 1H)

b) 5-Dimethoxymethyl-2-fluorobenzaldehyde

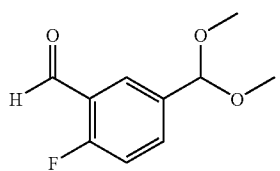

6.2 g of 2-Bromo-4-dimethoxymethyl-1-fluorobenzene was dissolved in 65 ml of tetrahydrofuran, and the solution was cooled to −60° C. under a nitrogen gas flow. 18 ml of 1.6M n-Butyl lithium in hexane was added dropwise and the mixture was stirred at −60° C. for 1 hour. 3.3 ml of N-Formylmorpholine was added thereto, and the reaction mixture was allowed to warm to room temperature. The mixture was stirred for 1 hour, then ice-cooled, and treated with water and ammonium chloride solution, then extracted with ethylacetate. The organic layer was washed with saturated brine, dried over anhydrous magnesium sulfate, and evaporated. The residue was subjected to silica gel column chromatography, to give 2.8 g of the title compound (8% ethyl acetate-hexane).

$^1$H-NMR (DMDO-d$_6$)

δ: 3.24 (s, 3H) 3.32 (s, 3H) 5.45 (s, 1H) 7.41 (t, J=10.0 Hz, 1H) 7.71 (t, J=8.0 Hz, 1H) 7.82 (d, J=8.0 Hz, 1H) 10.20 (s, 1H)

c) 4-Fluoro-3-hydroxymethylbenzaldehyde

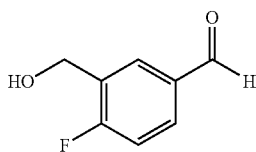

2.8 g of 5-Dimethoxymethyl-2-fluorobenzaldehyde was dissolved in 40 ml of diethyl ether, and 0.38 g of lithium aluminum hydride was added under ice-cooling. After being stirred at room temperature for 5 minutes, the reaction solution was ice-cooled and diethylether-water was added. When the insoluble precipitate adhered to the wall of the flask, the reaction solution was dried over anhydrous magnesium sulfate, then evaporated. The residue was dissolved in 25 ml of dichloromethane, and 8 ml of trifluoroacetic acid was added. The reaction mixture was stirred at room temperature for 2.5 hours, the reaction solution was diluted with water and the mixture was extracted with ethyl acetate. The organic layer was washed with saturated brine, dried over anhydrous magnesium sulfate, and then evaporated. The residue was subjected to silica gel column chromatography (30% ethyl acetate-hexane), to give 1.6 g of the title compound.

$^1$H-NMR (CDCl$_3$)

δ: 4.85 (s, 2H) 7.20 (t, J=10.0 Hz, 1H) 7.85 (t, J=8.0 Hz, 1H) 8.04 (d, J=8.0 Hz, 1H) 9.98 (s, 1H)

d) 3-(t-Butyldimethylsilanyloxymethyl)-4-fluorobenzaldehyde

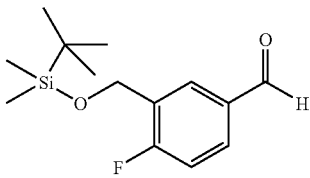

1.6 g of 4-Fluoro-3-hydroxymethylbenzaldehyde was dissolved in 20 ml of dichloromethane, and 1.4 g of imidazole and 1.75 g of t-butyldimethylchlorosilane were added under ice-cooling, then the mixture was stirred at room temperature for 16 hours. The reaction solution was diluted with water and the reaction mixture was extracted with ethyl acetate. The organic layer was washed with saturated brine, dried over anhydrous magnesium sulfate, and evaporated. The residue was subjected to silica gel column chromatography (18% ethyl acetate-hexane), to give 2.6 g of the title compound.

$^1$H-NMR (CDCl$_3$)

δ: 0.00 (s, 6H) 0.82 (s, 9H) 4.70 (s, 2H) 7.01 (t, J=10.0 Hz, 1H) 7.64 (t, J=8.0 Hz, 1H) 7.92 (d, J=8.0 Hz, 1H) 9.82 (s, 1H)

e) Ethyl 3-[3-(t-butyldimethylsilanyloxymethyl)-4-fluorophenyl]-2-isopropoxypropionate

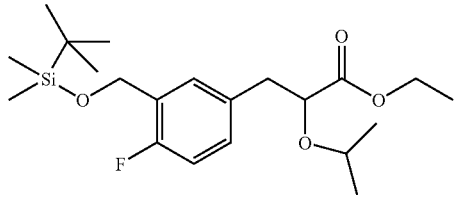

1.36 g of Ethyl 2-(diethylphosphoryl)-2-isopropylacetate was dissolved in 15 ml of tetrahydrofuran, and 0.19 g of 60% sodium hydride was added under ice-cooling, and the mixture was stirred for 20 minutes under ice-cooling. The reaction solution was treated with 1 g of 3-(t-butyldimethylsilanyloxymethyl)-4-fluorobenzaldehyde dissolved in 5 ml of tetrahydrofuran, and was stirred at room temperature for 16 hours. The reaction solution was treated with water and extracted with ethylacetate. The organic layer was washed with saturated brine, dried over anhydrous magnesium sulfate, and evaporated. The residue was subjected to silica gel column chromatography, and the fraction eluting with 14% ethyl acetate-hexane was concentrated. The residue was dissolved in 10 ml of ethanol and 10 ml of ethyl acetate, and 0.4 g of 10% palladium-barium sulfate was added, and the atmosphere was replaced with hydrogen, and the mixture was stirred at room temperature for 5 hours. Thereafter, the atmosphere was replaced with nitrogen and the catalyst was filtered off. The solvent was evaporated, and the residue was subjected to silica gel column chromatography (20% ethyl acetate-hexane), to give 1.2 g of the title compound.

$^1$H-NMR (CDCl$_3$)

δ: 0.00 (s, 6H) 0.82 (m, 12H) 1.04 (d, J=6.0 Hz, 3H) 1.13 (t, J=6.0 Hz, 1H) 2.84 (m, 2H) 3.49 (dq, J=6.0, 6.0 Hz, 1H) 3.91 (dd, J=7.6, 4.4 Hz, 1H) 4.06 (q, J=6.0 Hz, 2H) 4.65 (s, 2H) 6.80 (t, J=10.0 Hz, 1H) 6.98 (m, 1H) 7.28 (d, J=8.0 Hz, 1H)

f) Ethyl 3-(4-fluoro-3-hydroxymethylphenyl)-2-isopropoxypropionate

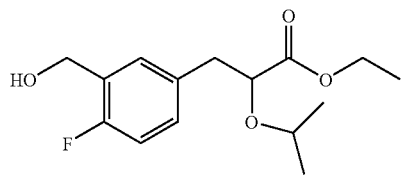

1.2 g of Ethyl 3-[3-(t-butyldimethylsilanyloxymethyl)-4-fluorophenyl]-2-isopropoxypropionate was dissolved in 15 ml of tetrahydrofuran, and 3.3 ml of 1.0M tetrabutyl ammonium fluoride in tetrahydrofuran was added. The mixture was stirred at room temperature for 2 hours. The reaction solution was diluted with water and extracted with ethyl acetate. The organic layer was washed with saturated brine, dried over anhydrous magnesium sulfate, and evaporated. The residue was subjected to silica gel column chromatography (30% ethyl acetate-hexane), to give 1.0 g of the title compound.

$^1$H-NMR (CDCl$_3$)

δ: 0.95 (d, J=6.0 Hz, 12H) 1.15 (d, J=6.0 Hz, 3H) 1.25 (t, J=6.0 Hz, 1H) 2.94 (m, 2H) 3.49 (dq, J=6.0, 6.0 Hz, 1H) 4.02 (dd, J=7.6, 4.4 Hz, 1H) 4.15 (q, J=6.0 Hz, 2H) 4.72 (s, 2H) 6.95 (t, J=10.0 Hz, 1H) 7.06 (m, 1H) 7.28 (d, J=8.0 Hz, 1H)

g) 3-(4-Fluoro-3-phenylcarbamoyloxymethylphenyl)-2-isopropoxypropanoic acid

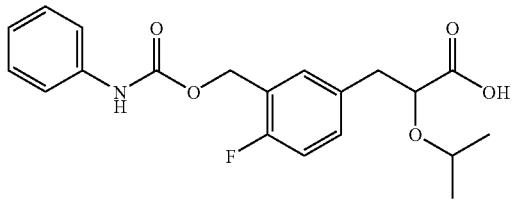

20 mg of Ethyl 3-(4-fluoro-3-hydroxymethylphenyl)-2-isopropoxypropionate and 15 mg of phenylisocyanate were dissolved in 0.6 ml of tetrahydrofuran, and 5 μl of pyridine was added thereto. The mixture was stirred at room temperature for 16 hours. The solvent was removed under a stream of nitrogen, and the residue was dissolved in 0.6 ml of ethanol, then 0.12 ml of 5N sodium hydroxide was added, and the mixture was stirred at room temperature for 1 hour. The reaction solution was diluted with 1 ml of water and 0.14 ml of 5N hydrochloric acid, and extracted with ethylacetate. The organic layer was collected, and the solvent was removed under a stream of nitrogen. The residue was purified by HPLC using a reverse phase system column and a water-acetonitrile-trifluoroacetic acid eluent, to give 3.1 mg of the title compound.

MS m/e (ESI) 398 (MNa⁺)

Example 539

3-[4-Fluoro-3-(4-methoxyphenylcarbamoyloxymethyl)phenyl]-2-isopropoxypropanoic acid

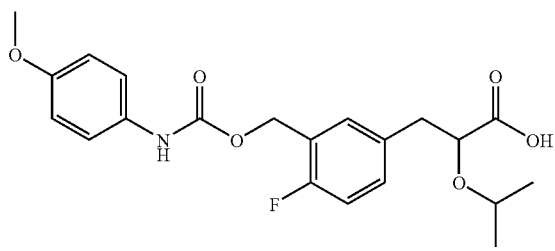

Using 4-methoxyphenylisocyanate, the title compound was obtained in the same manner as described in Example 538g).

MS m/e (ESI) 428 (MNa⁺)

Example 540

3-[3-(4-Chlorophenylcarbamoyloxymethyl)-4-fluorophenyl]-2-isopropoxypropanoic acid

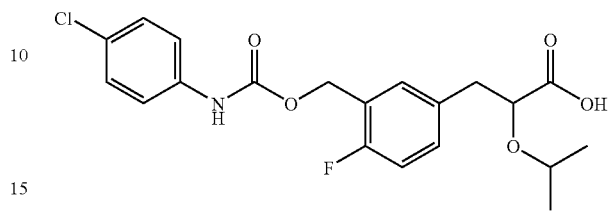

Using 4-chlorophenylisocyanate, the title compound was obtained in the same manner as described in Example 538g).

MS m/e (ESI) 432 (MNa⁺)

Example 541

3-[3-(3-Chlorophenylcarbamoyloxymethyl)-4-fluorophenyl]-2-isopropoxypropanoic acid

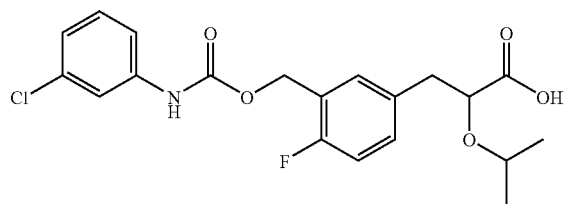

Using 3-chlorophenylisocyanate, the title compound was obtained in the same manner as described in Example 538g).

MS m/e (ESI) 432 (MNa⁺)

Example 542

3-[3-(2,4-Dichlorophenylcarbomoyloxymethyl)-4-fluorophenyl]-2-isopropoxypropanoic acid

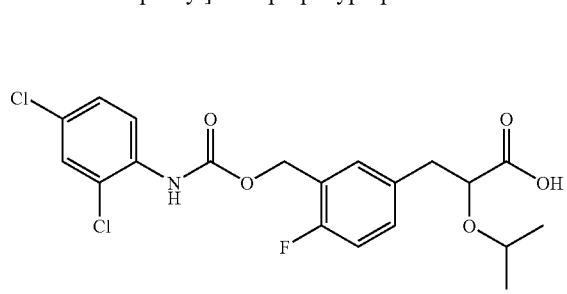

Using 2,4-dichlorophenylisocyanate, the title compound was obtained in the same manner as described in Example 538g).

MS m/e (ESI) 466 (MNa⁺)

Example 543

3-[4-Fluoro-3-(4-trifluoromethylphenylcarbam-oyloxymethyl)-phenyl]-2-isopropoxypropanoic acid

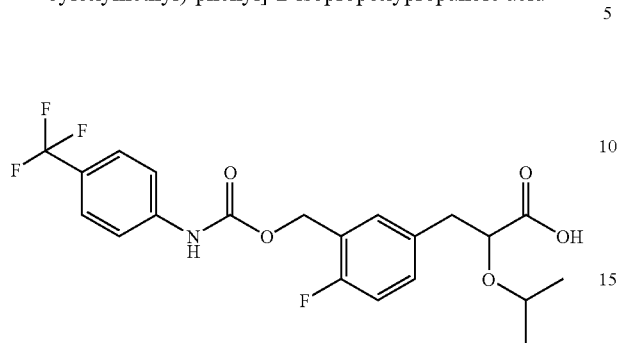

Using 4-trifluoromethylphenylisocyanate, the title compound was obtained in the same manner as described in Example 538g).

MS m/e (ESI) 466 (MNa+)

Example 544 a) 1-Methoxymethyl-1H-indol-3-aldehyde

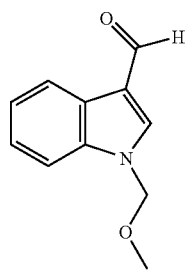

5 g of Indol-3-aldehyde was dissolved in 40 ml of N,N-dimethylformamide, and 1.38 g of 60% sodium hydride was added under ice-cooling. The reaction solution was stirred for 20 minutes with ice-cooling, then 3.2 ml of chloromethyl methyl ether was added, and stirring was continued at room temperature for 16 hours. The reaction solution was cooled in ice, treated with water and ammonium chloride solution, and extracted with ethyl acetate. The organic layer was washed with saturated brine, dried over anhydrous magnesium sulfate, and evaporated. The residue was subjected to silica gel column chromatography, to give 6.1 g of the title compound (20-44% ethyl acetate-hexane)

$^1$H-NMR (CDCl$_3$)

δ: 3.30 (s, 3H) 5.51 (s, 2H) 7.36 (m, 2H) 7.53 (d, J=8.0 Hz, 1H) 7.80 (s, 1H) 8.31 (d, J=8.0 Hz, 1H) 10.10 (s, 1H)

b) Ethyl 2-isopropoxy-3-(1-methoxymethyl-1H-indol-3-yl)propionate

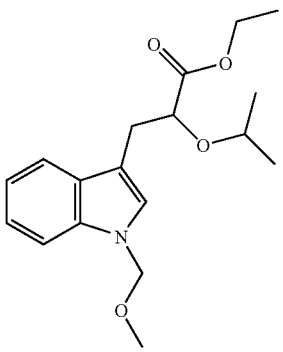

3.9 g of Ethyl 2-(diethylphosphoryl)-2-isopropylacetate was dissolved in 35 ml of tetrahydrofuran, and 0.51 g of 60% sodium hydride was added under ice-cooling, and the mixture was stirred for 20 minutes under ice-cooling. The reaction solution was treated with a solution of 2 g of 1-methoxymethyl-1H-indol-3-aldehyde in 10 ml of tetrahydrofuran, and then stirred at room temperature for 16 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography, and the fraction eluting with 22% ethyl acetate-hexane was evaporated, and the residue was dissolved in 30 ml of ethanol. To this solution was added 0.5 g of 10% palladium carbon, the atmosphere was replaced with hydrogen, and the mixture was stirred at room temperature for 3 days. The atmosphere was replaced with nitrogen, the catalyst was filtered off, and the solvent was evaporated, to give 2.3 g of the title compound.

$^1$H-NMR (CDCl$_3$)

δ: 1.00 (d, J=6.0 Hz, 3H) 1.20 (m, 6H) 3.10 (dd, J=14.0, 6.0 Hz, 1H) 3.20 (m, 4H) 3.55 (dq, J=6.0, 6.0 Hz, 1H) 4.15 (m, 3H) 5.40 (dd, J=6.0, 10.0 Hz, 2H) 7.18 (s, 1H) 7.15 (t, J=8.0 Hz, 1H) 7.20 (d, J=8.0 Hz, 1H) 7.44 (d, J=8.0 Hz, 1H) 7.63 (dd, J=2.0, 8.0 Hz, 1H)

c) Ethyl 3-(1H-indol-3-yl)-2-isopropoxypropionate

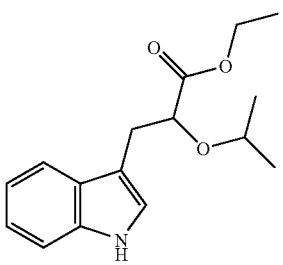

2.3 g of Ethyl 2-isopropoxy-3-(1-methoxymethyl-1H-indol-3-yl)propionate was dissolved in 25 ml of acetone, and 15 ml of 5N hydrochloric acid was added, and the mixture was stirred for 2 hours. The reaction solution was cooled with ice, treated with water and sodium hydrogencarbonate, and extracted with ethyl acetate. The organic layer was washed d) Ethyl 3-(1-carboxymethyl-1H-indol-3-yl)-2-isopropoxypropionate

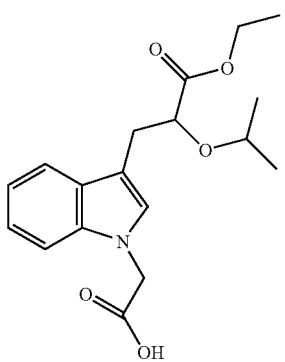

0.75 g of Ethyl 3-(1H-indol-3-yl)-2-isopropoxypropionate was dissolved in 10 ml of N,N-dimethylformamide, and 0.12 g of 60% sodium hydride was added under ice-cooling. The reaction mixture was stirred at room temperature for 30 minutes, 0.53 ml of t-butyl bromoacetate was added, and stirring was continued at room temperature for 16 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography, and the fraction eluted with 10% ethyl acetate-hexane was evaporated, and the residue was dissolved in 15 ml of dichloromethane. 3 ml of Trifluoroacetic acid was added under ice-cooling, and the mixture was stirred at 0° C. for 7 hours. The reaction solution was diluted with toluene, and the solvent was evaporated. The residue was subjected to silica gel column chromatography (33% ethyl acetate-hexane), to give 0.3 g of the title compound.

$^1$H-NMR (CDCl$_3$)

δ: 1.00 (d, J=6.0 Hz, 3H) 1.18 (m, 6H) 3.10 (dd, J=14.0, 6.0 Hz, 1H) 3.20 (dd, J=14.0, 4.4 Hz, 1H) 3.54 (dq, J=6.0, 6.0 Hz, 1H) 4.13 (m, 3H) 4.83 (s, 2H) 6.97 (s, 1H) 7.05-7.20 (m, 3H) 7.65 (d, J=8.0 Hz, 1H)

e) Ethyl 3-[1-(2-hydroxyethyl)-1H-indol-3-yl]-2-isopropoxypropionate

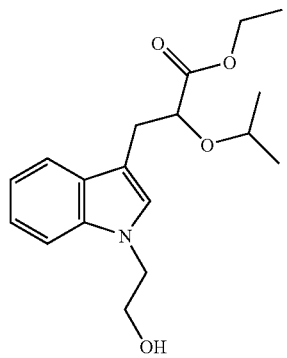

0.3 g of Ethyl 3-(1-carboxymethyl-1H-indol-3-yl)-2-isopropoxypropionate was dissolved in 10 ml of tetrahydrofuran, and 0.2 ml of triethylamine was added under ice-cooling, followed by 0.1 ml of ethyl chloroformate, then the mixture was stirred at 0° C. for 15 minutes. After filtering off the precipitated insoluble substances, the reaction solution was again cooled with ice, and 60 mg of sodium borohydride and water were added, and stirring was continued at room temperature for 1 hour. The reaction solution was cooled with ice, acidified with diluted hydrochloric acid, and extracted with ethyl acetate. The organic layer was washed with saturated brine, dried over anhydrous magnesium sulfate, and evaporated. The residue was subjected to silica gel column chromatography (33% ethyl acetate-hexane), to give 143 mg of the title compound.

$^1$H-NMR (CDCl$_3$)

δ: 0.98 (d, J=6.0 Hz, 3H) 1.15 (m, 6H) 3.00-3.15 (m, 2H) 3.50 (dq, J=6.0, 6.0 Hz, 1H) 3.85 (t, J=6.0 Hz, 2H) 4.06 (m, 3H) 4.17 (t, J=6.0 Hz, 2H) 7.00 (s, 1H) 7.05 (d, J=8.0 Hz, 1H) 7.13 (t, J=8.0 Hz, 1H) 7.28 (d, J=8.0 Hz, 1H) 7.57 (d, J=8.0 Hz, 1H)

f) 3-{1-[2-(4-Chlorophenylcarbamoyloxy)ethyl]-1H-indol-3-yl}-2-isopropoxypropanoic acid

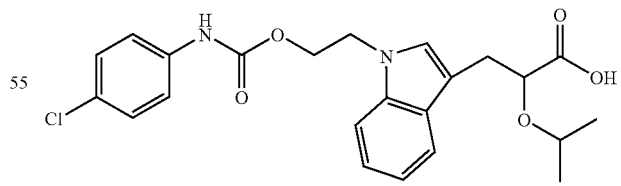

Using 4-chlorophenylisocyanate, the title compound was obtained in the same manner as described in Example 536g).

MS m/e (ESI) 445 (MH$^+$)

Example 545

3-{1-[2-(3-Chlorophenylcarbamoyloxy)ethyl]-1H-indol-3-yl}-2-isopropoxypropanoic acid

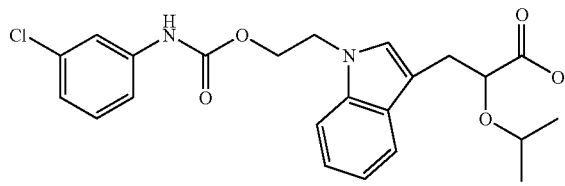

Using 3-chlorophenylisocyanate, the title compound was obtained in the same manner as described in Example 538g).
MS m/e (ESI) 445 (MH$^+$)

Example 546

2-Isopropoxy-3-{1-[2-(4-methoxyphenylcarbamoyloxy)ethyl]-1H-indol-3-yl}propanoic acid

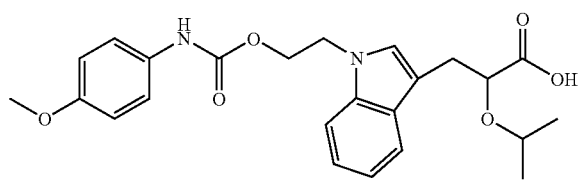

Using 4-methoxyphenylisocyanate, the title compound was obtained in the same manner as described in Example 538g).
MS m/e (ESI) 441 (MH$^+$)

Example 547

2-Isopropoxy-3-{1-[2-(4-trifluoromethylphenylcarbamoyloxy)-ethyl]-1H-indol-3-yl}propanoic acid

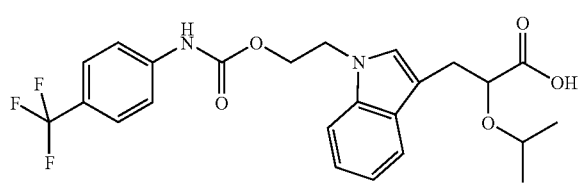

Using 4-trifluoromethylphenylisocyanate, the title compound was obtained in the same manner as described in Example 538g).
MS m/e (ESI) 479 (MH$^+$)

Example 548

2-Isopropoxy-3-{1-[2-(3-trifluoromethylphenylcarbamoyloxy)-ethyl]-1H-indol-3-yl}propanoic acid

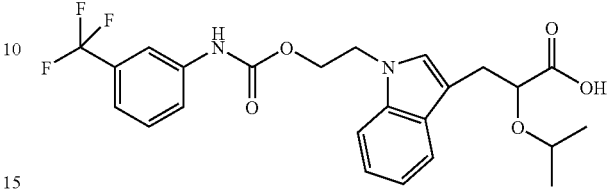

Using 3-trifluoromethylphenylisocyanate, the title compound was obtained in the same manner as described in Example 538g).
MS m/e (ESI) 479 (MH$^+$)

Example 549 a) Methyl 1-(2-benzyloxyethyl)-1H-indol-4-carboxylate

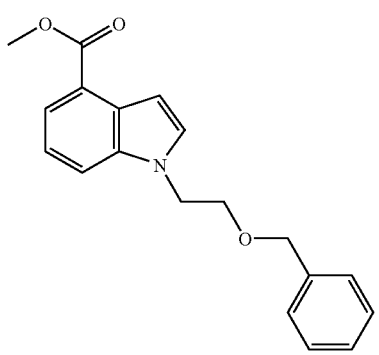

2.75 g of Methyl 1H-indol-4-carboxylate was dissolved in 10 ml of N,N-dimethylformamide, and 0.7 g of 60% sodium hydride was added under ice-cooling. The reaction solution was stirred at room temperature for 30 minutes, treated with 2.5 ml of benzyl 2-bromoethyl ether, and stirred at room temperature for a further 2 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography (8% ethyl acetate-hexane), to give 3.6 g of the title compound.
$^1$H-NMR (CDCl$_3$)

δ: 3.78 (t, J=6.0 Hz, 2H) 3.99 (s, 3H) 4.37 (t, J=6.0 Hz, 2H) 4.43 (s, 2H) 7.12-7.27 (m, 7H) 7.32 (s, 1H) 7.55 (d, J=8.0 Hz, 1H) 7.91 (d, J=8.0 Hz, 1H)

b) 1-(2-Benzyloxyethyl)-1H-indol-4-aldehyde

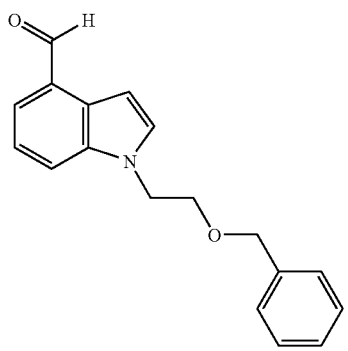

3.6 g of Methyl 1-(2-benzyloxyethyl)-1H-indol-4-carboxylate was dissolved in 40 ml of diethyl ether, and 0.44 g of lithium aluminum hydride was added under ice-cooling. After stirring at room temperature for 10 minutes, the reaction solution was cooled with ice, and diethyl ether and water were added. When the insoluble substances adhered to and solidified on the wall of the flask, the reaction solution was dried over anhydrous magnesium sulfate, then the solvent was evaporated. The residue was dissolved in 40 ml of dichloromethane, 20 g of manganese dioxide was added, and the mixture was stirred at room temperature for 2 hours. After filtering off the manganese dioxide through Celite, and washing through with ethyl acetate, the solvent was evaporated, to give 1.5 g of the title compound.
$^1$H-NMR (CDCl$_3$)
δ: 3.80 (t, J=6.0 Hz, 2H) 4.37 (t, J=6.0 Hz, 2H) 443 (s, 2H) 7.16 (m, 2H) 7.20-7.27 (m, 5H) 7.38 (s, 1H) 7.63 (m, 2H) 10.25 (s, 1H)

c) Ethyl 3-[1-(2-hydroxyethyl)-1H-indol-4-yl]-2-isopropoxypropionate

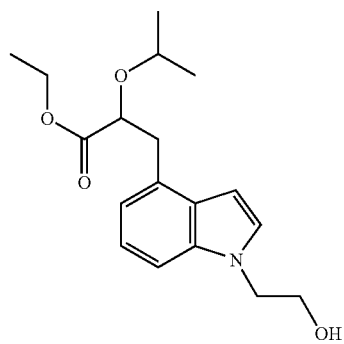

1.3 g of Ethyl 2-(diethylphosphoryl)-2-isopropylacetate was dissolved in 15 ml of tetrahydrofuran, and 0.18 g of 60% sodium hydride was added under ice-cooling, and the mixture was stirred for 20 minutes under ice-cooling. The reaction solution was treated with a solution of 1 g of 1-(2-benzyloxyethyl)-1H-indol-4-aldehyde in 5 ml of tetrahydrofuran, and stirred at room temperature for 16 hours. The reaction solution was cooled with ice, treated with water and ammonium chloride solution, and extracted with ethylacetate. The organic layer was washed with saturated brine, dried over anhydrous magnesium sulfate, and evaporated. The residue was subjected to silica gel column chromatography, and the fraction eluted with 20% ethyl acetate-hexane was evaporated and the residue was dissolved in 10 ml of ethanol and 10 ml of acetic acid. The solution was treated with 0.5 g of 10% palladium carbon, the atmosphere was replaced with hydrogen, and the mixture was stirred at room temperature for 24 hours. The atmosphere was replaced with nitrogen, the catalyst filtered off, and the solvent was evaporated, to give 0.2 g of the title compound.
$^1$H-NMR (CDCl$_3$)
δ: 0.92 (d, J=6.0 Hz, 6H) 1.13 (d, J=6.0 Hz, 3H) 1.17 (t, J=6.0 Hz, 1H) 3.23 (dd, J=14.0, 6.0 Hz, 1H) 3.32 (dd, J=14.0, 4.4 Hz, 1H) 3.47 (dq, J=6.0, 6.0 Hz, 1H) 3.96 (t, J=6.0 Hz, 2H) 4.14 (q, J=6.0 Hz, 2H) 4.22 (dd, J=7.6, 4.4 Hz, 1H) 4.29 (t, J=6.0 Hz, 2H) 6.60 (d, J=4.5 Hz, 1H) 7.00 (d, J=8.0 Hz, 1H) 7.10 (d, J=8.0 Hz, 1H) 7.15 (s, 1H) 7.25 (m, 1H)

d) 3-{1-[2-(4-Chlorophenylcarbamoyloxy)ethyl]-1H-indol-4-yl}-2-isopropoxypropanoic acid

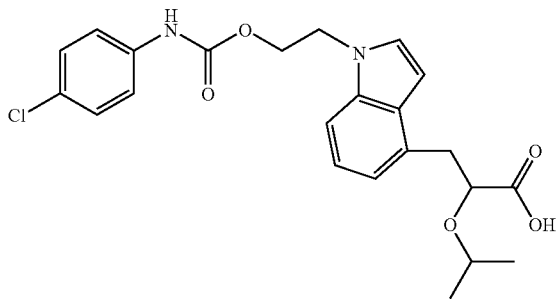

Using 4-chlorophenylisocyanate, the title compound was obtained in the same manner as described in Example 536g).
MS m/e (ESI) 445 (MH$^+$)

Example 550

3-{1-[2-(3-Chlorophenylcarbamoyloxy)ethyl]-1H-indol-4-yl}-2-isopropoxypropanoic acid

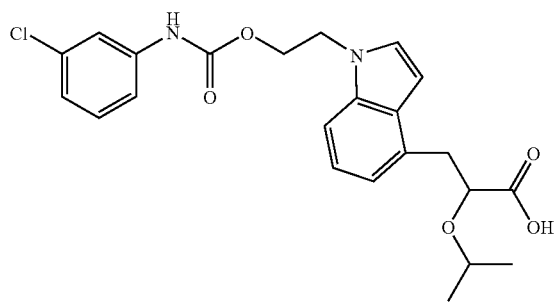

Using 3-chlorophenylisocyanate, the title compound was obtained in the same manner as described in Example 538g).
MS m/e (ESI) 445 (MH$^+$)

Example 551

2-Isopropoxy-3-{1-[2-(4-methoxyphenylcarbamoyloxy)ethyl]-1H-indol-4-yl}propanoic acid

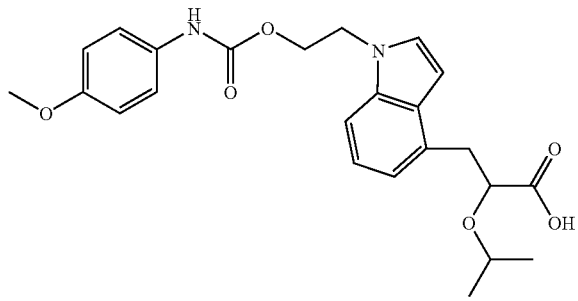

Using 4-methoxyphenylisocyanate, the title compound was obtained in the same manner as described in Example 538g).
MS m/e (ESI) 441 (MH$^+$)

Example 552

2-Isopropoxy-3-{1-[2-(3-trifluoromethylphenylcarbamoyloxy)-ethyl]-1H-indol-4-yl}propanoic acid

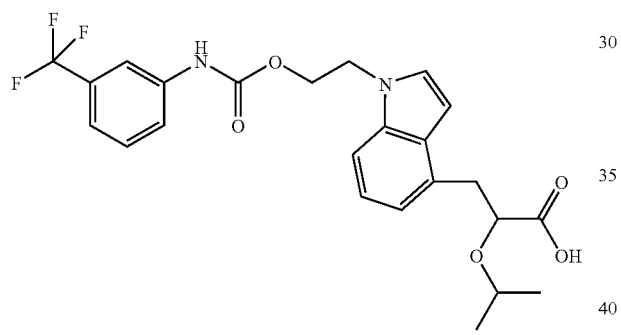

Using 3-trifluoromethylphenylisocyanate, the title compound was obtained in the same manner as described in Example 538g).
MS m/e (ESI) 479 (MH$^+$)

Example 553

3-{1-[2-(2,4-Dichlorophenylcarbamoyloxy)ethyl]-1H-indol-4-yl}-2-isopropoxypropanoic acid

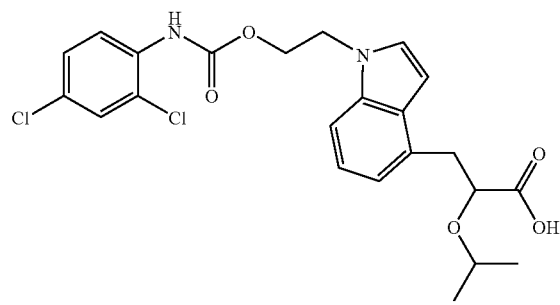

Using 2,4-dichlorophenylisocyanate, the title compound was obtained in the same manner as described in Example 538g).
MS m/e (ESI) 479 (MH$^+$)

Example 554

3-{1-[2-(2,4-Difluorophenylcarbamoyloxy)ethyl]-1H-indol-4-yl}-2-isopropoxypropanoic acid

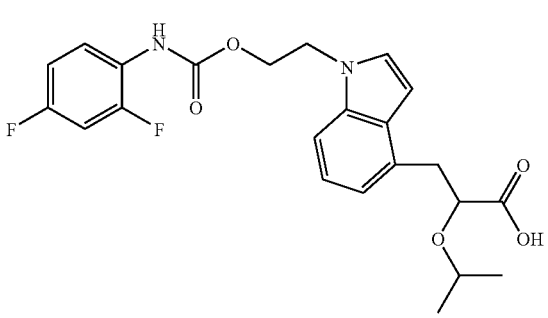

Using 2,4-difluorophenylisocyanate, the title compound was obtained in the same manner as described in Example 538g).
MS m/e (ESI) 447 (MH$^+$)

Example 555 a) Ethyl 3-(4-hydroxyphenyl)-2-isopropoxypropanoate

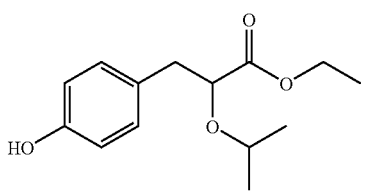

5.2 g of Ethyl 2-(diethylphosphoryl)-2-isopropylacetate was dissolved in 40 ml of tetrahydrofuran, and 0.53 g of 60% sodium hydride was added under ice-cooling, and the mixture was stirred for 20 minutes under ice-cooling. The reaction solution was treated with a solution of 3.0 g of 4-benzyloxy-benzaldehyde in 15 ml of tetrahydrofuran and 10 ml of N,N-dimethylformamide, and stirred at room temperature for 16 hours. The reaction solution was diluted with water, and extracted with ethyl acetate. The organic layer was washed with saturated brine, dried over anhydrous magnesium sulfate, and evaporated. The residue was subjected to silica gel column chromatography, and the fraction eluting with 5% ethyl acetate-hexane was concentrated. The residue was dissolved in 40 ml of ethanol, and 0.4g of 10% palladium carbon was added, the atmosphere was replaced with hydrogen, and the mixture was stirred at room temperature for 5 hours. Then, the atmosphere was replaced with nitrogen, the catalyst was filtered off, and the solvent was evaporated. The residue was subjected to silica gel column chromatography (20% ethyl acetate-hexane), to give 2.7 g of the title compound.
$^1$H NMR (CDCl$_3$)

δ: 0.98 (d, J=6.4 Hz, 6H) 1.16 (d, J=6.4 Hz, 3H) 1.24 (t, J=7.2 Hz, 3H) 2.85-2.95 (m, 2H) 3.52 (Sept, J=6.0 Hz, 1H) 4.05 (dd, J=4.8, 8.8 Hz, 1H) 4.12-4.19 (m, 2H) 4.86 (br, 1H) 6.73 (d, J=8.0 Hz, 2H) 7.10 (d, J=8.0 Hz, 2H)

b) Ethyl 2-isopropoxy-3-[4-(2-oxilanylmethoxy)phenyl]-propanoate

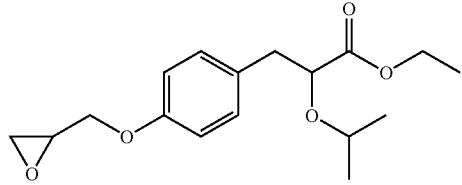

Using ethyl 3-(4-hydroxyphenyl)-2-isopropoxypropanoate, the title compound was obtained in the same manner as described in Production example 1b).

$^1$H NMR (CDCl$_3$)

δ: 0.96 (d, J=6.4 Hz, 3H) 1.15 (d, J=6.4 Hz, 3H) 1.24 (t, J=7.2 Hz, 3H) 2.75 (dd, J=2.8, 4.8 Hz, 1H) 2.83-2.93 (m, 3H) 3.34 (dt, J=2.8, 9.6 Hz, 1H) 3.50 (Sept, J=6.0 Hz, 1H) 3.94 (dd, J=5.6, 11.2 Hz, 1H) 4.00 (dd, J=4.8, 8.8 Hz, 1H) 4.15-4.22 (m, 2H) 6.82 (d, J=8.0 Hz, 2H) 7.15 (d, J=8.0 Hz, 2H)

c) 3-{4-[3-(2,4-Dichlorophenoxy)-2-hydroxypropoxy]phenyl}-2-isopropoxypropanoic acid

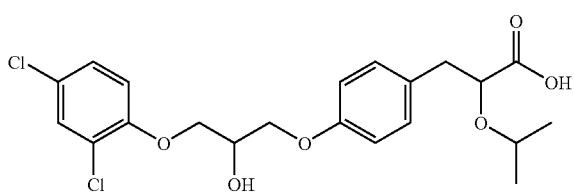

Using 2,4-dichlorophenol, the title compound was obtained in the same manner as described in Example 1c).

MS m/e (ESI) 443 (MH$^+$)

Example 556

3-{4-[3-(3,4-Dichlorophenoxy)-2-hydroxypropoxy]phenyl}-2-isopropoxypropanoic acid

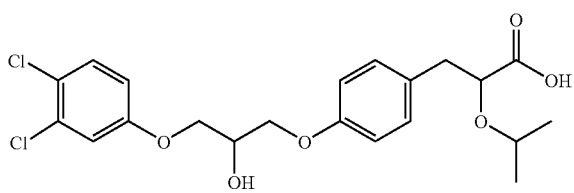

Using 3,4-dichlorophenol, the title compound was obtained in the same manner as described in Example 1c).

MS m/e (ESI) 465 (MNa$^+$)

Example 557

3-{4-[3-(4-Chloro-2-methylphenoxy)-2-hydroxypropoxy]phenyl}-2-isopropoxypropanoic acid

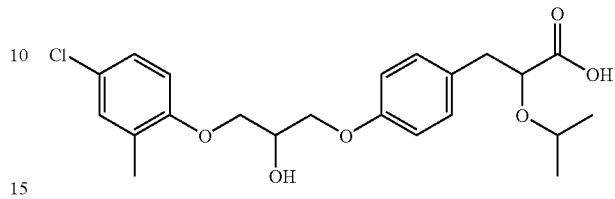

Using 4-chloro-2-methylphenol, the title compound was obtained in the same manner as described in Example 1c).

MS m/e (ESI) 445 (MNa$^+$)

Example 558

3-(4-[3-(2-Bromo-4-cyanophenoxy)-2-hydroxypropoxy]phenyl}-2-isopropoxypropanoic acid

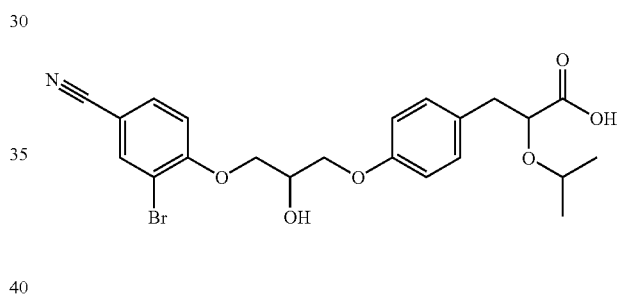

Using 2-bromo-4-cyanophenol, the title compound was obtained in the same manner as described in Example 1c).

MS m/e (ESI) 478 (MH$^+$)

Example 559

3-{4-[3-(4-Chloro-2-cyanophenoxy)-2-hydroxypropoxy]phenyl}-2-isopropoxypropanoic acid

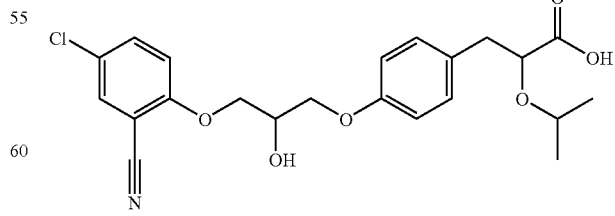

Using 4-chloro-2-cyanophenol, the title compound was obtained in the same manner as described in Example 1c).

MS m/e (ESI) 456 (MNa$^+$)

Example 560

3-{4-[3-(4-Chlorophenoxy)-2-hydroxypropoxy]phenyl}-2-isopropoxypropanoic acid

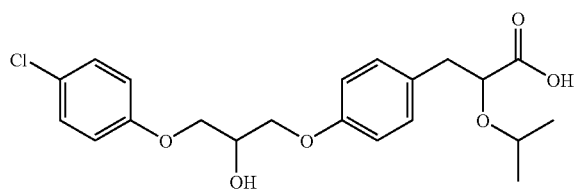

Using 4-chlorophenol, the title compound was obtained in the same manner as described in Example 1c).

MS m/e (ESI) 431 (MNa$^+$)

Example 561

3-{4-[3-(3-Chlorophenoxy)-2-hydroxypropoxy]phenyl}-2-isopropoxypropanoic acid

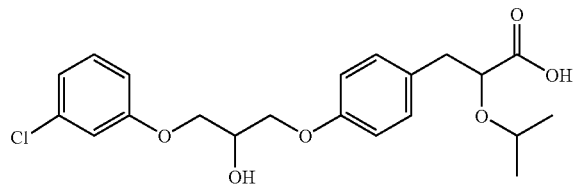

Using 3-chlorophenol, the title compound was obtained in the same manner as described in Example 1c).

MS m/e (ESI) 431 (MNa$^+$)

Example 562

3-[4-(2-Hydroxy-3-p-tolyloxypropoxy)phenyl]-2-isopropoxypropanoic acid

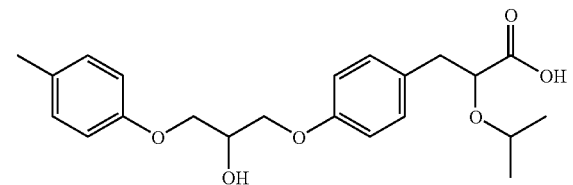

Using 4-methylphenol, the title compound was obtained in the same manner as described in Example 1c).

MS m/e (ESI) 411 (MNa$^+$)

Example 563

3-[4-(2-Hydroxy-3-m-tolyloxypropoxy)phenyl]-2-isopropoxypropanoic acid

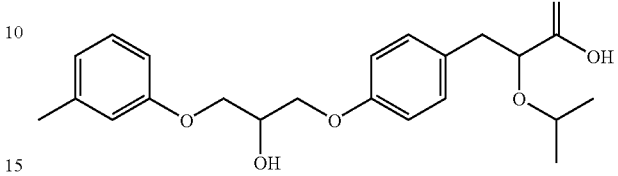

Using 3-methylphenol, the title compound was obtained in the same manner as described in Example 1c).

MS m/e (ESI) 389 (MH$^+$)

Example 564

3-{4-[3-(3,4-Dimethylphenoxy)-2-hydroxypropoxy]phenyl}-2-isopropoxypropanoic acid

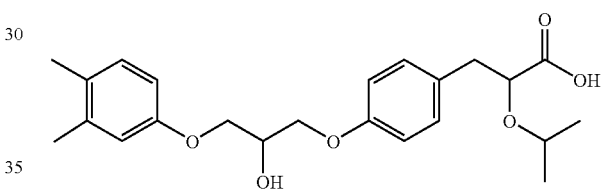

Using 3,4-dimethylphenol, the title compound was obtained in the same manner as described in Example 1c).

MS m/e (ESI) 425 (MNa$^+$)

Example 565

3-{4-[3-(4-t-Butylphenoxy)-2-hydroxypropoxy]phenyl}-2-isopropoxypropanoic acid

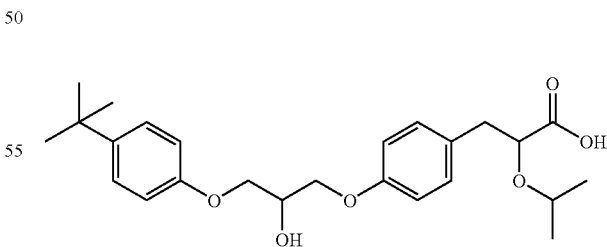

Using 4-t-butyl phenol, the title compound was obtained in the same manner as described in Example 1c).

MS m/e (ESI) 453 (MNa$^+$)

Example 566

3-{4-[3-(5-Chloro-2-methylphenoxy)-2-hydroxypropoxy]phenyl}-2-isopropoxypropanoic acid

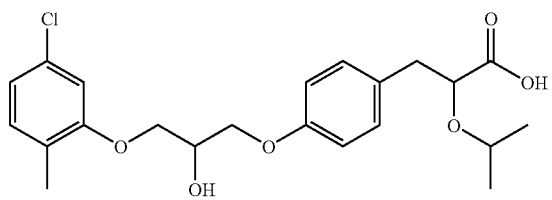

Using 5-chloro-2-methylphenol, the title compound was obtained in the same manner as described in Example 1c).
MS m/e (ESI) 445 (MNa$^+$)

Example 567

3-{4-[3-(3-Ethylphenoxy)-2-hydroxypropoxy]phenyl}-2-isopropoxypropanoic acid

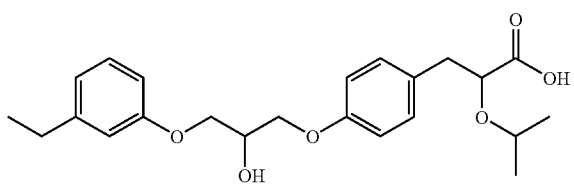

Using 3-ethylphenol, the title compound was obtained in the same manner as described in Example 1c).
MS m/e (ESI) 425 (MNa$^+$)

Example 568 a) 5-Benzyloxy-1-methyl-1H-indol-3-aldehyde

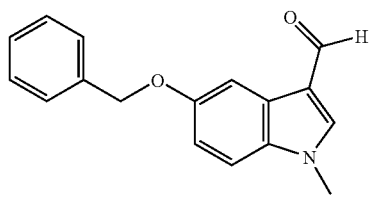

5g of 5-Benzyloxyindol-3-aldehyde was dissolved in 50 ml of N,N-dimethylformamide, and 0.84 g of 60% sodium hydride was added under ice-cooling. The reaction solution was stirred at room temperature for 30 minutes, 2.5 ml of methyl iodide was added and stirring was continued at room temperature for 16 hours. The reaction solution was cooled with ice, treated with water and ammonium chloride, and extracted with ethyl acetate and tetrahydrofuran. The organic layer was washed with saturated brine, dried over anhydrous magnesium sulfate, and evaporated. The residue was treated with diethyl ether and filtered, to give 4.6 g of the title compound.
$^1$H-NMR (CDCl$_3$)
δ: 3.83 (s, 3H) 5.15 (s, 2H) 7.06 (dd, J=2.0, 8.0 Hz, 1H) 7.26 (m, 2H) 7.33 (m, 1H) 7.40 (m, 2H) 7.50 (m, 2H) 7.62 (s, 1H) 7.91 (d, J=2.0 Hz, 1H) 9.92 (s, 1H)

b) Ethyl 3-(5-hydroxy-1-methyl-1H-indol-3-yl)-2-isopropoxypropionate

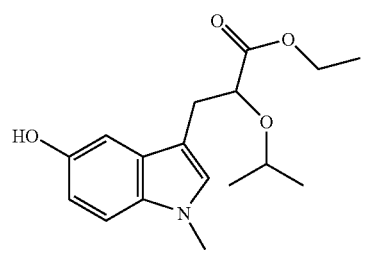

3.2 g of Ethyl 2-(diethylphosphoryl)-2-isopropylacetate was dissolved in 25 ml of tetrahydrofuran, and 0.44 g of 60% sodium hydride was added under ice-cooling, and stirring was continued for 20 minutes under ice-cooling. The reaction solution was treated with a solution of 2 g of 5-benzyloxy-1-methyl-1H-indol-3-aldehyde in 5 ml of tetrahydrofuran and 5 ml of N,N-dimethylformamide, and stirred at 50° C. for one hour and then at room temperature for 16 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography, and the fraction eluting with 20% ethylacetate-hexane was evaporated and the residue was dissolved in 10 ml of ethanol. 0.6 g of 10% Palladium carbon was added to this solution, the atmosphere was replaced with hydrogen, and the mixture was stirred at room temperature for 24 hours. The reaction atmosphere was replaced with nitrogen, the catalyst was filtered off, and the solvent was evaporated. The residue was subjected to silica gel column chromatography (30% ethyl acetate hexane), to give 2 g of the title compound.
$^1$H-NMR (CDCl$_3$)
δ: 1.00 (d, J=6.0 Hz, 3H) 1.18 (m, 6H) 3.05 (dd, J=14.0, 6.0 Hz, 1H) 3.12 (dd, J=14.0, 4.4 Hz, 1H) 3.55 (dq, J=6.0, 6.0 Hz, 1H) 3.70 (s, 3H) 4.15 (m, 3H) 6.77 (dd, J=2.0, 8.0 Hz, 1H) 6.91 (s, 1H) 7.02 (s, 1H) 7.11 (d, J=2.0 Hz, 1H)

c) Ethyl 2-isopropoxy-3-(1-methyl-5-oxilanylmethoxy-1H-indol-3-yl)propionate

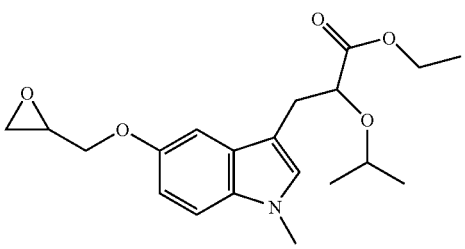

0.5 g of Ethyl 3-(5-hydroxy-1-methyl-1H-indol-3-yl)-2-isopropoxypropionate was dissolved in 13 ml of N,N-dimethylformamide, and 0.32 g of potassium carbonate and 0.05 g of cesium fluoride were added, then the mixture was stirred at room temperature for 30 minutes. The reaction solution was treated with 0.56 g of glycidylnosylate, and stirred at room temperature for a further 16 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography (16% ethyl acetate hexane), to give 0.4 g of the title compound.

$^1$H-NMR (CDCl$_3$)

δ: 1.00 (d, J=6.0 Hz, 3H) 1.18 (m, 6H) 2.78 (dd, J=2.0, 6.0 Hz, 1H) 2.90 (m, 1H) 3.05 (dd, J=14.0, 6.0 Hz, 1H) 3.13 (dd, J=14.0, 4.4 Hz, 1H) 3.40 (m, 1H) 3.55 (dq, J=6.0, 6.0 Hz, 1H) 3.70 (s, 3H) 4.02 (m, 1H) 4.13 (m, 3H) 4.26 (m, 1H) 6.88 (dd, J=2.0, 8.0 Hz, 1H) 6.91 (s, 1H) 7.09 (s, 1H) 7.16 (d, J=2.0 Hz, 1H)

d) 3-{5-[3-(2,4-Dichlorophenoxy)-2-hydroxypropoxy]-1-methyl-1H-indol-3-yl}-2-isopropoxypropanoic acid

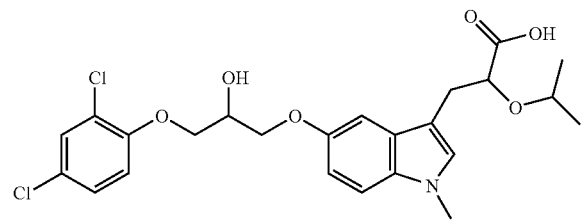

Using 2,4-dichlorophenol, the title compound was obtained in the same manner as described in Example 1c).
MS m/e (ESI) 496 (MH$^+$)

Example 569

3-{5-[3-(3,4-Dichlorophenoxy)-2-hydroxypropoxy]-1-methyl-1H-indol-3-yl}-2-isopropoxypropanoic acid

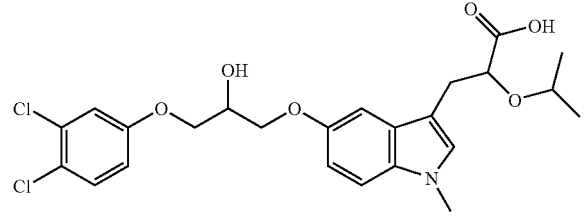

Using 3,4-dichlorophenol, the title compound was obtained in the same manner as described in Example 1c).
MS m/e (ESI) 496 (MH$^+$)

Example 570

3-{5-[3-(2-Bromo-4-cyanophenoxy)-2-hydroxypropoxy]-1-methyl-1H-indol-3-yl}-2-isopropoxypropanoic acid

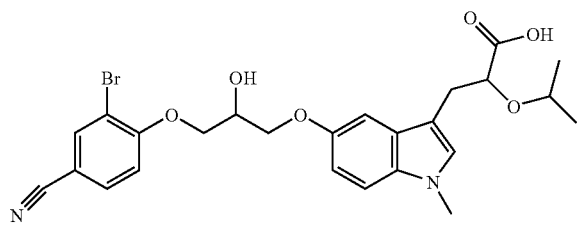

Using 2-bromo-4-cyanophenol, the title compound was obtained in the same manner as described in Example 1c).
MS m/e (ESI) 531 (MH$^+$)

Example 571

3-{5-[3-(3-Chloro-4-cyanophenoxy)-2-hydroxypropoxy]-1-methyl-1H-indol-3-yl}-2-isopropoxypropanoic acid

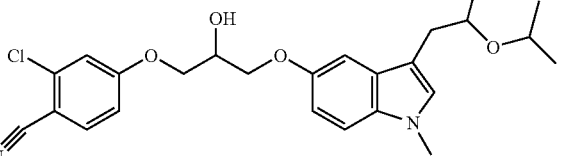

Using 3-chloro-4-cyanophenol, the title compound was obtained in the same manner as described in Example 1c).
MS m/e (ESI) 487 (MH$^+$)

Example 572

3-{5-[3-(4-Chloro-2-cyanophenoxy)-2-hydroxypropoxy]-1-methyl-1H-indol-3-yl}-2-isopropoxypropanoic acid

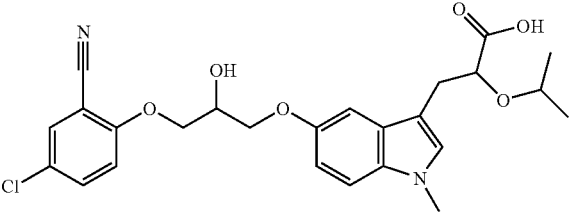

Using 4-chloro-2-cyanophenol, the title compound was obtained in the same manner as described in Example 1c).
MS m/e (ESI) 487 (MH$^+$)

Example 573

3-{5-[3-(4-Chlorophenoxy)-2-hydroxypropoxy]-1-methyl-1H-indol-3-yl}-2-isopropoxypropanoic acid

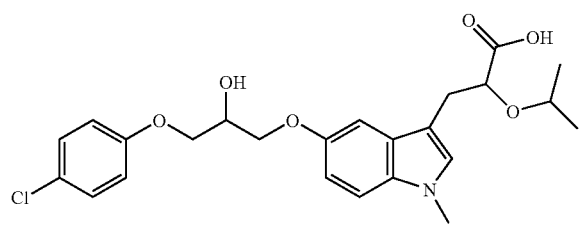

Using 4-chlorophenol, the title compound was obtained in the same manner as described in Example 1c).
MS m/e (ESI) 462 (MH$^+$)

Example 574

3-{5-[3-(3-Chlorophenoxy)-2-hydroxypropoxy]-1-methyl-1H-indol-3-yl}-2-isopropoxypropanoic acid

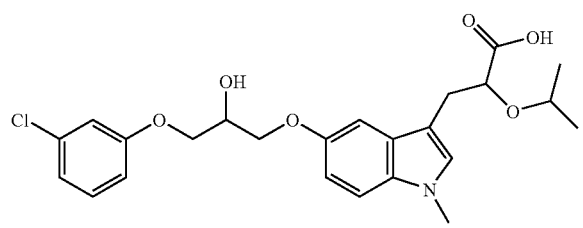

Using 3-chlorophenol, the title compound was obtained in the same manner as described in Example 1c).
MS m/e (ESI) 462 (MH$^+$)

Example 575

3-{5-[3-(2,5-Dichlorophenoxy)-2-hydroxypropoxy]-1-methyl-1H-indol-3-yl}-2-isopropoxypropanoic acid

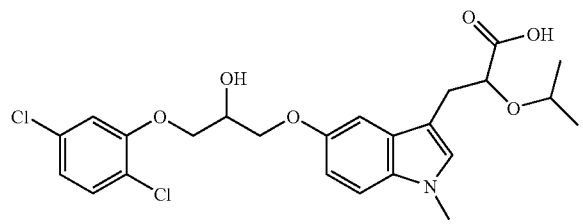

Using 2,5-dichlorophenol, the title compound was obtained in the same manner as described in Example 1c).
MS m/e (ESI) 496 (MH$^+$)

Example 576

3-{5-[3-(3-Chloro-4-fluorophenoxy)-2-hydroxypropoxy]-1-methyl-1H-indol-3-yl}-2-isopropoxypropanoic acid

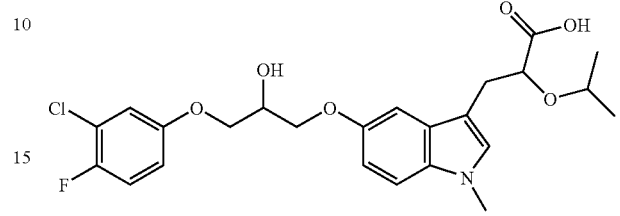

Using 3-chloro-4-fluorophenol, the title compound was obtained in the same manner as described in Example 1c).
MS m/e (ESI) 480 (MH$^+$)

Example 577

3-{5-[3-(2,4-Dimethylphenoxy)-2-hydroxypropoxy]-1-methyl-1H-indol-3-yl}-2-isopropoxypropanoic acid

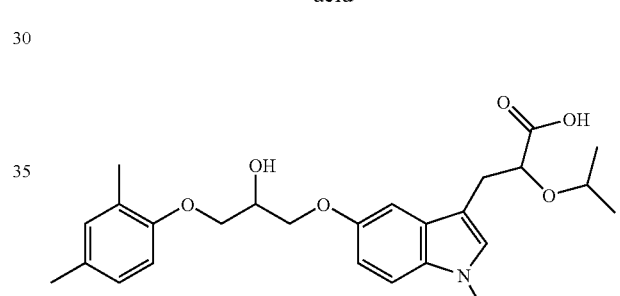

Using 2,4-dimethylphenol, the title compound was obtained in the same manner as described in Example 1c).
MS m/e (ESI) 456 (MH$^+$)

Example 578

3-{5-[3-(4-t-Butylphenoxy)-2-hydroxypropoxy]-1-methyl-1H-indol-3-yl}-2-isopropoxypropanoic acid

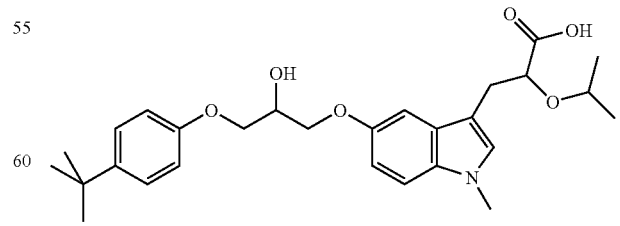

Using 4-t-butylphenol, the title compound was obtained in the same manner as described in Example 1c).
MS m/e (ESI) 484 (MH$^+$)

Example 579

3-{5-[3-(3-Ethylphenoxy)-2-hydroxypropoxy]-1-methyl-1H-indol-3-yl}-2-isopropoxypropanoic acid

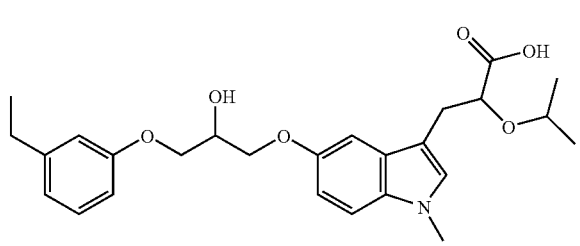

Using 3-ethylphenol, the title compound was obtained in the same manner as described in Example 1c).

MS m/e (ESI) 456 (MH$^+$)

Example 580 a) Ethyl 2-isopropoxy-3-(1-prop-2-ynyl-1H-indol-3-yl)propionate

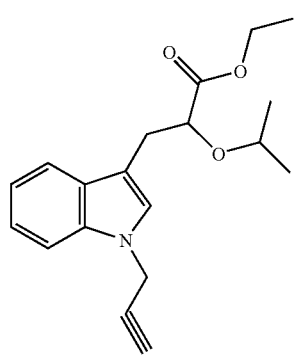

0.23 g of Ethyl 3-(1H-indol-3-yl)-2-isopropoxypropionate was dissolved in 5 ml of N,N-dimethylformamide, and 34 mg of 60% sodium hydride was added under ice-cooling. The reaction solution was stirred for 30 minutes under ice-cooling, then 0.09 ml of propargyl bromide was added, and stirring was continued at room temperature for 16 hours. The reaction solution was cooled with ice, treated with water and ammonium chloride solution, and extracted with ethyl acetate. The organic layer was washed with saturated brine, dried over anhydrous magnesium sulfate, and evaporated. The residue was subjected to silica gel column chromatography (9% ethyl acetate-hexane), to give 0.18 g of the title compound.

$^1$H-NMR (CDCl$_3$)

δ: 1.00 (d, J=6.0 Hz, 3H) 1.18 (m, 6H) 3.10 (dd, J=14.0, 6.0 Hz, 1H) 3.20 (dd, J=14.0, 4.4 Hz, 1H) 3.55 (dq, J=6.0, 6.0 Hz, 1H) 4.13 (m, 3H) 4.83 (s, 2H) 7.13 (m, 3H) 7.22 (d, J=8.0 Hz, 1H) 7.35 (d, J=8.0 Hz, 1H) 7.64 (d, J=8.0 Hz, 1H)

b) 3-{1-[3-(4-Chlorophenyl)prop-2-ynyl]-1H-indol-3-yl}-2-isopropoxypropanoic acid

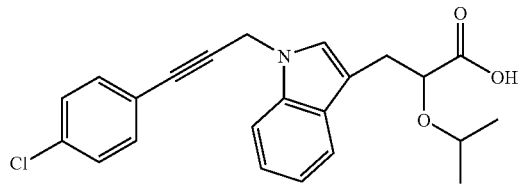

Using 1-chloro-4-iodobenzene, the title compound was obtained in the same manner as described in Example 77b).

MS m/e (ESI) 396 (MH$^+$)

Example 581

2-Isopropoxy-3-{1-[3-(4-methoxyphenyl)prop-2-ynyl]-1H-indol-3-yl}propanoic acid

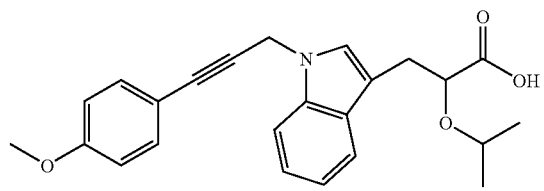

Using 4-iodoanisole, the title compound was obtained in the same manner as described in Example 77b).

MS m/e (ESI) 392 (MH$^+$)

Example 582

2-Isopropoxy-3-{1-[3-(3-methoxyphenyl)prop-2-ynyl]-1H-indol-3-yl}propanoic acid

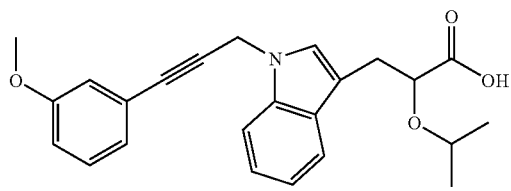

Using 3-iodoanisole, the title compound was obtained in the same manner as described in Example 77b).

MS m/e (ESI) 392 (MH$^+$)

Example 583

2-Isopropoxy-3-{1-[3-(4-trifluoromethylphenyl)prop-2-ynyl]-1H-indol-3-yl}propanoic acid

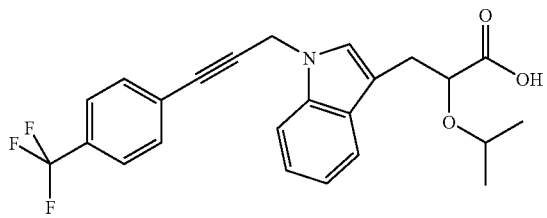

Using 4-iodobenzotrifluoride, the title compound was obtained in the same manner as described in Example 77b).
MS m/e (ESI) 430 (MH$^+$)

Example 584

2-Isopropoxy-3-{1-[3-(3-trifluoromethylphenyl)prop-2-ynyl]-1H-indol-3-yl}propanoic acid

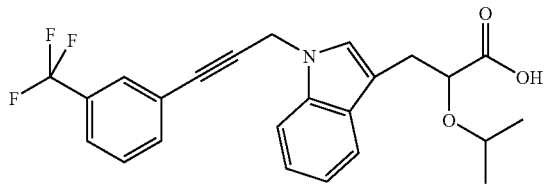

Using 3-iodobenzotrifluoride, the title compound was obtained in the same manner as described in Example 77b).
MS m/e (ESI) 430 (MH$^+$)

Example 585

3-{1-[3-(2,4-Dichlorophenyl)prop-2-ynyl]-1H-indol-3-yl}-2-isopropoxypropanoic acid

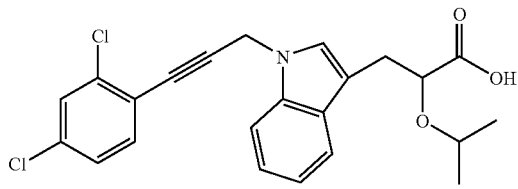

Using 2,4-dichloroiodobenzene, the title compound was obtained in the same manner as described in Example 77b).
$^1$H-NMR (CDCl$_3$)
δ: 1.04 (d, J=6.0 Hz, 3H) 1.15 (d, J=6.0 Hz, 3H) 3.15 (dd, J=14.0, 6.0 Hz, 1H) 3.31 (dd, J=14.0, 4.4 Hz, 1H) 3.61 (dq, J=6.0, 6.0 Hz, 1H) 4.23 (dd, J=7.6, 4.4 Hz, 1H) 5.11 (s, 2H) 7.15-7.20 (m, 3H) 7.25 (m, 1H) 7.34 (d, J=8.0 Hz, 1H) 7.40 (d, J=2.0 Hz, 2H) 7.44 (d, J=8.0 Hz, 1H) 7.67 (d, J=8.0 Hz, 1H)
MS m/e (ESI) 480 (MH$^+$)

Example 586

3-[4-(4-Trifluoromethylbenzyloxycarbonylamino)phenyl]-2-isopropoxypropanoic acid

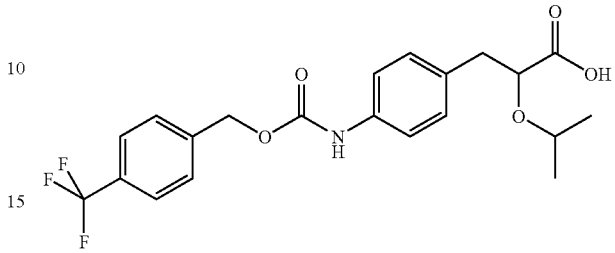

Using 4-trifluoromethylbenzyl alcohol, the title compound was obtained in the same manner as described in Example 493.
$^1$H-NMR (CDCl$_3$)
δ: 1.03 (d, J=6.0 Hz, 3H) 1.16 (d, J=6.0 Hz, 3H) 2.91 (dd, J=14.0, 6.0 Hz, 1H) 3.09 (dd, J=14.0, 4.4 Hz, 1H) 3.55 (dq, J=6.0, 6.0 Hz, 1H) 4.12 (dd, J=7.6, 4.4 Hz, 1H) 5.25 (s, 2H) 6.71 (s, 1H) 7.19 (d, J=8.0 Hz, 2H) 7.32 (d, J=8.0 Hz, 2H) 7.51 (d, J=8.0 Hz, 2H) 7.63 (d, J=8.0 Hz, 2H)

Example 587

3-{3-[3-(2,4-Dichlorophenoxy)-1-propynyl]-phenyl}-2(S)-isopropoxypropanoic acid

Production Example 587a

3-[3-(4-Benzyl-2-(oxo)-oxazolidin-3-yl)-2-isopropoxy-3-oxo-propyl]-phenyl trifluoromethanesulfonate

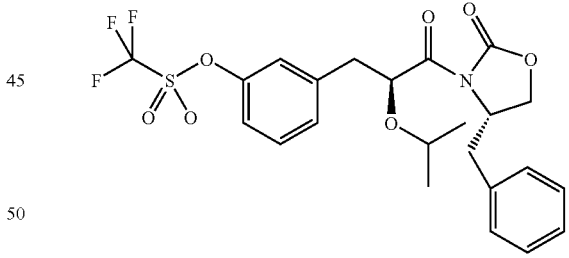

1.002 g of 4 (S)-Benzyl-3-[3-(3-hydroxyphenyl)-2(S)-isopropoxypropionyl]-oxazolidin-2-one was dissolved in 15 ml of dichloromethane, and 0.4 ml of triethylamine, 16 ml of N,N-dimethylaminopyridine and 950 mg of N-phenyltrifluoromethanesulfonylimide were added under ice-cooling. After being stirred overnight at room temperature, the reaction solution was diluted with ethyl acetate and the organic layer was successively washed with 1N hydrochloric acid and saturated brine, then dried over anhydrous magnesium sulfate. The solvent was evaporated and the residue was purified by silica gel column chromatography, to give 1.492 g of the title compound as a colorless oil in the 2:1 hexane-ethyl acetate fraction.
$^1$H NMR (CDCl$_3$)

δ: 0.91 (d, J=6.4 Hz, 3H) 1.15 (d, J=6.4 Hz, 3H) 2.78-2.90 (m, 2H) 3.02-3.09 (m, 1H) 3.36 (dd, J=2.4, 13.2 Hz, 1H) 3.45 (Sept, J=6.4 Hz, 1H) 4.18-4.24 (m, 2H) 4.64-4.69 (m, 1H) 5.23 (dd, J=2.4, 9.2 Hz, 1H) 7.14-7.41 (m, 9H)

Production Example 587b

4-Benzyl-3-{3-[3-(3-hydroxy-1-propynyl)phenyl]-2-isopropoxypropionyl}-oxazolidin-2-one

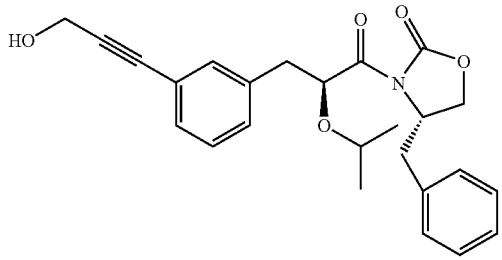

390 mg of 3-[3-(4-Benzyl-2-(oxo)-oxazolidin-3-yl)-2-isopropoxy-3-oxo-propyl]-phenyl trifluoromethanesulfonate was dissolved in 2 ml of N,N-dimethylformamide, 85 mg of propargyl alcohol, 8 mg of copper iodide, 45 mg of tetrakis(triphenylphosphine) palladium and 0.3 ml of triethylamine were added in succession, and the mixture was stirred overnight at 50° C. under a nitrogen atmosphere. The reaction solution was filtered through silica gel, and the filtrate was dissolved in ethyl acetate, washed with water, 1N hydrochloric acid and saturated brine. The organic layer was dried over anhydrous magnesium sulfate, and the solvent was evaporated. The residue was purified by silica gel column chromatography, to give 207 mg of the title compound as a colorless oil in the 3:2 hexane-ethyl acetate fraction.

$^1$H NMR (CDCl$_3$)

δ: 0.98 (d, J=6.0 Hz, 3H) 1.15 (d, J=6.0 Hz, 3H) 2.76-2.88 (m, 2H) 2.96 (dd, J=4.4, 13.2 Hz, 1H) 3.33 (dd, J=2.8, 10.4 Hz, 1H) 3.47 (Sept, J=6.0 Hz, 1H) 4.13-4.19 (m, 2H) 4.48 (d, J=6.0 Hz, 1H) 4.56-4.62 (m, 1H) 5.30 (dd, J=4.4, 9.2 Hz, 1H) 7.16-7.18 (m, 1H) 7.21-7.36 (m, 8H)

Production Example 587c

4-Benzyl-3-(3-{3-[3-(2,4-dichloro-phenoxy)-1-propynyl]-phenyl}-2-isopropoxypropionyl)-oxazolidin-2-one

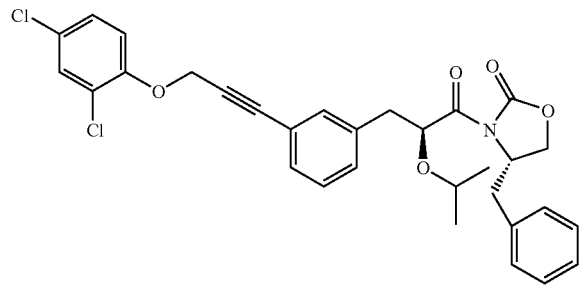

Using 4-benzyl-3-{3-[3-(3-hydroxy-1-propynyl)phenyl]-2-isopropoxypropionyl}oxazolidin-2-one, the title compound was obtained in the same manner as described in Production examples 102c) and Example 102d).

$^1$H NMR (CDCl$_3$)

δ: 0.98 (d, J=6.0 Hz, 3H) 1.15 (d, J=6.4 Hz, 3H) 2.77-2.93 (m, 2H) 2.96 (dd, J=4.4, 13.6 Hz, 1H) 3.32 (dd, J=3.6, 13.2 Hz, 1H) 3.45 (Sept, J=6.0 Hz, 1H) 4.13-4.19 (m, 2H) 4.57-4.61 (m, 1H) 4.97 (s, 2H) 5.27 (dd, J=4.0, 9.2 Hz, 1H) 7.10 (d, J=8.8 Hz, 1H) 7.17-7.39 (m, 11H)

Example 587d

3-{3-[3-(2,4-Dichlorophenoxy)-1-propynyl]-phenyl}-2(S)-isopropoxypropanoic acid

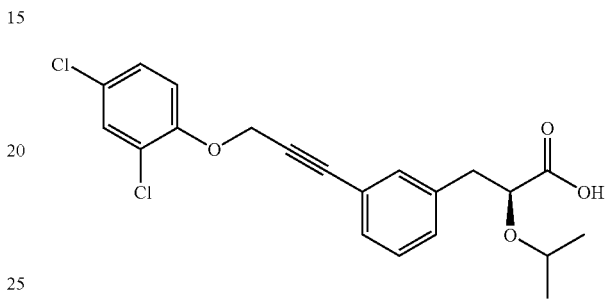

Using 4-benzyl-3-(3-{3-[3-(2,4-dichlorophenoxy)-1-propynyl]phenyl}-2-isopropoxypropionyl)oxazolidin-2-one, an hydrolysis reaction was conducted in the same manner as described in Production example 279d), and after purification by reverse-phase high performance liquid chromatography, the title compound was obtained.

MS m/e (ESI) 429 (MNa$^+$)

Example 588

3-{3-[3-(2,4-Dichlorophenyl)-2-propynyloxy]-phenyl}-2(S)-isopropoxypropanoic acid Production Example 588a 4-Benzyl-3-(3-{3-[3-(2,4-dichlorophenyl)-2-propynyloxy]-phenyl}-2-isopropoxypropanoyl)oxazolidin-2-one

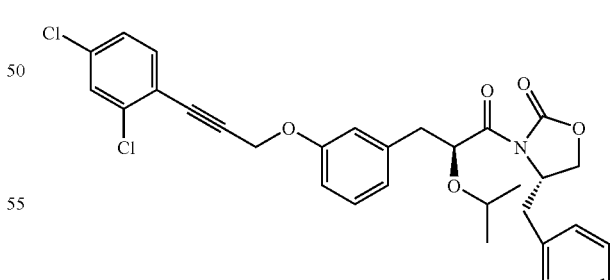

Using 4 (S)-benzyl-3-[3-(3-hydroxyphenyl)-2(S)-isopropoxypropynyl]oxazolidin-2-one and 1-(3-bromo-1-propynyl)-2,4-dichlorobenzene, the title compound was obtained in the same manner as described in Production example 77a).

$^1$H NMR (CDCl$_3$)

δ: 1.02 (d, J=6.0 Hz, 3H) 1.15 (d, J=6.0 Hz, 3H) 2.77 (dd, J=8.8, 13.2 Hz, 1H) 2.89-3.00 (m, 1H) 2.77-3.32 (m, 2H) 3.52

(Sept, J=6.0 Hz, 1H) 3.99 (t, J=8.4 Hz, 1H) 4.08-4.13 (m, 1H) 4.49-4.54 (m, 1H) 4.93 (s, 2H) 5.40 (dd, J=5.2, 8.4 Hz, 1H) 6.89-6.92 (m, 1H) 6.96 (d, J=5.6 Hz, 1H) 7.00 (br, 1H) 7.16-7.34 (m, 7H) 7.37-7.40 (m, 2H)

Example 588b

3-{3-[3-(2,4-Dichlorophenyl)-2-propynyloxy]phenyl}-2(S)-isopropoxypropanoic acid

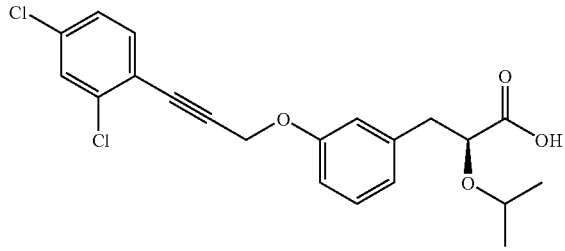

Using 4-benzyl-3-{3-(3-[3-(2,4-dichlorophenyl)-2-propynyloxy]phenyl}-2-isopropoxypropanoyl)oxazolidin-2-one, an hydrolysis reaction was conducted in the same manner as described in Production example 279d), and after purification by reverse-phase high performance liquid chromatography, the title compound was obtained.
MS m/e (ESI) 429 (MNa+)

Example 589

3-{3-[3-(4-Chlorophenyl)-2-propynyloxy]-phenyl}-2(S)-isopropoxypropanoic acid

Production Example 589a

4-Benzyl-3-(3-{3-[3-(4-chlorophenyl)-2-propynyloxy]-phenyl}-2-isopropoxypropanoyl)-oxazolidin-2-one

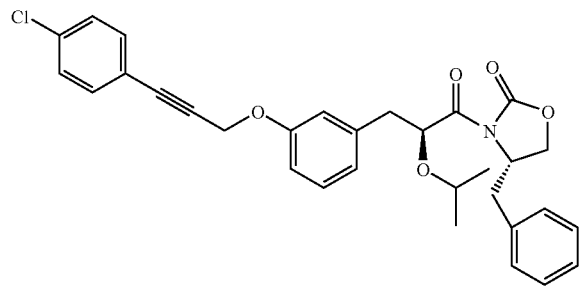

Using 4 (S)-benzyl-3-[3-(3-hydroxyphenyl)-2(S)-isopropoxypropynyl]oxazolidin-2-one and 1-(3-bromo-1-propynyl)-4-chlorobenzene, the title compound was obtained in the same manner as described in Production example 77a).
¹H NMR (CDCl₃)
δ: 1.02 (d, J=6.0 Hz, 3H) 1.15 (d, J=6.4 Hz, 3H) 2.77 (dd, J=9.6, 13.2 Hz, 1H) 2.93-2.98 (m, 1H) 3.29 (dd, J=4.0, 13.2 Hz, 1H) 3.52 (Sept, J=6.0 Hz, 1H) 3.99 (t, J=9.6 Hz, 1H) 4.08-4.15 (m, 1H) 4.50-4.54 (m, 1H) 4.88 (s, 2H) 5.40 (dd, J=5.6, 8.4 Hz, 1H) 6.87 (dd, J=2.4, 8.4 Hz, 1H) 6.96 (d, J=7.6 Hz, 1H) 7.00 (br, 1H) 7.18-7.21 (m, 2H) 7.27-7.37 (m, 8H)

Example 589b

3-{3-[3-(4-Chlorophenyl)-2-propynyloxy]-phenyl}-2(S)-isopropoxypropanoic acid

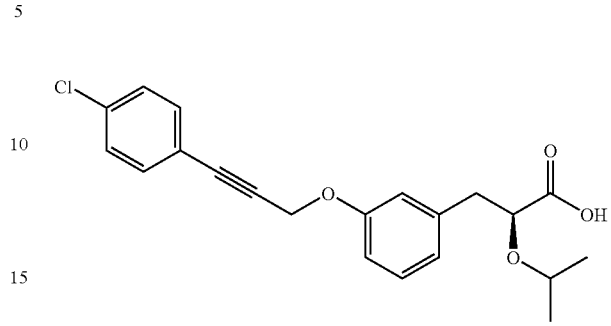

Using 4-benzyl-3-(3-{3-[3-(4-chlorophenyl)-2-propynyloxy]phenyl}-2-isopropoxypropanoyl)-oxazolidin-2-one, an hydrolysis reaction was conducted in the same manner as described in Production example 279d), and after purification by reverse-phase high performance liquid chromatography, the title compound was obtained.
MS m/e (ESI) 395 (MNa+)

Example 590

3-[3-(2,4-Dichlorobenzoylaminooxy)phenyl]-2-isopropoxypropanoic acid

Production Example 590a

3-[1,3,2]Dioxaborinan-2-yl-benzaldehyde

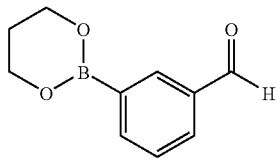

5.0 g of 3-Formylbenzene boronate was suspended in diethyl ether, and 3.7 ml of ethylene glycol was added, and the mixture was stirred at room temperature for 15 minutes. The solvent was concentrated, to give 10.36 g of the title compound as a colorless oil.

Production Example 590b

Ethyl 3-(3-boronyl-phenyl)-2-isopropoxyacrylate

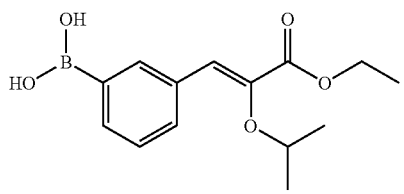

2.38 g of Ethyl (diethoxyphosphoryl) isopropoxyacrylate was dissolved in anhydrous tetrahydrofuran, and 316 mg of sodium hydride was added. This mixture was stirred at room temperature for 15 minutes, then a solution of 1.0 g of 3-[1,3,2]dioxaborinan-2-yl-benzaldehyde in N,N-dimethylformamide was added, and stirring was continued at room temperature for 1 hour. The reaction solution was diluted with ethyl acetate, washed with 1N hydrochloric acid and saturated brine. The organic layer was dried over anhydrous magnesium sulfate, and the solvent was evaporated. The residue was purified by silica gel column chromatography, to give 511 mg of the title compound as a colorless oil in the 3:2 hexane-ethyl acetate fraction.

Production Example 590c

Ethyl 3-(3-boronyl-phenyl)-2-isopropoxypropanoate

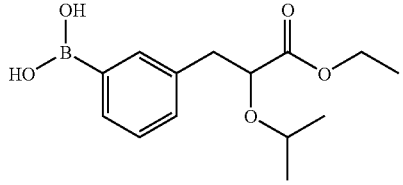

511 mg of Ethyl 3-(3-boronylphenyl)-2-isopropoxyacrylate was dissolved in anhydrous ethanol, and 10% palladium carbon was added, and the mixture was stirred overnight at room temperature under an hydrogen atmosphere. The reaction solution was filtered, and the filtrate was concentrated, to give 539 mg of the title compound.

Production Example 590d

Ethyl 3-[3-(1,3-dioxo-1,3-dihydroisoindol-2-yloxy)phenyl]-2-isopropoxypropanoate

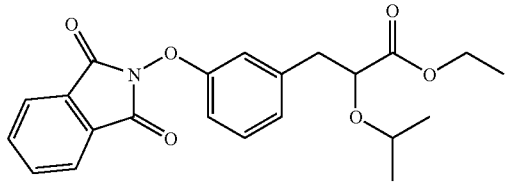

539 mg of Ethyl 3-(3-boronylphenyl)-2-isopropoxypropanoate, 389 mg of N-hydroxyphthalimide and 380 mg of copper (II) acetate were suspended in 10 ml of 1,2-dichloroehtane, and 0.2 ml of pyridine was added, and the mixture was stirred at room temperature for 3 days. The reaction solution was filtered through a silica gel column, and the filtrate was concentrated. The residue was purified by silica gel column chromatography, to give 275 mg of the title compound as a colorless oil in the 4:1 hexane-ethyl acetate fraction.

$^1$H NMR (CDCl$_3$)

δ: 0.99 (d, J=6.0 Hz, 3H) 1.10 (d, J=6.4 Hz, 3H) 1.23 (t, J=4.8 Hz, 3H) 2.89 (dd, J=9.6, 14.0 Hz, 1H) 2.97 (dd, J=4.4, 13.6 Hz, 1H) 3.46 (Sept, J=6.0 Hz, 1H) 4.00 (dd, J=4.4, 9.2 Hz, 1H) 4.13-4.21 (m, 2H) 7.01-7.06 (m, 3H) 7.25-7.28 (m, 1H) 7.81-7.84 (m, 2H) 7.89-7.93 (m, 2H)

Production Example 590e

Ethyl 3-(3-aminooxyphenyl-2-isopropoxypropanoate

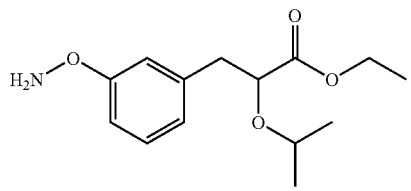

275 mg of Ethyl 3-[3-(1,3-dioxo-1,3-dihydroisoindol-2-yloxy)phenyl]-2-isopropoxypropionate was dissolved in ethanol, and 50 mg of hydrazine monohydrate was added. The mixture was stirred at 70° C. for 30 minutes, then the insoluble substances were filtered off. The filtrate was concentrated. The residue was purified by silica gel column chromatography, to give 163 mg of the title compound as a colorless oil in the 3:1 hexane-ethyl acetate fraction.

Example 590f

3-[3-(2,4-Dichlorobenzoylaminooxy)phenyl]-2-isopropoxypropanoic acid 10 mg of Ethyl 3-(3-aminooxyphenyl-2-isopropoxypropionate and 7 mg of 2,4-dichlorobenzoic acid were dissolved in 0.3 ml of N,N-dimethylformamide, 0.006 ml of diethyl phosphonate cyanide and 0.05 ml of triethylamine were added, and the mixture was stirred overnight at room temperature. The reaction solution was diluted with ethyl acetate and washed with water. The organic layer was concentrated, to give ethyl 3-[3-(2,4-dichlorobenzoylaminooxy)phenyl]-2-isopropoxypropionate. This product was then dissolved in 0.4 ml of ethanol, 0.1 ml of 5N sodium hydroxide was added, and the mixture was stirred overnight at room temperature. The reaction solution was treated with 1N hydrochloric acid, extracted with ethyl acetate, and the organic layer was concentrated. The residue was purified by reverse-phase high performance liquid chromatography, to give the title compound.

MS m/e (ESI) 434 (MNa$^+$)

Example 591

3-[3-(4-chloro-2-fluorobenzoylaminooxy)phenyl]-2-isopropoxypropanoic acid

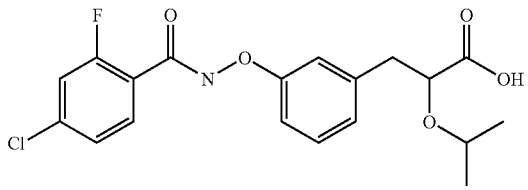

Using 4-chloro-2-fluorobenzoic acid, the title compound was obtained in the same manner as described in Example 590f)
MS m/e (ESI) 418 (MNa+)

Example 592

3-[3-(4-Trifluoromethyl-2-fluorobenzoylaminooxy)phenyl]-2-isopropoxypropanoic acid

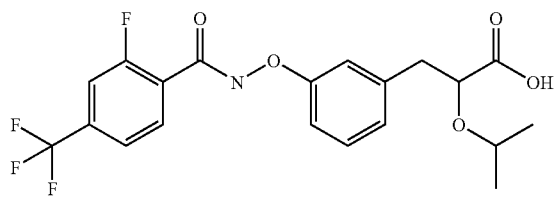

Using 4-trifluoromethyl-2-fluorobenzic acid, the title compound was obtained in the same manner as described in Example 590f).
MS m/e (ESI) 452 (MNa+)

Example 593

3-[3-(4-Propoxy-2-chlorobenzoylaminooxy)-phenyl]-2-isopropoxypropanoic acid

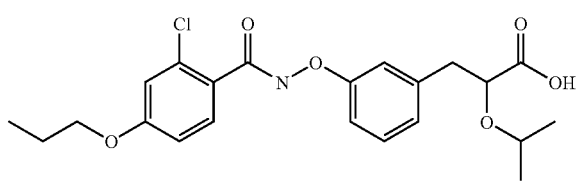

Using 4-propoxy-2-chlorobenzoic acid, the title compound was obtained in the same manner as described in Example 590f)
MS m/e (ESI) 458 (MNa+)

Example 594

2-Isopropoxy-3-{3-[(4-methyl-2-p-tolyl-thiazol-5-carbonyl)aminooxy]phenyl}propanoic acid

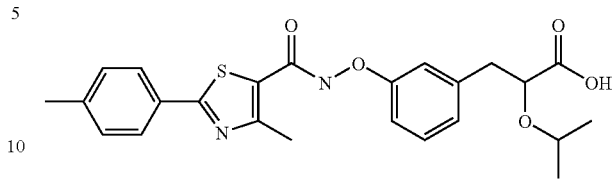

Using 4-methyl-2-p-tolylthiazol-5-carboxylic acid, the title compound was obtained in the same manner as described in Example 590f).
MS m/e (ESI) 477 (MNa+)

Example 595

2 (S)-3-{[3-(2,4-Dichlorophenyl)carbamoyloxymethyl-4-ethoxy]phenyl}-2-isopropoxypropanoic acid

Production Example 595a

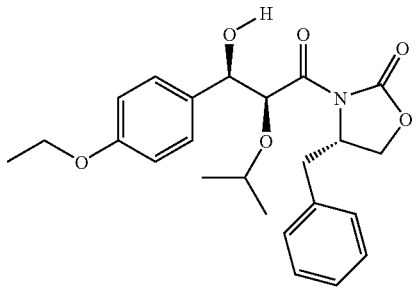

Under the similar conditions to those described in Production example 332a), 2.4 g of 4-ethoxybenzaldehyde and 5.6 g of (4S)-4-benzyl-3-(2-isopropoxyacetyl)-1,3-oxazolidin-2-one were reacted, to give 7.2 g of (4S)-3-[(3R,2S)-3-(4-ethoxyphenyl)-3-hydroxy-2-isopropoxypropanoyl]-4-benzyl-1,3-oxazolan-2-one as a colorless solid.
$^1$H-NMR (CDCl$_3$)
δ: 1.15 (d, J=6.0 Hz, 3H) 1.20 (d, J=6.0 Hz, 3H) 1.38 (t, J=7.0 Hz, 3H) 2.73 (dd, J=13.5, 10.0 Hz, 1H) 3.05 (d, J=5.4 Hz, 1H) 3.16 (dd, J=13.5, 3.6 Hz, 1H) 3.69 (sept, J=6.0 Hz, 1H) 3.70 (m, 1H) 3.99 (q, J=7.0 Hz, 2H) 4.05 (m, 1H) 4.43 (m, 1H) 4.79 (t, J=5.4 Hz, 1H) 5.41 (d, J=5.4 Hz, 1H) 6.82 (d, J=8.0 Hz, 2H) 7.19 (d, J=8.0 Hz, 2H) 7.24-7.35 (m, 5H)

Production Example 595b

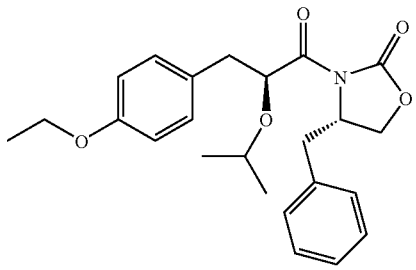

7.2 g of (4S)-3-[(3R,2S)-3-(4-Ethoxyphenyl)-3-hydroxy-2-isopropoxypropanoyl]-4-benzyl-1,3-oxazolan-2-one was dissolved in 200 ml of trifluoroacetic acid, 40 ml of triethylsilane was added, and the mixture was stirred for 24 hours. The solvent was evaporated, and the residue was purified by silica gel column chromatography (elution solvent: hexane-ethyl acetate), to give 7.0 g of (4S)-3-[(2S)-3-(4-ethoxyphenyl)-2-isopropoxypropanoyl]-4-benzyl-1,3-oxazolan-2-one as a colorless solid.

$^1$H-NMR (CDCl$_3$)

δ: 1.03 (d, J=6.0 Hz, 3H) 1.15 (d, J=6.0 Hz, 3H) 1.39 (t, J=7.2 Hz, 3H) 2.77 (dd, J=13.5, 9.9 Hz, 1H) 2.88 (dd, J=13.8, 8.4 Hz, 1H) 2.92 (dd, J=13.8, 6.0 Hz, 1H) 3.31 (dd, J=13.5, 3.6 Hz, 1H) 3.52 (sept, J=6.0 Hz, 1H) 3.97 (dd, J=9.0, 3.6 Hz, 1H) 3.98 (q, J=7.2 Hz, 2H) 4.13 (dd, J=9.0, 2.4 Hz, 1H) 4.51 (dtd, J=9.6, 3.6, 2.4 Hz, 1H) 5.35 (dd, J=8.4, 6.0 Hz, 1H) 6.79 (d, J=8.0 Hz, 2H) 7.20 (d, J=8.0 Hz, 2H) 7.20-7.34 (m, 5H)

Production Example 595c

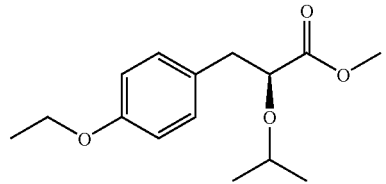

7.0 g of (4S)-3-[(2S)-3-(4-Ethoxyphenyl)-2-isopropoxypropanoyl]-4-benzyl-1,3-oxazolan-2-one was hydrolyzed and methylated in the same manner as described in Production example 332c), to give 3.9 g of methyl 2 (S)-isopropoxy-3-(4-ethoxyphenyl)-propanoate as a colorless oil.

$^1$H-NMR (CDCl$_3$)

δ: 0.95 (d, J=6.2 Hz, 3H) 1.13 (d, J=6.0 Hz, 3H) 1.39 (t, J=7.2 Hz, 3H) 2.87 (dd, J=13.7, 8.6 Hz, 1H) 2.94 (dd, J=13.7, 5.2 Hz, 1H) 3.48 (sept, J=6.2 Hz, 1H) 3.71 (s, 3H) 4.01 (q, J=7.2 Hz, 2H) 4.02 (dd, J=8.6, 6.2 Hz, 1H) 6.80 (d, J=8.0 Hz, 2H) 7.13 (d, J=8.0 Hz, 2H)

Production Example 595d

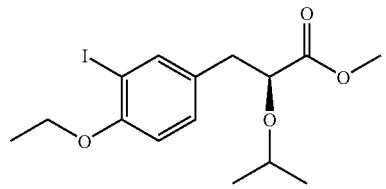

To a solution of 3.9 g of methyl 2 (S)-isopropoxy-3-(4-ethoxyphenyl) propanoate in dichloromethane (180 ml) were added 4.58 g of silver sulfate and 3.72 g of iodine, and the mixture was stirred for 18 hours. The reaction solution was poured into ethyl acetate (500 ml):water (200 ml), and excess iodine was decomposed with sodium thiosulfate. The organic layer was dried over magnesium sulfate, and the solvent was evaporated. The residue was purified by silica gel column chromatography (elution solvent: hexane-ethyl acetate), to give 3.9 g of methyl 2 (S)-isopropoxy-3-(4-ethoxy-3-iodophenyl)propanoate as a yellow oil.

$^1$H-NMR (CDCl$_3$)

δ: 0.97 (d, J=6.1 Hz, 3H) 1.15 (d, J=6.1 Hz, 3H) 1.46 (t, J=6.9 Hz, 3H) 2.83 (dd, J=13.6, 9.0 Hz, 1H) 2.99 (dd, J=13.6, 6.9 Hz, 1H) 3.48 (sept, J=6.1 Hz, 1H) 3.72 (s, 3H) 3.99 (dd, J=9.0 Hz, 1H) 4.06 (q, J=6.9 Hz, 2H) 6.71 (d, J=8.5 Hz, 1H) 7.15 (dd, J=8.5, 2.0 Hz, 1H) 7.67 (d, J=2.0 Hz, 1H)

Production Example 595e

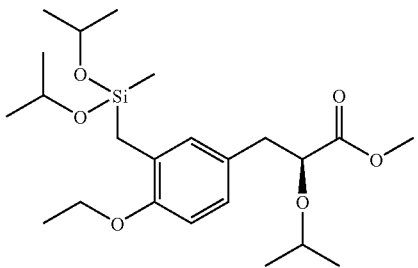

0.43 g of Magnesium, 1 ml of tetrahydrofuran and 1,2-dibromomethane were heated, and several drops of chloromethyl-diisopropoxy methylsilane were added. The solution was cooled to 0° C., and a solution of 3.7 g of silane in tetrahydrofuran-(30 ml) was added dropwise. After 30 minutes, this solution was added to a 0.5M zinc chloride solution in tetrahydrofuran (35.5 ml), and after stirring this mixture for 30 minutes, a solution of 3.9 g of methyl 2 (S)-isopropoxy-3-(4-ethoxy-3-iodophenyl)propanoate in tetrahydrofuran (50 ml) and 0.33 g of dichlorophosphinoferrocene palladium were added, and the mixture was heated under reflux for 40 hours. After adding an equivalent amount of zinc reagent, the solution was heated under reflux for another 16 hours. The reaction solution was poured into ethyl acetate (500 ml) and a saturated solution of ammonium chloride (300 ml). The organic layer was dried over magnesium sulfate. The solvent was evaporated and the residue was purified by silica gel column chromatography (elution solvent: hexane-ethyl acetate), to give 5.6 g of methyl 2 (S)-isopropoxy-3-{3-[(di-isopropoxymethyl)methylsilanyl)-methyl]-4-ethoxyphenyl}propanoate as a yellow oil.

$^1$H-NMR (CDCl$_3$)

δ: 0.01 (s, 3H) 0.97 (d, J=6.2 Hz, 3H) 1.13 (d, J=6.2 Hz, 3H) 1.14 (d, J=6.2 Hz, 6H) 1.17 (d, J=6.2 Hz, 6H) 1.41 (t, J=7.0 Hz, 3H) 2.15 (d, J=14.0 Hz, 1H) 2.19 (d, J=14.0 Hz, 1H) 2.82 (dd, J=13, 6, 8.3 Hz, 1H) 2.89 (dd, J=13.6, 5.5 Hz, 1H) 3.48 (sept, J=6.2 Hz, 1H) 3.70 (s, 3H) 3.98 (q, J=7.0 Hz, 2H) 4.01 (dd, J=8.3, 5.5 Hz, 1H) 4.13 (sept, J=6.2 Hz, 1H) 6.67 (d, J=8.3 Hz, 1H) 6.90 (dd, J=8.3, 2.2 Hz, 1H) 6.98 (d, J=2.2 Hz, 1H)

Production Example 595f

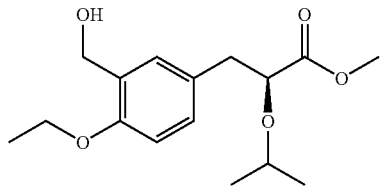

To a solution of 5.6 g of methyl 2 (S)-isopropoxy-3-{3-[(diisopropoxymethyl)methylsilanyl)methyl]-4-ethoxyphenyl}propanoate in tetrahydrofuran (13 ml) and methanol (13 ml) were added 0.75 g of potassium fluoride, 1.30 g of potassium hydrogencarbonate and 2.5 ml of 30% aqueous hydrogen peroxide solution. The mixture was stirred for 24 hours. 3.0 g of sodium thiosulfate was added, and the mixture was poured into ethyl acetate (200 ml): water (100 ml). The organic layer was dried over magnesium sulfate, and the solvent was evaporated. The residue was purified by silica gel column chromatography (elution solvent: hexane-ethyl acetate), to give 1.4 g of methyl 2 (S)-isopropoxy-3-(4-ethoxy-3-hydroxymethylphenyl)-propanoate as a colorless oil.

$^1$H-NMR (CDCl$_3$)

δ: 0.97 (d, J=6.2 Hz, 3H) 1.14 (d, J=6.2 Hz, 3H) 1.43 (t, J=7.0 Hz, 3H) 2.43 (t, J=5.9 Hz, 1H) 2.88 (dd, J=14.6, 9.0 Hz, 1H) 2.95 (dd, J=14.6, 5.2 Hz, 1H) 3.49 (sept, J=6.2 Hz, 1H) 3.72 (s, 3H) 4.03 (dd, J=9.0, 5.2 Hz, 1H) 4.07 (q, J=7.0 Hz, 2H) 4.66 (d, J=5.9 Hz, 1H) 6.78 (d, J=8.2 Hz, 1H) 7.11 (dd, J=8.2, 2.3 Hz, 1H) 7.13 (d, J=2.3 Hz, 1H)

Production Example 595g

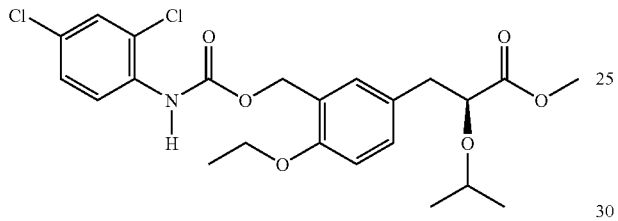

Under similar conditions to those described in Production example 147c), 2.5 g of methyl 2 (S)-isopropoxy-3-(4-ethoxy-3-hydroxymethylphenyl)propanoate and 1.9 g of 2,4-dichlorophenylisocyanate were reacted, to give 3.0 g of methyl 2 (S)-3-{[3-(2,4-dichlorophenyl)carbamoyloxymethyl-4-ethoxy]phenyl}-2-isopropoxypropanoate as a colorless solid.

$^1$H-NMR (CDCl$_3$)

δ: 0.96 (d, J=6.0 Hz, 3H) 1.13 (d, J=6.0 Hz, 3H) 1.41 (t, J=6.9 Hz, 3H) 2.89 (dd, J=13.8, 9.0 Hz, 1H) 2.95 (dd, J=13.8, 5.1 Hz, 1H) 3.49 (sept, J=6.0 Hz, 1H) 3.71 (s, 3H) 4.04 (d, J=9.0, 5.1 Hz, 1H) 4.05 (q, J=6.9 Hz, 2H) 5.26 (s, 2H) 6.81 (d, J=8.4 Hz, 1H) 7.15 (br. s, 1H) 7.17 (dd, J=8.4, 2.3 Hz, 1H) 7.21-7.23 (m, 2H) 7.35 (d, J=2.3 Hz, 1H) 8.18 (d, J=8.8 Hz, 1H)

Example 595h

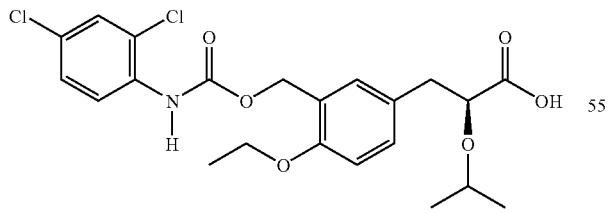

3.0 g of Methyl 2 (S)-3-{[3-(2,4-dichlorophenyl)carbamoyloxymethyl-4-ethoxy]phenyl}-2-isopropoxypropanoate was hydrolyzed in the same manner as described in Production example 147d, to give 1.6 g of 2 (S)-3-{[3-(2,4-dichlorophenyl)carbamoyloxymethyl-4-ethoxy]phenyl}-2-isopropoxypropanoic acid as a colorless solid.

$^1$H-NMR (CDCl$_3$)

δ: 1.04 (d, J=6.1 Hz, 3H) 1.15 (d, J=6.1 Hz, 3H) 1.41 (t, J=7.0 Hz, 3H) 2.91 (dd, J=14.0, 7.9 Hz, 1H) 3.08 (dd, J=14.0, 3.5 Hz, 1H) 3.55 (sept, J=6.1 Hz, 1H) 4.06 (q, J=7.0 Hz, 2H) 4.09 (dd, J=6.1, 3.5 Hz, 1H) 5.27 (s, 2H) 6.82 (d, J=8.3 Hz, 1H) 7.16 (br.s, 1H) 7.17 (dd, J=8.3, 2.2 Hz, 1H) 7.24 (dd, J=9.0, 2.2 Hz, 1H) 7.25 (d, J=2.2 Hz, 1H) 7.36 (d, J=2.2 Hz, 1H) 8.17 (d, J=9.0 Hz, 1H)

Example 596

3-{3-[(3,4-Dichlorobenzyloxycarbonylamino)methyl]-phenyl}-2(S)-isopropoxypropanoic acid

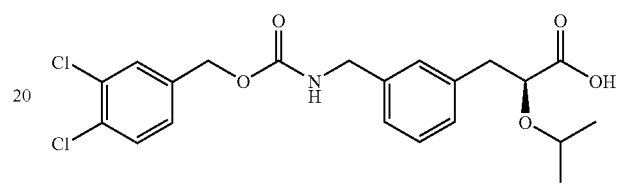

Using 3,4-dichlorobenzylchloride, the title compound was obtained in the same manner as described in Example 332e).

$^1$H NMR (CDCl$_3$)

δ: 1.00 (d, J=6.0 Hz, 3H) 1.15 (d, J=6.4 Hz, 3H) 2.95 (dd, J=8.0, 14.0 Hz, 1H) 3.12 (dd, J=4.0, 14.0 Hz, 1H) 3.54 (Sept, J=6.0 Hz, 1H) 4.12 (q, J=4.0 Hz, 1H) 4.37 (d, J=6.0 Hz, 2H) 5.08 (s, 2H) 5.10 (br, 1H) 7.12-7.22 (m, 4H) 7.25-7.29 (m, 1H) 7.41-7.47 (m, 2H)

MS m/e (ESI) 462 (MNa$^+$)

The invention claimed is:

1. A carboxylic acid compound represented by the following formula (I), a salt thereof, or an ester thereof

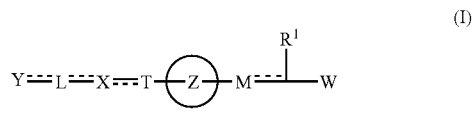

wherein

R$^1$ represents a C$_{1-6}$ alkoxy group;

L represents a single bond or a C$_{1-6}$ alkylene group which may have one or more substituents selected from C$_{1-6}$ alkyl groups;

M represents a C$_{1-6}$ alkylene group:

T represents a single bond, a C$_{1-3}$ alkylene group, or a C$_{2-3}$ alkynylene group;

W represents a carboxyl group;

----- represents a single bond or a double bond;

X is a group represented by the formula:

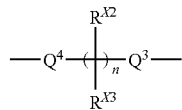

wherein n represents 1 to 5; $R^{X2}$ and $R^{X3}$ are the same as or different from each other and each represents a hydrogen atom, a hydroxy group, a halogen atom, a $C_{1-6}$ alkoxy group, or a $C_{1-6}$ hydroxyalkyl group, provided that at least one of $R^{x2}$ and $R^{x3}$ in the compound is a group other than a hydrogen atom; and $Q^3$ and $Q^4$ are the same as or different from each other and each represents an oxygen atom or (O)S(O);

Y is a phenyl group or a $C_{3-7}$ alicyclic hydrocarbon group, each of which may have one to 4 substituents selected from the group consisting of halogen atoms, cyano groups, $C_{1-6}$ alkyl groups, $C_{1-4}$ alkoxy groups, $C_{1-6}$ haloalkyl groups, and $C_{1-6}$ hydroxyalkyl groups; and the ring Z is a phenyl group.

2. The carboxylic acid compound according to claim 1, a salt thereof, or an ester thereof, wherein in the formula (I), Y is a phenyl group which may have one to 4 substituents selected from the group consisting of a halogen atom, a cyano group, a $C_{1-4}$ alkyl group, and a $C_{1-4}$ alkoxy group.

3. The carboxylic acid compound according to claim 1, a salt thereof, or an ester thereof, wherein in the formula (I), X is a group represented by the formula:

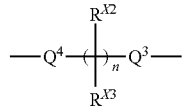

wherein $Q^3$ and $Q^4$ represent an oxygen atom; and n, $R^{X2}$ and $R^{X3}$ are as defined above.

4. The carboxylic acid according to claim 3, a salt thereof, or an ester thereof, wherein in the formula (I), X is a group represented by the formula:

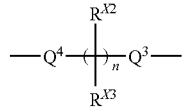

wherein $Q^3$ and $Q^4$ represent an oxygen atom; n represents 2 to 5; and $R^{X2}$ and $R^{X3}$ are as defined above; L is a single bond or a $C_{1-3}$ alkylene group; and T is a single bond or a $C_{1-3}$ alkylene group.

5. The carboxylic acid compound according to claim 4, a salt thereof, or an ester thereof, wherein in the formula (I), wherein M is a $C_{1-6}$ alkylene group; and $R^1$ is a $C_{1-6}$ alkoxy group.

6. The carboxylic acid compound according to claim 5, a salt thereof, or an ester thereof, wherein in the formula (I), the ring Z is a 1,3-phenylene group.

7. The carboxylic acid compound according to claim 4 or 6, a salt thereof, or an ester thereof, wherein in the formula (I), X is a group represented by the formula:

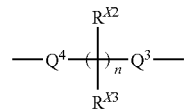

wherein $Q^3$ and $Q^4$ represent an oxygen atom; n represents 3 to 5; and $R^{X2}$ and $R^{X3}$ represent a hydrogen atom, hydroxyl group or fluorine atom.

8. The carboxylic acid compound according to claim 7, a salt thereof, or an ester thereof, wherein in the formula (I), X is represented by the formula:

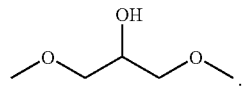

9. The carboxylic acid compound according to claim 7, a salt thereof, or an ester thereof, wherein in the formula (I), X is represented by the formula:

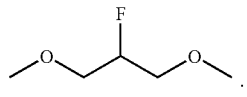

10. The carboxylic acid compound according to claim 7, a salt thereof or an ester thereof, wherein in the formula (I), M is a methylene group; and $R^1$ is a $C_{1-6}$ alkoxy group.

11. The carboxylic acid compound according to claim 4, a salt thereof, or an ester thereof, wherein in the formula (I), Y is a phenyl group.

12. The carboxylic acid compound according to claim 1, a salt thereof, or an ester thereof, wherein in the formula (I), a group represented by the formula:

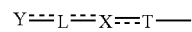

wherein each symbol represents a group as defined above and a group represented by the formula:

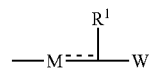

wherein each symbol represents a group as defined above are in a meta-position or a para-position on the ring Z.

13. The carboxylic acid compound according to claim 1, a salt thereof, or an ester thereof, wherein the compound represented by the formula (I) is one selected from:
- 3-{3-[3-(4-chloro-2-cyanophenoxy)-2-hydroxypropoxy]phenyl}-2-isopropoxypropanoic acid;
- 3-{3-[3-(2,4-dichlorophenoxy)-2(S)-hydroxypropoxy]phenyl}-2(S)-isopropoxypropanoic acid;
- 3-{3-[3-(4-chloro-2-cyanophenoxy)-2(S)-hydroxypropoxy]phenyl}-2(S)-isopropoxypropanoic acid;
- 3-(3-{2(S)-hydroxy-3-[3-(1-hydroxy-1-methylethyl)phenoxy]propoxy-}-phenyl)-2(S)-isopropoxypropanoic acid;

3-(3-{2(R)-hydroxy-3-[4-chlorophenoxy]propoxy}phenyl)-2(S)-isopropoxypropanoic acid;

3-(3-{2(S)-hydroxy-3-[2,4-dimethylphenoxy]propoxy}phenyl)-2(S)-isopropoxypropanoic acid;

3-(3-{2(S)-hydroxy-3-[4-chloro-2-fluorophenoxy]propoxy}phenyl)-2(S)-isopropoxypropanoic acid;

3-{3-[3-(2,4-dichlorophenoxy)-2 (R)-hydroxypropoxy]phenyl}-2(S)-isopropoxypropanoic acid;

3-{3-[3-(4-chloro-2-cyanophenoxy)-2 (R)-hydroxypropoxy]phenyl}-2(S)-isopropoxypropanoic acid;

3-(3-{2(R)-hydroxy-3-[2,4-dimethylphenoxy]propoxy}phenyl)-2(S)-isopropoxypropanoic acid;

3-{3-[3-(2,4-dichlorophenoxy)-2 (R)-fluoropropoxy]phenyl}-2(S)-isopropoxypropanoic acid;

3-{3-[3-(4-chlorophenoxy)-2(S)-fluoropropoxy]phenyl}-2(S)-isopropoxypropanoic acid;

3-{3-[3-(4-chloro-2-cyanophenoxy)-2 (R)-fluoropropoxy]phenyl}-2(S)-isopropoxypropanoic acid;

3-{3-[3-(2,4-dichlorophenoxy)-2(S)-fluoropropoxy]phenyl}-2(S)-isopropoxypropanoic acid;

3-{3-[3-(4-chlorophenoxy)-2 (R)-fluoropropoxy]phenyl}-2(S)-isopropoxypropanoic acid;

3-{3-[3-(4-chloro-2-cyanophenoxy)-2(S)-fluoropropoxy]phenyl}-2(S)-isopropoxypropanoic acid;

3-{3-[3-(2,4-dimethylphenoxy)-2(S)-fluoropropoxy]phenyl}-2(S)-isopropoxypropanoic acid; and 3-{4-[3-(4-chloro-2-cyanophenoxy)-2-hydroxypropoxy]phenyl}-2-isopropoxypropanoic acid.

14. A pharmaceutical composition comprising a carboxylic acid compound represented by the formula (I) as it is defined in claim 1, a salt thereof, or an ester thereof and a pharmaceutically acceptable carrier.

15. A carboxylic acid compound represented by the following formula, a salt thereof or an ester thereof

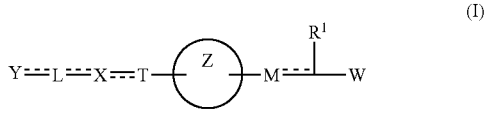
(I)

wherein
$R^1$ represents a $C_{1-3}$ alkoxy group;
L represents a single bond;
M represents a $C_{1-3}$ alkylene group;
T represents a single bond;
W represents a carboxyl group;

----- represents a single bond;
X is represented by the formula:

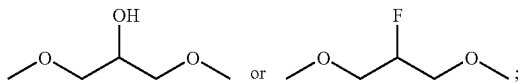

Y represents a phenyl group or a $C_{3-7}$ alicyclic hydrocarbon group, each of which may have 1 to 4 substituents selected from the group consisting of halogen atoms, cyano groups, $C_{1-6}$ alkyl groups, $C_{1-6}$ alkoxy groups, $C_{1-6}$ haloalkyl groups, and $C_{1-6}$ hydroxyalkyl groups; and the ring Z represents a phenyl group.

16. A compound selected from the group consisting of the compounds listed below, a salt thereof, or an ester thereof:

(1) 3-{3-[3-(4-chloro-2-cyanophenoxy)-2-hydroxypropoxy]phenyl}-2-isopropoxypropanoic acid;

(2) 3-{3-[3-(2,4-dichlorophenoxy)-2(S)-hydroxypropoxy]phenyl}-2(S)-isopropoxypropanoic acid;

(3) 3-{3-[3-(4-chloro-2-cyanophenoxy)-2(S)-hydroxypropoxy]phenyl}-2(S)-isopropoxypropanoic acid;

(4) 3-(3-{2(S)-hydroxy-3-[3-(1-hydroxy-1-methylethyl)phenoxy]propoxy}phenyl)-2(S)-isopropoxypropanoic acid;

(5) 3-(3-{2(R)-hydroxy-3-[4-chlorophenoxy]propoxy}phenyl)-2(S)-isopropoxypropanoic acid;

(6) 3-(3-{2(S)-hydroxy-3-[2,4-dimethylphenoxy]propoxy}phenyl)-2(S)-isopropoxypropanoic acid;

(7) 3-(3-{2(S)-hydroxy-3-[4-chloro-2-fluorophenoxy]propoxy}phenyl)-2(S)-isopropoxypropanoic acid;

(8) 3-{3-[3-(2,4-dichlorophenoxy)-2 (R)-hydroxypropoxy]phenyl}-2(S)-isopropoxypropanoic acid;

(9) 3-{3-[3-(4-chloro-2-cyanophenoxy)-2 (R)-hydroxypropoxy]phenyl}-2(S)-isopropoxypropanoic acid;

(10) 3-(3-{2(R)-hydroxy-3-[2,4-dimethylphenoxy]propoxy}phenyl)-2(S)-isopropoxypropanoic acid;

(11)-{3-[3-(2,4-dichlorophenoxy)-2 (R)-fluoropropoxy]phenyl}-2(S)-isopropoxypropanoic acid;

(12) 3-{3-[3-(4-chlorophenoxy)-2(S)-fluoropropoxy]phenyl}-2(S)-isopropoxypropanoic acid;

(13) 3-{3-[3-(4-chloro-2-cyanophenoxy)-2(R)-fluoropropoxy]phenyl}-2(S)-isopropoxypropanoic acid;

(14) 3-{3-[3-(2,4-dichlorophenoxy)-2(S)-fluoropropoxy]phenyl}-2(S)-isopropoxypropanoic acid;

(15) 3-{3-[3-(4-chlorophenoxy)-2(R)-fluoropropoxy]phenyl}-2(S)-isopropoxypropanoic acid;

(16) 3-{3-[3-(4-chloro-2-cyanophenoxy)-2(S)-fluoropropoxy]phenyl}-2(S)-isopropoxypropanoic acid;

(17) 3-{3-[3-(2,4-dimethylphenoxy)-2(S)-fluoropropoxy]phenyl}-2(S)-isopropoxypropanoic acid; and

(18) 3-{4-[3-(4-chloro-2-cyanophenoxy)-2-hydroxypropoxy]phenyl}-2-isopropoxypropanoic acid.

17. A pharmaceutical composition comprising the carboxylic acid compound according to claim 15, a salt thereof, or an ester thereof and a pharmaceutically acceptable carrier.

18. The compound 3-{3-[3-(4-chloro-2-cyanophenoxy)-2(S)-fluoropropoxy]phenyl}-2(S)-isopropoxypropanoic acid, represented by the following formula, a salt thereof or an ester thereof

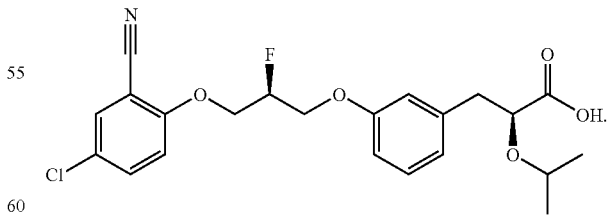

19. A pharmaceutical composition comprising the compound according to claim 18, a salt thereof, or an ester thereof and a pharmaceutically acceptable carrier.

* * * * *